US012385096B2

(12) United States Patent
Zimmermann et al.

(10) Patent No.: US 12,385,096 B2
(45) Date of Patent: *Aug. 12, 2025

(54) METHODS FOR CANCER DETECTION AND MONITORING

(71) Applicant: Natera, Inc., San Carlos, CA (US)

(72) Inventors: Bernhard Zimmermann, Manteca, CA (US); Raheleh Salari, San Carlos, CA (US); Ryan Swenerton, San Bruno, CA (US); Hsin-Ta Wu, Sunnyvale, CA (US); Himanshu Sethi, Sunnyvale, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/461,298

(22) Filed: Aug. 30, 2021

(65) Prior Publication Data

US 2022/0056509 A1 Feb. 24, 2022

Related U.S. Application Data

(63) Continuation of application No. 16/382,520, filed on Apr. 12, 2019, now Pat. No. 12,024,738.

(60) Provisional application No. 62/804,566, filed on Feb. 12, 2019, provisional application No. 62/777,973, filed on Dec. 11, 2018, provisional application No. 62/746,210, filed on Oct. 16, 2018, provisional application No. 62/715,143, filed on Aug. 6, 2018, provisional application No. 62/693,843, filed on Jul. 3, 2018, provisional application No. 62/669,330, filed on May 9, 2018, provisional application No. 62/657,727, filed on Apr. 14, 2018.

(51) Int. Cl.
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,957,654 A | 5/1976 | Ayres |
| 4,040,785 A | 8/1977 | Kim et al. |
| 4,683,195 A | 7/1987 | Mullis et al. |
| 4,942,124 A | 7/1990 | Church et al. |
| 5,180,812 A | 1/1993 | Dower et al. |
| 5,314,809 A | 5/1994 | Erlich et al. |
| 5,319,071 A | 6/1994 | Dower et al. |
| 5,464,937 A | 11/1995 | Sims et al. |
| 5,486,477 A | 1/1996 | Carver |
| 5,488,032 A | 1/1996 | Dower et al. |
| 5,492,888 A | 2/1996 | Dower et al. |
| 5,569,582 A | 10/1996 | Tavernarakis et al. |
| 5,595,890 A | 1/1997 | Newton et al. |
| 5,635,366 A | 6/1997 | Cooke et al. |
| 5,645,988 A | 7/1997 | Vande Woude et al. |
| 5,648,220 A | 7/1997 | Bianchi et al. |
| 5,714,320 A | 2/1998 | Kool |
| 5,716,776 A | 2/1998 | Bogart |
| 5,736,033 A | 4/1998 | Coleman et al. |
| 5,753,467 A | 5/1998 | Jensen et al. |
| 5,824,467 A | 10/1998 | Mascarenhas |
| 5,854,033 A | 12/1998 | Lizardi |
| 5,860,917 A | 1/1999 | Comanor et al. |
| 5,891,734 A | 4/1999 | Gill et al. |
| 5,952,170 A | 9/1999 | Stroun et al. |
| 5,962,223 A | 10/1999 | Whiteley et al. |
| 5,972,602 A | 11/1999 | Hyland et al. |
| 5,976,790 A | 11/1999 | Pinkel et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |

(Continued)

FOREIGN PATENT DOCUMENTS

| | | |
|---|---|---|
| BR | 112017023232 A2 | 8/2018 |
| CA | 2875281 A1 | 12/2013 |

(Continued)

OTHER PUBLICATIONS

US 8,501,409 B2, 08/2013, Simen et al. (withdrawn)

(Continued)

*Primary Examiner* — Carla J Myers

(57) ABSTRACT

The invention provides methods for detecting single nucleotide variants in breast cancer, bladder cancer, or colorectal cancer. Additional methods and compositions, such as reaction mixtures and solid supports comprising clonal populations of nucleic acids, are provided. For example, provided here is a method for monitoring and detection of early relapse or metastasis of breast cancer, bladder cancer, or colorectal cancer, comprising generating a set of amplicons by performing a multiplex amplification reaction on nucleic acids isolated from a sample of blood or urine or a fraction thereof from a patient who has been treated for a breast cancer, bladder cancer, or colorectal cancer, wherein each amplicon of the set of amplicons spans at least one single nucleotide variant locus of a set of patient-specific single nucleotide variant loci associated with the breast cancer, bladder cancer, or colorectal cancer; and determining the sequence of at least a segment of each amplicon of the set of amplicons that comprises a patient-specific single nucleotide variant locus, wherein detection of one or more patient-specific single nucleotide variants is indicative of early relapse or metastasis of breast cancer, bladder cancer, or colorectal cancer.

12 Claims, 140 Drawing Sheets

(56) References Cited

U.S. PATENT DOCUMENTS

| | | |
|---|---|---|
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,235,472 B1 | 2/2001 | Landegren et al. |
| 6,214,558 B1 | 4/2001 | Shuber et al. |
| 6,221,603 B1 | 4/2001 | Mahtani |
| 6,258,540 B1 | 7/2001 | Lo et al. |
| 6,300,077 B1 | 10/2001 | Shuber et al. |
| 6,329,179 B1 | 12/2001 | Kopreski |
| 6,335,167 B1 | 1/2002 | Pinkel et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,605,451 B1 | 8/2003 | Marmaro et al. |
| 6,617,137 B2 | 9/2003 | Dean et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,858,412 B2 | 2/2005 | Willis et al. |
| 6,927,028 B2 | 8/2005 | Lo et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,101,663 B2 | 9/2006 | Godfrey et al. |
| 7,153,656 B2 | 12/2006 | Nolan et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,410,764 B2 | 8/2008 | Gocke et al. |
| 7,414,118 B1 | 8/2008 | Mullah et al. |
| 7,442,506 B2 | 12/2008 | Dhallan |
| 7,459,273 B2 | 12/2008 | Jones et al. |
| 7,537,897 B2 | 5/2009 | Brenner et al. |
| 7,645,576 B2 | 1/2010 | Lo et al. |
| 7,655,399 B2 | 2/2010 | Cantor et al. |
| 7,700,325 B2 | 4/2010 | Cantor et al. |
| 7,718,367 B2 | 5/2010 | Lo et al. |
| 7,718,370 B2 | 6/2010 | Dhallan |
| 7,741,463 B2 | 6/2010 | Gormley et al. |
| 7,785,798 B2 | 8/2010 | Cantor et al. |
| 7,727,720 B2 | 9/2010 | Dhallan |
| 7,790,393 B2 | 9/2010 | Lyamichev et al. |
| 7,790,418 B2 | 9/2010 | Mayer |
| 7,805,282 B2 | 11/2010 | Casey |
| 7,838,647 B2 | 11/2010 | Hahn et al. |
| 7,981,609 B2 | 7/2011 | Rubin et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,236,503 B2 | 8/2012 | Faham et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,318,434 B2 | 11/2012 | Cuppens et al. |
| 8,323,897 B2 | 12/2012 | Andersen et al. |
| 8,372,584 B2 | 2/2013 | Shoemaker et al. |
| 8,389,557 B2 | 3/2013 | Singh et al. |
| 8,389,578 B2 | 3/2013 | Went et al. |
| 8,450,063 B2 | 5/2013 | Dube et al. |
| 8,467,976 B2 | 8/2013 | Lo et al. |
| 8,515,679 B2 | 8/2013 | Rabinowitz et al. |
| 8,532,930 B2 | 9/2013 | Rabinowitz et al. |
| 8,609,338 B2 | 12/2013 | Mitchell et al. |
| 8,679,741 B2 | 3/2014 | Hoyal-Wrightson et al. |
| 8,682,592 B2 | 3/2014 | Rabinowitz et al. |
| 8,703,652 B2 | 4/2014 | Quake et al. |
| 8,706,422 B2 | 4/2014 | Lo et al. |
| 8,748,103 B2 | 6/2014 | Faham et al. |
| 8,822,153 B2 | 9/2014 | Hayes et al. |
| 8,825,412 B2 | 9/2014 | Rabinowitz et al. |
| 9,005,894 B2 | 4/2015 | Ladner et al. |
| 9,051,602 B2 | 6/2015 | Oliphant et al. |
| 9,085,798 B2 | 7/2015 | Chee |
| 9,206,475 B2 | 12/2015 | Gerdes et al. |
| 9,228,234 B2 | 1/2016 | Rabinowitz et al. |
| 9,290,815 B2 | 3/2016 | Di Pasquale et al. |
| 9,323,888 B2 | 4/2016 | Rava et al. |
| 9,364,829 B2 | 6/2016 | Heid et al. |
| 9,404,150 B2 | 8/2016 | Lee et al. |
| 9,424,392 B2 | 8/2016 | Rabinowitz et al. |
| 9,453,257 B2 | 9/2016 | Hoyal-Wrightson et al. |
| 9,476,095 B2 | 10/2016 | Vogelstein et al. |
| 9,487,829 B2 | 11/2016 | Vogelstein et al. |
| 9,493,828 B2 | 11/2016 | Rava et al. |
| 9,506,119 B2 | 11/2016 | Faham et al. |
| 9,598,731 B2 | 3/2017 | Talasaz |
| 9,677,118 B2 | 6/2017 | Zimmermann et al. |
| 9,784,742 B2 | 10/2017 | Benz et al. |
| 9,926,593 B2 | 3/2018 | Ehrich et al. |
| 9,957,558 B2 | 5/2018 | Leamon et al. |
| 10,011,870 B2 | 7/2018 | Zimmermann et al. |
| 10,017,810 B2 | 7/2018 | Iafrate et al. |
| 10,041,127 B2 | 8/2018 | Talasaz |
| 10,061,890 B2 | 8/2018 | Rabinowitz et al. |
| 10,081,839 B2 | 9/2018 | Rabinowitz et al. |
| 10,083,273 B2 | 9/2018 | Rabinowitz et al. |
| 10,174,369 B2 | 1/2019 | Rabinowitz et al. |
| 10,179,937 B2 | 1/2019 | Babiarz et al. |
| 10,227,652 B2 | 3/2019 | Rabinowitz et al. |
| 10,229,244 B2 | 3/2019 | Ghosh |
| 10,240,202 B2 | 3/2019 | Rabinowitz et al. |
| 10,260,096 B2 | 4/2019 | Rabinowitz et al. |
| 10,262,755 B2 | 4/2019 | Babiarz et al. |
| 10,266,893 B2 | 4/2019 | Rabinowitz et al. |
| 10,308,981 B2 | 6/2019 | Sparks et al. |
| 10,316,362 B2 | 6/2019 | Babiarz et al. |
| 10,351,906 B2 | 7/2019 | Zimmermann et al. |
| 10,385,396 B2 | 8/2019 | Mitchell et al. |
| 10,392,664 B2 | 8/2019 | Rabinowitz et al. |
| 10,450,597 B2 | 10/2019 | Iafrate et al. |
| 10,472,680 B2 | 11/2019 | Mitchell et al. |
| 10,522,242 B2 | 12/2019 | Rabinowitz et al. |
| 10,526,658 B2 | 1/2020 | Babiarz et al. |
| 10,538,814 B2 | 1/2020 | Babiarz et al. |
| 10,557,172 B2 | 2/2020 | Babiarz et al. |
| 10,597,708 B2 | 3/2020 | Zimmermann et al. |
| 10,597,709 B2 | 3/2020 | Zimmermann et al. |
| 10,597,723 B2 | 3/2020 | Babiarz et al. |
| 10,640,819 B2 | 5/2020 | Rosenfeld et al. |
| 10,655,180 B2 | 5/2020 | Babiarz et al. |
| 10,683,552 B2 | 6/2020 | Giulio et al. |
| 10,711,309 B2 | 7/2020 | Rabinowitz et al. |
| 10,731,220 B2 | 8/2020 | Babiarz et al. |
| 10,774,380 B2 | 9/2020 | Ryan et al. |
| 10,793,912 B2 | 10/2020 | Babiarz et al. |
| 10,894,976 B2 | 1/2021 | Stray et al. |
| 11,111,543 B2 | 9/2021 | Rabinowitz et al. |
| 11,111,544 B2 | 9/2021 | Rabinowitz et al. |
| 11,111,545 B2 | 9/2021 | Babiarz et al. |
| 11,130,995 B2 | 9/2021 | Quake et al. |
| 11,319,596 B2 | 5/2022 | Babiarz et al. |
| 11,371,100 B2 | 6/2022 | Babiarz et al. |
| 11,519,035 B2 | 12/2022 | Rabinowtiz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2002/0119478 A1 | 8/2002 | Umansky et al. |
| 2002/0182622 A1 | 12/2002 | Nakamura et al. |
| 2002/0197630 A1 | 12/2002 | Knapp et al. |
| 2003/0009295 A1 | 1/2003 | Markowitz et al. |
| 2003/0040620 A1 | 2/2003 | Langmore et al. |
| 2003/0044388 A1 | 3/2003 | Lo et al. |
| 2003/0065535 A1 | 4/2003 | Karlov et al. |
| 2003/0077586 A1 | 4/2003 | Pavlovic et al. |

(56) References Cited

U.S. PATENT DOCUMENTS

| | | |
|---|---|---|
| 2003/0087276 A1 | 5/2003 | Kopreski et al. |
| 2003/0101000 A1 | 5/2003 | Bader et al. |
| 2003/0108900 A1 | 6/2003 | Oliphant et al. |
| 2003/0119004 A1 | 6/2003 | Wenz et al. |
| 2003/0138780 A1 | 7/2003 | Gill et al. |
| 2003/0148301 A1 | 8/2003 | Aono et al. |
| 2003/0191005 A1 | 10/2003 | Coelho et al. |
| 2003/0211489 A1 | 11/2003 | Shen et al. |
| 2003/0228613 A1 | 12/2003 | Bornarth et al. |
| 2003/0232348 A1 | 12/2003 | Jones et al. |
| 2003/0232353 A1 | 12/2003 | Kennedy et al. |
| 2003/0235848 A1 | 12/2003 | Neville et al. |
| 2004/0009518 A1 | 1/2004 | Lo et al. |
| 2004/0033596 A1 | 2/2004 | Threadgill et al. |
| 2004/0067493 A1 | 4/2004 | Matsuzaki et al. |
| 2004/0096874 A1 | 5/2004 | Neville et al. |
| 2004/0115629 A1 | 6/2004 | Panzer et al. |
| 2004/0117346 A1 | 6/2004 | Stoffel et al. |
| 2004/0126760 A1 | 7/2004 | Broude |
| 2004/0136967 A1 | 7/2004 | Weiss et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0185495 A1 | 9/2004 | Schueler et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0043894 A1 | 2/2005 | Fernandez |
| 2005/0049793 A1 | 3/2005 | Paterlini-brechot |
| 2005/0053950 A1 | 3/2005 | Ubani et al. |
| 2005/0064476 A1 | 3/2005 | Huang et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0164252 A1 | 7/2005 | Yeung |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2005/0282185 A1 | 12/2005 | Lo et al. |
| 2006/0014179 A1 | 1/2006 | Roberts |
| 2006/0019278 A1 | 1/2006 | Lo et al. |
| 2006/0040300 A1 | 2/2006 | Dapprich et al. |
| 2006/0046258 A1 | 3/2006 | Lapidus et al. |
| 2006/0051799 A1 | 3/2006 | Iwaki et al. |
| 2006/0052945 A1 | 3/2006 | Rabinowitz et al. |
| 2006/0057618 A1 | 3/2006 | Piper et al. |
| 2006/0068369 A1 | 3/2006 | Coelho et al. |
| 2006/0068394 A1 | 3/2006 | Langmore et al. |
| 2006/0088574 A1 | 4/2006 | Manning et al. |
| 2006/0088871 A1 | 4/2006 | Finkelstein et al. |
| 2006/0088912 A1 | 4/2006 | Yan et al. |
| 2006/0094010 A1 | 5/2006 | Giles et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216153 A1 | 9/2006 | Wobben et al. |
| 2006/0216738 A1 | 9/2006 | Wada et al. |
| 2006/0228721 A1 | 10/2006 | Leamon et al. |
| 2006/0234264 A1 | 10/2006 | Hardenbol |
| 2006/0248031 A1 | 11/2006 | Kates et al. |
| 2006/0281105 A1 | 12/2006 | Li et al. |
| 2006/0292599 A1 | 12/2006 | Ritz et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0037166 A1 | 2/2007 | Wohlgemuth et al. |
| 2007/0042384 A1 | 2/2007 | Li et al. |
| 2007/0059700 A1 | 3/2007 | Tao et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0134658 A1 | 6/2007 | Bohmer |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0231823 A1 | 10/2007 | McKernan et al. |
| 2007/0243549 A1 | 10/2007 | Bischoff |
| 2007/0259351 A1 | 11/2007 | Chinitz |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0161420 A1 | 7/2008 | Shuber et al. |
| 2008/0164204 A1 | 7/2008 | Hatamian et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0293589 A1 | 11/2008 | Shapero |
| 2008/0299562 A1 | 12/2008 | Oeth et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176234 A1 | 7/2009 | Drmanac et al. |
| 2009/0176662 A1 | 7/2009 | Rigatti et al. |
| 2009/0221620 A1 | 9/2009 | Luke et al. |
| 2009/0228299 A1 | 9/2009 | Kangarloo et al. |
| 2009/0233802 A1 | 9/2009 | Bignell et al. |
| 2009/0253183 A1 | 10/2009 | Han |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0012598 A1 | 1/2010 | Dicesare et al. |
| 2010/0035232 A1 | 2/2010 | Ecker et al. |
| 2010/0041048 A1 | 2/2010 | Diehl et al. |
| 2010/0086914 A1 | 4/2010 | Bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0155343 A1 | 6/2010 | Battles et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |

(56) References Cited

U.S. PATENT DOCUMENTS

| | | |
|---|---|---|
| 2010/0203538 A1 | 8/2010 | Dube et al. |
| 2010/0216145 A1 | 8/2010 | Duvdevani |
| 2010/0216151 A1 | 8/2010 | Lapdus et al. |
| 2010/0216153 A1 | 8/2010 | Lapidus et al. |
| 2010/0227329 A1 | 9/2010 | Cuppens |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2010/0326218 A1 | 12/2010 | Boeckh et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0110931 A1 | 5/2011 | Matsui |
| 2011/0111410 A1 | 5/2011 | Ryan et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0189677 A1 | 8/2011 | Adli et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0230358 A1 | 9/2011 | Rava |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0021442 A1 | 1/2012 | Buhimschi et al. |
| 2012/0028814 A1 | 2/2012 | Toloue et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0115140 A1 | 5/2012 | Rivkees et al. |
| 2012/0122701 A1 | 5/2012 | Ryan et al. |
| 2012/0122702 A1 | 5/2012 | Leproust et al. |
| 2012/0135872 A1 | 5/2012 | Chuu et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0251411 A1 | 10/2012 | Jeon |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0059733 A1 | 3/2013 | Lo et al. |
| 2013/0060483 A1 | 3/2013 | Struble et al. |
| 2013/0069869 A1 | 3/2013 | Akao et al. |
| 2013/0071844 A1 | 3/2013 | Makino et al. |
| 2013/0073214 A1 | 3/2013 | Hyland et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0143219 A1 | 6/2013 | Mitchell et al. |
| 2013/0150253 A1 | 6/2013 | Deciu et al. |
| 2013/0157870 A1 | 6/2013 | Pushkarev et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0231252 A1 | 9/2013 | Mitchell et al. |
| 2013/0237431 A1 | 9/2013 | Lo et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0274135 A1 | 10/2013 | Zhang et al. |
| 2013/0288252 A1 | 10/2013 | Sparks et al. |
| 2013/0303461 A1 | 11/2013 | Iafrate et al. |
| 2013/0310260 A1 | 11/2013 | Kim et al. |
| 2013/0323727 A1 | 12/2013 | Huang et al. |
| 2013/0323731 A1 | 12/2013 | Lo et al. |
| 2013/0325360 A1 | 12/2013 | Deciu et al. |
| 2013/0344066 A1 | 12/2013 | Faham et al. |
| 2014/0032128 A1 | 1/2014 | Rabinowitz et al. |
| 2014/0038830 A1 | 2/2014 | Srinivasan et al. |
| 2014/0045181 A1 | 2/2014 | Lo et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |
| 2014/0100121 A1 | 4/2014 | Lo et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0113795 A1 | 4/2014 | Emerson et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0186827 A1 | 7/2014 | Pieprzyk et al. |
| 2014/0193816 A1 | 7/2014 | Rabinowitz et al. |
| 2014/0206552 A1 | 7/2014 | Rabinowitz et al. |
| 2014/0227691 A1 | 8/2014 | May et al. |
| 2014/0227705 A1 | 8/2014 | Vogelstein et al. |
| 2014/0242588 A1 | 8/2014 | Van Den Boom et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1 | 10/2014 | Diehn et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0056617 A1 | 2/2015 | Whitt et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0099673 A1 | 4/2015 | Fodor |
| 2015/0147815 A1 | 5/2015 | Babiarz et al. |
| 2015/0157606 A1 | 6/2015 | Maneval et al. |
| 2015/0167069 A1 | 6/2015 | Schutz et al. |
| 2015/0167077 A1 | 6/2015 | Fehr et al. |
| 2015/0197786 A1 | 7/2015 | Osborne et al. |

(56) References Cited

U.S. PATENT DOCUMENTS

| | | |
|---|---|---|
| 2015/0211050 A1 | 7/2015 | Iafrate et al. |
| 2015/0218631 A1 | 8/2015 | Chuu et al. |
| 2015/0232938 A1 | 8/2015 | Mhatre |
| 2015/0246103 A1 | 9/2015 | Hazout |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0024581 A1 | 1/2016 | Sarwal et al. |
| 2016/0032396 A1 | 2/2016 | Diehn et al. |
| 2016/0046986 A1 | 2/2016 | Eltoukhy et al. |
| 2016/0053320 A1 | 2/2016 | Schuh et al. |
| 2016/0115541 A1 | 4/2016 | Schutz et al. |
| 2016/0138112 A1 | 5/2016 | Janne et al. |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0011166 A1 | 1/2017 | Rabinowitz et al. |
| 2017/0107576 A1 | 4/2017 | Babiarz et al. |
| 2017/0114411 A1 | 4/2017 | Mitchell |
| 2017/0121716 A1 | 5/2017 | Rodi et al. |
| 2017/0137882 A1 | 5/2017 | Goossens et al. |
| 2017/0145475 A1 | 5/2017 | Hunsley et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0298427 A1 | 10/2017 | Buis et al. |
| 2017/0314014 A1 | 11/2017 | Green et al. |
| 2017/0342477 A1 | 11/2017 | Jensen et al. |
| 2017/0362649 A1 | 12/2017 | Lieberman-Aiden et al. |
| 2018/0023128 A1 | 1/2018 | Yanai et al. |
| 2018/0025109 A1 | 2/2018 | Rabinowitz et al. |
| 2018/0105807 A1 | 4/2018 | Lo et al. |
| 2018/0127744 A1 | 5/2018 | Hu et al. |
| 2018/0142296 A1 | 5/2018 | Mitchell et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0187241 A1 | 7/2018 | Selvaraj et al. |
| 2018/0201995 A1 | 7/2018 | Rabinowitz et al. |
| 2018/0237841 A1 | 8/2018 | Stray et al. |
| 2018/0251553 A1 | 9/2018 | McGranahan et al. |
| 2018/0265917 A1 | 9/2018 | Barany et al. |
| 2018/0288982 A1 | 10/2018 | Sinha |
| 2018/0298439 A1 | 10/2018 | Ryan et al. |
| 2018/0300448 A1 | 10/2018 | Rabinowitz et al. |
| 2018/0303870 A1 | 10/2018 | Golobish et al. |
| 2018/0320171 A1 | 11/2018 | Withey |
| 2018/0320239 A1 | 11/2018 | Babiarz et al. |
| 2018/0371531 A1 | 12/2018 | Quake et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0112661 A1 | 4/2019 | Khan et al. |
| 2019/0153521 A1 | 5/2019 | Mitchell et al. |
| 2019/0153525 A1 | 5/2019 | Mitchell et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211376 A1 | 7/2019 | Quake et al. |
| 2019/0211385 A1 | 7/2019 | Sarwar et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256924 A1 | 8/2019 | Vogelstein et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360033 A1 | 11/2019 | Stamm et al. |
| 2019/0360036 A1 | 11/2019 | Rabinowitz et al. |
| 2019/0367972 A1 | 12/2019 | Mitchell et al. |
| 2020/0024653 A1 | 1/2020 | Bethke |
| 2020/0032323 A1 | 1/2020 | Talasaz et al. |
| 2020/0032340 A1 | 1/2020 | Mitchell et al. |
| 2020/0109449 A1 | 4/2020 | Stamm et al. |
| 2020/0121718 A1 | 4/2020 | Novik et al. |
| 2020/0123612 A1 | 4/2020 | Babiarz et al. |
| 2020/0126634 A1 | 4/2020 | Sigurjonsson et al. |
| 2020/0140950 A1 | 5/2020 | Babiarz et al. |
| 2020/0141925 A1 | 5/2020 | Liaw et al. |
| 2020/0149111 A1 | 5/2020 | Babiarz et al. |
| 2020/0157629 A1 | 5/2020 | Babiarz et al. |
| 2020/0165678 A1 | 5/2020 | Mitchell et al. |
| 2020/0172977 A1 | 6/2020 | Rabinowitz et al. |
| 2020/0181681 A1 | 6/2020 | Mitchell et al. |
| 2020/0181697 A1 | 6/2020 | Rabinowitz et al. |
| 2020/0190570 A1 | 6/2020 | Ryan et al. |
| 2020/0190573 A1 | 6/2020 | Rabinowitz et al. |
| 2020/0190591 A1 | 6/2020 | Rabinowitz et al. |
| 2020/0208196 A1 | 7/2020 | Zimmermann et al. |
| 2020/0208221 A1 | 7/2020 | Babiarz et al. |
| 2020/0224273 A1 | 7/2020 | Rabinowitz et al. |
| 2020/0232036 A1 | 7/2020 | Rabinowitz et al. |
| 2020/0232037 A1 | 7/2020 | Babiarz et al. |
| 2020/0248264 A1 | 8/2020 | Rabinowitz et al. |
| 2020/0248266 A1 | 8/2020 | Swanton et al. |
| 2020/0316498 A1 | 10/2020 | Mitchell |
| 2020/0318191 A1 | 10/2020 | Babiarz et al. |
| 2020/0347454 A1 | 11/2020 | Babiarz et al. |
| 2020/0350034 A1 | 11/2020 | Rabinowitz et al. |
| 2020/0362415 A1 | 11/2020 | Rabinowitz et al. |
| 2020/0370129 A1 | 11/2020 | Quinn et al. |
| 2020/0385809 A1 | 12/2020 | Ramani et al. |
| 2020/0407788 A1 | 12/2020 | Ryan et al. |
| 2020/0407798 A1 | 12/2020 | Babiarz et al. |
| 2021/0009990 A1 | 1/2021 | Stray et al. |

(56) References Cited

U.S. PATENT DOCUMENTS

| | | |
|---|---|---|
| 2021/0025005 A1 | 1/2021 | Babiarz et al. |
| 2021/0032692 A1 | 2/2021 | Mitchell et al. |
| 2021/0054459 A1 | 2/2021 | Rabinowitz et al. |
| 2021/0071246 A1 | 3/2021 | Zimmermann et al. |
| 2021/0139969 A1 | 5/2021 | Mitchell et al. |
| 2021/0139983 A1 | 5/2021 | Mitchell et al. |
| 2021/0139988 A1 | 5/2021 | Mitchell et al. |
| 2021/0155988 A1 | 5/2021 | Rabinowitz et al. |
| 2021/0189498 A1 | 6/2021 | Babiarz et al. |
| 2021/0198733 A1 | 7/2021 | Moshkevich et al. |
| 2021/0198742 A1 | 7/2021 | Rabinowitz et al. |
| 2021/0198743 A1 | 7/2021 | Rabinowitz et al. |
| 2021/0222230 A1 | 7/2021 | Zimmermann et al. |
| 2021/0222240 A1 | 7/2021 | Moshkevich et al. |
| 2021/0257048 A1 | 8/2021 | Zimmermann et al. |
| 2021/0269879 A1 | 9/2021 | Mitchell et al. |
| 2021/0301320 A1 | 9/2021 | Mitchell et al. |
| 2021/0324463 A1 | 10/2021 | Rabinowitz et al. |
| 2021/0327538 A1 | 10/2021 | Egilsson et al. |
| 2021/0327542 A1 | 10/2021 | Ryan et al. |
| 2021/0348229 A1 | 11/2021 | Maguire et al. |
| 2021/0355536 A1 | 11/2021 | Rabinowitz et al. |
| 2022/0025455 A1 | 1/2022 | Zimmermann et al. |
| 2022/0025456 A1 | 1/2022 | Rabinowitz et al. |
| 2022/0033908 A1 | 2/2022 | Rabinowitz et al. |
| 2022/0033909 A1 | 2/2022 | Babiarz et al. |
| 2022/0042103 A1 | 2/2022 | Rabinowitz et al. |
| 2022/0056534 A1 | 2/2022 | Rivers |
| 2022/0009866 A1 | 3/2022 | Rabinowitz et al. |
| 2022/0073978 A1 | 3/2022 | Rabinowitz et al. |
| 2022/0073979 A1 | 3/2022 | Rabinowitz et al. |
| 2022/0139495 A1 | 5/2022 | Rabinowitz et al. |
| 2022/0145391 A1 | 5/2022 | Mitchell et al. |
| 2022/0154249 A1 | 5/2022 | Zimmermann et al. |
| 2022/0154290 A1 | 5/2022 | Babiarz et al. |
| 2022/0195526 A1 | 6/2022 | Rabinowitz et al. |
| 2022/0213561 A1 | 7/2022 | Babiarz et al. |
| 2022/0251654 A1 | 8/2022 | Hafez et al. |
| 2022/0267849 A1 | 8/2022 | Mitchell et al. |
| 2022/0282335 A1 | 9/2022 | Babiarz et al. |
| 2022/0307086 A1 | 9/2022 | Babiarz et al. |
| 2022/0340963 A1 | 10/2022 | North et al. |
| 2022/0356522 A1 | 11/2022 | Mitchell et al. |
| 2022/0356526 A1 | 11/2022 | Babiarz et al. |
| 2022/0356530 A1 | 11/2022 | Sharma |
| 2022/0403461 A1 | 12/2022 | Kirkizlar et al. |
| 2022/0411875 A1 | 12/2022 | Rabinowitz et al. |
| 2023/0054494 A1 | 2/2023 | Rabinowitz et al. |
| 2023/0053752 A1 | 3/2023 | Rabinowitz et al. |
| 2023/0060579 A1 | 3/2023 | Bethke et al. |
| 2023/0193387 A1 | 6/2023 | Rabinowitz |
| 2023/0203573 A1 | 6/2023 | Swenerton et al. |
| 2023/0212693 A1 | 7/2023 | Rabinowitz et al. |
| 2023/0242998 A1 | 8/2023 | Babiarz et al. |
| 2023/0332221 A1 | 10/2023 | Zimmermann et al. |
| 2023/0343411 A1 | 10/2023 | Rabinowitz et al. |
| 2023/0360723 A1 | 11/2023 | Rabinowitz et al. |
| 2023/0368865 A1 | 11/2023 | Rabinowitz et al. |
| 2023/0383348 A1 | 11/2023 | Rabinowitz et al. |
| 2023/0420071 A1 | 12/2023 | Rabinowitz et al. |
| 2024/0002938 A1 | 1/2024 | Rabinowitz et al. |
| 2024/0038328 A1 | 2/2024 | Rabinowitz et al. |
| 2024/0060124 A1 | 2/2024 | Ryan et al. |
| 2024/0062846 A1 | 2/2024 | Rabinowitz |
| 2024/0068031 A1 | 2/2024 | Rabinowitz |
| 2024/0132957 A1 | 4/2024 | Mitchell et al. |
| 2024/0132960 A1 | 4/2024 | Demko |
| 2024/0158855 A1 | 5/2024 | Babiarz et al. |
| 2024/0185957 A1 | 6/2024 | Rabinowitz et al. |
| 2024/0271214 A1 | 8/2024 | Rabinowitz et al. |

FOREIGN PATENT DOCUMENTS

| | | |
|---|---|---|
| CN | 1650032 A | 8/2005 |
| CN | 1674028 A | 9/2005 |
| CN | 101675169 A | 3/2010 |
| CN | 102892901 A | 1/2013 |
| CN | 104736722 A | 6/2015 |
| CN | 105229175 A | 1/2016 |
| CN | 107365769 A | 11/2017 |
| CN | 107849604 A | 3/2018 |
| CN | 109661476 A | 4/2019 |
| EA | 201792389 A1 | 5/2018 |
| EP | 0270017 A2 | 6/1988 |
| EP | 1325963 A1 | 7/2003 |
| EP | 1524321 A1 | 4/2005 |
| EP | 1325963 B1 | 9/2006 |
| EP | 1524321 B1 | 7/2009 |
| EP | 2163622 A1 | 3/2010 |
| EP | 2128169 A1 | 12/2010 |
| EP | 2551356 A1 | 1/2013 |
| EP | 2653562 A1 | 10/2013 |
| EP | 2902500 A1 | 8/2015 |
| EP | 3026124 A1 | 6/2016 |
| EP | 2315849 B1 | 11/2017 |
| EP | 3285193 A1 | 2/2018 |
| EP | 2877594 B1 | 12/2019 |
| EP | 3187597 B1 | 6/2020 |
| EP | 3134541 B1 | 8/2020 |
| EP | 3760730 A1 | 1/2021 |
| EP | 3760731 A1 | 1/2021 |
| EP | 3760732 A1 | 1/2021 |
| EP | 3824470 | 5/2021 |
| EP | 3443119 B1 | 2/2022 |
| GB | 2488358 | 8/2012 |
| JP | 2965699 | 8/1999 |
| JP | 2002-530121 A | 9/2002 |
| JP | 2002-300894 A | 10/2002 |
| JP | 2003/521252 A | 7/2003 |
| JP | 2004502466 A | 1/2004 |
| JP | 2004121087 A | 4/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2008-263974 A | 11/2008 |
| JP | 2008/271980 A | 11/2008 |
| JP | 2010-509922 A | 4/2010 |
| JP | 2011/508662 A | 3/2011 |
| JP | 2011/516069 A | 5/2011 |
| JP | 2012-085556 A | 5/2012 |
| JP | 2013509883 A | 3/2013 |
| JP | 2014118334 A1 | 8/2014 |
| JP | 2015-535681 | 12/2015 |
| JP | 2016502849 A | 2/2016 |
| RU | 2290078 C1 | 12/2006 |
| WO | 95/01796 | 1/1995 |
| WO | 9623067 A1 | 8/1996 |
| WO | 1996036736 A2 | 11/1996 |
| WO | 98/39474 | 9/1998 |
| WO | 98/44151 | 10/1998 |
| WO | 9937773 A1 | 7/1999 |
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 2001/079851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |
| WO | 03/020974 A3 | 3/2003 |
| WO | 2003031646 A1 | 4/2003 |
| WO | 2003/050532 A1 | 6/2003 |
| WO | 2003062441 A1 | 7/2003 |
| WO | 2003/102595 A1 | 12/2003 |
| WO | 2003/106623 A2 | 12/2003 |
| WO | 2004/051218 A2 | 6/2004 |
| WO | 2004069849 A2 | 8/2004 |

(56) References Cited

FOREIGN PATENT DOCUMENTS

| | | |
|---|---|---|
| WO | 2004070005 A2 | 8/2004 |
| WO | 2004070007 A2 | 8/2004 |
| WO | 2004078999 A1 | 9/2004 |
| WO | 2004081183 | 9/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007070280 A2 | 6/2007 |
| WO | 2007070482 A2 | 6/2007 |
| WO | 2007075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A1 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/032779 A2 | 3/2009 |
| WO | 2009/036525 A2 | 3/2009 |
| WO | 2009030100 A1 | 3/2009 |
| WO | 2009032781 A2 | 3/2009 |
| WO | 2009033178 A1 | 3/2009 |
| WO | 2009049889 A1 | 4/2009 |
| WO | 2009017784 A2 | 5/2009 |
| WO | 2009064897 A2 | 5/2009 |
| WO | 2009091934 A1 | 7/2009 |
| WO | 2009092035 A2 | 7/2009 |
| WO | 2009/105531 A1 | 8/2009 |
| WO | 2009099602 A1 | 8/2009 |
| WO | 2009100029 A1 | 8/2009 |
| WO | 2009117122 A2 | 9/2009 |
| WO | 2009120808 A2 | 10/2009 |
| WO | 2009145828 A2 | 12/2009 |
| WO | 2009146335 A1 | 12/2009 |
| WO | 2010014920 A1 | 2/2010 |
| WO | 2010017214 A1 | 2/2010 |
| WO | 2010/033639 A2 | 3/2010 |
| WO | 2010/033652 A1 | 3/2010 |
| WO | 2010033578 A2 | 3/2010 |
| WO | 2010042831 A2 | 4/2010 |
| WO | 2010045617 A2 | 4/2010 |
| WO | 2010075459 | 7/2010 |
| WO | 2010/088288 A2 | 8/2010 |
| WO | 2010115016 A2 | 10/2010 |
| WO | 2010115154 A1 | 10/2010 |
| WO | 2010118016 A2 | 10/2010 |
| WO | 2010/127186 A1 | 11/2010 |
| WO | 2011015944 A2 | 2/2011 |
| WO | 2011/023078 A1 | 3/2011 |
| WO | 2011/032078 A1 | 3/2011 |
| WO | 2011041485 A1 | 4/2011 |
| WO | 2011/051283 A1 | 5/2011 |
| WO | 2011057061 A1 | 5/2011 |
| WO | 2011057094 | 5/2011 |
| WO | 2011/090556 A1 | 7/2011 |
| WO | 2011087760 | 7/2011 |
| WO | 2011094646 A1 | 8/2011 |
| WO | 2011102998 A2 | 8/2011 |
| WO | 2011/118603 | 9/2011 |
| WO | 2011109440 A1 | 9/2011 |
| WO | 2011118603 A1 | 9/2011 |
| WO | 2011/142836 A2 | 11/2011 |
| WO | 2011140433 A2 | 11/2011 |
| WO | 2011146632 A1 | 11/2011 |
| WO | 2012/019200 A2 | 2/2012 |
| WO | 2012/028746 A1 | 3/2012 |
| WO | 2012042374 A2 | 4/2012 |
| WO | 2012/058488 A1 | 5/2012 |
| WO | 2012-083189 A2 | 6/2012 |
| WO | 201283250 | 6/2012 |
| WO | 2012088456 A2 | 6/2012 |
| WO | 20120071621 | 6/2012 |
| WO | 2012092426 | 7/2012 |
| WO | 2012108920 A1 | 8/2012 |
| WO | 2012122374 A2 | 9/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 2013/123220 A1 | 8/2013 |
| WO | 2013/138510 A1 | 9/2013 |
| WO | 2013/138510 A9 | 9/2013 |
| WO | 20130130848 | 9/2013 |
| WO | 2013159035 A2 | 10/2013 |
| WO | 2013/169339 A1 | 11/2013 |
| WO | 2013/177220 A1 | 11/2013 |
| WO | 2013/181651 A1 | 12/2013 |
| WO | 2013190441 A2 | 12/2013 |
| WO | 2014/004726 A1 | 1/2014 |
| WO | 2014/014497 A1 | 1/2014 |
| WO | 20140018080 | 1/2014 |
| WO | 2014026277 A1 | 2/2014 |
| WO | 2014/035986 A1 | 3/2014 |
| WO | 2014039556 A1 | 3/2014 |
| WO | 2014099919 A2 | 6/2014 |
| WO | 2014/122288 A1 | 8/2014 |
| WO | 2014/1424290 | 8/2014 |
| WO | 2014/145078 A1 | 9/2014 |
| WO | 2014/145232 A2 | 9/2014 |
| WO | 2014/149134 A2 | 9/2014 |
| WO | 2014/150300 A2 | 9/2014 |
| WO | 2014/151117 A1 | 9/2014 |
| WO | 2014143989 A1 | 9/2014 |
| WO | 2014194113 A2 | 12/2014 |
| WO | 2015/006668 A1 | 1/2015 |
| WO | 2015035177 A1 | 3/2015 |
| WO | 2015134552 A1 | 3/2015 |
| WO | 2015/048535 A1 | 4/2015 |
| WO | 2015/070086 A1 | 5/2015 |
| WO | 2015069933 A1 | 5/2015 |
| WO | 2015/100427 A1 | 7/2015 |
| WO | 2015138997 A1 | 9/2015 |
| WO | 2015/148494 A1 | 10/2015 |
| WO | 2015/164432 A1 | 10/2015 |

(56) References Cited

FOREIGN PATENT DOCUMENTS

| | | |
|---|---|---|
| WO | 2015169947 A1 | 11/2015 |
| WO | 2015178978 A2 | 11/2015 |
| WO | 2016/009059 A1 | 1/2016 |
| WO | 2016001411 A1 | 1/2016 |
| WO | 2016009224 A1 | 1/2016 |
| WO | 2016028316 A1 | 2/2016 |
| WO | 2016/065295 A1 | 4/2016 |
| WO | 2016063122 A1 | 4/2016 |
| WO | 2016/077313 A1 | 5/2016 |
| WO | 2016123698 A1 | 8/2016 |
| WO | 2016/138080 A1 | 9/2016 |
| WO | 2016/183106 A1 | 11/2016 |
| WO | 2016176662 A1 | 11/2016 |
| WO | 2016/193490 A1 | 12/2016 |
| WO | 2016192956 A1 | 12/2016 |
| WO | 2017011329 A1 | 1/2017 |
| WO | 2017-045654 A1 | 3/2017 |
| WO | 2017/058784 A1 | 4/2017 |
| WO | 2017091865 A1 | 6/2017 |
| WO | 2017/176852 A1 | 10/2017 |
| WO | 2017/181146 A1 | 10/2017 |
| WO | 2017/181202 A2 | 10/2017 |
| WO | 2017190106 A1 | 11/2017 |
| WO | 2017205540 A1 | 11/2017 |
| WO | 2018/009723 A1 | 1/2018 |
| WO | 2018/083467 A1 | 5/2018 |
| WO | 2018085597 A1 | 5/2018 |
| WO | 2018085603 A1 | 5/2018 |
| WO | 2018/106798 A1 | 6/2018 |
| WO | 2018119422 A1 | 6/2018 |
| WO | 2018/136562 A2 | 7/2018 |
| WO | 2018/156418 A1 | 8/2018 |
| WO | 2018237078 A1 | 12/2018 |
| WO | 2018237081 A1 | 12/2018 |
| WO | 2019006561 A1 | 1/2019 |
| WO | 2019008408 A1 | 1/2019 |
| WO | 2019/046817 A1 | 3/2019 |
| WO | 2019053243 A1 | 3/2019 |
| WO | 2019109053 A1 | 6/2019 |
| WO | 2019118926 A1 | 6/2019 |
| WO | 2019/140298 A1 | 7/2019 |
| WO | 2019/161244 A1 | 8/2019 |
| WO | 2019/200228 A1 | 10/2019 |
| WO | 2019/241349 A1 | 12/2019 |
| WO | 2020/010255 A1 | 1/2020 |
| WO | 2020/018522 A1 | 1/2020 |
| WO | 2020/041449 A1 | 2/2020 |
| WO | 2020/076957 A1 | 4/2020 |
| WO | 2020/106987 A1 | 5/2020 |
| WO | 2020104670 A1 | 5/2020 |
| WO | 2020/131699 A2 | 6/2020 |
| WO | 2020131955 A1 | 6/2020 |
| WO | 2020/214547 A1 | 10/2020 |
| WO | 2020206290 A1 | 10/2020 |
| WO | 2020/247263 A1 | 12/2020 |
| WO | 2021/055968 A1 | 3/2021 |
| WO | 2007100911 A2 | 9/2021 |
| WO | 2021/243045 A1 | 12/2021 |
| WO | 2022/015676 A1 | 1/2022 |
| WO | 2022182878 | 9/2022 |
| WO | 2022197864 | 9/2022 |
| WO | 2023014597 A1 | 2/2023 |
| WO | 2023034090 A1 | 3/2023 |
| WO | 2023133131 A1 | 7/2023 |
| WO | 2011/130751 | 10/2023 |
| WO | 2023/192224 A1 | 10/2023 |
| WO | 2011/146942 A | 11/2023 |
| WO | 2011/153254 A2 | 12/2023 |
| WO | 2024/076485 A1 | 4/2024 |

OTHER PUBLICATIONS

Reinert et al JAMA. May 9, 2019. 5(8): 1124-1131 and Supplementary Online Content, p. 1-74 (Year: 2019).*
Abbosh et al Nature. Apr. 26, 2017. 545: 446-453 and Supplementary Information, total of 22 pages (Year: 2017).*
Sethi et al Cancer Research. 78(13), Abstract 4542, abstract published Jul. 1, 2018; AACR meeting held Apr. 14-18, 2018 (Year: 2018).*
Reinert et al. Annals Oncology. Oct. 2018. 29(8), p. viii 151, abstract 456PD (Year: 2018).*
"European Application No. 014198110, European Search Report Mailed Apr. 28, 2015, 3 pages."
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.
"Abstracts for CNAPS III Circulating Nucleic Acids in Plasma and Serum and Serum Proteomics", Clinical Chemistry, vol. 49, No. 11, 2003, 33 pages.
"Abstracts for CNAPS IV Circulating Nucleic Acids in Plasma/Serum", Fourth International Conference on Circulating Nucleic Acids in Plasma/Serum (CNAPS-IV), 2005, 40 pages.
"How Many Carbs in a Potato?, [Online]", New Health Guide, Nov. 1, 2014, 3 pages.
"Random variable", The Penguin Dictionary of Mathematics, 2008, 1 page.
Abaan, O. D. et al., "The Exomes of the NCI-60 Panel: A Genomic Resource for Cancer Biology and Systems Pharmacology", Cancer Res., vol. 73, No. 14, Jul. 15, 2013, 4372-4382.
Abbosh, C. et al., "Phylogenetic ctDNA analysis depicts early-stage lung cancer evolution", Nature, vol. 545, May 25, 2017, 446-451.
Abd-Elsalam, Kamel A. , "Bioinformatic Tools And Guideline for PCR Primer Design", African Journal of Biotechnology, vol. 2, 2003, pp. 91-95.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Academic Press, "Fixed Medium", 1996, 1 pg.
Adalsteinsson, V. A. et al., "Scalable whole-exome sequencing of cell-free DNA reveals high concordance with metastatic tumors", Nature Communications, vol. 18, No. 1324, 2017, 13 pages.
Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.
Agarwal, Ashwin. et al., "Commercial Landscape of Noninvasive Prenatal Testing in the United States", Prenatal Diagnosis, 33, 2013, 521-531.
Agbor-Enoh, S. et al., "Donor-derived cell-free DNA predicts allograft failure and mortality after lung transplantation", EBioMedicine, vol. 40, 2019, 541-553.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.
Alkan, Can et al., "Personalized Copy Number and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allan, J. et al., "Micrococcal Nuclease Does Not Substantially Bias Nucleosome Mapping", Journal of Molecular Biology, vol. 417, Jan. 30, 2012, 152-164.
Allawi, Hatim T. et al., "Thermodynamics of internal C•T Mismatches in DNA", Nucleic Acids Research, 26 (11), 1998, 2694-2701.
Ambardar, S. et al., "High Throughput Sequencing: An Overview of Sequencing Chemistry", Indian J. Microbiol., vol. 56, No. 4, 2016, 394-404.

(56) References Cited

OTHER PUBLICATIONS

Amicucci, P. et al., "Prenatal Diagnosis of Myotonic Dystrophy Using Fetal DNA Obtained from Maternal Plasma", Clinical Chemistry, vol. 46, No. 2, 2000, 301-302.
Andras, S. C. et al., "Strategies for Signal Amplification in Nucleic Acid Detection", Molecular Biotechnology, vol. 19, 2001, 29-44.
Anker, P. et al., "Circulating DNA in Plasma or Serum", Medicina, vol. 60, 2000, 699-702.
Anker, P. et al., "Detection of circulating tumour DNA in the blood (plasma/serum) of cancer patients", Cancer and Metastasis Reviews, vol. 18, 1999, 65-73.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Ansorge, Wilhelm J., "Next-generation DNA Sequencing Techniques", New Biotechnology, vol. 25, No. 4, Feb. 2, 2009, 195-203.
Antonarakis, S. E. et al., "Chromosome 21 and Down Syndrome: From Genomics to Pathophysiology", Nature Reviews Genetics, vol. 5, Oct. 2004, 725-738.
Aoki, Yasuhiro, "Statistical and Probabilistic Bases of Forensic DNA Testing", The Journal of the Iwate Medical Association, 2002, vol. 54, p. 81-94.
Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Auld, D. S., "Use of Chelating Agents to Inhibit Enzymes", Methods in Enzymology, vol. 158, 1988, 110-114.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6,, May 28, 2009, 581-591.
Bada, Michael A. et al., "Computational Modeling of Structural Experimental Data", Methods in Enzymology,317, 2000, 470-491.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Balavoine, Guillaume, "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Bale, J. R. et al., "Reducing Birth Defects: Meeting the Challenge in the Developing World", Institute of Medicine of the National Academies, 2003, 270 pgs.
Ballif, B. C. et al., "Detection of Low-Level Mosaicism by Array CGH in Routine Diagnostic Specimens", American Journal of Medical Genetics Part A, vol. 140A, 2006, 2757-2767.
Banfi, G. et al., "The role of ethylenediamine tetraacetic acid (EDTA) as in vitro anticoagulant for diagnostic purposes", Clin. Chem., vol. 45, No. 5, 2007, 565-576.
Barbazuk, et al., "SNP Discovery via 454 Transcriptome Sequencing", The Plant Journal, vol. 51, Jul. 27, 2007, 910-918.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al., "High-Resolution Profiling of Histone Methylations in the Human Genome", Cell, vol. 129, May 18, 2007, 823-837.
Bartlett, John M. et al., "PCR Protocols", PCR Protocols, vol. 226, 2003, 519 pages.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.
Baxter-Lowe, et al., "Tracking Microchimeric DNA In Plasma To Diagnose And Manage Organ Transplant Rejection", Clinical Chemistry, vol. 52, No. 4, Apr. 1, 2006, 559-561.
Beaumont, Mark A et al., "The Bayesian Revolution in Genetics", Nature Reviews Genetics, 5, 2004, 251-261.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Beck, J. et al., "Profile of the Circulating DNA in Apparently Healthy Individuals", Clinical Chemistry, vol. 55, No. 4, 2009, 730-738.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Belostotsky, Dmitry A. et al., "Plant Systems Biology", Methods in Molecular Biology, vol. 553, Aug. 25, 2009, 3-408.
Bender, et al., "A Multiplex SNP Typing Approach For The DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bennett, S. T. et al., "Toward the $1000 human genome", Pharmacogenomics, vol. 6, No. 4, 2005, 373-382.
Bentley, et al., "High-resolution, High-throughput HLA Genotyping by Next-generation Sequencing", Tissue Antigens, vol. 74, No. 5, Nov. 1, 2009, 393-403.
Bentley, David R et al., "Accurate Whole Human Genome Sequencing Using Reversible Terminator Chemistry", Nature, 456, 6, 2008, 53-59.
Bergen, A. W. et al., "Effects of DNA mass on multiple displacement whole genome amplification and genotyping performance", BMC Biotechnology, vol. 5, No. 24, Sep. 16, 2005, 11 pgs.

(56) References Cited

OTHER PUBLICATIONS

Bermudez, M. et al., "Single-cell sequencing and mini-sequencing for preimplantation genetic diagnosis", Prenatal Diagnosis, 23, 2003, 669- 677.
Beroud, C. et al., "Prenatal diagnosis of spinal muscular atrophy by genetic analysis of circulating fetal cells", The Lancet, vol. 361, Mar. 22, 2003, 1013-1014.
Bevinetto, Gina , Bevinetto (5 Foods All Pregnant Women Need, American Baby, available at http://www.parents.com/pregnancy/mybody/nutrition/5greatpregnancyfoods/, Apr. 15, 2008), 8 pgs.
Bianchi, D W. et al., "Fetal gender and aneuploidy detection using fetal cells maternal blood: analysis of NIFTY I data", Prenat Diagn 2002; 22, 2002, 609-615.
Bianchi, D W. et al., "Insights Into Fetal and Neonatal Development Through Analysis of Cell-Free RNA in Body Fluids", Early Human Development, vol. 86, No. 11, Nov. 2010, 747-752.
Bianchi, D. W. , "Circulating Fetal DNA: Its Origin and Diagnostic Potential—A Review", Placenta, vol. 25, Supplemental A, May 2004, S93-S101.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Bianchi, D. W. , "Review: Fetal Cells in the Maternal Circulation: Feasibility for Prenatal Diagnosis", British Journal of Haematology, vol. 105, 1999, 574-583.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Bisignano, et al., "PGD and Aneuploidy Screening for 24 Chromosomes: Advantages and Disadvantages of Competing Platforms", Reproductive BioMedicine Online, 23, 2011, 677-685.
Blomquist, T M. et al., "Targeted RNA-Sequencing with Competitive Multiplex—PCR Amplicon Libraries", Plos One, vol. 8, Issue 11, Nov. 2013, 14 pages.
Blow, N. , "The personal side of genomics", Nature, vol. 449, Oct. 4, 2007, 627-630.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.
Bodenreider, O. , "The Unified Medical Language System (UMLS): Integrating Biomedical Terminology", Nucleic Acids Research, 32, (Database issue), 2004, D267-D270.
Bordoni, et al., "Evaluation Of Human Gene Variant Detection In Amplicon Pools By The GS-FLX Parallel Pyrosequencer", BMC Genomics, vol. 9, Oct. 8, 2008, 1-8.
Boudsocq, F. et al., "Sulfolobus solfataricus P2 DNA polymerase IV (Dpo4): an archael DinB-like DNA polymerase with lesion-bypass properties akin to eukaryotic poln", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Breithaupt, Holger , "The Future of Medicine", EMBO Reports, 21(61), 2001, 465-467.

Brinza, D. et al., "2SNP: scalable phasing based on 2-SNP haplotypes", Bioinformatics, vol. 22, No. 3, 2006, 371-373.
Brockman, et al., "Quality Scores And SNP Detection In Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Brownie, Jannine et al., "The Elimination of Primer-Dimer Accumulation in PCR", Nucleic Acids Research, 25(16), 1997, 3235-3241.
Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.
Bryant, A. P. , "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance In The Diagnosis Of Acute Heart Transplant Rejection: A Review", Journal of Cardiovascular Magnetic Resonance, vol. 11, No. 1, Mar. 12, 2009, 1-11.
Butler, J. et al., "The Development of Reduced Size STR Amplicons as Tools for Analysis of Degraded DNA*", Journal of Forensic Sciences, vol. 48, No. 5, 2003, 1054-1064.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela , "Multiplex PCR and Emerging Technologies for the Detection of Respiratory Pathogens", Clinical Infectious Diseases, 52(4), 2011, S326-S330.
Calin, G. A. et al., "A MicroRNA Signature Associated with Prognosis and Progression in Chronic Lymphocytic Leukemia", N Engl J Med, vol. 353, 2005, 1793-1801.
Campbell, P. J. et al., "Subclonal phylogenetic structures in cancer revealed by ultra-deep sequencing", PNAS, vol. 105, No. 35, Sep. 2, 2008, 13081-13086.
Canick, J. A. et al., "The impact of maternal plasma DNA fetal fraction on next generation sequencing tests for common fetal aneuploidies", Prenatal Diagnosis, vol. 33, 2013, 667-674.
Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.

(56) References Cited

OTHER PUBLICATIONS

Carnevale, Alessandra et al., "Attitudes of Mexican Geneticists Towards Prenatal Diagnosis and Selective Abortion", American Journal of Medical Genetics, 75, 1998, 426-431.
Carvalho, B. et al., "Exploration, normalization, and genotype calls of high-density oligonucleotide SNP array data", Biostatistics, vol. 8, No. 2, 2007, 485-499.
Casbon, J. A. et al., "A method for counting PCR template molecules with application to next-generation sequencing", Nucleic Acids Research, vol. 39, No. 12, Apr. 13, 2011, 1-8.
Castleberry, C. D. et al., "Quantification of Circulating Cell—Free DNA in Pediatric Heart Transplant Recipients", Journal of Heart and Lung Transplantation, vol. 30, No. 4, Apr. 1, 2011, S139.
Chakraborty, R. et al., "Paternity Exclusion by DNA Markers: Effects of Paternal Mutations", Journal of Forensic Sciences, vol. 41, No. 4, Jul. 1996, 671-677.
Chan, Allen K. et al., "Cell-free Nucleic Acids In Plasma, Serum And Urine: A New Tool In Molecular Diagnosis", Annals of Clinical Biochemistry, vol. 40, Issue 2, Mar. 1, 2003, 122-130.
Chan, K.C. et al., "Size Distributions of Maternal and Fetal DNA in Maternal Plasma", Clinical Chemistry, vol. 50, No. 1, 2004, 88-92.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Chavali, Sreenivas et al., "Oligonucleotide Properties Determination And Primer Designing: A Critical Examination of Predictions", Bioinformatics, vol. 21, 2005, pp. 3918-3925.
Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.
Chen, Bing-Yuan et al., "PCR Cloning Protocols", PCR Cloning Protocols, vol. 192, 2002, 434 pages.
Chen, C. P. et al., "Fetal DNA in maternal plasma: the prenatal detection of a paternally inherited fetal aneuploidy", Prenatal Diagnosis, vol. 20, 2000, 353-357.
Chen, X. Q. et al., "Microsatallite alterations in plasma DNA of small cell lung cancer patients", Nature Medicine, vol. 2, No. 9, Sep. 1996, 1033-1035.
Chetty, Shilpa et al., "Uptake of Noninvasive Prenatal Testing (NIPT) in Women Following Positive Aneuploidy Screening", Prenatal Diagnosis,33, 2013, 542-546.
Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.
Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.
Chim, S. S. et al., "Detection and Characterization of Placental MicroRNAs in Maternal Plasma", Clinical Chemistry, vol. 54, No. 3, 2008, 482-490.
Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.
Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, R.W.K. et al., "Hypermethylation of RASSF1A in Human and Rhesus Placentas", The American Journal of Pathology, vol. 170, No. 3, Mar. 2007, 941-950.

Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.
Choi, M. et al., "Genetic diagnosis by whole exome capture and massively parallel DNA sequencing", PNAS, vol. 106, No. 45, Nov. 10, 2009, 19096-19101.
Choi, Y. et al., "Comparison of phasing strategies for whole human genomes", PLOS Genetics, Apr. 5, 2018, 26 pages.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Chung, G. T. et al., "Lack of Dramatic Enrichment of Fetal DNA in Maternal Plasma by Formaldehyde Treatment", Clinical Chemistry, vol. 51, No. 3, 2005, 655-658.
Church, et al., "Multiplex DNA Sequencing", Science, vol. 240, No. 4849, Apr. 8, 1988, 185-188.
Ciriello, G. et al., "Emerging landscape of oncogenic signatures across human cancers", Nature Genetics, vol. 45, No. 10, Oct. 2013, 1127-1135.
Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.
Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.
Cossu, Gianfranco et al., "Rh D/d Genotyping by Quantitative Polymerase Chain Reaction and Capillary Zone Electrophoresis", Electrophoresis, 17, 1996, 1911-1915.
Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.
Couraud, S. et al., "Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002", 2014, 13 pages.
Coyle, J. F. et al., "Standards for detailed clinical models as the basis for medical data exchange and decision support", International Journal of Medical Informatics, 69(2-3), 2003, 157-174.

(56) References Cited

OTHER PUBLICATIONS

Craig, D. W. et al., "Identification of genetic variants using barcoded multiplexed sequencing", Nature Methods, vol. 5, Oct. 2008, 887-893.
Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.
Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.
Cross, Jillian et al., "Resolution of trisomic mosaicism in prenatal diagnosis: estimated performance of a 50K SNP microarray", Prenat Diagn 2007; 27, 2007, 1197-1204.
Cunningham, K. S. et al., "An approach to endomyocardial biopsy interpretation", Journal of Clinical Pathology, vol. 59, No. 2, Mar. 2006, 121-129.
Dahl, et al., "Multigene Amplification and Massively Parallel Sequencing for Cancer Mutation Discovery", Proceedings of the National Academy of Sciences, vol. 104, No. 22, May 29, 2007, 9387-9392.
Dambrin, et al., "A New Rejection Criteria In The Heterotopically Placed Rat Heart By Non-invasive Measurement Of Dp/Dtmax", The Journal of Heart and Lung Transplantation, vol. 18, No. 6, Jun. 18, 1999, 524-531.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
Dawson, S.J. et al., "Analysis of Circulating Tumor DNA to Monitor Metastatic Breast Cancer", The New England Journal of Medicine, vol. 368, No. 13, Mar. 28, 2013, 1199-1209.
De Bruin, E. et al., "Spatial and temporal diversity in genomic instability processes defines lung cancer evolution", Science, vol. 346, No. 6206, Oct. 10, 2014, 251-256.
De Jong, M. M. et al., "Genes other than BRCA 1 and BRCA2 involved in breast cancer susceptibility", J. Med. Genet., vol. 39, 2009, 225-242.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.
Delaneau, O. et al., "Shape-IT: new rapid and accurate algorithm for haplotype inference", BMC Bioinformatics, vol. 9, No. 540, Dec. 16, 2008, 14 pages.
Delgado, P. O. et al., "Characterization of cell-free circulating DNA in plasma in patients with prostate cancer", Tumor Biol., vol. 34, 983-986, 2013.
Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Di, X. et al., "Dynamic model based algorithms for screening and genotyping", Bioinformatics, vol. 21, No. 9, 2005, 1958-1963.
Dias-Santagata, D. et al., "BRAF V600E Mutations Are Common in Pleomorphic Xanthoastrocytoma: Diagnostic and Therapeutic Implications", PLoS One, vol. 6, No. 3, Mar. 2011, 9 pages.
Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.
Dieffenbach, C W. et al., "General concepts for PCR primer design", Genome Research. PCR methods and Applications vol. 3, 1993, S30-S37.
Diehl, F. et al., "Circulating mutant DNA to assess tumor dynamics", Nature Medicine, vol. 14, No. 9, Jul. 31, 2008, 985-990.
Diehl, F. et al., "Detection and quantification of mutations in the plasma of patients with colorectal tumors", PNAS, vol. 102, No. 45, Nov. 8, 2005, 16368-16373.
Dietmaier, W. et al., "Multiple Mutation Analyses in Single Tumor Cells with Improved Whole Genome Amplification", American Journal of Pathology, vol. 154, No. 1, Jan. 1999, 83-95.
Ding, C et al., "Direct molecular haplotyping of long-range genomic DNA with M1-PCR", PNAS 100(13), 2003, 7449-7453.
Ding, C. et al., "MS analysis of single-nucleotide differences in circulating nucleic acids: Application to noninvasive prenatal diagnosis", PNAS, vol. 101, No. 29, Jul. 20, 2004, 10762-10767.
Dodge, Y. , "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na-K+ -Cl-Cotransporter (NKCC1) in Asthmatic Subjects", Genome Res., 11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Doostzadeh, et al., "High Throughput Automated Allele Frequency Estimation by Pyrosequencing", PLoS ONE, vol. 3, No. 7, Jul. 16, 2008, 1-4.
Dorit, D. L. , "cDNA Amplification Using One-sided (Anchored) Pcr", Current Protocols in Molecular Biology, vol. 17, 1992, pp. 15.6.1-15.6.10.
Dorit, Robert L. et al., "One-sided Anchored Polymerase Chain Reaction for Amplification and Sequencing of Complementary DNA", Methods in Enzymology, vol. 218 1993, pp. 36-47.
Dowd, P. et al., "On the mechanism of the anticlotting action of vitamin R quinone", Proc. Natl. Acad. Sci. USA, vol. 92, 1995, 8171-8175.
Downward, J. , "Targeting RAS Signalling Pathways in Cancer Therapy", Nature Reviews, vol. 3, Jan. 2003, 11-22.
Dressman, D. et al., "Transforming single DNA molecules into fluorescent magnetic particles for detection and enumeration of genetic variations", PNAS, vol. 100, No. 15, Jul. 22, 2003, 8817-8822.
Echeverri, et al., "Caffeine's Vascular Mechanisms of Action", International Journal of Vascular Medicine vol. 2010(2010), 10 pages, Aug. 25, 2010.
Edwards, M. C. et al., "Multiplex PCR: Advantages, Development, and Applications", Genome Research, vol. 3, 1994, S65-S75.
Efron, B. et al., "Bootstrap Methods for Standard Errors, Confidence Intervals, and Other Measures of Statistical Accuracy", Statistical Science, vol. 1, No. 1, 1986, 54-77.

(56) References Cited

OTHER PUBLICATIONS

Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series, 1261, 2004, 12-14.
Elnifro, Elfath M. , "Multiplex PCR: Optimization and Application in Diagnostic Virology", Clinical Microbiology Reviews, vol. 13, 2000, pp. 559-570.
Eltoukhy, H. et al., "Modeling and Base-Calling for DNA Sequencing-by-Synthesis", IEEE, 2006, II-1032-II-1035.
EP06838311.6, "European Communication and Extended European Search Report", mailed Dec. 30, 2008, 8 pgs.
EP08742125.1, "European Communication pursuant to Article 94(3) EPC and Examination Report", mailed Feb. 12, 2010, 5 pgs.
Erijman, Ariel et al., "Transfer-PCR (TPCR): A Highway For DNA Cloning and Protein Engineering", Journal of Structural Biology, vol. 175, 2011, pp. 171-177.
Erlich, R. L. et al., "Next-generation sequencing for HLA typing of class loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
European Commission, , "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.
Everitt, B. S. , "Medical Statistics From A to Z", 2003, 3 pages.
Fackenthal, J. D. et al., "Aberrant RNA splicing and its functional consequences in cancer cells", Disease Models & Mechanisms, vol. 1, 2008, 37-42.
Faham, M. et al., "Deep-sequencing approach for minimal residual disease detection in acute lymphoblastic leukemia", Blood Journal, vol. 120, No. 26, Dec. 20, 2012, 5173-5180.
Falcon, O. , "Screening for trisomy 21 by fetal tricuspid regurgitation, nuchal translucency and maternal serum free b-hCG and PAPP-A at 11 + 0 to 13 + 6 weeks", Ultrasound Obstet Gynecol, vol. 27, 2006, 151-155.
Fan, et al., "Whole-genome molecular haplotyping of single cells", Nature Biotechnology, vol. 29, No. 1, Jan. 1, 2011, 51-57.
Fan, C H. et al., "Detection of Aneuploidy with Digital Polymerase Chain Reaction", Analytical Chemistry, vol. 79, No. 19, Oct. 1, 2007, 7576-7579.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "In Principle Method for Noninvasive Determination of the Fetal Genome", Nat. Prec., 2010, 16 pgs.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, J.-B. et al., "Highly Parallel SNP Genotyping", Cold Spring Harbor Symposia on Quantitative Biology, vol. LXVIII, Feb. 2003, 69-78.
Fan, Jian-Bing et al., "Highly Parallel Genomic Assay", Nature Reviews, 7, 2006, 632-644.

Fat Secret, "5 Foods to Never Eat", https://www.fatsecret.com/calories-nutrition/food/white-bread/carboyhydrate (printed from internet Nov. 1, 2014)., 2 pages.
Fazio, Gennaro. et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Fitzgerald, , "Intravascular Ultrasound Imaging Of Coronary Arteries: Is Three Layers The Norm?", Circulation, vol. 86, No. 1, Jul. 1, 1992, 154-158.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Fouquet, C. et al., "Rapid and Sensitive p53 Alteration Analysis in Biopsies from Lung Cancer Patients Using a Functional Assay and A Universal Oligonudeotide Array: A Prospective Study", Clinical Cancer Research, vol. 10, May 15, 2004, 3479-3489.
Fournie, et al., "Plasma DNA As A Marker Of Cancerous Cell Death. Investigations In Patients Suffering From Lung Cancer And In Nude Mice Bearing Human Tumours", Cancer Letters, vol. 91, No. 2, May 8, 1995, 221-227.
Fredriksson, et al., "Multiplex amplification of all coding sequences within 10 cancer genes by Gene-Collector", Nucleic Acids Research, 2007, vol. 35, No. 7 e47, 1-6.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Freeman, Jennifer L. et al., "Copy Number Variation: New Insights in Genome Diversity", Genome Research, 16, 2006, 949-961.
Frohman, M A. et al., "On Beyond Classic RACE (Rapid Amplification of cDNA Ends)", Genome Research, vol. 4, 1994, S40-S58.
Frost, MacKenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

(56) References Cited

OTHER PUBLICATIONS

Fu, Yao-Wen et al., "Presence Of Donor-and-recipientderived Dna Microchimerism In The Cell-free Blood Samples Of Renal Transplantation Recipients Associates With The Acceptance Of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gao, et al., "Relation Of Donor Age And Preexisting Coronary Artery Disease On Angiography And Intracoronary Ultrasound To Later Development Of Accelerated Allograft Coronary Artery Disease", The American Journal of Cardiology, vol. 29, No. 3, Mar. 1, 1997, 623-629.
Gao, F. et al., "Characterizing Immunoglobulin Repertoire from Whole Blood by a Personal Genome Sequencer", PLOS One, vol. 8, No. 9, Sep. 13, 2013, 8 pgs.
Gao, Ming et al., "Characterization of dull1, a Maize Gene Coding for a Novel Starch Synthase", The Plant Cell, vol. 10, 1998, pp. 399-412.
Garcia Moreira, V. et al., "Cell-Free DNA as a Noninvasive Acute Rejection Marker in Renal Transplantation", Clinical Chemistry, vol. 55, No. 11, 2009, 1958-1966.
Garcia-Murillas, I. et al., "Mutation tracking in circulating tumor DNA predicts relapse in early breast cancer", Science Translational Medicine, vol. 7, No. 302, Aug. 26, 2015, 34 pgs.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Gautier, E. et al., "Fetal RhD genotyping by maternal serum analysis: A two-year experience", American Journal of Obstetrics and Gynecology, vol. 192, 2005, 666-669.
Geifman-Holtzman, et al., "Prenatal Diagnosis: Update On Invasive Versus Noninvasive Fetal Diagnostic Testing From Maternal Blood", Expert Review of Molecular Diagnostics, vol. 8, No. 6, Nov. 1, 2008, 727-751.
Geiss, G. K. et al., "Direct multiplexed measurement of gene expression with color-coded probe pairs", Nature Biotechnology, vol. 26, No. 3, Feb. 17, 2008, 317-325.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gholami, M. et al., "A tailed PCR procedure for cost-effective, two-order multiplex sequencing of candidate genes in polyploid plants", Plant Biotechnology Journal, vol. 10, 2012, 635-645.
Gielis, E. M. et al., "Cell-Free DNA: An Upcoming Biomarker in Transplantation", American Journal of Transplantation, vol. 15, 2015, 2541-2551.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Gineikiene, Egle et al., "Single Nucleotide Polymorphism-based System Improves The Applicability Of Quantitative PCR For Chimerism Monitoring", Journal of Molecular Diagnostics, vol. 11, No. 1, Jan. 1, 2009, 66-74.
Gingeras, et al., "Fifty Years of Molecular (DNA/RNA) Diagnostics", Clinical Chemistry, vol. 51, No. 3, Jan. 13, 2005, 661-671.
Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.

Gjertson, David W. et al., "Assessing Probability of Paternity and the Product Rule in DNA Systems", Genetica, 96, 1995, 89-98.
Gnirke, A. et al., "Solution hybrid selection with ultra-long oligonucleotides for massively parallel targeted sequencing", Nature Biotechnology, vol. 27, No. 2, Feb. 2009, 182-189.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.
Gordon, et al., "Disease-Specific Motifs Can Be Identified In Circulating Nucleic Acids From Live Elk And Cattle Infected With Transmissible Spongiform Encephalopathies", Nucleic Acids Research, vol. 37. No. 2, Feb. 1, 2009, 550-556.
Gorringe, et al., "Large-scale Genomic Analysis of Ovarian Carcinomas", Molecular oncology, vol. 3, No. 2, Apr. 1, 2009, 157-164.
Gouya, et al., "Coronary Artery Stenosis In High-risk Patients: 64-section Ct And Coronary Angiography-Prospective Study And Analysis of Discordance", Radiology, vol. 252, No. 2, Aug. 1, 2009, 377-385.
Greenwalt, T. et al., "The Quantification of Fetomaternal Hemorrhage by an Enzyme-Linked Antibody Test with Glutaraldehyde Fixation", Vox Sang, 63, 1992, 268-271.
Gregory, et al., "Comparison of Sixty-Four-Slice Multidetector Computed Tomographic Coronary Sngiography To Coronary Angiography With Intravascular Ultrasound For The Detection Of Transplant Vasculopathy", The American Journal of Cardiology, vol. 98, No. 7, Aug. 4, 2006, 877-884.
Griffiths, A. J. et al., "An Introduction to Genetic Analysis", Sixth Edition, 1996, 5 pages.
Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.
Grunenwald, H. , "Optimization of Polymerase Chain Reactions", Methods in Biology, vol. 226, 2003, 89-99.
Gu, H. et al., "Diagnostic role of microRNA expression profile in the serum of pregnant women with fetuses with neural tube defects", Journal of Neurochemistry, vol. 122, 2012, 641-649.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Gunderson, K. L. et al., "A genome-wide scalable SNP genotyping assay using microarray technology", Nature Genetics, vol. 37, No. 5, May 2005, 549-554.
Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.
Guo, H. et al., "A Specific and Versatile Genome Walking Technique", Gene, vol. 381, 2006, 18-23.
Gwee, Pai-Chung et al., "Simultaneous Genotyping of Seven Single-nucleotide Polymorphisms in the Mdr1 Gene by Single-tube Multiplex Minisequencing", Pai-Chung Gwee. et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.
Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.
Hahn, S. et al., "Current applications of single-cell PCR", CMLS Cellular and Molecular. Life Sciences, vol. 57, 2000, 96-105.
Hahn, S. et al., "Quantification of Circulating DNA: In the Preparation Lies the Rub", Clinical Chemistry, vol. 47, No. 9, 2001, 1577-1578.

(56) References Cited

OTHER PUBLICATIONS

Halford, William P., "The Essential Prerequisites for Quantitative RT-PCR", Nature Biotechnology, vol. 17, 1999, 1 page.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Handley, D. et al., "Noninvasive prenatal chromosomal aneuploidy detection using plasma cell-free nucleic acid", Expert Rev Obstet. Gynecol, vol. 5, No. 5, 2010, 581-590.
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P., "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hartwell, L. H. et al., "Chapter 11: The Direct Detection of Genotype Distinguishes Individual Genomes", Genetics: From Genes To Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes To Genomes, Second Edition, 2004, 441-486.
Hattori, M. et al., "The DNA sequence of human chromosome 21", Nature, vol. 405, May 18, 2000, 311-319.
Hawkins, T. et al., "Whole genome amplification—applications and advances", Current Opinion in Biotechnology, 13, 2002, 65-67.
Hayden, et al., "Multiplex-Ready PCR: A new method for multiplexed SSR and SNP genotyping", BMC Genomics 2008, 9(80), 1-12.
He, Qz et al., "A method for improving the accuracy of non-invasive prenatal screening by cell-free foetal DNA size selection", British Journal of Biomedical science, vol. 75, No. 3, Jul. 2018, 133-138.
Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method For Assessment Of Hematopoietic Chimerism After Allogeneic Stem Cell Transplantation", Blood, vol. 101, No. 1, Jan. 1, 2003, 363-369.
Hodges, et al., "Genome-wide In Situ Exon Capture For Selective Resequencing", Nature Genetics, vol. 39, No. 12, Nov. 4, 2007, 1522-1527.
Hodgkinson, C. L. et al., "Tumorigenicity and genetic profiling of circulating tumor cells in small-cell lung cancer", Nature Medicine, vol. 20, No. 8, Aug. 2014, 897-905.
Hoffmann, Steven et al., "Donor Genomics Influence Graft Events: The Effect Of Donor Polymorphisms On Acute Rejection And Chronic Allograft Nephropathy", Kidney International, vol. 66, No. 4, Oct. 1, 2004, 1686-1693.
Hojsgaard, S. et al., "BIFROST—Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR" BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Holt, et al., "Detecting SNPS And Estimating Allele Frequencies In Clonal Bacterial Populations By Sequencing Pooled DNA", Bioinformatics, vol. 25, No. 16, Aug. 15, 2009, 2074-2075.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Horai, et al., "Novel Implantable Device To Detect Cardiac Allograft Rejection", Circulation, vol. 120, No. Suppl 1, Sep. 15, 2009, 185-190.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Hosmillo, Myra D. et al., "Development of Universal SYBR Green Real-time RT-PCR for The Rapid Detection and Quantitation of Bovine and Porcine Toroviruses", Journal of Virological Methods, vol. 168, 2010, pp. 212-217.
Hosono, S. et al., "Unbiased Whole-Genome Amplification Directly From Clinical Samples", Genome Research, vol. 13, 2003, 954-964.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Howie, et al., "Fast and accurate genotype imputation in genome-wide association studies through pre-phasing", Nature Genetics, vol. 44, No. 8, Jul. 22, 2012, 955-959.
Howie, B. N. et al., "A Flexible and Accurate Genotype Imputation Method for the Next Generation of Genome-Wide Association Studies", PLoS Genetics, vol. 5, No. 6, Jun. 2009, 15 pages.
Hu, Dong Gui et al., "Aneuploidy Detection in Single Cells Using DNA Array-Based Comparative Genomic Hybridization", Molecular Human Reproduction, 10(4), 2004, 283-289.
Hu, Hao et al., "Mutation Screening in 86 Known X-linked Mental Retardation Genes by Droplet-based Multiplex Pcr and Massive

(56) References Cited

OTHER PUBLICATIONS

Parallel Sequencing", Hao Hu. et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.
Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.
Huang, D. J. et al., "Reliable detection of Trisomy 21 using MALDI-TOF mass spectrometry", Genetics in Medicine, vol. 8, Nov. 2006, 728-734.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Huang, J. et al., "Whole genome DNA copy number changes identified by high density oligonucleotide arrays", Human Genomics, vol. 1, No. 4, May 2004, 287-299.
Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.
Hug, H. et al., "Measurement of the number of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Hung, E.C.W. et al., "Detection of circulating fetal nucleic acids: a review of methods and applications", J. Clin. Pathol., vol. 62, 2009, 308-313.
Hyndman, D L. et al., "PCR Primer Design", Methods in Molecular Biology, vol. 226, Second Edition, 2003, 81-88.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina, "Automated GoldenGate™ Genotyping on the BeadStation 500", Pub. No. 970-2004-002, 2004, 2 pages.
Illumina, "Genomic Sequencing", Data Sheet: Sequencing, 2010, 38939-38944.
Illumina, "GoldenGate" Assay Workflow: Illumina's GoldenGate assay protocol provides high-quality, high-multiplex genotyping results with a streamlined workflow, Pub. No. 370-2004-006, 2004, 2 pages.
Illumina, "HiSeq 2500 Sequencing System", System Specification Sheet: Sequencing, available via URL https://www.illumina.com/documents/products/datasheets/datasheet_hiseq2500.pdf, 2015, 4 pgs.
Illumina, "History of Sequencing by Synthesis", https://www.illumina.com/science/technology/next-generation-sequencing/illumina-sequencing-history.html, 2020, 3 pages.
Illumina, "Illumina Extends BeadArray Technology to Address Wider Range of SNP Genotyping Projects; New Microarray Offerings Enable Genotyping at 384 and 786 Multiplex", Businesswire, May 4, 2004, 2 pages.
Illumina, "Illumina® Beadstation 500: A Scalable System That Grows With Your Research Requirements", Pub. No. 970-2005-003, Jul. 1, 2005, 4 pages.
Illumina, "Illumina Announces Benchtop SNP Genotyping System", Press Release, Nov. 5, 2003, 3 pages.
Illumina, "Illumina Begins Shipment of BeadStation 500G Benchtop Genotyping System", Press Release, Apr. 15, 2004, 3 pages.
Illumina, "MiSeq System Information Sheet", 2018, 3 pgs.
Illumina, "Patent Owner Illumina's Preliminary Response to Petition", Oct. 17, 2018, 75 pgs.
Illumina, "Petition for Inter Partes Review of U.S. Pat. No. 8,682,592", Jun. 13, 2019, 91 pages.
Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.

Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Illumina, "Preparing Samples for Sequencing Genomic DNA", Part # 11251892 Rev. A, 2007, 18 pages.
Illumina, "Preparing Samples for Sequencing Genomic DNA", Part # 1003806 Rev. A, 2007, 20 pages.
Illumina, "Products & Services", Product Literature, Mar. 21, 2007, 3 pages.
Illumina, "Technology: Solexa Sequencing Technology", May 21, 2007, 1 page.
Illumina, "TruSeq™ RNA and DNA Library Preparation Kits v2", Data Sheet: Illumina® Sequencing, 2014, 4.
Illumina Catalog, "Paired-End Sample Preparation Guide, Illumina Catalog# PE-930-1 001, Part# 1005063 Rev. E", 2011, 1-40.
Illumina, Inc., "Declaration of David Peters, PH.D. in Support of Petition for Inter Partes Review of U.S. Pat. No. 8,682,592", Jun. 13, 2019, 136 pages.
*Illumina, Inc.* V. *Natera, Inc.*, "Order Re: Claim Construction", Jan. 30, 2019, 16 pgs.
Imielinski, M. et al., "Mapping the Hallmarks of Lung Adenocarcinoma with Massively Parallel Sequencing", Cell, vol. 150, Sep. 14, 2012, 1107-1120.
Ingman, et al., "SNP Frequency Estimation Using Massively Parallel Sequencing of Pooled DNA", European Journal of Human Genetics, vol. 17, No. 3, Oct. 15, 2008, 383-386.
Innan, H. et al., "The Pattern of Polymorphism on Human Chromosome 21", Genome Research, vol. 13, 2003, 1158-1168.
Interewicz, B. et al., "DNA Released from Ischemic and Rejecting Organs as an Indicator of Graft Cellular Damage", Annals of Transplantation, vol. 9, No. 2, May 1, 2004, 42-45.
International Human, Genome Sequencing Consortium , "Finishing the Euchromatic Sequence of the Human Genome", Nature, vol. 431, Oct. 21, 2004, 931-945.
Ishii, et al., "Optimization of Annealing Temperature To Reduce Bias Caused by a Primer Mismatch in Multitemplate PCR", Applied and Environmental Microbiology, Aug. 2001, p. 3753-3755,.
Iskow, R. C. et al., "Natural Mutagenesis of Human Genomes by Endogenous Retrotransposons", Cell, vol. 141, Jun. 25, 2010, 1253-1261.
Ivanov, M. et al., "Non-random fragmentation patterns in circulating cell-free DNA reflect epigenetic regulation", BMC Genomics, vol. 16 (Suppl 13):S1, Jun. 2015, 12 pgs.
Jabara, C. B. et al., "Accurate sampling and deep sequencing of the HIV-1 protease gene using a Primer ID", PNAS, vol. 108, No. 50, Dec. 13, 2011, 20166-20171.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T. , "Next generation sequencing technologies", Drug Discovery Today: Technologies, vol. 2, No. 3, 2005, 255-260.
Jen, J. et al., "An Overview on the Isolation and Analysis of Circulating Tumor DNA in Plasma and Serum", Annals New York Academy of Sciences, 2000, 8-12.
Jenkins, S. et al., "High-throughput SNP genotyping", Comparative and Functional Genomics, vol. 3, Dec. 5, 2001, 57-66.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jett, K. et al., "Clinical and genetic aspects of neurofibromatosis 1", Genetics In Medicine, vol. 12, No. 1, Jan. 2010, 11 pages.

(56) References Cited

OTHER PUBLICATIONS

Jewesburty, E.C.O. , "Reactions after Transfusion of Stored Blood", The British Medical Journal, vol. 1, No. 4191, 1941, 664-665.
Jiang, P. et al., "The Long and Short of Circulating Cell-Free DNA and the Ins and Outs of Molecular Diagnostics", Trends in Genetics, vol. 32, No. 6, Jun. 2016, 360-371.
Johnson, D. S. et al., "Genome-Wide Mapping of in Vivo Protein-DNA Interactions", Science, vol. 316, Jun. 8, 2007, 1497-1502.
Johnson, D.S. et al., "Comprehensive Analysis of Karyotypic Mosaicism Between Trophectoderm and Inner Cell Mass", Molecular Human Reproduction, 16(12), 2010, 944-949.
Johnson, J. B. et al., "Differential mechanisms of complementmediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Johnson D.S, et al., "Preclinical Validation of a Microarray Method for Full Molecular Karyotyping of Blastomeres in a 24-h Protocol", Human Reproduction, 25 (4), 2010, 1066-1075.
Jung, K. et al., "Cell-free DNA in the blood as a solid tulnor biomarker—A critical appraisal of the literature", Clinica Chimica Acta, vol. 411, 2010, 1611-1624.
Juppner, H. et al., "Functional Properties of the PTH/PTHrP Receptor", Bone, vol. 17, No. 2 Supplement, Aug. 1995, 39S-42S.
Kalendar, Ruslan et al., "Java Web Tools for PCR, in Silico PCR, and Oligonucleotide Assembly and Analysis", Genomics, vol. 98, 2011, pp. 137-144.
Kamat, A. A. et al., "Quantification of total plasma cell-free DNA in ovarian cancer using real-time PCR", Ann N Y Acad Sci., vol. 1075, Sep. 2006, 230-234.
Kamel, A. M. et al., "A simple strategy for breakpoint fragment determination in chronic myeloid leukemia", Cancer Genetics and Cytogenetics, vol. 122, 2000, 110-115.
Kane, M. et al., "Application of Less Primer Method to Commercial Kits", Forensic Science International: Genetics Supplement Series, vol. 1, Issue 1, 2008, 41-43.
Kane, M. , "Application of Less Primer Method To Multiplex PCR", International Congress Series, vol. 1288, 2006, pp. 694-696.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Kapadia, Samir R. et al., "Impact of Intravascular Ultrasound in Understanding Transplant Coronary Artery Disease", Current Opinion In Cardiology, vol. 14, No. 2, Mar. 1, 1999, 1-19.
Kaplinski, Lauris et al., "MultiPLX: Automatic Grouping and Evaluation of PCR Primers", Bioinformatics, 21(8), 2005, 1701-1702.
Karger, et al., "DNA Sequencing By Capillary Electrophoresis" Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis Of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Kazakov, V.I. et al., "Extracellular DNA in the Blood of Pregnant Women", Tsitologia, vol. 37, No. 3, 1995, 1-8.
Keith, L. et al., "Clinical Experience With the Prevention of Rh-Isoimmunization: A Historical Comparative Analysis", American Journal of Reproductive Immunology, vol. 5, 1984, 84-89.
Keller, M. C. et al., "Non-Pathological Paternal Isodisomy of Chromosome 2 Detected From a Genome-Wide SNP Scan", American Journal of Medical Genetics, Part A, 2009, 1823-1826.

Kennedy, S. R. et al., "Detecting ultralow-frequency mutations by Duplex Sequencing", Nature Protocols, vol. 9, No. 11, 2014, 2586-2606.
Kibbe, Warren A. , "Oligocalc: An Online Oligonucleotide Properties Calculator", Nucleic Acids Research, vol. 35, 2007, pp. W43-W46.
Kiernan, J. A. , "Formaldehyde, formalin, paraformaldehyde and glutaraldehyde: What they are and what they do.", Microscopy Today, vol. 1, 2000, 8-12.
Kijak, G. et al., "Discrepant Results in the Interpretation of HIV-1 Drug-Resistance Genotypic Data Among Widely Used Algorithms", HIV Medicine, 4, 2003, 72-78.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kimmel, G. et al., "GERBIL: Genotype resolution and block identification using likelihood", PNAS, vol. 102, No. 1, Jan. 4, 2005, 158-162.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kirkness, E. F. et al., "Sequencing of isolated sperm cells for direct haplotyping of a human genome", Genome Research, vol. 23, 2013, 826-832.
Kivioja, T. et al., "Counting absolute number of molecules using unique molecular identifiers", Nature Proceedings, Apr. 14, 2011, 18 pgs.
Kivioja, T. et al., "Counting absolute numbers of molecules using unique molecular identifiers", Nature Methods, Advance Online Publication, Nov. 20, 2011, 1-5.
Kivioja, T. et al., "Counting absolute numbers of molecules using unique molecular identifiers", Nature Methods, vol. 9, No. 1, Jan. 2012, 72-76.
Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection In Massively Parallel Sequencing Of Individual And Pooled Samples", Bioinformatics, vol. 25, No. 17, Jun. 19, 2009, 2283-2285.
Koelman, et al., "Donor-derived Soluble HLA Plasma Levels Can Not Be Used To Monitor Graft Rejection In Heart Transplant Recipients", Transplant Immunology, vol. 8, No. 1, Mar. 1, 2000, 57-64.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Konfortov, B A. et al., "A High-Resolution HAPPY Map of Dictyostelium discoideum Chromosome 6", Genome Research, vol. 10, No. 11, Nov. 2000, 1737-1742.
Konfortov, Bernard A. et al., "An Efficient Method for Multi-Locus Molecular Haplotyping", Nucleic Acids Research, 35(1), e6, 2007, 8 pgs.

(56) References Cited

OTHER PUBLICATIONS

Kopreski, MS et al., "Detection of mutant K-ras DNA in plasma or serum of patients with colorectal cancer", British Journal of Cancer, vol. 76, No. 10, 1997, 1293-1299.

Koressaar, Triinu et al., "Enhancements and Modifications of Primer Design Program Primer3", Bioinformatics, vol. 23, 2007, pp. 1289-1291.

Korn, et al., "Integrated Genotype Calling And Association Analysis Of SNPS, Common Copy Number Polymorphisms And Rare CNVS", Nature Genetics, vol. 40, No. 10, Oct. 1, 2008, 1253-1260.

Krjutskov, K. et al., "Development of a single tube 640-plex genotyping method for detection of nucleic acid variations on microarrays", Nucleic Acids Research, vol. 36, No. 12, May 23, 2008, 7 pages.

Kuhn, H. et al., "Rolling-circle amplification under topological constraints", Nucleic Acids Research, vol. 30, No. 2, 2002, 574-580.

Kukita, Y. et al., "High-fidelity target sequencing of individual molecules identified using barcode sequences: de nova detection and absolute quantitation of mutations in plasma cell-free DNA from cancer patients", DNA Research, vol. 22, No. 4, Jun. 29, 2015, 269-277.

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.

Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.

Kunishima, S. et al., "First description of somatic mosaicism in MYH9 disorders", British Journal of Haematology, vol. 128, 2005, 360-365.

Kwok, P. Y., "High-throughput genotyping assay approaches", Pharmacogenomics, vol. 1, No. 1, 2000, 1-5.

Lambert, et al., "Quantification of Maternal Microchimerism by HLA-Specific Real-time Polymerase Chain Reaction", Arthritis and Rheumatism, vol. 50, No. 3, Mar. 1, 2004, 906-914.

Lambert-Messerlian, G. et al., "Adjustment of Serum Markers in First Trimester Screening", Journal of Medical Screening, 16 (2), 2009, 102-103.

Landegren, U. et al., "Padlock and proximity probes for in situ and array-based analyses: tools for the post-genomic era", Comparative and Functional Genomics, vol. 4, 2003, 525-530.

Lander, E. S. et al., "Initial sequencing and analysis of the human genome", Nature, vol. 409, Feb. 15, 2001, 860-921.

Langmore, J., "Quality Control and Pre-Qualifications of NGS Libraries Made from Clinical Samples", ABRF 2013 Satellite Workshop, Mar. 2, 2013, 35 pages.

Lapaire, O. et al., "Array-CGH analysis of cell-free fetal DNA in 10 mL of amniotic fluid supernatant", Prenatal Diagnosis, vol. 27, May 17, 2007, 616-621.

Lapierre, J.M. et al., "Analysis of uncultured amniocytes by comparative genomic hybridization: a prospective prenatal study", Prenatal Diagnosis, vol. 20, 2000, 123-131.

Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.

Larsen, J. B. et al., "Single-step Nested Multiplex PCR to Differentiate Between Various Bivalve Larvae", Marine Biology, vol. 146, 2005, pp. 1119-1129.

Lasken, R. S. et al., "Whole genome amplification: abundant supplies of DNA from precious samples or clinical specimens", Trends in Biotechnology, vol. 21, No. 12, Dec. 2003, 531-535.

Lathi, Ruth B. et al., "Informatics Enhanced SNP Microarray Analysis of 30 Miscarriage Samples Compared to Routine Cytogenetics", PLoS ONE, 7(3), 2012, 5 pgs.

Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.

Lavebratt, Catharina et al., "Pyrosequencing-based SNP Allele Frequency Estimation In DNA Pools", Human Mutation, vol. 23, Issue 1, Dec. 19, 2003, 92-97.

Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.

Leamon, John H. et al., "A massively parallel PicoTiterPlate based platform for discrete picoliter-scale polymerase chain reactions", Electrophoresis, vol. 24, No. 21, Nov. 1, 2003, 3769-3777.

Leary, R. J. et al., "Development of Personalized Tumor Biomarkers Using Massively Parallel Sequencing", Science Translational Medicine, vol. 2, No. 20, Feb. 24, 2010, 1-8.

Leary, Rebecca J et al., "Detection of Chromosomal Alterations in the Circulation of Cancer Patients with Whole-Genome Sequencing", Science Translational Medicine, 4, 162, 2012, 12.

Lecomte, T. et al., "Detection of Free-Circulating Tumor-Associated DNA in Plasma of Colorectal Cancer Patients and Its Association With Prognosis", Int. J. Cancer, vol. 100, 2002, 542-548.

Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.

Lee, T. et al., "Down syndrome and cell-free fetal DNA in archived maternal serum", AmJ Obstet Gynecol, vol. 187, No. 5, 1217-1221, Nov. 2002.

Lee, T.H. et al., "Quantitation of genomic DNA in plasma and serum samples: higher concentrations of genomic DNA found in serum than in plasma", Transfusion, vol. 41, Feb. 2001, 276-282.

Levsky, J. M. et al., "Fluorescence in situ hybridization: past, present and future", Journal of Cell Science, vol. 116, No. 14, 2003, 2833-2838.

Levsky, Jeffrey M. et al., "Efficacy of Coronary Ct Angiography: Where We Are, Where We Are Going and Where We Want to Be", Journal Of Cardiovascular Computed Tomography, vol. 3, Supplement 2, Nov. 2, 2009, s99-s108.

Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.

Li, et al., "Mapping Short DNA Sequencing Reads And Calling Variants Using Mapping Quality Scores", Genome Research, vol. 18, No. 11,, Aug. 19, 2008, 1851-1858.

Li, et al., "Multiplex Padlock Targeted Sequencing Reveals Human Hypermutable CpG Variations", Genome Research, vol. 19, No. 9, Jun. 12, 2009, 1606-1615.

Li, et al., "SOAP2: An Improved Ultrafast Tool For Short Read Alignment", Bioinformatics, vol. 25, No. 15, Aug. 1, 2009, 1966-1967.

Li, B., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.

Li, R. et al., "SNP detection for massively parallel whole-genome resequencing", Genome Research, vol. 19, 2009, 1124-1132.

Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.

Li, Ying et al., "Detection of Donor-specific DNA Polymorphisms in the Urine of Renal Transplant Recipients", Clinical Chemistry, vol. 49, No. 4, Apr. 1, 2003, 655-658.

Li, Ying et al., "Ready detection of donor-specific single-nucleotide polymorphisms in the urine of renal transplant recipients by matrix-

(56) References Cited

OTHER PUBLICATIONS assisted laser desorption/ionization time-of-flight mass spectrometry", Ying Li. et al., "Ready detection of donor-specific single-nucleotide polymorphisms in the urine of renal transplant recipients by matrix-assisted laser desorption/ionization time-of-flight mass spectrometry", Clin Chem, Oct. 2005, vol. 51,Issue. 10,pp. 1903-1904, Oct. 1, 2005, 1903-1904.

Li, Ying et al., "Size Separation of Circulatory DNA in Maternal Plasma Permits Ready Detection of Fetal DNA Polymorphisms", Clinical Chemistry, 50, 6, 2004, 1002-1011.

Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).

Lichtenstein, A. V. et al., "Circulating Nucleic Acids and Apoptosis", Annals New York Academy of Sciences, vol. 945, Aug. 1, 2001, 239-249.

Liew, Michael et al., "Genotyping of Single-Nucleotide Polymorphisms", Clinical Chemistry, 50(7), 2004, 1156-1164.

Life Technologies, "Ion AmpliSeq Comprehensive Cancer Panel", 2012, 2 pgs.

Life Technologies, "Ion AmpliSeq™ Designer provides full flexibility to sequence genes of your choice", 2012, 4 pages.

Liljedahl, Ulrika et al., "Detecting Imbalanced Expression Of SNP Alleles by Minisequencing On Microarrays", BMC Biotechnology, vol. 4, Article No. 24, Oct. 22, 2004, 1-10.

Lindberg, J. et al., "Exome Sequencing of Prostate Cancer Supports the Hypothesis of Independent Tumour Origins", European Urology, vol. 63, 2013, 347-353.

Lindroos, Katarina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.

Lo, et al., "Digital PCR for the Molecular Detection of Fetal Chromosomal Aneuploidy", PNAS, vol. 104, No. 32, Aug. 7, 2007, 13116-13121.

Lo, et al., "Fetal Nucleic Acids in Maternal Blood: the Promises", Clin. Chem. Lab. Med., 50(6), 2012, 995-998.

Lo, et al., "Free Fetal DNA in Maternal Circulation", JAMA, 292(23), (Letters to the Editor), 2004, 2835-2836.

Lo, et al., "Next-generation Sequencing Of Plasma/Serum DNA: An Emerging Research And Molecular Diagnostic Tool", Clinical Chemistry, vol. 55, No. 4, Apr. 1, 2009, 607-608.

Lo, "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet, 2, 8676, 1989, 1363-1365.

Lo, et al., "Presence Of Donor-specific Dna In Plasma Of Kidney And Liver-transplant Recipients", Lancet, vol. 351, No. 9112, May 2, 1998, 1329-1330.

Lo, et al., "Rapid Clearance of Fetal DNA from Maternal Plasma", Am. J. Hum. Genet., 64, 1999, 218-224.

Lo, et al., "Strategies for the Detection of Autosomal Fetal DNA Sequence from Maternal Peripheral Blood", Annals New York Academy of Sciences,731, 1994, 204-213.

Lo, et al., "Two-way cell traffic between mother and fetus: biologic and clinical implications", Blood, 88(11), Dec. 1, 1996, 4390-4395.

Lo, Y M. et al., "Circulating Nucleic Acids in Plasma and Serum: An Overview", Annals of the New York Academy of Sciences, vol. 945, Sep. 1, 2001, 1-7.

Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.

Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.

Lo, Y.M. Dennis et al., "Maternal Plasma DNA Sequencing Reveals the Genome-Wide Genetic and Mutational Profile of the Fetus", Science Translational Medicine,, 2 (61), 2010, 13.

Lo, Y.M. Dennis et al., "Plasma placental RNA allelic ratio permits noninvasive prenatal chromosomal aneuploidy detection", Nature Medicine, 13 (2), 2007, 218-223.

Lo, Y.M. Dennis et al., "Presence of Fetal DNA in Maternal Plasma and Serum", The Lancet, 350, 1997, 485-487.

Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.

Lo, Y.M.D. , "Fetal DNA in Maternal Plasma: Biology and Diagnostic Applications", Clinical Chemistry, vol. 46, No. 12, 2000, 1903-1906.

Lo, Y.M.D. et al., "Prenatal diagnosis: progress through plasma nucleic acids", Nature Reviews, vol. 8, 2007, 71-77.

Lo, Y-M D. , "Non-invasive prenatal diagnosis using fetal cells in maternal blood", J. Clin. Pathol., vol. 47, 1994, 1060-1065.

Lo, Y-M.D et al., "Detection of Single-Copy Fetal DNA Sequence from Maternal Blood", The Lancet, 335, 1990, 1463-1464.

Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.

Lo, Y-M.D. et al., "Detection of Fetal RhD Sequence from Peripheral Blood of Sensitized RhD-Negative Pregnant Women", British Journal of Haematology, 87, 1994, 658-660.

Lo, Y-M.D. et al., "Prenatal Determination of Fetal RhD Status by Analysis of Peripheral Blood of Rhesus Negative Mothers", The Lancet, 341, 1993, 1147-1148.

Loh, Elwyn , "Anchored PCR: Amplification with Single-sided Specificity", Methods, vol. 2, 1991, pp. 11-19.

Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.

Lu, I. et al., "Establishment of a system based on universal multiplex-PCR for screening genetically modified crops", Anal. Bioanal. Chem, vol. 396, Oct. 24, 2009, 2055-2064.

Lu, S. et al., "Probing Meiotic Recombination and Aneuploidy of Single Sperm Cells by Whole-Genome Sequencing", Science, vol. 338, Dec. 21, 2012, 1627-1630.

Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.

Lui, Yanni Y. et al., "Circulating DNA in Plasma and Serum: Biology, Preanalytical Issues And Diagnostic Applications", Clinical Chemistry and Laboratory Medicine, vol. 40, No. 10, Oct. 29, 2002, 962-968.

Lui, Yanni Y. et al., "Origin of Plasma Cell-Free DNA after Solid Organ Transplantation", Clinical Chemistry, vol. 49, No. 3, Mar. 1, 2003, 495-496.

Lun, Fiona M. et al., "Microfluidics Digital PCR Reveals A Higher Than Expected Fraction Of Fetal DNA In Maternal Plasma", Clinical Chemistry, vol. 54, No. 10, Aug. 14, 2008, 1664-1672.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Ma, Xiaotu et al., "Rise and fall of subclones from diagnosis to relapse in pediatric B-acute lymphoblastic leukaemia", Nature Communications, vol. 6, Mar. 19, 2015, 1-12.

Mackiewicz, D. et al., "Distribution of Recombination Hotspots in the Human Genome—A Comparison of Computer Simulations with Real Data", PLOS One, vol. 8, No. 6, Jun. 2013, 11 pages.

Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.

(56) References Cited

OTHER PUBLICATIONS

Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Mardis, E. R. , "The impact of next-generation sequencing technology on genetics", Trends in Genetics, vol. 24, No. 3, Feb. 11, 2008, 133-141.
Marguiles, M. et al., "Genome Sequencing in Open Microfabricated High Density Picoliter Reactors", Nature, vol. 437, No. 7057, Sep. 15, 2005, 376-380.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
Marianes, Alexis E. et al., "Targets of Somatic Hypermutation within Immunoglobulin Light Chain Genes in Zebrafish", Immunology, vol. 132, 2010, pp. 240-255.
Markoulatos, P. et al., "Multiplex Polymerase Chain Reaction: A Practical Approach", Journal of Clinical Laboratory Analysis, vol. 16, 2002, 47-51.
Maron, Jill L. et al., "Cell-free Fetal DNA Plasma Extraction and Real-time Polymerase Chain Reaction Quantification", Methods In Molecular Medicine, vol. 132, Aug. 1, 2007, 51-63.
Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.
Martinez-Lopez, J. et al., "Real-time PCR Quantification of Haematopoietic Chimerism after Transplantation: A Comparison Between TaqMan And Hybridization Probes Technologies", International Journal of Laboratory Hematology, vol. 32, Issue 1, Part 1, May 12, 2009, e17-e25.
Martins, et al., "Quantification Of Donor-derived DNA In Serum: A New Approach Of Acute Rejection Diagnosis In A Rat Kidney Transplantation Model", Transplantation Proceedings, vol. 37, No. 1,, Jan. 1, 2005, 87-88.
Masuzaki, H. et al., "Detection of cell free placental DNA in maternal plasma: direct evidence from three cases of confined placental mosaicism", J Med Genet, vol. 41, 2004, 289-292.
Matsubara, T. et al., "Pantropic Retroviral Vectors Integrate and Express In Cells of the Malaria Mosquito, Anopheles gambiae", PNAS, vol. 93, 1996, pp. 6181-6185.
Matsuzaki, H. et al., "Genotyping over 100,000 SNPs on a pair of oligonucleotide arrays", Nature Methods, vol. 1, No. 2, Nov. 2004, 109-111.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
McDonald, J. P. et al., "Novel thermostable Y-family polymerases: applications for the PCR amplification of damaged or ancient DNAs", Nucleic Acids Research, vol. 34, No. 4, 2006, 1102-1111.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, "Medical Definition of Stimulant", http://www.merriam-webster.com/medical/stimulant, Mar. 14, 2016, 7 pages.
Merriam-Webster, "Universal Definition", Merriam-Webster.com, 3 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Mertes, F. et al., "Targeted enrichment of genomic DNA regions for next-generation sequencing", Briefings in Functional Genomics, vol. 10, No. 6, Nov. 26, 2011, 374-386.
Messmer, Trudy O. et al., "Application of a Nested, Multiplex PCR to Psittacosis Outbreaks", Journal of Clinical Microbiology, vol. 35, No. 8, 1997, pp. 2043-2046.
Metzker, M. L. et al., "Polymerase Chain Reaction", Encyclopedia of Medical Devices and Instrumentation, vol. 5, Second Edition, 2006, 380-387.
Metzker, M. L. et al., "Quantitation of Mixed-Base Populations of HIV-1 Variants by Automated DNA Sequencing with BODIPY* Dye-Labeled Primers", BioTechniques, vol. 25, Sep. 1998, 446-462.
Meuzelaar, Linda S. et al., "Megaplex PCR: A Strategy for Multiplex Amplification", Nature Methods, vol. 4, 2007, pp. 835-837.
Meyer, M et al., "Illumina Sequencing Library Preparation for Highly Multiplexed Target Capture and Sequencing", Cold Spring Harbor Protocols, vol. 2010, Issue 6, Jun. 2010, 1-10.
Meyerson, M. et al., "Advances in understanding cancer genomes through second-generation sequencing", Nature Reviews: Genetics, vol. 11, Oct. 2010, 685-696.
Mikkelsen, T. S. et al., "Genome-wide maps of chromatin state in pluripotent and lineage-committed cells", Nature, vol. 448, No. 2, Aug. 2007, 553-562.
Milani, et al., "Genotyping Single Nucleotide Polymorphisms By Multiplex Minisequencing Using Tag-arrays", DNA Microarrays for Biomedical Research, vol. 529, Jan. 16, 2009, 215-229.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, Sep. 30, 2004, 1-4.
Minkoff, E. et al., "Stem Cells, Cell Division, and Cancer", Biology Today Third Edition, Chapter 12, 2004, 10 pages.
Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.
Mitra, S. et al., "Chapter 4 Classification Techniques", Introduction to Machine Learning and Bioinformatics, First Edition, 2008, 101-127.
Morand, et al., "Hesperidin contributes to the vascular protective effects of orange juice: a randomized crossover study in healthy volunteers", Am J Clin Nutr. Jan. 2011;93(1 ):73-80. Epub Nov. 10, 2010.
Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.

(56) References Cited

OTHER PUBLICATIONS

Moreira, et al., "Increase In And Clearance Of Cell-free Plasma DNA In Hemodialysis Quantified By Real-time PCR", Clinical Chemistry and Laboratory Medicine, vol. 44, No. 12, Dec. 13, 2006, 1410-1415.
Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.
Munne, S. et al., "Chromosome Abnormalities in Human Embryos", Textbook of Assisted Reproductive Techniques, 2004, pp. 355-377.
Munne, S. et al., "Chromosome abnormalities in human embryos", European Society of Human Reproduction and Embryology: Human Reproduction Update, vol. 4, No. 6, 1998, 842-855.
Munne, S. et al., "Improved implantation after preimplantation genetic diagnosis of aneuploidy", Reproductive BioMedicine Online, vol. 7., No. 1., May 15, 2003, 91-97.
Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.
Murtaza, M. et al., "Non-Invasive Analysis of Acquired Resistance to Cancer Therapy by Sequencing of Plasma DNA", Nature (doi: 10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.
Nakamura, N. et al., "Ex Vivo Liver Perfusion with Arterial Blood from A Pig with Ischemic Liver Failure", Artificial Organs, vol. 23, No. 2, 1999, 153-160.
Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Natera, Inc., "Declaration of Sandra L. Haberny", May 16, 2019, 3 pages.
Natera, Inc., "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., "Exhibit 8 Ehrich Invalidity Chart", Aug. 20, 2018, 16 pages.
Natera, Inc., "Exhibits A-H to Haberny Declaration", May 16, 2019, 192 pages.
Natera, Inc., "Motion to Dismiss", May 16, 2019, 2 pages.
Natera, Inc., "Natera Inc.'s First Amended Answer, Affirmative Defenses and Counterclaims", Aug. 16, 2018, 28 pages.
Natera, Inc., "Natera, Inc.'s Supplemental Objections and Response to Plaintiff Illumina, Inc.'s Interrogatory No. 8", Mar. 20, 2019, 29 pages.
Natera, Inc., "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
National Institutes of Health, , "Genetics Home Reference: Your Guide to Understanding Genetic Conditions", Feb. 28, 2014, 2 pgs.
Nawroz, H et al., "Microsatellite Alterations in Serum DNA of Head and Neck Cancer Patients", Nature Medicine, vol. 2, No. 9, Sep. 1996, 1035-1037.
NCBI, "Blast of AAAAAAAAATTTAAAAAAAAATTT", 2015, 9 pages.
NCBI, "db SNP rs2056688", 2015, 3 pages.
NCBI, "dbSNP record for rs1294331", Retrieved from the Internet: <URL: www.ncbi.nlm.nih.gov/snp/?term=rs 1294331 >, 2019, 2 pgs.
NCBI, "dbSNP record for rs1872575", Retrieved from the Internet: <URL: www.ncbi.nlm.nih.gov/snp/?term=rs1872575, 2019, 2 pgs.
NCBI, "dbSNP record for rs2362450", Retrieved from the Internet: <URL: www.ncbi.nlm.nih.gov/snp/?term=rs2362450>, 2019, 1 pg.
NCBI, "dbSNP record for rs2384571", Retrieved from the Internet: <URL: www.ncbi.nlm.nih.gov/snp/?term=rs2384571>, 2019, 2 pgs.
NCBI, "dbSNP record for rs2498982", Retrieved from the Internet: <URL: www.ncbi.nlm.nih.gov/snp/?term=rs2498982>, 2019, 3 pgs.
NCBI, "dbSNP record for rs3731877", Retrieved from the Internet: <URL: www.ncbi.nlm.nih.gov/snp/?term=rs3731877>, 2019, 2 pgs.
Neve, B. et al., "Rapid SNP Allele Frequency Determination in Genomic DNA Pools by Pyrosequencing", BioTechniques, vol. 32, No. 5, May 1, 2002, 1138-1142.
New England Biolabs, "NucleicAcids, Linkers and Primers: Random Primers", 1998/99Catalog, 1998, 121 and 284.
Newman, A. M. et al., "Integrated digital error suppression for improved detection of circulating tumor DNA", Nature Biotechnology, vol. 34, No. 5, May 2016, 547-555.
Ng, et al., "Multiplex Sequencing Of Paired-end Ditags (MS-PET): A Strategy For The Ultra-high-throughput Analysis Of Transcriptomes And Genomes", Nucleic Acids Research, vol. 34, No. 12, Jul. 13, 2006, 1-10.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T. , "A high-plex PCR approach for massively parallel sequencing", BioTechniques, vol. 55, No. 2, Aug. 2013, 69-74.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H. et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nilsson, M. et al., "Padlock Probes: Circularizing Oligonucleotides for Localized DNA Detection", Science, vol. 265, Sep. 10, 1994, 2085-2088.
Nishigaki, K. et al., "Random PCR-Based Genome Sequencing: A Non-Divide-and-Conquer Strategy", DNA Research, vol. 7, 2000, 19-26.
Nishiwaki, Morie et al., "Genotyping of Human Papillomaviruses by A Novel One-step Typing Method With Multiplex PCR and Clinical Applications", Journal of Clinical Microbiology, vol. 46, 2008, pp. 1161-1168.
Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.
Nui, A. et al., "The Functional Integrity of a Normothermic Perfusion System Using Artificial Blood in Pig Liver", Journal of Surgical Research, Vo. 131, 2006, 189-198.
Nygren, et al., "Quantification of Fetal DNA by Use of Methylation-Based DNA Discrimination", Clinical Chemistry 56:10 1627-1635 (2010).
O'Connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.

(56) References Cited

OTHER PUBLICATIONS

Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.
Ogino, S. et al., "Bayesian Analysis and Risk Assessment in Genetic Counseling and Testing", Journal of Molecular Diagnostics, 6 (1), 2004, 9 pgs.
Ohara, O et al., "One-sided Polymerase Chain Reaction: The Amplification of cDNA", Proceedings of the National Academy of Sciences, vol. 86, 1989, 5673-5677.
Ohira, T. et al., "Tumor vol. determines the feasibility of cell-free DNA sequencing for mutation detection in non-small cell lung cancer", Cancer Science, vol. 107, 2016, 1660-1666.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Okou, et al., "Microarray-based Genomic Selection For High-throughput Resequencing", Nature Methods, vol. 4, No. 11, Oct. 14, 2007, 907-909.
Okou, David T. et al., "Combining Microarray-based Genomic Selection (MGS) with The Illumina Genome Analyzer Platform To Sequence Diploid Target Regions", Annals of Human Genetics, vol. 73, No. 5, Aug. 6, 2009, 502-513.
Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.
Oliphant, A. et al., "Bead.Array™ Technology: Enabling an Accurate, Cost-Effective Approach to High-Throughput Genotyping", Bio Techniques, vol. 32, Jun. 2002, S56-S6.
Olivarius, S et al., "High-throughput Verification of Transcriptional starting Sites by Deep-RACE", Bio Techniques, vol. 46, No. 2, Feb. 2009, 130-132.
Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.
Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.
Olivier, et al., "The Invader Assay for SNP Genotyping", Mutation Research, vol. 573, No. 1-2, Jun. 3, 2005, 103-110.
Olney, R. S. et al., "Chorionic Villus Sampling and Amniocentesis: Recommendations for Prenatal Counseling", MMWR: Recommendations and Reports, 44(RR-9), Jul. 21, 1995, 1-12.
O'Malley, R. et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta, 30, 2009, 891-897.
Orsouw, et al., "Complexity Reduction Of Polymorphic Sequences (Crops): A Novel Approach For Large-scale Polymorphism Discovery In Complex Genomes", PLoS ONE, vol. 11:e1172, Nov. 14, 2017, 1-10.
Owczarzy, Richard et al., "Melting Temperatures of Nucleic Acids: Discrepancies in Analysis", Biophysical Chemistry, vol. 117, 2005, pp. 207-215.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.
Pakstis, et al., "Candidate SNPs For A Universal Individual Identification Panel", Human Genetics, vol. 121, No. 3-4,, Feb. 27, 2007, 305-317.
Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Palomaki, G. E. et al., "DNA sequencing of maternal plasma to detect Down syndrome: An international clinical validation study", Genetics In Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Panjkovich, Alejandro et al., "Comparison of Different Melting Temperature Calculation Methods for Short DNA Sequences", Bioinformatics, vol. 21, 2005, pp. 711-722.
Papadopoulou, E. et al., "Cell-Free DNA and RNA in Plasma as a New Molecular Marker for Prostate Cancer", Oncology Research, vol. 14, 2004, 439-445.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Parker, A. V. et al., "The Effect of Sodium Citrate on the Stimulation of Polymorphonuclear Leukocytes", Investigative Ophthalmology & Visual Science, vol. 26, 1985, 1257-1261.
Paruzynski, A. et al., "Genome-wide high-throughput integrome analyses by nrLAM-PCR and next-generation sequencing", Nature Protocols, vol. 5, No. 8, Jul. 8, 2010, 1379-1395.
Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.
Pastinen, T. et al., "Minisequencing: A Specific Tool for DNA Analysis and Diagnostics on Oligonucleotide Arrays", Genome Research, vol. 7, 1997, 606-614.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Patil, N. et al., "Blocks of Limited Haplotype Diversity Revealed by High-Resolution Scanning of Human Chromosome 21", Science, vol. 294, Nov. 23, 2001, 1719-1723.
Paunio, T et al., "Preimplantation diagnosis by whole-genome amplification, PCR amplification, and solid-phase minisequencing of blastomere DNA", Clinical Chemistry, vol. 42, No. 9, 1996, 1382-1390.
PCT/US2006/045281, "International Preliminary Report on Patentability", mailed May 27, 2008, 1 pg.
PCT/US2006/045281, "International Search Report and Written Opinion", mailed Sep. 28, 2007, 7 pgs.
PCT/US2008/003547, "International Search Report", mailed Apr. 15, 2009, 5 pgs.
PCT/US2009/034506, "International Search Report", mailed Jul. 8, 2009, 2 pgs.
PCT/US2009/045335, "International Search Report", mailed Jul. 27, 2009, 1 pg.
PCT/US2009/052730, "International Search Report", mailed Sep. 28, 2009, 1 pg.

(56) References Cited

OTHER PUBLICATIONS

PCT/US2010/050824, "International Search Report", mailed Nov. 15, 2010, 2 pgs.
PCT/US2011/037018, "International Search Report", mailed Sep. 27, 2011, 2 pgs.
PCT/US2011/061506, "International Search Report", mailed Mar. 16, 2012, 1 pgs.
PCT/US2011/066938, "International Search Report", mailed Jun. 20, 2012, 1 pg.
PCT/US2012066339, "International Search Report", mailed Mar. 5, 2013, 1 pg.
PCT/US2013/028378, "International Search Report and Written Opinion", mailed May 28, 2013, 11 pgs.
PCT/US2013/57924, "International Search Report and Written Opinion", mailed Feb. 18, 2014, 8 pgs.
PCT/US2014/051926, "International Search Report and Written Opinion", Dec. 9, 2014, 3 pgs.
Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pelizzari, C. A. et al., "Quantitative analysis of DNA array autoradiographs", Nucleic Acids Research, vol. 28, No. 22, 2000, 4577-4581.
Pena, Sergio D.J. et al., "Paternity Testing in the DNA Era", Trends In Genetics, 10, 6, 1994, 204-209.
Perakis, S. et al., "Advances in Circulating Tumor DNA Analysis", Advances in Clinical Chemistry, vol. 80, 2017, 73-153.
Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M. , "Overcoming the Challenges of Multiplex PCR", Biocompare Editorial Article, 2012, 1-5.
Perry, George H. et al., "The Fine-Scale and Complex Architecture of Human Copy-Number Variation", The American Journal of Human Genetics, 82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, D. , "List of Materials Considered By David Peters, Ph.D.", Jun. 13, 2019, 2 pages.
Peters, David P. et al., "Noninvasive Prenatal Diagnosis of a Fetal Microdeletion Syndrome", New England Journal of Medicine, 365(19), 2011, 1847-1848.
Pfaffl, Michael W. , "Quantification Strategies in Real-time PCR", A-Z of quantitative PCR, 2004, pp. 87-112.
Pfaffl, Michael W. , "Relative Expression Software Tool (REST ©) for Group-Wise Comparison and Statistical Analysis of Relative Expression Results in real-Time PCR", Nucleic Acids Research, 30(9), 2002, 10 pgs.
Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.
Phillips, C. et al., "Resolving Relationship Tests that Show Ambiguous STR Results Using Autosomal SNPs as Supplementary Markers", Forensic Science International: Genetics 2, 2008, 198-204.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pirker, C. et al., "Whole Genome Amplification for CGH Analysis: Linker-Adapter PCR as the Method of Choice for Difficult and Limited Samples", Cytometry Part A, vol. 61A, 2004, 26-34.
Podder, Mohua et al., "Robust SN P genotyping by multiplex PCR and arrayed primer", BMC Medical Genomics, 1(5), 2008, 1-15.
Poirier, K. et al., "Maternal mosaicism for mutations in the ARX gene in a family with X linked mental retardation", Human Genetics, vol. 118, Aug. 3, 2005, 45-48.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Price, T.S et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Profitt, J et al., "Isolation And Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Puszyk, William M. et al., "Noninvasive Prenatal Diagnosis Of Aneuploidy Using Cell-free Nucleic Acids In Maternal Blood: Promises And Unanswered Questions", Prenatal Diagnosis, vol. 28, No. 1, Nov. 16, 2007, 1-6.
Qiagen, "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.
Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.
Quan, P. C. et al., "Studies on the mechanism of NK cell lysis", The Journal of Immunology, vol. 128, 1982, 1786-1791.
Quinlan, M. P. , "Amniocentesis: Indications and Risks", American Medical Association Journal of Ethics: Virtual Mentor, vol. 10, No. 5, May 2008, 304-306.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, M. , "A System and Method for Integrating, Validating and Applying Genetic and Clinical Data to Enhance Medical Decisions", Nov. 29, 2005, 155 pgs.
Rabinowitz, Matthew et al., "Origins and rates of aneuploidy inhuman blastomeres", Fertility and Sterility, vol. 97, No. 2, Feb. 2012, 395-401.
Rabinowitz, Matthew et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J. , "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.

(56) References Cited

OTHER PUBLICATIONS

Raindance Technologies, "Multiplexing with RainDrop Digital PCR", Application Note, 2013, 2 pgs.
Raindance Technologies, et al., "RainDance Technologies Introduces the RDT 1000", RainDance Technologies, Nov. 12, 2008.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.
Rechitsky, Svetlana et al., "Preimplantation Genetic Diagnosis with HLA Matching", Reproductive Bio Medicine Online, 9, 2, 2004, 210-221.
Reeves, R. H. et al., "Too much of a good thing: mechanisms of gene action in Down syndrome", Trends in Genetics, vol. 17, No. 2, Feb. 2, 2001, 83-88.
Reinert, T. et al., "Analysis of circulating tumour DNA to monitor disease burden following colorectal cancer surgery", Gut, vol. 65, 2016, 625-634.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Rhoads, A. et al., "PacBio Sequencing and Its Applications", Genomics Proteomics Bioinformatics, vol. 13, Nov. 2, 2015, 278-289.
Ricciotti, Hope , "Eating by Trimester", Online]. Retrieved from Internet:<http://www.youandyourfamily.com/article.php?story=Eating+by+Trimester>, 2014, 3.
Riley, D. E. , "DNA Testing: An Introduction For Non-Scientists An Illustrated Explanation", Scientific Testimony: An Online Journal, http://www.scientific.org/tutorials/articles/riley/riley.html, Apr. 6, 2005, 22 pages.
Riva, F. , "Patient-Specific Circulating Tumor DNA Detection during Neoadjuvant Chemotherapy in Triple-Negative Breast Cancer", Clinical Chemistry, vol. 63, No. 3, 2017, 691-699.
Robertson, G. et al., "Genome-wide profiles of STAT1 DNA association using chromatin immunoprecipitation and massively parallel sequencing", Nature Methods, vol. 4, No. 8, Aug. 2007, 651-657.
Roche Diagnostics, et al., "Versatile Nucleic Acid Purification", MagnaPure Manual, Feb. 3, 2012.
Rogaeva, E. et al., "The Solved and Unsolved Mysteries of the Genetics of Early-Onset Alzheimer's Disease", NeuroMolecular Medicine, vol. 2, 2002, 1-10.
Roman, B. L. et al., "Non-Radioisotopic AFLP Method Using PCR Primers Fluorescently Labeled with CyA 5", BioTechniques, vol. 26, Feb. 1999, 236-238.
Roper, Stephen M. et al., "Forensic Aspects of DNA-Based Human Identity Testing", Journal of Forensic Nursing, 4, 2008, 150-156.
Rosado, J. A. et al., "Tyrosine kinases activate store-mediated Ca2+ entry in human platelets through the reorganization of the actin cytoskeleton", Biochem. J., vol. 351, 2000, 429-437.
Rosen, D. R. et al., "Mutations in Cu/Zn superoxide dismutase gene are associated with familial amyotrophic lateral sclerosis", Nature, vol. 362, Mar. 4, 1993, 59-62.
Ross, P. et al., "Quantitative Approach to Single-Nucleotide Polymorphism Analysis Using MALDI-TOF Mass Spectrometry", BioTechniques, vol. 29, Sep. 2000, 620-629.
Rothberg, et al., "The Development and Impact of 454 Sequencing", Nature Biotechnology, vol. 26, No. 10, Oct. 9, 2008, 1117-1124.
Roux, K. , "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Ruano, G. et al., "Haplotype of multiple polymorphisms resolved by enzymatic amplification of single DNA molecules", Proc. Nati. Acad. Sci. USA, vol. 87, Aug. 1990, 6296-6300.
Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine And Hygiene, vol. 60, 1999, pp. 183-187.
Ruschendorf, et al., "Alohomora: A Tool For Linkage Analysis Using 10K SNP Array Data", Bioinformatics Applications Notes, vol. 21, No. 9, Jan. 12, 2005, 2123-2125.
Russell, L. M. , "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Ryan, B. M. et al., "A prospective study of circulating mutant KRAS2 in the serum of patients with colorectal neoplasia: strong prognostic indicator in postoperative follow up", Gut, vol. 52, 2003, 101-108.
Rychlik, et al., "Optimization of the annealing temperature for DNA amplification in vitro", Nucleic Acids Research, 18(21), 1990, 6409-6412.
Sahota, A. , "Evaluation of Seven PCR-Based Assays for the Analysis of Microchimerism", Clinical Biochemistry, vol. 31, No. 8., 1998, 641-645.
Sahukhal, G. S. et al., "msaABCR operon positively regulates biofilm development by repressing proteases and autolysis in Staphlococcus aureus", FEMS Microbiology Letters, vol. 362, No. 4, 2015, 1-10.
Saito, H. et al., "Prenatal DNA diagnosis of a single-gene disorder from maternal plasma", The Lancet, vol. 356, Sep. 30, 2000, 1170.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Sanchez, C. et al., "New insights into structural features and optimal detection of circulating tumor DNA determined by single-strand DNA analysis", Nature Partner Journals, vol. 3, No. 31, Nov. 23, 2018, 12 pgs.
Sander, Chris , "Genetic Medicine and the Future of Health Care", Science, 287(5460), 2000, 1977-1978.
Sanger, et al., "Nucleotide Sequence of Bacteriophage Lambda DNA", Journal of Molecular Biology, vol. 162, No. 4, Dec. 25, 1982, 729-773.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Santalucia, Jr., J. , "Physical Principles and Visual-OMP Software for Optimal PCR Design", Methods in Molecular Biology, vol. 402, 2007, 3-33.
Sasabe, Yutaka , "Genetic Diagnosis of Gametes and Embryos Resulting from ART", Japanese Journal of Fertility and Sterility, vol. 46, No. 1, 2001, 43-46.
Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.
Schaaf, C. P. et al., "Copy Number and SNP Arrays In Clinical Diagnostics", Annu. Rev. Genomics Hum. Genet., vol. 12, 2011, 25-51.
Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.

(56) References Cited

OTHER PUBLICATIONS

Schmitt, M. W. et al., "Detection of ultra-rare mutations by next-generation sequencing", PNAS, vol. 109, No. 36, Sep. 4, 2012, 14508-14513.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schoumans, J et al., "Detection of chromosomal imbalances in children with idiopathic mental retardation by array based comparative genomic hybridisation (array-CGH)", JMed Genet, 42, 2005, 699-705.
Schubert, "Picking out prenatal DNA", Nature Medicine, vol. 10, No. 785, Aug. 2004, 1 page.
Schwarzenbach, H. et al., "Cell~free nucleic acids as biomarkers in cancer patients", Nature Reviews: Cancer, vol. 11, Jun. 2011, 426-437.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Schwarzenbach, H. et al., "Evaluation of cell-free tumour DNA and RNA in patients with breast cancer and benign breast disease", Molecular BioSystems, vol. 7, 2011, 2848-2854.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Sham, P. et al., "DNA Pooling: A Tool for Large-Scale Association Studies", Nature Reviews Genetics, vol. 3, Nov. 2002, 862-871.
Shapero, M. H. et al., "MARA: A Novel Approach for Highly Multiplexed Locus-specific SNP Genotyping Using High-density DNA Oligonucleotide Arrays", Nucleic Acids Research, vol. 32, No. 22, 2004, 1-9.
Sharples, et al., "Diagnostic Accuracy Of Coronary Angiography And Risk Factors For Post-heart-transplant Cardiac Allograft Vasculopathy", Transplantation, vol. 76, No. 4, Aug. 27, 2003, 679-682.
Shaw-Smith, et al., "Microarray Based Comparative Genomic Hybridisation (array-CGH) Detects Submicroscopic Chromosomal Deletions and Duplications in Patients with Learning Disability/ Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.
Shen, Zhiyong , "MPprimer: a program for reliable multiplex PCR primer design", BMC Bioinformatics 2010, 11:143, 1-7.
Shendure, J. et al., "Accurate Multiplex Polony Sequencing of an Evolved Bacterial Genome", Science, Nov. 30, 2007, 18-24.
Shendure, J. et al., "Next-generation DNA sequencing", Nature Biotechnology, vol. 26, No. 10, Oct. 2008, 1135-1145.
Sherlock, J et al., "Assessment of Diagnostic Quantitative Fluorescent Multiplex Polymerase Chain Reaction Assays Performed on Single Cells", Annals of Human Genetics, 62, 1, 1998, 9-23.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Shokralla, S. et al., "Next-generation DNA barcoding: using next-generation sequencing to enhance and accelerate DNA barcode capture from single specimens", Molecular Ecology Resources, vol. 14, 2014, 892-901.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Shyamala, Venkatakrishna et al., "Genome Walking by Single-Specific-Primer Polymerase Chain Reaction: SSP-PCR", Gene, vol. 84, 1989, pp. 1-8.
Siebert, P. D. et al., "An improved PCR method for walking in uncloned genomic DNA", Nucleic Acids Research, vol. 23, No. 6, 1995, 1087-1088.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Simpson, J. et al., "Fetal Cells in Maternal Blood: Overview and Historical Perspective", Annals New York Academy of Sciences, 731, 1994, 1-8.
Singh, Vinayak K. et al., "PCR Primer Design", Molecular Biology Today, vol. 2, 2001, pp. 27-32.
Sint, Daniela et al., "Advances in Multiplex PCR: Balancing Primer Efficiencies and Improving Detection Success", Methods in Ecology and Evolution, 3, 2012, 898-905.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Snijders, Antoine et al., "Assembly of Microarrays for Genome-Wide Measurement of DNA Copy Number", Nature Genetic, 29, 2001, 263-264.
Snyder, T. M. et al., "Universal noninvasive detection of solid organ transplant rejection", PNAS, vol. 108, No. 15, Apr. 12, 2011, 6229-6234.
Societies Related to Genetic Med, , "Guideline related to genetic examination", Japanese Society for Genetic Counseling, Japanese Society for Gene Diagnosis and Therapy, Japan Society of Obstetrics and Gynecology, 2003, 2-15.
Solexa, "Application Note: DNA Sequencing", 2006, 1-2.
Solomon, M. J. et al., "Formaldehyde-mediated DNA-protein crosslinking: A probe for in vivo chromatin structures", Proc. Natl. Acad. Sci. USA, vol. 82, 1985, 6470-6474.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
sourceforge.net, "Primer3", 2009, 1 pg.

(56) References Cited

OTHER PUBLICATIONS

Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.

Sparks, Andrew B. et al., "Selective Analysis of Cell-Free DNA in Maternal Blood for Evaluation of Fetal Trisomy", Prenatal Diagnosis, 32, 2012, 1-7.

Spencer, K. et al., "Maternal serum levels of dimeric inhibin A in pregnancies affected by trisomy 21 in the first trimester", Prenatal Diagnosis, vol. 21, 2001, 441-444.

Spencer, K. et al., "Maternal serum levels of total activin-A in first-trimester trisomy 21 pregnancies", Prenatal Diagnosis, vol. 21, 2001, 270-273.

Spertini, D. et al., "Screening of Transgenic Plants by Amplification of Unknown Genomic DNA Flanking T-DNA", BioTechniques, vol. 27, Aug. 1999, 308-314.

Spes, et al., "Diagnostic And Prognostic Value Of Serial Dobutamine Stress Echocardiography For Noninvasive Assessment Of Cardiac Allograft Vasculopathy: A Comparison With Coronary Angiography And Intravascular Ultrasound", Circulation, vol. 100, No. 5, Aug. 3, 1999, 509-515.

Spindler, K.L. G. et al., "Cell-free DNA in healthy individuals, noncancerous disease and strong prognostic value in colorectal cancer", International Journal of Cancer, vol. 135, 2014, 2984-2991.

Spindler, K.-L. G. et al., "Cell-Free DNA in Metastatic Colorectal Cancer: A Systematic Review and Meta-Analysis", The Oncologist, vol. 22, 2017, 1049-1055.

Spiro, Alexander et al., "A Bead-Based Method for Multiplexed Identification and Quantitation of DNA Sequences Using Flow Cytometry", Applied and Environmental Microbiology, 66, 10, 2000, 4258-4265.

Spits, C et al., "Optimization and Evaluation of Single-Cell Whole Genome Multiple Displacement Amplification", Human Mutation, 27(5), 496-503, 2006.

Srinivasan, et al., "Noninvasive Detection of Fetal Subchromosome Abnormalities via Deep Sequencing of Maternal Plasma", The American Journal of Human Genetics 92, 167-176, Feb. 7, 2013.

Stephens, M. et al., "Accounting for Decay of Linkage Disequilibrium in Haplotype Inference and Missing-Data Imputation", Am. J. Hum. Genet., vol. 76, 2005, 449-462.

Stephens, Mathews et al., "A Comparison of Bayesian Methods for Haplotype Reconstruction from Population Genotype Data", Am. J. Hum. Genet.,73, 2003, 1162-1169.

Stevens, Robert et al., "Ontology-Based Knowledge Representation for Bioinformatics", Briefings in Bioinformatics, 1, 4, 2000, 398-414.

Stewart, C. M. et al., "Circulating cell-free DNA for non-invasive cancer management", Cancer Genetics, vol. 228-229, 2018, 169-179.

Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.

Steyerberg, E.W. et al., "Application of Shrinkage Techniques in Logistic Regression Analysis: A Case Study", Statistica Neerlandica, 55(1), 2001, 76-88.

Stiller, et al., "Direct Multiplex Sequencing (DMPS)—A Novel Method For Targeted High-thoroughput Sequencing Of Ancient And Highly Degraded DNA", Genome Research, vol. 19, No. 10, Jul. 27, 2009, 1843-1848.

Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.

Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.

Strom, C. et al., "Three births after preimplantation genetic diagnosis for cystic fibrosis with sequential first and second polar body analysis", American Journal of Obstetrics and Gynecology, 178 (6), 1998, 1298-1306.

Strom, Charles M. et al., "Neonatal Outcome of Preimplantation Genetic Diagnosis by Polar Body Removal: The First 109 Infants", Pediatrics, 106( 4), 2000, 650-653.

Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.

Su, S.Y. et al., ""Inferring combined CNV/SNP haplotypes from genotype data"", Bioinformatics, vol. 26, No. 11,1, Jun. 1, 2010, 1437-1445.

Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.

Sun, Guihua et al., "SNPs in human miRNA genes affect biogenesis and function", RNA, 15(9), 2009, 1640-1651.

Swarup, V. et al., "Circulating (cell-free) nucleic acids—A promising, non-invasive tool for early detection of several human diseases", FEBS Letters, vol. 581, 2007, 795-799.

Sweet-Kind Singer, J. A. et al., "Log-penalized linear regression", IEEE International Symposium on Information Theory, 2003. Proceedings, 2003, 286.

Swinkels, D. W. et al., "Effects of Blood-Processing Protocols on Cell-free DNA Quantification in Plasma", Clinical Chemistry, vol. 49, No. 3, 2003, 525-526.

Syvanen, A.C. , "Toward genome-wide SNP genotyping", Nature Genetics Supplement, vol. 37, Jun. 2005, S5-S10.

Taback, B. et al., "Quantification of Circulating DNA in the Plasma and Serum of Cancer Patients", Ann. N.Y. Acad. Sci, vol. 1022, 2004, 17-24.

Takala, et al., "A High-throughput Method for Quantifying Alleles and Haplotypes of The Malaria Vaccine Candidate Plasmodium Falciparum Merozoite Surface Protein-1 19 kDa", Malaria Journal, vol. 5:31, Apr. 20, 2006, 1-10.

Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.

Takara Biomedicals, "Competitive PCR Guide", Lit. # L0126, Aug. 1999, 9 pages.

Takashima, Y. et al., "Expansion-contraction of photoresponsive artificial muscle regulated by host-guest interactions", Nature Communications, vol. 3, No. 1270, Dec. 11, 2012, 8 pages.

Taliun, D. et al., "Efficient haplotype block recognition of very long and dense genetic sequences", BMC Bioinformatics, vol. 15 (10), 2014, 1-18.

Tamura, et al., "Sibling Incest and formulation of paternity probability: case report", Legal Medicine, 2000, vol. 2, p. 189-196.

Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v. 144, No. 1, p. 35-39.

Tang, N. et al., "Detection of Fetal-Derived Paternally Inherited X-Chromosome Polymorphisms in Maternal Plasma", Clinical Chemistry, 45 (11), 1999, 2033-2035.

Tebbutt, S. J. et al., "Microarray genotyping resource to determine population stratification in genetic association studies of complex disease", BioTechniques, vol. 37, Dec. 2004, 977-985.

Ten Bosch, J. , "Keeping Up With the Next Generation Massively Parallel Sequencing in Clinical Diagnostics", Journal of Molecular Diagnostics, vol. 10, No. 6, 2008, 484-492.

Tewhey, R. et al., "Microdroplet-based PCR enrichment for large-scale targeted sequencing", Nature Biotechnology, vol. 27, No. 11, Nov. 2009, 1025-1031.

Tewhey, R. et al., "The importance of phase information for human genomics", Nature Reviews Genetics, vol. 12, No. 3, Mar. 1, 2011, 215-223.

Thavarajah, R. et al., "Chemical and physical basics of routine formaldehyde fixation", Journal of Oral and Maxillofacial Pathology, vol. 16, No. 3, 2012, 400-405.

(56) References Cited

OTHER PUBLICATIONS

The Bump Message Boards, The Bump (Panorama Test, attached), Jul. 1, 2013, 8 pages.
The International HapMap Consort, "The International HapMap Project", Nature, vol. 426, Dec. 18, 2003, 789-796.
Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.
Thornton, Brenda et al., "Real-time Pcr (qPCR) Primer Design Using Free Online Software", Biochemistry and Molecular Biology Education, vol. 39, 2011, pp. 145-154.
Tiersch, T. R. et al., "Reference Standards for Flow Cytometry and Application in Comparative Studies of Nuclear DNA Content", Cytometry, vol. 10, Mar. 21, 1989, 706-710.
Tong, et al., "Diagnostic Developments Involving Cell-free (Circulating) Nucleic Acids", Clinica Chimica Acta, vol. 363, No. (1-2), Aug. 26, 2005, 187-196.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Toshikazu, et al., "Estimation Of Haplotype Frequencies, Linkage-disequilibrium Measures, And Combination of Haplotype Copies in Each Pool By Use Of Pooled DNA Data", American Journal of Human Genetics, vol. 72, Jan. 17, 2003, 384-398.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.
Tounta, G. et al., "A Multiplex PCR for Non-invasive Fetal RHD Genotyping Using Cell-free Fetal DNA", in vivo, vol. 25, 2011, 411-418.
Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.
Troeger, C. et al., "Approximately Half of The Erythroblasts in Maternal Blood are of Fetal Origin", Molecular Human Reproduction, vol. 5, No. 12, Dec. 1, 1999, 1162-1165.
Troutt, et al., "Ligation-anchored PCR: A Simple Amplification Technique with Single-sided Specificity", Proceedings of the National Academy of Sciences, vol. 89, Oct. 1992, 9823-9825.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsang, Jason C. et al., "Circulating Nucleic Acids in Plasma/Serum", Pathology, vol. 39, No. 2, Apr. 1, 2007, 197-207.
Tsangaris, G. T. et al., "Proteomic analysis of amniotic fluid in pregnancies with Down syndrome", Proteomics, vol. 6, 2006, 4410-4419.
Tsui, N. B. et al., "Systematic micro-array based identification of placental mRNA in maternal plasma: towards non-invasive prenatal gene expression profiling", J. Med. Genet, vol. 41, 2004, 461-467.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.

Tu, J. et al., "Pair-barcode high-throughput sequencing for large-scale multiplexed sample analysis", BMC Genomics, vol. 13, No. 43, Jan. 25, 2012, 1-9.
Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.
Turner, E. et al., "Massively Parallel Exon Capture and Library-Free Resequencing Across 16 Genomes", Nature Methods, 6 (5), 2009, 315-316.
Tuzcu, et al., "Intravascular Ultrasound Evidence Of Angiographically Silent Progression In Coronary Atherosclerosis Predicts Long-term Morbidity And Mortality After Cardiac Transplantation", The American Journal of Cardiology, vol. 45, No. 9, May 3, 2005, 1538-1542.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell-free RNA from bodily fluids", Cancer Epidemiology, vol. 35, 2011, 580-589.
Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.
Urbaniak, S. J. et al., "RhD haemolytic disease of the fetus and the newborn", Blood Reviews, vol. 14, 2000, 44-61.
Urbanova, M. et al., "Circulating Nucleic Acids as a New Diagnostic Tool", Cellular & Molecular Biology Letters, vol. 15, 2010, 242-259.
Vallone, P. M. et al., "A multiplex allele-specific primer extension assay for forensically informative SNPs distributed throughout the mitochondrial genome", Int J Legal Medicine, vol. 118, Feb. 4, 2004, 147-157.
Vallone, Peter, "AutoDimer: a Screening Tool for Primer-Dimer and Hairpin Structures", Bio Techniques, 37, 2004, 226-231.
Vallone, Peter M. et al., "Demonstration of Rapid Multiplex PCR Amplification Involving 16 Genetic Loci", Forensic Science International: Genetics, vol. 3, 2008, pp. 42-45.
Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.
Van Uitert, I. et al., "The influence of different membrane components on the electrical stability of bilayer lipid membranes", Biochimica et Biophysica Acta, vol. 1798, 2010, 21-31.
Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.
Varley, Katherine Elena et al., "Nested Patch PCR Enables Highly Multiplexed Mutation Discovery in Candidate Genes", Genome Res., 18(11), 2008, 1844-1850.
Verlaan, et al., "Allele-specific Chromatin Remodeling in The ZPBP22/GSDMB/ORMDL3 Locus Associated with the Risk of Asthma And Autoimmune Disease", The American Journal of Human Genetics, vol. 85, No. 3, Sep. 11, 2009, 377-393.
Verlaan, et al., "Targeted Screening of Cis-Regulatory Variation in Human Haplotypes", Genome Research, vol. 19, No. 1, Jan. 1, 2009, 118-127.
Verlinsky, Y. et al., "Over a Decade of Experience with Preimplantation Genetic Diagnosis", Fertility and Sterility, 82 (2), 2004, 302-303.
Vlaminck, I. D. et al., "Circulating Cell-Free DNA Enables Non-invasive Diagnosis of Heart Transplant Rejection", Sci Transl Med., vol. 6, No. 241, Jun. 18, 2018, 26 pages.
Voelkerding, et al., "Next-generation Sequencing: From Basic Research To Diagnostics", Clinical Chemistry, vol. 55, No. 4, Apr. 1, 2009, 641-658.
Vogelstein, B. et al., "Digital PCR", Proc. Natl. Acad. Sci. USA, vol. 96, Aug. 1999, 9236-9241.
Von Ahsen, Nicolas et al., "Oligonucleotide Melting Temperatures under PCR Conditions: Nearest-Neighbor Corrections for Mg2+,

(56) References Cited

OTHER PUBLICATIONS

Deoxynucleotide Triphosphate, and Dimethyl Sulfoxide Concentrations with Comparison to Alternative Empirical Formulas", Clinical Chemistry, vol. 47, 2001, pp. 1956-1961.
Von Eggeling, F. et al., "Applications of Random PCR", Cellular and Molecular Biology, vol. 41, No. 5, 1995, 653-670.
Wagner, Jasenka et al., "Non-Invasive Prenatal Paternity Testing from Maternal Blood", Int. J. Legal Med., 123, 2009, 75-79.
Wang, D. G. et al., "Large-Scale Identification, Mapping, and Genotyping of Single-Nucleotide Polymorphisms in the Human Genome", Science, vol. 280, May 15, 1998, 1077-1082.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, J. et al., "Genome-wide Single-Cell Analysis of Recombination Activity and De Novo Mutation Rates in Human Sperm", Cell, vol. 150, Jul. 20, 2012, 402-412.
Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.
Wang, T.L. et al., "Digital karyotyping", PNAS, vol. 99, No. 25, Dec. 10, 2002, 16156-16161.
Wang, W.-P. et al., "Multiplex single nucleotide polymorphism genotyping by adapter ligation-mediated allele-specific amplification", Analytical Biochemistry, vol. 355, May 5, 2006, 240-248.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Wartell, Roger M. et al., "Thermal Denaturation of DNA Molecules: A Comparison of Theory with Experiment", Physics Reports, vol. 126, 1985, pp. 67-107.
Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Watt, Heather L. , "Sex Diagnosis of Preimplantation Porcine Embryos through PCR Amplification of The Sry Gene", Sex Diagnosis of Preimplantation Porcine Embryos Through PCR Amplification of the SRY Gene (1998) ("Watt (1998)"), 1998, 151 pages.
Wei, C. et al., "Detection and Quantification by Homogeneous PCR of Cell-free Fetal DNA in Maternal Plasma", Clinical Chemistry, vol. 47, No. 2, 2001, 336-338.
Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.
Weiss, C. A. , "Chapter 8: Confidence Intervals for One Population Mean", Introductory Statistics, Sixth Edition, 2002, 340-381.
Wellnhofer, et al., "Angiographic Assessment Of Cardiac Allograft Vasculopathy: Results Of A Consensus Conference Of The Task Force For Thoracic Organ Transplantation of the German Cardiac Society", Transplant International, vol. 23, No. 11, Aug. 19, 2010, 1094-1104.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
What To Expect Message Boards, What To Expect (Weird Harmony results), May 1, 2015, 7 pages.
Widlak, P. et al., "Cleavage Preferences of the Apoptotic Endonuclease DFF 40 (Caspase-activated DNase or Nuclease) on Naked DNA and Chromatin Substrates", The Journal of Biological Chemistry, vol. 275, No. 11, Mar. 17, 2000, 8228-8232.
Wiedmann, Ralph T. et al., "SNP Discovery in Swine by Reduced Representation and High Throughput Pyrosequencing", BMC Genetics, vol. 9, Article No. 81, Dec. 4, 2008, 1-7.
Wikipedia, "Buffy coat", Retrieved from "https://en.wikipedia.orgJw/index.php?title=Buffy_coat&oldid=900992886", Jun. 9, 2019, 2 pgs.
Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.
Wikipedia, "Stimulant", 17 pages.
Wilkening, Stefan et al., "Determination of Allele Frequency In Pooled DNA: Comparison of Three PCR-based Methods", Bio Techniques, vol. 39, No. 6, May 30, 2005, 853-857.
Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Winsor, E. J. et al., "Maternal Cell Contamination in Uncultured Amniotic Fluid", Prenatal Diagnosis, vol. 16, 1996, 49-54.
Witherspoon, David J. et al., "Mobile Element Scanning (Me-scan) by Targeted High-throughput Sequencing", BMC Genomics, vol. 410, 2010, 15 pages.
Wittwer, C. T. et al., "Real-Time Multiplex PCR Assays", Methods, vol. 25, 2001, 430-448.
Wong, K. H. et al., "Multiplex Illumina Sequencing Using DNA Barcoding", Current Protocols in Molecular Biology, vol. 101, Jan. 2013, 7.11.1-7.11.11.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wright, Caroline et al., "Cell-free Fetal Nucleic Acids for Noninvasive Prenatal Diagnosis", PHG Foundation, Jan. 1, 2009, 1-64.
Wu, T.L. et al., "Cell-free DNA: measurement in various carcinomas and establishment of normal reference range", Clinica Chimica Acta, vol. 321, 2002, 77-87.
Wu, Y. Y. et al., "Rapid and/or high-throughput genotyping for human red blood cell, platelet and leukocyte antigens, and forensic applications", Clinica Chimica Acta, vol. 363, 2006, 165-176.

(56) References Cited

OTHER PUBLICATIONS

Xia, et al., "Simultaneous Quantitative Assessment Of Circulating Cell-free Mitochondrial And Nuclear DNA By Multiplex Real-time PCR", Genetics and Molecular Biology, vol. 32, No. 1, Mar. 1, 2009, 20-24.

Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.

Xian, et al., "Advances On Circulating Fetal DNA In Maternal Plasma", Chinese Medical Journal, vol. 120, No. 14, Jul. 2, 2007, 1256-1259.

Xie, et al., "CNV-SEQ, A New Method to Detect Copy Number Variation Using Highthroughput Sequencing", BMC Bioinformatics, vol. 10:80, Mar. 6, 2009, 1-9.

Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.

Xu, S. et al., "Circulating tumor DNA identified by targeted sequencing in advanced-stage non-small cell lung cancer patients", Cancer Letters, vol. 370, 2016, 324-331.

Xu, W. et al., "A Novel Universal Primer-Multiplex-PCR Method with Sequencing Gel Electrophoresis Analysis", PLOS One, vol. 7, No. 1, Jan. 17, 2012, 10 pgs.

Xue, et al., "Optimizing The Yield And Utility Of Circulating Cell-free DNA From Plasma And Serum", Clinica Chimica Acta, vol. 404, No. 2, Jun. 27, 2009, 100-104.

Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.

Yamada, T. et al., "PrimerStation: a highly specific multiplex genomic PCR primer design server for the human genome", Nucleic Acids Research, vol. 34, 2006, W665-W669.

Yang, Lin et al., "64-MDCT Coronary Angiography of Patients With Atrial Fibrillation: Influence of Heart Rate On Image Quality and Efficacy In Evalution of Coronary Artery Disease", AJR, vol. 193, No. 3, Sep. 1, 2009, 795-801.

Yaron, Y. , "The implications of non-invasive prenatal testing failures: a review of an under-discussed phenomenon", Prenatal Diagnosis, vol. 36, 2016, 391-396.

Yeh, Iwei et al., "Knowledge Acquisition, Consistency Checking and Concurrency Control for Gene Ontology (GO)", Bioinformatics, 19, 2, 2003, 241-248.

Yijen, et al., "Noninvasive Evaluation Of Cardiac Allograft Rejection By Cellular And Functional Cardiac Magnetic Resonance", JACC: Cardiovacular Imaging, vol. 2, No. 6, Jun. 1, 2009, 731-741.

Yilmaz, A. et al., "Comparative Evaluation of Left and Right Ventricular Endomyocardial Biopsy", Circulation, vol. 122, No. 9, Aug. 31, 2010, 900-909.

You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.

Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.

Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.

Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.

Zachariah, R. et al., "Circulating cell-free DNA as a potential biomarker for minimal and mild endometriosis", Reproductive BioMedicine Online, vol. 18, No. 3, Jan. 27, 2009, 4007-411.

Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.

Zhang, et al., "Use Of PCR And PCR-SSP For Detection Of Urinary Donor-Origin Dna In Renal Transplant Recipients With Acute Rejection", Chinese Medical Journal, vol. 116, No. 2, Feb. 2003, 191-194.

Zhang, J. et al., "Presence of Donor-and Recipient-derived DNA in Cell-free Urine Samples of Renal Transplantation Recipients: Urinary DNA Chimerism", Clinical Chemistry, vol. 45, No. 10, 1999, 1741-1746.

Zhang, Kun et al., "Digital RNA Alleotyping Reveals Tissue-specific and Allele-specific Gene Expression in Human", Nature Methods, vol. 6, No. 8, Jul. 20, 2009, 613-618.

Zhang, L. et al., "Whole genome amplification from a single cell: Implications for genetic analysis", Proc. Nat'l. Acad. Sci. USA, vol. 89, Jul. 1992, 5847-5851.

Zhang, Rui et al., "Quantifying RNA allelic ratios by microfluidic multiplex PCR and sequencing", Nature Methods, 11(1), 2014, 51-56.

Zhao, et al., "Urinary Thromboxane B2 In Cardiac Transplant Patients As A Screening Method Of Rejection", Prostaglandins, vol. 54, No. 6, Dec. 1, 1997, 881-889.

Zhao, Xiaojun. et al., "An Integrated View of Copy Number and Allelic Alterations in the Cancer Genome Using Single Nucleotide Polymorphism Arrays", Cancer Research, 64, 2004, 3060-3071.

Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.

Zheng, Z et al., "Anchored Multiplex PCR for Targeted Next-generation Sequencing", Nature Medicine, vol. 20, No. 12, Dec. 2014, 1479-1486.

Zhong, X Y. et al., "Detection of Fetal Rhesus D And Sex Using Fetal DNA from Maternal Plasma by Multiplex Polymerase Chain Reaction", British Journal of Obstetrics and Gynaecology, vol. 107, Jun. 2000, 766-769.

Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.

Zhong, Xiao Y. et al., "Cell-free DNA In Urine: A Marker for Kidney Graft Rejection, but Not for Prenatal Diagnosis?", Annals of the New York Academy of Sciences, vol. 945, Sep. 1, 2001, 250-257.

Zhou, et al., "Pyrosequencing, A High-throughput Method For Detecting Single Nucleotide Polymorphisms In The Dihydrofolate Reductase And Dihydropteroate Synthetase Genes Of Plasmodiym Falciparum", Journal of Clinical Microbiology, vol. 44, No. 11, Nov. 1, 2006, 3900-3910.

Zhou, W. et al., "Counting Alleles Reveals a Connection Between Chromosome 18q Loss and Vascular Invasion", Nature Biotechnology, 19, 2001, 78-81.

Zhou, W. et al., "Counting alleles to predict recurrence of early-stage colorectal cancers", The Lancet, vol. 359, Jan. 19, 2002, 219-225.

Zimmer, et al., "Transplant Coronary Artery Disease", JACC: Cardiovascular Interventions, vol. 3, No. 4, Apr. 1, 2010, 367-377.

Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.

Zimmermann, B. , "Declaration Under 37 CFR 1.32", filed in U.S. Appl. No. 14/171,587, filed Feb. 3, 2014, 4 pgs.

Zimmermann, B. et al., "Digital PCR: a powerful new tool for noninvasive prenatal diagnosis?", Prenatal Diagnosis, vol. 28, Nov. 10, 2008, 1087-1093.

Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.

Zimmermann, B. et al., "Novel Real-Time Quantitative PCR Test for Trisomy 21", Clinical Chemistry, vol. 48, No. 2, 2002, 362-363.

(56) References Cited

OTHER PUBLICATIONS

Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Zlotogora, J., "Penetrance and expressivity in the molecular age", Genetics in Medicine, vol. 5, No. 5, 2003, 347-352.
Bau, Stephan, et al., "Targeted next-generation sequencing by specific capture of multiple genomic loci using low-volume microfluidic DNA arrays", Anal Bioanal Chem, 2009, 171-175.
Anman, et al., "Analytical and Clinical Validation of a Digital Sequencing Panel for Quantitative, Highly Accurate Evaluation of Cell-Free Circulating Tumor DNA", PLOS ONE, 2015, 1-27.
Lee, et al., "ERBB2 kinase domain mutation in the lung squamous cell carcinoma", Cancer Letters, 2006, 89-94.
Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.
Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.
Goessl, C. et al., "DNA Alterations in Body Fluids as Molecular Tumor Markers for Urological Malignancies", European Urology, vol. 41, 2002, 668-676.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1.
Vargas, D. Y. et al., "Multiplex Real-Time PCR Assays that Measure the Abundance of Extremely Rare Mutations Associated with Cancer", PLOS One, vol. 11, No. 5, May 31, 2016, 26 pgs.
Wong, I. H. et al., "Quantitative Analysis of Tumor-derived Methylated p16INK4a Sequences in Plasma, Serum, and Blood Cells of Hepatocellular Carcinoma Patients", Clinical Cancer Research, vol. 9, Mar. 2003, 1047-1052.
18820195.8, "Extended European Search Report", mailed Jan. 27, 2021, 9 pages.
18821381.3, "Extended European Search Report", mailed Feb. 15, 2021, 9 pages.
Adamek, Martina et al., "A fast and simple method for detecting and quantifying donor-derived cell-free DNA in sera of solid organ transplant recipients as a biomarker for graft function", Clinical Chemistry and Laboratory Medicine: Journal of the Forum of the European Societies of Clinical Chemistry, vol. 54, No. 7, doi:10.1515/CCLM-2015-0622, ISSN 1437-4331, (Jul. 1, 2016), pp. 1147-1155.
Agbor-Enoh, et al., "Applying rigor and reproducibility standards to assay donor-derived cell-free DNA as a non-invasive method for detection of acute rejection and graft injury after heart transplantation", J Heart Lung Transplant, 36(9):1004-1012. doi: 10.1016/j.healun.2017.05.026. Epub May 20, 2017., 17 pages.
Agbor-Enoh, et al., "Cell-Free DNA to Detect Heart Allograft Acute Rejection", Circulation, Mar. 23, 2021;143(12): doi: 10.1161/CIRCULATIONAHA.120.049098. Epub Jan. 13, 2021, 1184-1197.
Ahmadian, A. et al., "Analysis of the p53 Tumor Suppressor Gene by Pyrosequencing", BioTechniques, vol. 28, Jan. 2000, 140-147.
Ahmed, et al., "Cell Free DNA and Procalcitonin as Early Markers of Complications in ICU Patients with Multiple Trauma and Major Surgery", Clin Lab, Dec. 1, 2016;62(12); doi: 10.7754/Clin.Lab.2016.160615., 2395-2404.

Alachkar, "Serum and urinary biomarkers in acute kidney transplant rejection", Nephrol Ther., Feb. 2012;8(1): doi: 10.1016/j.nephro.2011.07.409. Epub Oct. 21, 2011, 13-19.
Almeida, et al., "Evaluation of 16 SNPs allele-specific to quantify post hSCT chimerism by SYBR green-based qRT-PCR", J Clin Pathol., Mar. 2013;66(3):. doi: 10.1136/jclinpath-2012-201224. Epub Jan. 2, 2013., 238-242.
Andargie, et al., "Cell-free DNA maps COVID-19 tissue injury and risk of death and can cause tissue injury", JCI Insight, Apr. 8, 2021;6(7):e147610. doi: 10.1172/jci.insight.147610, 20 pages.
Arshad, et al., "Elevated Cell-Free Mitochondrial DNA in Filtered Plasma Is Associated with HIV Infection and Inflammation", J Acquir Immune Defic Syndr., May 1, 2018;78(1): doi: 10.1097/QAI.0000000000001650., 111-118.
Avanzini, Stefano et al., "A mathematical model of ctDNA shedding predicts tumor detection size", Science Advances, vol. 6, Issue eabc4308, Dec. 11, 2020, 9 pages.
Avriel, et al., "Admission Cell Free DNA Levels Predict 28-Day Mortality in Patients with Severe Sepsis in Intensive Care", PLoS One., Jun. 23, 2014;9(6):e100514. doi: 10.1371/journal.pone.0100514. eCollection 2014., 7 pages.
Ayyadevara, et al., "Discrimination of primer 3'-nucleotide mismatch by taq DNA polymerase during polymerase chain reaction", Anal Biochem. Aug. 15, 2000, 284(1), 11-18.
Bai, et al., "Detection and quantification of heteroplasmic mutant mitochondrial DNA by real-time amplification refractory mutation system quantitative PCR analysis: a single-step approach", Clin Chem., Jun. 2004; 50(6); Epub Apr. 8, 2004., 996-1001.
Benesova, et al., "Mutation-based detection and monitoring of cell-free tumor DNA in peripheral blood of cancer patients", Analytical Biochemistry, vol. 433, 2013, 227-234.
Benn, Peter et al., "Current Controversies in Prenatal Diagnosis 2: NIPT results suggesting maternal cancer should always be disclosed", Prenetal Diagnosis, vol. 39, No. 5, 2018, 339-343.
Bergallo, et al., "A novel TaqMAMA assay for allelic discrimination of TLR9 rs352140 polymorphism", J Virol Methods, May 2017;243. doi: 10.1016/j.jviromet.2017.01.015. Epub Jan. 28, 2017., 25-30.
Bergallo, et al., "Evaluation of IFN-γ polymorphism+874 T/A in patients with recurrent tonsillitis by PCR real time mismatch amplification mutation assay (MAMA real time PCR)", Cytokine., Feb. 2015; 71(2): Epub Dec. 2014., 278-282.
Bewersdorf, Jan Philipp et al., "From clonal hematopoiesis to myeloid leukemia and what happens in between: Will improved understanding lead to new therapeutic and preventive opportunities?", Blood Reviews, vol. 37, 2019, 6.
Bezieau, et al., "High incidence of N and K-Ras activating mutations in multiple myeloma and primary plasma cell leukemia at diagnosis", Hum Mutat., Sep. 2001;18(3):. doi: 10.1002/humu.1177, 212-224.
Bianchi, Diana W. et al., "Noninvasive Prenatal Testing and Incidental Detection of Occult Maternal Malignancies", Jama the Journal of the American Medical Association, vol. 314, No. 2, 2015, 162.
Bienkowski, et al., "Liquid biopsy for minimally invasive heart transplant monitoring: a pilot study", J Clin Pathol., Aug. 2020;73(8): doi: 10.1136/jclinpath-2019-205926. Epub Dec. 5, 2019., 507-510.
Birkenkamp-Demtroder, et al., "Longitudinal assessment of multiplex patient-specific ctDNA biomarkers in bladder cancer for diagnosis, surveillance and recurrence", Annals of Oncology, Oxford University Press NLD, vol. 29, No. Supplement 8, 2018, viii26.
Blomquist, et al., "Targeted RNA-Sequencing with Competitive Multiplex-PCR Amplicon Libraries", PLOS ONE, 2013, vol. 8, Issue 11.
Board, et al., "Detection of PIK3CA mutations in circulating free DNA in patients with breast cancer", Breast Cancer Res Treat, Apr. 2010;120(2): doi: 10.1007/s10549-010-0747-9. Epub Jan. 28, 2010, 461-467.
Board, et al., "Multiplexed assays for detection of mutations in PIK3CA", Clin Chem., Apr. 2008; 54(4), 757-760.
Bolotin, D. A. et al., "MIXCR: software for comprehensive adaptive immunity profiling", Nature, vol. 12, No. 5, May 2015, 380-381.

(56) References Cited

OTHER PUBLICATIONS

Braun, et al., "Limitation of Circulating cfDNA Under the Use of a Cytokine Elimination Adsorber (CytoSorb) in Cardiac Surgery", The Thoracic and Cardiovascular Surgeon, Jan. 2018; 66(S01): S1-S110, 1 page.
Brochet, X. et al., "IMGT/V-QUEST: the highly customized and integrated system for IG and TR standardized V-J and V-D-J sequence analysis", Nucleic Acids Research, vol. 36, May 23, 2008, W503-W508.
Bronkhorst, et al., "The emerging role of cell-free DNA as a molecular marker for cancer management", Biomol Detect Quantif, Mar. 18, 2019;17:100087. doi: 10.1016/j.bdq.2019.100087., 23 pages.
Bunnapradist, S. et al., "Using both the fraction and Quantity of Donor-Derived Cell-free DNA to Detect Kidney Allograft Rejection", JASN, vol. 32, 2021, 2439-2441.
Burgstaller, et al., "Mitochondrial DNA heteroplasmy in ovine fetuses and sheep cloned by somatic cell nuclear transfer", BMC Dev Biol., Dec. 21, 2007;7:141, 10 pages.
Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.
Cabel, et al., "Circulating tumor DNA changes for early monitoring of anti-PD1 immunotherapy: a proof-of-concept study", Ann Oncol., Aug. 1, 2017;28(8); doi: 10.1093/annonc/mdx212., 1996-2001.
Cagliani, et al., "Deoxyribonuclease Reduces Tissue Injury and Improves Survival After Hemorrhagic Shock", J Surg Res., May 2020;249: doi: 10.1016/j.jss.2019.11.036. Epub Jan. 8, 2020., 104-113.
Castells, et al., "K-ras mutations in DNA extracted from the plasma of patients with pancreatic carcinoma: diagnostic utility and prognostic significance", J Clin Oncol., Feb. 1999;17(2): doi: 10.1200/JCO.1999.17.2.578., 578-584.
Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, S139.
Cawkwell, L. et al., "Rapid detection of allele loss in colorectal tumours using microsatellites and fluorescent DNA technology", Br. J. Cancer, vol. 67, 1993, 1262-1267.
Chan, et al., "Bioinformatics analysis of circulating cell-free DNA sequencing data", Clin Biochem., Oct. 2015;48(15); doi: 10.1016/j.clinbiochem.2015.04.022. Epub May 9, 2015., 962-975.
Chan, Allen et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry, 2013, 211-224.
Chan, Allen, "Scanning for Cancer Genomic Changes in Plasma: Toward an Era of Personalized Blood-Based Tumor Markers", Clinical Chemistry, 2013, 1553-1555.
Chang, et al., "Identification of individual DNA molecule of Mycobacterium tuberculosis by nested PCR-RLFP and capillary electrophoresis", National Library of Medicine, 2008, 182-8.
Chen, et al., "Non-invasive prenatal diagnosis using fetal DNA in maternal plasma: a preliminary study for identification of paternally-inherited alleles using single nucleotide polymorphisms", BMJ Open, Jul. 22, 2015;5(7):e007648. doi: 10.1136/bmjopen-2015-007648., 8 pages.
Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.
Chen, KE et al., "Multiplex PCR with the Blunt Hairpin Primers for Next Generation Sequencing", Biotechnology and Bioprocess Engineering, vol. 22, 2017, 347-351.
Chen, Kevin et al., "Commercial ctDNA Assays for Minimal Residual Disease Detection of Solid Tumors", Molecular Diagnosis & Therapy, vol. 25, Issue 6, Nov. 1, 2021, 757-774.
Cheng, et al., "Cell-Free DNA in Blood Reveals Significant Cell, Tissue and Organ Specific injury and Predicts COVID-19 Severity", medRxiv., Jul. 29, 2020;2020.07.27.20163188. doi: 10.1101/2020.07.27.20163188., 16 pages.
Chiu, et al., "Effects of blood-processing protocols on fetal and total DNA quantification in maternal plasma", Clin Chem., Sep. 2001;47(9): PubMed PMID: 11514393., 1607-1613.
Chiu, et al., "Noninvasive prenatal exclusion of congenital adrenal hyperplasia by maternal plasma analysis: a feasibility study", Clin Chem., May 2002;48(5), 778-780.
Chothia, C et al., "Canonical structures for the hypervariable regions of immunoglobulins", Journal of Molecular Biology, vol. 196, No. 4, Aug. 20, 1987, 901-917.
Chu, et al., "A novel approach toward the challenge of accurately quantifying fetal DNA in maternal plasma", Prenat Diagn., Dec. 2010;30(12-13): doi: 10.1002/pd.2656, 1226-1229.
Chun, et al., "Dual priming oligonucleotide system for the multiplex detection of respiratory viruses and SNP genotyping of CYP2C19 gene", Nucleic Acids Research, vol. 35, No. 6, 2007, 1-6.
Chung, et al., "Cell-free DNA fetal fraction and pregnancy outcome", American Journal of Obstetrics & Gynecology, vol. 222, No. 1, 2019, S157.
Clementi, et al., "The Role of Cell-Free Plasma DNA in Critically Ill Patients with Sepsis", Blood Purif., 2016;41(1-3): doi: 10.1159/000440975. Epub Oct. 20, 2015, 34-40.
Coombs, Catherine et al., "Therapy-Related Clonal Hematopoiesis in Patients with Non-hematologic Cancers Is Common and Associated with Adverse Clinical Outcomes", Cell Stem Cell, vol. 21, No. 3, 2017, 374.
Costa, J.-M. et al., "Fetal RHD genotyping in maternal serum during the first trimester of pregnancy", British Journal of Haematology, vol. 119, 2002, 255-260.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Daly, "Circulating donor-derived cell-free DNA: a true biomarker for cardiac allograft rejection?", Ann Transl Med., Mar. 2015;3(4):47. doi:10.3978/j.issn.2305-5839.2015.01.35, 6 pages.
Dandel, et al., "Non-invasive cardiac allograft rejection surveillance: reliability and clinical value for prevention of heart failure", Heart Fail Rev., Mar. 2021;26(2): doi: 10.1007/s10741-020-10023-3. Epub Sep. 5, 2020., 319-336.
Daniels, G. et al., "Fetal blood group genotyping from DNA from maternal plasma: an important advance in the management and prevention of haemolytic disease of the fetus and newborn", Vox Sanguinis, vol. 87, 2004, 223-232.
Dastsooz, et al., "Multiplex ARMS PCR to Detect 8 Common Mutations of ATP7B Gene in Patients With Wilson Disease", Hepat Mon., May 16, 2013;13(5):e8375. doi: 10.5812/hepatmon.8375. eCollection 2013., 7 pages.
De Vlaminck, et al., "Circulating cell-free DNA enables noninvasive diagnosis of heart transplant rejection", Sci Transl Med., Jun. 18, 2014;6(241):241ra77. doi: 10.1126/scitranslmed.3007803, 20 pages.
De Vlaminck, et al., "Circulating cell-free DNA enables noninvasive diagnosis of heart transplant rejection", Sci Transl Med., Jun. 18, 2014;6(241):241ra77. Supplemental Materials., 6 pages.
De Vlaminck, et al., "Noninvasive monitoring of infection and rejection after lung transplantation", Proc Natl Acad Sci U S A, Oct. 27, 2015;112(43): doi: 10.1073/pnas.1517494112. Epub Oct. 12, 2015., 13336-13341.
Delgado, et al., "Characterization of cell-free circulating DNA in plasma in patients with prostate cancer", Tumour Biol., Apr. 2013;34(2): doi: 10.1007/s13277-012-0634-6. Epub Dec. 27, 2012, 983-986.
Deshpande, et al., "Relationship Between Donor Fraction Cell-Free DNA and Treatment for Rejection in Heart Transplantation", Pediatric Transplantation, Jun. 2022; 26(4):e14264. https://doi.org/10.1111/petr.14264, 11 pages.
Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.

(56) References Cited

OTHER PUBLICATIONS

Dey, et al., "A plasma telomeric cell-free DNA level in unaffected women with BRCA1 or/and BRCA2 mutations: a pilot study. Oncotarget", Oncotarget, Dec. 29, 2017;9(3): doi: 10.18632/oncotarget. 23767.eCollection Jan. 9, 2018., 4214-4222.

Dharajiya, Nilesh et al., "Incidental Detection of Maternal Neoplasia in Noninvasive Prenatal Testing", Clinical Chemistry, vol. 64, No. 2, 2018, 329-335.

Diaz, et al., "Liquid Biopsies: Genotyping Circulating Tumor Dna", Journal of Clinical Oncology, vol. 32, No. 6, 2014, 579-586.

Diehl, et al., "Detection and quantification of mutations in the plasma of patients with colorectal tumors", Proceedings of the National Academy of Sciences, vol. 102, 2005, 16368-16373.

Ding, et al., "New Progress in Plasma Cell-free DNA in Clinical Applications", Progress in Modern Biomedicine, 2016; 18: 3476, 3593-3596.

Dwivedi, et al., "Prognostic utility and characterization of cell-free DNA in patients with severe sepsis", Crit Care, Aug. 13, 2012;16(4):R151. doi: 10.1186/cc11466., 11 pages.

Ehlayel, A. et al., "Emerging monitoring technologies in kidney transplantation", Pediatric Nephrology, vol. 36, 2021, 3077-3087.

Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.

Fire, et al., "Rolling replication of short DNA circles", PNAS, 1995, 4641-4645.

Fleischhacker, et al., "Circulating nucleic acids (CNAs) and cancer—a survey", Biochim Biophys Acta, Jan. 2007;1775(1): doi: 10.1016/j.bbcan.2006.10.001. Epub Oct. 7, 2006., 181-232.

García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 1958-1966.

Garnacho-Montero, et al., "Prognostic and diagnostic value of eosinopenia, C-reactive protein, procalcitonin, and circulating cell-free DNA in critically ill patients admitted with suspicion of sepsis", Crit Care, Jun. 5, 2014;18(3):R116. doi: 10.1186/cc13908, 9 pages.

Ge, et al., "Haplotype block: a new type of forensic DNA markers", Int J Legal Med, 2010, 353-361.

Ghanta, et al., "Non-invasive prenatal detection of trisomy 21using tandem single nucleotide polymorphisms", PLoS One, Oct. 8, 2010;5(10):e13184. doi: 10.1371/journal.pone.0013184, 10 pages.

Gielis, et al., "Cell-Free DNA: An Upcoming Biomarker in Transplantation", Am J Transplant, Oct. 2015;15(10): doi: 10.1111/ajt. 13387. Epub Jul. 16, 2015, 2541-2551.

Gielis, et al., "Plasma donor-derived cell-free DNA kinetics after kidney transplantation using a single tube multiplex PCR assay", PLoS One, 2018; 13(12): e0208207, 16 pages.

Giulio, Genovese et al., "Hematopoiesis and Blood-Cancer Risk Inferred from Blood DNA Sequence", The New England Journal of Medicine, vol. 371, No. 26, 2014, 2477-2487.

Glaab, et al., "A novel assay for allelic discrimination that combines the fluorogenic 5' nuclease polymerase chain reaction (TaqMan) and mismatch amplification mutation assay", Mutat Res., Nov. 29, 1999;430(1), 1-12.

Glaab, W. E. et al., "A novel assay for allelic discrimination that combines the fluorogenic 5' nuclease polymerase chain reaction (TaqMan) and mismatch amplification mutation assay", Mutation Research, vol. 430, 1999, 12 pgs.

Gordon, et al., "An Algorithm Measuring Donor Cell-Free DNA in Plasma of Cellular and Solid Organ Transplant Recipients That Does Not Require Donor or Recipient Genotyping", Front Cardiovasc Med., Sep. 22, 2016;3:33. eCollection 2016., 10 pages.

Gordon, Paul et al., "An Algorithm Measuring Donor Cell-Free DNA in Plasma of Cellular and Solid Organ Transplant Recipients That Does Not Require Donor or Recipient Genotyping", Frontiers in Cardiovascular Medicine, 2016, vol. 3.

Gormally, et al., "Amount of DNA in plasma and cancer risk: a prospective study", Int J Cancer, Sep. 20, 2004;111(5): doi: 10.1002/ijc.20327, 746-749.

Gotoh, et al., "Prediction of MYCN amplification in neuroblastoma using serum DNA and real-time quantitative polymerase chain reaction", J Clin Oncol., Aug. 1, 2005;23(22): PubMed PMID: 16051962., 5205-5210.

Grenda, R., "Torque teno (TTV) viral load as a biomarker of immunosuppressive strength after kidney transplantation in children", Pediatric Nephrology, vol. 36, May 27, 2020, 3 pages.

Gripp, et al., "*Homo sapiens* KRAS proto-oncogene, GTPase (KRAS), RefSeqGene (LRG_344) on chromosome 12", GenBank Submission; Accession No. NG_007524, version NG_007524.2, Aug. 16, 2020., 16 Pages.

Grskovic, et al., "Validation of a Clinical-Grade Assay to Measure Donor-Derived Cell-Free DNA in Solid Organ Transplant Recipients", J Mol Diagn., Nov. 2016;18(6): doi: 10.1016/j.jmoldx.2016. 07.003. Epub 2016, 890-902.

Guedj, et al., "A refined molecular taxonomy of breast cancer", Oncogene, Mar. 1, 2012;31(9):1196-206. doi: 10.1038/onc.2011. 301. Epub Jul. 25, 2011., 34 pages.

Gusella, J. et al., "Precise localization of human B-globin gene complex on chromosome 11*", Proc. Natl. Acad. Sci USA, vol. 76, No. 10, Oct. 1979, 5239-5243.

Hainer & Fazzio, "High-Resolution Chromatin Profiling Using Cut&Run", Current Protocols in Molecular Biology, 2019, 1-22.

Hasi, et al., "Acetaldehyde dehydrogenase 2 SNP rs671 and susceptibility to essential hypertension in Mongolians: a case control study", Genet Mol Res., Mar. 29, 2011;10(1). doi: 10.4238/vol10-1gmr1056., 537-543.

Hidestrand, et al., "Highly sensitive noninvasive cardiac transplant rejection monitoring using targeted quantification of donor-specific cell-free deoxyribonucleic acid", J Am Coll Cardiol., Apr. 1, 2014;63(12). doi:10.1016/j.jacc.2013.09.029. Epub Oct. 16, 2013., 1224-1226.

Hidestrand, et al., "Highly Sensitive Transplant Rejection Surveillance Using Targeted Detection of Donor Specific Cell Free DNA", J Heart Lung Transplant, Apr. 2012; 31(4), S91-S92.

Hidestrand, et al., "Influence of temperature during transportation on cellfree DNA analysis", Fetal Diagn Ther., 2012; 31, 122-128.

Hidestrand, et al., "Quantification of Circulating Donor Specific Cell Free DNA Is an Exquisitely Sensitive Non-Invasive Indicator of Injury to the Donor Heart", J Heart Lung Transplant, 2013; 32, S101-S102.

Hiendleder, et al., "Functional genomics: tools for improving farm animal health and welfare", Rev. Sci. Tech. Off. Int. Epiz., 24 (1), 2005, 354-377.

Hoerning, et al., "Quantitative real-time ARMS-qPCR for mitochondrial DNA enables accurate detection of microchimerism in renal transplant recipients", Pediatr Transplant, Dec. 2011;15(8). doi: 10.1111/j.1399-3046.2011.01581.x. Epub Oct. 4, 2011, 809-818.

Hou, et al., "Application of tetra primer ARMS-PCR approach for detection of Fusarium graminearum genotypes with resistance to carbendazim", Australian Plant Pathology, Jan. 1, 2013; 42(1), 73-78.

Huang, et al., "Circulating cell-free DNA levels correlate with postresuscitation survival rates in out-of-hospital cardiac arrest patients", Resuscitation, Feb. 2012;83(2): doi: 10.1016/j.resuscitation. 2011.07.039. Epub Aug. 22, 2011., 213-218.

Huang, et al., "*Homo sapiens* TSC complex subunit 1 (TSC1), RefSeqGene (LRG_486) on chromosome 9", GenBank Submission; Accession No. NG_012386, version NG_012386.1, Sep. 21, 2020, 20 Pages.

Hudecova, "Digital PCR analysis of circulating nucleic acids", Clin Biochem., Oct. 2015;48(15): doi: 10.1016/j.clinbiochem.2015.03. 015. Epub Mar. 28, 2015, 948-956.

Hugon, et al., "Influence of intention to adhere, beliefs and satisfaction about medicines on adherence in solid organ transplant recipients", Transplantation., Jul. 27, 2014;98(2): doi: 10.1097/TP. 0000000000000221, 222-228.

Illumina, "HumanOmni1-Quad BeadChip", Illumina DNA Analysis, Pub. No. 370-21009-007, 2009, 1 page.

Illumina, "HumanOmni2.5-8 BeadChips: Next-Generation GWAS Content for Genotyping and CNV Analysis", Data Sheet: DNA Analysis, Pub. No. 370-2011-008, 2011, 1 page.

Illumina, "Illumina Adapter Sequences", Published by Illumina, 2018, 1-45.

(56) References Cited

OTHER PUBLICATIONS

Jaiswal, Siddhartha et al., "Clonal hematopoiesis in human aging and disease", Science, vol. 366, No. 6465, 2019, 4.

Ji, Xing et al., "Copy number variation profile in noninvasive prenatal testing (NIPT) can identify co-existing maternal malignancies: Case reports and a literature review", Taiwanese Journal of Obstetrics and Gynecology, vol. 57, No. 6, 2018, 871-877.

Jing, et al., "Cell-free DNA: characteristics, detection and its applications in myocardial infarction", Curr Pharm Des., 2013;19(28): doi: 10.2174/1381612811319280012., 5135-5145.

Jordan, et al., "Donor-derived Cell-free DNA Identifies Antibody-mediated Rejection in Donor Specific Antibody Positive Kidney Transplant Recipients", Transplant Direct, 2018;4(9):e379, 5 pages.

Jordens, et al., "Amplification with molecular beacon primers and reverse line blotting for the detection and typing of human papillomaviruses", Journal of Virological Methods, vol. 89, 2000, 29-37.

Jung, et al., "Cell-free DNA in the blood as a solid tumor biomarker—a critical appraisal of the literature", Clin Chim Acta., Nov. 11, 2010;411(21-22): doi: 10.1016/j.cca.2010.07.032. Epub Aug. 2, 2010., 1611-1624.

Jung, Klaus et al., "Increased cell-free DNA in plasma of patients with metastatic spread in prostate cancer", Cancer Letters, 2004, 173-180.

Kaboev, et al., "PCR hot start using primers with the structure of molecular beacons (hairpin-like structure)", Nucleic Acids Research, vol. 28, 2000, 1-2.

Kane, et al., "Application of less primer method to PCR", DNA Polymorphism, 2004, vol. 13, pp. 34-37.

Karapetis, et al., "K-ras mutations and benefit from cetuximab in advanced colorectal cancer", N Engl J Med., Oct. 23, 2008;359(17). doi: 10.1056/NEJMoa0804385., 1757-1765.

Keshavjee, S. H. et al., "The role of dextran 40 and potassium in extended hypothermic lung preservation for transplantation", The Journal of Thoracic and Cardiovascular Surgery, vol. 103, No. 2, 1992.

Khater & Khauli, "Pseudorejection and true rejection after kidney transplantation: classification and clinical significance", Urol Int., 90(4), 2012, 373-80.

Khush, et al., "Circulating cell-free DNA as a non-invasive marker of pediatric heart transplant rejection and immunosuppressive treatment", J Heart Lung Transplantation, Apr. 2016. 35(4):Abstract 181, S75.

Khush, et al., "Noninvasive detection of graft injury after heart transplant using donorderived cellfree DNA: A prospective multi-center study", Am J Transplant, Oct. 2019;19(10): doi: 10.1111/ajt.15339. Epub Apr. 8, 2019., 2889-2899.

Kim, et al., "Personalized therapy on the horizon for squamous cell carcinoma of the lung", Lung Cancer, vol. 80, 2013, 249-255.

Kindel, et al., "Early Changes in Donor Fraction Cell-free DNA in Newly Transplanted Heart Transplant Patients", ISHLT DF cfDNA declanation poster, 2018, 1 Page.

Kirkizlar, et al., "Detection of Clonal and Subclonal Copy-Number Variants in Cell-Free DNA from Patients with Breast Cancer Using a Massively Multiplexed PCR Methodology", Transl Oncol., Oct. 2015;8(5): doi: 10.1016/j.tranon.2015.08.004., 407-416.

Kirsch-Gerweck, et al., "HaploBlocks: Efficient Detection of Positive Selection in Large Population Genomic Datasets", Mol. Biol. Evol., 2023.

Kittler, R. et al., "A Whole Genome Amplification Method to Generate Long Fragments from Low Quantities of Genomic DNA", Analytical Biochemistry, vol. 300, 2002, 237-244.

Kiyomi, Morita et al., "Clearance of Somatic Mutations at Remission and the Risk of Relapse in Acute Myeloid Leukemia", J Clin Oncol, vol. 36, No. 18, 2018, 1788-1797.

Koeppe, et al., "HIV-1-Specific CD4+ T-Cell Responses Are Not Associated with Significant Viral Epitope Variation in Persons With Persistent Plasma Viremia", J Acquir Immune Defic Syndr, 2006, 41:140-148.

Krishnakumar, S. et al., "A comprehensive assay for targeted multiplex amplification of human DNA sequences", PNAS, vol. 105, No. 27, Jul. 8, 2008, 9296-9301.

Ku, et al., "Exome versus transcriptome sequencing in identifying coding region variants", Expert Review of Molecular Diagnostics, vol. 12, 2012, 241-251.

Kulifaj, D. et al., "Development of a standardized real time PCR for Torque teno viruses (TTV) viral load detection and quantification: A new tool for immune monitoring", Journal of Clinical Virology, vol. 105, 2018, 118-127.

Kuo, et al., "Preimplantation and prenatal genetic diagnosis of aromatic L-amino acid decarboxylase deficiency with an amplification refractory mutation system-quantitative polymerase chain reaction", Taiwan J Obstet Gynecol, Dec. 2011;50(4): doi: 10.1016/j.tjog.2011.10.012., 468-473.

Kustanovich, et al., "Life and death of circulating cell-free DNA", Cancer Biol Ther., 2019;20(8): doi: 10.1080/15384047.2019.1598759. Epub Apr. 16, 2019, 1057-1067.

Lajin, et al., "A quadruplex tetra-primer ARMS-PCR method for the simultaneous detection of TP53 Arg72Pro, IVS3 16bp Del/Ins and IVS6+62A>G, and NQO1 C609T polymorphisms", Gene., Aug. 10, 2012;504(2): Epub May 23, 2012., 268-273.

Lajoie, B. R. et al., "The Hitchhiker's Guide to Hi-C Analysis: Practical guidelines", Methods: Author manuscript, vol. 72, Jan. 2015, 65-75.

Landegren, U. et al., "Reading Bits of Genetic Information: Methods for Single-Nucleotide Polymorphism Analysis", Genome Research, vol. 8, No. 8, 769-776, 1997.

Lang, et al., "Optimized allele-specific real-time PCR assays for the detection of common mutations in KRAS and BRAF", J Mol Diagn., Jan. 2011;13(1): doi: 10.1016/j.jmoldx.2010.11.007. Epub Dec. 23, 2010., 23-28.

Laurent-Puig, et al., "Clinical relevance of KRAS-mutated subclones detected with picodroplet digital PCR in advanced colorectal cancer treated with anti-EGFR therapy", Clin Cancer Res., Mar. 1, 2015;21(5): doi: 10.1158/1078-0432.CCR-14-0983. Epub Sep. 23, 2014., 1087-1097.

Lecomte, et al., "Detection of free-circulating tumor-associated DNA in plasma of colorectal cancer patients and its association with prognosis", Int J Cancer, Aug. 10, 2002;100(5): doi: 10.1002/ijc.10526., 542-548.

Lee, et al., "Allele-Specific Quantitative PCR for Accurate, Rapid, and Cost-Effective Genotyping", Hum Gene Ther., Jun. 2016;27(6): doi: 10.1089/hum.2016.011. Epub Mar. 17, 2016., 425-435.

Lefebure, et al., "Prognostic value of circulating mutant DNA in unresectable metastatic colorectal cancer", Ann Surg., Feb. 2010;251(2): doi: 10.1097/SLA.0b013e3181c35c87, 275-280.

Lenaerts, Liesbeth et al., "Noninvasive Prenatal Testing and Detection of Occult Maternal Malignancies", Clinical Chemistry, vol. 65, No. 12, 2019, 1484-1486.

Levy, et al., "Analysis of Cell-Free DNA to Assess Risk of Tumoremia Following Endoscopic Ultrasound Fine-Needle Aspiration of Pancreatic Adenocarcinomas", Clin Gastroenterol Hepatol., Oct. 2018;16(10): e1. doi: 10.1016/j.cgh.2018.02.048. Epub Mar. 8, 2018., 1632-1640.

Li, et al., "Multiplex co-amplification of 24 retinoblastoma gene exons after pre-amplification by long-distance PCR", Nucleic Acids Res., Feb. 1, 1996;24(3), 538-539.

Liang, et al., "Cationic nanoparticle as an inhibitor of cell-free DNA-induced inflammation", Nat Commun., Oct. 16, 2018;9(1):4291. doi: 10.1038/s41467-018-06603-5, 14 pages.

Lievre, et al., "KRAS mutations as an independent prognostic factor in patients with advanced colorectal cancer treated with cetuximab", J Clin Oncol., Jan. 20, 2008;26(3): doi: 10.1200/JCO.2007.12.5906., 374-379.

Lin, et al., "A new diagnostic system for ultra-sensitive and specific detection and quantification of Candidatus Liberibacter asiaticus, the bacterium associated with citrus Huanglongbing", J Microbial Methods, 2010, 17-25.

Liu, et al., "ABO chimerism determined by real-time polymerase chain reaction analysis after ABO-incompatible haematopoietic stem cell transplantation", Blood Tranfus, Jan. 2013;11(1): doi: 10.2450/2012.0013-12. Epub Jul. 4, 2012., 43-52.

(56) References Cited

OTHER PUBLICATIONS

Liu, et al., "Comparison of next-generation sequencing systems", J Biomed Biotechnol., 2012;2012: doi: 10.1155/2012/251364. Epub Jul. 5, 2012., 1-11.
Livergood, "Adverse perinatal outcomes and cell free DNA no calls: Beyond low fetal fraction", American Journal of Obstetrics & Gynecology, vol. 218, No. 1, 2018, S169.
Lizardi, et al., "Mutation detection and single-molecule counting using isothermal rolling-circle amplification", Nature Genetics, 1998, 225-232.
Llop, et al., "Development of a highly sensitive nested-PCR procedure using a single closed tube for detection of Erwinia amylovora in asymptomatic plant material", Appl Environ Microbial., 2000, 2071-8.
Lo, et al., "Plasma placental RNA allelic ratio permits noninvasive prenatal chromosomal aneuploidy detection", Nat Med., Feb. 2007;13(2): doi: 10.1038/nm1530. Epub Jan. 7, 2007., 218-223.
Lo, et al., "Transplantation monitoring by plasma DNA sequencing", Clin Chem., Jul. 2011;57(7): doi: 10.1373/clinchem.2011. 166686. PubMed PMID: 21566070., 941-942.
Lo, Y.M. D. et al., "Prenatal Diagnosis of Fetal RhD Status by Molecular Analysis of Maternal Plasma", The New England Journal of Medicine, vol. 339, No. 24, 1998, 1734-1738.
Luo, et al., "Detection of usual and atypical aldehyde dehydrogenase alleles by mismatch amplification mutation assay", Clin Chem Lab Med., Dec. 2001;39(12): doi: 10.1515/CCLM.2001.189., 1195-1197.
Maheswaran, S. et al., "Detection of Mutations in EGFR in Circulating Lung-Cancer Cells", N Engl J Med, vol. 359, No. 4, Jul. 24, 2008, 366- 377.
Mak, et al., "Rapid diagnosis of Wilson disease by a 28-mutation panel: real-time amplification refractory mutation system in diagnosing acute Wilsonian liver failure", Clin Chim Acta., Dec. 2008; 398(1-2): doi: 10.1016/j.cca.2008.08.002. Epub Aug. 8, 2008., 39-42.
Mamanova, L. et al., "Target-enrichment strategies for next-generation sequencing", Nat Methods, vol. 7, No. 2, 2010, 111-118.
Mamun, et al., "The *Escherichia coli* UVM response is accompanied by an SOS-independent error-prone DNA replication activity demonstrable in vitro", Molecular Microbiology, 2000, 368-380.
Manage, et al., "Genotyping single nucleotide polymorphisms in human genomic DNA with an automated and self-contained PCR cassette", J Mol Diagn., Sep. 2014;16(5): doi:10.1016/j.jmoldx. 2014.04.004. Epub Jul. 2, 2014., 550-557.
Margulies, et al., "Genome Sequencing in Open Microfabricated High Density Picoliter Reactors", Nature, 437(7057), 2005, 376-380.
Martinez-Herrero, et al., "Cancer protection elicited by a single nucleotide polymorphism close to the adrenomedullin gene", J Clin Endocrinol Metab., Apr. 2013;98(4): doi: 10.1210/jc.2012-4193. Epub Feb. 28, 2013., E807-E810.
Marusyk, et al., "Causes and consequences", Biochimica et Biophysica Acta, vol. 1805, 2010, 105-117.
Mehra, et al., "Gene expression profiles and B-type natriuretic peptide elevation in heart transplantation: more than a hemodynamic marker", Circulation, Jul. 4, 2006;114(1 Suppl), I21-I26.
Mehra, et al., "International Society for Heart and Lung Transplantation working formulation of a standardized nomenclature for cardiac allograft vasculopathy-2010", J Heart Lung Transplant, Jul. 2010;29(7) .doi: 10.1016/j.healun.2010.05.017., 717-727.
Mengel, et al., "The molecular phenotype of heart transplant biopsies: relationship to histopathological and clinical variables", Am J Transplant, Sep. 2010;10(9): doi: 10.1111/j.1600-6143.2010.03182. x., 2105-2115.
Metzker, Michael, Declaration of Michael L. Metzker, Ph.D. from IPR2018-01317, 2004.
Misale, et al., "Emergence of KRAS mutations and acquired resistance to anti-EGFR therapy in colorectal cancer", Nature, Jun. 28, 2012;486(7404): doi: 10.1038/nature11156., 532-536.

Mouliere, et al., "Circulating Cell-Free DNA from Colorectal Cancer Patients May Reveal High KRAS or BRAF Mutation Load", Transl Oncol., Jun. 1, 2013;6(3): doi: 10.1593/tlo.12445. Print Jun. 2013., 319-328.
Mueller, P. R. et al., "In Vivo Footprinting of a Muscle Specific Enhancer by Ligation Mediated PCR", Science, vol. 249, Nov. 10, 1989, 780-786.
Myers, et al., "ACB-PCR quantification of somatic oncomutation", Methods Mol Biol., 2014;1105: doi:10.1007/978-1-62703-739-6_ 27, 345-363.
Namlos, H.M. et al., "Use of liquid biopsies to monitor disease progression in a sarcoma patient: a case report", BMC Cancer, vol. 17, No. 1, 2017, 2-3.
Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.
Newton, et al., "Analysis of any point mutation in DNA. The amplification refractory mutation system (ARMS)", Nucleic Acids Res., Apr. 11, 1989;17(7): doi: 10.1093/nar/17.7.2503, 2503-2516.
Nilsson, et al., "Analyzing genes using closing and replicating circles", Trends in Biotechnology, 24, 2006, 83-88.
No Author Listed, "Jury Rules in Favor of Natera, Finding All Asserted Patents Valid and Infrindged by ArcherDX/Invitae; Awards $19.35 Million in Past Damages for Royalties and Lost Profits", Natera Press Release, 2023, 4 pgs.
No Author Listed, "*Natera Inc.* vs. *ArcherDx* Verdict Form, Case 1:20-cv-00125-GBW", 2023, 1-12.
No Author Listed, "The Journal of Heart and Lung Transplantation", Apr. 2012., vol. 31, Issue 4, Supplement, pp. A1-A4, S1-S310. https://www.google.de/searchq=The+Journal+of+Heart+and+Lung+ Transplantation+Volume+31,+Issue+4,+Supplement&sourceid=ie7 &rls=com.microsoft:en-US:IE-Address&ie=&oe=#spf= 1604593918239, Last Accessed: Oct. 13, 2015., A1-A4.
No Author Listed, NIH, "Quantitative Detection of Circulating Donor-Specific DNA in Organ Transplant Recipients (DTRT-Multi-Center Study) (DTRT)", ClinicalTrials.gov Identifier: NCT02109575., Apr. 10, 2014, Last updated Mar. 26, 2021, 9 pages.
North, et al., "Cell-free DNA donor fraction analysis in pediatric and adult heart transplant patients by multiplexed allele-specific quantitative PCR: Validation of a rapid and highly sensitive clinical test for stratification of rejection probability", PLoS One, Jan. 13, 2020;15(1): e0227385. doi: 10.1371/journal.pone.0227385. eCollection 2020., 48 pages.
Norton, et al., "Perinatal and genetic outcomes associated with no call cfDNA results in 18,496 pregnancies", American Journal of Obstetrics & Gynecology, vol. 224, No. 2, 2021, S3.
Oeth, et al., "Qualitative and quantitative genotyping using single base primer extension coupled with matrix-assisted laser desorption/ionization time-of-flight mass spectrometry (MassARRAY®).", Methods Mol. Biol., 2009; 578, 307-343.
Ohya, K et al., "Detection of the CTG Repeat Expansion in Congenital Myotonic Dystrophy", Jpn J. Human Genet, vol. 42, 1997, 169-180.
Orou, et al., "Allele-specific competitive blocker PCR: a one-step method with applicability to pool screening", Hum Mutat., 1995;6(2): doi: 10.1002/humu.1380060209., 163-169.
Parsons, et al., "Allele-specific competitive blocker-PCR detection of rare base substitution", Methods Mol Biol., 2005;291, 235-245.
PCT/US2017/059808, "International Preliminary Report on Patentability", mailed May 16, 2019, 8 pages.
PCT/US2017/059808, "International Search Report and Written Opinion for Application", mailed Jan. 25, 2018, 12 pages.
PCT/US2018/038598, "International Preliminary Report on Patentability", mailed Jan. 2, 2020, 6 pages.
PCT/US2018/038598, "International Search Report and Written Opinion", mailed Sep. 7, 2018, 8 pages.
PCT/US2018/038609, "International Preliminary Report on Patentability", mailed Jan. 2, 2020, 7 pages.
PCT/US2018/038609, "International Search Report and Written Opinion", mailed Sep. 10, 2018, 9 pages.

(56) References Cited

OTHER PUBLICATIONS

Peng, et al., "Comparison of K-ras mutations in lung, colorectal and gastric cancer", Oncol Lett., Aug. 2014;8(2): doi: 10.3892/ol.2014. 2205. Epub May 30, 2014., 561-565.
Peng, Q et al., "Reducing amplification artifacts in high multiplex amplicon sequencing by using molecular barcodes", BMC Genomics, vol. 16. No. 586, 2015, 12 pages.
Peyster, et al., "Advanced Morphologic Analysis for Diagnosing Allograft Rejection: The Case of Cardiac Transplant Rejection", Transplantation, Aug. 2018;102(8): doi: 10.1097/TP. 0000000000002189., 1230-1239.
Price, et al., "Cost-effective interrogation of single nucleotide polymorphisms using the mismatch amplification mutation assay and capillary electrophoresis", Electrophoresis, Dec. 2010;31(23-24): doi: 10.1002/elps.201000379., 3881-3888.
Purhonen, et al., "Human plasma cell-free DNA as a predictor of infectious complications of neutropenic fever in hematological patients", Infect Dis (Lond)., Apr. 2015;47(4): doi: 10.3109/00365548. 2014.985711. Epub Feb. 9, 2015., 255-259.
Qin, et al., "Quantitative assessment of hematopoietic chimerism by quantitative real-time polymerase chain reaction of sequence polymorphism systems after hematopoietic stem cell transplantation", Chin Med J (Engl), Aug. 2011;124(15), 2301-2308.
Quail, et al., "A tale of three next generation sequencing platforms: comparison of Ion torrent, pacific biosciences and illumina MiSeq sequencers", BMC Genomics, Jul. 24, 2012;13:341. doi: 10.1186/ 1471-2164-13-341, 13 pages.
Raemdonck, Dirk Van et al., "Ex-vivo lung perfusion", Transplant International, vol. 28, Issue 6, Special Issue: Focus Issue: Machine Perfusion, 2014, 643-656.
Ragalie, et al., "Description of Longitudinal Measurement of Donor Fraction of Cell-Free DNA and Correlation to Clinical Outcomes", ISHLT poster, 2018, 1 page.
Ragalie, et al., "Noninvasive Assay for Donor Fraction of Cell-Free DNA in Pediatric Heart Transplant Recipients", J Am Coll Cardiol., Jun. 26, 2018;71(25): doi: 10.1016/j.jacc.2018.04.026, 2982-2983.
Rechitsky, S. et al., "Allele Dropout in Polar Bodies and Blastomeres", Journal of Assisted Reproduction and Genetics, vol. 15, No. 5, 1998, 253-257.
Richmond, et al., "Donor fraction cell-free DNA and rejection in adult and pediatric heart transplantation", J Heart Lung Transplant, May 2020;39(5): doi: 10.1016/j.healun.2019.11.015. Epub Nov. 29, 2019., 454-463.
Roedder, et al., "Biomarkers in solid organ transplantation: establishing personalized transplantation medicine", Genome Med., Jun. 8, 2011;3(6):37, 12 pages.
Sanmamed, et al., "Quantitative cell-free circulating BRAFV600E mutation analysis by use of droplet digital PCR in the follow-up of patients with melanoma being treated with BRAF inhibitors", Clin Chem., Jan. 2015;61(1): doi: 10.1373/clinchem.2014.230235. Epub Nov. 19, 2014., 297-304.
Sapio, et al., "Detection of BRAF mutation in thyroid papillary carcinomas by mutant allele-specific PCR amplification (MASA)", Eur J Endocrinol., Feb. 2006;154(2): doi: 10.1530/eje.1.02072, 341-348.
Saukkonen, et al., "Cell-free plasma DNA as a predictor of outcome in severe sepsis and septic shock.", Clin Chem., Jun. 2008;54(6): doi: 10.1373/clinchem.2007.101030. Epub Apr. 17, 2008. PubMed PMID: 18420731., 1000-1007.
Scheffer, et al., "Association between low fetal fraction in cell-free DNA testing and adverse pregnancy outcome: A systematic review", Prenatal Diagnosis, vol. 41, No. 10, 2021, 1287-1295.
Schnittger, et al., "Development and validation of a real-time quantification assay to detect and monitor BRAFV600E mutations in hairy cell leukemia", Blood., Mar. 29, 2012;119(13): doi: 10.1182/ blood-2011-10-383323. Epub Feb. 13, 2012., 3151-3154.
Schutz, et al., "Graft-derived cell-free DNA, a noninvasive early rejection and graft damage marker in liver transplantation: A prospective, observational, multicenter cohort study", PLoS Med., Apr. 25, 2017;14(4):e1002286. doi: 10.1371/journal.pmed. 1002286. eCollection Apr. 2017., 19 pages.
Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.
Schwarzenbach, et al., "Cell-free nucleic acids as biomarkers in cancer patients", Nat Rev Cancer, Jun. 2011;11(6): doi: 10.1038/ nrc3066. Epub May 12, 2011, 426-437.
Scott, et al., "Elevated nuclear and mitochondrial cell-free deoxyribonucleic acid measurements are associated with death after infant cardiac surgery", J Thorac Cardiovasc Surg., Aug. 2022;164(2): doi: 10.1016/j.jtcvs.2021.10.066. Epub Dec. 24, 2021., 367-375.
Scott, et al., "Total Cell-Free DNA Predicts Death and Infection Following Pediatric and Adult Heart Transplantation", Ann Thorac Surg., Oct. 2021;112(4): doi: 10.1016/j.athoracsur.2020.08.006. Epub Oct. 8, 2020., 1282-1289.
Sefrioui, et al., "Clinical value of chip-based digital-PCR platform for the detection of circulating DNA in metastatic colorectal cancer", Dig Liver Dis., Oct. 2015;47(10): doi: 10.1016/j.dld.2015.05. 023. Epub Jun. 5, 2015, 884-890.
Selzner, Markus et al., "Normothermic Ex Vivo Liver Perfusion Using Steen Solution as Perfusate for Human Liver Transplantation: First North American Results", Liver Transplantation, vol. 22, Issue 11, 2016.
Sethi, Himanshu et al., "Analytical validation of the Signatera (TM) RUO assay, a highly sensitive patient-specific multiplex PCR NGS-based noninvasive cancer recurrence detection and therapy monitoring assay", Cancer Research, vol. 78, No. 13, 2018, 4542.
Sheffield, et al., "Attachment of a 40-base-pair G + C-rich sequence (GC-clamp) to genomic DNA fragments by the polymerase chain reaction results in improved detection of single-base changes", Proc Natl Acad Sci U S A, Jan. 1989;86(1), 232-236.
Shi, et al., "Development of a single multiplex amplification refractory mutation system PCR for the detection of rifampin-resistant *Mycobacterium tuberculosis*", Gene., Nov. 1, 2013; 530(1): Epub Aug. 19, 2013, 95-99.
Shimabukuro-Vornhagen, et al., "Cytokine release syndrome", J Immunother Cancer, Jun. 15, 2018;6(1):56. doi: 10.1186/s40425-018-0343-9, 14 pages.
Sigdel, et al., "A rapid noninvasive assay for the detection of renal transplant injury", Transplantation, Jul. 15, 2013;96(1): doi: 10.1097/ TP.0b013e318295ee5a., 97-101.
Sigdel, Tara et al., "Optimizing Detection of Kidney Transplant Injury by Assessment of Donor-Derived Cell-Free DNA via Massively Multiplex PCR", Journal of Clinical Medicine, vol. 8, No. 1, 2018, 19.
Sigdel, Tara et al., "Plasma Donor-Derived Cell-Free DNA Quantification by massively multiplex PCR Distinguishes Kidney Transplant Acute Rejection", Transplantation, vol. 102, No. 7s, 2018, s178-s179.
Singh, et al., "Aspergillus infections in transplant recipients", Clin Microbiol Rev., Jan. 2005;18(1), 44-69.
Snyder, et al., "Universal noninvasive detection of solid organ transplant rejection", Proc Natl Acad Sci U S A, Apr. 12, 2011;108(15); doi: 10.1073/pnas.1013924108. Epub Mar. 28, 2011. PubMed PMID: 21444804; PubMed Central PMCID: PMC3076856., 6229-6234.
Sparks, et al., "Noninvasive prenatal detection and selective analysis of cell-free DNA obtained from maternal blood: evaluation for trisomy 21 and trisomy 18", Am J Obstet Gynecol., Apr. 2012;206(4): doi: 10.1016/j.ajog.2012.01.030. Epub Jan. 26, 2012, 319.e1-319. e9.
Sparks, et al., "Selective analysis of cell-free DNA in maternal blood for evaluation of fetal trisomy", Prenat Diagn., Jan. 2012;32(1). Epub Jan. 6, 2012., 3-9.
Spindler, et al., "Cell-free DNA in healthy individuals, noncancerous disease and strong prognostic value in colorectal cancer", Int J Cancer, Dec. 15, 2014;135(12): doi: 10.1002/ijc.28946. Epub Jun. 17, 2014, 2984-2991.
Spindler, et al., "KRAS-mutated plasma DNA as predictor of outcome from irinotecan monotherapy in metastatic colorectal cancer", Br J Cancer, Dec. 10, 2013;109(12). doi: 10.1038/bjc.2013. 633. Epub Nov. 21, 2013., 3067-3072.

(56) References Cited

OTHER PUBLICATIONS

Spindler, et al., "Quantitative cell-free DNA, KRAS, and BRAF mutations in plasma from patients with metastatic colorectal cancer during treatment with cetuximab and irinotecan", Clin Cancer Res., Feb. 15, 2012;18(4). doi: 10.1158/1078-0432.CCR-11-0564. Epub Jan. 6, 2012., 1177-1185.
Steensma, D. P. et al., "Clonal hematopoiesis of indeterminate potential and its distinction from myelodysplastic syndromes", Blood, vol. 126, No. 1, 2015, 9-16.
Stein, "Next-Generation Sequencing Update", Genetic Engineering & Biotechnology News, Sep. 1, 2008; 28(15). https://www.genengnews.com/magazine/97/next-generation-sequencing-update/, 10 pages.
Steinborn, et al., "Coexistence of Bos taurus and B. indicus mitochondrial DNAs in nuclear transfer-derived somatic cattle clones", Genetics, Oct. 2002; 162(2), 823-829.
Stemmer, et al., "Use of magnetic beads for plasma cell-free DNA extraction: toward automation of plasma DNA analysis for molecular diagnostics", Clin Chem., Nov. 2003;49(11): PubMed PMID: 14578335., 1953-1955.
Stone, J. P. et al., "Altered Immunogenicity of Donor Lungs via Removal of Passenger Leukocytes Using Ex Vivo Lung Perfusion", American Journal of Transplantation, vol. 16, 2016, 33-43.
Strausberg, et al., "*Homo sapiens* placenta-specific 4, mRNA (cDNA clone MGC:120720 IMAGE:7939530), complete cds", GenBank Submission; Accession No. BC093685, version BC093685.1., Jan. 18, 2007, 2 Pages.
Strohmeier, et al., "Multiplex genotyping of KRAS point mutations in tumor cell DNA by allele-specific real-time PCR on a centrifugal microfluidic disk segment", Microchimica Acta., 2014;181 (13-14), 1681-1688.
Suzuki, et al., "Characterization of circulating DNA in healthy human plasma", Clin Chim Acta., Jan. 2008;387(1-2): doi: 10.1016/j.cca.2007.09.001. Epub Sep. 8, 2007., 55-58.
Swinkels, et al., "Effects of blood-processing protocols on cell-free DNA quantification in plasma", Clin Chem., Mar. 2003;49(3): PubMed PMID: 12600978, 525-526.
Tabernero, et al., "Analysis of circulating DNA and protein biomarkers to predict the clinical activity of regorafenib and assess prognosis in patients with metastatic colorectal cancer: a retrospective, exploratory analysis of the CORRECT trial", Lancet Oncol., Aug. 2015;16(8): doi: 10.1016/S1470-2045(15)00138-2. Epub Jul. 13, 2015., 937-948.
Taira, et al., "Novel high-speed droplet-allele specific-polymerase chain reaction: application in the rapid genotyping of single nucleotide polymorphisms", Clin Chim Acta., Sep. 23, 2013;424: doi: 10.1016/j.cca.2013.04.024. Epub May 17, 2013., 39-46.
Taira, et al., "Quantitative monitoring of single nucleotide mutations by allele-specific quantitative PCR can be used for the assessment of minimal residual disease in patients with hematological malignancies throughout their clinical course", Clin Chim Acta., Jan. 14, 2011;412(1-2): doi: 10.1016/j.cca.2010.09.011. Epub Sep. 16, 2010., 53-58.
Takai, et al., "Clinical utility of circulating tumor DNA for molecular assessment in pancreatic cancer", Sci Rep., Dec. 16, 2015;5:18425. doi: 10.1038/srep18425., 10 pages.
Taly, et al., "Multiplex picodroplet digital PCR to detect KRAS mutations in circulating DNA from the plasma of colorectal cancer patients", Clin Chem., Dec. 2013;59(12): doi: 10.1373/clinchem.2013.206359. Epub Aug. 12, 2013., 1722-1731.
Tamkovich, et al., "Circulating nucleic acids in blood of healthy male and female donors", Clin Chem., Jul. 2005; 51(7): PubMed PMID: 15976134., 1317-1319.
Tanem, et al., "Abstract 16873: Association of Preoperative Cell-Free DNA Levels and Outcome Following Pediatric Cardiopulmonary Bypass", Circulation, Nov. 17, 2020; 142(S3): https://doi.org/10.1161/circ.142.suppl_3.16873., 1-6.
Thierry, et al., "A Targeted Q-PCR-Based Method for Point Mutation Testing by Analyzing Circulating DNA for Cancer Management Care", Methods Mol Biol., 2016;1392: doi: 10.1007/978-1-4939-3360-0_1, 1-16.
Thierry, et al., "Clinical validation of the detection of KRAS and BRAF mutations from circulating tumor DNA", Nat Med., Apr. 2014;20(4): doi: 10.1038/nm.3511. Epub Mar. 23, 2014., 430-435.
Tie, et al., "Circulating tumor DNA as an early marker of therapeutic response in patients with metastatic colorectal cancer", Annals of Oncology, vol. 26, No. 8, 2015, 1715-1722.
Tomita-Mitchell, et al., "Human gene copy number spectra analysis in congenital heart malformations", Physiol Genomics, May 1, 2012;44(9): doi: 10.1152/physiolgenomics.00013.2012. Epub Feb. 7, 2012., 518-541.
Tong, et al., "Diagnostic developments involving cell-free (circulating) nucleic acids", Clin Chim Acta., Jan. 2006;363(1-2): Epub Aug. 26, 2005. Review. PubMed PMID: 16126188, 187-196.
Toth, T. et al., "Prenatal Detection of Trisomy 13 From Amniotic Fluid by Quantitative Fluorescent Polymerase Chain Reaction", Prenatal Diagnosis, vol. 18, 1998, 669-674.
Tungwiwat, et al., "Non-invasive fetal sex determination using a conventional nested PCR analysis of fetal DNA in maternal plasma", Clinica Chimica Acta, vol. 334, No. 1-2, 2003, 173-177.
Valenza, F. et al., "The Consumption of Glucose During Ex Vivo Lung Perfusion Correlates with Lung Edema", Transplantation Proceedings, vol. 43, 2011, 993-996.
Van Orsouw, et al., "Rapid design of denaturing gradient-based two-dimensional electrophoretic gene mutational scanning tests", Nucleic Acids Res., May 15, 1998;26(10), 2398-2406.
Vandekerkhove, G et al., "Circulating Tumor DNA Reveals Clinically Actionable Somatic Genome of Metastatic Bladder Cancer", Clinical Cancer Research, 2017, 6487-6497.
Vannucchi, et al., "A quantitative assay for JAK2(V617F) mutation in myeloproliferative disorders by ARMS-PCR and capillary electrophoresis", Leukemia, Jun. 2006;20(6), 1055-1060.
Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.
Veseloskva, "The use of cell-free nucleic acids in maternal plasma for non-invasive prenatal diagnosis of monogenic diseases, placental insufficiency-related complications and Down syndrome", Thesis from Charles University in Prague, 2011, 104 pages.
Volckmar, et al., "A field guide for cancer diagnostics using cell-free DNA: From principles to practice and clinical applications", Genes Chromosomes Cancer, 2018, 123-139.
Wagner, F. F. et al., "RHD gene deletion occurred in the Rhesus box", Blood, vol. 95, No. 12, 2000, 3662-3668.
Wang, et al., "DNA Degradation Test Predicts Success in Whole-Genome Amplification from Diverse Clinical Samples", Journal of Molecular Diagnostics, vol. 9, 2007, 441-451.
Wang, et al., "Molecular inversion probes: a novel microarray technology and its application in cancer research", Cancer Genetics, 205, 2012, 341-355.
Wangkumhang, et al., "WASP: a Web-based Allele-Specific PCR assay designing tool for detecting SNPs and mutations", BMC Genomics, Aug. 14, 2007;8:275, 9 Pages.
Wangkumhang, P. et al., "WASP: a Web-based Allele-Specific PCR assay designing tool for detecting SNPs and mutations", BMC Genomics, vol. 8, No. 275, Aug. 14, 2007, 9 pgs.
Wapner, et al., "Expanding the scope of noninvasive prenatal testing: detection of fetal microdeletion syndromes", Am J Obstet Gynecol., Mar. 2015;212(3): doi: 10.1016/j.ajog.2014.11.041. Epub Dec. 2, 2014., 332.e1-332.e9.
Whitlam, J. B. et al., "Diagnostic application of kidney allograft-derived absolute cell-free DNA levels during transplant dysfunction", Am J Transplant, vol. 19, 2019, 1037-1049.
Wilkins, et al., "IMP PCR primers detect single nucleotide polymorphisms for *Anopheles gambiae* species identification, Mopti and Savanna rDNA types, and resistance to dieldrin in Anopheles arabiensis", Malar J., Dec. 19, 2006;5:125., 7 pages.
Wood, et al., "Molecular histology of lung cancer: From targets to treatments", Cancer Treatment Reviews, vol. 41, 2015, 361-375.
Woude, et al., "Methods of identifying drugs with selective effects against cancer cells", Oct. 7, 1997, Nucleic acid sequence search reports AC: 151794, Accession I51796., 2 Pages.

(56) References Cited

OTHER PUBLICATIONS

Xie, et al., "Designing highly multiplex PCR primer sets with Simulated Annealing Design using Dimer Likelihood Estimation (SADDLE)", Nat Commun., vol. 13, No. 1, 2022, 1881.

Yamada, et al., "Detection of K-ras gene mutations in plasma DNA of patients with pancreatic adenocarcinoma: correlation with clinicopathological features", Clin Cancer Res., Jun. 1998;4(6), 1527-1532.

Yamauchi Medical Clinic, "Chromosome abnormality", http://www.yamauchi-iin.com/kaisetu/1241.htm, (Dec. 10, 2015 updated), Dec. 10, 2015, 3 pages.

Ye, et al., "Primer-BLAST: a tool to design target-specific primers for polymerase chain reaction", BMC Bioinformatics, 13:134, 2012, 11 pages.

Yi, et al., "PCR/LDR/capillary electrophoresis for detection of single-nucleotide differences between fetal and maternal DNA in maternal plasma", Prenat Diagn., Mar. 2009;29(3): doi: 10.1002/pd.2072., 217-222.

Zangwill, et al., "Effect of endomyocardial biopsy on levels of donor- specific cell-free DNA", J Heart Lung Transplant, Oct. 2019;38(10): doi: 10.1016/j.healun.2019.06.005. Epub Jun. 28, 2019., 1118-1120.

Zhang, et al., "A novel multiplex tetra-primer ARMS-PCR for the simultaneous genotyping of six single nucleotide polymorphisms associated with female cancers", PLOS One, Apr. 1, 20137;8(4):e62126. doi: 10.1371/journal.pone.0062126. Print 2013., 8 pages.

Zheng, et al., "Whole-exome sequencing to identify novel somatic mutations in squamous cell lung cancers", International Journal of Oncology, vol. 43, 2015, 755-764.

Antoniou, A. et al., "Data augmentation generative adversarial networks.", arXiv preprint arXiv:1711.04340, (Year: 2017), Nov. 12, 2017, 14 pages.

Li, Ying et al., "Biochemical and Clinical Diagnostic Aspects of Circulating Nucleic Acids", Dissertation, 2005, 103 Pages.

Liao, W et al., "Noninvasive detection of tumor-associated mutations from circulating cell-free DNA in hepatocellular carcinoma patients by targeted deep sequencing.", Oncotarget, 7(26), (Year: 2016), Jun. 28, 2016, 40481-40490.

Malapelle, U. et al., "Next generation sequencing techniques in liquid biopsy: focus on non-small cell lung cancer patients.", Transl Lung Cancer Res., 5(5), (Year: 2016), Oct. 2016, 505-510.

Min, S. et al., "Deep learning in bioinformatics.", Brief Bioinform., 18(5), (Year: 2017), Sep. 1, 2017, 851-869.

Moscow, J. A. et al., "Engraftment of MDR1 and NeoR Gene-Transduced Hematopoietic Cells After Breast Cancer Chemotherapy", Blood, vol. 94, No. 1, 1999, 52-61.

Neocleous, A. C. et al., "First Trimester Noninvasive Prenatal Diagnosis: A Computational Intelligence Approach", in IEEE Journal of Biomedical and Health Informatics, vol. 20, No. 5, (Year: 2016), Sep. 2016, pp. 1427-1438.

Oustimov, A. , "Artificial neural networks in the cancer genomics frontier.", Translational cancer research., 3(3), (Year: 2014), Jun. 2014, 11 pages.

Puszyk, William , "Epigenetics of cell-free plasma DNA for non-invasive prenatal diagnosis of fetal aneuploidies", Diss. University of Warwick, 2008, 199 pages.

Stephens, Z. D. et al., "Simulating Next-Generation Sequencing Datasets from Empirical Mutation and Sequencing Models.", PLoS One., 11(11):e0167047. (Year: 2016), Nov. 28, 2016, 18 pages.

* cited by examiner

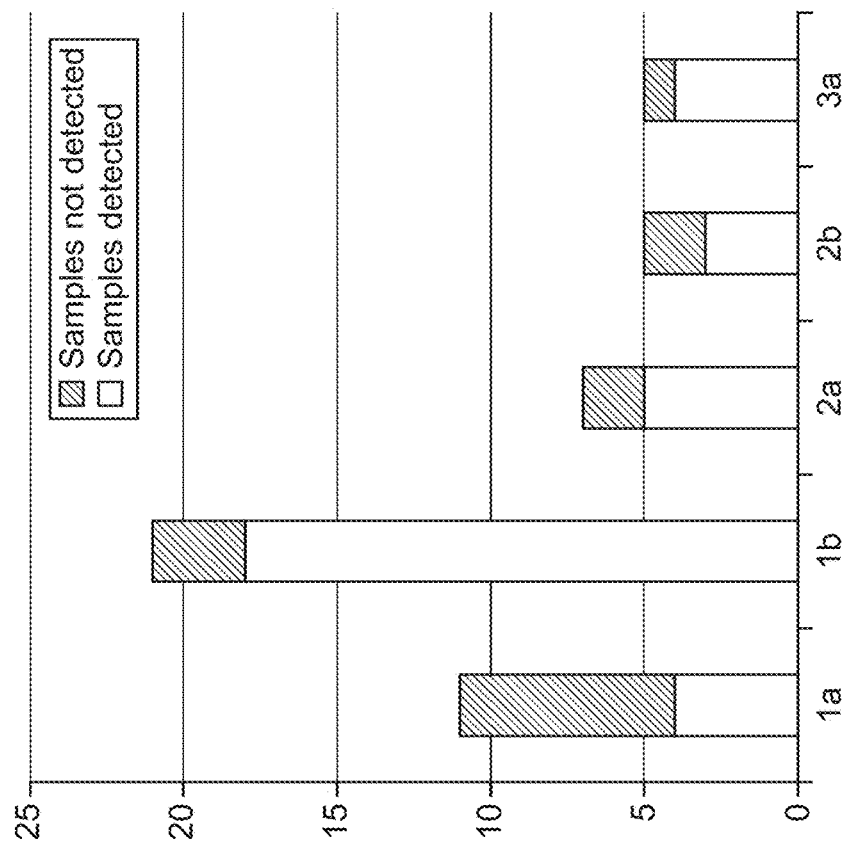
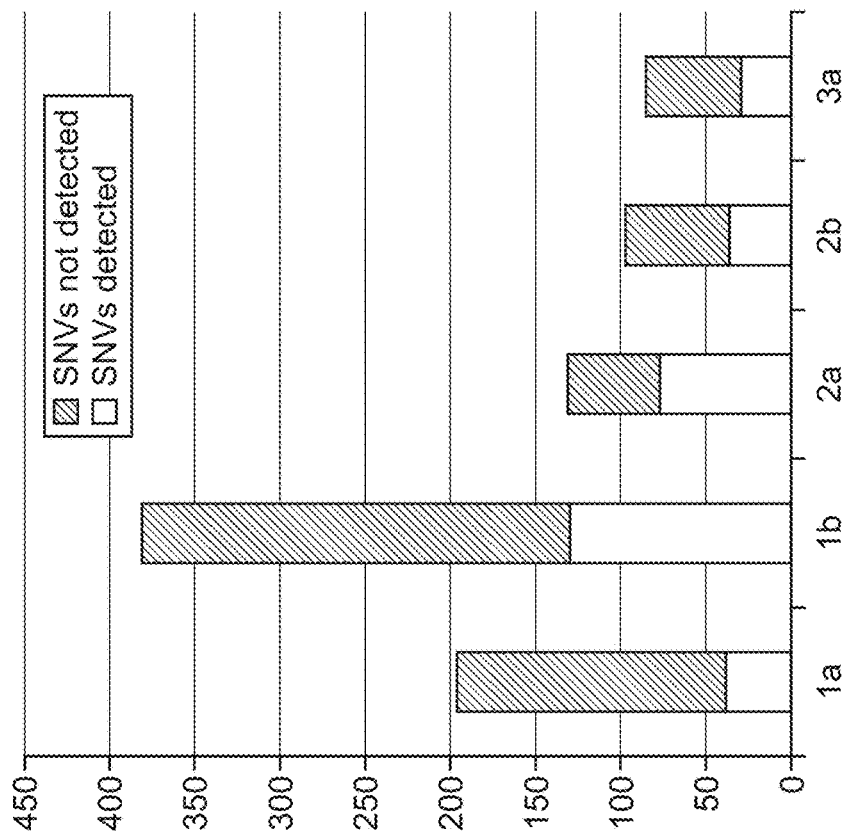
FIG. 8A
FIG. 8B

| Sample ID | cfDNA concentration (ng/ul) | Genome copy equivalents into Library Prep | cfDNA size profile | Hemolysis |
|---|---|---|---|---|
| U_LTX144 | 0.09 | 1,017 | 3 | 2 |
| B_LTX135 | 0.21 | 2,578 | 2 | 0 |
| B_LTX160 | 0.25 | 3,021 | 2 | 1 |
| M_LTX085 | 0.27 | 3,300 | 2 | 0 |
| B_LTX065 | 0.30 | 3,564 | 2 | 0 |
| U_LTX092 | 0.31 | 3,689 | 3 | 2 |
| M_LTX013 | 0.32 | 3,853 | 2 | 0 |
| B_LTX163 | 0.32 | 3,919 | 1 | 0 |
| B_LTX075 | 0.39 | 4,733 | 1 | 0 |
| M_LTX175 | 0.41 | 4,929 | 1 | 0 |
| A_LTX055 | 0.42 | 5,042 | 2 | 0 |
| A_LTX210 | 0.43 | 5,167 | 2 | 0 |
| A_LTX049 | 0.45 | 5,465 | 2 | 0 |
| M_LTX073 | 0.45 | 5,480 | 1 | 0 |
| U_LTX103 | 0.46 | 5,611 | 2 | 0 |
| A_LTX102 | 0.48 | 5,817 | 1 | 0 |
| B_LTX165 | 0.50 | 6,049 | 2 | 0 |
| U_LTX111 | 0.50 | 6,068 | 2 | 0 |
| U_LTX180 | 0.52 | 6,245 | 2 | 0 |
| U_LTX058 | 0.65 | 7,898 | 2 | 1 |
| U_LTX091 | 0.66 | 8,030 | 2 | 0 |
| U_LTX206 | 0.68 | 8,271 | 2 | 1 |
| U_LTX036 | 0.69 | 8,293 | 1 | 0 |
| B_LTX048 | 0.73 | 8,800 | 2 | 0 |
| U_LTX107 | 0.73 | 8,878 | 2 | 0 |
| L_LTX062 | 0.74 | 8,934 | 2 | 0 |
| B_LTX046 | 0.74 | 9,015 | 2 | 0 |
| L_LTX041 | 0.82 | 9,940 | 1 | 0 |
| U_LTX076 | 0.83 | 10,009 | 2 | 0 |
| B_LTX059 | 0.84 | 10,201 | 2 | 0 |
| M_LTX093 | 0.87 | 10,556 | 2 | 0 |
| U_LTX097 | 0.91 | 10,995 | 2 | 0 |
| U_LTX185 | 1.00 | 12,055 | 2 | 0 |

FIG. 16

| | | | | |
|---|---|---|---|---|
| U_LTX022 | 1.04 | 12,536 | 3 | 1 |
| L_LTX115 | 1.21 | 14,602 | 2 | 0 |
| B_LTX033 | 1.25 | 15,187 | 1 | 0 |
| M_LTX025 | 1.43 | 17,334 | 3 | 1 |
| R_LTX120 | 1.63 | 19,693 | 1 | 0 |
| B_LTX034 | 1.85 | 22,361 | 2 | 1 |
| A_LTX021 | 1.85 | 22,400 | 1 | 0 |
| B_LTX084 | 1.89 | 22,889 | 1 | 0 |
| M_LTX015 | 1.91 | 23,193 | 1 | 0 |
| M_LTX032 | 1.95 | 23,637 | 1 | 2 |
| M_LTX063 | 2.06 | 25,007 | 1 | 0 |
| M_LTX028 | 2.35 | 28,476 | 1 | 0 |
| M_LTX074 | 2.54 | 30,752 | 1 | 0 |
| B_LTX038 | 3.12 | 37,767 | 1 | 0 |
| M_LTX149 | 3.89 | 47,165 | 2 | 1 |
| U_LTX126 | 6.75 | 50,000 | 2 | 1 |
| U_LTX001 | 7.24 | 50,000 | 1 | 0 |

FIG. 16 (Cont.)

| Sample | Total assays | Detected in plasma | Negative |
|---|---|---|---|
| LTX001 | 17 | 2 | 15 |
| LTX013 | 15 | 2 | 13 |
| LTX015 | 19 | 17 | 2 |
| LTX021 | 19 | 0 | 19 |
| LTX022 | 20 | 17 | 3 |
| LTX025 | 19 | 15 | 4 |
| LTX028 | 19 | 13 | 6 |
| LTX032 | 17 | 12 | 5 |
| LTX033 | 18 | 13 | 5 |
| LTX034 | 18 | 0 | 18 |
| LTX036 | 19 | 1 | 18 |
| LTX038 | 19 | 16 | 3 |
| LTX041 | 19 | 1 | 18 |
| LTX046 | 18 | 0 | 18 |
| LTX048 | 17 | 1 | 16 |
| LTX049 | 18 | 1 | 17 |
| LTX055 | 21 | 0 | 21 |
| LTX058 | 18 | 8 | 10 |
| LTX059 | 18 | 9 | 9 |
| LTX062 | 18 | 0 | 18 |
| LTX063 | 20 | 15 | 5 |
| LTX065 | 15 | 0 | 15 |
| LTX073 | 22 | 0 | 22 |
| LTX074 | 19 | 7 | 12 |
| LTX075 | 19 | 1 | 18 |
| LTX076 | 20 | 19 | 1 |
| LTX084 | 14 | 0 | 14 |

FIG. 17

| | | | |
|---|---|---|---|
| LTX085 | 15 | 3 | 12 |
| LTX091 | 18 | 0 | 18 |
| LTX092 | 21 | 18 | 3 |
| LTX093 | 16 | 14 | 2 |
| LTX097 | 18 | 14 | 4 |
| LTX102 | 20 | 0 | 20 |
| LTX103 | 13 | 1 | 12 |
| LTX107 | 19 | 13 | 6 |
| LTX111 | 17 | 5 | 12 |
| LTX115 | 19 | 0 | 19 |
| LTX120 | 18 | 17 | 1 |
| LTX126 | 19 | 6 | 13 |
| LTX135 | 17 | 4 | 13 |
| LTX144 | 19 | 0 | 19 |
| LTX149 | 17 | 12 | 5 |
| LTX160 | 17 | 3 | 14 |
| LTX163 | 19 | 0 | 19 |
| LTX165 | 19 | 11 | 8 |
| LTX175 | 21 | 9 | 12 |
| LTX180 | 17 | 0 | 17 |
| LTX185 | 18 | 0 | 18 |
| LTX210 | 18 | 10 | 8 |

FIG. 17 (Cont.)

| Sample | Chr. | Position | | Ref | Mut | Ref VAF Plasma | Mut VAF Plasma | Total DOR | Mut DOR |
|---|---|---|---|---|---|---|---|---|---|
| LTX032 | 6 | 161530837 | | T | G | 99.691% | 0.286% | 63656 | 182 |
| LTX063 | 1 | 27102067 | | T | G | 99.802% | 0.156% | 52495 | 82 |
| LTX063 | 10 | 108378017 | | T | A | 99.839% | 0.143% | 56002 | 80 |
| LTX092 | 2 | 216252943 | | G | T | 99.484% | 0.478% | 42289 | 202 |
| LTX107 | 3 | 156272874 | | A | G | 94.884% | 5.116% | 3968 | 203 |
| LTX149 | 14 | 70633967 | | G | T | 99.754% | 0.211% | 50808 | 107 |
| LTX149 | 1 | 160136470 | | T | G | 99.418% | 0.538% | 31966 | 172 |

FIG. 18

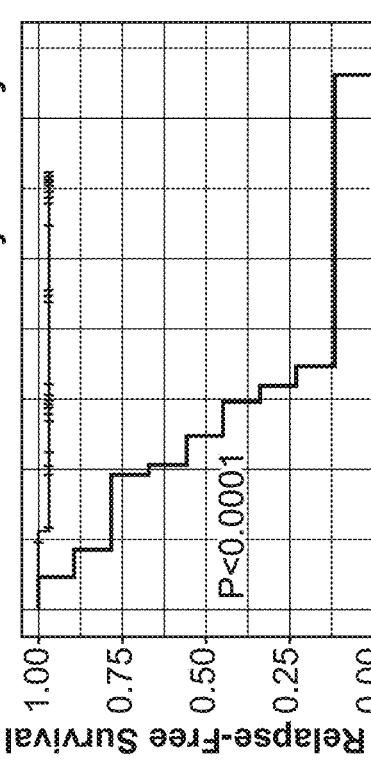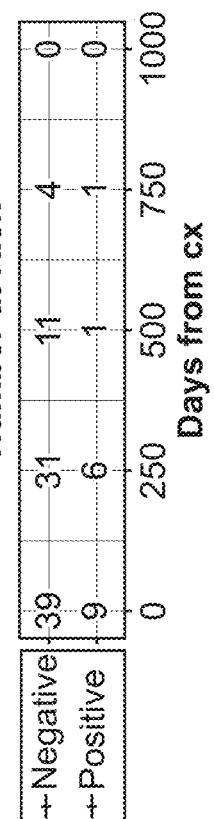
FIG. 31A
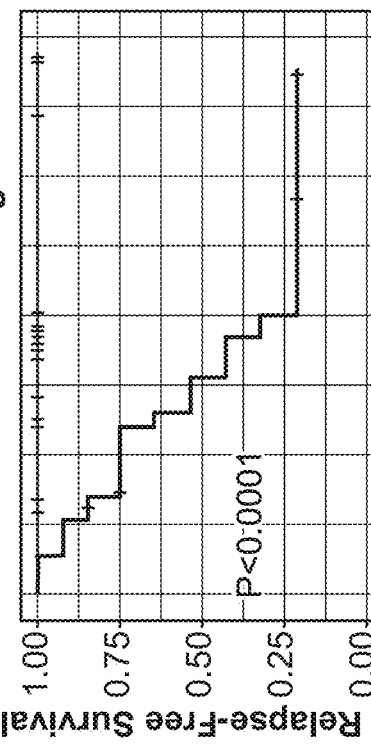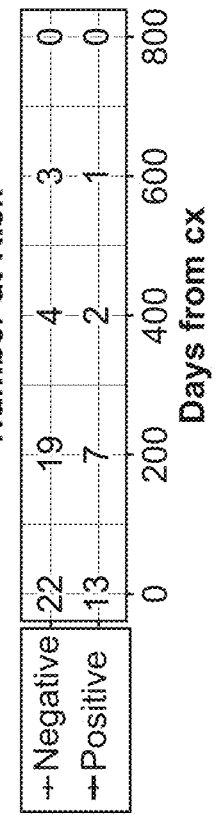
FIG. 31B

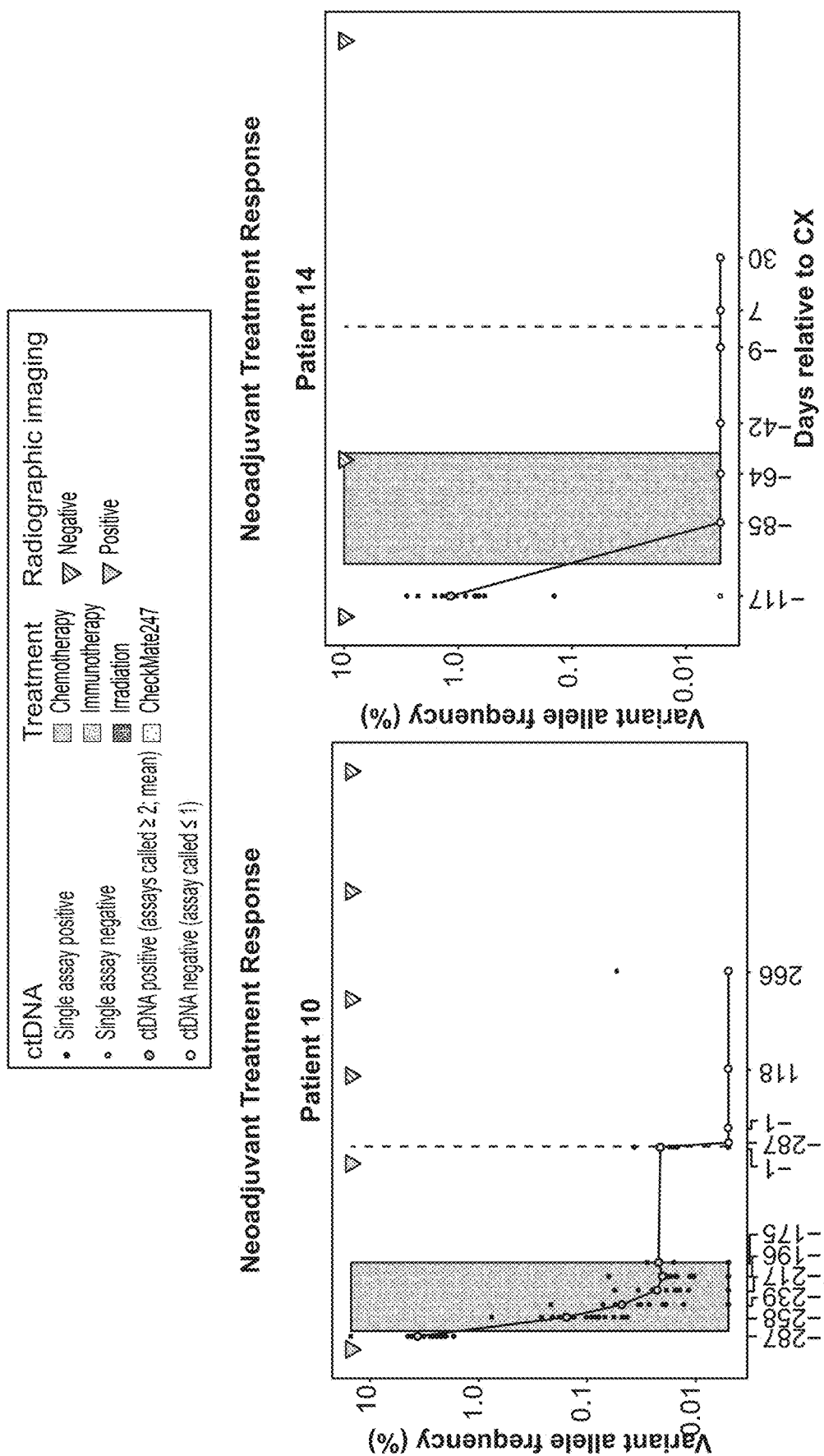

FIG. 38A

| | | | | | | | | | | | | | | | | | |
|---|---|---|---|---|---|---|---|---|---|---|---|---|---|---|---|---|---|
| CD004 | 30m | | 8 | 8 | Negative | IIC | HR+/HER2- | 306 | A | 5 | 5 | PLA | 21.3 | 0 | | | |
| CD004 | 30m | | 8 | 8 | Negative | IIC | HR+/HER2- | 306 | B | 2 | 5 | PLA | 21.3 | 0 | 0.006997 | 0.02209 | 0.0289803 |
| CD005 | baseline | 01/02/2015 | 8 | 0 | Negative | IIC | HR+/HER2- | 206 | A | 2 | 2 | PLA | 17.14 | 12 | 0.000358 | 0.01161 | 0.0073504 |
| CD005 | baseline | 01/02/2015 | 8 | 0 | Negative | IIC | HR+/HER2- | 206 | B | 2 | 2 | PLA | 17.14 | 4 | 0.006684 | 0.05302 | 0.0238656 |
| CD005 | 6m | 01/02/2015 | 8 | 0 | Negative | IIC | HR+/HER2- | 206 | B | 2 | 5 | MIX | 17.14 | 12 | 0.008582 | 0.01093 | 0.009921 |
| CD005 | 6m | 01/02/2015 | 8 | 0 | Negative | IIC | HR+/HER2- | 206 | A | 3 | 8 | MIX | 66 | 3 | | | |
| CD006 | baseline | | 8 | 0 | Negative | IA | HR+/HER2- | 74 | A | 5 | 7 | MIX | 21.44 | 0 | | | |
| CD006 | baseline | | 8 | 0 | Negative | IA | HR+/HER2- | 74 | B | 4 | 7 | MIX | 21.44 | 0 | | | |
| CD006 | 18m | | 8 | 3 | Negative | IA | HR+/HER2- | 74 | A | 4 | 5 | MIX | 20.67 | 0 | | | |
| CD006 | 18m | | 8 | 3 | Negative | IA | HR+/HER2- | 74 | B | 4 | 5 | MIX | 20.67 | 0 | | | |
| CD006 | 24m | | 8 | 4 | Negative | IA | HR+/HER2- | 74 | A | 4 | 6 | PLA | 37.67 | 0 | | | |
| CD006 | 24m | | 8 | 4 | Negative | IA | HR+/HER2- | 74 | B | 3 | 6 | PLA | 37.67 | 0 | | | |
| CD006 | 30m | | 8 | 5 | Negative | IA | HR+/HER2- | 74 | A | 3 | 4 | MIX | 43.23 | 0 | | | |
| CD006 | 30m | | 8 | 5 | Negative | IA | HR+/HER2- | 74 | B | 4 | 6 | MIX | 43.23 | 0 | | | |
| CD007 | baseline | | 7 | 0 | Positive | IIC | HR+/HER2+ | 72 | A | 6 | 6 | PLA | 22.19 | 0 | | | |
| CD007 | 6m | | 7 | 1 | Positive | IIC | HR+/HER2+ | 72 | A | 1 | 4 | MIX | 18.16 | 0 | 0.000672 | 0.00067 | 0.0006718 |
| CD007 | 18m | | 7 | 3 | Positive | IIC | HR+/HER2+ | 72 | A | 2 | 5 | MIX | 17.33 | 1 | | | |
| CD007 | 24m | | 7 | 4 | Positive | IIC | HR+/HER2+ | 72 | A | 3 | 6 | MIX | 13.01 | 0 | | | |
| CD007 | 30m | | 7 | 5 | Positive | IIC | HR+/HER2+ | 72 | A | 3 | 3 | MIX | 27.12 | 0 | | | |
| CD007 | 36m | | 7 | 6 | Positive | IIC | HR+/HER2+ | 72 | A | 4 | 4 | MIX | 9.01 | 0 | | | |
| CD008 | baseline | | 8 | 0 | Negative | IA | HR+/HER2- | 108 | A | 3 | 3 | MIX | 18.83 | 0 | | | |
| CD008 | 6m | | 8 | 1 | Negative | IA | HR+/HER2- | 108 | A | 1 | 4 | MIX | 27.39 | 0 | | | |
| CD008 | 12m | | 8 | 2 | Negative | IA | HR+/HER2- | 108 | A | 1 | 6 | MIX | 9.04 | 0 | | | |
| CD008 | 18m | | 8 | 3 | Negative | IA | HR+/HER2- | 108 | A | 3 | 4 | MIX | 13.65 | 1 | 0.000755 | 0.00076 | 0.0007553 |
| CD008 | 30m | | 8 | 5 | Negative | IA | HR+/HER2- | 108 | B | 2 | 6 | PLA | 23.95 | 0 | | | |
| CD009 | baseline | 10/28/2014 | 8 | 0 | Negative | IB | HR+/HER2- | 105 | A | 5 | 5 | MIX | 66 | 1 | 8.02E-05 | 8E-05 | 8.022E-05 |
| CD009 | baseline | 10/28/2014 | 8 | 0 | Negative | IB | HR+/HER2- | 105 | B | 3 | 5 | MIX | 66 | 0 | | | |
| CD010 | baseline | 07/08/2016 | 8 | 0 | Negative | IA | HR+/HER2- | 147 | A | 3 | 8 | MIX | 35.69 | 0 | | | |
| CD010 | 6m | 07/08/2016 | 8 | 1 | Negative | IA | HR+/HER2- | 147 | B | 3 | 8 | MIX | 35.69 | 0 | | | |
| CD010 | EoS | 07/08/2016 | 8 | | Negative | IA | HR+/HER2- | 147 | A | 2 | 4 | MIX | 32.73 | 0 | | | |
| CD010 | EoS | 07/08/2016 | 8 | | Negative | IA | HR+/HER2- | 147 | B | 4 | 4 | MIX | 32.73 | 0 | | | |
| CD011 | baseline | | 8 | 0 | Negative | IA | HR+/HER2- | 80 | A | 5 | 5 | MIX | 66 | 0 | | | |
| CD011 | 6m | | 8 | 1 | Negative | IA | HR+/HER2- | 80 | A | 5 | 6 | PLA | 30.37 | 0 | | | |
| CD011 | 12m | | 8 | 2 | Negative | IA | HR+/HER2- | 80 | A | 5 | 6 | PLA | 51.4 | 0 | | | |
| CD011 | 18m | | 8 | 3 | Negative | IA | HR+/HER2- | 80 | B | 2 | 5 | MIX | 31.59 | 0 | | | |
| CD011 | 24m | | 8 | 4 | Negative | IA | HR+/HER2- | 80 | A | 4 | 7 | MIX | 35 | 0 | | | |
| CD011 | 30m | | 8 | 5 | Negative | IA | HR+/HER2- | 80 | A | 7 | 8 | MIX | 45.12 | 0 | | | |
| CD011 | EoS | | 8 | 6 | Negative | IA | HR+/HER2- | 80 | A | 5 | 5 | MIX | 66 | 0 | | | |
| CD012 | baseline | | 8 | 0 | Negative | IB | HR+/HER2- | 243 | A | 6 | 6 | PLA | 41.33 | 0 | | | |
| CD012 | 6m | | 4 | 1 | Negative | IB | HR+/HER2- | 243 | B | 6 | 5 | MIX | 23.61 | 0 | | | |
| CD012 | 6m | | 4 | 1 | Negative | IB | HR+/HER2- | 243 | A | 6 | 7 | PLA | 43.97 | 0 | | | |
| CD012 | 12m | | 4 | 2 | Negative | IB | HR+/HER2- | 243 | B | 3 | 3 | PLA | 43.97 | 0 | | | |
| CD012 | 12m | | 4 | 2 | Negative | IB | HR+/HER2- | 243 | A | | | PLA | 18.15 | 0 | | | |

| | | | | | | | | | | | | | | | | |
|---|---|---|---|---|---|---|---|---|---|---|---|---|---|---|---|---|
| CD037 | 18m | 3 | | 0 | 0 | Positive | IIC | HR+/HER2+ | 146 | A | 5 | 5 | PLA | 47.32 | 16 | 0.001498 | 0.01077 | 0.004768 |
| CD037 | 18m | 3 | | 0 | 0 | Positive | IIC | HR+/HER2+ | 146 | B | 5 | 5 | PLA | 47.32 | 14 | 0.001077 | 0.00918 | 0.004732 |
| CD037 | EoS | 4 | | 0 | 0 | Positive | IIC | HR+/HER2+ | 146 | B | 3 | 3 | PLA | 64.15 | 16 | 0.000155 | 0.00404 | 0.001337 |
| CD037 | EoS | 4 | 06/07/2017 | 0 | 0 | Positive | IIC | HR+/HER2+ | 146 | A | 7 | 7 | PLA | 64.15 | 11 | 0.000433 | 0.00261 | 0.001335 |
| CD038 | baseline | 0 | 06/07/2017 | 8 | 8 | Negative | IIA | HR+/HER2- | 273 | B | 4 | 8 | MIX | 25.27 | 0 | | | |
| CD038 | baseline | 0 | 06/07/2017 | 8 | 8 | Negative | IIA | HR+/HER2- | 273 | A | 4 | 8 | MIX | 25.27 | 0 | | | |
| CD038 | 6m | 1 | | 8 | 8 | Negative | IA | HR+/HER2- | 273 | A | 5 | 4 | MIX | 40.63 | 0 | | | |
| CD038 | 6m | 1 | | 8 | 8 | Negative | IA | HR+/HER2- | 273 | B | 4 | 4 | MIX | 40.63 | 0 | | | |
| CD038 | 12m | 2 | | 8 | 8 | Negative | IA | HR+/HER2- | 273 | B | 4 | 4 | MIX | 14 | 0 | | | |
| CD038 | 12m | 2 | | 8 | 8 | Negative | IA | HR+/HER2- | 273 | A | 4 | 4 | MIX | 14 | 0 | | | |
| CD038 | 18m | 3 | | 8 | 8 | Negative | IA | HR+/HER2- | 273 | A | 5 | 5 | PLA | 37.21 | 0 | | | |
| CD038 | 18m | 3 | | 8 | 8 | Negative | IA | HR+/HER2- | 273 | B | 3 | 6 | PLA | 37.21 | 0 | | | |
| CD039 | baseline | 0 | | 6 | 6 | Negative | IB | HR+/HER2- | 170 | B | 3 | 6 | PLA | 57 | 0 | | | |
| CD039 | baseline | 0 | | 6 | 6 | Negative | IB | HR+/HER2- | 170 | A | 6 | 6 | PLA | 57 | 0 | | | |
| CD039 | 12m | 2 | | 6 | 6 | Negative | IB | HR+/HER2- | 170 | A | 6 | 5 | MIX | 34.04 | 0 | | | |
| CD039 | 12m | 2 | | 6 | 6 | Negative | IB | HR+/HER2- | 170 | B | 5 | 4 | MIX | 34.04 | 0 | | | |
| CD039 | 18m | 3 | | 6 | 6 | Negative | IB | HR+/HER2- | 170 | B | 4 | 4 | PLA | 66 | 0 | | | |
| CD039 | 18m | 3 | | 6 | 6 | Negative | IB | HR+/HER2- | 170 | A | 4 | 5 | PLA | 66 | 0 | | | |
| CD040 | baseline | 0 | 09/05/2016 | 7 | 7 | Positive | IB | HR+/HER2- | 64 | A | 5 | 5 | MIX | 35.68 | 5 | 7.44E-05 | 0.00046 | 0.002294 |
| CD040 | baseline | 0 | 09/05/2016 | 7 | 7 | Positive | IB | HR+/HER2- | 64 | B | 3 | 6 | MIX | 35.68 | 2 | 0.000616 | 0.00077 | 0.006938 |
| CD040 | 6m | 1 | 09/05/2016 | 7 | 7 | Positive | IB | HR+/HER2- | 64 | B | 3 | 3 | MIX | 46.72 | 5 | 0.002295 | 0.108 | 0.004904 |
| CD040 | 6m | 1 | 09/05/2016 | 7 | 7 | Positive | IB | HR+/HER2- | 64 | A | 6 | 5 | MIX | 46.72 | 5 | 0.00195 | 0.00526 | 0.003152 |
| CD040 | EoS | 2 | 09/05/2016 | 7 | 7 | Positive | IB | HR+/HER2- | 64 | B | 3 | 4 | MIX | 51.28 | 6 | 0.107785 | 0.26712 | 0.207409 |
| CD040 | EoS | 2 | | 7 | 7 | Positive | IB | HR+/HER2- | 64 | A | 3 | 5 | MIX | 51.28 | 5 | | | |
| CD041 | baseline | 0 | | 7 | 7 | Negative | IIA | HR+/HER2- | 250 | B | 3 | 3 | MIX | 66 | 0 | | | |
| CD041 | baseline | 0 | | 7 | 7 | Negative | IIA | HR+/HER2- | 250 | A | 3 | 6 | MIX | 66 | 0 | | | |
| CD041 | 6m | 1 | | 7 | 7 | Negative | IIA | HR+/HER2- | 250 | B | 3 | 6 | MIX | 39.36 | 0 | | | |
| CD041 | 6m | 1 | | 7 | 7 | Negative | IIA | HR+/HER2- | 250 | A | 3 | 6 | MIX | 39.36 | 0 | | | |
| CD041 | 12m | 2 | | 7 | 7 | Negative | IIA | HR+/HER2- | 250 | A | 3 | 6 | MIX | 22.87 | 0 | 0.00068 | 0.00068 | 0.006777 |
| CD041 | 12m | 2 | | 7 | 7 | Negative | IIA | HR+/HER2- | 250 | B | 4 | 5 | MIX | 22.87 | 0 | | | |
| CD041 | 18m | 3 | | 7 | 7 | Negative | IIA | HR+/HER2- | 250 | B | 3 | 5 | PLA | 47.98 | 0 | | | |
| CD041 | 18m | 3 | | 7 | 7 | Negative | IIA | HR+/HER2- | 250 | A | 3 | 3 | PLA | 47.98 | 0 | | | |
| CD042 | baseline | 0 | | 8 | 8 | Negative | IB | HR+/HER2- | 74 | B | 3 | 7 | MIX | 13.9 | 1 | 0.000435 | 0.00043 | 0.000434 |
| CD042 | baseline | 0 | | 8 | 8 | Negative | IB | HR+/HER2- | 74 | A | 4 | 7 | MIX | 13.9 | 0 | | | |
| CD042 | 6m | 1 | | 8 | 8 | Negative | IB | HR+/HER2- | 74 | B | 4 | 6 | MIX | 18.46 | 0 | | | |
| CD042 | 6m | 1 | | 8 | 8 | Negative | IB | HR+/HER2- | 74 | A | 4 | 6 | MIX | 18.46 | 0 | | | |
| CD042 | 12m | 2 | | 8 | 8 | Negative | IB | HR+/HER2- | 74 | A | 4 | 6 | MIX | 36.06 | 1 | | | |
| CD042 | 12m | 2 | | 8 | 8 | Negative | IB | HR+/HER2- | 74 | B | 6 | 6 | MIX | 36.06 | 0 | | | |
| CD043 | baseline | 0 | | 8 | 8 | Negative | IB | HR+/HER2- | 77 | B | 6 | 5 | PLA | 25.94 | 0 | | | |
| CD043 | 6m | 1 | | 8 | 8 | Negative | IB | HR+/HER2- | 77 | A | 6 | 6 | MIX | 66 | 11 | 0.004197 | 0.11205 | 0.06385 |
| CD044 | baseline | 0 | RIP 25/5/2016 | 8 | 8 | Negative | IB | HR+/HER2- | 222 | B | 6 | 6 | MIX | 2.96 | 7 | 0.003353 | 0.16115 | 0.087006 |
| CD044 | baseline | 0 | RIP 25/5/2016 | 3 | 3 | Negative | IB | HR+/HER2- | 222 | A | 3 | 5 | MIX | 2.96 | 3 | | 0.0078 | 0.0056029 |
| CD044 | baseline | 0 | 02/04/2016 | 3 | 3 | Negative | IB | HR+/HER2- | 222 | A | 2 | 5 | MIX | 2.96 | 2 | 0.001982 | 0.00296 | 0.0024724 |
| CD044 | 6m | 1 | 02/04/2016 | 3 | 3 | Negative | IB | HR+/HER2- | 222 | A | 5 | 5 | PLA | 61.71 | 0 | | | |

FIG. 38G

| | | | | | | | | | | | | | | | |
|---|---|---|---|---|---|---|---|---|---|---|---|---|---|---|---|
| CD044 | 6m | 1 | 02/04/2016 | 3 | 9 | Negative | IB | HR+/HER2- | 222 | B | 5 | 5 | PLA | 61.71 | 0 | | | 0.038198 | | 0.0614012 |
| CD044 | EoS | 2 | 02/04/2016 | 3 | 9 | Negative | IB | HR+/HER2- | 222 | A | 6 | 6 | PLA | 18.36 | 9 | | | 0.10089 | 0.0736886 |
| CD044 | EoS | 2 | 02/04/2016 | 3 | 9 | Negative | IB | HR+/HER2- | 222 | B | 6 | 6 | PLA | 18.36 | 4 | | | 0.048183 0.11888 | |
| CD046 | baseline | 0 | | 5 | 9 | Positive | IB | HR+/HER2+ | 154 | A | 5 | 5 | PLA | 26.97 | 1 | | | 0.000362 0.00036 0.003624 |
| CD046 | 6m | 1 | | 5 | 9 | Positive | IB | HR+/HER2+ | 154 | A | 6 | 6 | PLA | 4.3 | 0 | | | | |
| CD046 | 12m | 2 | | 5 | 9 | Positive | IB | HR+/HER2+ | 154 | A | 5 | 5 | PLA | 16.33 | 2 | | | | |
| CD047 | baseline | 0 | 02/08/2016 | 0 | 0 | Negative | IIA | TNBC | 62 | A | 2 | 5 | MIX | 16.2 | 15 | | | 0.000549 0.00191 0.0012305 |
| CD047 | 6m | 1 | 02/08/2016 | 0 | 0 | Negative | IIA | TNBC | 62 | A | 1 | 6 | cfDNA | 23.3 | 15 | | | 0.134777 0.2537 0.1933538 |
| CD047 | 12m | 2 | 02/08/2016 | 0 | 0 | Negative | IIA | TNBC | 62 | A | | 4 | MIX | 66 | 5 | | | 0.341113 0.6443 0.5367268 |
| CD048 | baseline | 0 | 11/18/2015 | 5 | 2 | Negative | IIA | HR+/HER2- | 54 | A | 1 | | cfDNA | 3.64 | 14 | | | 0.002077 0.00663 0.003626 |
| CD048 | 6m | 1 | 11/18/2015 | 5 | 2 | Negative | IB | HR+/HER2- | 83 | A | 2 | 5 | MIX | 23.18 | 0 | | | 0.000733 0.19579 0.1048331 |
| CD049 | baseline | 0 | 12/31/2015 | 0 | 0 | Negative | IIB | TNBC | 83 | A | 2 | 5 | MIX | 30.52 | 10 | | 0.0194 | 0.06551 | 0.032892 |
| CD049 | 6m | 1 | 12/31/2015 | 0 | 0 | Negative | IIB | TNBC | 83 | A | 1 | 4 | MIX | 26.79 | 10 | | 0.018564 | 0.067 | 0.036457 |
| CD049 | EoS | 2 | 12/31/2015 | 0 | 0 | Negative | IIB | TNBC | 83 | A | 1 | 4 | MIX | 16.26 | 5 | | | | |
| CD050 | baseline | 0 | 10/17/2016 | 0 | 0 | Negative | IIB | TNBC | 151 | A | 1 | 4 | MIX | 30.79 | 11 | | 0.000389 0.00292 0.0015608 |

FIG. 38H

| Her2 status | number of patients |
|---|---|
| Negative | 41 |
| Positive | 9 |

| Natera's Group | number of patients |
|---|---|
| HR-/HER2+ | 1 |
| HR+/HER2- | 34 |
| HR+/HER2+ | 8 |
| TNBC | 7 |

| Patient | Timepoint | Failure reason | Mitigation |
|---|---|---|---|
| 002-007 | all | Tumor and matched normal WES data did not match | exclude |
| 001-013 | all (pool B) | Low read in plasma sequencing | use pool A results |
| 001-029 | 6 (pool B) | Low read in plasma sequencing | resequence |
| 001-088R | 2 | Low read in plasma sequencing | resequence |
| 001-096R | 3 | Low read in plasma sequencing | resequence |
| 001-003 | 4 (pool A) | Swapped with 001-092-003 | rerun |
| 001-092 | 3 | Swapped with 001-003-004 | rerun |
| 001-013 | 2 | Was processed as 001-077-2 | rerun |
| 001-077 | 2 | Missing | Investigate |
| 001-033 | 3 | Swapped with 002-004R-002 | rerun |
| 002-004R | 2 | Swapped with 001-033-003 | rerun |

FIG. 43

| Patient | Sample ID | Size of Tumour | Tumour Type | Tumour Grade | Tumour Stage | ER status | PGR status | Her2 status | Stage | Natera's Group | Total timepoints | Positive timepoints |
|---|---|---|---|---|---|---|---|---|---|---|---|---|
| 001-004R | 1004 | 55 | Invasive ductal | 2 | T3 N2 M0 | 4 | 0 | Negative | IIIA | HR+/HER2- | 1 | 1 |
| 001-111R | 1111 | 75 | Invasive ductal | 2 | T3 N1 M0 | 8 | 8 | Negative | IIIA | HR+/HER2- | 1 | 1 |
| 003-048R | 3048 | 30 | Invasive ductal | 3 | T2 N1 M0 | 0 | 0 | Negative | IIB | TNBC | 1 | 1 |
| 001-072 | 1072 | 42 | Invasive lobular | 2 | T2 N2 M0 | 8 | 0 | Negative | IIIA | HR+/HER2- | 5 | 1 |
| 001-011R | 1011 | 100 | Invasive ductal | 2 | T3 N3 M0 | 8 | 0 | Negative | IIIC | HR+/HER2- | 2 | 2 |
| 001-088R | 1088 | 18 | Invasive lobular | 2 | T1 N3 M0 | 8 | 8 | Negative | IIIC | HR+/HER2- | 2 | 2 |
| 003-019R | 3019 | 58 | Invasive ductal | 3 | T3 N1 M0 | 5 | 2 | Negative | IIIA | HR+/HER2- | 3 | 2 |
| 002-004R | 2004 | 29 | Invasive ductal | 3 | T2 N1 M0 | 3 | 9 | Negative | IIB | HR+/HER2- | 2 | 2 |
| 003-023R | 3023 | 32 | Invasive ductal | 3 | T2 N1 M0 | 0 | 0 | Negative | IIB | TNBC | 3 | 3 |
| 001-091R | 1091 | 32 | Invasive ductal | 3 | T2 N3 M0 | 0 | 0 | Positive | IIIC | HR+/HER2+ | 3 | 3 |
| 001-096R | 1096 | 35 | Invasive ductal | 3 | T2 N1 M0 | 7 | 6 | Positive | IIB | HR+/HER2+ | 3 | 3 |
| 003-018R | 3018 | 42 | Invasive ductal | 3 | T2 N2 M0 | 0 | 0 | Negative | IIIA | TNBC | 3 | 3 |
| 001-055R | 1055 | 38 | Invasive ductal | 3 | T2 N1 M0 | 0 | 0 | Negative | IIB | TNBC | 4 | 3 |
| 001-074R | 1074 | 9 | Invasive ductal | 2 | T1 N0 M0 | 0 | 0 | Negative | IA | TNBC | 4 | 4 |
| 001-051R | 1051 | 35 | Invasive lobular | 2 | T2 N3 M0 | 8 | 5 | Negative | IIIC | HR+/HER2- | 5 | 4 |
| 001-031 | 1031 | 78 | Invasive ductal | 3 | T3 N3 M0 | 8 | 2 | Negative | IIIC | HR+/HER2- | 7 | 4 |

FIG. 45

| Breast Cancer Subtypes | Total Patients | Relapses | % Detected | PPV | NPV | Median Lead Time (days) |
|---|---|---|---|---|---|---|
| HR+/HER2- | 34 | 11 | 82% | 100% | 92% | 301 |
| HER2+ | 8 | 2 | 100% | 100% | 100% | 164 |
| TNBC | 7 | 5 | 100% | 100% | 100% | 258 |
| TOTAL | 49 | 18 | 89% | 100% | 94% | 266 |

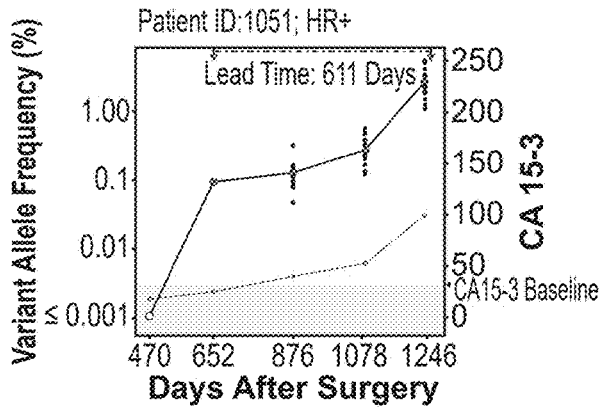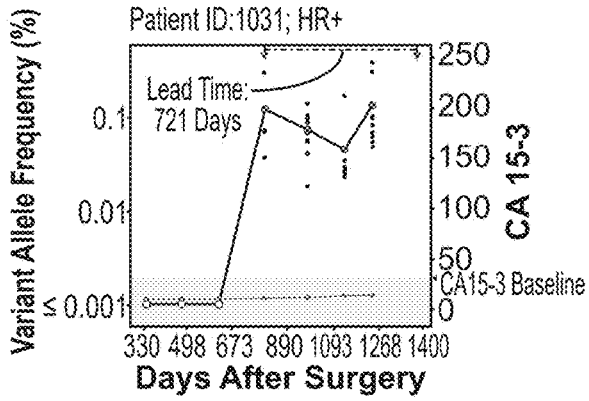
FIG. 63A  FIG. 63B
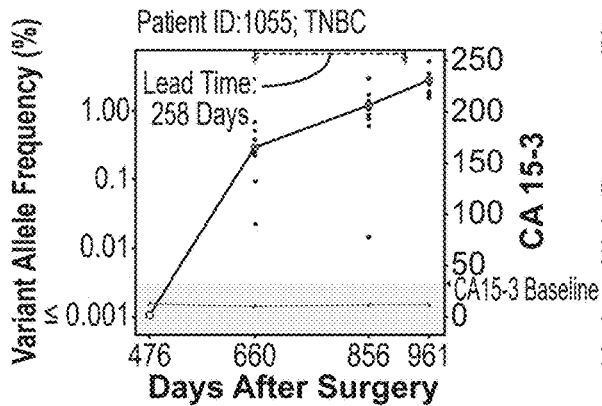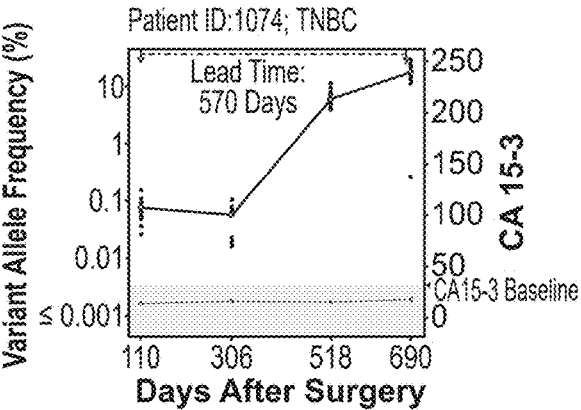
FIG. 63C  FIG. 63D
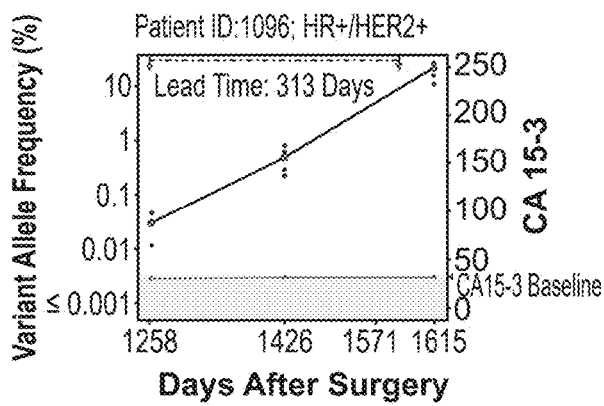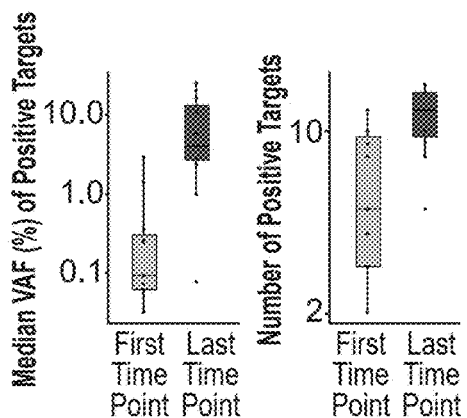
FIG. 63E  FIG. 63F

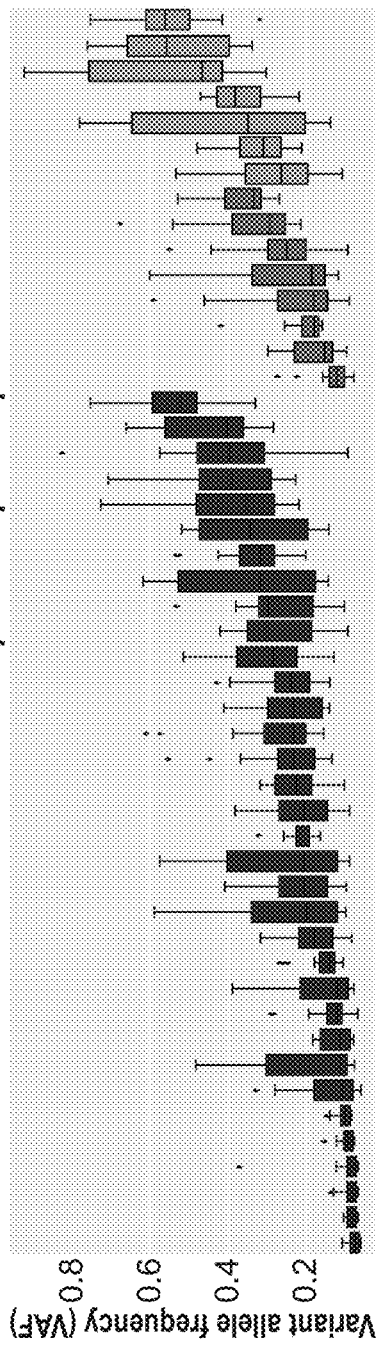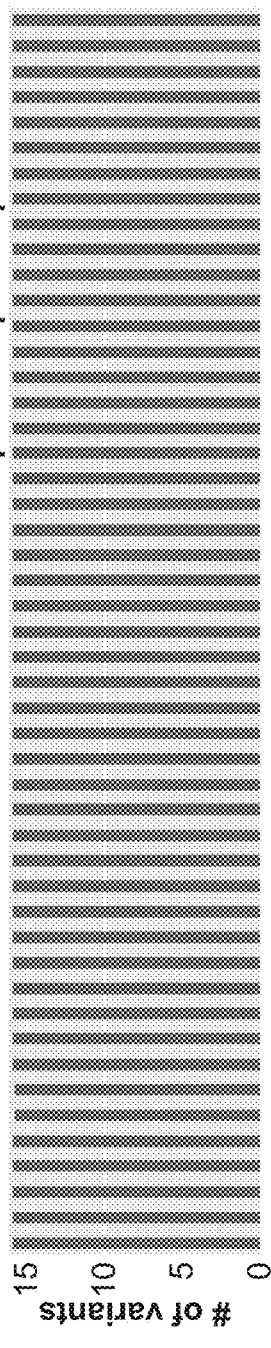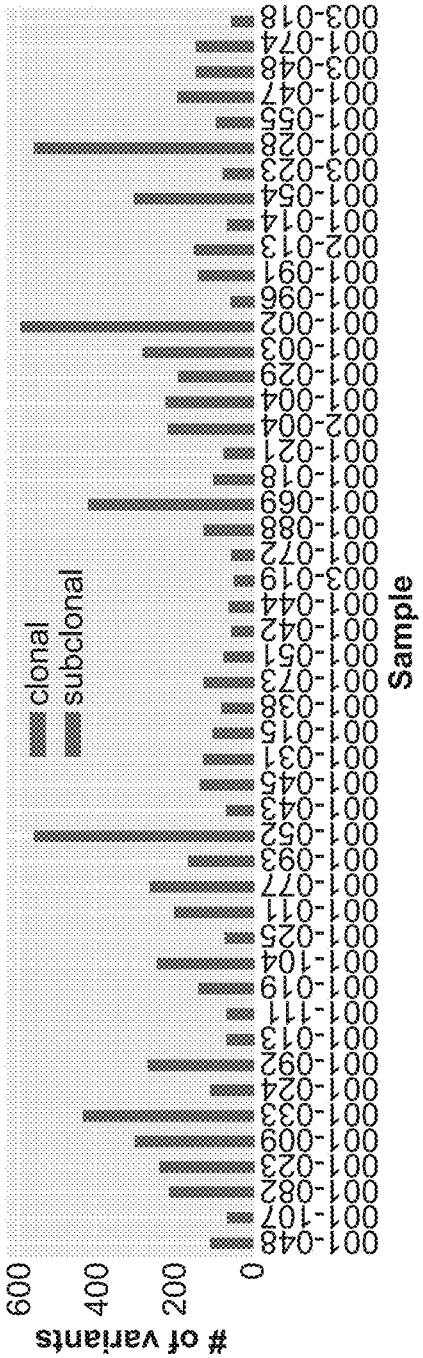

| Tumor DNA Concentration (%) | Tumor DNA Concentration Range (%) | Sensitivity Per Sample (%) |
|---|---|---|
| 0.00375 | 0.0025-0.005 | 44.7-70.8 |
| 0.0075 | 0.005-0.01 | 58.9-83.3 |
| 0.015 | 0.01-0.02 | 98.5-100.0 |
| 0.025 | 0.02-0.03 | 100 |
| 0.04 | 0.03-0.05 | 100 |
| 0.0625 | 0.05-0.075 | 100 |
| 0.0875 | 0.075-0.1 | 100 |
| 0.2 | 0.1-0.3 | 100 |
| 0.4 | 0.3-0.5 | 100 |
| 0.75 | 0.5-1.0 | 100 |

| Table 1. Characteristics of the Patients at Baseline* | |
|---|---|
| Characteristic | N = 49 |
| Median age at diagnosis (range)- yr | 57 (38-81) |
| Estrogen Receptor status- no.(%) | |
| Positive | 37 (76) |
| Negative | 12 (24) |
| Progesterone Receptor status- no.(%) | |
| Positive | 32 (65) |
| Negative | 17 (35) |
| HER2 status- no.(%)‡ | |
| Positive | 8 (16) |
| Negative | 41 (84) |
| Tumour Stage- no. (%) | |
| IA | 1 (2) |
| IIA | 1 (2) |
| IIB | 14 (29) |
| IIIA | 17 (35) |
| IIIB | 2 (4) |
| IIIC | 14 (28) |
| Size of tumour-mean (range)- cm | 3.8 (0.9-10) |
| Treatment – No.(%) | |
| NACT | 9 (18) |
| ACT | 33 (67) |
| none | 7 (15) |

FIG. 69

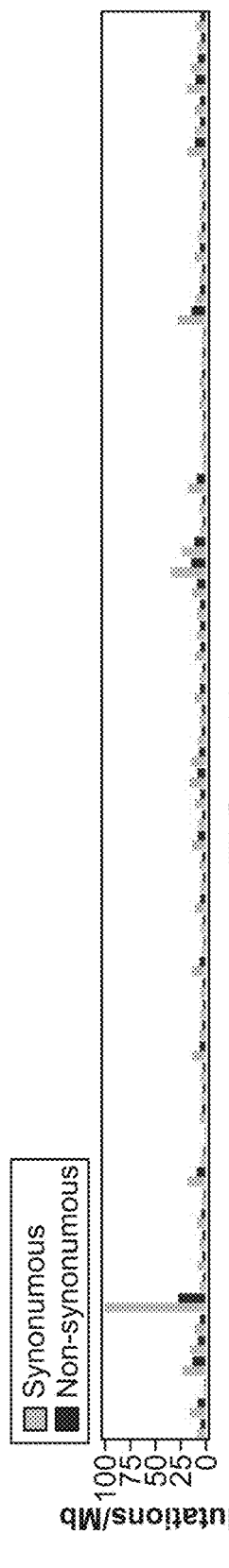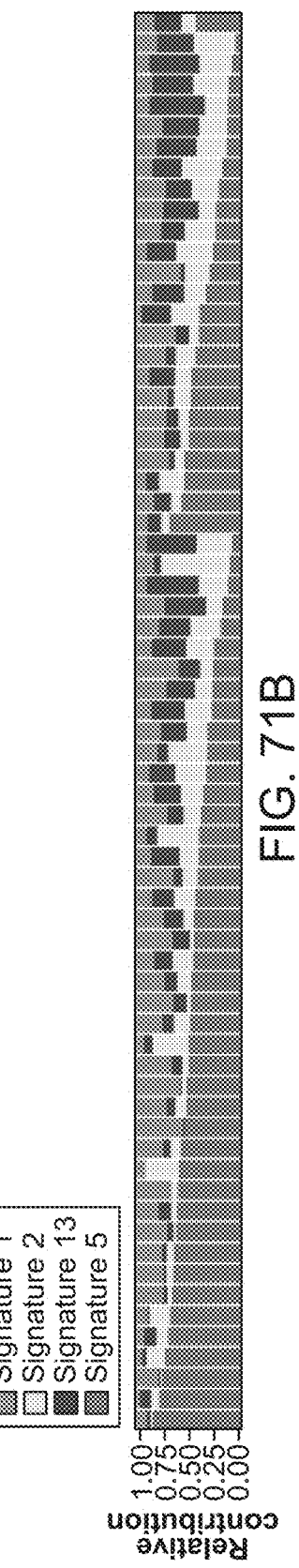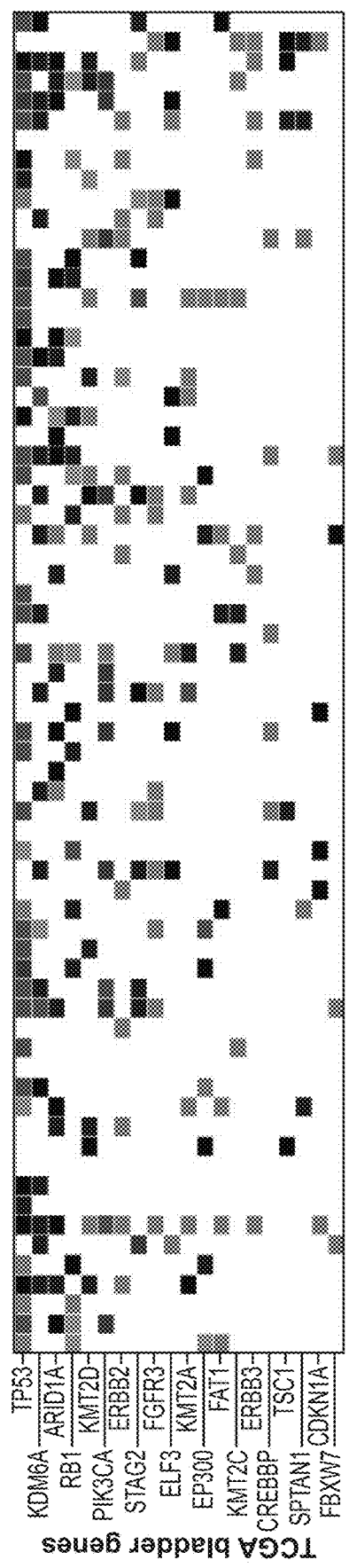

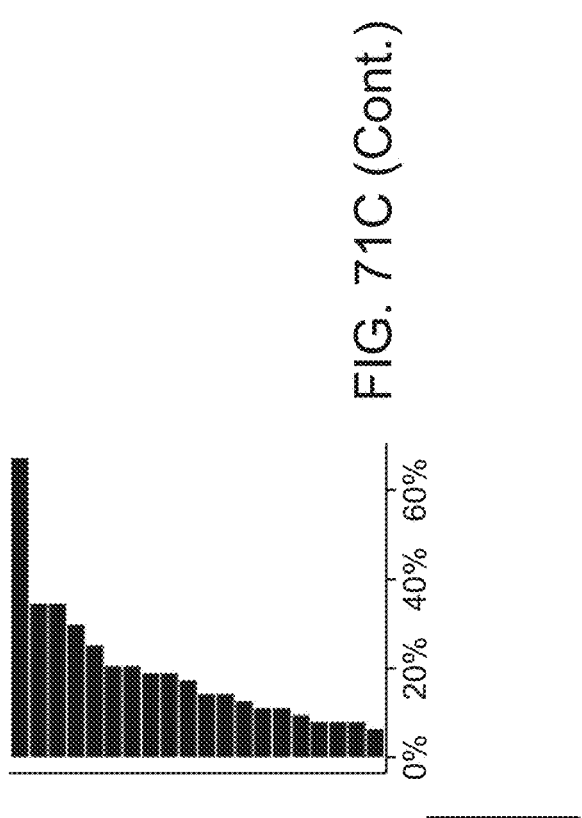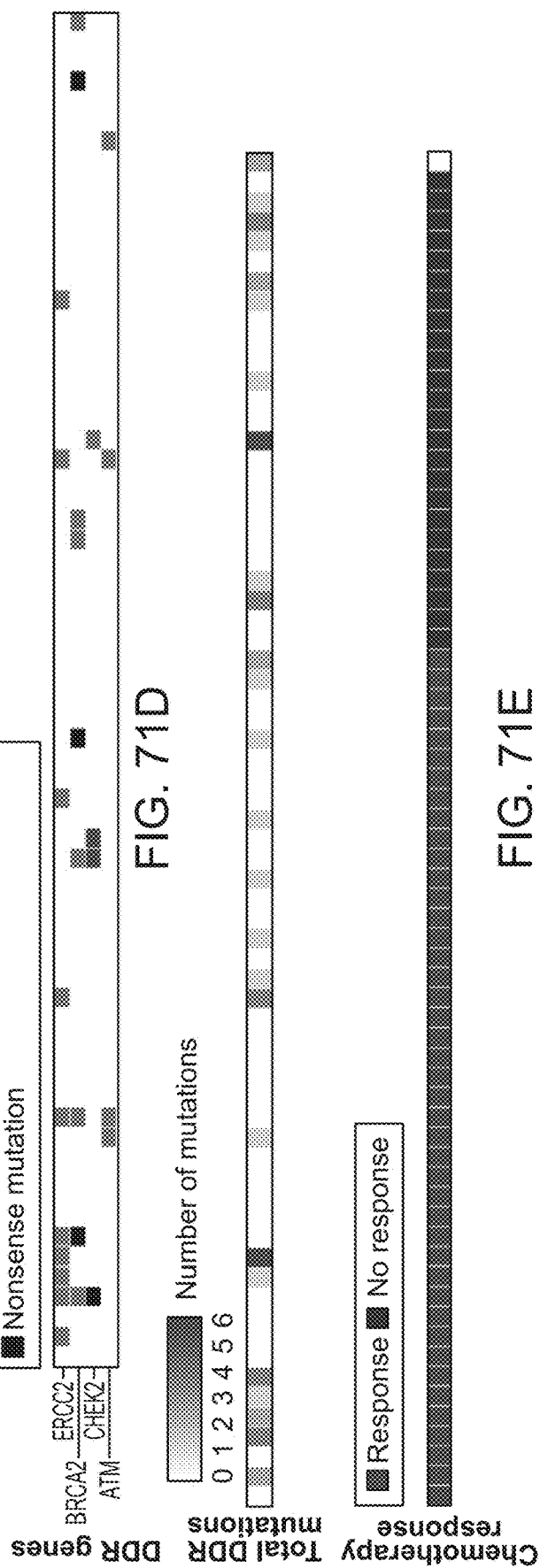

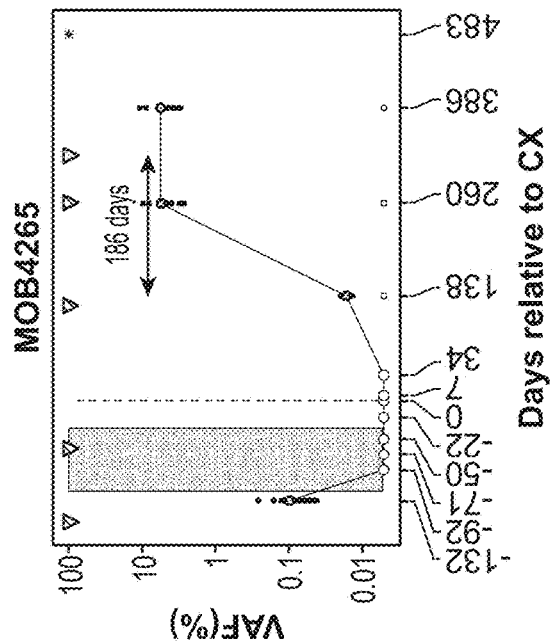
FIG. 76F
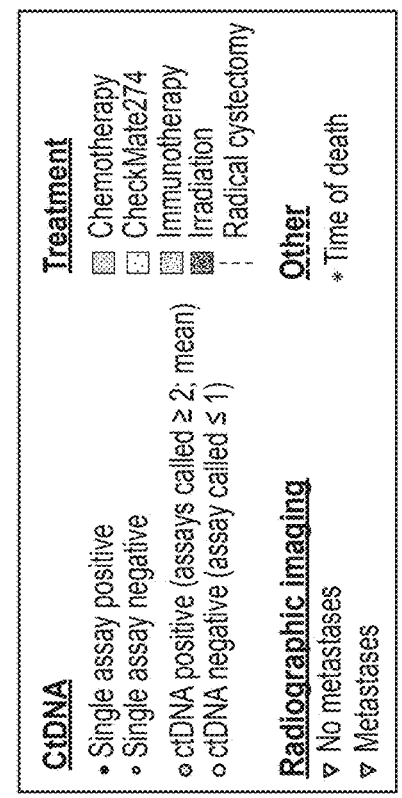
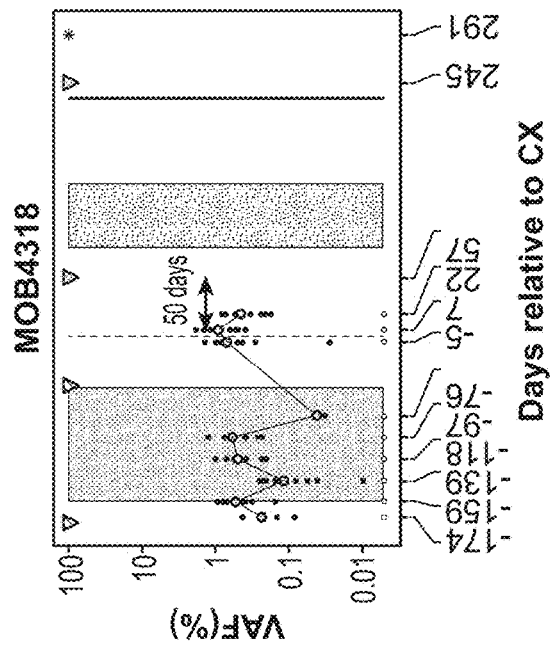
FIG. 76E
FIG. 76G

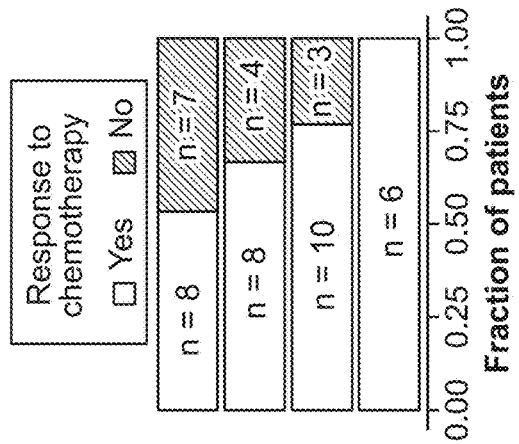
FIG. 78D
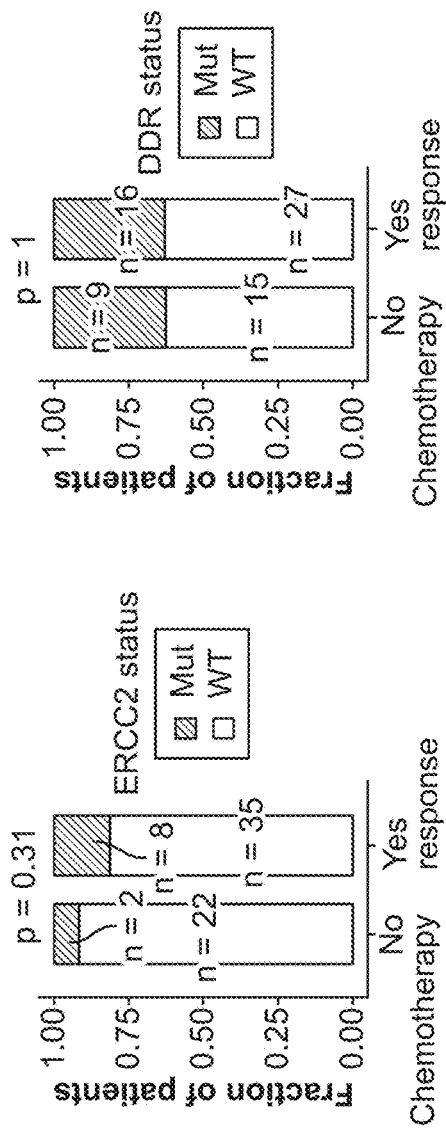
FIG. 78E
FIG. 78F
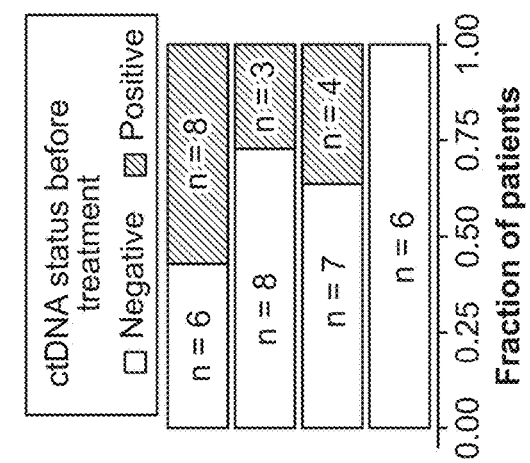
FIG. 78G
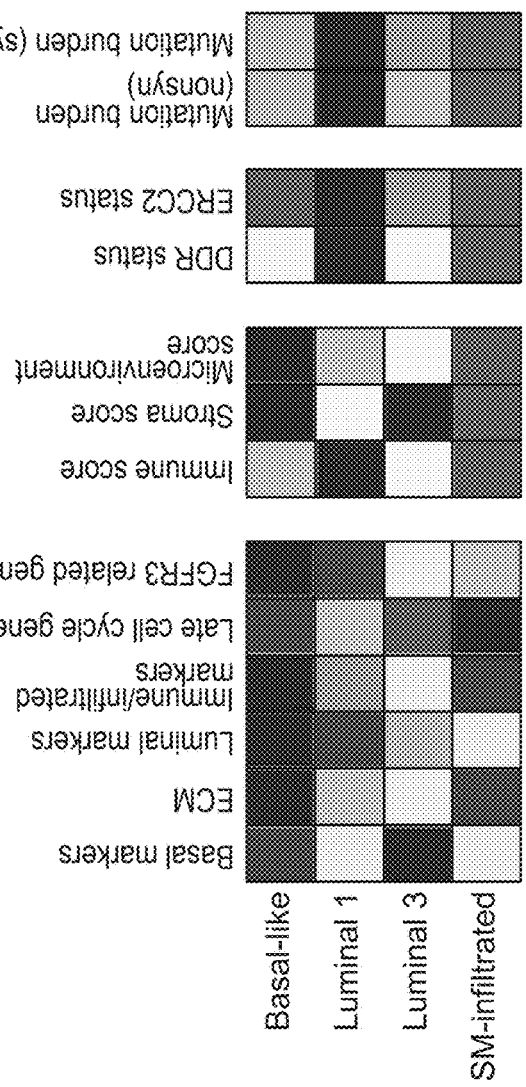
FIG. 78H

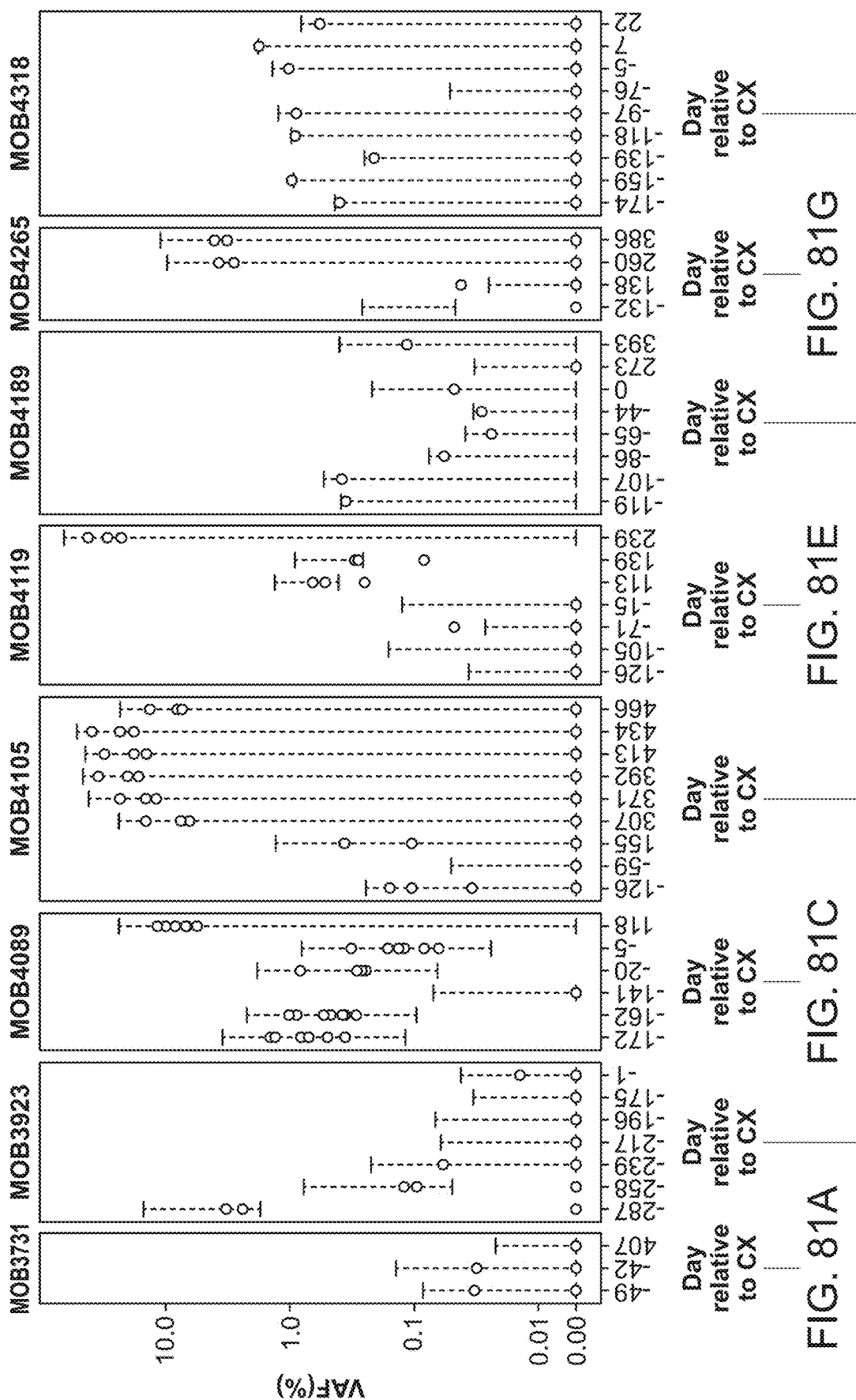

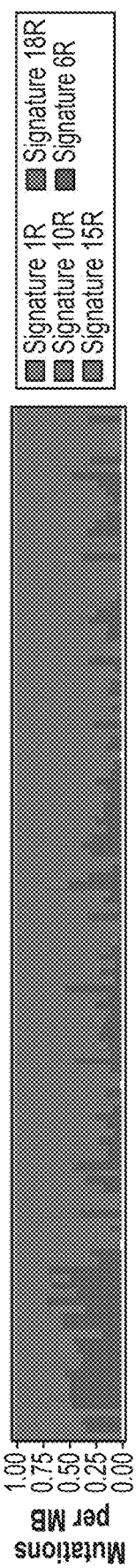
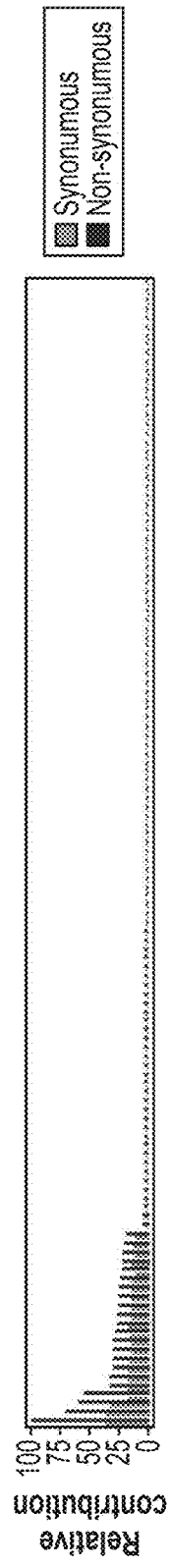
FIG. 83A
FIG. 83B

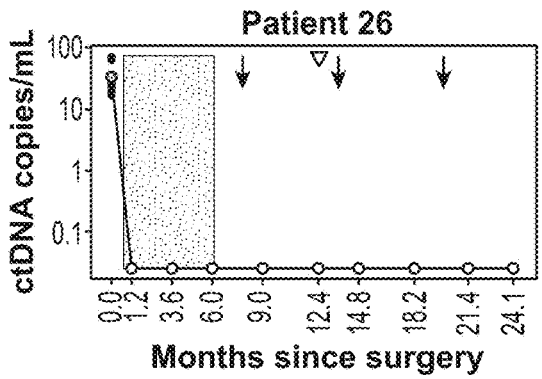
FIG. 86Y
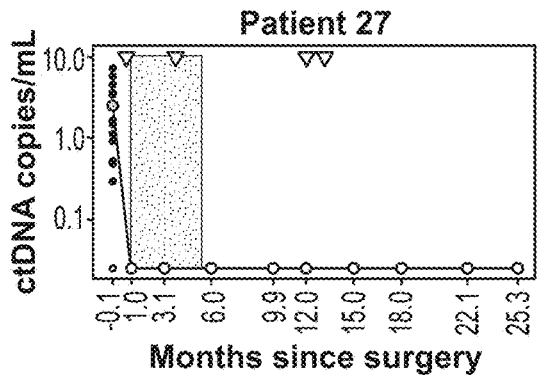
FIG. 86Z
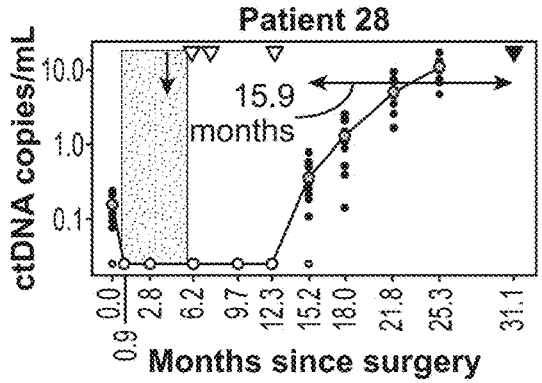
FIG. 86A1
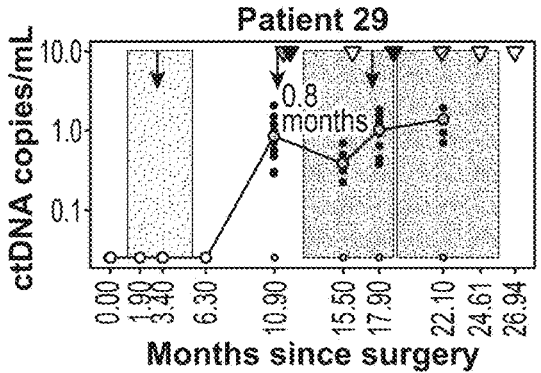
FIG. 86B1
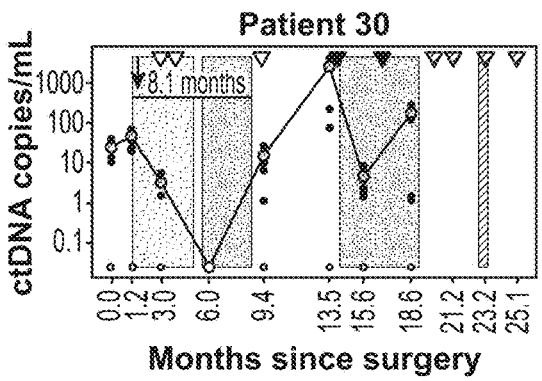
FIG. 86C1
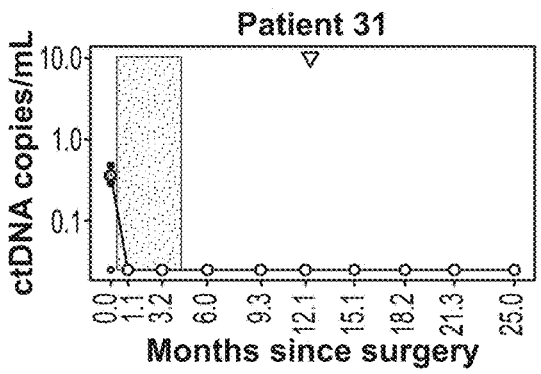
FIG. 86D1
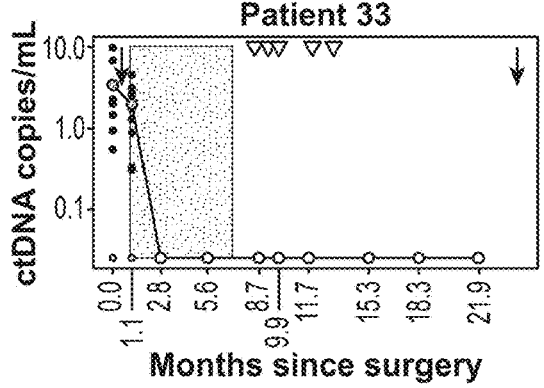
FIG. 86E1
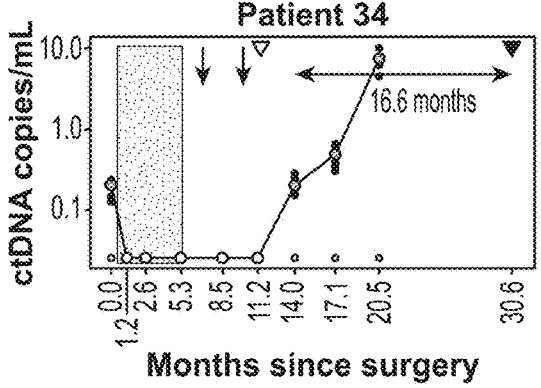
FIG. 86F1

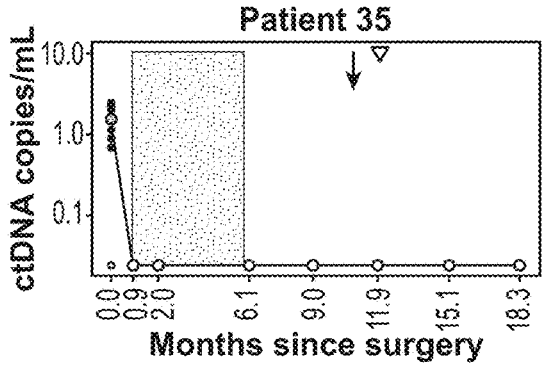
FIG. 86G1
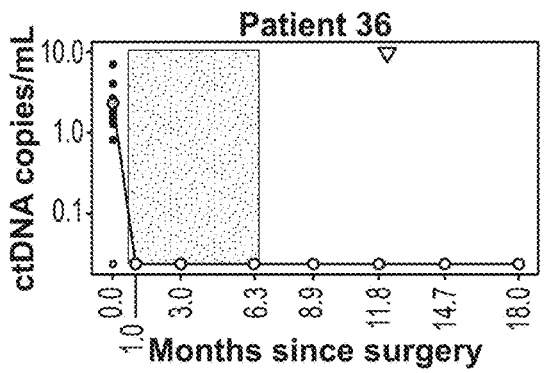
FIG. 86H1
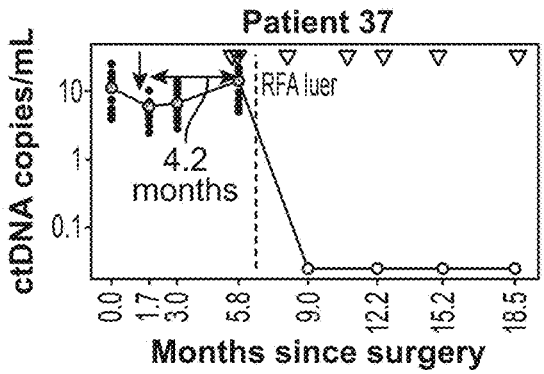
FIG. 86I1
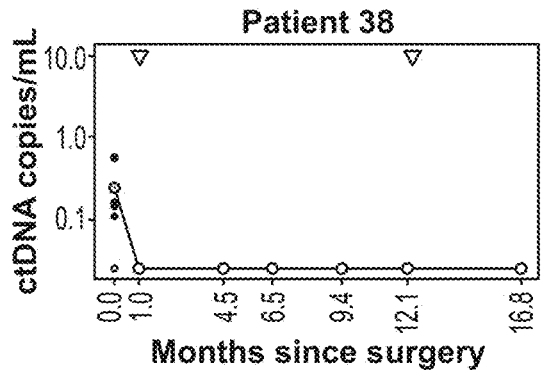
FIG. 86J1
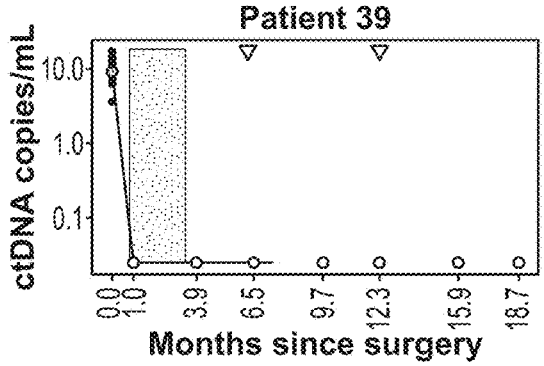
FIG. 86K1
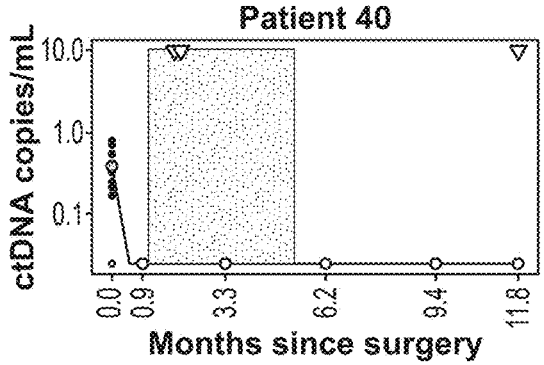
FIG. 86L1
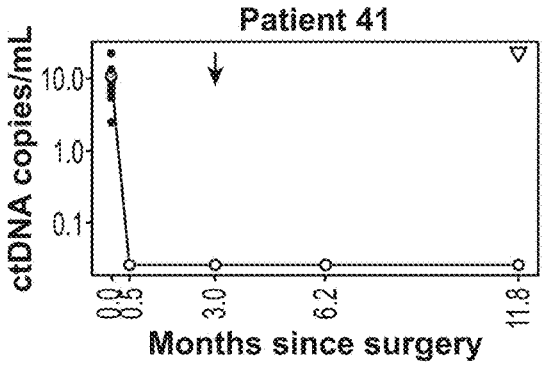
FIG. 86M1
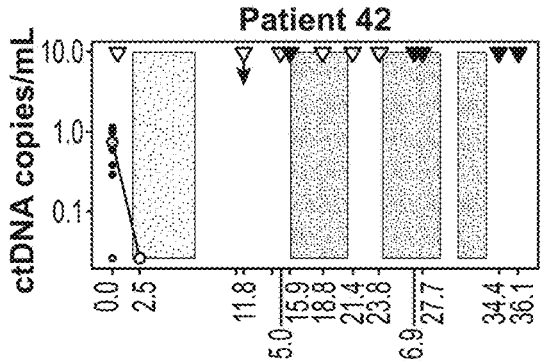
FIG. 86N1

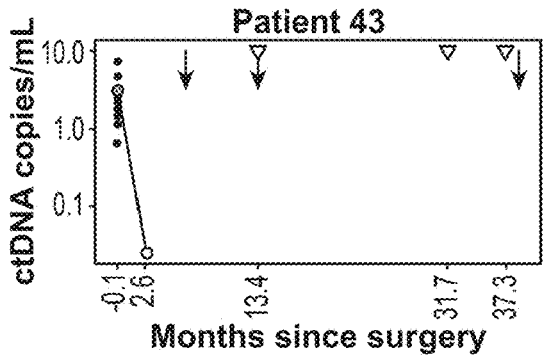
FIG. 86O1
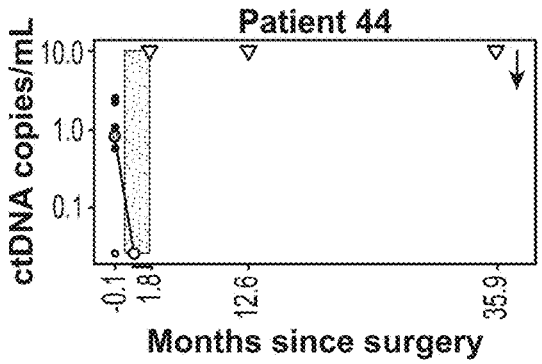
FIG. 86P1
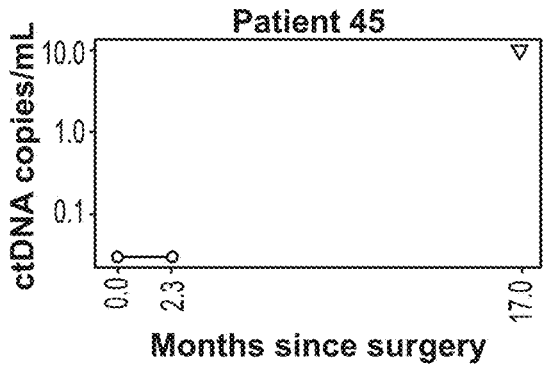
FIG. 86Q1
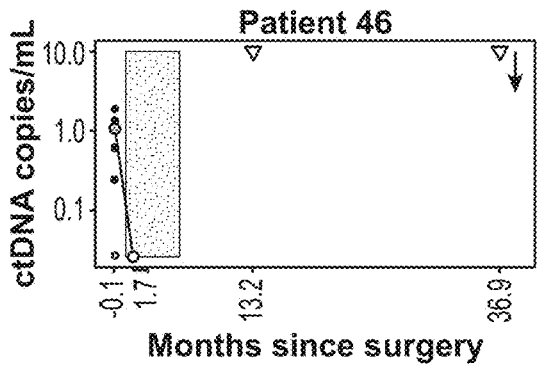
FIG. 86R1
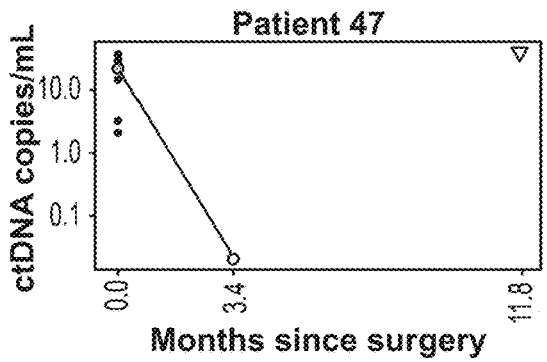
FIG. 86S1
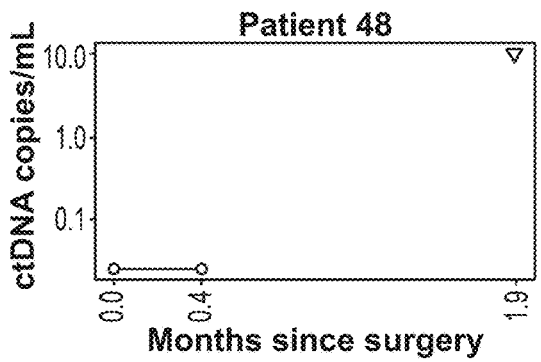
FIG. 86T1
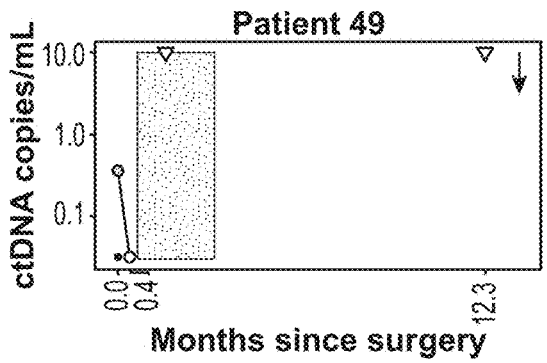
FIG. 86U1
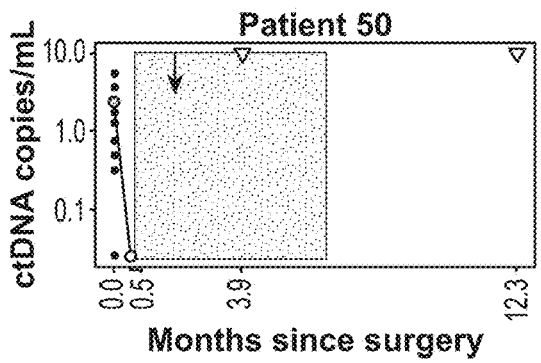
FIG. 86V1

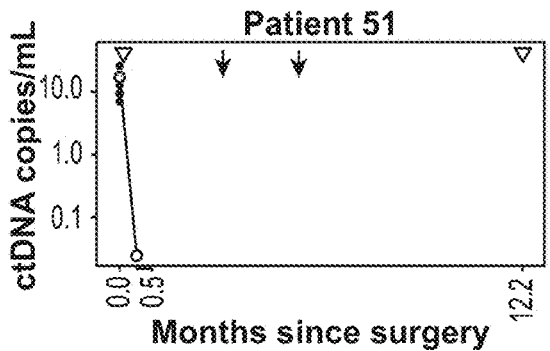
FIG. 86W1
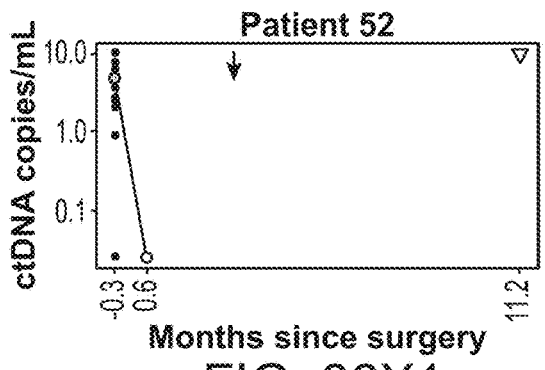
FIG. 86X1
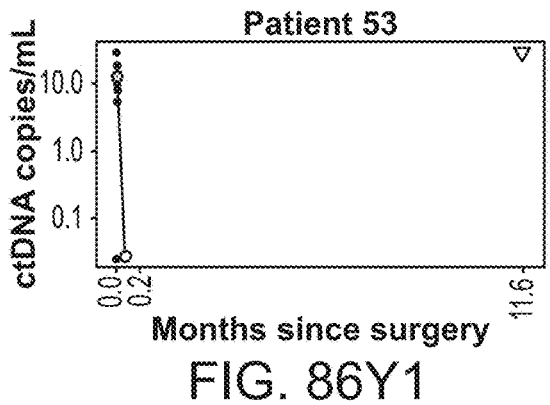
FIG. 86Y1
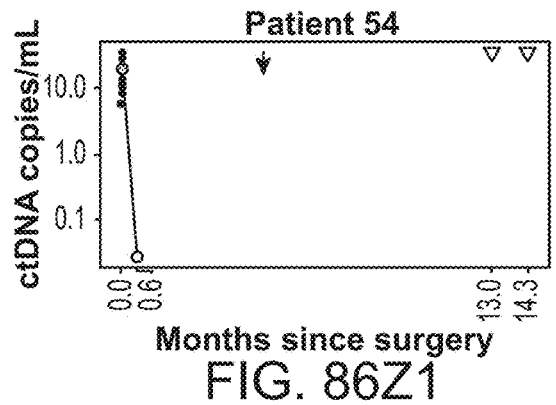
FIG. 86Z1
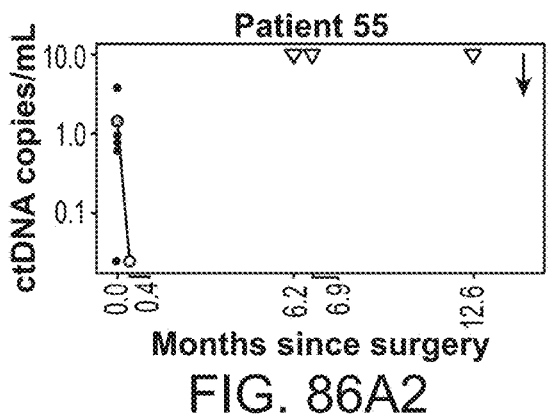
FIG. 86A2
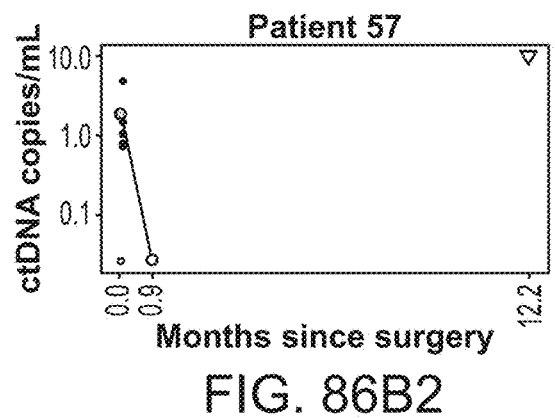
FIG. 86B2
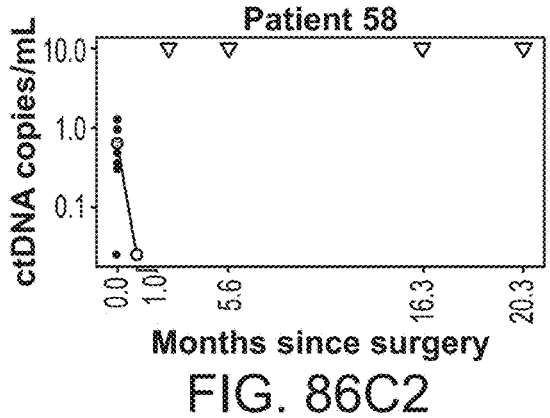
FIG. 86C2
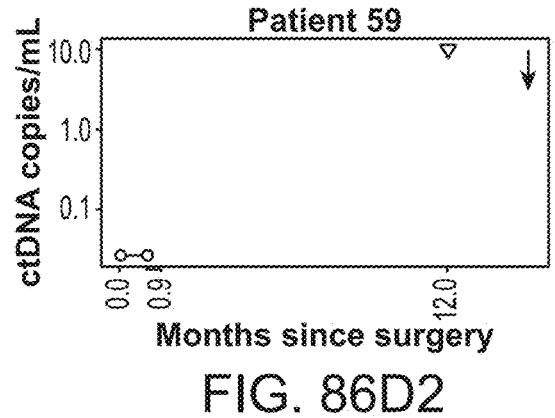
FIG. 86D2

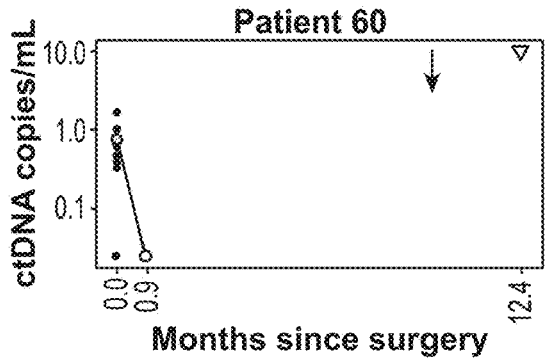
FIG. 86E2
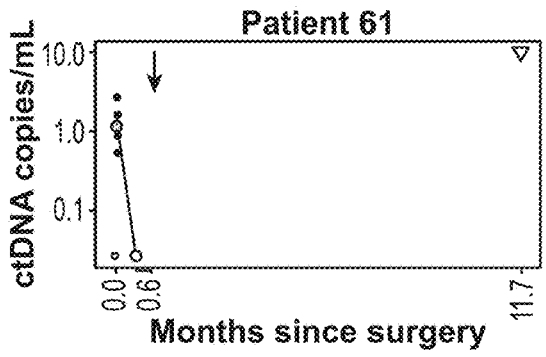
FIG. 86F2
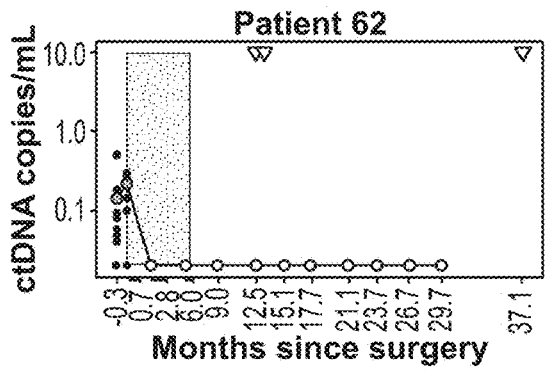
FIG. 86G2
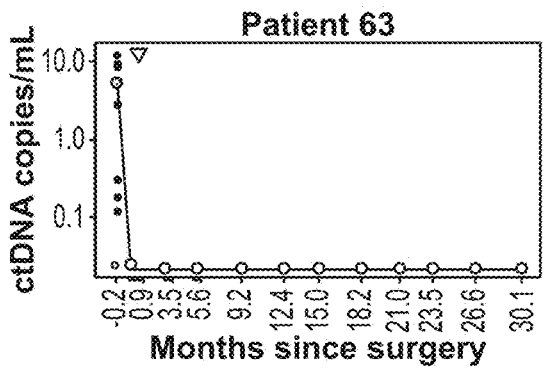
FIG. 86H2
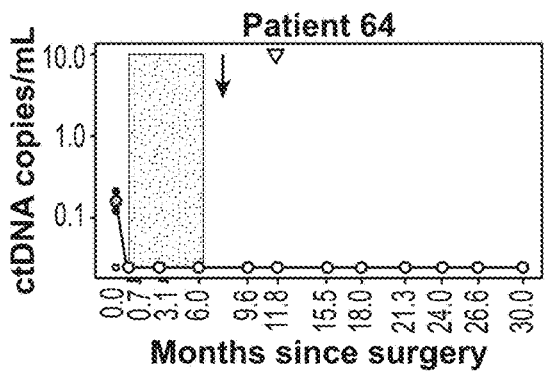
FIG. 86I2
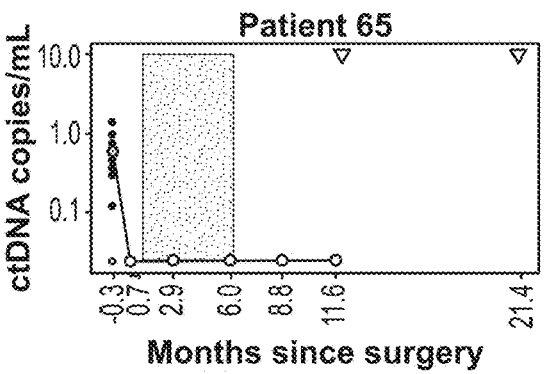
FIG. 86J2
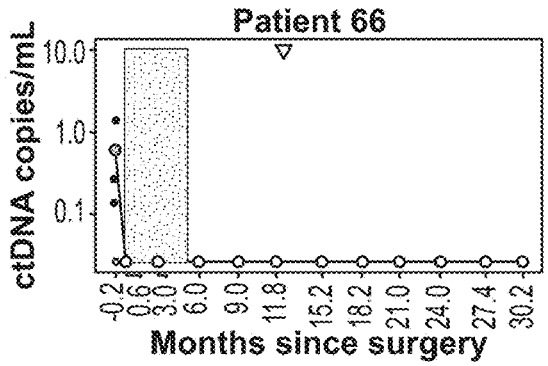
FIG. 86K2
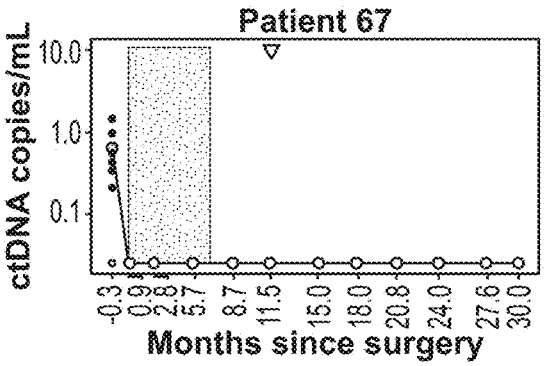
FIG. 86L2

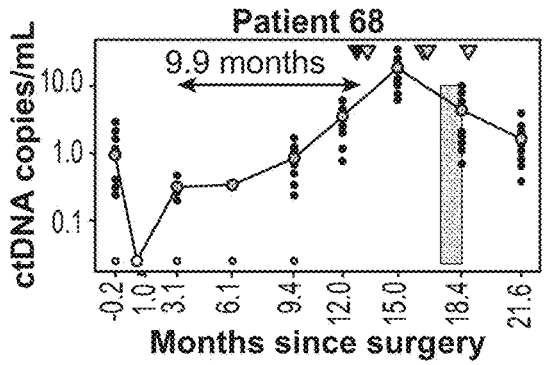
FIG. 86M2
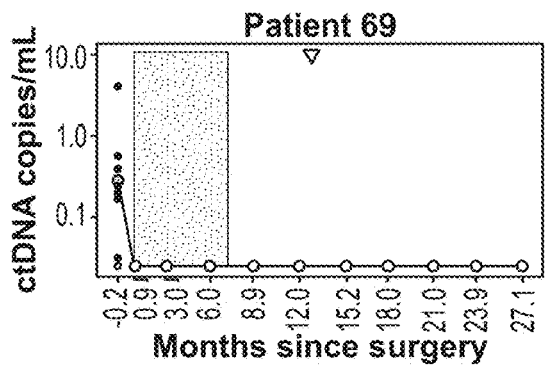
FIG. 86N2
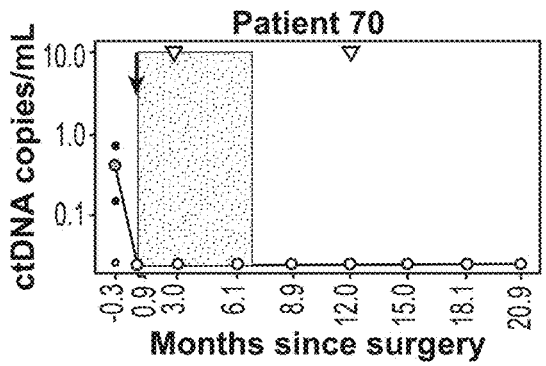
FIG. 86O2
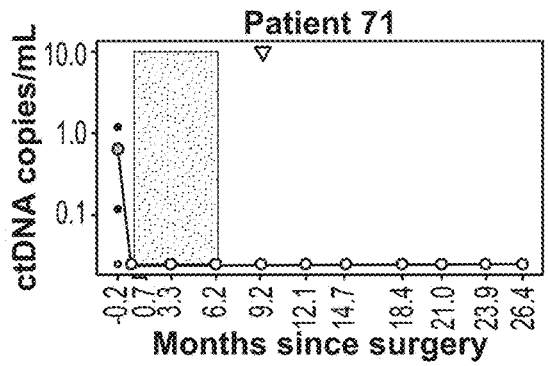
FIG. 86P2
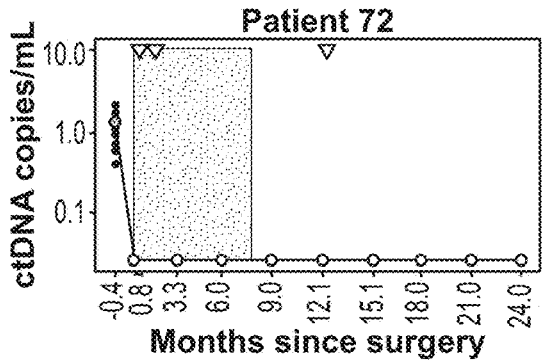
FIG. 86Q2
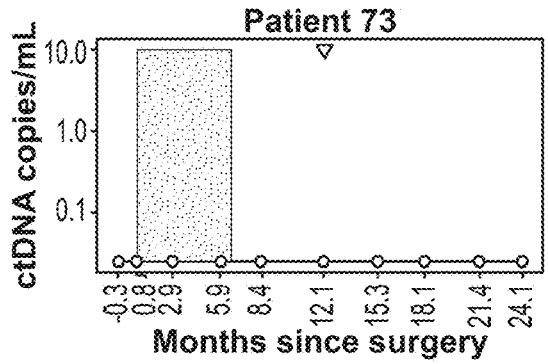
FIG. 86R2
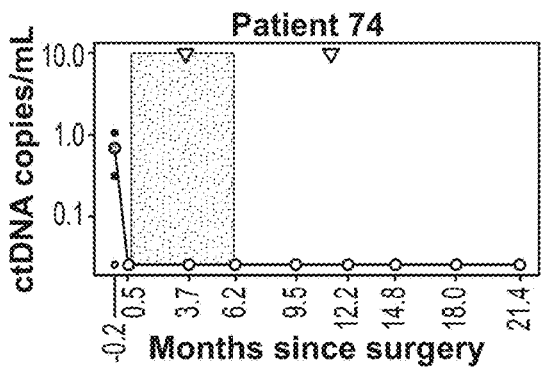
FIG. 86S2
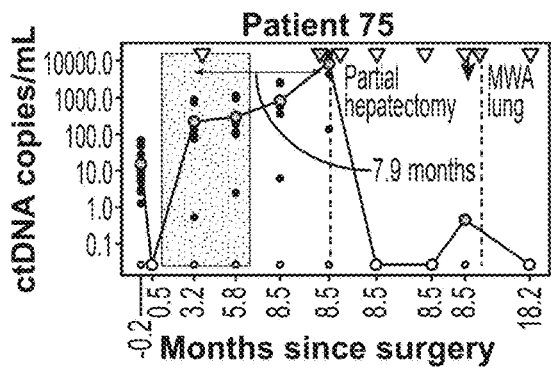
FIG. 86T2

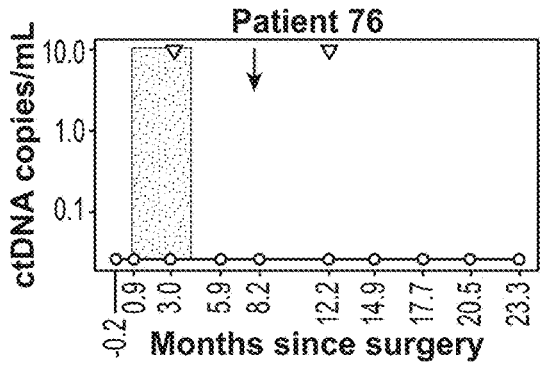
FIG. 86U2
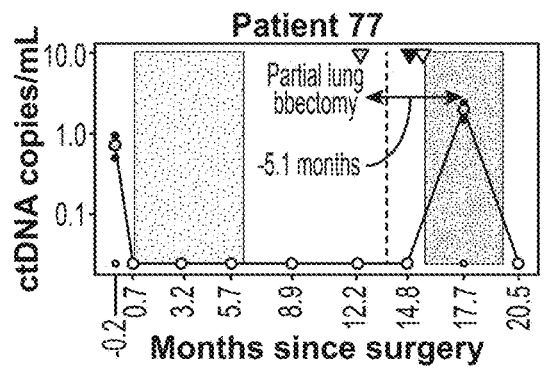
FIG. 86V2
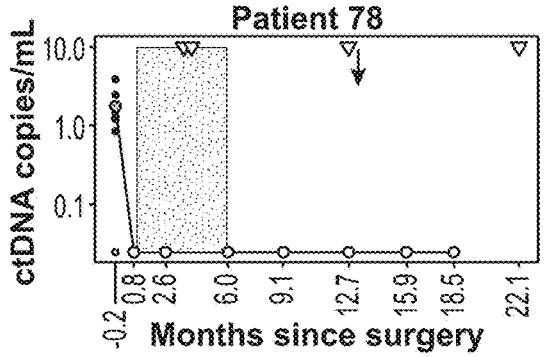
FIG. 86W2
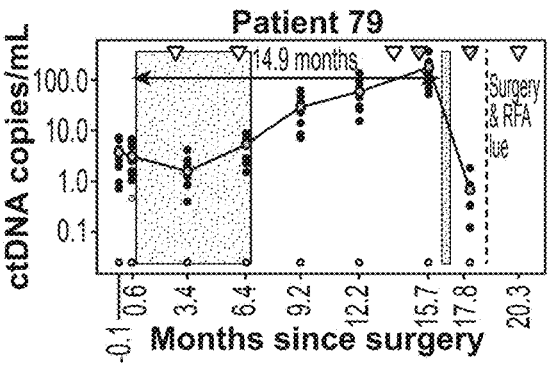
FIG. 86X2
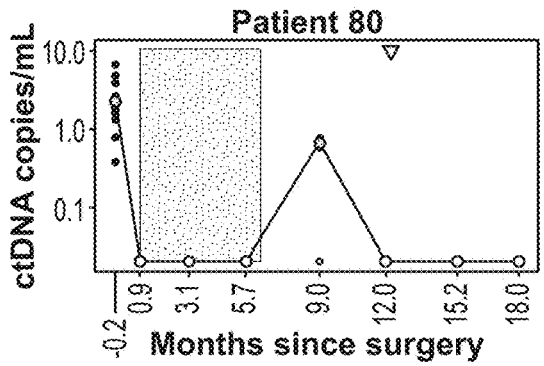
FIG. 86Y2
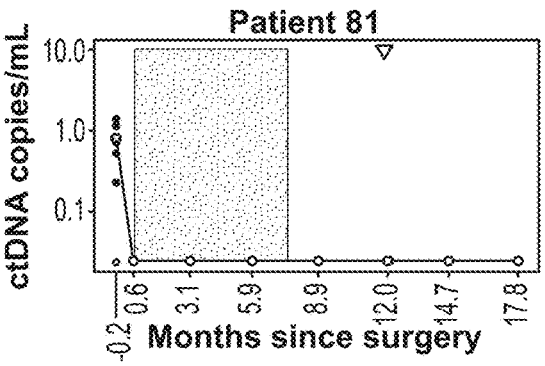
FIG. 86Z2
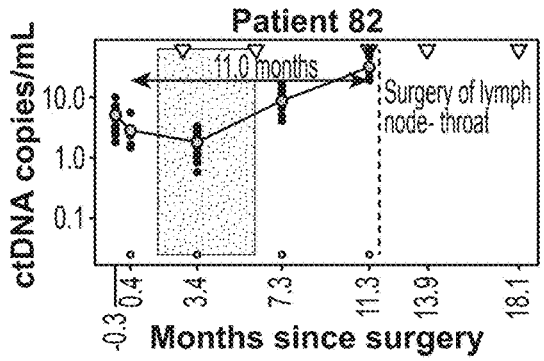
FIG. 86A3
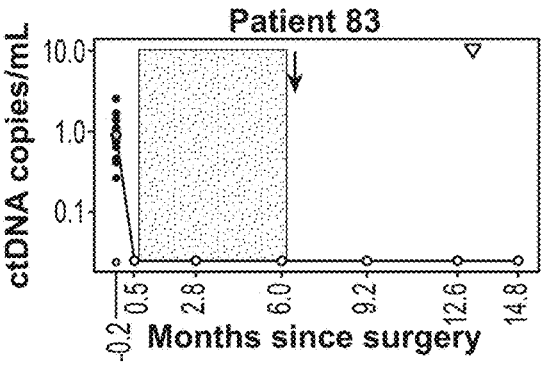
FIG. 86B3

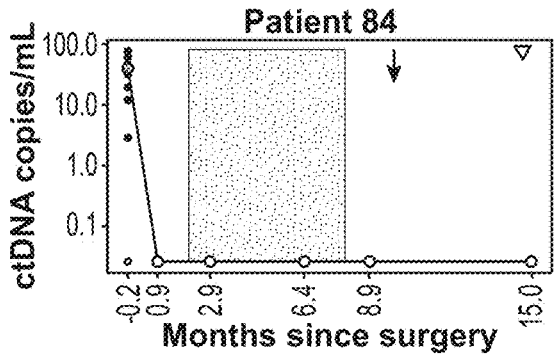
FIG. 86C3
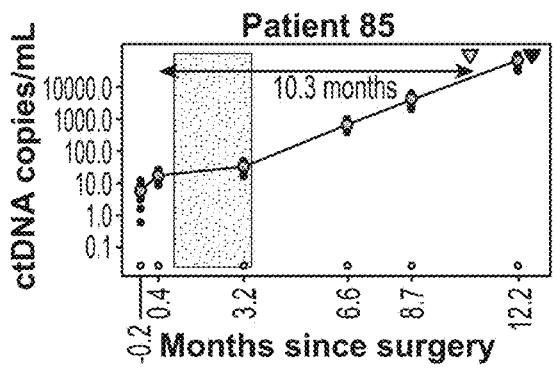
FIG. 86D3
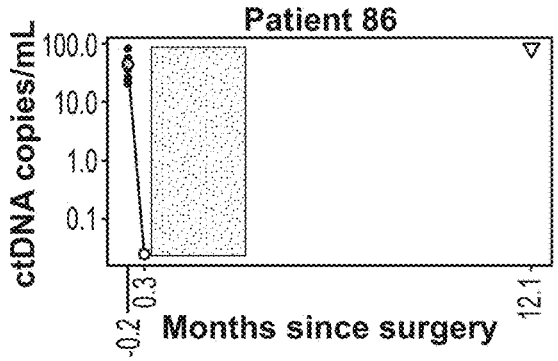
FIG. 86E3
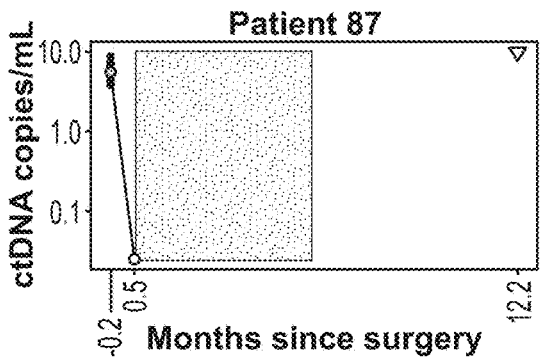
FIG. 86F3
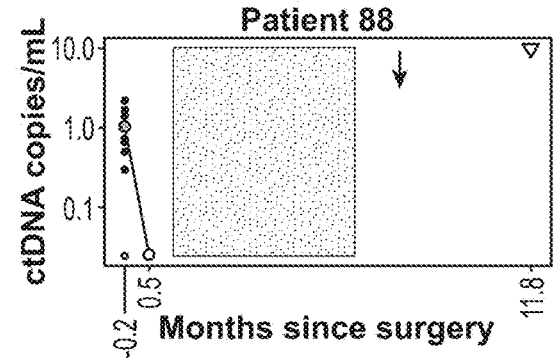
FIG. 86G3
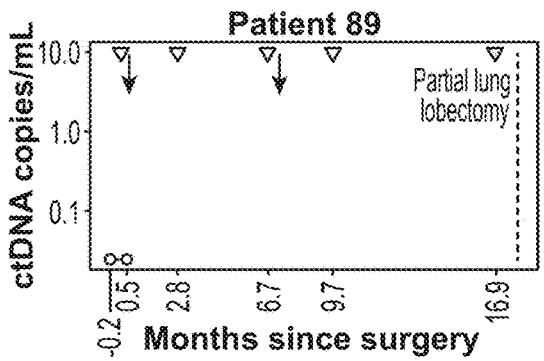
FIG. 86H3
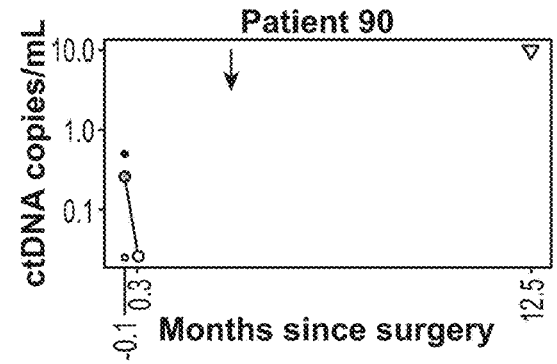
FIG. 86I3
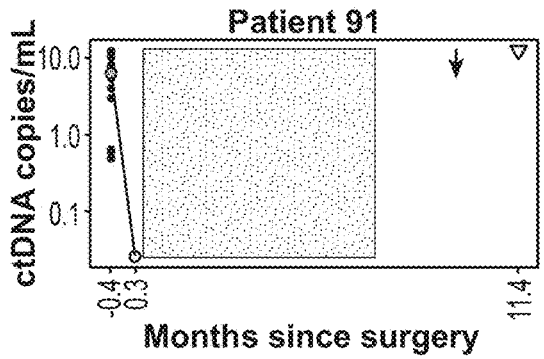
FIG. 86J3

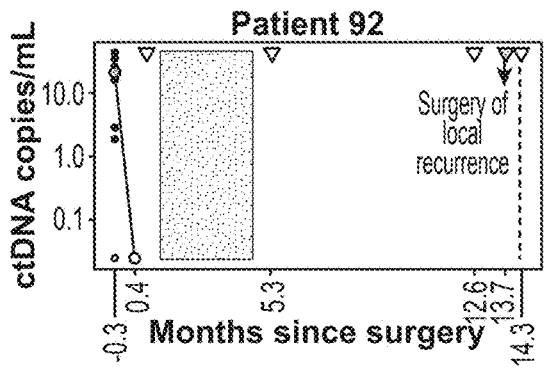
FIG. 86K3
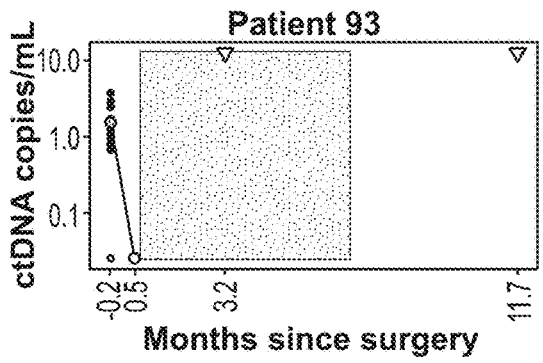
FIG. 86L3
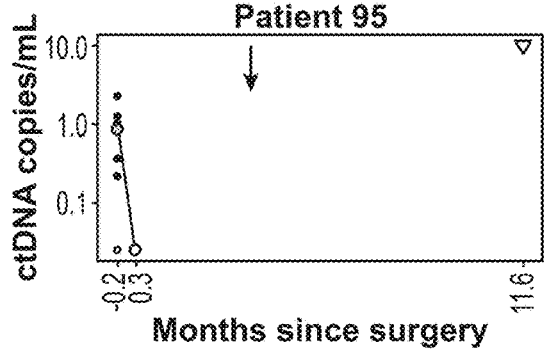
FIG. 86M3
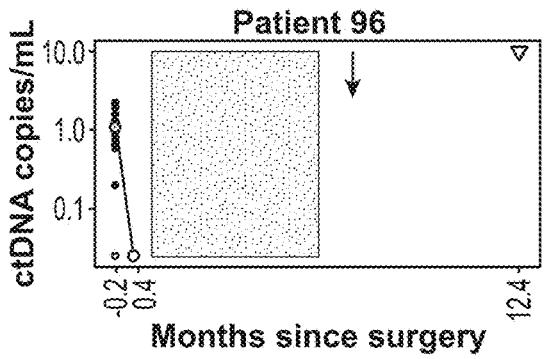
FIG. 86N3
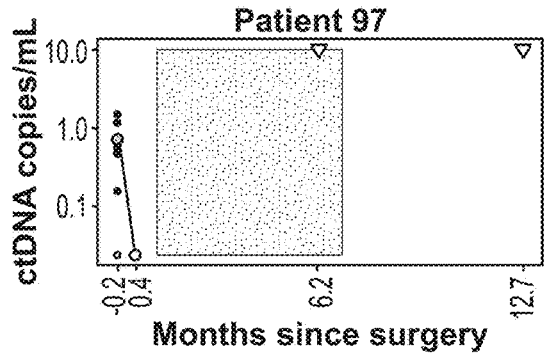
FIG. 86O3
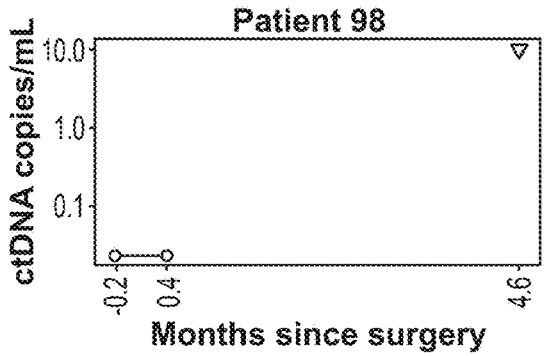
FIG. 86P3
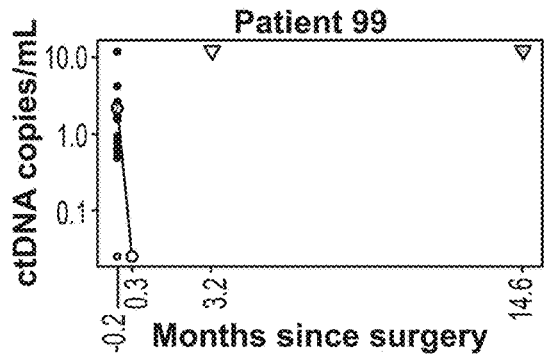
FIG. 86Q3
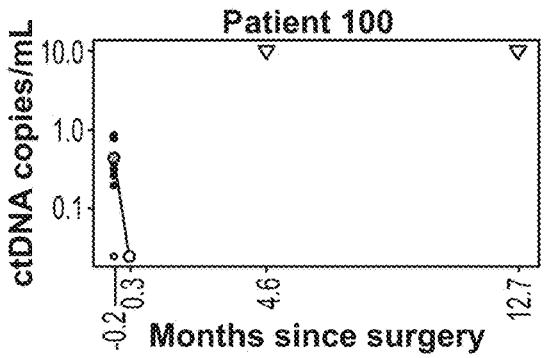
FIG. 86R3

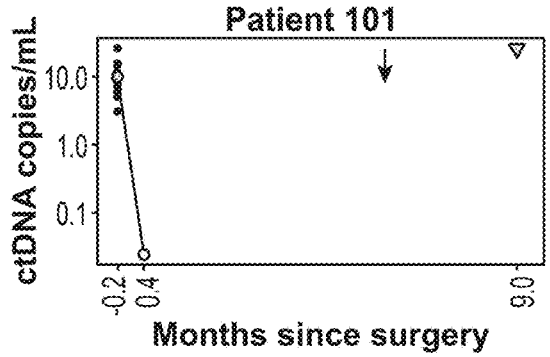
FIG. 86S3
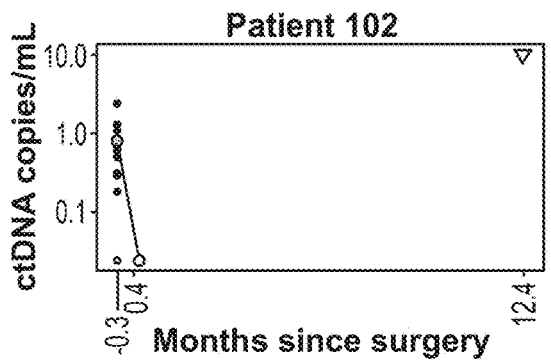
FIG. 86T3
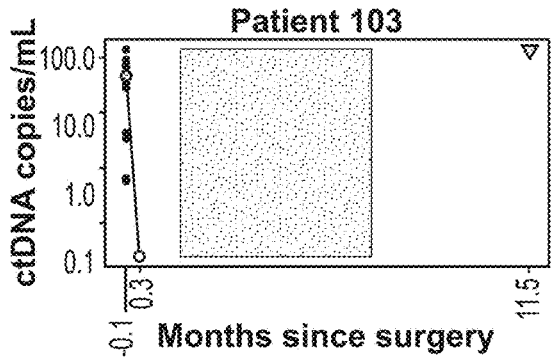
FIG. 86U3
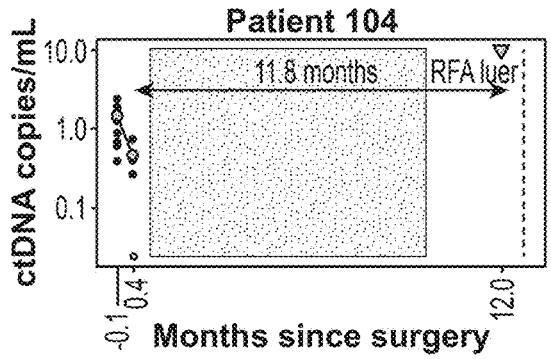
FIG. 86V3
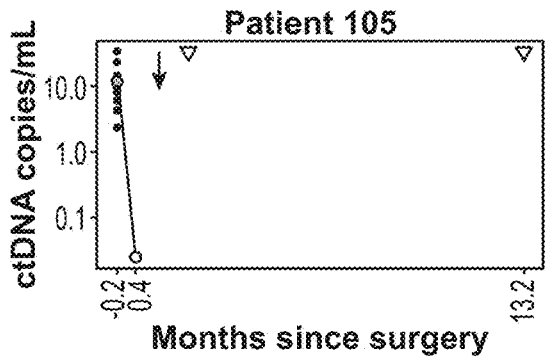
FIG. 86W3
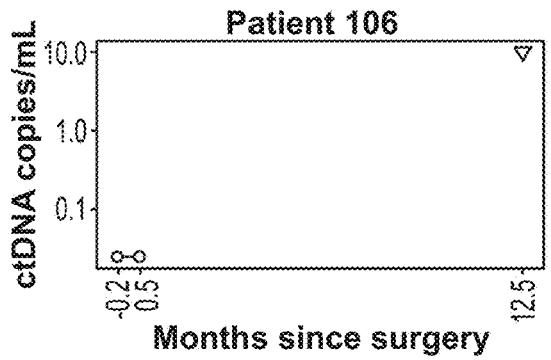
FIG. 86X3
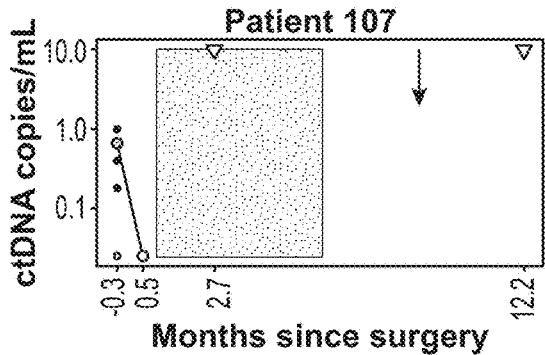
FIG. 86Y3
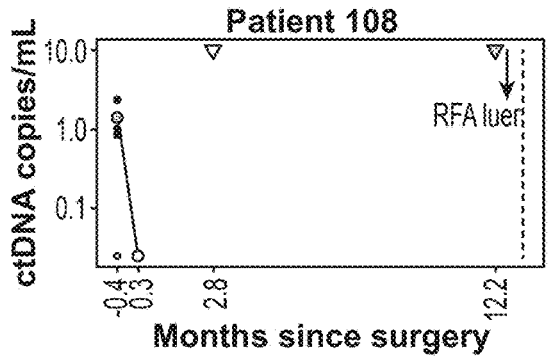
FIG. 86Z3

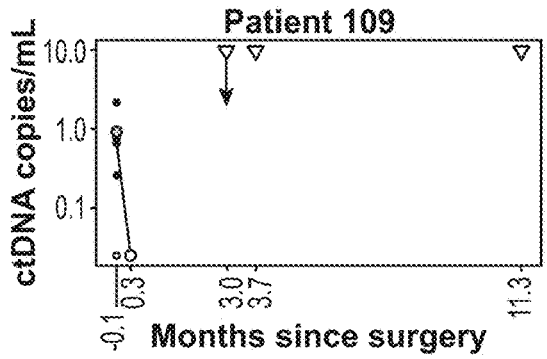
FIG. 86A4
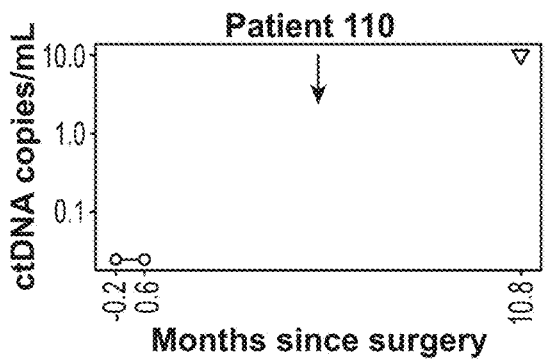
FIG. 86B4
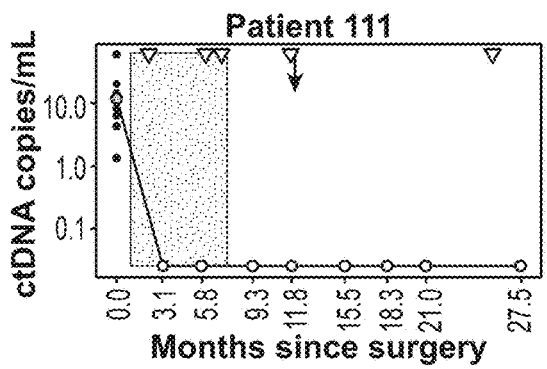
FIG. 86C4
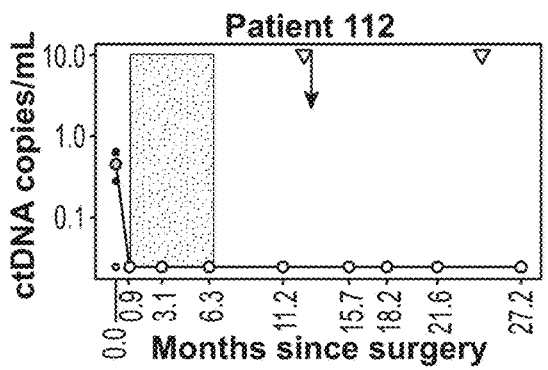
FIG. 86D4
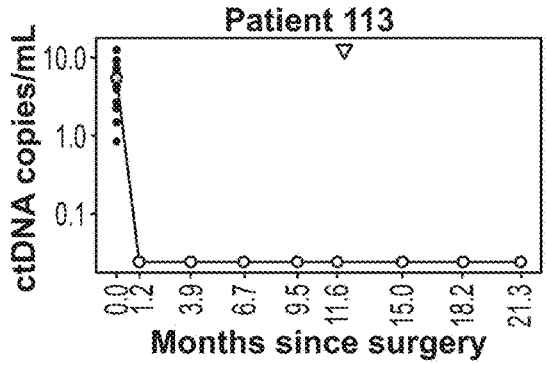
FIG. 86E4
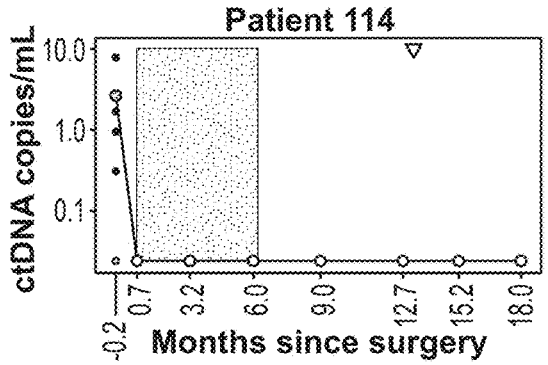
FIG. 86F4
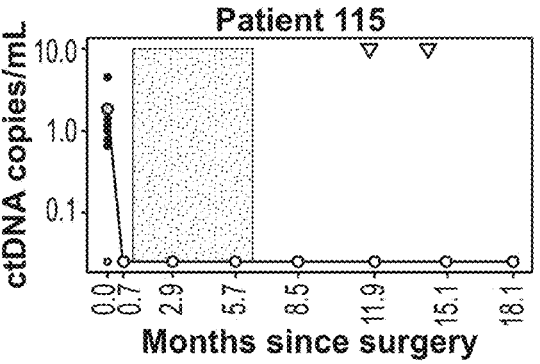
FIG. 86G4
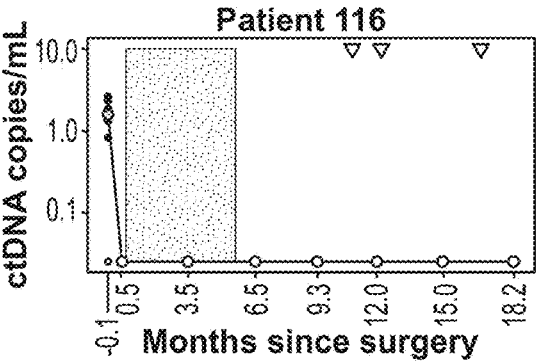
FIG. 86H4

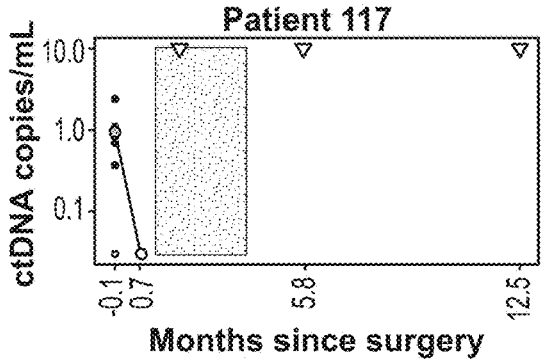
FIG. 86I4
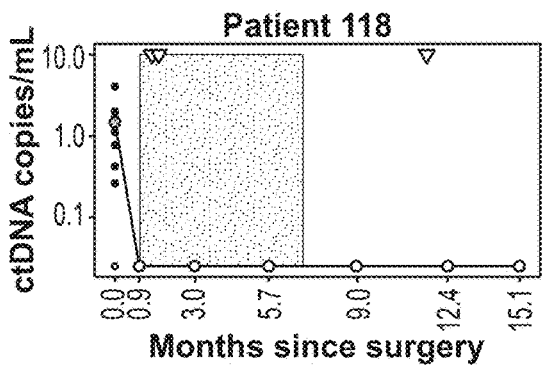
FIG. 86J4
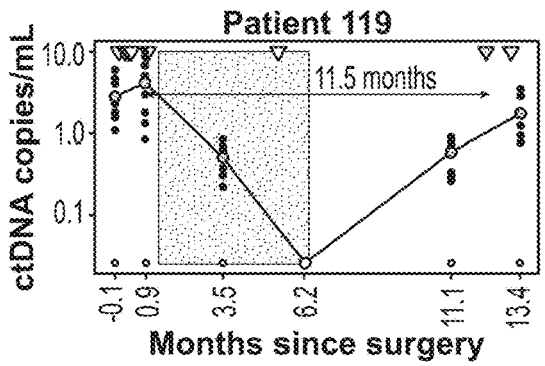
FIG. 86K4
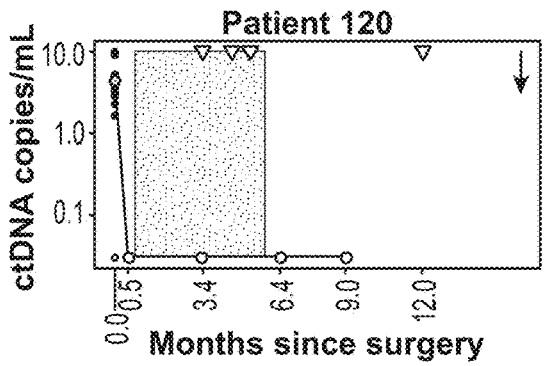
FIG. 86L4
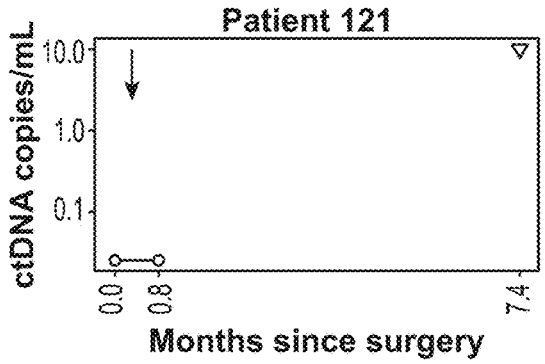
FIG. 86M4
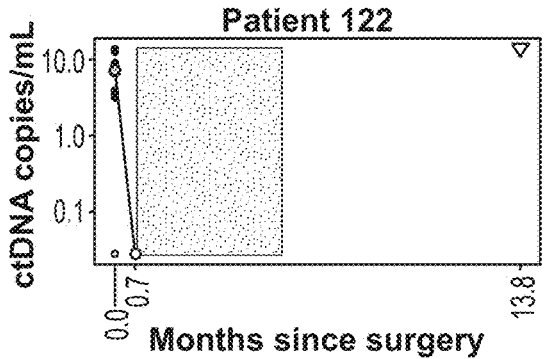
FIG. 86N4
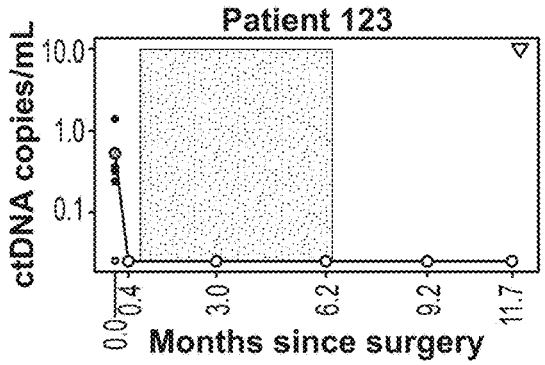
FIG. 86O4
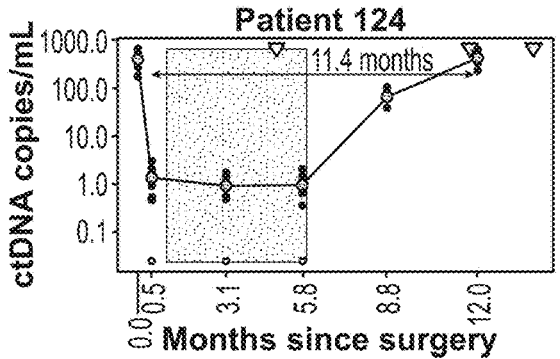
FIG. 86P4

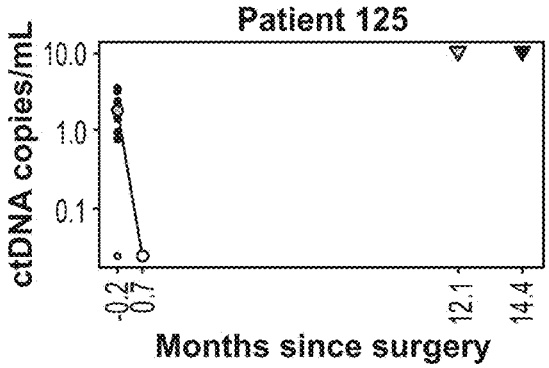
FIG. 86Q4
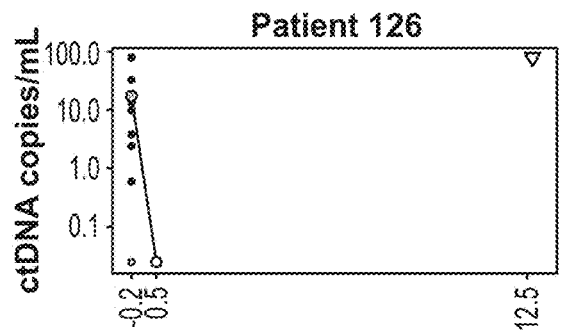
FIG. 86R4
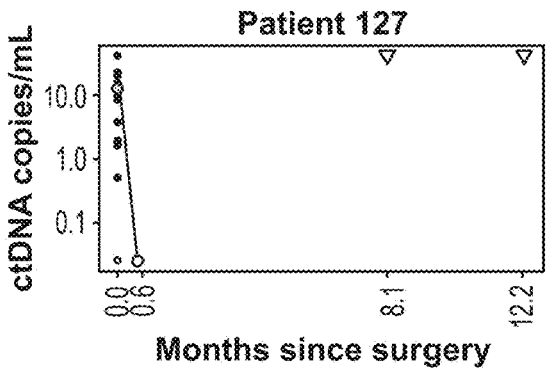
FIG. 86S4
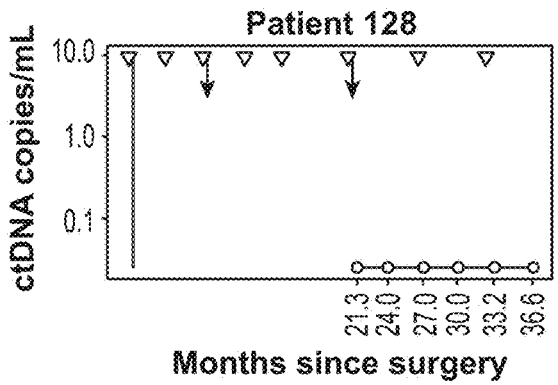
FIG. 86T4
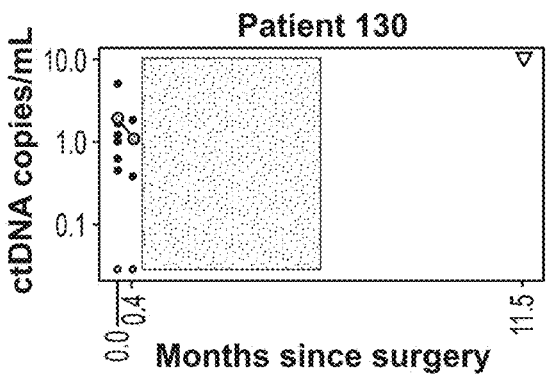
FIG. 86U4

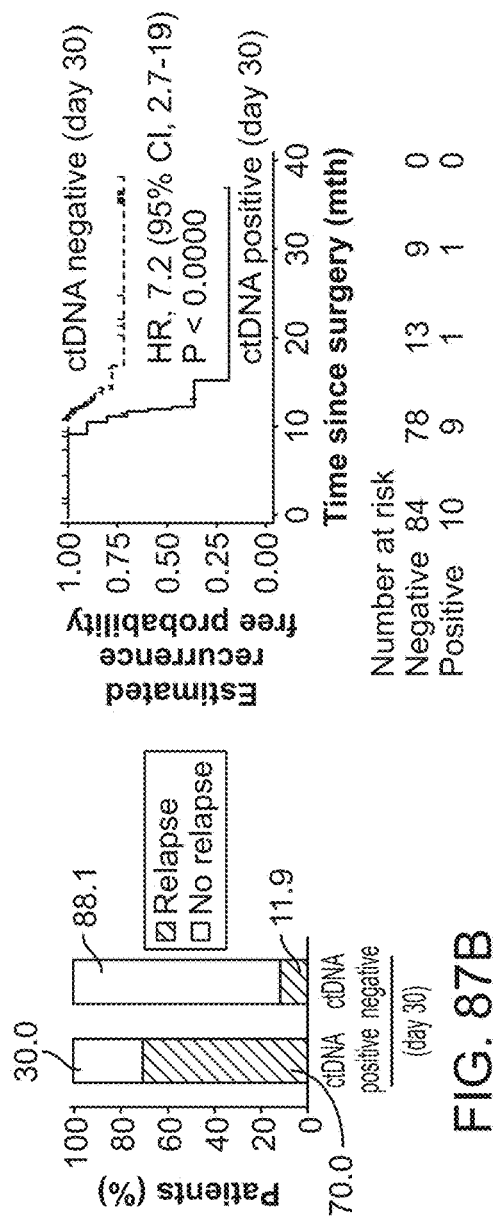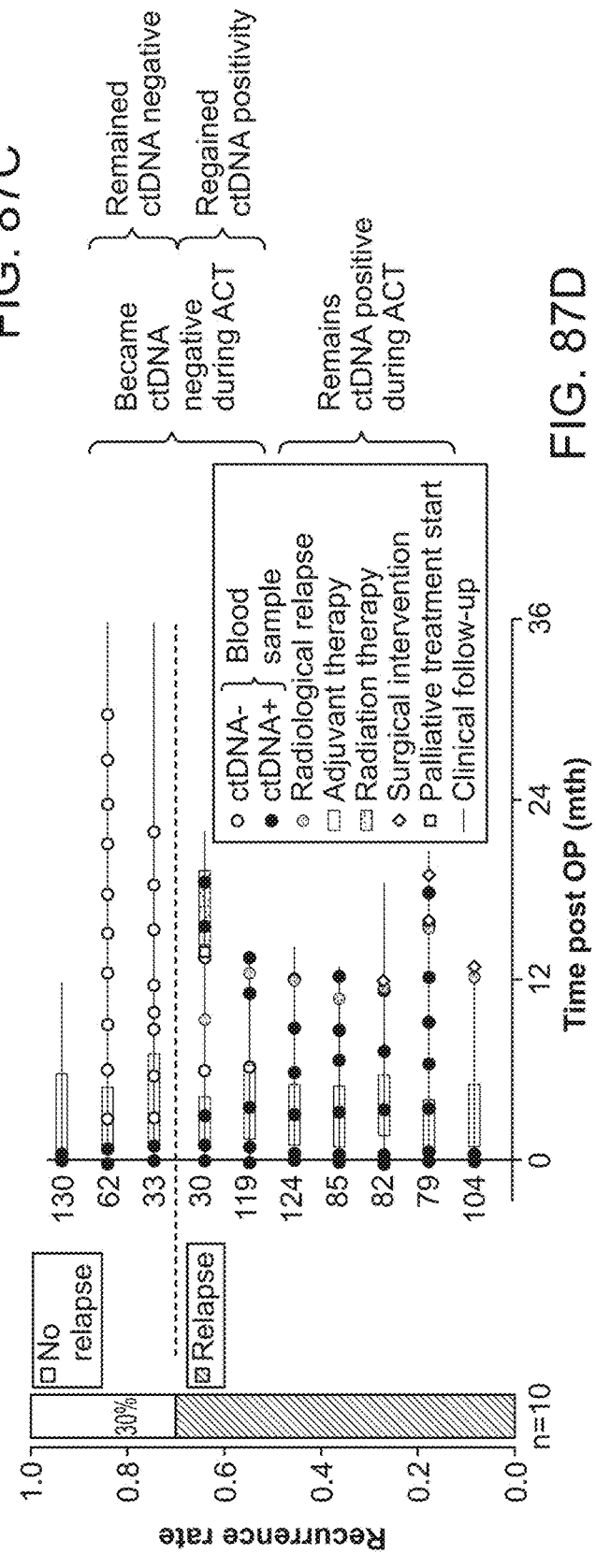
FIG. 87A
FIG. 87B
FIG. 87C
FIG. 87D

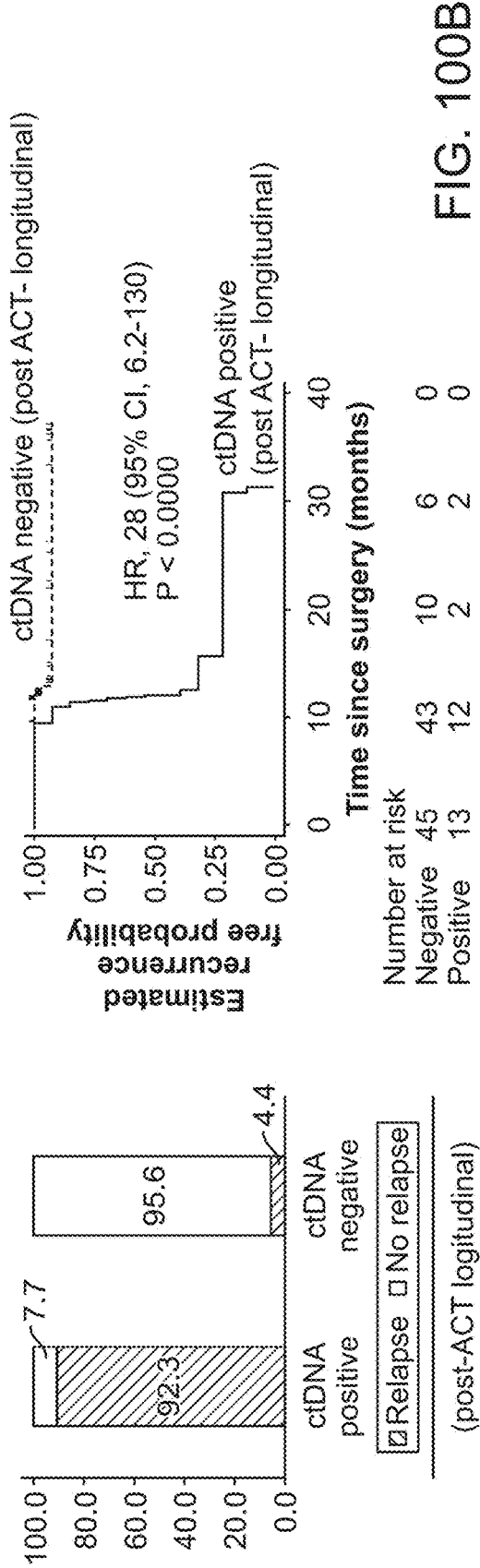
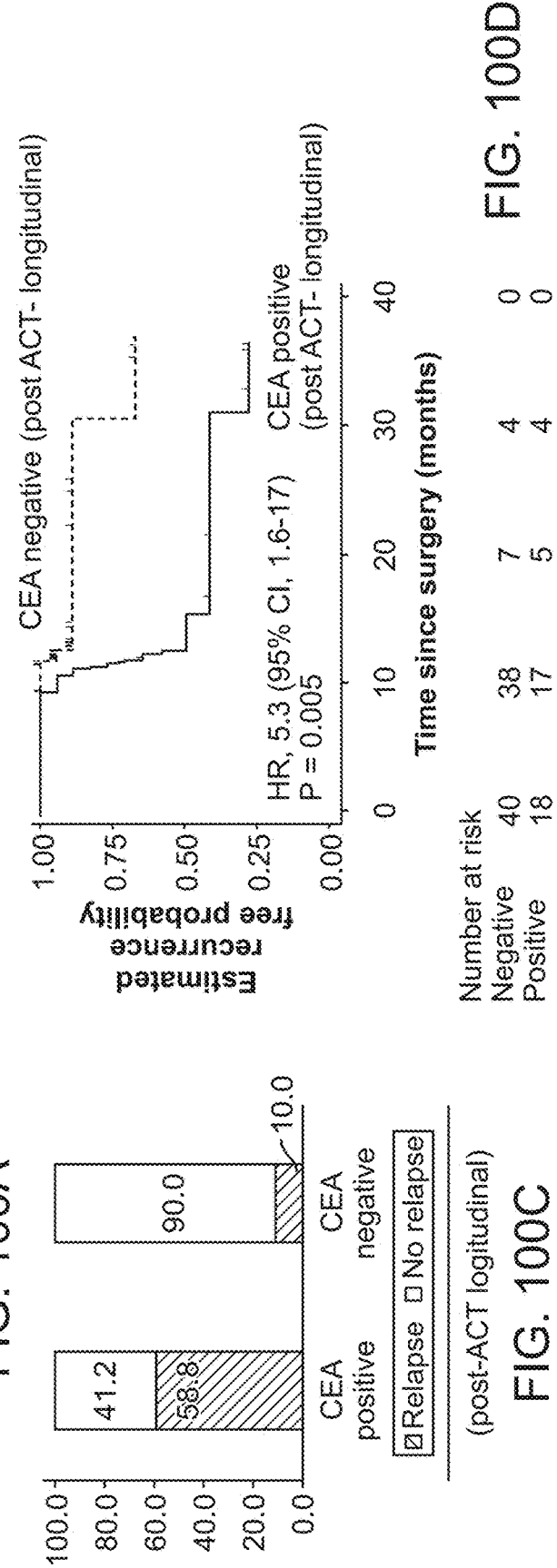
FIG. 100A
FIG. 100B
FIG. 100C
FIG. 100D

METHODS FOR CANCER DETECTION AND MONITORING

CROSS REFERENCE TO RELATED APPLICATIONS

This application is a continuation of U.S. application Ser. No. 16/382,520 filed Apr. 14, 2019. U.S. application Ser. No. 16/382,520 claims priority to U.S. Provisional Application No. 62/657,727 filed Apr. 14, 2018; U.S. Provisional Application No. 62/669,330 filed May 9, 2018; U.S. Provisional Application No. 62/693,843 filed Jul. 3, 2018; U.S. Provisional Application No. 62/715,143 filed Aug. 6, 2018; U.S. Provisional Application No. 62/746,210 filed Oct. 16, 2018; U.S. Provisional Application No. 62/777,973 filed Dec. 11, 2018; and U.S. Provisional Application No. 62/804,566 filed Feb. 12, 2019. Each of these applications cited above is hereby incorporated by reference in its entirety.

BACKGROUND OF THE INVENTION

Detection of early relapse or metastasis of cancers has traditionally relied on imaging and tissue biopsy. The biopsy of tumor tissue is invasive and carries risk of potentially contributing to metastasis or surgical complications, while imaging-based detection is not sufficiently sensitive to detect relapse or metastasis in an early stage. Better and less invasive methods are needed for detecting relapse or metastasis of cancers.

SUMMARY OF THE INVENTION

One aspect of the invention described herein relates to a method for monitoring and detection of early relapse or metastasis of cancer (e.g., breast cancer, bladder cancer, or colorectal cancer), comprising generating a set of amplicons by performing a multiplex amplification reaction on nucleic acids isolated from a sample of blood or urine or a fraction thereof from a patient who has been treated for a cancer (e.g., breast cancer, bladder cancer, or colorectal cancer), wherein each amplicon of the set of amplicons spans at least one single nucleotide variant locus of a set of patient-specific single nucleotide variant loci associated with the cancer (e.g., breast cancer, bladder cancer, or colorectal cancer); and determining the sequence of at least a segment of each amplicon of the set of amplicons that comprises a patient-specific single nucleotide variant locus, wherein detection of one or more (or two or more, or three or more, or four or more, or five or more, or six or more, or seven or more, or eight or more, or nine or more, or ten or more) patient-specific single nucleotide variants is indicative of early relapse or metastasis of cancer (e.g., breast cancer, bladder cancer, or colorectal cancer).

In addition to breast cancer, bladder cancer, and colorectal cancer, the methods described herein can also be used for monitoring and detection of early relapse or metastasis of other types of cancer, such as: acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor.

In some embodiments, nucleic acids are isolated from a tumor of the patient and somatic mutations are identified in the tumor for the set of patient-specific single nucleotide variant loci before determining the sequence of at least a segment of each amplicon of the set of amplicons for the sample of blood or urine or fraction thereof, and wherein the single nucleotide variants.

In some embodiments, the method comprising collecting and sequencing blood or urine samples from the patient longitudinally.

In some embodiments, at least 2 or at least 5 SNVs are detected and the presence of the at least 2 or at least 5 SNVs is indicative of early relapse or metastasis of breast cancer, bladder cancer, or colorectal cancer.

In some embodiments, the breast cancer, bladder cancer, or colorectal cancer is a stage 1 or stage 2 breast cancer, bladder cancer, or colorectal cancer. In some embodiments, the breast cancer, bladder cancer, or colorectal cancer is a stage 3 or stage 4 breast cancer, bladder cancer, or colorectal cancer.

In some embodiments, the individual has been treated with surgery before isolation of the blood or urine sample.

In some embodiments, the individual has been treated with chemotherapy before isolation of the blood or urine sample.

In some embodiments, the individual has been treated with an adjuvant or neoadjuvant before isolation of the blood or urine sample.

In some embodiments, the individual has been treated with radiotherapy before isolation of the blood or urine sample.

In some embodiments, the method further comprises comprising administering a compound to the individual, where the compound is known to be specifically effective in treating breast cancer, bladder cancer, or colorectal cancer having one or more of the determined single nucleotide variants.

In some embodiments, the method further comprises determining the variant allele frequency for each of the single nucleotide variants from the sequence determination.

In some embodiments, a breast cancer, bladder cancer, or colorectal cancer treatment plan is identified based on the variant allele frequency determinations.

In some embodiments, the method further comprises administering a compound to the individual, where the compound is known to be specifically effective in treating breast cancer, bladder cancer, or colorectal cancer having one of the single nucleotide variants with a variable allele frequency greater than at least one half of the other single nucleotide variants that were determined.

In some embodiments, the sequence is determined by high throughput DNA sequencing of the plurality of single nucleotide variance loci.

In some embodiments, the method further comprises detecting a clonal single nucleotide variant in the breast cancer, bladder cancer, or colorectal cancer by determining the variant allele frequency for each of the SNV loci based on the sequence of the plurality of copies of the series of amplicons, wherein a higher relative allele frequency compared to the other single nucleotide variants of the plurality of single nucleotide variant loci is indicative of a clonal single nucleotide variant in the breast cancer, bladder cancer, or colorectal cancer.

In some embodiments, the method further comprises administering a compound to the individual that targets the one or more clonal single nucleotide variants, but not the other single nucleotide variants.

In some embodiments, a variant allele frequency of greater than 1.0% is indicative a clonal single nucleotide variant.

In some embodiments, the method further comprises forming an amplification reaction mixture by combining a polymerase, nucleotide triphosphates, nucleic acid fragments from a nucleic acid library generated from the sample, and a set of primers that each binds within 150 base pairs of a single nucleotide variant loci, or a set of primer pairs that each span a region of 160 base pairs or less comprising a single nucleotide variant loci, and subjecting the amplification reaction mixture to amplification conditions to generate the set of amplicons.

In some embodiments, determining whether a single nucleotide variant is present in the sample, comprises identifying a confidence value for each allele determination at each of the set of single nucleotide variance loci based at least in part on a depth of read for the loci.

In some embodiments, a single nucleotide variant call is made if the confidence value for the presence a single nucleotide variant is greater than 90%.

In some embodiments, a single nucleotide variant call is made if the confidence value for the presence a single nucleotide variant is greater than 95%.

In some embodiments, the set of single nucleotide variance loci comprises all of the single nucleotide variance loci identified in the TCGA and COSMIC data sets for breast cancer, bladder cancer, or colorectal cancer.

In some embodiments, the set of single nucleotide variance sites comprises all of the single nucleotide variance sites identified in the TCGA and COSMIC data sets for breast cancer, bladder cancer, or colorectal cancer.

In some embodiments, the method is performed with a depth of read for the set of single nucleotide variance loci of at least 1,000.

In some embodiments, the set of single nucleotide variant loci comprises 25 to 1000 single nucleotide variance loci known to be associated with breast cancer, bladder cancer, or colorectal cancer.

In some embodiments, an efficiency and an error rate per cycle are determined for each amplification reaction of the multiplex amplification reaction of the single nucleotide variance loci, and the efficiency and the error rate are used to determine whether a single nucleotide variant at the set of single variant loci is present in the sample.

In some embodiments, the amplification reaction is a PCR reaction and the annealing temperature is between 1 and 15° C. greater than the melting temperature of at least 50% of the primers of the set of primers.

In some embodiments, the amplification reaction is a PCR reaction and the length of the annealing step in the PCR reaction is between 15 and 120 minutes.

In some embodiments, the amplification reaction is a PCR reaction and the length of the annealing step in the PCR reaction is between 15 and 120 minutes.

In some embodiments, the primer concentration in the amplification reaction is between 1 and 10 nM.

In some embodiments, the primers in the set of primers, are designed to minimize primer dimer formation.

In some embodiments, the amplification reaction is a PCR reaction, the annealing temperature is between 1 and 15° C. greater than the melting temperature of at least 50% of the primers of the set of primers, the length of the annealing step in the PCR reaction is between 15 and 120 minutes, the primer concentration in the amplification reaction is between 1 and 10 nM, and the primers in the set of primers, are designed to minimize primer dimer formation.

In some embodiments, the multiplex amplification reaction is performed under limiting primer conditions.

Another aspect of the invention described herein relates to composition comprising circulating tumor nucleic acid fragments comprising a universal adapter, wherein the circulating tumor nucleic acids originated from a breast cancer, bladder cancer, or colorectal cancer.

In some embodiments, the circulating tumor nucleic acids originated from a sample of blood or urine or a fraction thereof, of an individual with breast cancer, bladder cancer, or colorectal cancer.

Another aspect of the invention described herein relates to composition comprising a solid support comprising a plurality of clonal populations of nucleic acids, wherein the clonal populations comprise amplicons generated from a sample of circulating free nucleic acids, wherein the circulating tumor nucleic acids originated from a breast cancer, bladder cancer, or colorectal cancer.

In some embodiments, the circulating free nucleic acids originated from a sample of blood or urine or a fraction thereof, of an individual with breast cancer, bladder cancer, or colorectal cancer.

In some embodiments, the nucleic acid fragments in different clonal populations comprise the same universal adapter.

In some embodiments, the clonal populations of nucleic acids are derived from nucleic acid fragments from a set of samples from two or more individuals.

In some embodiments, the nucleic acid fragments comprise one of a series of molecular barcodes corresponding to a sample in the set of samples.

A further aspect of the invention described herein relates to a method for monitoring and detection of early relapse or metastasis of breast cancer, bladder cancer, or colorectal cancer, comprising selecting a set of at least 8 or 16 patient-specific single nucleotide variant loci based on somatic mutations identified in a tumor sample of a patient who has been diagnosed with a breast cancer, bladder cancer, or colorectal cancer; longitudinally collecting one or more blood or urine samples from the patient after the patient has been treated with surgery, first-line chemotherapy, and/or adjuvant therapy; generating a set of amplicons by performing a multiplex amplification reaction on nucleic acids isolated from each blood or urine sample or a fraction thereof, wherein each amplicon of the set of amplicons spans at least one single nucleotide variant locus of the set of patient-specific single nucleotide variant loci associated with the breast cancer, bladder cancer, or colorectal cancer; and determining the sequence of at least a segment of each amplicon of the set of amplicons that comprises a patient-specific single nucleotide variant locus, wherein detection of one or more (or two or more, or three or more, or four or more, or five or more, or six or more, or seven or more, or eight or more, or nine or more, or ten or more) patient-specific single nucleotide variants from the blood or urine sample is indicative of early relapse or metastasis of breast cancer, bladder cancer, or colorectal cancer.

A further aspect of the invention described herein relates to a method for treating breast cancer, bladder cancer, or colorectal cancer, comprising treating a patient who has been diagnosed with a breast cancer, bladder cancer, or colorectal cancer with surgery, first-line chemotherapy, and/or adjuvant therapy; longitudinally collecting one or more blood or urine samples from the patient; generating a set of amplicons by performing a multiplex amplification reaction on nucleic acids isolated from each blood or urine sample or a fraction thereof, wherein each amplicon of the set of amplicons spans at least one single nucleotide variant locus of a set of at least 8 or 16 patient-specific single nucleotide variant loci associated with the breast cancer, bladder cancer, or colorectal cancer, which have been selected based on somatic mutations identified in a tumor sample of the patient; determining the sequence of at least a segment of each amplicon of the set of amplicons that comprises a patient-specific single nucleotide variant locus, wherein detection of one or more (or two or more, or three or more, or four or more, or five or more, or six or more, or seven or more, or eight or more, or nine or more, or ten or more) patient-specific single nucleotide variants from the blood or urine sample is indicative of early relapse or metastasis of breast cancer, bladder cancer, or colorectal cancer; and administering a compound to the individual, where the compound is known to be effective in treating breast cancer, bladder cancer, or colorectal cancer having one or more of the single nucleotide variants detected from the blood or urine sample.

A further aspect of the invention described herein relates to a method for monitoring or predicting response to treatment of breast cancer, bladder cancer, or colorectal cancer, comprising longitudinally collecting one or more blood or urine samples from a patient that is undergoing treatment of a breast cancer, bladder cancer, or colorectal cancer; generating a set of amplicons by performing a multiplex amplification reaction on nucleic acids isolated from each blood or urine sample or a fraction thereof, wherein each amplicon of the set of amplicons spans at least one single nucleotide variant locus of a set of at least 8 or 16 patient-specific single nucleotide variant loci associated with the breast cancer, bladder cancer, or colorectal cancer, which have been selected based on somatic mutations identified in a tumor sample of the patient; and determining the sequence of at least a segment of each amplicon of the set of amplicons that comprises a patient-specific single nucleotide variant locus, wherein detection of one or more (or two or more, or three or more, or four or more, or five or more, or six or more, or seven or more, or eight or more, or nine or more, or ten or more) patient-specific single nucleotide variants from the blood or urine sample is indicative of poor response to the treatment of breast cancer, bladder cancer, or colorectal cancer.

In some embodiments, the methods described herein comprise detecting ctDNA in plasma of breast cancer patients before therapy, and/or during neoadjuvant therapy (e.g., after cycle 1, cycle 2, cycle 3, cycle 4, etc.). In some embodiments, a treatment plan is defined based on ctDNA concentration determination (e.g. presence/absence) and rate of decline during neo-adjuvant therapy.

In some embodiments, the methods described herein comprise assessing ctDNA presence and levels for every cancer patient (i.e. targeting mutations that are actually present in the tumor). In some embodiment, the methods described herein comprise detecting 2 or more, 4 or more, 10 or more, 16 or more, 32 or more, 50 or more, 64 or more, or 100 or more of mutations that are actually present in a patients tumor(s).

According to some embodiments of the present invention, at least 50%, or least 60%, or at least 70%, or at least 80%, or at least 90%, or about 100% of patients that will have metastatic recurrence (e.g. after neo-adjuvant therapy and surgery) have ctDNA detectable at baseline.

According to some embodiments of the present invention, at least 50%, or least 60%, or at least 70%, or at least 80%, or at least 90%, or about 100% of patients that will have metastatic recurrence (e.g. after neo-adjuvant therapy and surgery) have ctDNA detectable after cycle 1 of neoadjuvant therapy.

According to some embodiments of the present invention, at least 50%, or least 60%, or at least 70%, or at least 80%, or at least 90%, or about 100% of patients that will have metastatic recurrence (e.g. after neo-adjuvant therapy and surgery) have ctDNA detectable after cycle 2 of neoadjuvant therapy.

According to some embodiments of the present invention, at least 50%, or least 60%, or at least 70%, or at least 80%, or at least 90%, or about 100% of patients that will have metastatic recurrence (e.g. after neo-adjuvant therapy and surgery) have ctDNA detectable after neoadjuvant therapy and before surgery.

According to some embodiments of the present invention, at least 50%, or least 60%, or at least 70%, or at least 80%, or at least 90%, or about 100% of patients that will have metastatic recurrence (e.g. after neo-adjuvant therapy and surgery) have ctDNA detectable after surgery.

According to some embodiments of the present invention, at least 50%, or least 60%, or at least 70%, or at least 80%, or at least 90%, or about 100% of patients that have ctDNA detectable (e.g. after surgery) will have metastatic without further treatment recurrence (e.g. after neo-adjuvant therapy and surgery).

According to some embodiments of the present invention, at least 50%, or least 60%, or at least 70%, or at least 80%, or at least 90%, or about 100% of patients that have increasing ctDNA levels between baseline and cycle 1, or cycle 2, etc., will have metastatic relapse after surgery if no additional treatment is administered.

In some embodiments, the methods described herein comprise detecting occurrence, recurrence, or metastasis of certain subtypes of cancers, including certain subtypes of breast cancer. In some embodiments, the methods described herein comprise detecting occurrence, recurrence, or metastasis of HR+/HER2− tumor including HR+/HER2− breast cancer (e.g., hormone receptor positive-ERα+ and/or PR+). HR+ tumors typically are less aggressive and have a favorable prognosis with a 5-year survival rate of over 90%.

In some embodiments, the methods described herein comprise detecting occurrence, recurrence, or metastasis of HER2+ tumor including HER2+ breast cancer (human epidermal growth factor receptor 2 positive). HER2+ tumors are generally more invasive, have a worse prognosis, and are more likely to recur and metastasize than HR+/HER2− breast cancers.

In some embodiments, the methods described herein comprise detecting occurrence, recurrence, or metastasis of HR−/HER2− tumor including HR−/HER2− breast cancer (TNBC or triple negative BC). Triple-negative breast cancers (TNBCs) do not express ERα, PR, or HER2. These tumors tend to be the most aggressive and have the worst prognosis of all the breast cancer subtypes.

In some embodiments, the method described herein is capable of detecting patient-specific single nucleotide variants in at least 75%, at least 80%, at least 85%, at least 90%, or at least 95% of patients having early relapse or metastasis of cancer.

In some embodiments, the method described herein is capable of detecting patient-specific single nucleotide variants at least 80%, at least 85%, at least 90%, at least 95%, or at least 98% of patients having early relapse or metastasis of HER2+ breast cancer.

In some embodiments, the method described herein is capable of detecting patient-specific single nucleotide variants least 80%, at least 85%, at least 90%, at least 95%, or at least 98% of patients having early relapse or metastasis of triple negative breast cancer.

In some embodiments, the method described herein is capable of detecting patient-specific single nucleotide variants in at least 75%, at least 80%, at least 85%, at least 90%, or at least 95% of patients having early relapse or metastasis of HR+/HER2− breast cancer.

In some embodiments, the method described herein is capable of detecting patient-specific single nucleotide variants in patients having early relapse or metastasis of cancer at least 100 days, at least 150 days, at least 200 days, at least 250 days, or at least 300 days prior to clinical relapse or metastasis of cancer detectable by imaging, and/or at least 100 days, at least 150 days, at least 200 days, at least 250 days, or at least 300 days prior to elevation of CA15-3 level.

In some embodiments, the method described herein is capable of detecting patient-specific single nucleotide variants in patients having early relapse or metastasis of HER2+ breast cancer at least 100 days, at least 150 days, at least 200 days, at least 250 days, or at least 300 days prior to clinical relapse or metastasis of HER2+ breast cancer detectable by imaging, and/or at least 100 days, at least 150 days, at least 200 days, at least 250 days, or at least 300 days prior to elevation of CA15-3 level.

In some embodiments, the method described herein is capable of detecting patient-specific single nucleotide variants in patients having early relapse or metastasis of triple negative breast cancer at least 100 days, at least 150 days, at least 200 days, at least 250 days, or at least 300 days prior to clinical relapse or metastasis of triple negative breast cancer detectable by imaging, and/or at least 100 days, at least 150 days, at least 200 days, at least 250 days, or at least 300 days prior to elevation of CA15-3 level.

In some embodiments, the method described herein is capable of detecting patient-specific single nucleotide variants in patients having early relapse or metastasis of HR+/HER2-breast cancer at least 100 days, at least 150 days, at least 200 days, at least 250 days, or at least 300 days prior to clinical relapse or metastasis of HR+/HER2− breast cancer detectable by imaging, and/or at least 100 days, at least 150 days, at least 200 days, at least 250 days, or at least 300 days prior to elevation of CA15-3 level.

In some embodiments, the method described herein does not detect patient-specific single nucleotide variants in at least 95%, at least 98%, at least 99%, at least 99.5%, at least 99.8%, or at least 99.9% of patients lacking early relapse or metastasis of cancer.

In some embodiments, the method described herein does not detect patient-specific single nucleotide variants in at least 95%, at least 98%, at least 99%, at least 99.5%, at least 99.8%, or at least 99.9% of patients lacking early relapse or metastasis of HER2+ breast cancer.

In some embodiments, the method described herein does not detect patient-specific single nucleotide variants in at least 95%, at least 98%, at least 99%, at least 99.5%, at least 99.8%, or at least 99.9% of patients lacking early relapse or metastasis of triple negative breast cancer.

In some embodiments, the method described herein does not detect patient-specific single nucleotide variants in at least 95%, at least 98%, at least 99%, at least 99.5%, at least 99.8%, or at least 99.9% of patients lacking early relapse or metastasis of HR+/HER2− breast cancer.

In some embodiments, the method described herein has a specificity of at least 95%, at least 98%, at least 99%, at least 99.5%, at least 99.8%, or at least 99.9% in detecting early relapse or metastasis of cancer when two or more patient-specific single nucleotide variants are detected above a predetermined confidence threshold (e.g., 0.95, 0.96, 0.97, 0.98, or 0.99).

In some embodiments, the method described herein has a specificity of at least 95%, at least 98%, at least 99%, at least 99.5%, at least 99.8%, or at least 99.9% in detecting early relapse or metastasis of HER2+ breast cancer when two or more patient-specific single nucleotide variants are detected above a predetermined confidence threshold (e.g., 0.95, 0.96, 0.97, 0.98, or 0.99).

In some embodiments, the method described herein has a specificity of at least 95%, at least 98%, at least 99%, at least 99.5%, at least 99.8%, or at least 99.9% in detecting early relapse or metastasis of triple negative breast cancer when two or more patient-specific single nucleotide variants are detected above a predetermined confidence threshold (e.g., 0.95, 0.96, 0.97, 0.98, or 0.99).

In some embodiments, the method described herein has a specificity of at least 95%, at least 98%, at least 99%, at least 99.5%, at least 99.8%, or at least 99.9% in detecting early relapse or metastasis of HR+/HER2− breast cancer when two or more patient-specific single nucleotide variants are detected above a predetermined confidence threshold (e.g., 0.95, 0.96, 0.97, 0.98, or 0.99).

In some embodiments, the method described herein detects patient-specific single nucleotide variants in at least 75%, at least 80%, at least 85%, at least 90%, or at least 95% of patients having early relapse or metastasis of muscle invasive bladder cancer (MIBC).

In some embodiments, the method described herein detects patient-specific single nucleotide variants in patients having early relapse or metastasis of cancer at least 100 days, at least 150 days, at least 200 days, or at least 250 days prior to clinical relapse or metastasis of MIBC detectable by imaging.

In some embodiments, the method described herein does not detect patient-specific single nucleotide variants in at least 95%, at least 98%, at least 99%, at least 99.5%, at least 99.8%, or at least 99.9% of patients lacking early relapse or metastasis of MIBC.

In some embodiments, the method described herein has a specificity of at least 95%, at least 98%, at least 99%, at least 99%, at least 99.5%, at least 99.8%, or at least 99.9% in detecting early relapse or metastasis of MIBC when two or more patient-specific single nucleotide variants are detected above a predetermined confidence threshold (e.g., 0.95, 0.96, 0.97, 0.98, or 0.99).

In addition or alternative to single-nucleotide variants, the methods described herein can also be based on the detection of other genomic variants, such as indels, multiple nucleotide variants, and/or gene fusions.

Accordingly, an additional aspect of the invention described herein relates to a method for monitoring and detection of early relapse or metastasis of breast cancer, bladder cancer, or colorectal cancer, comprising selecting a plurality of genomic variant loci (e.g., SNV, indel, multiple nucleotide variant, and gene fusion) based on somatic mutations identified in a tumor sample of a patient who has been diagnosed with a breast cancer, bladder cancer, or colorectal cancer; longitudinally collecting one or more blood or urine samples from the patient after the patient has been treated with surgery, first-line chemotherapy, and/or adjuvant therapy; generating a set of amplicons by performing a multiplex amplification reaction on nucleic acids isolated from each blood or urine sample or a fraction thereof, wherein each amplicon of the set of amplicons spans at least one genomic variant locus of the set of patient-specific genomic variant loci associated with the breast cancer, bladder cancer, or colorectal cancer; and determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of early relapse or metastasis of breast cancer, bladder cancer, or colorectal cancer.

An additional aspect of the invention described herein relates to a method for treating breast cancer, bladder cancer, or colorectal cancer, comprising treating a patient who has been diagnosed with a breast cancer, bladder cancer, or colorectal cancer with surgery, first-line chemotherapy, and/or adjuvant therapy; longitudinally collecting one or more blood or urine samples from the patient; generating a set of amplicons by performing a multiplex amplification reaction on nucleic acids isolated from each blood or urine sample or a fraction thereof, wherein each amplicon of the set of amplicons spans at least one genomic variant locus (e.g., SNV, indel, multiple nucleotide variant, and gene fusion) of a set of at least 8 or 16 patient-specific genomic variant loci associated with the breast cancer, bladder cancer, or colorectal cancer, which have been selected based on somatic mutations identified in a tumor sample of the patient; determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of early relapse or metastasis of breast cancer, bladder cancer, or colorectal cancer; and administering a compound to the individual, where the compound is known to be effective in treating breast cancer, bladder cancer, or colorectal cancer having one or more of the genomic variants detected from the blood or urine sample.

An additional aspect of the invention described herein relates to a method for monitoring or predicting response to treatment of breast cancer, bladder cancer, or colorectal cancer, comprising longitudinally collecting one or more blood or urine samples from a patient that is undergoing treatment of a breast cancer, bladder cancer, or colorectal cancer; generating a set of amplicons by performing a multiplex amplification reaction on nucleic acids isolated from each blood or urine sample or a fraction thereof, wherein each amplicon of the set of amplicons spans at least one genomic variant locus (e.g., SNV, indel, multiple nucleotide variant, and gene fusion) of a set of at least 8 or 16 patient-specific genomic variant loci associated with the breast cancer, bladder cancer, or colorectal cancer, which have been selected based on somatic mutations identified in a tumor sample of the patient; and determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of poor response to the treatment of breast cancer, bladder cancer, or colorectal cancer.

In addition or alternative to patient-specific genomic variants, the methods described herein can also be based on the detection of recurring cancer-associated mutations (e.g., hotspot cancer mutations, drug resistant markers, cancer panel mutations) that are recurring in many cancer patients.

Accordingly, an additional aspect of the invention described herein relates to a method for monitoring and detection of early relapse or metastasis of breast cancer, bladder cancer, or colorectal cancer, comprising selecting a plurality of recurring cancer-associated mutations; longitudinally collecting one or more blood or urine samples from the patient after the patient has been treated with surgery, first-line chemotherapy, and/or adjuvant therapy; generating a set of amplicons by performing a multiplex amplification reaction on nucleic acids isolated from each blood or urine sample or a fraction thereof, wherein each amplicon of the set of amplicons spans at least one of the set of recurring mutations associated with the breast cancer, bladder cancer, or colorectal cancer; and determining the sequence of at least a segment of each amplicon of the set of amplicons that comprises a recurring cancer-associated mutation, wherein detection of one or more (or two or more, or three or more, or four or more, or five or more, or six or more, or seven or more, or eight or more, or nine or more, or ten or more) recurring cancer-associated mutations from the blood or urine sample is indicative of early relapse or metastasis of breast cancer, bladder cancer, or colorectal cancer.

An additional aspect of the invention described herein relates to a method for treating breast cancer, bladder cancer, or colorectal cancer, comprising treating a patient who has been diagnosed with a breast cancer, bladder cancer, or colorectal cancer with surgery, first-line chemotherapy, and/or adjuvant therapy; longitudinally collecting one or more blood or urine samples from the patient; generating a set of amplicons by performing a multiplex amplification reaction on nucleic acids isolated from each blood or urine sample or a fraction thereof, wherein each amplicon of the set of amplicons spans at least one recurring cancer-associated mutation (e.g., hotspot cancer mutation, drug resistant marker, cancer panel mutation) of a set of at least 8 or 16 recurring mutations associated with the breast cancer, bladder cancer, or colorectal cancer; determining the sequence of at least a segment of each amplicon of the set of amplicons that comprises a recurring cancer-associated mutation, wherein detection of one or more (or two or more, or three or more, or four or more, or five or more, or six or more, or seven or more, or eight or more, or nine or more, or ten or more) recurring cancer-associated mutations from the blood or urine sample is indicative of early relapse or metastasis of breast cancer, bladder cancer, or colorectal cancer; and administering a compound to the individual, where the compound is known to be effective in treating breast cancer, bladder cancer, or colorectal cancer having one or more of the recurring cancer-associated mutations detected from the blood or urine sample.

An additional aspect of the invention described herein relates to a method for monitoring or predicting response to treatment of breast cancer, bladder cancer, or colorectal cancer, comprising longitudinally collecting one or more blood or urine samples from a patient that is undergoing treatment of a breast cancer, bladder cancer, or colorectal cancer; generating a set of amplicons by performing a multiplex amplification reaction on nucleic acids isolated from each blood or urine sample or a fraction thereof, wherein each amplicon of the set of amplicons spans at least one recurring cancer-associated mutation (e.g., hotspot cancer mutation, drug resistant marker, cancer panel mutation) of a set of at least 8 or 16 recurring mutations associated with the breast cancer, bladder cancer, or colorectal cancer; and determining the sequence of at least a segment of each amplicon of the set of amplicons that comprises a recurring cancer-associated mutation, wherein detection of one or more (or two or more, or three or more, or four or more, or five or more, or six or more, or seven or more, or eight or more, or nine or more, or ten or more) recurring cancer-associated mutations from the blood or urine sample is indicative of poor response to the treatment of breast cancer, bladder cancer, or colorectal cancer.

In addition or alternative to initially identifying somatic mutations from a tumor sample of a patient who has been diagnosed with a breast cancer, bladder cancer, or colorectal cancer, the methods described herein can also be based on the identifying somatic mutations from other biological samples of the patients, such as blood, serum, plasma, urine, hair, tears, saliva, skin, fingernails, feces, bile, lymph, cervical mucus, or semen.

Accordingly, an additional aspect of the invention described herein relates to a method for monitoring and detection of early relapse or metastasis of breast cancer, bladder cancer, or colorectal cancer, comprising selecting a plurality of genomic variant loci (e.g., SNV, indel, multiple nucleotide variant, and gene fusion) based on somatic mutations identified in a biological sample comprising cancer-associated mutations (e.g., blood, serum, plasma, urine, hair, tears, saliva, skin, fingernails, feces, bile, lymph, cervical mucus, or semen) of a patient who has been diagnosed with a breast cancer, bladder cancer, or colorectal cancer; longitudinally collecting one or more blood or urine samples from the patient after the patient has been treated with surgery, first-line chemotherapy, and/or adjuvant therapy; generating a set of amplicons by performing a multiplex amplification reaction on nucleic acids isolated from each blood or urine sample or a fraction thereof, wherein each amplicon of the set of amplicons spans at least one genomic variant locus of the set of patient-specific genomic variant loci associated with the breast cancer, bladder cancer, or colorectal cancer; and determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of early relapse or metastasis of breast cancer, bladder cancer, or colorectal cancer.

An additional aspect of the invention described herein relates to a method for treating breast cancer, bladder cancer, or colorectal cancer, comprising treating a patient who has been diagnosed with a breast cancer, bladder cancer, or colorectal cancer with surgery, first-line chemotherapy, and/or adjuvant therapy; longitudinally collecting one or more blood or urine samples from the patient; generating a set of amplicons by performing a multiplex amplification reaction on nucleic acids isolated from each blood or urine sample or a fraction thereof, wherein each amplicon of the set of amplicons spans at least one genomic variant locus (e.g., SNV, indel, multiple nucleotide variant, and gene fusion) of a set of at least 8 or 16 patient-specific genomic variant loci associated with the breast cancer, bladder cancer, or colorectal cancer, which have been selected based on somatic mutations identified in a biological sample of the patient comprising cancer-associated mutations (e.g., blood, serum, plasma, urine, hair, tears, saliva, skin, fingernails, feces, bile, lymph, cervical mucus, or semen); determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of early relapse or metastasis of breast cancer, bladder cancer, or colorectal cancer; and administering a compound to the individual, where the compound is known to be effective in treating breast cancer, bladder cancer, or colorectal cancer having one or more of the genomic variants detected from the blood or urine sample.

An additional aspect of the invention described herein relates to a method for monitoring or predicting response to treatment of breast cancer, bladder cancer, or colorectal cancer, comprising longitudinally collecting one or more blood or urine samples from a patient that is undergoing treatment of a breast cancer, bladder cancer, or colorectal cancer; generating a set of amplicons by performing a multiplex amplification reaction on nucleic acids isolated from each blood or urine sample or a fraction thereof, wherein each amplicon of the set of amplicons spans at least one genomic variant locus (e.g., SNV, indel, multiple nucleotide variant, and gene fusion) of a set of at least 8 or 16 patient-specific genomic variant loci associated with the breast cancer, bladder cancer, or colorectal cancer, which have been selected based on somatic mutations identified in a biological sample of the patient comprising cancer-associated mutations (e.g., blood, serum, plasma, urine, hair, tears, saliva, skin, fingernails, feces, bile, lymph, cervical mucus, or semen); and determining the sequence of at least a segment of each amplicon of the set of amplicons that comprises a patient-specific genomic variant locus, wherein detection of one or more (or two or more, or three or more, or four or more, or five or more, or six or more, or seven or more, or eight or more, or nine or more, or ten or more) patient-specific genomic variants from the blood or urine sample is indicative of poor response to the treatment of breast cancer, bladder cancer, or colorectal cancer.

Other embodiments and features and advantages of the disclosed inventions will be apparent from the following detailed description and from the claims.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 8A-B. SNV detection (left) and sample detection (right) in plasma by tumor stage.

FIG. 16 is a table of cfDNA analysis showing DNA concentration, genome copy equivalents into library prep, plasma hemolysis grade, and cDNA profile in all samples.

FIG. 17 is a table of SNVs detected in the plasma for each sample.

FIG. 18 is a table of additional SNVs detected in plasma.

FIG. 31A-B: Relapse-Free Survival and ctDNA Status at Diagnosis and Post Cystectomy.

FIG. 32A-B: Neoadjuvant Treatment Response.

Figure 38A:
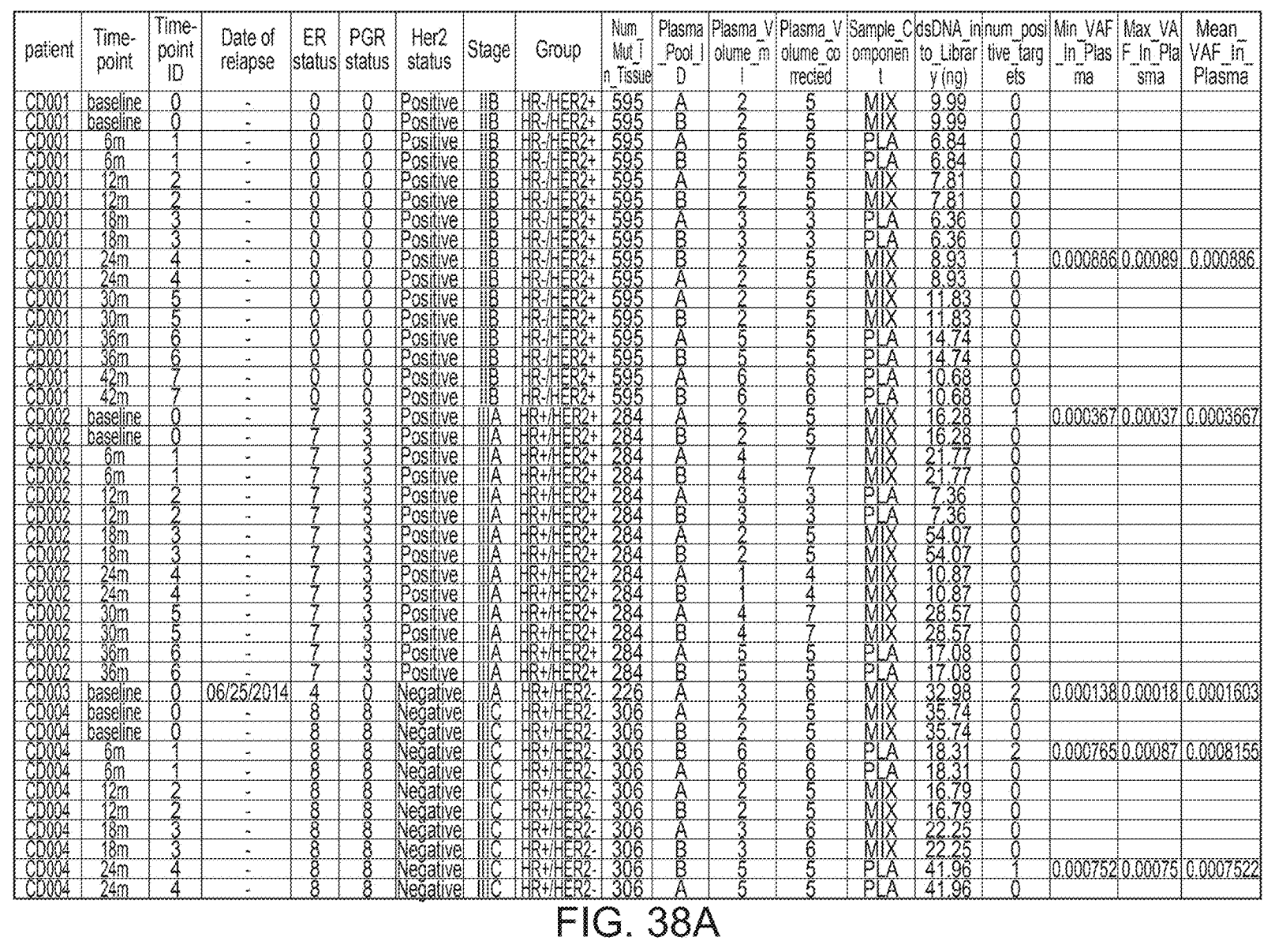
Figure 38F:
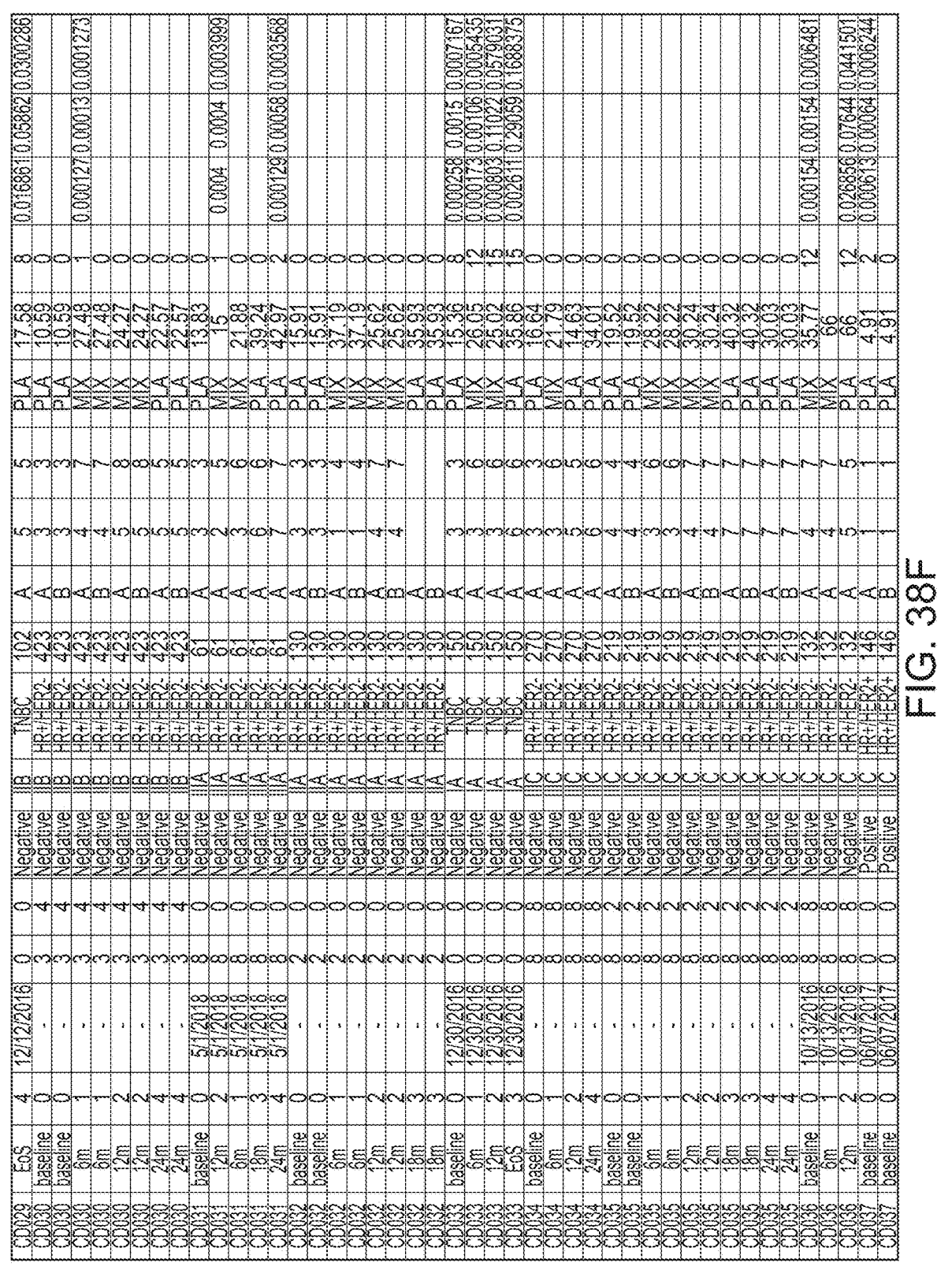

FIG. 38A-H: is a table of information regarding the samples analyzed in the study of Example 6. FIG. 38A is part 1 of the table. FIG. 38B is a continuation of the table. FIG. 38C is a continuation of the table. FIG. 38D is a continuation of the table. FIG. 38E is a continuation of the table. FIG. 38F is a continuation of the table. FIG. 38G is a continuation of the table. FIG. 38H is a continuation of the table.

FIG. 43: Plasma sample reruns for the breast cancer study in Example 6. 319 sequenced samples with 214 unique plasma samples are represented for 49 patients.

FIG. 45: Summary of 16 Patients with ctDNA detected.

FIG. 63: (A-F) Plasma levels of ctDNA across multiple plasma time points for five breast cancer patients (one per panel). Primary tumor and matched normal whole-exome sequencing identified patient-specific somatic mutations. Using the analytically-validated Signatera™ RUO workflow, each patient specific assay was designed to target 16 somatic SNV and INDEL variants using massively parallel sequencing (median depth >100,000× per target). Mean VAFs are denoted by circle and solid line represent average VAF profile over time. The lead time is calculated by difference in clinical relapse and molecular relapse. CA15-3 levels is graphed over time and the baseline levels are marked in light shade. (F) Summary of VAFs and number of targets detected at molecular and clinical relapse for all ctDNA positive samples, excluding patients with only one time point.

FIG. 64A-C: Signatera variant selection strategy for the 49 patient specific panels. (Top) Tumor tissue VAF distribution in patients custom panel. (Middle) The number of inferred clonal and subclonal variants in patients' custom panel. The median number of clonal variants in 49 custom panel is 13 out of 16. (Bottom) The number of inferred clonal and subclonal variants in patients' WES data.

FIG. 69: After screening and recruitment patients were followed up with 6 monthly blood samples. HER2 status was determined by immunohistochemical and fluorescence in situ hybridization assays. A patient was considered to have HER2-positive cancer if either assay was positive. NACT: neoadjuvant chemotherapy; ACT: adjuvant chemotherapy.

FIG. 71A-G: Patient summary for the muscle invasive bladder cancer study in Example 9. FIG. 71A shows the rate of synonymous and non-synonymous mutations called from WES. One patient's tumor was hypermutated with a mutational burden of 126 mutations/Mb and displayed a POLD1 mutation which previously has been associated with hypermutators (Campbell, B. B. et al. Comprehensive Analysis of Hypermutation in Human Cancer. Cell 171, 1042-1056.e10 (2017). FIG. 71B shows the relative contribution of bladder cancer associated mutational signatures. FIG. 71C shows mutations in frequently mutated genes in bladder cancer (TCGA) (Robertson, A. G. et al. Comprehensive Molecular Characterization of Muscle-Invasive Bladder Cancer. Cell 171, 540-556.e25 (2017)). FIG. 71D shows deleterious mutations in DNA damage response (DDR) associated genes mutated in more than 5% of the 68 samples. FIG. 71E shows total number of deleterious DDR mutations. FIG. 71F shows clinical and histopathological characteristics. FIG. 71G shows summarized ctDNA status.

FIG. 75D shows association between disease recurrence and ctDNA status before chemotherapy, before cystectomy and after cystectomy as well as disease recurrence and lymph node status before cystectomy. FIG. 75E shows association between ctDNA status before cystectomy (CX) and pathology status at cystectomy (CX). Assessment of statistical significance was performed using Wilcoxon rank-sum test for continuous variables and Fisher's Exact test for categorical variables.

FIG. 76A-G: Graphs showing ctDNA changes in individual disease courses for the muscle invasive bladder cancer study in Example 9. FIG. 76A-G shows representation of detailed disease courses, applied treatments and associated longitudinal ctDNA analyses from selected patients. ctDNA status, applied treatment and imaging results are presented according to the legend. Positive lead times for ctDNA based recurrence detection are indicated.

FIG. 78A-H: Graphs showing predictive markers of chemotherapy response for the muscle invasive bladder cancer study in Example 9. FIG. 78A shows association between disease recurrence and response to chemotherapy. FIG. 78B shows relative signature 5 contribution for all patients stratified by response to chemotherapy and ERCC2 mutation status, respectively. FIG. 78C shows fraction of patients responding to therapy in relation to ERCC2 mutation status. FIG. 78D RNA subtype figures_NEW figure. FIG. 78E shows association between ctDNA and response to chemotherapy for patients being ctDNA negative throughout the whole disease course, patients where ctDNA level drops down to zero and patients where ctDNA level remains to be positive. FIG. 78F shows the level of ctDNA for all patients with detectable ctDNA before, during and after chemotherapy. Patients are grouped by response to chemotherapy and recurrence status is indicated.

FIG. 81A-H: Graphs depicting variance allele frequency (VAF %) at different days relative to cystectomy (CX) from 8 patients from the muscle invasive bladder cancer study in Example 9.

FIG. 83A-E: Graphs showing clinical, histopathological and molecular parameters for all 125 patients. FIG. 83A shows the relative contribution of the five most prevalent colorectal cancer associated mutational signatures. FIG. 83B shows the rate of synonymous and non-synonymous mutations called from WES. FIG. 83C depicts a graph showing mutations in frequently mutated genes in colorectal cancer (TCGA) {Cancer Genome Atlas, 2012 #52}. FIG. 83D shows clinical and histopathological characteristics. FIG. 83E shows a graph summarizing pre- and post-OP ctDNA status.

FIG. 85A shows library preparation DNA input amount. Up to 66 ng of cell-free DNA (cfDNA) from each plasma sample was used as input into library preparation protocol. Library DNA input amount ranged between 1 to 66 ng with the median of 45.66. The purified libraries were quality controlled before proceeding to the next step. One sample failed library preparation QC. FIG. 85B shows sequencing coverage. Assays with coverage less than 5000× were excluded from analyses. Subsequently, samples with less than 8 passing assays failed sequencing coverage QC. One sample failed the sequencing coverage requirement. The median depth of read for the assays passed coverage QC was 105,000×. FIG. 85C shows sequencing error rate measured in all plasma samples. Average transition error rate is 5e-5 and average transversion error rate is 8e-6.

FIG. 87A-F shows ctDNA status pre-operative (pre-op), at day 30 post-operative and during adjuvant chemotherapy (ACT). FIG. 87A shows pre-op detection of ctDNA. FIG. 87B shows recurrence rate. FIG. 87C shows Kaplan-Meier estimates of TTR for 94 stage I-III patients, stratified by postoperative day 30 ctDNA status. FIG. 87D shows ACT effect on ctDNA-positive patients, assessed by recurrence rate and longitudinal ctDNA status. FIG. 87E shows recurrence rate stratified by ctDNA status at first visit post-ACT. FIG. 87F shows Kaplan-Meier estimates of TTR for 58 ACT treated patients, stratified by ctDNA status at first post-ACT visit.

FIG. 93A shows the recurrence rate stratified by longitudinal ctDNA status. FIG. 93B shows Kaplan-Meier estimates of TTR for 75 patients with longitudinal samples, stratified by longitudinal ctDNA status. FIG. 93C shows a graph comparing time to radiological and ctDNA recurrence. FIG. 93D shows that ctDNA variance allele frequency (VAF) in plasma increased towards the radiologic relapse. Early timepoints before and during ACT omitted.

FIG. 97A shows percentage of ctDNA+ recurrence patients with actionable mutations detected during surveillance. First ctDNA+ sample (Left column) and all ctDNA+ plasma samples (Right column). FIG. 97B shows actionable variants called in blood. Correlation between mean blood VAFs calculated using Signatera ctDNA+ assays and variance allele frequencies (VAFs) of actionable mutations, plotted with logarithmic scales on both the horizontal and vertical axes. FIG. 97C shows serial ctDNA profiling of two representative recurrence patients with actionable mutations.

FIG. 100A-D: Graphs showing the association between ctDNA status and recurrence subsequent to definitive treatment. FIG. 100A shows the recurrence rate stratified by longitudinal ctDNA status, and Kaplan-Meier estimates of TTR for 58 patients with longitudinal samples, stratified by longitudinal ctDNA analysis. FIG. 100B shows the recurrence rate stratified by CEA analysis, and Kaplan-Meier estimates of TTR for 58 patients with longitudinal samples, stratified by CEA analysis.

Figure 1:
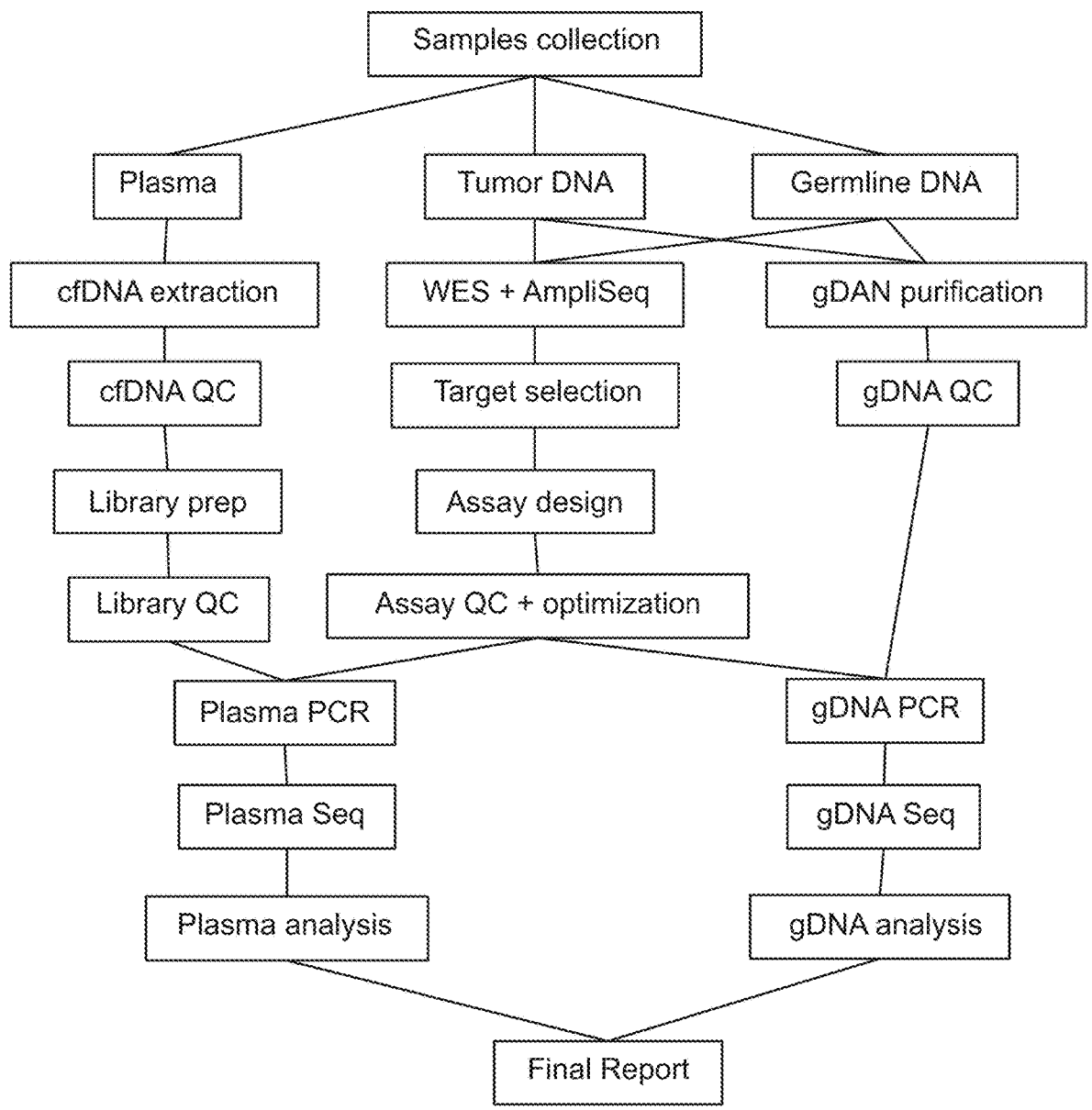
FIG. 1 is a workflow Diagram.
Figure 2:
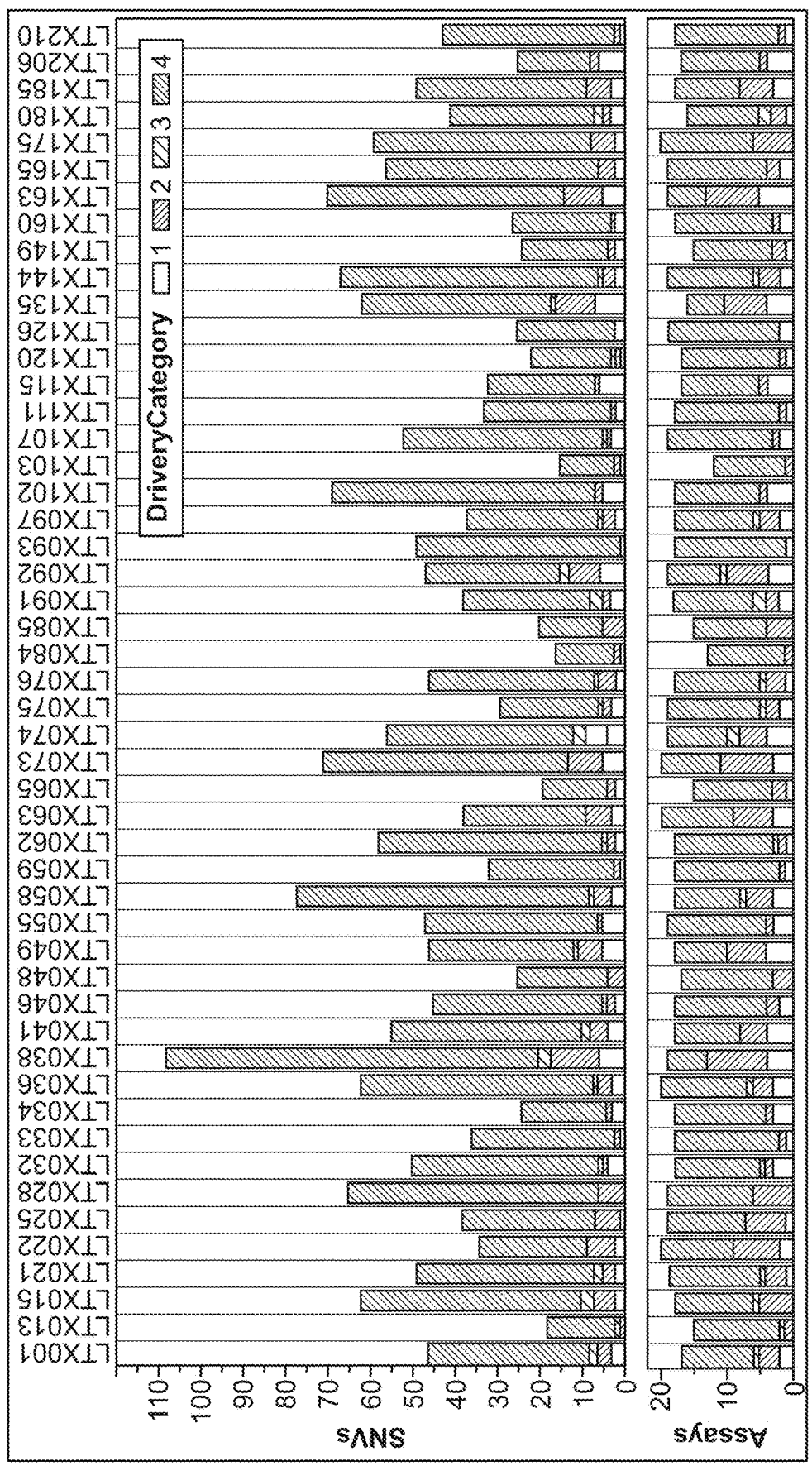
FIG. 2 Top panel: the number of SNVs per sample; bottom panel: the working assays, sorted by driver category.

The above-identified figures are provided by way of representation and not limitation.

DETAILED DESCRIPTION OF THE INVENTION

Methods and compositions provided herein improve the detection, diagnosis, staging, screening, treatment, and management of cancer (e.g., breast cancer, bladder cancer, or colorectal cancer). Methods provided herein, in illustrative embodiments analyze single nucleotide variant mutations (SNVs) in circulating fluids, especially circulating tumor DNA. The methods provide the advantage of identifying more of the mutations that are found in a tumor and clonal as well as subclonal mutations, in a single test, rather than multiple tests that would be required, if effective at all, that utilize tumor samples. The methods and compositions can be helpful on their own, or they can be helpful when used along with other methods for detection, diagnosis, staging, screening, treatment, and management of cancer (e.g., breast cancer, bladder cancer, or colorectal cancer), for example to help support the results of these other methods to provide more confidence and/or a definitive result.

Accordingly, provided herein in one embodiment, is a method for determining the single nucleotide variants present in a cancer (e.g., breast cancer, bladder cancer, or colorectal cancer) by determining the single nucleotide variants present in a ctDNA sample from an individual, such as an individual having or suspected of having cancer (e.g., breast cancer, bladder cancer, or colorectal cancer) using a ctDNA SNV amplification/sequencing workflow provided herein.

The terms "cancer" and "cancerous" refer to or describe the physiological condition in animals that is typically characterized by unregulated cell growth. A "tumor" comprises one or more cancerous cells. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor.

In another embodiment, provided herein is a method for detecting cancer (e.g., breast cancer, bladder cancer, or colorectal cancer) in a sample of blood or a fraction thereof from an individual, such as an individual suspected of having a cancer, that includes determining the single nucleotide variants present in a sample by determining the single nucleotide variants present in a ctDNA sample using a ctDNA SNV amplification/sequencing workflow provided herein. The presence of 1, 2, 3, 4, 5, 6, 7, 8, 9, 10, 11, 12, 13, 14, or 15 SNVs on the low end of the range, and 2, 3, 4, 5, 6, 7, 8, 9, 10, 11, 12, 13, 14, 15, 16, 17, 18, 19, 20, 21, 22, 23, 24, 25, 30, 40, or 50 SNVs on the high end of the range, in the sample at the plurality of single nucleotide loci is indicative of the presence of cancer (e.g., breast cancer, bladder cancer, or colorectal cancer).

Figure 12:
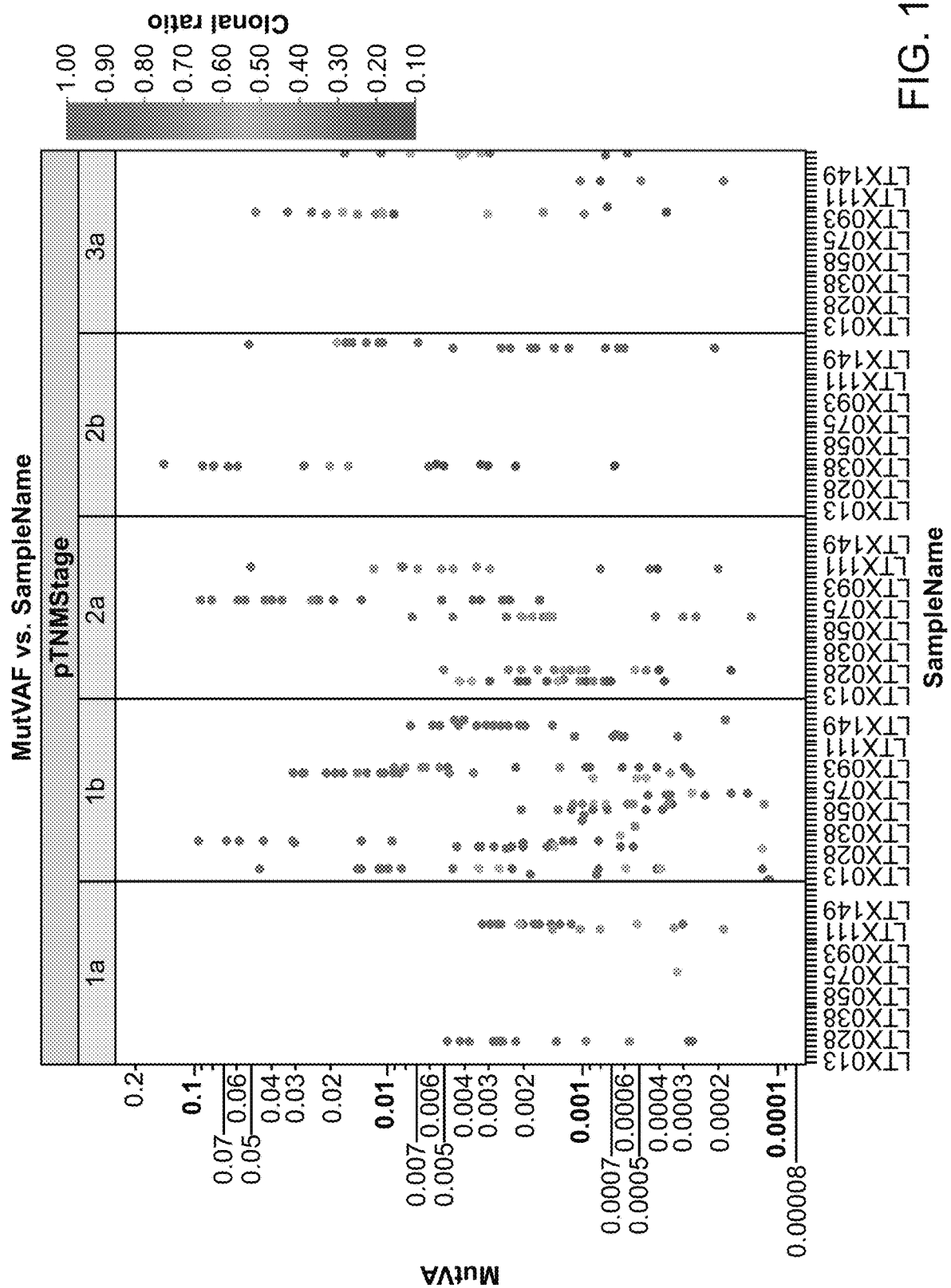
FIG. 12 shows the clonal ratios and mutant variant allele frequency (MutVAF) of each detected SNV. The total SNVs detected from each sample are placed in a single column and the samples are categorized by tumor stage (pTNMstage). Samples with no detected SNVs are included. The clonal ratio is defined as the ratio between the number of tumor subsections in which SNV was observed and the total number of subsections analyzed from that tumor.
Figure 13:
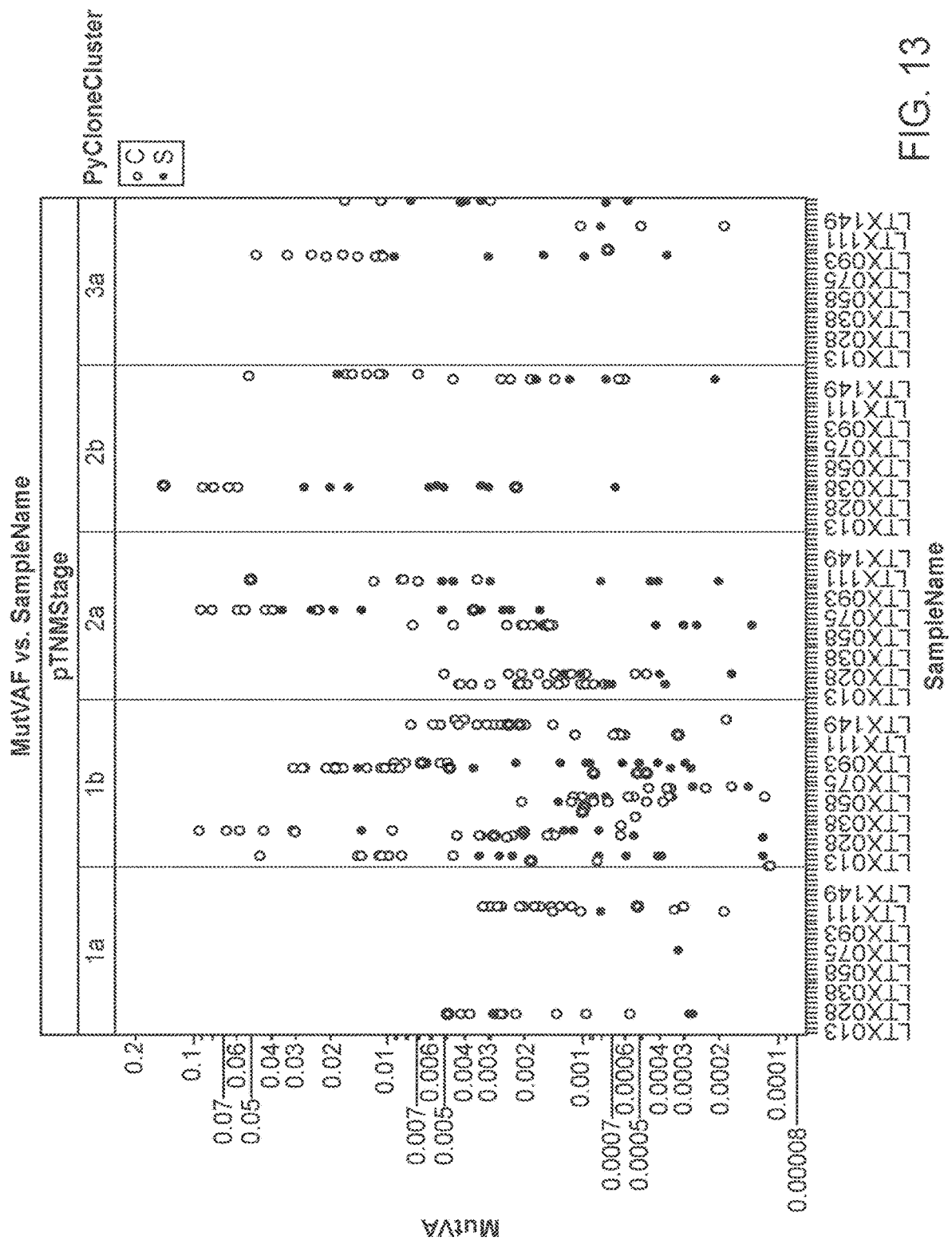
FIG. 13 shows the clonal status (open circle for clonal and filled circle for subclonal) and mutant variant allele frequency (MutVAF) of each detected SNV, The total SNVs detected from each sample are placed in a single column and the samples are categorized by tumor stage (pTNMstage). Samples with no detected SNVs are included. The clonal status was determined by PyCloneChswr using, whole exome sequencing data from the tumor tissue.
Figure 14:
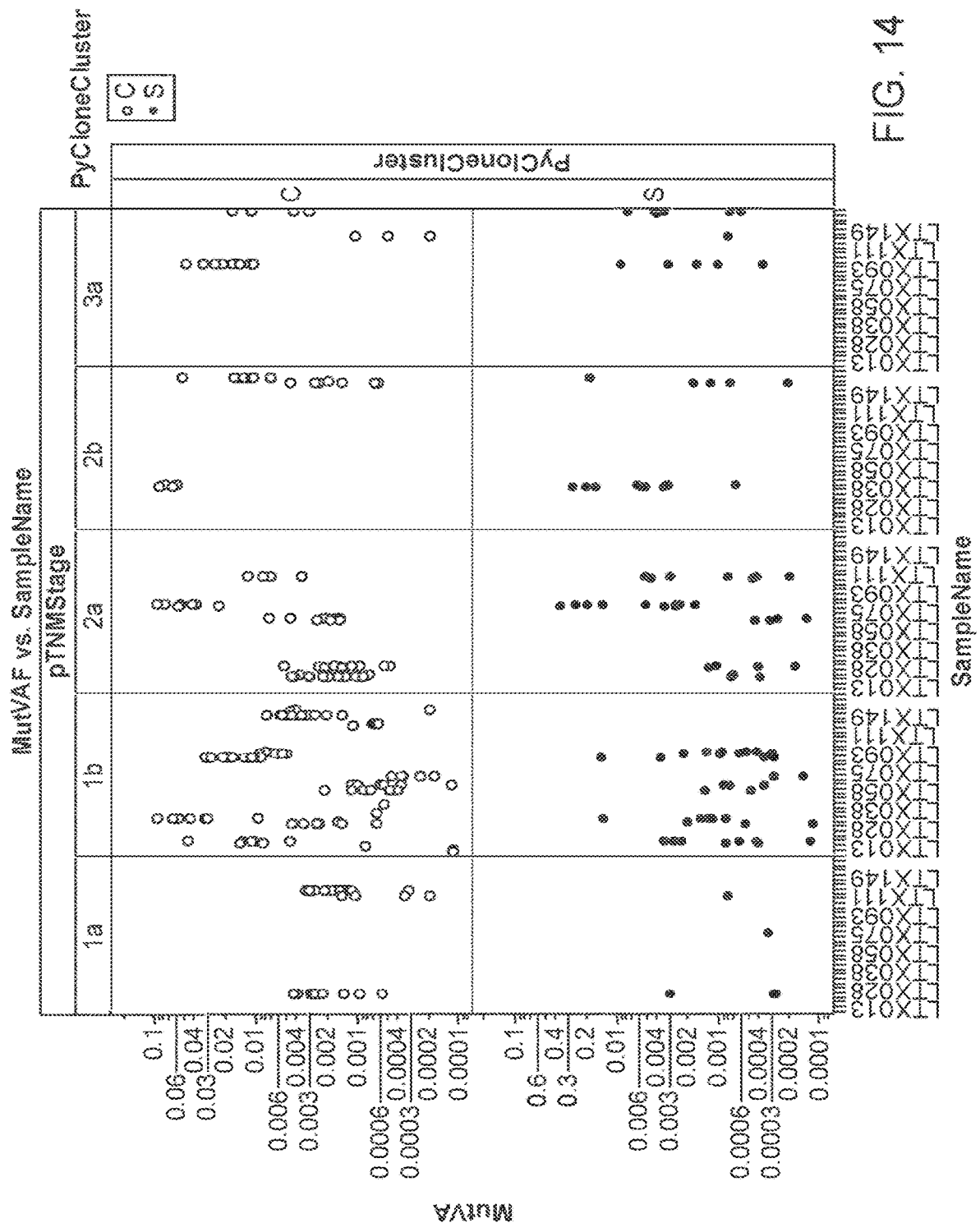
FIG. 14 shows the clonal status (open circle for clonal and filled circle for subclonal and mutant variant allele frequency (MutVAF) of each detected SNV where the top panel shows only the clonal SNVs and the bottom panel shows only the subclonal SNVs. The total SNVs detected from each sample are placed in a single column and the samples are categorized by tumor stage (pTNMstage). Samples with no detected SNVs are included. The clonal status was determined by PyCloneChswr using whole exome sequencing data from the tumor tissue.

In another embodiment, provided herein is a method for detecting a clonal single nucleotide variant in a tumor of an individual (e.g., breast cancer, bladder cancer, or colorectal cancer). The method includes performing a ctDNA SNV amplification/sequencing workflow as provided herein, and determining the variant allele frequency for each of the SNV loci based on the sequence of the plurality of copies of the series of amplicons. A higher relative allele frequency compared to the other single nucleotide variants of the plurality of single nucleotide variant loci is indicative of a clonal single nucleotide variant in the tumor. Variant allele frequencies are well known in the sequencing art. Support for this embodiment, is provided, for example in FIGS. 12-14.

In certain embodiments, the method further includes determining a treatment plan, therapy and/or administering a compound to the individual that targets the one or more clonal single nucleotide variants. In certain examples, subclonal and/or other clonal SNVs are not targeted by therapy. Specific therapies and associated mutations are provided in other sections of this specification and are known in the art. Accordingly, in certain examples, the method further includes administering a compound to the individual, where the compound is known to be specifically effective in treating cancer (e.g., breast cancer, bladder cancer, or colorectal cancer) having one or more of the determined single nucleotide variants.

In certain aspects of this embodiment, a variant allele frequency of greater than 0.25%, 0.5%, 0.75%, 1.0%, 5% or 10% is indicative a clonal single nucleotide variant. These cutoffs are supported by the data in tabular form FIG. 20A-B.

In certain examples of this embodiment, the cancer is a stage 1a, 1b, or 2a breast cancer, bladder cancer, or colorectal cancer. In certain examples of this embodiment, the cancer is a stage 1a or 1b breast cancer, bladder cancer, or colorectal cancer. In certain examples of the embodiment, the individual is not subjected to surgery. In certain examples of the embodiment, the individual is not subjected to a biopsy.

In some examples of this embodiment, a clonal SNV is identified or further identified if other testing such as direct tumor testing suggest an on-test SNV is a clonal SNV, for any SNV on test that has a variable allele frequency greater than at least one quarter, one third, one half, or three quarters of the other single nucleotide variants that were determined.

In some embodiments, methods herein for detecting SNVs in ctDNA can be used instead of direct analysis of DNA from a tumor. Results provided herein demonstrate that SNVs that are much more likely to be clonal SNVs have higher VAFs (See e.g. FIGS. 12-14).

In certain examples of any of the method embodiments provided herein, before a targeted amplification is performed on ctDNA from an individual, data is provided on SNVs that are found in a tumor from the individual. Accordingly, in these embodiments, a SNV amplification/sequencing reaction is performed on one or more tumor samples from the individual. In this methods, the ctDNA SNV amplification/sequencing reaction provided herein is still advantageous because it provides a liquid biopsy of clonal and subclonal mutations. Furthermore, as provided herein, clonal mutations can be more unambiguously identified in an individual that has cancer (e.g., breast cancer, bladder cancer, or colorectal cancer), if a high VAF percentage, for example, more than 1, 2, 3, 4, 5, 6, 7, 8, 9, 10% VAF in a ctDNA sample from the individual is determined for an SNV.

In certain embodiment, method provided herein can be used to determine whether to isolate and analyze ctDNA from circulating free nucleic acids from an individual with cancer (e.g., breast cancer, bladder cancer, or colorectal cancer). First, it is determined whether the cancer is breast cancer, bladder cancer, or colorectal cancer. If the cancer is a breast cancer, bladder cancer, or colorectal cancer, circulating free nucleic acids are isolated from individual. The method in some examples, further includes determining the stage of the cancer.

In some methods, provided herein are inventive compositions and/or solid supports. A composition comprising circulating tumor nucleic acid fragments comprising a universal adapter, wherein the circulating tumor nucleic acids originated from breast cancer, bladder cancer, or colorectal cancer.

In some embodiments, provided herein is an inventive composition that includes circulating tumor nucleic acid fragments comprising a universal adapter, wherein the circulating tumor nucleic acids originated from a sample of blood or a fraction thereof, of an individual with cancer (e.g., breast cancer, bladder cancer, or colorectal cancer). These methods typically include formation of ctDNA fragment that include a universal adapter. Furthermore, such methods typically include the formation of a solid support especially a solid support for high throughput sequencing, that includes a plurality of clonal populations of nucleic acids, wherein the clonal populations comprise amplicons generated from a sample of circulating free nucleic acids, wherein the ctDNA. In illustrative embodiments based on the surprising results provided herein, the ctDNA originated from cancer (e.g., breast cancer, bladder cancer, or colorectal cancer).

Similarly, provided herein as an embodiment of the invention is a solid support comprising a plurality of clonal populations of nucleic acids, wherein the clonal populations comprise nucleic acid fragments generated from a sample of circulating free nucleic acids from a sample of blood or a fraction thereof, from an individual with cancer (e.g., breast cancer, bladder cancer, or colorectal cancer).

In certain embodiments, the nucleic acid fragments in different clonal populations comprise the same universal adapter. Such a composition is typically formed during a high throughput sequencing reaction in methods of the present invention.

The clonal populations of nucleic acids can be derived from nucleic acid fragments from a set of samples from two or more individuals. In these embodiments, the nucleic acid fragments comprise one of a series of molecular barcodes corresponding to a sample in the set of samples.

Detailed analytical methods are provided herein as SNV Methods 1 and SNV Method 2 in the analytical section herein. Any of the methods provided herein can further include analytical steps provided herein. Accordingly, in certain examples, the methods for determining whether a single nucleotide variant is present in the sample, includes identifying a confidence value for each allele determination at each of the set of single nucleotide variance loci, which can be based at least in part on a depth of read for the loci. The confidence limit can be set at least 75%, 80%, 85%, 90%, 95%, 96%, 96%, 98%, or 99%. The confidence limit can be set at different levels for different types of mutations.

The method can performed with a depth of read for the set of single nucleotide variance loci of at least 5, 10, 15, 20, 25, 50, 100, 150, 200, 250, 500, 1,000, 10,000, 25,000, 50,000, 100,000, 250,000, 500,000, or 1 million.

In certain embodiments, a method of any of the embodiments herein includes determining an efficiency and/or an error rate per cycle are determined for each amplification reaction of the multiplex amplification reaction of the single nucleotide variance loci. The efficiency and the error rate can then be used to determine whether a single nucleotide variant at the set of single variant loci is present in the sample. More detailed analytical steps provided in SNV Method 2 provided in the analytical method can be included as well, in certain embodiments.

In illustrative embodiments, of any of the methods herein the set of single nucleotide variance loci includes all of the single nucleotide variance loci identified in the TCGA and COSMIC data sets for cancer (e.g., breast cancer, bladder cancer, or colorectal cancer).

In certain embodiments of any of the methods herein the set of single nucleotide variant loci include 2, 3, 4, 5, 6, 7, 8, 9, 10, 15, 20, 25, 30, 40, 50, 75, 100, 250, 500, 1000, 2500, 5000, or 10,000 single nucleotide variance loci known to be associated with cancer (e.g., breast cancer, bladder cancer, or colorectal cancer) on the low end of the range, and, 5, 6, 7, 8, 9, 10, 15, 20, 25, 30, 40, 50, 75, 100, 250, 500, 1000, 2500, 5000, 10,000, 20,000 and 25,000 on the high end of the range.

In any of the methods for detecting SNVs herein that include a ctDNA SNV amplification/sequencing workflow, improved amplification parameters for multiplex PCR can be employed. For example, wherein the amplification reaction is a PCR reaction and the annealing temperature is between 1, 2, 3, 4, 5, 6, 7, 8, 9, or 10° C. greater than the melting temperature on the low end of the range, and 2, 3, 4, 5, 6, 7, 8, 9, 10, 11, 12, 13, 14 or 150 on the high end the range for at least 10, 20, 25, 30, 40, 50, 06, 70, 75, 80, 90, 95 or 100% the primers of the set of primers.

In certain embodiments, wherein the amplification reaction is a PCR reaction the length of the annealing step in the PCR reaction is between 10, 15, 20, 30, 45, and 60 minutes on the low end of the range, and 15, 20, 30, 45, 60, 120, 180, or 240 minutes on the high end of the range. In certain embodiments, the primer concentration in the amplification, such as the PCR reaction is between 1 and 10 nM. Furthermore, in exemplary embodiments, the primers in the set of primers, are designed to minimize primer dimer formation.

Accordingly, in an example of any of the methods herein that include an amplification step, the amplification reaction is a PCR reaction, the annealing temperature is between 1 and 10° C. greater than the melting temperature of at least 90% of the primers of the set of primers, the length of the annealing step in the PCR reaction is between 15 and 60 minutes, the primer concentration in the amplification reaction is between 1 and 10 nM, and the primers in the set of primers, are designed to minimize primer dimer formation. In a further aspect of this example, the multiplex amplification reaction is performed under limiting primer conditions.

In another embodiment, provided herein is a method for supporting a cancer (e.g., breast cancer, bladder cancer, or colorectal cancer) diagnosis for an individual, such as an individual suspected of having cancer (e.g., breast cancer, bladder cancer, or colorectal cancer), from a sample of blood or a fraction thereof from the individual, that includes performing a ctDNA SNV amplification/sequencing workflow as provided herein, to determine whether one or more single nucleotide variants are present in the plurality of single nucleotide variant loci. In this embodiment, the following elements, statements, guidelines or rules apply: the absence of a single nucleotide variant supports a diagnosis of stage 1a, 1b, or 2a adenocarcinoma, the presence of a single nucleotide variant supports a diagnosis of squamous cell carcinoma or a stage 2b or 3a adenocarcinoma, and/or the presence of ten or more single nucleotide variants supports a diagnosis of squamous cell carcinoma or a stage 2b or 3 adenocarcinoma.

Figure 15:
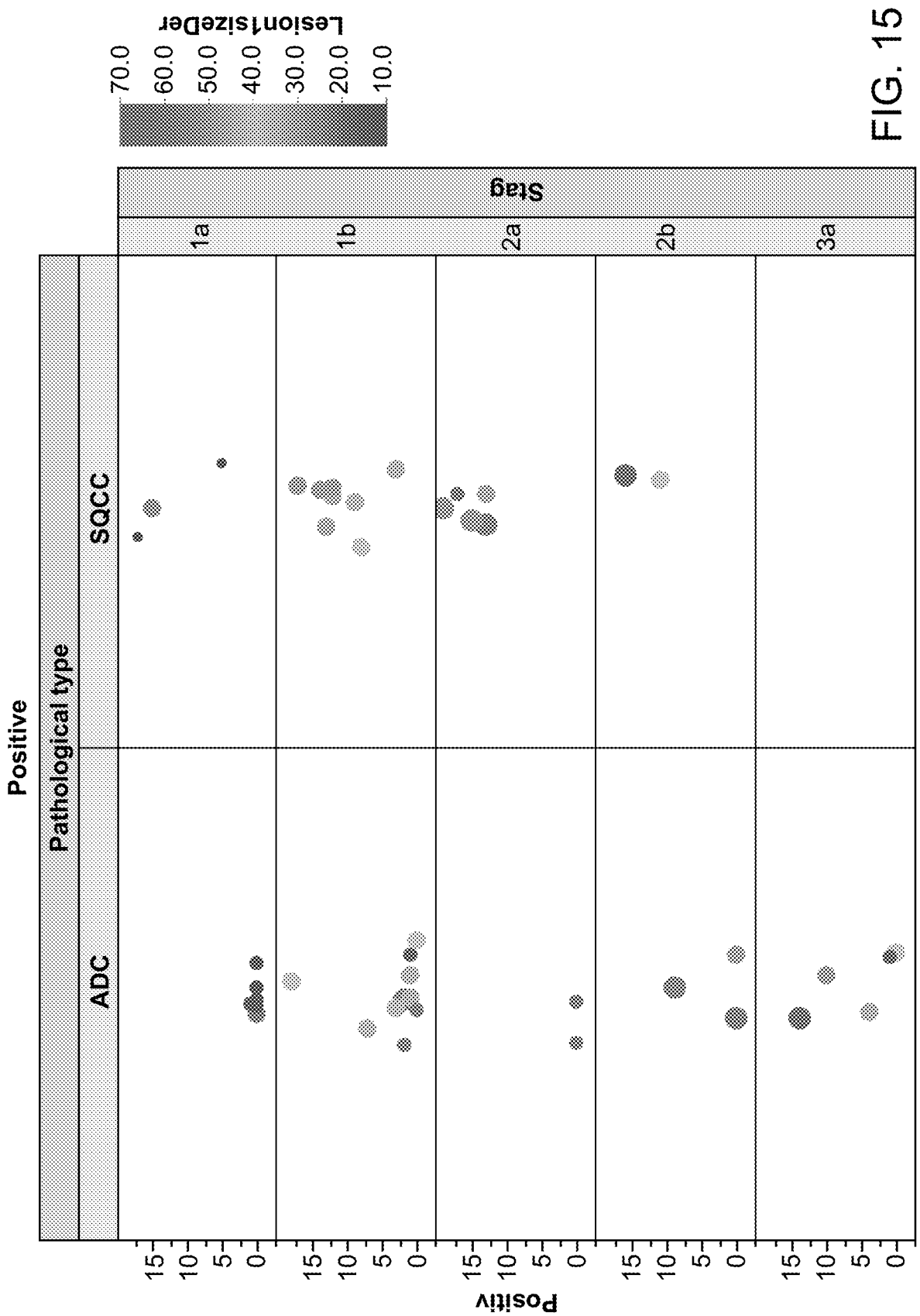
FIG. 15 shows the number of SNVs detected in plasma as a function of histological type and tumor size, The histological type and tumor stage were determined by the pathology report.
Figure 19:
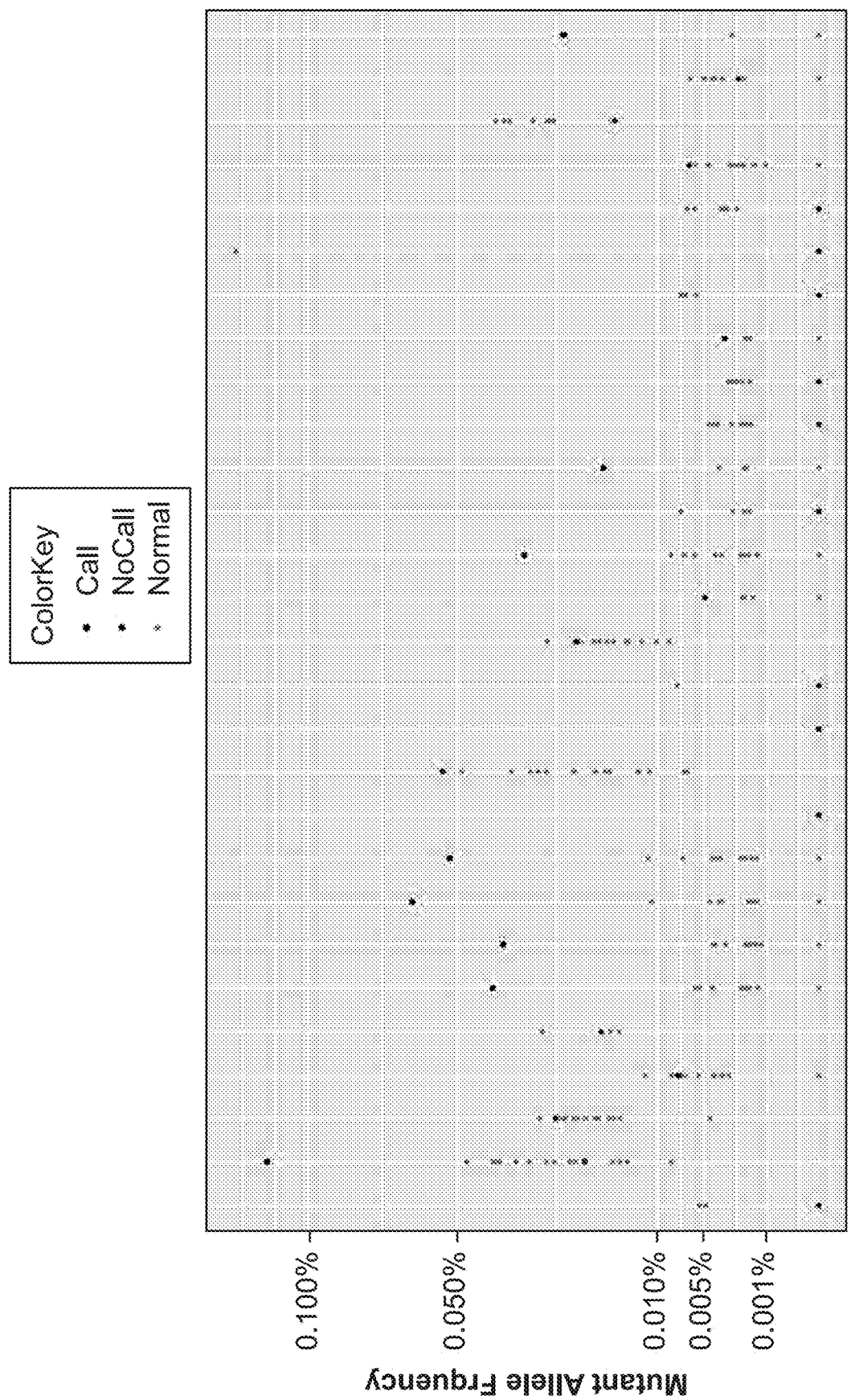
FIG. 19 is an example of detected assays and their background allele fractions for a plasma sample at relapse time (LTX103).
Figure 20A:
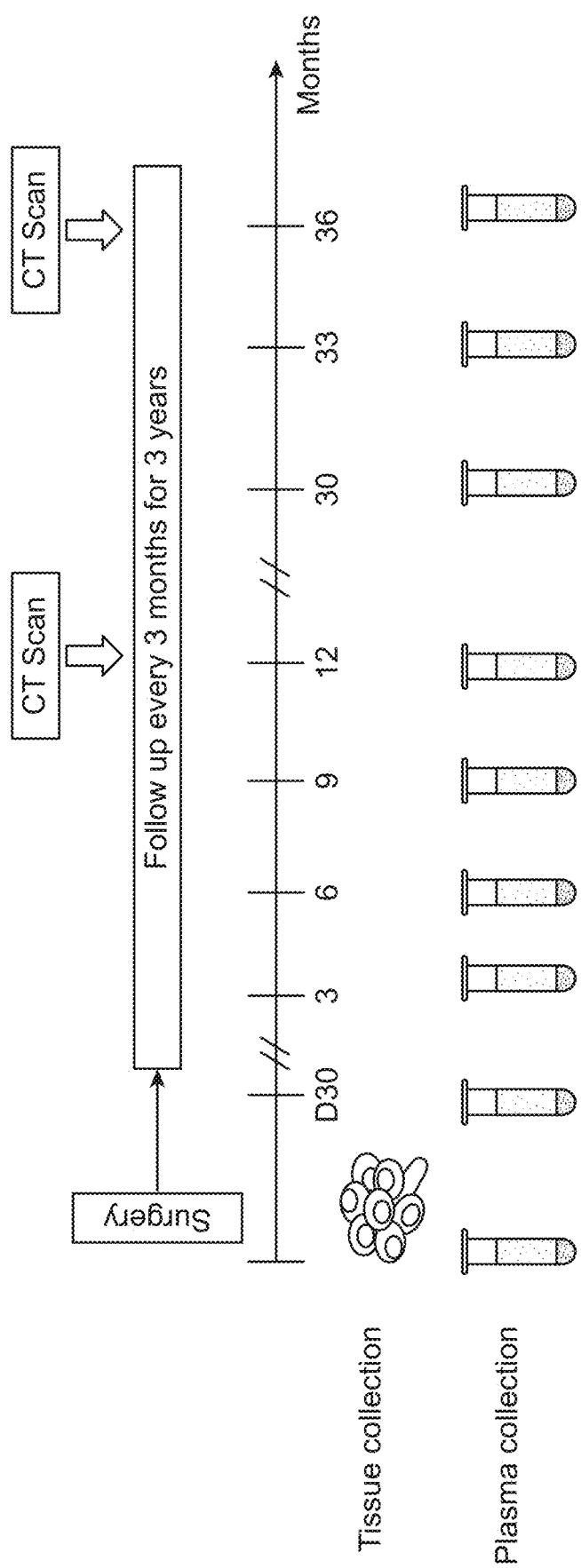
FIG. 20A-B: Schematic of Clinical and Molecular Protocols.
Figure 20B:
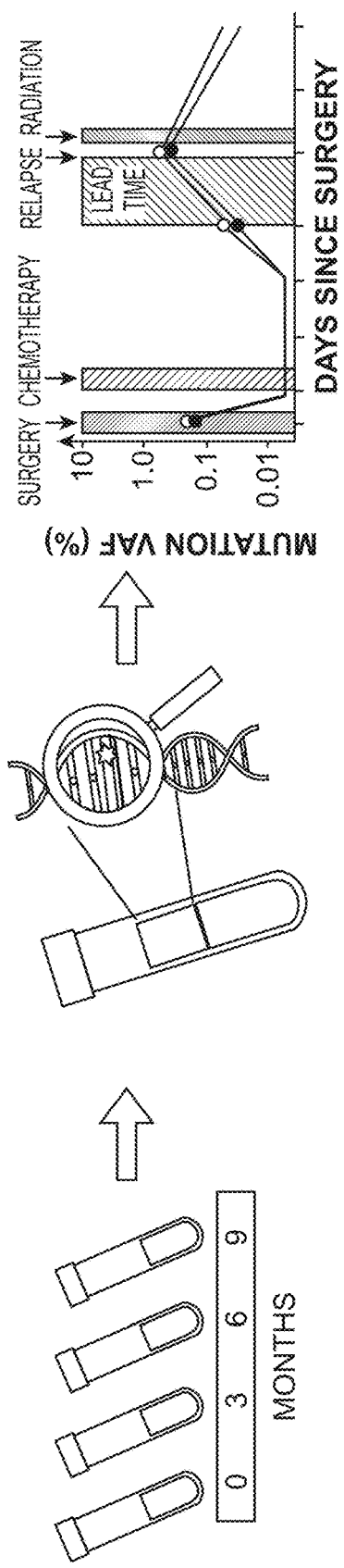
Figure 21:
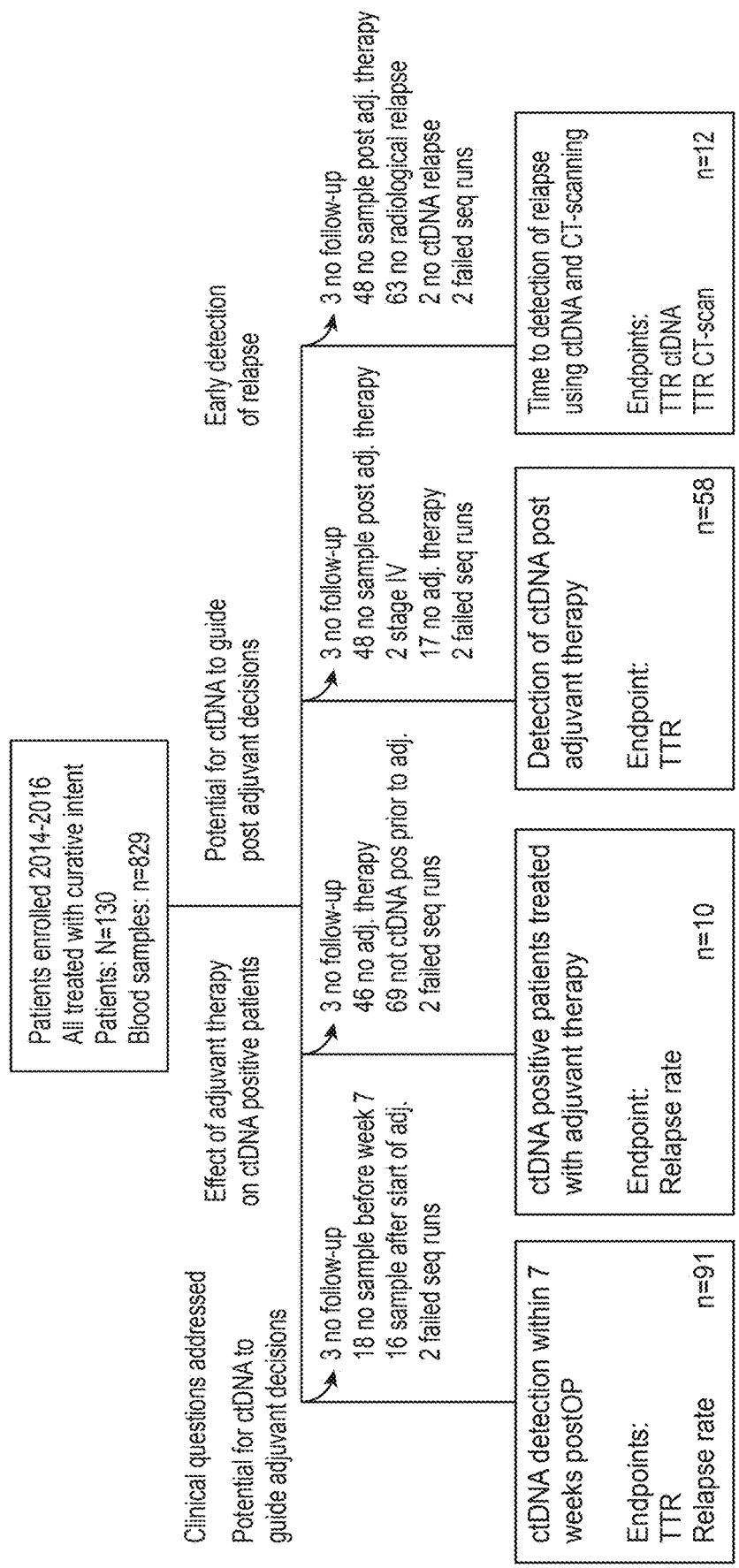
FIG. 21: Study Overview.

These results identify analysis using a ctDNA SNV amplification/sequencing workflow of lung ADC and SCC samples from an individual as a valuable method for identifying SNVs found in an ADC tumor, especially for stage 2b and 3a ADC tumors, and especially an SCC tumor at any stage (See e.g. FIG. 15 and FIG. 20A-B).

In certain embodiments, methods herein for detecting SNVs can be used to direct a therapeutic regimen. Therapies are available and under development that target specific mutations associated with ADC and SCC (Nature Review Cancer. 14:535-551 (2014). For example, detection of an EGFR mutation at L858R or T790M can be informative for selecting a therapy. Erlotinib, gefitinib, afatinib, AZK9291, CO-1686, and HM61713 are current therapies approved in the U.S. or in clinical trials, that target specific EGFR mutations. In another example, a G12D, G12C, or G12V mutation in KRAS can be used to direct an individual to a therapy of a combination of Selumetinib plus docetaxel. As another example, a mutation of V600E in BRAF can be used to direct a subject to a treatment of Vemurafenib, dabrafenib, and trametinib.

A sample analyzed in methods of the present invention, in certain illustrative embodiments, is a blood sample, or a fraction thereof. Methods provided herein, in certain embodiments, are specially adapted for amplifying DNA fragments, especially tumor DNA fragments that are found in circulating tumor DNA (ctDNA). Such fragments are typically about 160 nucleotides in length.

It is known in the art that cell-free nucleic acid (cfNA), e.g cfDNA, can be released into the circulation via various forms of cell death such as apoptosis, necrosis, autophagy and necroptosis. The cfDNA, is fragmented and the size distribution of the fragments varies from 150-350 bp to >10000 bp. (see Kalnina et al. *World J Gastroenterol.* 2015 Nov. 7; 21(41): 11636-11653). For example the size distributions of plasma DNA fragments in hepatocellular carcinoma (HCC) patients spanned a range of 100-220 bp in length with a peak in count frequency at about 166 bp and the highest tumor DNA concentration in fragments of 150-180 bp in length (see: Jiang et al. *Proc Nat Acad Sci USA* 112:E1317-E1325).

In an illustrative embodiment the circulating tumor DNA (ctDNA) is isolated from blood using EDTA-2Na tube after removal of cellular debris and platelets by centrifugation. The plasma samples can be stored at −80° C. until the DNA is extracted using, for example, QIAamp DNA Mini Kit (Qiagen, Hilden, Germany), (e.g. Hamakawa et al., *Br J Cancer.* 2015; 112:352-356). Hamakava et al. reported median concentration of extracted cell free DNA of all samples 43.1 ng per ml plasma (range 9.5-1338 ng ml/) and a mutant fraction range of 0.001-77.8%, with a median of 0.90%.

In certain illustrative embodiments the sample is a tumor. Methods are known in the art for isolating nucleic acid from a tumor and for creating a nucleic acid library from such a DNA sample given the teachings here. Furthermore, given the teachings herein, a skilled artisan will recognize how to create a nucleic acid library appropriate for the methods herein from other samples such as other liquid samples where the DNA is free floating in addition to ctDNA samples.

Methods of the present invention in certain embodiments, typically include a step of generating and amplifying a nucleic acid library from the sample (i.e. library preparation). The nucleic acids from the sample during the library preparation step can have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

A number of the embodiments provided herein, include detecting the SNVs in a ctDNA sample. Such methods in illustrative embodiments, include an amplification step and a sequencing step (Sometimes referred to herein as a 37 ctDNA SNV amplification/sequencing workflow). In an illustrative example, a ctDNA amplification/sequencing workflow can include generating a set of amplicons by performing a multiplex amplification reaction on nucleic acids isolated from a sample of blood or a fraction thereof from an individual, such as an individual suspected of having cancer, for example breast cancer, bladder cancer, or colorectal cancer, wherein each amplicon of the set of amplicons spans at least one single nucleotide variant loci of a set of single nucleotide variant loci, such as an SNV loci known to be associated with cancer (e.g., breast cancer, bladder cancer, or colorectal cancer); and determining the sequence of at least a segment of at each amplicon of the set of amplicons, wherein the segment comprises a single nucleotide variant loci. In this way, this exemplary method determines the single nucleotide variants present in the sample.

Exemplary ctDNA SNV amplification/sequencing workflows in more detail can include forming an amplification reaction mixture by combining a polymerase, nucleotide triphosphates, nucleic acid fragments from a nucleic acid library generated from the sample, and a set of primers that each binds an effective distance from a single nucleotide variant loci, or a set of primer pairs that each span an effective region that includes a single nucleotide variant loci. The single nucleotide variant loci, in exemplary embodiments, is one known to be associated with cancer, for example breast cancer, bladder cancer, or colorectal cancer. Then, subjecting the amplification reaction mixture to amplification conditions to generate a set of amplicons comprising at least one single nucleotide variant loci of a set of single nucleotide variant loci, preferably known to be associated with cancer (e.g., breast cancer, bladder cancer, or colorectal cancer); and determining the sequence of at least a segment of each amplicon of the set of amplicons, wherein the segment comprises a single nucleotide variant loci.

The effective distance of binding of the primers can be within 1, 2, 3, 4, 5, 6, 7, 8, 9, 10, 11, 12, 13, 14, 15, 20, 25, 30, 35, 40, 45, 50, 75, 100, 125, or 150 base pairs of a SNV loci. The effective range that a pair of primers spans typically includes an SNV and is typically 160 base pairs or less, and can be 150, 140, 130, 125, 100, 75, 50 or 25 base pairs or less. In other embodiments, the effective range that a pair of primers spans is 20, 25, 30, 40, 50, 60, 70, 75, 100, 110, 120, 125, 130, 140, or 150 nucleotides from an SNV loci on the low end of the range, and 25, 30, 40, 50, 60, 70, 75, 100, 110, 120, 125, 130, 140, or 150, 160, 170, 175, or 200 on the high end of the range.

Further details regarding methods of amplification that can be used in a ctDNA SNV amplification/sequencing workflow to detect SNVs for use in methods of the invention are provided in other sections of this specification.

SNV Calling Analytics

During performance of the methods provided herein, nucleic acid sequencing data is generated for amplicons created by the tiled multiplex PCR. Algorithm design tools are available that can be used and/or adapted to analyze this data to determine within certain confidence limits, whether a mutation, such as a SNV is present in a target gene.

Sequencing Reads can be demultiplexed using an in-house tool and mapped using the Burrows-Wheeler alignment software, Bwa mem function (BWA, Burrows-Wheeler Alignment Software (see Li H. and Durbin R. (2010) Fast and accurate long-read alignment with Burrows-Wheeler Transform. Bioinformatics, Epub. [PMID: 20080505]) on single end mode using pear merged reads to the hg19 genome. Amplification statistics QC can be performed by analyzing total reads, number of mapped reads, number of mapped reads on target, and number of reads counted.

In certain embodiments, any analytical method for detecting an SNV from nucleic acid sequencing data detection can be used with methods of the invention methods of the invention that include a step of detecting an SNV or determining whether an SNV is present. In certain illustrative embodiments, methods of the invention that utilize SNV METHOD 1 below are used. In other, even more illustrative embodiments, methods of the invention that include a step of detecting an SNV or determining whether an SNV is present at an SNV loci, utilize SNV METHOD 2 below.

SNV METHOD 1: For this embodiment, a background error model is constructed using normal plasma samples, which were sequenced on the same sequencing run to account for run-specific artifacts. In certain embodiments, 5, 10, 15, 20, 25, 30, 40, 50, 100, 150, 200, 250, or more than 250 normal plasma samples are analyzed on the same sequencing run. In certain illustrative embodiments, 20, 25, 40, or 50 normal plasma samples are analyzed on the same sequencing run. Noisy positions with normal median variant allele frequency greater than a cutoff are removed. For example this cutoff in certain embodiments is >0.1%, 0.2%, 0.25%, 0.5%, 1%, 2%, 5%, or 10%. In certain illustrative embodiments noisy positions with normal medial variant allele frequency greater than 0.5% are removed. Outlier samples were iteratively removed from the model to account for noise and contamination. In certain embodiments, samples with a Z score of greater than 5, 6, 7, 8, 9, or 10 are removed from the data analysis. For each base substitution of every genomic loci, the depth of read weighted mean and standard deviation of the error are calculated. Tumor or cell-free plasma samples' positions with at least 5 variant reads and a Z-score of 10 against the background error model for example, can be called as a candidate mutation.

SNV METHOD 2: For this embodiment Single Nucleotide Variants (SNVs) are determined using plasma ctDNA data. The PCR process is modeled as a stochastic process, estimating the parameters using a training set and making the final SNV calls for a separate testing set. The propagation of the error across multiple PCR cycles is determined, and the mean and the variance of the background error are calculated, and in illustrative embodiments, background error is differentiated from real mutations.

The following parameters are estimated for each base:
p=efficiency (probability that each read is replicated in each cycle)
$p_e$=error rate per cycle for mutation type e (probability that an error of type e occurs)
$X_0$=initial number of molecules As a read is replicated over the course of PCR process, the more errors occur. Hence, the error profile of the reads is determined by the degrees of separation from the original read. We refer to a read as $k^{th}$ generation if it has gone through k replications until it has been generated.

Let us define the following variables for each base:
$X_{ij}$=number of generation i reads generated in the PCR cycle j
$Y_{ij}$=total number of generation i reads at the end of cycle j
$X_{ij}^e$=number of generation i reads with mutation e generated in the PCR cycle j Moreover, in addition to normal molecules $X_0$, if there are additional $f_e X_0$ molecules with the mutation e at the beginning of the PCR process (hence fe/(1+fe) will be the fraction of mutated molecules in the initial mixture).

Given the total number of generation i−1 reads at cycle j−1, the number of generation i reads generated at cycle j has a binomial distribution with a sample size of $Y_{i-1,j-1}$ and probability parameter of p. Hence, $E(X_{ij}, |Y_{i-1,j-1}, p)=p Y_{i-1,j-1}$ and $Var(X_{ij}, |Y_{i-1,j-1}, p)=p(1-p) Y_{i-1,j-1}$.

We also have $$Y_{ij} = \sum_{k=i}^{j} X_{ik}.$$

Hence, by recursion, simulation or similar methods, we can determine $E(X_{ij})$. Similarly, we can determine $Var(X_{ij})=E(Var(X_{ij}, |p))+Var(E(X_{ij}, |p))$ using the distribution of p.

finally, $E(X_{ij}^e|Y_{i-1,j-1}, p_e)=p_e Y_{i-1,j-1}$ and $Var(X_{ij}^e|Y_{i-1,j-1}, p)=p_e(1-p_e)Y_{i-1,j-1}$, and we can use these to compute $E(X_{ij}^e)$ and $Var(X_{ij}^e)$.

In certain embodiments, SNV Method 2 is performed as follows:
a) Estimate a PCR efficiency and a per cycle error rate using a training data set;
b) Estimate a number of starting molecules for the testing data set at each base using the distribution of the efficiency estimated in step (a);
c) If needed, update the estimate of the efficiency for the testing data set using the starting number of molecules estimated in step (b);
d) Estimate the mean and variance for the total number of molecules, background error molecules and real mutation molecules (for a search space consisting of an initial percentage of real mutation molecules) using testing set data and parameters estimated in steps (a), (b) and (c);
e) Fit a distribution to the number of total error molecules (background error and real mutation) in the total molecules, and calculate the likelihood for each real mutation percentage in the search space; and
f) Determine the most likely real mutation percentage and calculate the confidence using the data from in step (e).

A confidence cutoff can be used to identify an SNV at an SNV loci. For example, a 90%, 95%, 96%, 97%, 98%, or 99% confidence cutoff can be used to call an SNV.

Exemplary SNV Method 2 Algorithm

The algorithm starts by estimating the efficiency and error rate per cycle using the training set. Let n denote the total number of PCR cycles.

The number of reads $R_b$ at each base b can be approximated by $(1+p_b)^n X_0$, where $p_b$ is the efficiency at base b. Then $(R_b/X_0)^{1/n}$ can be used to approximate $1+p_b$. Then, we can determine the mean and the standard variation of $p_b$ across all training samples, to estimate the parameters of the probability distribution (such as normal, beta, or similar distributions) for each base.

Similarly the number of error e reads $R_b^e$ at each base b can be used to estimate $p_e$. After determining the mean and the standard deviation of the error rate across all training samples, we approximate its probability distribution (such as normal, beta, or similar distributions) whose parameters are estimated using this mean and standard deviation values.

Next, for the testing data, we estimate the initial starting copy at each base as $$\int_0^1 \frac{R_b}{(1+p_b)^n} f(p_b) dp_b$$

where f(·) is an estimated distribution from the training set.

$$\int_0^1 \frac{R_b}{(1+p_b)^n} f(p_b) dp_b$$

where f(·) is an estimated distribution from the training set.

Hence, we have estimated the parameters that will be used in the stochastic process. Then, by using these estimates, we can estimate the mean and the variance of the molecules created at each cycle (note that we do this separately for normal molecules, error molecules, and mutation molecules).

Finally, by using a probabilistic method (such as maximum likelihood or similar methods), we can determine the best $f_e$ value that fits the distribution of the error, mutation, and normal molecules the best. More specifically, we estimate the expected ratio of the error molecules to total molecules for various $f_e$ values in the final reads, and determine the likelihood of our data for each of these values, and then select the value with the highest likelihood.

Primer tails can improve the detection of fragmented DNA from universally tagged libraries. If the library tag and the primer-tails contain a homologous sequence, hybridization can be improved (for example, melting temperature (Tm) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used.

In one embodiment, Libraries are generated from the samples above by ligating adaptors to the ends of DNA fragments in the samples, or to the ends of DNA fragments generated from DNA isolated from the samples. The fragments can then be amplified using PCR, for example, according to the following exemplary protocol:

95° C., 2 min; 15×[95° C., 20 sec, 55° C., 20 sec, 68° C., 20 sec], 68° C. 2 min, 4° C. hold.

Many kits and methods are known in the art for generation of libraries of nucleic acids that include universal primer binding sites for subsequent amplification, for example clonal amplification, and for subsequence sequencing. To help facilitate ligation of adapters library preparation and amplification can include end repair and adenylation (i.e. A-tailing). Kits especially adapted for preparing libraries from small nucleic acid fragments, especially circulating free DNA, can be useful for practicing methods provided herein. For example, the NEXTflex Cell Free kits available from Bioo Scientific( ) or the Natera Library Prep Kit (available from Natera, Inc. San Carlos, CA). However, such kits would typically be modified to include adaptors that are customized for the amplification and sequencing steps of the methods provided herein. Adaptor ligation can be performed using commercially available kits such as the ligation kit found in the AGILENT SURESELECT kit (Agilent, CA).

Target regions of the nucleic acid library generated from DNA isolated from the sample, especially a circulating free DNA sample for the methods of the present invention, are then amplified. For this amplification, a series of primers or primer pairs, which can include between 5, 10, 15, 20, 25, 50, 100, 125, 150, 250, 500, 1000, 2500, 5000, 10,000, 20,000, 25,000, or 50,000 on the low end of the range and 15, 20, 25, 50, 100, 125, 150, 250, 500, 1000, 2500, 5000, 10,000, 20,000, 25,000, 50,000, 60,000, 75,000, or 100,000 primers on the upper end of the range, that each bind to one of a series of primer binding sites.

Primer designs can be generated with Primer3 (Untergrasser A, Cutcutache I, Koressaar T, Ye J, Faircloth B C, Remm M, Rozen S G (2012) "Primer3—new capabilities and interfaces." Nucleic Acids Research 40(15):e115 and Koressaar T, Remm M (2007) "Enhancements and modifications of primer design program Primer3." Bioinformatics 23(10):1289-91) source code available at primer3.sourceforge.net). Primer specificity can be evaluated by BLAST and added to existing primer design pipeline criteria:

Primer specificities can be determined using the BLASTn program from the ncbi-blast-2.2.29+ package. The task option "blastn-short" can be used to map the primers against hg19 human genome. Primer designs can be determined as "specific" if the primer has less than 100 hits to the genome and the top hit is the target complementary primer binding region of the genome and is at least two scores higher than other hits (score is defined by BLASTn program). This can be done in order to have a unique hit to the genome and to not have many other hits throughout the genome.

The final selected primers can be visualized in IGV (James T. Robinson, Helga Thorvaldsdóttir, Wendy Winckler, Mitchell Guttman, Eric S. Lander, Gad Getz, Jill P. Mesirov. Integrative Genomics Viewer. Nature Biotechnology 29, 24-26 (2011)) and UCSC browser (Kent W J, Sugnet C W, Furey T S, Roskin K M, Pringle T H, Zahler A M, Haussler D. The human genome browser at UCSC. Genome Res. 2002 June; 12(6):996-1006) using bed files and coverage maps for validation.

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a set of forward and reverse primers specific for target regions that contain SNVs. The reaction mixtures provided herein, themselves forming in illustrative embodiments, a separate aspect of the invention.

An amplification reaction mixture useful for the present invention includes components known in the art for nucleic acid amplification, especially for PCR amplification. For example, the reaction mixture typically includes nucleotide triphosphates, a polymerase, and magnesium. Polymerases that are useful for the present invention can include any polymerase that can be used in an amplification reaction especially those that are useful in PCR reactions. In certain embodiments, hot start Taq polymerases are especially useful. Amplification reaction mixtures useful for practicing the methods provided herein, such as AmpliTaq Gold master mix (Life Technologies, Carlsbad, CA), are available commercially.

Amplification (e.g. temperature cycling) conditions for PCR are well known in the art. The methods provided herein can include any PCR cycling conditions that result in amplification of target nucleic acids such as target nucleic acids from a library. Non-limiting exemplary cycling conditions are provided in the Examples section herein.

There are many workflows that are possible when conducting PCR; some workflows typical to the methods disclosed herein are provided herein. The steps outlined herein are not meant to exclude other possible steps nor does it imply that any of the steps described herein are required for the method to work properly. A large number of parameter variations or other modifications are known in the literature, and may be made without affecting the essence of the invention.

In certain embodiments of the method provided herein, at least a portion and in illustrative examples the entire sequence of an amplicon, such as an outer primer target amplicon, is determined. Methods for determining the sequence of an amplicon are known in the art. Any of the sequencing methods known in the art, e.g. Sanger sequencing, can be used for such sequence determination. In illustrative embodiments high throughput next-generation sequencing techniques (also referred to herein as massively parallel sequencing techniques) such as, but not limited to, those employed in MYSEQ (ILLUMINA), HISEQ (ILLUMINA), ION TORRENT (LIFE TECHNOLOGIES), GENOME ANALYZER ILX (ILLUMINA), GS FLEX+ (ROCHE 454), can be used for sequencing the amplicons produced by the methods provided herein.

High throughput genetic sequencers are amenable to the use of barcoding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest (or expression level in the case of cDNA containing preparations). Biases in amplification efficiency can be taken into account in such quantitative determination.

Target Genes

Target genes of the present invention in exemplary embodiments, are cancer-related genes, and in many illustrative embodiments, cancer-related genes. A cancer-related gene (for example, a cancer-related gene or a bladder cancer-related gene or a colorectal cancer-related gene) refers to a gene associated with an altered risk for a cancer (e.g. breast cancer, bladder cancer, or colorectal cancer) or an altered prognosis for a cancer. Exemplary cancer-related genes that promote cancer include oncogenes; genes that enhance cell proliferation, invasion, or metastasis; genes that inhibit apoptosis; and pro-angiogenesis genes. Cancer-related genes that inhibit cancer include, but are not limited to, tumor suppressor genes; genes that inhibit cell proliferation, invasion, or metastasis; genes that promote apoptosis; and anti-angiogenesis genes.

An embodiment of the mutation detection method begins with the selection of the region of the gene that becomes the target. The region with known mutations is used to develop primers for mPCR-NGS to amplify and detect the mutation.

Methods provided herein can be used to detect virtually any type of mutation, especially mutations known to be associated with cancer and most particularly the methods provided herein are directed to mutations, especially SNVs, associated with cancer, specifically breast cancer, bladder cancer, or colorectal cancer. Exemplary SNVs can be in one or more of the following genes: EGFR, FGFR1, FGFR2, ALK, MET, ROS1, NTRK1, RET, HER2, DDR2, PDG-FRA, KRAS, NF1, BRAF, PIK3CA, MEK1, NOTCH1, MLL2, EZH2, TET2, DNMT3A, SOX2, MYC, KEAP1, CDKN2A, NRG1, TP53, LKB1, and PTEN, which have been identified in various lung cancer samples as being mutated, having increased copy numbers, or being fused to other genes and combinations thereof (Non-small-cell lung cancers: a heterogeneous set of diseases. Chen et al. Nat. Rev. Cancer. 2014 Aug. 14(8):535-551). In another example, the list of genes are those listed above, where SNVs have been reported, such as in the cited Chen et al. reference.

Amplification (e.g. PCR) Reaction Mixtures:

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a series of forward target-specific outer primers and a first strand reverse outer universal primer. Another illustrative embodiment is a reaction mixture that includes forward target-specific inner primers instead of the forward target-specific outer primers and amplicons from a first PCR reaction using the outer primers, instead of nucleic acid fragments from the nucleic acid library. The reaction mixtures provided herein, themselves forming in illustrative embodiments, a separate aspect of the invention. In illustrative embodiments, the reaction mixtures are PCR reaction mixtures. PCR reaction mixtures typically include magnesium.

In some embodiments, the reaction mixture includes ethylenediaminetetraacetic acid (EDTA), magnesium, tetramethyl ammonium chloride (TMAC), or any combination thereof. In some embodiments, the concentration of TMAC is between 20 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 8 mM.

The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 and 60 mM, or 60 and 80 mM $(NH_4)_2SO_4$, inclusive. In some embodiments, the ammonium [$NH_4^+$] concentration is between 0 and 160 mM, such as between 0 to 50, 50 to 100, or 100 to 160 mM, inclusive. In some embodiments, the sum of the potassium and ammonium concentration ([$K^+$]+[$NH_4^+$]) is between 0 and 160 mM, such as between 0 to 25, 25 to 50, 50 to 150, 50 to 75, 75 to 100, 100 to 125, or 125 to 160 mM, inclusive. An exemplary buffer with [$K^+$]+[$NH_4^+$]=120 mM is 20 mM KCl and 50 mM $(NH_4)_2SO_4$. In some embodiments, the buffer includes 25 to 75 mM Tris, pH 7.2 to 8, 0 to 50 mM KCl, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). Polymerases In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203). In some embodiments, AmpliTaq Gold® DNA Polymerase is used. In some embodiments a PrimeSTAR GXL DNA polymerase, a high fidelity polymerase that provides efficient PCR amplification when there is excess template in the reaction mixture, and when amplifying long products, is used (Takara Clontech, Mountain View, CA). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Missouri, catalog No. 100). In some embodiments, the polymerase is a PHUSION DNA polymerase, such as PHUSION High Fidelity DNA polymerase (M0530S, New England BioLabs, Inc.) or PHUSION Hot Start Flex DNA polymerase (M0535S, New England Bio-Labs, Inc.). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). In some embodiments, the polymerase is a T4 DNA polymerase (M0203S, New England BioLabs, Inc.).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

PCR Methods

In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments a QIAGEN Multiplex PCR Kit is used (QIAGEN catalog No. 206143). For 100×50 µl multiplex PCR reactions, the kit includes 2× QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1x QIAGEN MM final concentration (the recommended concentration), 7.5 nM of each primer in the library, 50 mM TMAC, and 7 ul DNA template in a 20 ul final volume is used. In some embodiments, the PCR thermocycling conditions include 95° C. for 10 minutes (hot start); 20 cycles of 96° C. for 30 seconds; 65° C. for 15 minutes; and 72° C. for 30 seconds; followed by 72° C. for 2 minutes (final extension); and then a 4° C. hold.

In some embodiments, 2× QIAGEN MM final concentration (twice the recommended concentration), 2 nM of each primer in the library, 70 mM TMAC, and 7 ul DNA template in a 20 ul total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20, 25, 30, 45, 60, 120, or 180 minutes; and optionally 72° C. for 30 seconds); followed by 72° C. for 2 minutes (final extension); and then a 4° C. hold.

Another exemplary set of conditions includes a semi-nested PCR approach. The first PCR reaction uses 20 ul a reaction volume with 2× QIAGEN MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 ul of the resulting product, diluted 1:200, is used as input in a second PCR reaction. This reaction uses a 10 ul reaction volume with 1× QIAGEN MM final concentration, 20 nM of each inner forward primer, and 1 uM of reverse primer tag. Thermocycling parameters include 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold. The annealing temperature can optionally be higher than the melting temperatures of some or all of the primers, as discussed herein (see U.S. patent application Ser. No. 14/918,544, filed Oct. 20, 2015, which is herein incorporated by reference in its entirety).

The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5° C. below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing may be tolerated. In some embodiments of the present inventions, the $T_A$ is higher than $T_m$, where at a given moment only a small fraction of the targets have a primer annealed (such as only ~1-5%). If these get extended, they are removed from the equilibrium of annealing and dissociating primers and target (as extension increases $T_m$ quickly to above 70° C.), and a new ~1-5% of targets has primers. Thus, by giving the reaction a long time for annealing, one can get ~100% of the targets copied per cycle.

In various embodiments, the annealing temperature is between 1, 2, 3, 4, 5, 6, 7, 8, 9, 10, 11, 12, 13° C. and 2, 3, 4, 5, 6, 7, 8, 9, 10, 11, 12, 13, or 15° C. on the high end of the range, greater than the melting temperature (such as the empirically measured or calculated $T_m$) of at least 25, 50, 60, 70, 75, 80, 90, 95, or 100% of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 3 to 8, 5 to 10, 5 to 8, 8 to 10, 10 to 12, or 12 to 15° C., inclusive) greater than the melting temperature (such as the empirically measured or calculated $T_m$) of at least 25%, 50%, 60%, 70%, 75%, 80%, 90%, 95%, or all of the non-identical primers, and the length of the annealing step (per PCR cycle) is between 5 and 180 minutes, such as 15 and 120 minutes, 15 and 60 minutes, 15 and 45 minutes, or 20 and 60 minutes, inclusive.

Exemplary Multiplex PCR Methods

In various embodiments, long annealing times (as discussed herein and exemplified in Example 10) and/or low primer concentrations are used. In fact, in certain embodiments, limiting primer concentrations and/or conditions are used. In various embodiments, the length of the annealing step is between 15, 20, 25, 30, 35, 40, 45, or 60 minutes on the low end of the range and 20, 25, 30, 35, 40, 45, 60, 120, or 180 minutes on the high end of the range. In various embodiments, the length of the annealing step (per PCR cycle) is between 30 and 180 minutes. For example, the annealing step can be between 30 and 60 minutes and the concentration of each primer can be less than 20, 15, 10, or 5 nM. In other embodiments the primer concentration is 1, 2, 3, 4, 5, 6, 7, 8, 9, 10, 15, 20, or 25 nM on the low end of the range, and 2, 3, 4, 5, 6, 7, 8, 9, 10, 15, 20, 25, and 50 on the high end of the range.

At high level of multiplexing, the solution may become viscous due to the large amount of primers in solution. If the solution is too viscous, one can reduce the primer concentration to an amount that is still sufficient for the primers to bind the template DNA. In various embodiments, between 1,000 and 100,000 different primers are used and the concentration of each primer is less than 20 nM, such as less than 10 nM or between 1 and 10 nM, inclusive.

Detection of Copy Number Variation (CNV)

In addition to SNVs and indels, methods for monitoring and detection of early relapse and metastasis described herein can also benefit from detection of CNVs.

In one aspect, the present invention generally relates, at least in part, to improved methods of determining the presence or absence of copy number variations, such as deletions or duplications of chromosome segments or entire chromosomes. The methods are particularly useful for detecting small deletions or duplications, which can be difficult to detect with high specificity and sensitivity using prior methods due to the small amount of data available from the relevant chromosome segment. The methods include improved analytical methods, improved bioassay methods, and combinations of improved analytical and bioassay methods. Methods of the invention can also be used to detect deletions or duplications that are only present in a small percentage of the cells or nucleic acid molecules that are tested. This allows deletions or duplications to be detected prior to the occurrence of disease (such as at a precancerous stage) or in the early stages of disease, such as before a large number of diseased cells (such as cancer cells) with the deletion or duplication accumulate. The more accurate detection of deletions or duplications associated with a disease or disorder enable improved methods for diagnosing, prognosticating, preventing, delaying, stabilizing, or treating the disease or disorder. Several deletions or duplications are known to be associated with cancer or with severe mental or physical handicaps.

In another aspect, the present invention generally relates, at least in part, to improved methods of detecting single nucleotide variations (SNVs). These improved methods include improved analytical methods, improved bioassay methods, and improved methods that use a combination of improved analytical and bioassay methods. The methods in certain illustrative embodiments are used to detect, diagnose, monitor, or stage cancer, for example in samples where the SNV is present at very low concentrations, for example less than 10%, 5%, 4%, 3%, 2.5%, 2%, 1%, 0.5%, 0.25%, or 0.1% relative to the total number of normal copies of the SNV locus, such as circulating free DNA samples. That is, these methods in certain illustrative embodiments are particularly well suited for samples where there is a relatively low percentage of a mutation or variant relative to the normal polymorphic alleles present for that genetic loci. Finally, provided herein are methods that combine the improved methods for detecting copy number variations with the improved methods for detecting single nucleotide variations.

Successful treatment of a disease such as cancer often relies on early diagnosis, correct staging of the disease, selection of an effective therapeutic regimen, and close monitoring to prevent or detect relapse. For cancer diagnosis, histological evaluation of tumor material obtained from tissue biopsy is often considered the most reliable method. However, the invasive nature of biopsy-based sampling has rendered it impractical for mass screening and regular follow up. Therefore, the present methods have the advantage of being able to be performed non-invasively if desired for relatively low cost with fast turnaround time. The targeted sequencing that may be used by the methods of the invention requires less reads than shotgun sequencing, such as a few million reads instead of 40 million reads, thereby decreasing cost. The multiplex PCR and next generation sequencing that may be used increase throughput and reduces costs.

In some exemplary embodiments, analysis of AAI patterns in ctDNA provide more detailed insights into the clonal architecture of tumors to help predict their therapeutic responses and optimize treatment strategies. Therefore, in certain embodiments, mmPCR-NGS panels are selected that target clinically actionable CNVs and SNVs. Such panels in certain illustrative embodiments, are particularly useful for patients with cancers where CNVs represent a substantial proportion of the mutation load, as is common in breast, ovarian, and lung cancer.

In some embodiments, the methods are used to detect a deletion, duplication, or single nucleotide variant in an individual. A sample from the individual that contains cells or nucleic acids suspected of having a deletion, duplication, or single nucleotide variant may be analyzed. In some embodiments, the sample is from a tissue or organ suspected of having a deletion, duplication, or single nucleotide variant, such as cells or a mass suspected of being cancerous. The methods of the invention can be used to detect deletion, duplication, or single nucleotide variant that are only present in one cell or a small number of cells in a mixture containing cells with the deletion, duplication, or single nucleotide variant and cells without the deletion, duplication, or single nucleotide variant. In some embodiments, cfDNA or cfRNA from a blood sample from the individual is analyzed. In some embodiments, cfDNA or cfRNA is secreted by cells, such as cancer cells. In some embodiments, cfDNA or cfRNA is released by cells undergoing necrosis or apoptosis, such as cancer cells. The methods of the invention can be used to detect deletion, duplication, or single nucleotide variant that are only present in a small percentage of the cfDNA or cfRNA. In some embodiments, one or more cells from an embryo are tested.

In addition to determining the presence or absence of copy number variation, one or more other factors can be analyzed if desired. These factors can be used to increase the accuracy of the diagnosis (such as determining the presence or absence of cancer or an increased risk for cancer, classifying the cancer, or staging the cancer) or prognosis. These factors can also be used to select a particular therapy or treatment regimen that is likely to be effective in the subject. Exemplary factors include the presence or absence of polymorphisms or mutation; altered (increased or decreased) levels of total or particular cfDNA, cfRNA, microRNA (miRNA); altered (increased or decreased) tumor fraction; altered (increased or decreased) methylation levels, altered (increased or decreased) DNA integrity, altered (increased or decreased) or alternative mRNA splicing.

The following sections describe methods for detecting deletions or duplications using phased data (such as inferred or measured phased data) or unphased data; samples that can be tested; methods for sample preparation, amplification, and quantification; methods for phasing genetic data; polymorphisms, mutations, nucleic acid alterations, mRNA splicing alterations, and changes in nucleic acid levels that can be detected; databases with results from the methods, other risk factors and screening methods; cancers that can be diagnosed or treated; cancer treatments; cancer models for testing treatments; and methods for formulating and administering treatments.

Exemplary Methods for Determining Ploidy Using Phased Data

Some of the methods of the invention are based in part on the discovery that using phased data for detecting CNVs decreases the false negative and false positive rates compared to using unphased data. This improvement is greatest for samples with CNVs present in low levels. Thus, phase data increases the accuracy of CNV detection compared to using unphased data (such as methods that calculate allele ratios at one or more loci or aggregate allele ratios to give an aggregated value (such as an average value) over a chromosome or chromosome segment without considering whether the allele ratios at different loci indicate that the same or different haplotypes appear to be present in an abnormal amount). Using phased data allows a more accurate determination to be made of whether differences between measured and expected allele ratios are due to noise or due to the presence of a CNV. For example, if the differences between measured and expected allele ratios at most or all of the loci in a region indicate that the same haplotype is overrepresented, then a CNV is more likely to be present. Using linkage between alleles in a haplotype allows one to determine whether the measured genetic data is consistent with the same haplotype being overrepresented (rather than random noise). In contrast, if the differences between measured and expected allele ratios are only due to noise (such as experimental error), then in some embodiments, about half the time the first haplotype appears to be overrepresented and about the other half of the time, the second haplotype appears to be overrepresented.

In some embodiments, phased genetic data is used to determine if there is an overrepresentation of the number of copies of a first homologous chromosome segment as compared to a second homologous chromosome segment in the genome of an individual (such as in the genome of one or more cells or in cfDNA or cfRNA). Exemplary overrepresentations include the duplication of the first homologous chromosome segment or the deletion of the second homologous chromosome segment. In some embodiments, there is not an overrepresentation since the first and homologous chromosome segments are present in equal proportions (such as one copy of each segment in a diploid sample). In some embodiments, calculated allele ratios in a nucleic acid sample are compared to expected allele ratios to determine if there is an overrepresentation as described further below. In this specification the phrase "a first homologous chromosome segment as compared to a second homologous chromosome segment" means a first homolog of a chromosome segment and a second homolog of the chromosome segment.

In some embodiments, the method includes obtaining phased genetic data for the first homologous chromosome segment comprising the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising, for each of the alleles at each of the loci in the set of polymorphic loci, the amount of each allele present in a sample of DNA or RNA from one or more target cells and one or more non-target cells from the individual. In some embodiments, the method includes enumerating a set of one or more hypotheses specifying the degree of overrepresentation of the first homologous chromosome segment; calculating, for each of the hypotheses, expected genetic data for the plurality of loci in the sample from the obtained phased genetic data for one or more possible ratios of DNA or RNA from the one or more target cells to the total DNA or RNA in the sample; calculating (such as calculating on a computer) for each possible ratio of DNA or RNA and for each hypothesis, the data fit between the obtained genetic data of the sample and the expected genetic data for the sample for that possible ratio of DNA or RNA and for that hypothesis; ranking one or more of the hypotheses according to the data fit; and selecting the hypothesis that is ranked the highest, thereby determining the degree of overrepresentation of the number of copies of the first homologous chromosome segment in the genome of one or more cells from the individual.

In some embodiments, the method involves obtaining phased genetic data using any of the methods described herein or any known method. In some embodiments, the method involves simultaneously or sequentially in any order (i) obtaining phased genetic data for the first homologous chromosome segment comprising the identity of the allele present at that locus on the first homologous chromosome segment for each locus in a set of polymorphic loci on the first homologous chromosome segment, (ii) obtaining phased genetic data for the second homologous chromosome segment comprising the identity of the allele present at that locus on the second homologous chromosome segment for each locus in the set of polymorphic loci on the second homologous chromosome segment, and (iii) obtaining measured genetic allelic data comprising the amount of each allele at each of the loci in the set of polymorphic loci in a sample of DNA from one or more cells from the individual.

In some embodiments, the method involves calculating allele ratios for one or more loci in the set of polymorphic loci that are heterozygous in at least one cell from which the sample was derived. In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. The calculated allele ratios may be calculated using any of the methods described herein or any standard method (such as any mathematical transformation of the calculated allele ratios described herein).

In some embodiments, the method involves determining if there is an overrepresentation of the number of copies of the first homologous chromosome segment by comparing one or more calculated allele ratios for a locus to an allele ratio that is expected for that locus if the first and second homologous chromosome segments are present in equal proportions. In some embodiments, the expected allele ratio assumes the possible alleles for a locus have an equal likelihood of being present. In some embodiments in which the calculated allele ratio for a particular locus is the measured quantity of one of the alleles divided by the total measured quantity of all the alleles for the locus, the corresponding expected allele ratio is 0.5 for a biallelic locus, or ⅓ for a triallelic locus. In some embodiments, the expected allele ratio is the same for all the loci, such as 0.5 for all loci. In some embodiments, the expected allele ratio assumes that the possible alleles for a locus can have a different likelihood of being present, such as the likelihood based on the frequency of each of the alleles in a particular population that the subject belongs in, such as a population based on the ancestry of the subject. Such allele frequencies are publicly available (see, e.g., HapMap Project; Perlegen Human Haplotype Project; web at ncbi.nlm.nih.gov/projects/SNP/; Sherry S T, Ward M H, Kholodov M, et al. dbSNP: the NCBI database of genetic variation. Nucleic Acids Res. 2001 Jan. 1; 29(1):308-11, which are each incorporated by reference in its entirety). In some embodiments, the expected allele ratio is the allele ratio that is expected for the particular individual being tested for a particular hypothesis specifying the degree of overrepresentation of the first homologous chromosome segment. For example, the expected allele ratio for a particular individual may be determined based on phased or unphased genetic data from the individual (such as from a sample from the individual that is unlikely to have a deletion or duplication such as a noncancerous sample) or data from one or more relatives from the individual.

In some embodiments, a calculated allele ratio is indicative of an overrepresentation of the number of copies of the first homologous chromosome segment if either (i) the allele ratio for the measured quantity of the allele present at that locus on the first homologous chromosome divided by the total measured quantity of all the alleles for the locus is greater than the expected allele ratio for that locus, or (ii) the allele ratio for the measured quantity of the allele present at that locus on the second homologous chromosome divided by the total measured quantity of all the alleles for the locus is less than the expected allele ratio for that locus. In some embodiments, a calculated allele ratio is only considered indicative of overrepresentation if it is significantly greater or lower than the expected ratio for that locus. In some embodiments, a calculated allele ratio is indicative of no overrepresentation of the number of copies of the first homologous chromosome segment if either (i) the allele ratio for the measured quantity of the allele present at that locus on the first homologous chromosome divided by the total measured quantity of all the alleles for the locus is less than or equal to the expected allele ratio for that locus, or (ii) the allele ratio for the measured quantity of the allele present at that locus on the second homologous chromosome divided by the total measured quantity of all the alleles for the locus is greater than or equal to the expected allele ratio for that locus. In some embodiments, calculated ratios equal to the corresponding expected ratio are ignored (since they are indicative of no overrepresentation).

In various embodiments, one or more of the following methods is used to compare one or more of the calculated allele ratios to the corresponding expected allele ratio(s). In some embodiments, one determines whether the calculated allele ratio is above or below the expected allele ratio for a particular locus irrespective of the magnitude of the difference. In some embodiments, one determines the magnitude of the difference between the calculated allele ratio and the expected allele ratio for a particular locus irrespective of whether the calculated allele ratio is above or below the expected allele ratio. In some embodiments, one determines whether the calculated allele ratio is above or below the expected allele ratio and the magnitude of the difference for a particular locus. In some embodiments, one determines whether the average or weighted average value of the calculated allele ratios is above or below the average or weighted average value of the expected allele ratios irrespective of the magnitude of the difference. In some embodiments, one determines the magnitude of the difference between the average or weighted average value of the calculated allele ratios and the average or weighted average value of the expected allele ratios irrespective of whether the average or weighted average of the calculated allele ratio is above or below the average or weighted average value of the expected allele ratio. In some embodiments, one determines whether the average or weighted average value of the calculated allele ratios is above or below the average or weighted average value of the expected allele ratios and the magnitude of the difference. In some embodiments, one determines an average or weighted average value of the magnitude of the difference between the calculated allele ratios and the expected allele ratios.

In some embodiments, the magnitude of the difference between the calculated allele ratio and the expected allele ratio for one or more loci is used to determine whether the overrepresentation of the number of copies of the first homologous chromosome segment is due to a duplication of the first homologous chromosome segment or a deletion of the second homologous chromosome segment in the genome of one or more of the cells.

In some embodiments, an overrepresentation of the number of copies of the first homologous chromosome segment is determined to be present if one or more of following conditions is met. In some embodiments, the number of calculated allele ratios that are indicative of an overrepresentation of the number of copies of the first homologous chromosome segment is above a threshold value. In some embodiments, the number of calculated allele ratios that are indicative of no overrepresentation of the number of copies of the first homologous chromosome segment is below a threshold value. In some embodiments, the magnitude of the difference between the calculated allele ratios that are indicative of an overrepresentation of the number of copies of the first homologous chromosome segment and the corresponding expected allele ratios is above a threshold value. In some embodiments, for all calculated allele ratios that are indicative of overrepresentation, the sum of the magnitude of the difference between a calculated allele ratio and the corresponding expected allele ratio is above a threshold value. In some embodiments, the magnitude of the difference between the calculated allele ratios that are indicative of no overrepresentation of the number of copies of the first homologous chromosome segment and the corresponding expected allele ratios is below a threshold value. In some embodiments, the average or weighted average value of the calculated allele ratios for the measured quantity of the allele present on the first homologous chromosome divided by the total measured quantity of all the alleles for the locus is greater than the average or weighted average value of the expected allele ratios by at least a threshold value. In some embodiments, the average or weighted average value of the calculated allele ratios for the measured quantity of the allele present on the second homologous chromosome divided by the total measured quantity of all the alleles for the locus is less than the average or weighted average value of the expected allele ratios by at least a threshold value. In some embodiments, the data fit between the calculated allele ratios and allele ratios that are predicted for an overrepresentation of the number of copies of the first homologous chromosome segment is below a threshold value (indicative of a good data fit). In some embodiments, the data fit between the calculated allele ratios and allele ratios that are predicted for no overrepresentation of the number of copies of the first homologous chromosome segment is above a threshold value (indicative of a poor data fit).

In some embodiments, an overrepresentation of the number of copies of the first homologous chromosome segment is determined to be absent if one or more of following conditions is met. In some embodiments, the number of calculated allele ratios that are indicative of an overrepresentation of the number of copies of the first homologous chromosome segment is below a threshold value. In some embodiments, the number of calculated allele ratios that are indicative of no overrepresentation of the number of copies of the first homologous chromosome segment is above a threshold value. In some embodiments, the magnitude of the difference between the calculated allele ratios that are indicative of an overrepresentation of the number of copies of the first homologous chromosome segment and the corresponding expected allele ratios is below a threshold value. In some embodiments, the magnitude of the difference between the calculated allele ratios that are indicative of no overrepresentation of the number of copies of the first homologous chromosome segment and the corresponding expected allele ratios is above a threshold value. In some embodiments, the average or weighted average value of the calculated allele ratios for the measured quantity of the allele present on the first homologous chromosome divided by the total measured quantity of all the alleles for the locus minus the average or weighted average value of the expected allele ratios is less than a threshold value. In some embodiments, the average or weighted average value of the expected allele ratios minus the average or weighted average value of the calculated allele ratios for the measured quantity of the allele present on the second homologous chromosome divided by the total measured quantity of all the alleles for the locus is less than a threshold value. In some embodiments, the data fit between the calculated allele ratios and allele ratios that are predicted for an overrepresentation of the number of copies of the first homologous chromosome segment is above a threshold value. In some embodiments, the data fit between the calculated allele ratios and allele ratios that are predicted for no overrepresentation of the number of copies of the first homologous chromosome segment is below a threshold value. In some embodiments, the threshold is determined from empirical testing of samples known to have a CNV of interest and/or samples known to lack the CNV.

In some embodiments, determining if there is an overrepresentation of the number of copies of the first homologous chromosome segment includes enumerating a set of one or more hypotheses specifying the degree of overrepresentation of the first homologous chromosome segment. On exemplary hypothesis is the absence of an overrepresentation since the first and homologous chromosome segments are present in equal proportions (such as one copy of each segment in a diploid sample). Other exemplary hypotheses include the first homologous chromosome segment being duplicated one or more times (such as 1, 2, 3, 4, 5, or more extra copies of the first homologous chromosome compared to the number of copies of the second homologous chromosome segment). Another exemplary hypothesis includes the deletion of the second homologous chromosome segment. Yet another exemplary hypothesis is the deletion of both the first and the second homologous chromosome segments. In some embodiments, predicted allele ratios for the loci that are heterozygous in at least one cell are estimated for each hypothesis given the degree of overrepresentation specified by that hypothesis. In some embodiments, the likelihood that the hypothesis is correct is calculated by comparing the calculated allele ratios to the predicted allele ratios, and the hypothesis with the greatest likelihood is selected.

In some embodiments, an expected distribution of a test statistic is calculated using the predicted allele ratios for each hypothesis. In some embodiments, the likelihood that the hypothesis is correct is calculated by comparing a test statistic that is calculated using the calculated allele ratios to the expected distribution of the test statistic that is calculated using the predicted allele ratios, and the hypothesis with the greatest likelihood is selected.

In some embodiments, predicted allele ratios for the loci that are heterozygous in at least one cell are estimated given the phased genetic data for the first homologous chromosome segment, the phased genetic data for the second homologous chromosome segment, and the degree of overrepresentation specified by that hypothesis. In some embodiments, the likelihood that the hypothesis is correct is calculated by comparing the calculated allele ratios to the predicted allele ratios; and the hypothesis with the greatest likelihood is selected.

Use of Mixed Samples

It will be understood that for many embodiments, the sample is a mixed sample with DNA or RNA from one or more target cells and one or more non-target cells. In some embodiments, the target cells are cells that have a CNV, such as a deletion or duplication of interest, and the non-target cells are cells that do not have the copy number variation of interest (such as a mixture of cells with the deletion or duplication of interest and cells without any of the deletions or duplications being tested). In some embodiments, the target cells are cells that are associated with a disease or disorder or an increased risk for disease or disorder (such as cancer cells), and the non-target cells are cells that are not associated with a disease or disorder or an increased risk for disease or disorder (such as noncancerous cells). In some embodiments, the target cells all have the same CNV. In some embodiments, two or more target cells have different CNVs. In some embodiments, one or more of the target cells has a CNV, polymorphism, or mutation associated with the disease or disorder or an increased risk for disease or disorder that is not found it at least one other target cell. In some such embodiments, the fraction of the cells that are associated with the disease or disorder or an increased risk for disease or disorder out of the total cells from a sample is assumed to be greater than or equal to the fraction of the most frequent of these CNVs, polymorphisms, or mutations in the sample. For example if 6% of the cells have a K-ras mutation, and 8% of the cells have a BRAF mutation, at least 8% of the cells are assumed to be cancerous.

In some embodiments, the ratio of DNA (or RNA) from the one or more target cells to the total DNA (or RNA) in the sample is calculated. In some embodiments, a set of one or more hypotheses specifying the degree of overrepresentation of the first homologous chromosome segment are enumerated. In some embodiments, predicted allele ratios for the loci that are heterozygous in at least one cell are estimated given the calculated ratio of DNA or RNA and the degree of overrepresentation specified by that hypothesis are estimated for each hypothesis. In some embodiments, the likelihood that the hypothesis is correct is calculated by comparing the calculated allele ratios to the predicted allele ratios, and the hypothesis with the greatest likelihood is selected.

In some embodiments, an expected distribution of a test statistic calculated using the predicted allele ratios and the calculated ratio of DNA or RNA is estimated for each hypothesis. In some embodiments, the likelihood that the hypothesis is correct is determined by comparing a test statistic calculated using the calculated allele ratios and the calculated ratio of DNA or RNA to the expected distribution of the test statistic calculated using the predicted allele ratios and the calculated ratio of DNA or RNA, and the hypothesis with the greatest likelihood is selected.

In some embodiments, the method includes enumerating a set of one or more hypotheses specifying the degree of overrepresentation of the first homologous chromosome segment. In some embodiments, the method includes estimating, for each hypothesis, either (i) predicted allele ratios for the loci that are heterozygous in at least one cell given the degree of overrepresentation specified by that hypothesis or (ii) for one or more possible ratios of DNA or RNA, an expected distribution of a test statistic calculated using the predicted allele ratios and the possible ratio of DNA or RNA from the one or more target cells to the total DNA or RNA in the sample. In some embodiments, a data fit is calculated by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, one or more of the hypotheses are ranked according to the data fit, and the hypothesis that is ranked the highest is selected. In some embodiments, a technique or algorithm, such as a search algorithm, is used for one or more of the following steps: calculating the data fit, ranking the hypotheses, or selecting the hypothesis that is ranked the highest. In some embodiments, the data fit is a fit to a beta-binomial distribution or a fit to a binomial distribution. In some embodiments, the technique or algorithm is selected from the group consisting of maximum likelihood estimation, maximum a-posteriori estimation, Bayesian estimation, dynamic estimation (such as dynamic Bayesian estimation), and expectation-maximization estimation. In some embodiments, the method includes applying the technique or algorithm to the obtained genetic data and the expected genetic data.

In some embodiments, the method includes creating a partition of possible ratios that range from a lower limit to an upper limit for the ratio of DNA or RNA from the one or more target cells to the total DNA or RNA in the sample. In some embodiments, a set of one or more hypotheses specifying the degree of overrepresentation of the first homologous chromosome segment are enumerated. In some embodiments, the method includes estimating, for each of the possible ratios of DNA or RNA in the partition and for each hypothesis, either (i) predicted allele ratios for the loci that are heterozygous in at least one cell given the possible ratio of DNA or RNA and the degree of overrepresentation specified by that hypothesis or (ii) an expected distribution of a test statistic calculated using the predicted allele ratios and the possible ratio of DNA or RNA. In some embodiments, the method includes calculating, for each of the possible ratios of DNA or RNA in the partition and for each hypothesis, the likelihood that the hypothesis is correct by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, the combined probability for each hypothesis is determined by combining the probabilities of that hypothesis for each of the possible ratios in the partition; and the hypothesis with the greatest combined probability is selected. In some embodiments, the combined probability for each hypothesis is determining by weighting the probability of a hypothesis for a particular possible ratio based on the likelihood that the possible ratio is the correct ratio.

In some embodiments, a technique selected from the group consisting of maximum likelihood estimation, maximum a-posteriori estimation, Bayesian estimation, dynamic estimation (such as dynamic Bayesian estimation), and expectation-maximization estimation is used to estimate the ratio of DNA or RNA from the one or more target cells to the total DNA or RNA in the sample. In some embodiments, the ratio of DNA or RNA from the one or more target cells to the total DNA or RNA in the sample is assumed to be the same for two or more (or all) of the CNVs of interest. In some embodiments, the ratio of DNA or RNA from the one or more target cells to the total DNA or RNA in the sample is calculated for each CNV of interest.

Exemplary Methods for Using Imperfectly Phased Data

It will be understood that for many embodiments, imperfectly phased data is used. For example, it may not be known with 100% certainty which allele is present for one or more of the loci on the first and/or second homologous chromosome segment. In some embodiments, the priors for possible haplotypes of the individual (such as haplotypes based on population based haplotype frequencies) are used in calculating the probability of each hypothesis. In some embodiments, the priors for possible haplotypes are adjusted by either using another method to phase the genetic data or by using phased data from other subjects (such as prior subjects) to refine population data used for informatics based phasing of the individual.

In some embodiments, the phased genetic data comprises probabilistic data for two or more possible sets of phased genetic data, wherein each possible set of phased data comprises a possible identity of the allele present at each locus in the set of polymorphic loci on the first homologous chromosome segment and a possible identity of the allele present at each locus in the set of polymorphic loci on the second homologous chromosome segment. In some embodiments, the probability for at least one of the hypotheses is determined for each of the possible sets of phased genetic data. In some embodiments, the combined probability for the hypothesis is determined by combining the probabilities of the hypothesis for each of the possible sets of phased genetic data; and the hypothesis with the greatest combined probability is selected.

Any of the methods disclosed herein or any known method may be used to generate imperfectly phased data (such as using population based haplotype frequencies to infer the most likely phase) for use in the claimed methods. In some embodiments, phased data is obtained by probabilistically combining haplotypes of smaller segments. For example, possible haplotypes can be determined based on possible combinations of one haplotype from a first region with another haplotype from another region from the same chromosome. The probability that particular haplotypes from different regions are part of the same, larger haplotype block on the same chromosome can be determined using, e.g., population based haplotype frequencies and/or known recombination rates between the different regions.

In some embodiments, a single hypothesis rejection test is used for the null hypothesis of disomy. In some embodiments, the probability of the disomy hypothesis is calculated, and the hypothesis of disomy is rejected if the probability is below a given threshold value (such as less than 1 in 1,000). If the null hypothesis is rejected, this could be due to errors in the imperfectly phased data or due to the presence of a CNV. In some embodiments, more accurate phased data is obtained (such as phased data from any of the molecular phasing methods disclosed herein to obtain actual phased data rather than bioinformatics-based inferred phased data). In some embodiments, the probability of the disomy hypothesis is recalculated using the more accurate phased data to determine if the disomy hypothesis should still be rejected. Rejection of this hypothesis indicates that a duplication or deletion of the chromosome segment is present. If desired, the false positive rate can be altered by adjusting the threshold value.

Further Exemplary Embodiments for Determining Ploidy Using Phased Data

In illustrative embodiments, provided herein is a method for determining ploidy of a chromosomal segment in a sample of an individual. The method includes the following steps: receiving allele frequency data comprising the amount of each allele present in the sample at each loci in a set of polymorphic loci on the chromosomal segment; generating phased allelic information for the set of polymorphic loci by estimating the phase of the allele frequency data; generating individual probabilities of allele frequencies for the polymorphic loci for different ploidy states using the allele frequency data; generating joint probabilities for the set of polymorphic loci using the individual probabilities and the phased allelic information; and selecting, based on the joint probabilities, a best fit model indicative of chromosomal ploidy, thereby determining ploidy of the chromosomal segment.

As disclosed herein, the allele frequency data (also referred to herein as measured genetic allelic data) can be generated by methods known in the art. For example, the data can be generated using qPCR or microarrays. In one illustrative embodiment, the data is generated using nucleic acid sequence data, especially high throughput nucleic acid sequence data.

In certain illustrative examples, the allele frequency data is corrected for errors before it is used to generate individual probabilities. In specific illustrative embodiments, the errors that are corrected include allele amplification efficiency bias. In other embodiments, the errors that are corrected include ambient contamination and genotype contamination. In some embodiments, errors that are corrected include allele amplification bias, sequencing errors, ambient contamination and genotype contamination.

In certain embodiments, the individual probabilities are generated using a set of models of both different ploidy states and allelic imbalance fractions for the set of polymorphic loci. In these embodiments, and other embodiments, the joint probabilities are generated by considering the linkage between polymorphic loci on the chromosome segment.

Accordingly, in one illustrative embodiment that combines some of these embodiments, provided herein is a method for detecting chromosomal ploidy in a sample of an individual, that includes the following steps: receiving nucleic acid sequence data for alleles at a set of polymorphic loci on a chromosome segment in the individual; detecting allele frequencies at the set of loci using the nucleic acid sequence data; correcting for allele amplification efficiency bias in the detected allele frequencies to generate corrected allele frequencies for the set of polymorphic loci; generating phased allelic information for the set of polymorphic loci by estimating the phase of the nucleic acid sequence data; generating individual probabilities of allele frequencies for the polymorphic loci for different ploidy states by comparing the corrected allele frequencies to a set of models of different ploidy states and allelic imbalance fractions of the set of polymorphic loci; generating joint probabilities for the set of polymorphic loci by combining the individual probabilities considering the linkage between polymorphic loci on the chromosome segment; and selecting, based on the joint probabilities, the best fit model indicative of chromosomal aneuploidy.

As disclosed herein, the individual probabilities can be generated using a set of models or hypothesis of both different ploidy states and average allelic imbalance fractions for the set of polymorphic loci. For example, in a particularly illustrative example, individual probabilities are generated by modeling ploidy states of a first homolog of the chromosome segment and a second homolog of the chromosome segment. The ploidy states that are modeled include the following: (1) all cells have no deletion or amplification of the first homolog or the second homolog of the chromosome segment; (2) at least some cells have a deletion of the first homolog or an amplification of the second homolog of the chromosome segment; and (3) at least some cells have a deletion of the second homolog or an amplification of the first homolog of the chromosome segment.

It will be understood that the above models can also be referred to as hypothesis that are used to constrain a model. Therefore, demonstrated above are 3 hypothesis that can be used.

The average allelic imbalance fractions modeled can include any range of average allelic imbalance that includes the actual average allelic imbalance of the chromosomal segment. For example, in certain illustrative embodiments, the range of average allelic imbalance that is modeled can be between 0, 0.1, 0.2, 0.25, 0.3, 0.4, 0.5, 0.6, 0.75, 1, 2, 2.5, 3, 4, and 5% on the low end, and 1, 2, 2.5, 3, 4, 5, 10, 15, 20, 25, 30, 40, 50, 60, 70 80 90, 95, and 99% on the high end. The intervals for the modeling with the range can be any interval depending on the computing power used and the time allowed for the analysis. For example, 0.01, 0.05, 0.02, or 0.1 intervals can be modeled.

In certain illustrative embodiments, the sample has an average allelic imbalance for the chromosomal segment of between 0.4% and 5%. In certain embodiments, the average allelic imbalance is low. In these embodiments, average allelic imbalance is typically less than 10%. In certain illustrative embodiments, the allelic imbalance is between 0.25, 0.3, 0.4, 0.5, 0.6, 0.75, 1, 2, 2.5, 3, 4, and 5% on the low end, and 1, 2, 2.5, 3, 4, and 5% on the high end. In other exemplary embodiments, the average allelic imbalance is between 0.4, 0.45, 0.5, 0.6, 0.7, 0.8, 0.9, or 1.0% on the low end and 0.5, 0.6, 0.7, 0.8, 0.9, 1.0, 1.5, 2.0, 3.0, 4.0, or 5.0% on the high end. For example, the average allelic imbalance of the sample in an illustrative example is between 0.45 and 2.5%. In another example, the average allelic imbalance is detected with a sensitivity of 0.45, 0.5, 0.6, 0.8, 0.8, 0.9, or 1.0%. That is, the test method is capable of detecting chromosomal aneuploidy down to an AAI of 0.45, 0.5, 0.6, 0.8, 0.8, 0.9, or 1.0%. In An exemplary sample with low allelic imbalance in methods of the present invention include plasma samples from individuals with cancer having circulating tumor DNA or plasma samples from pregnant females having circulating fetal DNA.

It will be understood that for SNVs, the proportion of abnormal DNA is typically measured using mutant allele frequency (number of mutant alleles at a locus/total number of alleles at that locus). Since the difference between the amounts of two homologs in tumours is analogous, we measure the proportion of abnormal DNA for a CNV by the average allelic imbalance (AAI), defined as |(H1−H2)|/(H1+H2), where Hi is the average number of copies of homolog i in the sample and Hi/(H1+H2) is the fractional abundance, or homolog ratio, of homolog i. The maximum homolog ratio is the homolog ratio of the more abundant homolog.

Assay drop-out rate is the percentage of SNPs with no reads, estimated using all SNPs. Single allele drop-out (ADO) rate is the percentage of SNPs with only one allele present, estimated using only heterozygous SNPs. Genotype confidence can be determined by fitting a binomial distribution to the number of reads at each SNP that were B-allele reads, and using the ploidy status of the focal region of the SNP to estimate the probability of each genotype.

For tumor tissue samples, chromosomal aneuploidy (exemplified in this paragraph by CNVs) can be delineated by transitions between allele frequency distributions. In plasma samples of cancer patients, individuals suspected of having cancer, individuals who previously were diagnosed with cancer, or as a cancer screen for at-risk individuals or the general population, CNVs can be identified by a maximum likelihood algorithm that searches for plasma CNVs in regions known to exhibit aneuploidy in cancer, and/or where the tumor sample from the same individual also has CNVs. In illustrative embodiments, the algorithm uses haplotype phase information of the individual whose sample is being analyzed for the presence of circulating tumor DNA to fit measured and corrected test sample allele counts to expected allele counts, for example using a joint distribution mode. Such haplotype phase information can be deduced from any sample from an individual that includes mostly, or at least 60, 70, 80, 90, 95, 96, 97, 98, 99% or all normal cell DNA, such as, but not limited to, a buffy coat sample, a saliva sample, or a skin sample, from parental genotypic information, or by de novo haplotype phasing, which could be achieved by a variety of methods (See e.g., Snyder, M., et al., Haplotype-resolved genome sequencing: experimental methods and applications. Nat Rev Genet 16, 344-358 (2015)), such as haplotyping by dilution (Kaper, F., et al., Whole-genome haplotyping by dilution, amplification, and sequencing. Proc Natl Acad Sci USA 110, 5552-5557 (2013)) or long-read sequencing (Kuleshov, V. et al. Whole-genome haplotyping using long reads and statistical methods. Nat Biotech 32, 261-266 (2014)). This algorithm can model expected allelic frequencies across all allelic imbalance ratios at 0.025% intervals for three sets of hypotheses: (1) all cells are normal (no allelic imbalance), (2) some/all cells have a homolog 1 deletion or homolog 2 amplification, or (3) some/all cells have a homolog 2 deletion or homolog 1 amplification. The likelihood of each hypothesis can be determined at each SNP using a Bayesian classifier based on a beta binomial model of expected and observed allele frequencies at all heterozygous SNPs, and then the joint likelihood across multiple SNPs can be calculated, in certain illustrative embodiments taking linkage of the SNP loci into consideration, as exemplified herein. In fact, in illustrative embodiments normal cell haplotype phase information obtained as disclosed above, is used by the algorithm to fit the measured and typically corrected test sample allele counts to expected allele counts using a joint distribution model The maximum likelihood hypothesis can then be selected.

Consider a chromosomal region with an average of N copies in the tumor, and let c denote the fraction of DNA in plasma derived from the mixture of normal and tumour cells in a disomic region. AAI is calculated as:

$$AAI = \frac{c|N-2|}{2 + c(N-2)_-}$$

In certain illustrative examples, the allele frequency data is corrected for errors before it is used to generate individual probabilities. Different types of error and/or bias correction are disclosed herein. In specific illustrative embodiments, the errors that are corrected are allele amplification efficiency bias. In other embodiments, the errors that are corrected include sequencing errors, ambient contamination and genotype contamination. In some embodiments, errors that are corrected include allele amplification bias, sequencing errors, ambient contamination and genotype contamination.

It will be understood that allele amplification efficiency bias can be determined for an allele as part of an experiment or laboratory determination that includes an on test sample, or it can be determined at a different time using a set of samples that include the allele whose efficiency is being calculated. Ambient contamination and genotype contamination are typically determined on the same run as the on-test sample analysis.

In certain embodiments, ambient contamination and genotype contamination are determined for homozygous alleles in the sample. It will be understood that for any given sample from an individual some loci in the sample, will be heterozygous and others will be homozygous, even if a locus is selected for analysis because it has a relatively high heterozygosity in the population. It is advantageous in some embodiments, to determine ploidy of a chromosomal segment using heterozygous loci for an individual, whereas ambient and genotype contamination can be calculated using homozygous loci.

In certain illustrative examples, the selecting is performed by analyzing a magnitude of a difference between the phased allelic information and estimated allelic frequencies generated for the models.

In illustrative examples, the individual probabilities of allele frequencies are generated based on a beta binomial model of expected and observed allele frequencies at the set of polymorphic loci. In illustrative examples, the individual probabilities are generated using a Bayesian classifier.

In certain illustrative embodiments, the nucleic acid sequence data is generated by performing high throughput DNA sequencing of a plurality of copies of a series of amplicons generated using a multiplex amplification reaction, wherein each amplicon of the series of amplicons spans at least one polymorphic loci of the set of polymorphic loci and wherein each of the polymeric loci of the set is amplified. In certain embodiments, the multiplex amplification reaction is performed under limiting primer conditions for at least ½ of the reactions. In some embodiments, limiting primer concentrations are used in ⅒, ⅕, ¼, ⅓, ½, or all of the reactions of the multiplex reaction. Provided herein are factors to consider to achieve limiting primer conditions in an amplification reaction such as PCR.

In certain embodiments, methods provided herein detect ploidy for multiple chromosomal segments across multiple chromosomes. Accordingly, the chromosomal ploidy in these embodiments is determined for a set of chromosome segments in the sample. For these embodiments, higher multiplex amplification reactions are needed. Accordingly, for these embodiments the multiplex amplification reaction can include, for example, between 2,500 and 50,000 multiplex reactions. In certain embodiments, the following ranges of multiplex reactions are performed: between 100, 200, 250, 500, 1000, 2500, 5000, 10,000, 20,000, 25000, 50000 on the low end of the range and between 200, 250, 500, 1000, 2500, 5000, 10,000, 20,000, 25000, 50000, and 100,000 on the high end of the range.

In illustrative embodiments, the set of polymorphic loci is a set of loci that are known to exhibit high heterozygosity. However, it is expected that for any given individual, some of those loci will be homozygous. In certain illustrative embodiments, methods of the invention utilize nucleic acid sequence information for both homozygous and heterozygous loci for an individual. The homozygous loci of an individual are used, for example, for error correction, whereas heterozygous loci are used for the determination of allelic imbalance of the sample. In certain embodiments, at least 10% of the polymorphic loci are heterozygous loci for the individual.

As disclosed herein, preference is given for analyzing target SNP loci that are known to be heterozygous in the population. Accordingly, in certain embodiments, polymorphic loci are chosen wherein at least 10, 20, 25, 50, 75, 80, 90, 95, 99, or 100% of the polymorphic loci are known to be heterozygous in the population.

As disclosed herein, in certain embodiments the sample is a plasma sample from a pregnant female.

In some examples, the method further comprises performing the method on a control sample with a known average allelic imbalance ratio. The control can have an average allelic imbalance ratio for a particular allelic state indicative of aneuploidy of the chromosome segment, of between 0.4 and 10% to mimic an average allelic imbalance of an allele in a sample that is present in low concentrations, such as would be expected for a circulating free DNA from a tumor.

In some embodiments, PlasmArt controls, as disclosed herein, are used as the controls. Accordingly, in certain aspects the is a sample generated by a method comprising fragmenting a nucleic acid sample known to exhibit a chromosomal aneuploidy into fragments that mimic the size of fragments of DNA circulating in plasma of the individual. In certain aspects a control is used that has no aneuploidy for the chromosome segment.

In illustrative embodiments, data from one or more controls can be analyzed in the method along with a test sample. The controls for example, can include a different sample from the individual that is not suspected of containing Chromosomal aneuploidy, or a sample that is suspected of containing CNV or a chromosomal aneuploidy. For example, where a test sample is a plasma sample suspected of containing circulating free tumor DNA, the method can be also be performed for a control sample from a tumor from the subject along with the plasma sample. As disclosed herein, the control sample can be prepared by fragmenting a DNA sample known to exhibit a chromosomal aneuploidy. Such fragmenting can result in a DNA sample that mimics the DNA composition of an apoptotic cell, especially when the sample is from an individual afflicted with cancer. Data from the control sample will increase the confidence of the detection of Chromosomal aneuploidy.

In certain embodiments of the methods of determining ploidy, the sample is a plasma sample from an individual suspected of having cancer. In these embodiments, the method further comprises determining based on the selecting whether copy number variation is present in cells of a tumor of the individual. For these embodiments, the sample can be a plasma sample from an individual. For these embodiments, the method can further include determining, based on the selecting, whether cancer is present in the individual.

These embodiments for determining ploidy of a chromosomal segment, can further include detecting a single nucleotide variant at a single nucleotide variance location in a set of single nucleotide variance locations, wherein detecting either a chromosomal aneuploidy or the single nucleotide variant or both, indicates the presence of circulating tumor nucleic acids in the sample.

These embodiments can further include receiving haplotype information of the chromosome segment for a tumor of the individual and using the haplotype information to generate the set of models of different ploidy states and allelic imbalance fractions of the set of polymorphic loci.

As disclosed herein, certain embodiments of the methods of determining ploidy can further include removing outliers from the initial or corrected allele frequency data before comparing the initial or the corrected allele frequencies to the set of models. For example, in certain embodiments, loci allele frequencies that are at least 2 or 3 standard deviations above or below the mean value for other loci on the chromosome segment, are removed from the data before being used for the modeling.

As mentioned herein, it will be understood that for many of the embodiments provided herein, including those for determining ploidy of a chromosomal segment, imperfectly or perfectly phased data is preferably used. It will also be understood, that provided herein are a number of features that provide improvements over prior methods for detecting ploidy, and that many different combinations of these features could be used.

In certain embodiments provided herein are computer systems and computer readable media to perform any methods of the present invention. These include systems and computer readable media for performing methods of determining ploidy. Accordingly, and as non-limiting examples of system embodiments, to demonstrate that any of the methods provided herein can be performed using a system and a computer readable medium using the disclosure herein, in another aspect, provided herein is a system for detecting chromosomal ploidy in a sample of an individual, the system comprising: an input processor configured to receive allelic frequency data comprising the amount of each allele present in the sample at each loci in a set of polymorphic loci on the chromosomal segment; a modeler configured to: generate phased allelic information for the set of polymorphic loci by estimating the phase of the allele frequency data; and generate individual probabilities of allele frequencies for the polymorphic loci for different ploidy states using the allele frequency data; and generate joint probabilities for the set of polymorphic loci using the individual probabilities and the phased allelic information; and a hypothesis manager configured to select, based on the joint probabilities, a best fit model indicative of chromosomal ploidy, thereby determining ploidy of the chromosomal segment.

In certain embodiments of this system embodiment, the allele frequency data is data generated by a nucleic acid sequencing system. In certain embodiments, the system further comprises an error correction unit configured to correct for errors in the allele frequency data, wherein the corrected allele frequency data is used by the modeler for to generate individual probabilities. In certain embodiments the error correction unit corrects for allele amplification efficiency bias. In certain embodiments, the modeler generates the individual probabilities using a set of models of both different ploidy states and allelic imbalance fractions for the set of polymorphic loci. The modeler, in certain exemplary embodiments generates the joint probabilities by considering the linkage between polymorphic loci on the chromosome segment.

In one illustrative embodiment, provided herein is a system for detecting chromosomal ploidy in a sample of an individual, that includes the following: an input processor configured to receive nucleic acid sequence data for alleles at a set of polymorphic loci on a chromosome segment in the individual and detect allele frequencies at the set of loci using the nucleic acid sequence data; an error correction unit configured to correct for errors in the detected allele frequencies and generate corrected allele frequencies for the set of polymorphic loci; a modeler configured to: generate phased allelic information for the set of polymorphic loci by estimating the phase of the nucleic acid sequence data; generate individual probabilities of allele frequencies for the polymorphic loci for different ploidy states by comparing the phased allelic information to a set of models of different ploidy states and allelic imbalance fractions of the set of polymorphic loci; and generate joint probabilities for the set of polymorphic loci by combining the individual probabilities considering the relative distance between polymorphic loci on the chromosome segment; and a hypothesis manager configured to select, based on the joint probabilities, a best fit model indicative of chromosomal aneuploidy.

In certain exemplary system embodiments provided herein the set of polymorphic loci comprises between 1000 and 50,000 polymorphic loci. In certain exemplary system embodiments provided herein the set of polymorphic loci comprises 100 known heterozygosity hot spot loci. In certain exemplary system embodiments provided herein the set of polymorphic loci comprise 100 loci that are at or within 0.5 kb of a recombination hot spot.

In certain exemplary system embodiments provided herein the best fit model analyzes the following ploidy states of a first homolog of the chromosome segment and a second homolog of the chromosome segment: (1) all cells have no deletion or amplification of the first homolog or the second homolog of the chromosome segment; (2) some or all cells have a deletion of the first homolog or an amplification of the second homolog of the chromosome segment; and (3) some or all cells have a deletion of the second homolog or an amplification of the first homolog of the chromosome segment.

In certain exemplary system embodiments provided herein the errors that are corrected comprise allelic amplification efficiency bias, contamination, and/or sequencing errors. In certain exemplary system embodiments provided herein the contamination comprises ambient contamination and genotype contamination. In certain exemplary system embodiments provided herein the ambient contamination and genotype contamination is determined for homozygous alleles.

In certain exemplary system embodiments provided herein the hypothesis manager is configured to analyze a magnitude of a difference between the phased allelic information and estimated allelic frequencies generated for the models. In certain exemplary system embodiments provided herein the modeler generates individual probabilities of allele frequencies based on a beta binomial model of expected and observed allele frequencies at the set of polymorphic loci. In certain exemplary system embodiments provided herein the modeler generates individual probabilities using a Bayesian classifier.

In certain exemplary system embodiments provided herein the nucleic acid sequence data is generated by performing high throughput DNA sequencing of a plurality of copies of a series of amplicons generated using a multiplex amplification reaction, wherein each amplicon of the series of amplicons spans at least one polymorphic loci of the set of polymorphic loci and wherein each of the polymeric loci of the set is amplified. In certain exemplary system embodiments provided herein, wherein the multiplex amplification reaction is performed under limiting primer conditions for at least ½ of the reactions. In certain exemplary system embodiments provided herein, wherein the sample has an average allelic imbalance of between 0.4% and 5%.

In certain exemplary system embodiments provided herein, the sample is a plasma sample from an individual suspected of having cancer, and the hypothesis manager is further configured to determine, based on the best fit model, whether copy number variation is present in cells of a tumor of the individual.

In certain exemplary system embodiments provided herein the sample is a plasma sample from an individual and the hypothesis manager is further configured to determine, based on the best fit model, that cancer is present in the individual. In these embodiments, the hypothesis manager can be further configured to detect a single nucleotide variant at a single nucleotide variance location in a set of single nucleotide variance locations, wherein detecting either a chromosomal aneuploidy or the single nucleotide variant or both, indicates the presence of circulating tumor nucleic acids in the sample.

In certain exemplary system embodiments provided herein, the input processor is further configured to receiving haplotype information of the chromosome segment for a tumor of the individual, and the modeler is configured to use the haplotype information to generate the set of models of different ploidy states and allelic imbalance fractions of the set of polymorphic loci.

In certain exemplary system embodiments provided herein, the modeler generates the models over allelic imbalance fractions ranging from 0% to 25%.

It will be understood that any of the methods provided herein can be executed by computer readable code that is stored on nontransitory computer readable medium. Accordingly, provided herein in one embodiment, is a nontransitory computer readable medium for detecting chromosomal ploidy in a sample of an individual, comprising computer readable code that, when executed by a processing device, causes the processing device to: receive allele frequency data comprising the amount of each allele present in the sample at each loci in a set of polymorphic loci on the chromosomal segment; generate phased allelic information for the set of polymorphic loci by estimating the phase of the allele frequency data; generate individual probabilities of allele frequencies for the polymorphic loci for different ploidy states using the allele frequency data; generate joint probabilities for the set of polymorphic loci using the individual probabilities and the phased allelic information; and select, based on the joint probabilities, a best fit model indicative of chromosomal ploidy, thereby determining ploidy of the chromosomal segment.

In certain computer readable medium embodiments, the allele frequency data is generated from nucleic acid sequence data. certain computer readable medium embodiments further comprise correcting for errors in the allele frequency data and using the corrected allele frequency data for the generating individual probabilities step. In certain computer readable medium embodiments the errors that are corrected are allele amplification efficiency bias. In certain computer readable medium embodiments the individual probabilities are generated using a set of models of both different ploidy states and allelic imbalance fractions for the set of polymorphic loci. In certain computer readable medium embodiments the joint probabilities are generated by considering the linkage between polymorphic loci on the chromosome segment.

In one particular embodiment, provided herein is a nontransitory computer readable medium for detecting chromosomal ploidy in a sample of an individual, comprising computer readable code that, when executed by a processing device, causes the processing device to: receive nucleic acid sequence data for alleles at a set of polymorphic loci on a chromosome segment in the individual; detect allele frequencies at the set of loci using the nucleic acid sequence data; correcting for allele amplification efficiency bias in the detected allele frequencies to generate corrected allele frequencies for the set of polymorphic loci; generate phased allelic information for the set of polymorphic loci by estimating the phase of the nucleic acid sequence data; generate individual probabilities of allele frequencies for the polymorphic loci for different ploidy states by comparing the corrected allele frequencies to a set of models of different ploidy states and allelic imbalance fractions of the set of polymorphic loci; generate joint probabilities for the set of polymorphic loci by combining the individual probabilities considering the linkage between polymorphic loci on the chromosome segment; and select, based on the joint probabilities, the best fit model indicative of chromosomal aneuploidy.

In certain illustrative computer readable medium embodiments, the selecting is performed by analyzing a magnitude of a difference between the phased allelic information and estimated allelic frequencies generated for the models.

In certain illustrative computer readable medium embodiments the individual probabilities of allele frequencies are generated based on a beta binomial model of expected and observed allele frequencies at the set of polymorphic loci.

It will be understood that any of the method embodiments provided herein can be performed by executing code stored on nontransitory computer readable medium.

Exemplary Embodiments for Detecting Cancer

In certain aspects, the present invention provides a method for detecting cancer. The sample, it will be understood can be a tumor sample or a liquid sample, such as plasma, from an individual suspected of having cancer. The methods are especially effective at detecting genetic mutations such as single nucleotide alterations such as SNVs, or copy number alterations, such as CNVs in samples with low levels of these genetic alterations as a fraction of the total DNA in a sample. Thus the sensitivity for detecting DNA or RNA from a cancer in samples is exceptional. The methods can combine any or all of the improvements provided herein for detecting CNV and SNV to achieve this exceptional sensitivity.

Accordingly, in certain embodiments provided herein, is a method for determining whether circulating tumor nucleic acids are present in a sample in an individual, and a nontransitory computer readable medium comprising computer readable code that, when executed by a processing device, causes the processing device to carry out the method. The method includes the following steps: analyzing the sample to determine a ploidy at a set of polymorphic loci on a chromosome segment in the individual; and determining the level of average allelic imbalance present at the polymorphic loci based on the ploidy determination, wherein an average allelic imbalance equal to or greater than 0.4%, 0.45%, 0.5%, 0.6%, 0.7%, 0.75%, 0.8%, 0.9%, or 1% is indicative of the presence of circulating tumor nucleic acids, such as ctDNA, in the sample.

In certain illustrative examples, an average allelic imbalance greater than 0.4, 0.45, or 0.5% is indicative the presence of ctDNA. In certain embodiments the method for determining whether circulating tumor nucleic acids are present, further comprises detecting a single nucleotide variant at a single nucleotide variance site in a set of single nucleotide variance locations, wherein detecting either an allelic imbalance equal to or greater than 0.5% or detecting the single nucleotide variant, or both, is indicative of the presence of circulating tumor nucleic acids in the sample. It will be understood that any of the methods provided for detecting chromosomal ploidy or CNV can be used to determine the level of allelic imbalance, typically expressed as average allelic imbalance. It will be understood that any of the methods provided herein for detecting an SNV can be used to detect the single nucleotide for this aspect of the present invention.

In certain embodiments the method for determining whether circulating tumor nucleic acids are present, further comprises performing the method on a control sample with a known average allelic imbalance ratio. The control, for example, can be a sample from the tumor of the individual. In some embodiments, the control has an average allelic imbalance expected for the sample under analysis. For example, an AAI between 0.5% and 5% or an average allelic imbalance ratio of 0.5%.

In certain embodiments, the analyzing step in the method for determining whether circulating tumor nucleic acids are present, includes analyzing a set of chromosome segments known to exhibit aneuploidy in cancer. In certain embodiments, the analyzing step in the method for determining whether circulating tumor nucleic acids are present, includes analyzing between 1,000 and 50,000 or between 100 and 1000, polymorphic loci for ploidy. In certain embodiments, the analyzing step in the method for determining whether circulating tumor nucleic acids are present, includes analyzing between 100 and 1000 single nucleotide variant sites. For example, in these embodiments the analyzing step can include performing a multiplex PCR to amplify amplicons across the 1000 to 50,000 polymeric loci and the 100 to 1000 single nucleotide variant sites. This multiplex reaction can be set up as a single reaction or as pools of different subset multiplex reactions. The multiplex reaction methods provided herein, such as the massive multiplex PCR disclosed herein provide an exemplary process for carrying out the amplification reaction to help attain improved multiplexing and therefore, sensitivity levels.

In certain embodiments, the multiplex PCR reaction is carried out under limiting primer conditions for at least 10%, 20%, 25%, 50%, 75%, 90%, 95%, 98%, 99%, or 100% of the reactions. Improved conditions for performing the massive multiplex reaction provided herein can be used.

In certain aspects, the above method for determining whether circulating tumor nucleic acids are present in a sample in an individual, and all embodiments thereof, can be carried out with a system. The disclosure provides teachings regarding specific functional and structural features to carry out the methods. As a non-limiting example, the system includes the following:

An input processor configured to analyze data from the sample to determine a ploidy at a set of polymorphic loci on a chromosome segment in the individual; and An modeler configured to determine the level of allelic imbalance present at the polymorphic loci based on the ploidy determination, wherein an allelic imbalance equal to or greater than 0.5% is indicative of the presence of circulating.

Exemplary Embodiments for Detecting Single Nucleotide Variants

In certain aspects, provided herein are methods for detecting single nucleotide variants in a sample. The improved methods provided herein can achieve limits of detection of 0.015, 0.017, 0.02, 0.05, 0.1, 0.2, 0.3, 0.4 or 0.5 percent SNV in a sample. All the embodiments for detecting SNVs can be carried out with a system. The disclosure provides teachings regarding specific functional and structural features to carry out the methods. Furthermore, provided herein are embodiments comprising a nontransitory computer readable medium comprising computer readable code that, when executed by a processing device, causes the processing device to carry out the methods for detectings SNVs provided herein.

Accordingly, provided herein in one embodiment, is a method for determining whether a single nucleotide variant is present at a set of genomic positions in a sample from an individual, the method comprising: for each genomic position, generating an estimate of efficiency and a per cycle error rate for an amplicon spanning that genomic position, using a training data set; receiving observed nucleotide identity information for each genomic position in the sample; determining a set of probabilities of single nucleotide variant percentage resulting from one or more real mutations at each genomic position, by comparing the observed nucleotide identity information at each genomic position to a model of different variant percentages using the estimated amplification efficiency and the per cycle error rate for each genomic position independently; and determining the most-likely real variant percentage and confidence from the set of probabilities for each genomic position.

In illustrative embodiments of the method for determining whether a single nucleotide variant is present, the estimate of efficiency and the per cycle error rate is generated for a set of amplicons that span the genomic position. For example, 2, 3, 4, 5, 10, 15, 20, 25, 50, 100 or more amplicons can be included that span the genomic position.

In illustrative embodiments of the method for determining whether a single nucleotide variant is present, the observed nucleotide identity information comprises an observed number of total reads for each genomic position and an observed number of variant allele reads for each genomic position.

In illustrative embodiments of the method for determining whether a single nucleotide variant is present, the sample is a plasma sample and the single nucleotide variant is present in circulating tumor DNA of the sample.

In another embodiment provided herein is a method for estimating the percent of single nucleotide variants that are present in a sample from an individual. The method includes the following steps: at a set of genomic positions, generating an estimate of efficiency and a per cycle error rate for one or more amplicon spanning those genomic positions, using a training data set; receiving observed nucleotide identity information for each genomic position in the sample; generating an estimated mean and variance for the total number of molecules, background error molecules and real mutation molecules for a search space comprising an initial percentage of real mutation molecules using the amplification efficiency and the per cycle error rate of the amplicons; and determining the percentage of single nucleotide variants present in the sample resulting from real mutations by determining a most-likely real single nucleotide variant percentage by fitting a distribution using the estimated means and variances to an observed nucleotide identity information in the sample.

In illustrative examples of this method for estimating the percent of single nucleotide variants that are present in a sample, the sample is a plasma sample and the single nucleotide variant is present in circulating tumor DNA of the sample.

The training data set for this embodiment of the invention typically includes samples from one or preferably a group of healthy individuals. In certain illustrative embodiments, the training data set is analyzed on the same day or even on the same run as one or more on-test samples. For example, samples from a group of 2, 3, 4, 5, 10, 15, 20, 25, 30, 36, 48, 96, 100, 192, 200, 250, 500, 1000 or more healthy individuals can be used to generate the training data set. Where data is available for larger number of healthy individuals, e.g. 96 or more, confidence increases for amplification efficiency estimates even if runs are performed in advance of performing the method for on-test samples. The PCR error rate can use nucleic acid sequence information generated not only for the SNV base location, but for the entire amplified region around the SNV, since the error rate is per amplicon. For example, using samples from 50 individuals and sequencing a 20 base pair amplicon around the SNV, error frequency data from 1000 base reads can be used to determine error frequency rate.

Typically the amplification efficiency is estimating by estimating a mean and standard deviation for amplification efficiency for an amplified segment and then fitting that to a distribution model, such as a binomial distribution or a beta binomial distribution. Error rates are determined for a PCR reaction with a known number of cycles and then a per cycle error rate is estimated.

In certain illustrative embodiments, estimating the starting molecules of the test data set further includes updating the estimate of the efficiency for the testing data set using the starting number of molecules estimated in step (b) if the observed number of reads is significantly different than the estimated number of reads. Then the estimate can be updated for a new efficiency and/or starting molecules.

The search space used for estimating the total number of molecules, background error molecules and real mutation molecules can include a search space from 0.1%, 0.2%, 0.25%, 0.5%, 1%, 2.5%, 5%, 10%, 15%, 20%, or 25% on the low end and 1%, 2%, 2.5%, 5%, 10%, 12.5%, 15%, 20%, 25%, 50%, 75%, 90%, or 95% on the high end copies of a base at an SNV position being the SNV base. Lower ranges, 0.1%, 0.2%, 0.25%, 0.5%, or 1% on the low end and 1%, 2%, 2.5%, 5%, 10%, 12.5%, or 15% on the high end can be used in illustrative examples for plasma samples where the method is detecting circulating tumor DNA. Higher ranges are used for tumor samples.

A distribution is fit to the number of total error molecules (background error and real mutation) in the total molecules to calculate the likelihood or probability for each possible real mutation in the search space. This distribution could be a binomial distribution or a beta binomial distribution.

The most likely real mutation is determined by determining the most likely real mutation percentage and calculating the confidence using the data from fitting the distribution. As an illustrative example and not intended to limit the clinical interpretation of the methods provided herein, if the mean mutation rate is high then the percent confidence needed to make a positive determination of an SNV is lower. For example, if the mean mutation rate for an SNV in a sample using the most likely hypothesis is 5% and the percent confidence is 99%, then a positive SNV call would be made. On the other hand for this illustrative example, if the mean mutation rate for an SNV in a sample using the most likely hypothesis is 1% and the percent confidence is 50%, then in certain situations a positive SNV call would not be made. It will be understood that clinical interpretation of the data would be a function of sensitivity, specificity, prevalence rate, and alternative product availability.

In one illustrative embodiment, the sample is a circulating DNA sample, such as a circulating tumor DNA sample.

In another embodiment, provided herein is a method for detecting one or more single nucleotide variants in a test sample from an individual. The method according to this embodiment, includes the following steps:

determining a median variant allele frequency for a plurality of control samples from each of a plurality of normal individuals, for each single nucleotide variant position in a set of single nucleotide variance positions based on results generated in a sequencing run, to identify selected single nucleotide variant positions having variant median allele frequencies in normal samples below a threshold value and to determine background error for each of the single nucleotide variant positions after removing outlier samples for each of the single nucleotide variant positions; determining an observed depth of read weighted mean and variance for the selected single nucleotide variant positions for the test sample based on data generated in the sequencing run for the test sample; and identifying using a computer, one or more single nucleotide variant positions with a statistically significant depth of read weighted mean compared to the background error for that position, thereby detecting the one or more single nucleotide variants.

In certain embodiments of this method for detecting one or more SNVs the sample is a plasma sample, the control samples are plasma samples, and the detected one or more single nucleotide variants detected is present in circulating tumor DNA of the sample. In certain embodiments of this method for detecting one or more SNVs the plurality of control samples comprises at least 25 samples. In certain illustrative embodiments, the plurality of control samples is at least 5, 10, 15, 20, 25, 50, 75, 100, 200, or 250 samples on the low end and 10, 15, 20, 25, 50, 75, 100, 200, 250, 500, and 1000 samples on the high end.

In certain embodiments of this method for detecting one or more SNVs, outliers are removed from the data generated in the high throughput sequencing run to calculate the observed depth of read weighted mean and observed variance are determined. In certain embodiments of this method for detecting one or more SNVs the depth of read for each single nucleotide variant position for the test sample is at least 100 reads.

In certain embodiments of this method for detecting one or more SNVs the sequencing run comprises a multiplex amplification reaction performed under limited primer reaction conditions. Improved methods for performing multiplex amplification reactions provided herein, are used to perform these embodiments in illustrative examples.

Not to be limited by theory, methods of the present embodiment utilize a background error model using normal plasma samples, that are sequenced on the same sequencing run as an on-test sample, to account for run-specific artifacts. Noisy positions with normal median variant allele frequencies above a threshold, for example >0.1%, 0.2%, 0.25%, 0.5% 0.75%, and 1.0%, are removed.

Outlier samples are iteratively removed from the model to account for noise and contamination. For each base substitution of every genomic loci, the depth of read weighted mean and standard deviation of the error are calculated. In certain illustrative embodiments, samples, such as tumor or cell-free plasma samples, with single nucleotide variant positions with at least a threshold number of reads, for example, at least 2, 3, 4, 5, 6, 7, 8, 9, 10, 15, 20, 25, 50, 100, 250, 500, or 1000 variant reads and al Z-score greater than 2.5, 5, 7.5 or 10 against the background error model in certain embodiments, are counted as a candidate mutation.

In certain embodiments, a depth of read of greater than 100, 250, 500, 1,000, 2000, 2500, 5000, 10,000, 20,000, 25,0000, 50,000, or 100,000 on the low end of the range and 2000, 2500, 5,000, 7,500, 10,000, 25,000, 50,000, 100,000, 250,000 or 500,000 reads on the high end, is attained in the sequencing run for each single nucleotide variant position in the set of single nucleotide variant positions. Typically, the sequencing run is a high throughput sequencing run. The mean or median values generated for the on-test samples, in illustrative embodiments are weighted by depth of reads. Therefore, the likelihood that a variant allele determination is real in a sample with 1 variant allele detected in 1000 reads is weighed higher than a sample with 1 variant allele detected in 10,000 reads. Since determinations of a variant allele (i.e. mutation) are not made with 100% confidence, the identified single nucleotide variant can be considered a candidate variant or a candidate mutations.

Exemplary Test Statistic for Analysis of Phased Data

An exemplary test statistic is described below for analysis of phased data from a sample known or suspected of being a mixed sample containing DNA or RNA that originated from two or more cells that are not genetically identical. Left denote the fraction of DNA or RNA of interest, for example the fraction of DNA or RNA with a CNV of interest, or the fraction of DNA or RNA from cells of interest, such as cancer cells. In some embodiments for cancer testing, f denotes the fraction of DNA or RNA from cancer cells in a mixture of cancer and normal cells, or f denotes the fraction of cancer cells in a mixture of cancer and normal cells. Note that this refers to the fraction of DNA from cells of interest assuming two copies of DNA are given by each cell of interest. This differs from the DNA fraction from cells of interest at a segment that is deleted or duplicated.

The possible allelic values of each SNP are denoted A and B. AA, AB, BA, and BB are used to denote all possible ordered allele pairs. In some embodiments, SNPs with ordered alleles AB or BA are analyzed. Let $N_i$ denote the number of sequence reads of the ith SNP, and $A_i$ and $B_i$ denote the number of reads of the ith SNP that indicate allele A and B, respectively. It is assumed:

$$N_i = A_i + B_i.$$

The allele ratio $R_i$ is defined:

$$R_i \triangleq \frac{A_i}{N_i}.$$

Let T denote the number of SNPs targeted.

Without loss of generality, some embodiments focus on a single chromosome segment. As a matter of further clarity, in this specification the phrase "a first homologous chromosome segment as compared to a second homologous chromosome segment" means a first homolog of a chromosome segment and a second homolog of the chromosome segment. In some such embodiments, all of the target SNPs are contained in the segment chromosome of interest. In other embodiments, multiple chromosome segments are analyzed for possible copy number variations.

MAP Estimation

This method leverages the knowledge of phasing via ordered alleles to detect the deletion or duplication of the target segment. For each SNP i, define $$X_i \triangleq \begin{cases} 1 & R_i < 0.5 \text{ and } SNP\ i\ AB \\ 0 & R_i \geq 0.5 \text{ and } SNP\ i\ AB \\ 0 & R_i < 0.5 \text{ and } SNP\ i\ BA \\ 1 & R_i \geq 0.5 \text{ and } SNP\ i\ BA \end{cases}$$

Then define
$$S \triangleq \Sigma_{All\ SNPs}\ X_i.$$

The distributions of the $X_i$ and S under various copy number hypotheses (such as hypotheses for disomy, deletion of the first or second homolog, or duplication of the first or second homolog) are described below.

Disomy Hypothesis

Under the hypothesis that the target segment is not deleted or duplicated, $$X_i = \begin{cases} 0 & wp\ 1 - p\left(\frac{1}{2}, N_i\right) \\ 1 & wp\ p\left(\frac{1}{2}, N_i\right) \end{cases}$$

where $$p(b, n) \triangleq Pr\left\{X \sim Bino(b, n) \geq \frac{n}{2}\right\}.$$

If we assume a constant depth of read N, this gives us a Binomial distribution S with parameters
p(½,N) and T.

Deletion Hypotheses

Under the hypothesis that the first homolog is deleted (i.e., an AB SNP becomes B, and a BA SNP becomes A), then $R_i$ has a Binomial distribution with parameters 1−1/2−f and T for AB 2−f SNPs, and 1/2−f and T for BA SNPs. Therefore, $$X_i = \begin{cases} 0 & wp\ 1 - p\left(\frac{1}{2-f}, N_i\right) \\ 1 & wp\ p\left(\frac{1}{2-f}, N_i\right) \end{cases}$$

If we assume a constant depth of read N, this gives a Binomial distribution S with parameters
p(1/2−f, N) and T.

Under the hypothesis that the second homolog is deleted (i.e., an AB SNP becomes A, and a BA SNP becomes B), then $R_1$ has a Binomial distribution with parameters 1/2−f and T for AB SNPs, and 1−1/2−f and T for BA SNPs. Therefore, $$X_i = \begin{cases} 0 & wp\ p\left(\frac{1}{2-f}, N_i\right) \\ 1 & wp\ 1 - p\left(\frac{1}{2-f}, N_i\right) \end{cases}$$

If we assume a constant depth of read N, this gives a Binomial distribution S with parameters
p(1/2−f,N) and T.

Duplication Hypotheses

Under the hypothesis that the first homolog is duplicated (i.e., an AB SNP becomes A, and a BA SNP becomes BBA), then $R_i$ has a Binomial distribution with parameters 1+f/2+f and T for AB SNPs, and 1−1+f/2+f and T for BA SNPs. Therefore, $$X_i = \begin{cases} 0 & wp\ p\left(\frac{1+f}{2+f}, N_i\right) \\ 1 & wp\ 1 - p\left(\frac{1+f}{2+f}, N_i\right) \end{cases}$$

If we assume a constant depth of read N, this gives us a Binomial distribution S with parameters
1−p(1+f/2+f, N) and T.

Under the hypothesis that the second homolog is duplicated (i.e., an AB SNP becomes ABB, and a BA SNP becomes BAA), then $R_i$ has a Binomial distribution with parameters 1−1+f/2+f and T for AB SNPs, and 1+f/2+f and T for BA SNPs. Therefore, $$X_i = \begin{cases} 0 & wp\ 1 - p\left(\frac{1+f}{2+f}, N_i\right) \\ 1 & wp\ p\left(\frac{1+f}{2+f}, N_i\right) \end{cases}$$

If we assume a constant depth of read N, this gives a Binomial distribution S with parameters
p(1+f/2+f, N) and T.

Classification

As demonstrated in the sections above, $X_i$ is a binary random variable with $$Pr\{X_1 = 1\} = \begin{cases} p\left(\frac{1}{2}, N_i\right) & \text{given disomy} \\ p\left(\frac{1}{2-f}, N_i\right) & \text{homolog 1 deletion} \\ 1 - p\left(\frac{1}{2-f}, N_i\right) & \text{homolog 2 deletion} \\ 1 - p\left(\frac{1+f}{2+f}, N_i\right) & \text{homolog 1 duplication} \\ p\left(\frac{1+f}{2+f}, N_i\right) & \text{homolog 2 duplication} \end{cases}$$

This allows one to calculate the probability of the test statistic S under each hypothesis. The probability of each hypothesis given the measured data can be calculated. In some embodiments, the hypothesis with the greatest probability is selected. If desired, the distribution on S can be simplified by either approximating each $N_i$ with a constant depth of reach N or by truncating the depth of reads to a constant N. This simplification gives $$S \sim \begin{cases} Bino\left(p\left(\frac{1}{2}, N\right), T\right) & \text{given disomy} \\ Bino\left(p\left(\frac{1}{2-f}, N\right), T\right) & \text{homolog 1 deletion} \\ Bino\left(1 - p\left(\frac{1}{2-f}, N\right), T\right) & \text{homolog 2 deletion} \\ Bino\left(1 - p\left(\frac{1+f}{2+f}, N\right), T\right) & \text{homolog 1 duplication} \\ Bino\left(p\left(\frac{1+f}{2+f}, N\right), T\right) & \text{homolog 2 duplication} \end{cases}$$

The value for f can be estimate by selecting the most likely value off given the measured data, such as the value of f that generates the best data fit using an algorithm (e.g., a search algorithm) such as maximum likelihood estimation, maximum a-posteriori estimation, or Bayesian estimation. In some embodiments, multiple chromosome segments are analyzed and a value for f is estimated based on the data for each segment. If all the target cells have these duplications or deletions, the estimated values for f based on data for these different segments are similar. In some embodiments, f is experimentally measured such as by determining the fraction of DNA or RNA from cancer cells based on methylation differences (hypomethylation or hypermethylation) between cancer and non-cancerous DNA or RNA.

Single Hypothesis Rejection

The distribution of S for the disomy hypothesis does not depend on f. Thus, the probability of the measured data can be calculated for the disomy hypothesis without calculating f. A single hypothesis rejection test can be used for the null hypothesis of disomy. In some embodiments, the probability of S under the disomy hypothesis is calculated, and the hypothesis of disomy is rejected if the probability is below a given threshold value (such as less than 1 in 1,000). This indicates that a duplication or deletion of the chromosome segment is present. If desired, the false positive rate can be altered by adjusting the threshold value.

Exemplary Methods for Analysis of Phased Data

Exemplary methods are described below for analysis of data from a sample known or suspected of being a mixed sample containing DNA or RNA that originated from two or more cells that are not genetically identical. In some embodiments, phased data is used. In some embodiments, the method involves determining, for each calculated allele ratio, whether the calculated allele ratio is above or below the expected allele ratio and the magnitude of the difference for a particular locus. In some embodiments, a likelihood distribution is determined for the allele ratio at a locus for a particular hypothesis and the closer the calculated allele ratio is to the center of the likelihood distribution, the more likely the hypothesis is correct. In some embodiments, the method involves determining the likelihood that a hypothesis is correct for each locus. In some embodiments, the method involves determining the likelihood that a hypothesis is correct for each locus, and combining the probabilities of that hypothesis for each locus, and the hypothesis with the greatest combined probability is selected. In some embodiments, the method involves determining the likelihood that a hypothesis is correct for each locus and for each possible ratio of DNA or RNA from the one or more target cells to the total DNA or RNA in the sample. In some embodiments, a combined probability for each hypothesis is determined by combining the probabilities of that hypothesis for each locus and each possible ratio, and the hypothesis with the greatest combined probability is selected.

In one embodiment, the following hypotheses are considered: $H_{11}$ (all cells are normal), $H_{10}$ (presence of cells with only homolog 1, hence homolog 2 deletion), $H_{01}$ (presence of cells with only homolog 2, hence homolog 1 deletion), $H_{21}$ (presence of cells with homolog 1 duplication), $H_{12}$ (presence of cells with homolog 2 duplication). For a fraction f of target cells such as cancer cells or mosaic cells (or the fraction of DNA or RNA from the target cells), the expected allele ratio for heterozygous (AB or BA) SNPs can be found as follows:

$$r(AB, H_{11}) = r(BA, H_{11}) = 0.5,$$ Equation (1)

$$r(AB, H_{10}) = r(BA, H_{01}) = \frac{1}{2-f},$$

$$r(AB, H_{01}) = r(BA, H_{10}) = \frac{1-f}{2-f},$$

$$r(AB, H_{21}) = r(BA, H_{12}) = \frac{1+f}{2+f},$$

$$r(AB, H_{12}) = r(BA, H_{21}) = \frac{1}{2+f}.$$

Bias, Contamination, and Sequencing Error Correction:

The observation $D_s$ at the SNP consists of the number of original mapped reads with each allele present, $n_A^o$ and $n_B^o$. Then, we can find the corrected reads $n_A$ and $n_B$ using the expected bias in the amplification of A and B alleles.

Let $c_a$ to denote the ambient contamination (such as contamination from DNA in the air or environment) and $r(c_a)$ to denote the allele ratio for the ambient contaminant (which is taken to be 0.5 initially). Moreover, $c_g$ denotes the genotyped contamination rate (such as the contamination from another sample), and $r(c_g)$ is the allele ratio for the contaminant. Let $s_e(A,B)$ and $s_e(B,A)$ denote the sequencing errors for calling one allele a different allele (such as by erroneously detecting an A allele when a B allele is present).

One can find the observed allele ratio $q(r, c_a, r(c_a), c_g, r(c_g), s_e(A,B), s_e(B,A))$ for a given expected allele ratio r by correcting for ambient contamination, genotyped contamination, and sequencing error.

Since the contaminant genotypes are unknown, population frequencies can be used to find $P(r(c_g))$. More specifically, let p be the population frequency for one of the alleles (which may be referred to as a reference allele). Then, we have $P(r(c_g)=0)=(1-p)^2$, $P(r(c_g)=0)=2p(1-p)$, and $P(r(cg)=0)=p^2$. The conditional expectation over $r(c_g)$ can be used to determine the $E[q(r, c_a, r(c_a), c_g, r(c_g), s_e(A,B), s_e(B,A))]$. Note that the ambient and genotyped contamination are determined using the homozygous SNPs, hence they are not affected by the absence or presence of deletions or duplications. Moreover, it is possible to measure the ambient and genotyped contamination using a reference chromosome if desired.

Likelihood at Each SNP:

The equation below gives the probability of observing $n_A$ and $n_B$ given an allele ratio r:

$$P(n_A, n_B|r) = p_{bino}(n_A; n_A+n_B, r) = \binom{n_A+n_B}{n_A} r^{n_A}(1-r)^{n_B}.$$

Let $D_s$ denote the data for SNP s. For each hypothesis $h \in \{H_{11}, H_{01}, H_{10}, H_{21}, H_{12}\}$, one can let $r=r(AB,h)$ or $r=r(BA,h)$ in the equation (1) and find the conditional expectation over $r(c_g)$ to determine the observed allele ratio $E[q(r, c_a, r(c_a), c_g, r(c_g))]$. Then, letting $r=E[q(r, c_a, r(c_a), c_g, r(c_g), s_e(A,B), s_e(B,A))]$ in equation (2) one can determine $P(D_s|h,f)$.

Search Algorithm:

In some embodiments, SNPs with allele ratios that seem to be outliers are ignored (such as by ignoring or eliminating SNPs with allele ratios that are at least 2 or 3 standard deviations above or below the mean value). Note that an advantage identified for this approach is that in the presence of higher mosaicism percentage, the variability in the allele ratios may be high, hence this ensures that SNPs will not be trimmed due to mosaicism.

Let $F=\{f_1, \ldots, f_N\}$ denote the search space for the mosaicism percentage (such as the tumor fraction). One can determine $P(D_s|h,f)$ at each SNP s and $f \in F$, and combine the likelihood over all SNPs.

The algorithm goes over each f for each hypothesis. Using a search method, one concludes that mosaicism exists if there is a range F* off where the confidence of the deletion or duplication hypothesis is higher than the confidence of the no deletion and no duplication hypotheses. In some embodiments, the maximum likelihood estimate for $P(D_s|h,f)$ in F* is determined. If desired, the conditional expectation over $f \in F^*$ may be determined. If desired, the confidence for each hypothesis can be determined.

In some embodiments, a beta binomial distribution is used instead of binomial distribution. In some embodiments, a reference chromosome or chromosome segment is used to determine the sample specific parameters of beta binomial.

Theoretical Performance Using Simulations:

If desired, one can evaluate the theoretical performance of the algorithm by randomly assigning number of reference reads to a SNP with given depth of read (DOR). For the normal case, use p=0.5 for the binomial probability parameter, and for deletions or duplications, p is revised accordingly. Exemplary input parameters for each simulation are as follows: (1) number of SNPs S (2) constant DOR D per SNP, (3) p, and (4) number of experiments.

First Simulation Experiment:

This experiment focused on $S \in [500, 1000]$, $D \in [500, 1000]$ and $p \in [0\%, 1\%, 2\%, 3\%, 4\%, 5\%]$. We performed 1,000 simulation experiments in each setting (hence 24,000 experiments with phase, and 24,000 without phase). We simulated the number of reads from a binomial distribution (if desired, other distributions can be used). The false positive rate (in the case of p=0%) and false negative rate (in the case of p>0%) were determined both with or without phase information. Note that phase information is very helpful, especially for S=1000, D=1000. Although for S=500, D=500, the algorithm has the highest false positive rates with or without phase out of the conditions tested.

Phase information is particularly useful for low mosaicism percentages (<3%). Without phase information, a high level of false negatives were observed for p=1% because the confidence on deletion is determined by assigning equal chance to $H_{10}$ and $H_{01}$, and a small deviation in favor of one hypothesis is not sufficient to compensate for the low likelihood from the other hypothesis. This applies to duplications as well. Note also that the algorithm seems to be more sensitive to depth of read compared to number of SNPs. For the results with phase information, we assume that perfect phase information is available for a high number of consecutive heterozygous SNPs. If desired, haplotype information can be obtained by probabilistically combining haplotypes on smaller segments.

Second Simulation Experiment:

This experiment focused on $S \in [100, 200, 300, 400, 500]$, $D \in [1000, 2000, 3000, 4000, 5000]$ and $p \in [0\%, 1\%, 1.5\%, 2\%, 2.5\%, 3\%]$ and 10000 random experiments at each setting. The false positive rate (in the case of p=0%) and false negative rate (in the case of p>0%) were determined both with or without phase information. The false negative rate is below 10% for D≥3000 and N≥200 using haplotype information, whereas the same performance is reached for D=5000 and N≥400. The difference between the false negative rate was particularly stark for small mosaicism percentages. For example, when p=1%, a less than 20% false negative rate is never reached without haplotype data, whereas it is close to 0% for N≥300 and D≥3000. For p=3%, a 0% false negative rate is observed with haplotype data, while N≥300 and D≥3000 is needed to reach the same performance without haplotype data.

Exemplary Methods for Detecting Deletions and Duplications without Phased Data

In some embodiments, unphased genetic data is used to determine if there is an overrepresentation of the number of copies of a first homologous chromosome segment as compared to a second homologous chromosome segment in the genome of an individual (such as in the genome of one or more cells or in cfDNA or cfRNA). In some embodiments, phased genetic data is used but the phasing is ignored. In some embodiments, the sample of DNA or RNA is a mixed sample of cfDNA or cfRNA from the individual that includes cfDNA or cfRNA from two or more genetically different cells. In some embodiments, the method utilizes the magnitude of the difference between the calculated allele ratio and the expected allele ratio for each of the loci.

In some embodiments, the method involves obtaining genetic data at a set of polymorphic loci on the chromosome or chromosome segment in a sample of DNA or RNA from one or more cells from the individual by measuring the quantity of each allele at each locus. In some embodiments, allele ratios are calculated for the loci that are heterozygous in at least one cell from which the sample was derived. In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. The calculated allele ratios and expected allele ratios may be calculated using any of the methods described herein or any standard method (such as any mathematical transformation of the calculated allele ratios or expected allele ratios described herein).

In some embodiments, a test statistic is calculated based on the magnitude of the difference between the calculated allele ratio and the expected allele ratio for each of the loci. In some embodiments, the test statistic A is calculated using the following formula $$\Delta = \frac{\sum_{All\ Loci}(\delta_i - \mu_i)}{\sqrt{\sum_{All\ Loci} \sigma_i^2}}$$

wherein $\delta_i$ is the magnitude of the difference between the calculated allele ratio and the expected allele ratio for the ith loci;
wherein $\mu_i$ is the mean value of $\delta_i$; and
wherein $\mu_i$ is the standard deviation of $\delta_i$.

For example, we can define $\delta_i$ as follows when the expected allele ratio is 0.5:

$$\delta_i \triangleq \left| \frac{1}{2} - R_i \right|.$$

Values for $\mu_i$ and $\sigma_i$ can be computed using the fact that $R_i$ is a Binomial random variable. In some embodiments, the standard deviation is assumed to be the same for all the loci. In some embodiments, the average or weighted average value of the standard deviation or an estimate of the standard deviation is used for the value of $\sigma_i^2$. In some embodiments, the test statistic is assumed to have a normal distribution. For example, the central limit theorem implies that the distribution of $\Delta$ converges to a standard normal as the number of loci (such as the number of SNPs T) grows large.

In some embodiments, a set of one or more hypotheses specifying the number of copies of the chromosome or chromosome segment in the genome of one or more of the cells are enumerated. In some embodiments, the hypothesis that is most likely based on the test statistic is selected, thereby determining the number of copies of the chromosome or chromosome segment in the genome of one or more of the cells. In some embodiments, a hypotheses is selected if the probability that the test statistic belongs to a distribution of the test statistic for that hypothesis is above an upper threshold; one or more of the hypotheses is rejected if the probability that the test statistic belongs to the distribution of the test statistic for that hypothesis is below an lower threshold; or a hypothesis is neither selected nor rejected if the probability that the test statistic belongs to the distribution of the test statistic for that hypothesis is between the lower threshold and the upper threshold, or if the probability is not determined with sufficiently high confidence. In some embodiments, an upper and/or lower threshold is determined from an empirical distribution, such as a distribution from training data (such as samples with a known copy number, such as diploid samples or samples known to have a particular deletion or duplication). Such an empirical distribution can be used to select a threshold for a single hypothesis rejection test. Note that the test statistic $\Delta$ is independent of S and therefore both can be used independently, if desired.

Exemplary Methods for Detecting Deletions and Duplications Using Allele Distributions or Patterns This section includes methods for determining if there is an overrepresentation of the number of copies of a first homologous chromosome segment as compared to a second homologous chromosome segment. In some embodiments, the method involves enumerating (i) a plurality of hypotheses specifying the number of copies of the chromosome or chromosome segment that are present in the genome of one or more cells (such as cancer cells) of the individual or (ii) a plurality of hypotheses specifying the degree of overrepresentation of the number of copies of a first homologous chromosome segment as compared to a second homologous chromosome segment in the genome of one or more cells of the individual. In some embodiments, the method involves obtaining genetic data from the individual at a plurality of polymorphic loci (such as SNP loci) on the chromosome or chromosome segment. In some embodiments, a probability distribution of the expected genotypes of the individual for each of the hypotheses is created. In some embodiments, a data fit between the obtained genetic data of the individual and the probability distribution of the expected genotypes of the individual is calculated. In some embodiments, one or more hypotheses are ranked according to the data fit, and the hypothesis that is ranked the highest is selected. In some embodiments, a technique or algorithm, such as a search algorithm, is used for one or more of the following steps: calculating the data fit, ranking the hypotheses, or selecting the hypothesis that is ranked the highest. In some embodiments, the data fit is a fit to a beta-binomial distribution or a fit to a binomial distribution. In some embodiments, the technique or algorithm is selected from the group consisting of maximum likelihood estimation, maximum a-posteriori estimation, Bayesian estimation, dynamic estimation (such as dynamic Bayesian estimation), and expectation-maximization estimation. In some embodiments, the method includes applying the technique or algorithm to the obtained genetic data and the expected genetic data.

In some embodiments, the method involves enumerating (i) a plurality of hypotheses specifying the number of copies of the chromosome or chromosome segment that are present in the genome of one or more cells (such as cancer cells) of the individual or (ii) a plurality of hypotheses specifying the degree of overrepresentation of the number of copies of a first homologous chromosome segment as compared to a second homologous chromosome segment in the genome of one or more cells of the individual. In some embodiments, the method involves obtaining genetic data from the individual at a plurality of polymorphic loci (such as SNP loci) on the chromosome or chromosome segment. In some embodiments, the genetic data includes allele counts for the plurality of polymorphic loci. In some embodiments, a joint distribution model is created for the expected allele counts at the plurality of polymorphic loci on the chromosome or chromosome segment for each hypothesis. In some embodiments, a relative probability for one or more of the hypotheses is determined using the joint distribution model and the allele counts measured on the sample, and the hypothesis with the greatest probability is selected.

In some embodiments, the distribution or pattern of alleles (such as the pattern of calculated allele ratios) is used to determine the presence or absence of a CNV, such as a deletion or duplication. If desired the parental origin of the CNV can be determined based on this pattern.

Exemplary Counting Methods/Quantitative Methods

In some embodiments, one or more counting methods (also referred to as quantitative methods) are used to detect one or more CNS, such as deletions or duplications of chromosome segments or entire chromosomes. In some embodiments, one or more counting methods are used to determine whether the overrepresentation of the number of copies of the first homologous chromosome segment is due to a duplication of the first homologous chromosome segment or a deletion of the second homologous chromosome segment. In some embodiments, one or more counting methods are used to determine the number of extra copies of a chromosome segment or chromosome that is duplicated (such as whether there are 1, 2, 3, 4, or more extra copies). In some embodiments, one or more counting methods are used to differentiate a sample has many duplications and a smaller tumor fraction from a sample with fewer duplications and a larger tumor fraction. For example, one or more counting methods may be used to differentiate a sample with four extra chromosome copies and a tumor fraction of 10% from a sample with two extra chromosome copies and a tumor fraction of 20%. Exemplary methods are disclosed, e.g. U.S. Publication Nos. 2007/0184467; 2013/0172211; and 2012/0003637; U.S. Pat. Nos. 8,467,976; 7,888,017; 8,008,018; 8,296,076; and 8,195,415; U.S. Ser. No. 62/008,235, filed Jun. 5, 2014, and U.S. Ser. No. 62/032,785, filed Aug. 4, 2014, which are each hereby incorporated by reference in its entirety.

In some embodiment, the counting method includes counting the number of DNA sequence-based reads that map to one or more given chromosomes or chromosome segments. Some such methods involve creation of a reference value (cut-off value) for the number of DNA sequence reads mapping to a specific chromosome or chromosome segment, wherein a number of reads in excess of the value is indicative of a specific genetic abnormality.

In some embodiments, the total measured quantity of all the alleles for one or more loci (such as the total amount of a polymorphic or non-polymorphic locus) is compared to a reference amount. In some embodiments, the reference amount is (i) a threshold value or (ii) an expected amount for a particular copy number hypothesis. In some embodiments, the reference amount (for the absence of a CNV) is the total measured quantity of all the alleles for one or more loci for one or more chromosomes or chromosomes segments known or expected to not have a deletion or duplication. In some embodiments, the reference amount (for the presence of a CNV) is the total measured quantity of all the alleles for one or more loci for one or more chromosomes or chromosomes segments known or expected to have a deletion or duplication. In some embodiments, the reference amount is the total measured quantity of all the alleles for one or more loci for one or more reference chromosomes or chromosome segments. In some embodiments, the reference amount is the mean or median of the values determined for two or more different chromosomes, chromosome segments, or different samples. In some embodiments, random (e.g., massively parallel shotgun sequencing) or targeted sequencing is used to determine the amount of one or more polymorphic or non-polymorphic loci.

In some embodiments utilizing a reference amount, the method includes (a) measuring the amount of genetic material on a chromosome or chromosome segment of interest; (b) comparing the amount from step (a) to a reference amount; and (c) identifying the presence or absence of a deletion or duplication based on the comparison.

In some embodiments utilizing a reference chromosome or chromosome segment, the method includes sequencing DNA or RNA from a sample to obtain a plurality of sequence tags aligning to target loci. In some embodiments, the sequence tags are of sufficient length to be assigned to a specific target locus (e.g., 15-100 nucleotides in length); the target loci are from a plurality of different chromosomes or chromosome segments that include at least one first chromosome or chromosome segment suspected of having an abnormal distribution in the sample and at least one second chromosome or chromosome segment presumed to be normally distributed in the sample. In some embodiments, the plurality of sequence tags are assigned to their corresponding target loci. In some embodiments, the number of sequence tags aligning to the target loci of the first chromosome or chromosome segment and the number of sequence tags aligning to the target loci of the second chromosome or chromosome segment are determined. In some embodiments, these numbers are compared to determine the presence or absence of an abnormal distribution (such as a deletion or duplication) of the first chromosome or chromosome segment.

In some embodiments, the value of f (such as tumor fraction) is used in the CNV determination, such as to compare the observed difference between the amount of two chromosomes or chromosome segments to the difference that would be expected for a particular type of CNV given the value of f (see, e.g., US Publication No 2012/0190020; US Publication No 2012/0190021; US Publication No 2012/0190557; US Publication No 2012/0191358, which are each hereby incorporated by reference in its entirety). For example, the difference in the amount of a chromosome segment that is duplicated in a tumor compared to a disomic reference chromosome segment increases as the tumor fraction increases. In some embodiments, the method includes comparing the relative frequency of a chromosome or chromosome segment of interest to a reference chromosomes or chromosome segment (such as a chromosome or chromosome segment expected or known to be disomic) to the value of f to determine the likelihood of the CNV. For example, the difference in amounts between the first chromosomes or chromosome segment to the reference chromosome or chromosome segment can be compared to what would be expected given the value of f for various possible CNVs (such as one or two extra copies of a chromosome segment of interest).

The following prophetic examples illustrate the use of a counting method/quantitative method to differentiate between a duplication of the first homologous chromosome segment and a deletion of the second homologous chromosome segment. If one considers the normal disomic genome of the host to be the baseline, then analysis of a mixture of normal and cancer cells yields the average difference between the baseline and the cancer DNA in the mixture. For example, imagine a case where 10% of the DNA in the sample originated from cells with a deletion over a region of a chromosome that is targeted by the assay. In some embodiments, a quantitative approach shows that the quantity of reads corresponding to that region is expected to be 95% of what is expected for a normal sample. This is because one of the two target chromosomal regions in each of the tumor cells with a deletion of the targeted region is missing, and thus the total amount of DNA mapping to that region is 90% (for the normal cells) plus ½×10% (for the tumor cells)=95%. Alternately in some embodiments, an allelic approach shows that the ratio of alleles at heterozygous loci averaged 19:20. Now imagine a case where 10% of the DNA in the sample originated from cells with a five-fold focal amplification of a region of a chromosome that is targeted by the assay. In some embodiments, a quantitative approach shows that the quantity of reads corresponding to that region is expected to be 125% of what is expected for a normal sample. This is because one of the two target chromosomal regions in each of the tumor cells with a five-fold focal amplification is copied an extra five times over the targeted region, and thus the total amount of DNA mapping to that region is 90% (for the normal cells) plus (2+5)×10%/2 (for the tumor cells)=125%. Alternately in some embodiments, an allelic approach shows that the ratio of alleles at heterozygous loci averaged 25:20. Note that when using an allelic approach alone, a focal amplification of five-fold over a chromosomal region in a sample with 10% cfDNA may appear the same as a deletion over the same region in a sample with 40% cfDNA; in these two cases, the haplotype that is under-represented in the case of the deletion appears to be the haplotype without a CNV in the case with the focal duplication, and the haplotype without a CNV in the case of the deletion appears to be the over-represented haplotype in the case with the focal duplication. Combining the likelihoods produced by this allelic approach with likelihoods produced by a quantitative approach differentiates between the two possibilities.

Exemplary Counting Methods/Quantitative Methods Using Reference Samples

An exemplary quantitative method that uses one or more reference samples is described in U.S. Ser. No. 62/008,235, filed Jun. 5, 2014 and U.S. Ser. No. 62/032,785, filed Aug. 4, 2014, which is hereby incorporated by reference in its entirety. In some embodiments, one or more reference samples most likely to not have any CNVs on one or more chromosomes or chromosomes of interest (e.g., a normal sample) are identified by selecting the samples with the highest fraction of tumor DNA, selecting the samples with the z-score closest to zero, selecting the samples where the data fits the hypothesis corresponding to no CNVs with the highest confidence or likelihood, selecting the samples known to be normal, selecting the samples from individuals with the lowest likelihood of having cancer (e.g., having a low age, being a male when screening for breast cancer, having no family history, etc.), selecting the samples with the highest input amount of DNA, selecting the samples with the highest signal to noise ratio, selecting samples based on other criteria believed to be correlated to the likelihood of having cancer, or selecting samples using some combination of criteria. Once the reference set is chosen, one can make the assumption that these cases are disomic, and then estimate the per-SNP bias, that is, the experiment-specific amplification and other processing bias for each locus. Then, one can use this experiment-specific bias estimate to correct the bias in the measurements of the chromosome of interest, such as chromosome 21 loci, and for the other chromosome loci as appropriate, for the samples that are not part of the subset where disomy is assumed for chromosome 21. Once the biases have been corrected for in these samples of unknown ploidy, the data for these samples can then be analyzed a second time using the same or a different method to determine whether the individuals are afflicted with trisomy 21. For example, a quantitative method can be used on the remaining samples of unknown ploidy, and a z-score can be calculated using the corrected measured genetic data on chromosome 21. Alternately, as part of the preliminary estimate of the ploidy state of chromosome 21, a tumor fraction for samples from an individual suspected of having cancer can be calculated. The proportion of corrected reads that are expected in the case of a disomy (the disomy hypothesis), and the proportion of corrected reads that are expected in the case of a trisomy (the trisomy hypothesis) can be calculated for a case with that tumor fraction. Alternately, if the tumor fraction was not measured previously, a set of disomy and trisomy hypotheses can be generated for different tumor fractions. For each case, an expected distribution of the proportion of corrected reads can be calculated given expected statistical variation in the selection and measurement of the various DNA loci. The observed corrected proportion of reads can be compared to the distribution of the expected proportion of corrected reads, and a likelihood ratio can be calculated for the disomy and trisomy hypotheses, for each of the samples of unknown ploidy. The ploidy state associated with the hypothesis with the highest calculated likelihood can be selected as the correct ploidy state.

In some embodiments, a subset of the samples with a sufficiently low likelihood of having cancer may be selected to act as a control set of samples. The subset can be a fixed number, or it can be a variable number that is based on choosing only those samples that fall below a threshold. The quantitative data from the subset of samples may be combined, averaged, or combined using a weighted average where the weighting is based on the likelihood of the sample being normal. The quantitative data may be used to determine the per-locus bias for the amplification the sequencing of samples in the instant batch of control samples. The per-locus bias may also include data from other batches of samples. The per-locus bias may indicate the relative over- or under-amplification that is observed for that locus compared to other loci, making the assumption that the subset of samples do not contain any CNVs, and that any observed over or under-amplification is due to amplification and/or sequencing or other bias. The per-locus bias may take into account the GC content of the amplicon. The loci may be grouped into groups of loci for the purpose of calculating a per-locus bias. Once the per-locus bias has been calculated for each locus in the plurality of loci, the sequencing data for one or more of the samples that are not in the subset of the samples, and optionally one or more of the samples that are in the subset of samples, may be corrected by adjusting the quantitative measurements for each locus to remove the effect of the bias at that locus. For example, if SNP 1 was observed, in the subset of patients, to have a depth of read that is twice as great as the average, the adjustment may involve replacing the number of reads corresponding from SNP 1 with a number that is half as great. If the locus in question is a SNP, the adjustment may involve cutting the number of reads corresponding to each of the alleles at that locus in half. Once the sequencing data for each of the loci in one or more samples has been adjusted, it may be analyzed using a method for the purpose of detecting the presence of a CNV at one or more chromosomal regions.

In an example, sample A is a mixture of amplified DNA originating from a mixture of normal and cancerous cells that is analyzed using a quantitative method. The following illustrates exemplary possible data. A region of the q arm on chromosome 22 is found to only have 90% as much DNA mapping to that region as expected; a focal region corresponding to the HER2 gene is found to have 150% as much DNA mapping to that region as expected; and the p-arm of chromosome 5 is found to have 105% as much DNA mapping to it as expected. A clinician may infer that the sample has a deletion of a region on the q arm on chromosome 22, and a duplication of the HER2 gene. The clinician may infer that since the 22q deletions are common in breast cancer, and that since cells with a deletion of the 22q region on both chromosomes usually do not survive, that approximately 20% of the DNA in the sample came from cells with a 22q deletion on one of the two chromosomes. The clinician may also infer that if the DNA from the mixed sample that originated from tumor cells originated from a set of genetically tumor cells whose HER2 region and 22q regions were homogenous, then the cells contained a five-fold duplication of the HER2 region.

In an example, Sample A is also analyzed using an allelic method. The following illustrates exemplary possible data. The two haplotypes on same region on the q arm on chromosome 22 are present in a ratio of 4:5; the two haplotypes in a focal region corresponding to the HER2 gene are present in ratios of 1:2; and the two haplotypes in the p-arm of chromosome 5 are present in ratios of 20:21. All other assayed regions of the genome have no statistically significant excess of either haplotype. A clinician may infer that the sample contains DNA from a tumor with a CNV in the 22q region, the HER2 region, and the 5p arm. Based on the knowledge that 22q deletions are very common in breast cancer, and/or the quantitative analysis showing an underrepresentation of the amount of DNA mapping to the 22q region of the genome, the clinician may infer the existence of a tumor with a 22q deletion. Based on the knowledge that HER2 amplifications are very common in breast cancer, and/or the quantitative analysis showing an over-representation of the amount of DNA mapping to the HER2 region of the genome, the clinician may infer the existence of a tumor with a HER2 amplification.

Exemplary Reference Chromosomes or Chromosome Segments

In some embodiments, any of the methods described herein are also performed on one or more reference chromosomes or chromosomes segments and the results are compared to those for one or more chromosomes or chromosome segments of interest.

In some embodiments, the reference chromosome or chromosome segment is used as a control for what would be expected for the absence of a CNV. In some embodiments, the reference is the same chromosome or chromosome segment from one or more different samples known or expected to not have a deletion or duplication in that chromosome or chromosome segment. In some embodiments, the reference is a different chromosome or chromosome segment from the sample being tested that is expected to be disomic. In some embodiments, the reference is a different segment from one of the chromosomes of interest in the same sample that is being tested. For example, the reference may be one or more segments outside of the region of a potential deletion or duplication. Having a reference on the same chromosome that is being tested avoids variability between different chromosomes, such as differences in metabolism, apoptosis, histones, inactivation, and/or amplification between chromosomes. Analyzing segments without a CNV on the same chromosome as the one being tested can also be used to determine differences in metabolism, apoptosis, histones, inactivation, and/or amplification between homologs, allowing the level of variability between homologs in the absence of a CNV to be determined for comparison to the results from a potential CNV. In some embodiments, the magnitude of the difference between the calculated and expected allele ratios for a potential CNV is greater than the corresponding magnitude for the reference, thereby confirming the presence of a CNV.

In some embodiments, the reference chromosome or chromosome segment is used as a control for what would be expected for the presence of a CNV, such as a particular deletion or duplication of interest. In some embodiments, the reference is the same chromosome or chromosome segment from one or more different samples known or expected to have a deletion or duplication in that chromosome or chromosome segment. In some embodiments, the reference is a different chromosome or chromosome segment from the sample being tested that is known or expected to have a CNV. In some embodiments, the magnitude of the difference between the calculated and expected allele ratios for a potential CNV is similar to (such as not significantly different) than the corresponding magnitude for the reference for the CNV, thereby confirming the presence of a CNV. In some embodiments, the magnitude of the difference between the calculated and expected allele ratios for a potential CNV is less than (such as significantly less) than the corresponding magnitude for the reference for the CNV, thereby confirming the absence of a CNV. In some embodiments, one or more loci for which the genotype of a cancer cell (or DNA or RNA from a cancer cell such as cfDNA or cfRNA) differs from the genotype of a noncancerous cell (or DNA or RNA from a noncancerous cell such as cfDNA or cfRNA) is used to determine the tumor fraction. The tumor fraction can be used to determine whether the overrepresentation of the number of copies of the first homologous chromosome segment is due to a duplication of the first homologous chromosome segment or a deletion of the second homologous chromosome segment. The tumor fraction can also be used to determine the number of extra copies of a chromosome segment or chromosome that is duplicated (such as whether there are 1, 2, 3, 4, or more extra copies), such as to differentiate a sample with four extra chromosome copies and a tumor fraction of 10% from a sample with two extra chromosome copies and a tumor fraction of 20%. The tumor fraction can also be used to determine how well the observed data fits the expected data for possible CNVs. In some embodiments, the degree of overrepresentation of a CNV is used to select a particular therapy or therapeutic regimen for the individual. For example, some therapeutic agents are only effective for at least four, six, or more copies of a chromosome segment.

In some embodiments, the one or more loci used to determine the tumor fraction are on a reference chromosome or chromosomes segment, such as a chromosome or chromosome segment known or expected to be disomic, a chromosome or chromosome segment that is rarely duplicated or deleted in cancer cells in general or in a particular type of cancer that an individual is known to have or is at increased risk of having, or a chromosome or chromosome segment that is unlikely to be aneuploid (such segment that is expected to lead to cell death if deleted or duplicated). In some embodiments, any of the methods of the invention are used to confirm that the reference chromosome or chromosome segment is disomic in both the cancer cells and noncancerous cells. In some embodiments, one or more chromosomes or chromosomes segments for which the confidence for a disomy call is high are used.

Exemplary loci that can be used to determine the tumor fraction include polymorphisms or mutations (such as SNPs) in a cancer cell (or DNA or RNA such as cfDNA or cfRNA from a cancer cell) that aren't present in a noncancerous cell (or DNA or RNA from a noncancerous cell) in the individual. In some embodiments, the tumor fraction is determined by identifying those polymorphic loci where a cancer cell (or DNA or RNA from a cancer cell) has an allele that is absent in noncancerous cells (or DNA or RNA from a noncancerous cell) in a sample (such as a plasma sample or tumor biopsy) from an individual; and using the amount of the allele unique to the cancer cell at one or more of the identified polymorphic loci to determine the tumor fraction in the sample. In some embodiments, a noncancerous cell is homozygous for a first allele at the polymorphic locus, and a cancer cell is (i) heterozygous for the first allele and a second allele or (ii) homozygous for a second allele at the polymorphic locus. In some embodiments, a noncancerous cell is heterozygous for a first allele and a second allele at the polymorphic locus, and a cancer cell is (i) has one or two copies of a third allele at the polymorphic locus. In some embodiments, the cancer cells are assumed or known to only have one copy of the allele that is not present in the noncancerous cells. For example, if the genotype of the noncancerous cells is AA and the cancer cells is AB and 5% of the signal at that locus in a sample is from the B allele and 95% is from the A allele, then the tumor fraction of the sample is 10%. In some embodiments, the cancer cells are assumed or known to have two copies of the allele that is not present in the noncancerous cells. For example, if the genotype of the noncancerous cells is AA and the cancer cells is BB and 5% of the signal at that locus in a sample is from the B allele and 95% is from the A allele, the tumor fraction of the sample is 5%. In some embodiments, multiple loci for which the cancer cells have an allele not in the noncancerous cells are analyzed to determine which of the loci in the cancer cells are heterozygous and which are homozygous. For example for loci in which the noncancerous cells are AA, if the signal from the B allele is ~5% at some loci and ~10% at some loci, then the cancer cells are assumed to be heterozygous at loci with ~5% B allele, and homozygous at loci with ~10% B allele (indicating the tumor fraction is ~10%).

Exemplary loci that can be used to determine the tumor fraction include loci for which a cancer cell and noncancerous cell have one allele in common (such as loci in which the cancer cell is AB and the noncancerous cell is BB, or the cancer cell is BB and the noncancerous cell is AB). The amount of A signal, the amount of B signal, or the ratio of A to B signal in a mixed sample (containing DNA or RNA from a cancer cell and a noncancerous cell) is compared to the corresponding value for (i) a sample containing DNA or RNA from only cancer cells or (ii) a sample containing DNA or RNA from only noncancerous cells. The difference in values is used to determine the tumor fraction of the mixed sample.

In some embodiments, loci that can be used to determine the tumor fraction are selected based on the genotype of (i) a sample containing DNA or RNA from only cancer cells, and/or (ii) a sample containing DNA or RNA from only noncancerous cells. In some embodiments, the loci are selected based on analysis of the mixed sample, such as loci for which the absolute or relative amounts of each allele differs from what would be expected if both the cancer and noncancerous cells have the same genotype at a particular locus. For example, if the cancer and noncancerous cells have the same genotype, the loci would be expected to produce 0% B signal if all the cells are AA, 50% B signal if all the cells are AB, or 100% B signal if all the cells are BB. Other values for the B signal indicate that the genotype of the cancer and noncancerous cells are different at that locus and thus that locus can be used to determine the tumor fraction.

In some embodiments, the tumor fraction calculated based on the alleles at one or more loci is compared to the tumor fraction calculated using one or more of the counting methods disclosed herein.

Exemplary Methods for Detecting a Phenotype or Analyzing Multiple Mutations

In some embodiments, the method includes analyzing a sample for a set of mutations associated with a disease or disorder (such as cancer) or an increased risk for a disease or disorder. There are strong correlations between events within classes (such as M or C cancer classes) which can be used to improve the signal to noise ratio of a method and classify tumors into distinct clinical subsets. For example, borderline results for a few mutations (such as a few CNVs) on one or more chromosomes or chromosomes segments considered jointly may be a very strong signal. In some embodiments, determining the presence or absence of multiple polymorphisms or mutations of interest (such as 2, 3, 4, 5, 8, 10, 12, 15, or more) increases the sensitivity and/or specificity of the determination of the presence or absence of a disease or disorder such as cancer, or an increased risk for with a disease or disorder such as cancer. In some embodiments, the correlation between events across multiple chromosomes is used to more powerfully look at a signal compared to looking at each of them individually. The design of the method itself can be optimized to best categorize tumors. This may be incredibly useful for early detection and screening—vis-a-vis recurrence where sensitivity to one particular mutation/CNV may be paramount. In some embodiments, the events are not always correlated but have a probability of being correlated. In some embodiments, a matrix estimation formulation with a noise covariance matrix that has off diagonal terms is used.

In some embodiments, the invention features a method for detecting a phenotype (such as a cancer phenotype) in an individual, wherein the phenotype is defined by the presence of at least one of a set of mutations. In some embodiments, the method includes obtaining DNA or RNA measurements for a sample of DNA or RNA from one or more cells from the individual, wherein one or more of the cells is suspected of having the phenotype; and analyzing the DNA or RNA measurements to determine, for each of the mutations in the set of mutations, the likelihood that at least one of the cells has that mutation. In some embodiments, the method includes determining that the individual has the phenotype if either (i) for at least one of the mutations, the likelihood that at least one of the cells contains that mutations is greater than a threshold, or (ii) for at least one of the mutations, the likelihood that at least one of the cells has that mutations is less than the threshold, and for a plurality of the mutations, the combined likelihood that at least one of the cells has at least one of the mutations is greater than the threshold. In some embodiments, one or more cells have a subset or all of the mutations in the set of mutations. In some embodiments, the subset of mutations is associated with cancer or an increased risk for cancer. In some embodiments, the set of mutations includes a subset or all of the mutations in the M class of cancer mutations (Ciriello, Nat Genet. 45(10):1127-

1133, 2013, doi: 10.1038/ng.2762, which is hereby incorporated by reference in its entirety). In some embodiments, the set of mutations includes a subset or all of the mutations in the C class of cancer mutations (Ciriello, supra). In some embodiments, the sample includes cell-free DNA or RNA. In some embodiments, the DNA or RNA measurements include measurements (such as the quantity of each allele at each locus) at a set of polymorphic loci on one or more chromosomes or chromosome segments of interest.

Exemplary Combinations of Methods

To increase the accuracy of the results, two or more methods (such as any of the methods of the invention or any known method) for detecting the presence or absence of a CNV are performed. In some embodiments, one or more methods for analyzing a factor (such as any of the method described herein or any known method) indicative of the presence or absence of a disease or disorder or an increased risk for a disease or disorder are performed.

In some embodiments, standard mathematical techniques are used to calculate the covariance and/or correlation between two or more methods. Standard mathematical techniques may also be used to determine the combined probability of a particular hypothesis based on two or more tests. Exemplary techniques include meta-analysis, Fisher's combined probability test for independent tests, Brown's method for combining dependent p-values with known covariance, and Kost's method for combining dependent p-values with unknown covariance. In cases where the likelihoods are determined by a first method in a way that is orthogonal, or unrelated, to the way in which a likelihood is determined for a second method, combining the likelihoods is straightforward and can be done by multiplication and normalization, or by using a formula such as:

$$R_{comb} = R_1 R_2 / [R_1 R_2 + (1-R_1)(1-R_2)]$$

$R_{comb}$ is the combined likelihood, and $R_1$ and $R_2$ are the individual likelihoods. For example, if the likelihood of trisomy from method 1 is 90%, and the likelihood of trisomy from method 2 is 95%, then combining the outputs from the two methods allows the clinician to conclude that the fetus is trisomic with a likelihood of $(0.90)(0.95)/[(0.90)(0.95)+(1-0.90)(1-0.95)]=99.42\%$. In cases where the first and the second methods are not orthogonal, that is, where there is a correlation between the two methods, the likelihoods can still be combined.

Exemplary methods of analyzing multiple factors or variables are disclosed in U.S. Pat. No. 8,024,128 issued on Sep. 20, 2011; U.S. Publication No. 2007/0027636, filed Jul. 31, 2006; and U.S. Publication No. 2007/0178501, filed Dec. 6, 2006, which are each hereby incorporated by reference in its entirety).

In various embodiments, the combined probability of a particular hypothesis or diagnosis is greater than 80, 85, 90, 92, 94, 96, 98, 99, or 99.9%, or is greater than some other threshold value.

Limit of Detection

As demonstrated by experiments provided in the Examples section, methods provided herein are capable of detecting an average allelic imbalance in a sample with a limit of detection or sensitivity of 0.45% AAI, which is the limit of detection for aneuploidy of an illustrative method of the present invention. Similarly, in certain embodiments, methods provided herein are capable of detecting an average allelic imbalance in a sample of 0.45, 0.5, 0.6, 0.8, 0.8, 0.9, or 1.0%. That is, the test method is capable of detecting chromosomal aneuploidy in a sample down to an AAI of 0.45, 0.5, 0.6, 0.8, 0.8, 0.9, or 1.0%. As demonstrated by experiments provided in the Examples section, methods provided herein are capable of detecting the presence of an SNV in a sample for at least some SNVs, with a limit of detection or sensitivity of 0.2%, which is the limit of detection for at least some SNVs in one illustrative embodiment. Similarly, in certain embodiments, the method is capable of detecting an SNV with a frequency or SNV AAI of 0.2, 0.3, 0.4, 0.5, 0.6, 0.8, 0.8, 0.9, or 1.0%. That is, the test method is capable of detecting an SNV in a sample down to a limit of detection of 0.2, 0.3, 0.4, 0.5, 0.6, 0.8, 0.8, 0.9, or 1.0% of the total allele counts at the chromosomal locus of the SNV.

In some embodiments, a limit of detection of a mutation (such as an SNV or CNV) of a method of the invention is less than or equal to 10, 5, 2, 1, 0.5, 0.1, 0.05, 0.01, or 0.005%. In some embodiments, a limit of detection of a mutation (such as an SNV or CNV) of a method of the invention is between 15 to 0.005%, such as between 10 to 0.005%, 10 to 0.01%, 10 to 0.1%, 5 to 0.005%, 5 to 0.01%, 5 to 0.1%, 1 to 0.005%, 1 to 0.01%, 1 to 0.1%, 0.5 to 0.005%, 0.5 to 0.01%, 0.5 to 0.1%, or 0.1 to 0.01, inclusive.

In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules with that locus in a sample (such as a sample of cfDNA or cfRNA) is detected (or is capable of being detected). For example, the mutation can be detected even if less than or equal to 10, 5, 2, 1, 0.5, 0.1, 0.05, 0.01, or 0.005% of the DNA or RNA molecules that have that locus have that mutation in the locus (instead of, for example, a wild-type or non-mutated version of the locus or a different mutation at that locus). In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules in a sample (such as a sample of cfDNA or cfRNA) is detected (or is capable of being detected). In some embodiments in which the CNV is a deletion, the deletion can be detected even if it is only present in less than or equal to 10, 5, 2, 1, 0.5, 0.1, 0.05, 0.01, or 0.005% of the DNA or RNA molecules that have a region of interest that may or may not contain the deletion in a sample. In some embodiments in which the CNV is a deletion, the deletion can be detected even if it is only present in less than or equal to 10, 5, 2, 1, 0.5, 0.1, 0.05, 0.01, or 0.005% of the DNA or RNA molecules in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules that have a region of interest that may or may not be duplicated in a sample in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules in a sample.

Exemplary Samples

In some embodiments of any of the aspects of the invention, the sample includes cellular and/or extracellular genetic material from cells suspected of having a deletion or duplication, such as cells suspected of being cancerous. In some embodiments, the sample comprises any tissue or bodily fluid suspected of containing cells, DNA, or RNA having a deletion or duplication, such as tumors or other samples that include cancer cells, DNA, or RNA. The genetic measurements used as part of these methods can be made on any sample comprising DNA or RNA, for example but not limited to, tissue, blood, serum, plasma, urine, hair, tears, saliva, skin, fingernails, feces, bile, lymph, cervical mucus, semen, tumor, or other cells or materials comprising nucleic acids. Samples may include any cell type or DNA or RNA from any cell type may be used (such as cells from any organ or tissue suspected of being cancerous, or neurons). In some embodiments, the sample includes nuclear and/or mitochondrial DNA. In some embodiments, the sample is from any of the target individuals disclosed herein. In some embodiments, the target individual cancer patient.

Exemplary samples include those containing cfDNA or cfRNA. In some embodiments, cfDNA is available for analysis without requiring the step of lysing cells. Cell-free DNA may be obtained from a variety of tissues, such as tissues that are in liquid form, e.g., blood, plasma, lymph, ascites fluid, or cerebral spinal fluid. In some cases, cfDNA is comprised of DNA derived from fetal cells. In some cases, the cfDNA is isolated from plasma that has been isolated from whole blood that has been centrifuged to remove cellular material. The cfDNA may be a mixture of DNA derived from target cells (such as cancer cells) and non-target cells (such as non-cancer cells).

In some embodiments, the sample contains or is suspected to contain a mixture of DNA (or RNA), such as mixture of DNA (or RNA) originating from cancer cells and DNA (or RNA) originating from noncancerous (i.e. normal) cells. In some embodiments, at least 0.5, 1, 3, 5, 7, 10, 15, 20, 30, 40, 50, 60, 70, 80, 90, 92, 94, 95, 96, 98, 99, or 100% of the cells in the sample are cancer cells. In some embodiments, at least 0.5, 1, 3, 5, 7, 10, 15, 20, 30, 40, 50, 60, 70, 80, 90, 92, 94, 95, 96, 98, 99, or 100% of the DNA (such as cfDNA) or RNA (such as cfRNA) in the sample is from cancer cell(s). In various embodiments, the percent of cells in the sample that are cancerous cells is between 0.5 to 99%, such as between 1 to 95%, 5 to 95%, 10 to 90%, 5 to 70%, 10 to 70%, 20 to 90%, or 20 to 70%, inclusive. In some embodiments, the sample is enriched for cancer cells or for DNA or RNA from cancer cells. In some embodiments in which the sample is enriched for cancer cells, at least 0.5, 1, 2, 3, 4, 5, 6, 7, 10, 15, 20, 30, 40, 50, 60, 70, 80, 90, 92, 94, 95, 96, 98, 99, or 100% of the cells in the enriched sample are cancer cells. In some embodiments in which the sample is enriched for DNA or RNA from cancer cells, at least 0.5, 1, 2, 3, 4, 5, 6, 7, 10, 15, 20, 30, 40, 50, 60, 70, 80, 90, 92, 94, 95, 96, 98, 99, or 100% of the DNA or RNA in the enriched sample is from cancer cell(s). In some embodiments, cell sorting (such as Fluorescent Activated Cell Sorting (FACS)) is used to enrich for cancer cells (Barteneva et. al., Biochim Biophys Acta., 1836(1):105-22, August 2013. doi: 10.1016/j.bbcan.2013.02.004. Epub 2013 Feb. 24, and Ibrahim et al., Adv Biochem Eng Biotechnol. 106:19-39, 2007, which are each hereby incorporated by reference in its entirety).

In some embodiments, the sample is enriched for fetal cells. In some embodiments in which the sample is enriched for fetal cells, at least 0.5, 1, 2, 3, 4, 5, 6, 7% or more of the cells in the enriched sample are fetal cells. In some embodiments, the percent of cells in the sample that are fetal cells is between 0.5 to 100%, such as between 1 to 99%, 5 to 95%, 10 to 95%, 10 to 95%, 20 to 90%, or 30 to 70%, inclusive. In some embodiments, the sample is enriched for fetal DNA. In some embodiments in which the sample is enriched for fetal DNA, at least 0.5, 1, 2, 3, 4, 5, 6, 7% or more of the DNA in the enriched sample is fetal DNA. In some embodiments, the percent of DNA in the sample that is fetal DNA is between 0.5 to 100%, such as between 1 to 99%, 5 to 95%, 10 to 95%, 10 to 95%, 20 to 90%, or 30 to 70%, inclusive.

In some embodiments, the sample includes a single cell or includes DNA and/or RNA from a single cell. In some embodiments, multiple individual cells (e.g., at least 5, 10, 20, 30, 40, or 50 cells from the same subject or from different subjects) are analyzed in parallel. In some embodiments, cells from multiple samples from the same individual are combined, which reduces the amount of work compared to analyzing the samples separately. Combining multiple samples can also allow multiple tissues to be tested for cancer simultaneously (which can be used to provide or more thorough screening for cancer or to determine whether cancer may have metastasized to other tissues).

In some embodiments, the sample contains a single cell or a small number of cells, such as 2, 3, 5, 6, 7, 8, 9, or 10 cells. In some embodiments, the sample has between 1 to 100, 100 to 500, or 500 to 1,000 cells, inclusive. In some embodiments, the sample contains 1 to 10 picograms, 10 to 100 picograms, 100 picograms to 1 nanogram, 1 to 10 nanograms, 10 to 100 nanograms, or 100 nanograms to 1 microgram of RNA and/or DNA, inclusive.

In some embodiments, the sample is embedded in parafilm. In some embodiments, the sample is preserved with a preservative such as formaldehyde and optionally encased in paraffin, which may cause cross-linking of the DNA such that less of it is available for PCR. In some embodiments, the sample is a formaldehyde fixed-paraffin embedded (FFPE) sample. In some embodiments, the sample is a fresh sample (such as a sample obtained with 1 or 2 days of analysis). In some embodiments, the sample is frozen prior to analysis. In some embodiments, the sample is a historical sample.

These samples can be used in any of the methods of the invention.

Exemplary Sample Preparation Methods

In some embodiments, the method includes isolating or purifying the DNA and/or RNA. There are a number of standard procedures known in the art to accomplish such an end. In some embodiments, the sample may be centrifuged to separate various layers. In some embodiments, the DNA or RNA may be isolated using filtration. In some embodiments, the preparation of the DNA or RNA may involve amplification, separation, purification by chromatography, liquid separation, isolation, preferential enrichment, preferential amplification, targeted amplification, or any of a number of other techniques either known in the art or described herein. In some embodiments for the isolation of DNA, RNase is used to degrade RNA. In some embodiments for the isolation of RNA, DNase (such as DNase I from Invitrogen, Carlsbad, CA, USA) is used to degrade DNA. In some embodiments, an RNeasy mini kit (Qiagen), is used to isolate RNA according to the manufacturer's protocol. In some embodiments, small RNA molecules are isolated using the mirVana PARIS kit (Ambion, Austin, TX, USA) according to the manufacturer's protocol (Gu et al., J. Neurochem. 122:641-649, 2012, , which is hereby incorporated by reference in its entirety). The concentration and purity of RNA may optionally be determined using Nanovue (GE Healthcare, Piscataway, NJ, USA), and RNA integrity may optionally be measured by use of the 2100 Bioanalyzer (Agilent Technologies, Santa Clara, CA, USA) (Gu et al., J. Neurochem. 122:641-649, 2012, , which is hereby incorporated by reference in its entirety). In some embodiments, TRIZOL or RNAlater (Ambion) is used to stabilize RNA during storage.

In some embodiments, universal tagged adaptors are added to make a library. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. In some embodiments, adaptor ligation is performed using the ligation kit found in the AGILENT SURESELECT kit. In some embodiments, the library is amplified using universal primers. In an embodiment, the amplified library is fractionated by size separation or by using products such as AGENCOURT AMPURE beads or other similar methods. In some embodiments, PCR amplification is used to amplify target loci. In some embodiments, the amplified DNA is sequenced (such as sequencing using an ILLUMINA IIGAX or HiSeq sequencer). In some embodiments, the amplified DNA is sequenced from each end of the amplified DNA to reduce sequencing errors. If there is a sequence error in a particular base when sequencing from one end of the amplified DNA, there is less likely to be a sequence error in the complementary base when sequencing from the other side of the amplified DNA (compared to sequencing multiple times from the same end of the amplified DNA).

In some embodiments, whole genome application (WGA) is used to amplify a nucleic acid sample. There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. In some embodiments, WGA is not performed.

In some embodiments, selective amplification or enrichment are used to amplify or enrich target loci. In some embodiments, the amplification and/or selective enrichment technique may involve PCR such as ligation mediated PCR, fragment capture by hybridization, Molecular Inversion Probes, or other circularizing probes. In some embodiments, real-time quantitative PCR (RT-qPCR), digital PCR, or emulsion PCR, single allele base extension reaction followed by mass spectrometry are used (Hung et al., J Clin Pathol 62:308-313, 2009, which is hereby incorporated by reference in its entirety). In some embodiments, capture by hybridization with hybrid capture probes is used to preferentially enrich the DNA. In some embodiments, methods for amplification or selective enrichment may involve using probes where, upon correct hybridization to the target sequence, the 3-prime end or 5-prime end of a nucleotide probe is separated from the polymorphic site of a polymorphic allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals In some embodiments, PCR (referred to as mini-PCR) is used to generate very short amplicons (U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, filed Nov. 18, 2011, and U.S. Ser. No. 61/994,791, filed May 16, 2014, which are each hereby incorporated by reference in its entirety). cfDNA (such as necroptically- or apoptotically-released cancer cfDNA) is highly fragmented. For fetal cfDNA, the fragment sizes are distributed in approximately a Gaussian fashion with a mean of 160 bp, a standard deviation of 15 bp, a minimum size of about 100 bp, and a maximum size of about 220 bp. The polymorphic site of one particular target locus may occupy any position from the start to the end among the various fragments originating from that locus. Because cfDNA fragments are short, the likelihood of both primer sites being present the likelihood of a fragment of length L comprising both the forward and reverse primers sites is the ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. In certain embodiments that relate most preferably to cfDNA from samples of individuals suspected of having cancer, the cfDNA is amplified using primers that yield a maximum amplicon length of 85, 80, 75 or 70 bp, and in certain preferred embodiments 75 bp, and that have a melting temperature between 5° and 65° C., and in certain preferred embodiments, between 54-60.5° C. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons are less than 100 bp, less than 90 bp, less than 80 bp, less than 70 bp, less than 65 bp, less than 60 bp, less than 55 bp, less than 50 bp, or less than 45 bp.

In some embodiments, amplification is performed using direct multiplexed PCR, sequential PCR, nested PCR, doubly nested PCR, one-and-a-half sided nested PCR, fully nested PCR, one sided fully nested PCR, one-sided nested PCR, hemi-nested PCR, hemi-nested PCR, triply hemi-nested PCR, semi-nested PCR, one sided semi-nested PCR, reverse semi-nested PCR method, or one-sided PCR, which are described in U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, and U.S. Ser. No. 61/994, 791, filed May 16, 2014, which are hereby incorporated by reference in their entirety. If desired, any of these methods can be used for mini-PCR.

If desired, the extension step of the PCR amplification may be limited from a time standpoint to reduce amplification from fragments longer than 200 nucleotides, 300 nucleotides, 400 nucleotides, 500 nucleotides or 1,000 nucleotides. This may result in the enrichment of fragmented or shorter DNA (such as fetal DNA or DNA from cancer cells that have undergone apoptosis or necrosis) and improvement of test performance.

In some embodiments, multiplex PCR is used. In some embodiments, the method of amplifying target loci in a nucleic acid sample involves (i) contacting the nucleic acid sample with a library of primers that simultaneously hybridize to least 100; 200; 500; 750; 1,000; 2,000; 5,000; 7,500; 10,000; 20,000; 25,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, at least 50, 60, 70, 80, 90, 95, 96, 97, 98, 99, or 99.5% of the targeted loci are amplified. In various embodiments, less than 60, 50, 40, 30, 20, 10, 5, 4, 3, 2, 1, 0.5, 0.25, 0.1, or 0.05% of the amplified products are primer dimers. In some embodiments, the primers are in solution (such as being dissolved in the liquid phase rather than in a solid phase). In some embodiments, the primers are in solution and are not immobilized on a solid support. In some embodiments, the primers are not part of a microarray. In some embodiments, the primers do not include molecular inversion probes (MIPs).

In some embodiments, two or more (such as 3 or 4) target amplicons (such as amplicons from the miniPCR method disclosed herein) are ligated together and then the ligated products are sequenced. Combining multiple amplicons into a single ligation product increases the efficiency of the subsequent sequencing step. In some embodiments, the target amplicons are less than 150, 100, 90, 75, or 50 base pairs in length before they are ligated. The selective enrichment and/or amplification may involve tagging each individual molecule with different tags, molecular barcodes, tags for amplification, and/or tags for sequencing. In some embodiments, the amplified products are analyzed by sequencing (such as by high throughput sequencing) or by hybridization to an array, such as a SNP array, the ILLUMINA INFINIUM array, or the AFFYMETRIX gene chip. In some embodiments, nanopore sequencing is used, such as the nanopore sequencing technology developed by Genia (see, for example, the world wide web at geniachip.com/technology, which is hereby incorporated by reference in its entirety). In some embodiments, duplex sequencing is used (Schmitt et al., "Detection of ultra-rare mutations by next-generation sequencing," Proc Natl Acad Sci USA. 109(36): 14508-14513, 2012, which is hereby incorporated by reference in its entirety). This approach greatly reduces errors by independently tagging and sequencing each of the two strands of a DNA duplex. As the two strands are complementary, true mutations are found at the same position in both strands. In contrast, PCR or sequencing errors result in mutations in only one strand and can thus be discounted as technical error. In some embodiments, the method entails tagging both strands of duplex DNA with a random, yet complementary double-stranded nucleotide sequence, referred to as a Duplex Tag. Double-stranded tag sequences are incorporated into standard sequencing adapters by first introducing a single-stranded randomized nucleotide sequence into one adapter strand and then extending the opposite strand with a DNA polymerase to yield a complementary, double-stranded tag. Following ligation of tagged adapters to sheared DNA, the individually labeled strands are PCR amplified from asymmetric primer sites on the adapter tails and subjected to paired-end sequencing. In some embodiments, a sample (such as a DNA or RNA sample) is divided into multiple fractions, such as different wells (e.g., wells of a WaferGen SmartChip). Dividing the sample into different fractions (such as at least 5, 10, 20, 50, 75, 100, 150, 200, or 300 fractions) can increase the sensitivity of the analysis since the percent of molecules with a mutation are higher in some of the wells than in the overall sample. In some embodiments, each fraction has less than 500, 400, 200, 100, 50, 20, 10, 5, 2, or 1 DNA or RNA molecules. In some embodiments, the molecules in each fraction are sequenced separately. In some embodiments, the same barcode (such as a random or non-human sequence) is added to all the molecules in the same fraction (such as by amplification with a primer containing the barcode or by ligation of a barcode), and different barcodes are added to molecules in different fractions. The barcoded molecules can be pooled and sequenced together. In some embodiments, the molecules are amplified before they are pooled and sequenced, such as by using nested PCR. In some embodiments, one forward and two reverse primers, or two forward and one reverse primers are used.

In some embodiments, a mutation (such as an SNV or CNV) that is present in less than 10, 5, 2, 1, 0.5, 0.1, 0.05, 0.01, or 0.005% of the DNA or RNA molecules in a sample (such as a sample of cfDNA or cfRNA) is detected (or is capable of being detected). In some embodiments, a mutation (such as an SNV or CNV) that is present in less than 1,000, 500, 100, 50, 20, 10, 5, 4, 3, or 2 original DNA or RNA molecules (before amplification) in a sample (such as a sample of cfDNA or cfRNA from, e.g., a blood sample) is detected (or is capable of being detected). In some embodiments, a mutation (such as an SNV or CNV) that is present in only 1 original DNA or RNA molecule (before amplification) in a sample (such as a sample of cfDNA or cfRNA from, e.g., a blood sample) is detected (or is capable of being detected).

For example, if the limit of detection of a mutation (such as a single nucleotide variant (SNV)) is 0.1%, a mutation present at 0.01% can be detected by dividing the fraction into multiple, fractions such as 100 wells. Most of the wells have no copies of the mutation. For the few wells with the mutation, the mutation is at a much higher percentage of the reads. In one example, there are 20,000 initial copies of DNA from the target locus, and two of those copies include a SNV of interest. If the sample is divided into 100 wells, 98 wells have the SNV, and 2 wells have the SNV at 0.5%. The DNA in each well can be barcoded, amplified, pooled with DNA from the other wells, and sequenced. Wells without the SNV can be used to measure the background amplification/sequencing error rate to determine if the signal from the outlier wells is above the background level of noise.

In some embodiments, the amplified products are detected using an array, such as an array especially a microarray with probes to one or more chromosomes of interest (e.g., chromosome 13, 18, 21, X, Y, or any combination thereof). It will be understood for example, that a commercially available SNP detection microarray could be used such as, for example, the Illumina (San Diego, CA) GoldenGate, DASL, Infinium, or CytoSNP-12 genotyping assay, or a SNP detection microarray product from Affymetrix, such as the OncoScan microarray.

In some embodiments involving sequencing, the depth of read is the number of sequencing reads that map to a given locus. The depth of read may be normalized over the total number of reads. In some embodiments for depth of read of a sample, the depth of read is the average depth of read over the targeted loci. In some embodiments for the depth of read of a locus, the depth of read is the number of reads measured by the sequencer mapping to that locus. In general, the greater the depth of read of a locus, the closer the ratio of alleles at the locus tend to be to the ratio of alleles in the original sample of DNA. Depth of read can be expressed in variety of different ways, including but not limited to the percentage or proportion. Thus, for example in a highly parallel DNA sequencer such as an Illumina HISEQ, which, e.g., produces a sequence of 1 million clones, the sequencing of one locus 3,000 times results in a depth of read of 3,000 reads at that locus. The proportion of reads at that locus is 3,000 divided by 1 million total reads, or 0.3% of the total reads.

In some embodiments, allelic data is obtained, wherein the allelic data includes quantitative measurement(s) indicative of the number of copies of a specific allele of a polymorphic locus. In some embodiments, the allelic data includes quantitative measurement(s) indicative of the number of copies of each of the alleles observed at a polymorphic locus. Typically, quantitative measurements are obtained for all possible alleles of the polymorphic locus of interest. For example, any of the methods discussed in the preceding paragraphs for determining the allele for a SNP or SNV locus, such as for example, microarrays, qPCR, DNA sequencing, such as high throughput DNA sequencing, can be used to generate quantitative measurements of the number of copies of a specific allele of a polymorphic locus. This quantitative measurement is referred to herein as allelic frequency data or measured genetic allelic data. Methods using allelic data are sometimes referred to as quantitative allelic methods; this is in contrast to quantitative methods which exclusively use quantitative data from non-polymorphic loci, or from polymorphic loci but without regard to allelic identity. When the allelic data is measured using high-throughput sequencing, the allelic data typically include the number of reads of each allele mapping to the locus of interest.

In some embodiments, non-allelic data is obtained, wherein the non-allelic data includes quantitative measurement(s) indicative of the number of copies of a specific locus. The locus may be polymorphic or non-polymorphic. In some embodiments when the locus is non-polymorphic, the non-allelic data does not contain information about the relative or absolute quantity of the individual alleles that may be present at that locus. Methods using non-allelic data only (that is, quantitative data from non-polymorphic alleles, or quantitative data from polymorphic loci but without regard to the allelic identity of each fragment) are referred to as quantitative methods. Typically, quantitative measurements are obtained for all possible alleles of the polymorphic locus of interest, with one value associated with the measured quantity for all of the alleles at that locus, in total. Non-allelic data for a polymorphic locus may be obtained by summing the quantitative allelic for each allele at that locus. When the allelic data is measured using high-throughput sequencing, the non-allelic data typically includes the number of reads of mapping to the locus of interest. The sequencing measurements could indicate the relative and/or absolute number of each of the alleles present at the locus, and the non-allelic data includes the sum of the reads, regardless of the allelic identity, mapping to the locus. In some embodiments the same set of sequencing measurements can be used to yield both allelic data and non-allelic data. In some embodiments, the allelic data is used as part of a method to determine copy number at a chromosome of interest, and the produced non-allelic data can be used as part of a different method to determine copy number at a chromosome of interest. In some embodiments, the two methods are statistically orthogonal, and are combined to give a more accurate determination of the copy number at the chromosome of interest.

In some embodiments obtaining genetic data includes (i) acquiring DNA sequence information by laboratory techniques, e.g., by the use of an automated high throughput DNA sequencer, or (ii) acquiring information that had been previously obtained by laboratory techniques, wherein the information is electronically transmitted, e.g., by a computer over the internet or by electronic transfer from the sequencing device.

Additional exemplary sample preparation, amplification, and quantification methods are described in U.S. application Ser. No. 13/683,604, filed Nov. 21, 2012 (U.S. Publication No. 2013/0123120 and U.S. Ser. No. 61/994,791, filed May 16, 2014, which is hereby incorporated by reference in its entirety). These methods can be used for analysis of any of the samples disclosed herein.

Exemplary Quantification Methods for Cell-Free DNA

If desired, that amount or concentration of cfDNA or cfRNA can be measured using standard methods. In some embodiments, the amount or concentration of cell-free mitochondrial DNA (cf mDNA) is determined. In some embodiments, the amount or concentration of cell-free DNA that originated from nuclear DNA (cf nDNA) is determined. In some embodiments, the amount or concentration of cf mDNA and cf nDNA are determined simultaneously.

In some embodiments, qPCR is used to measure cf nDNA and/or cfm DNA (Kohler et al. "Levels of plasma circulating cell free nuclear and mitochondrial DNA as potential biomarkers for breast tumors." Mol Cancer 8:105, 2009, 8:doi: 10.1186/1476-4598-8-105, which is hereby incorporated by reference in its entirety). For example, one or more loci from cf nDNA (such as Glyceraldehyd-3-phosphat-dehydrogenase, GAPDH) and one or more loci from cf mDNA (ATPase 8, MTATP 8) can be measured using multiplex qPCR. In some embodiments, fluorescence-labelled PCR is used to measure cf nDNA and/or cf mDNA (Schwarzenbach et al., "Evaluation of cell-free tumour DNA and RNA in patients with breast cancer and benign breast disease." Mol Biosys 7:2848-2854, 2011, which is hereby incorporated by reference in its entirety). If desired, the normality distribution of the data can be determined using standard methods, such as the Shapiro-Wilk-Test. If desired, cf nDNA and mDNA levels can be compared using standard methods, such as the Mann-Whitney-U-Test. In some embodiments, cf nDNA and/or mDNA levels are compared with other established prognostic factors using standard methods, such as the Mann-Whitney-U-Test or the Kruskal-Wallis-Test.

Exemplary RNA Amplification, Quantification, and Analysis Methods

Any of the following exemplary methods may be used to amplify and optionally quantify RNA, such as such as cfRNA, cellular RNA, cytoplasmic RNA, coding cytoplasmic RNA, non-coding cytoplasmic RNA, mRNA, miRNA, mitochondrial RNA, rRNA, or tRNA. In some embodiments, the miRNA is any of the miRNA molecules listed in the miRBase database available at the world wide web at mirbase.org, which is hereby incorporated by reference in its entirety. Exemplary miRNA molecules include miR-509; miR-21, and miR-146a.

In some embodiments, reverse-transcriptase multiplex ligation-dependent probe amplification (RT-MLPA) is used to amplify RNA. In some embodiments, each set of hybridizing probes consists of two short synthetic oligonucleotides spanning the SNP and one long oligonucleotide (Li et al., Arch Gynecol Obstet. "Development of noninvasive prenatal diagnosis of trisomy 21 by RT-MLPA with a new set of SNP markers," Jul. 5, 2013, DOI 10.1007/s00404-013-2926-5; Schouten et al. "Relative quantification of 40 nucleic acid sequences by multiplex ligation-dependent probe amplification." Nucleic Acids Res 30:e57, 2002; Deng et al. (2011) "Non-invasive prenatal diagnosis of trisomy 21 by reverse transcriptase multiplex ligation-dependent probe amplification," Clin, Chem. Lab Med. 49:641-646, 2011, which are each hereby incorporated by reference in its entirety).

In some embodiments, RNA is amplified with reverse-transcriptase PCR. In some embodiments, RNA is amplified with real-time reverse-transcriptase PCR, such as one-step real-time reverse-transcriptase PCR with SYBR GREEN I as previously described (Li et al., Arch Gynecol Obstet. "Development of noninvasive prenatal diagnosis of trisomy 21 by RT-MLPA with a new set of SNP markers," Jul. 5, 2013, DOI 10.1007/s00404-013-2926-5; Lo et al., "Plasma placental RNA allelic ratio permits noninvasive prenatal chromosomal aneuploidy detection," Nat Med 13:218-223, 2007; Tsui et al., Systematic micro-array based identification of placental mRNA in maternal plasma: towards non-invasive prenatal gene expression profiling. J Med Genet 41:461-467, 2004; Gu et al., J. Neurochem. 122:641-649, 2012, which are each hereby incorporated by reference in its entirety).

In some embodiments, a microarray is used to detect RNA. For example, a human miRNA microarray from Agilent Technologies can be used according to the manufacturer's protocol. Briefly, isolated RNA is dephosphorylated and ligated with pCp-Cy3. Labeled RNA is purified and hybridized to miRNA arrays containing probes for human mature miRNAs on the basis of Sanger miRBase release 14.0. The arrays is washed and scanned with use of a microarray scanner (G2565BA, Agilent Technologies). The intensity of each hybridization signal is evaluated by Agilent extraction software v9.5.3. The labeling, hybridization, and scanning may be performed according to the protocols in the Agilent miRNA microarray system (Gu et al., J. Neurochem. 122:641-649, 2012, which is hereby incorporated by reference in its entirety).

In some embodiments, a TaqMan assay is used to detect RNA. An exemplary assay is the TaqMan Array Human MicroRNA Panel v1.0 (Early Access) (Applied Biosystems), which contains 157 TaqMan MicroRNA Assays, including the respective reverse-transcription primers, PCR primers, and TaqMan probe (Chim et al., "Detection and characterization of placental microRNAs in maternal plasma," Clin Chem. 54(3):482-90, 2008, which is hereby incorporated by reference in its entirety).

If desired, the mRNA splicing pattern of one or more mRNAs can be determined using standard methods (Fackenthall and Godley, Disease Models & Mechanisms 1: 37-42, 2008, doi:10.1242/dmm.000331, which is hereby incorporated by reference in its entirety). For example, high-density microarrays and/or high-throughput DNA sequencing can be used to detect mRNA splice variants.

In some embodiments, whole transcriptome shotgun sequencing or an array is used to measure the transcriptome.
Exemplary Amplification Methods Improved PCR amplification methods have also been developed that minimize or prevent interference due to the amplification of nearby or adjacent target loci in the same reaction volume (such as part of the sample multiplex PCR reaction that simultaneously amplifies all the target loci). These methods can be used to simultaneously amplify nearby or adjacent target loci, which is faster and cheaper than having to separate nearby target loci into different reaction volumes so that they can be amplified separately to avoid interference.

In some embodiments, the amplification of target loci is performed using a polymerase (e.g., a DNA polymerase, RNA polymerase, or reverse transcriptase) with low 5'→3' exonuclease and/or low strand displacement activity. In some embodiments, the low level of 5'→3' exonuclease reduces or prevents the degradation of a nearby primer (e.g., an unextended primer or a primer that has had one or more nucleotides added to during primer extension). In some embodiments, the low level of strand displacement activity reduces or prevents the displacement of a nearby primer (e.g., an unextended primer or a primer that has had one or more nucleotides added to it during primer extension). In some embodiments, target loci that are adjacent to each other (e.g., no bases between the target loci) or nearby (e.g., loci are within 50, 40, 30, 20, 15, 10, 9, 8, 7, 6, 5, 4, 3, 2, or 1 base) are amplified. In some embodiments, the 3' end of one locus is within 50, 40, 30, 20, 15, 10, 9, 8, 7, 6, 5, 4, 3, 2, or 1 base of the 5' end of next downstream locus.

In some embodiments, at least 100, 200, 500, 750, 1,000; 2,000; 5,000; 7,500; 10,000; 20,000; 25,000; 30,000; 40,000; 50,000; 75,000; or 100,000 different target loci are amplified, such as by the simultaneous amplification in one reaction volume In some embodiments, at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, at least 50, 60, 70, 80, 90, 95, 96, 97, 98, 99, or 99.5% of the targeted loci are amplified (e.g, amplified at least 5, 10, 20, 30, 50, or 100-fold compared to the amount prior to amplification), such as by the simultaneous amplification in one reaction volume. In various embodiments, the amount target loci that are amplified (e.g, amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, fewer non-target amplicons are produced, such as fewer amplicons formed from a forward primer from a first primer pair and a reverse primer from a second primer pair. Such undesired non-target amplicons can be produced using prior amplification methods if, e.g., the reverse primer from the first primer pair and/or the forward primer from the second primer pair are degraded and/or displaced.

In some embodiments, these methods allows longer extension times to be used since the polymerase bound to a primer being extended is less likely to degrade and/or displace a nearby primer (such as the next downstream primer) given the low 5'→3' exonuclease and/or low strand displacement activity of the polymerase. In various embodiments, reaction conditions (such as the extension time and temperature) are used such that the extension rate of the polymerase allows the number of nucleotides that are added to a primer being extended to be equal to or greater than 80, 90, 95, 100, 110, 120, 130, 140, 150, 175, or 200% of the number of nucleotides between the 3' end of the primer binding site and the 5'end of the next downstream primer binding site on the same strand.

In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In some embodiments, the low level of 5'→3' exonuclease of the polymerase is less than 80, 70, 60, 50, 40, 30, 20, 10, 5, 1, or 0.1% of the activity of the same amount of *Thermus aquaticus* polymerase ("Taq" polymerase, which is a commonly used DNA polymerase from a thermophilic bacterium, PDB IBGX, EC 2.7.7.7, Murali et al., "Crystal structure of Taq DNA polymerase in complex with an inhibitory Fab: the Fab is directed against an intermediate in the helix-coil dynamics of the enzyme," Proc. Natl. Acad. Sci. USA 95:12562-12567, 1998, which is hereby incorporated by reference in its entirety) under the same conditions. In some embodiments, the low level of strand displacement activity of the polymerase is less than 80, 70, 60, 50, 40, 30, 20, 10, 5, 1, or 0.1% of the activity of the same amount of Taq polymerase under the same conditions.

In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs, Inc.; Frey and Suppman *BioChemica.* 2:34-35, 1995; Chester and Marshak Analytical Biochemistry. 209:284-290, 1993, which are each hereby incorporated by reference in its entirety). The PHUSION DNA polymerase is a *Pyrococcus*-like enzyme fused with a processivity-enhancing domain. PHUSION DNA polymerase possesses 5'→3' polymerase activity and 3'→5' exonuclease activity, and generates blunt-ended products. PHUSION DNA polymerase lacks 5'→3' exonuclease activity and strand displacement activity.

In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). Q5® High-Fidelity DNA polymerase is a high-fidelity, thermostable, DNA polymerase with 3'→5' exonuclease activity, fused to a processivity-enhancing Sso7d domain. Q5® High-Fidelity DNA polymerase lacks 5'→3' exonuclease activity and strand displacement activity.

In some embodiments, the polymerase is a T4 DNA polymerase (M0203S, New England BioLabs, Inc.; Tabor and Struh. (1989). "DNA-Dependent DNA Polymerases," In Ausebel et al. (Ed.), *Current Protocols in Molecular Biology.* 3.5.10-3.5.12. New York: John Wiley & Sons, Inc., 1989; Sambrook et al. *Molecular Cloning: A Laboratory Manual.* (2nd ed.), 5.44-5.47. Cold Spring Harbor: Cold Spring Harbor Laboratory Press, 1989, which are each hereby incorporated by reference in its entirety). T4 DNA Polymerase catalyzes the synthesis of DNA in the 5'→3' direction and requires the presence of template and primer. This enzyme has a 3'→5' exonuclease activity which is much more active than that found in DNA Polymerase I. T4 DNA polymerase lacks 5'→3' exonuclease activity and strand displacement activity.

In some embodiments, the polymerase is a *Sulfolobus* DNA Polymerase IV (M0327S, New England BioLabs, Inc.; (Boudsocq, et al. (2001). *Nucleic Acids Res.,* 29:4607-4616, 2001; McDonald, et al. (2006). *Nucleic Acids Res.,* 34:1102-1111, 2006, which are each hereby incorporated by reference in its entirety). *Sulfolobus* DNA Polymerase IV is a thermostable Y-family lesion-bypass DNA Polymerase that efficiently synthesizes DNA across a variety of DNA template lesions McDonald, J. P. et al. (2006). *Nucleic Acids Res.,* 34, 1102-1111, which is hereby incorporated by reference in its entirety). *Sulfolobus* DNA Polymerase IV lacks 5'→3' exonuclease activity and strand displacement activity.

In some embodiments, if a primer binds a region with a SNP, the primer may bind and amplify the different alleles with different efficiencies or may only bind and amplify one allele. For subjects who are heterozygous, one of the alleles may not be amplified by the primer. In some embodiments, a primer is designed for each allele. For example, if there are two alleles (e.g., a biallelic SNP), then two primers can be used to bind the same location of a target locus (e.g., a forward primer to bind the "A" allele and a forward primer to bind the "B" allele). Standard methods, such as the dbSNP database, can be used to determine the location of known SNPs, such as SNP hot spots that have a high heterozygosity rate.

In some embodiments, the amplicons are similar in size. In some embodiments, the range of the length of the target amplicons is less than 100, 75, 50, 25, 15, 10, or 5 nucleotides. In some embodiments (such as the amplification of target loci in fragmented DNA or RNA), the length of the target amplicons is between 50 and 100 nucleotides, such as between 60 and 80 nucleotides, or 60 and 75 nucleotides, inclusive. In some embodiments (such as the amplification of multiple target loci throughout an exon or gene), the length of the target amplicons is between 100 and 500 nucleotides, such as between 150 and 450 nucleotides, 200 and 400 nucleotides, 200 and 300 nucleotides, or 300 and 400 nucleotides, inclusive.

In some embodiments, multiple target loci are simultaneously amplified using a primer pair that includes a forward and reverse primer for each target locus to be amplified in that reaction volume. In some embodiments, one round of PCR is performed with a single primer per target locus, and then a second round of PCR is performed with a primer pair per target locus. For example, the first round of PCR may be performed with a single primer per target locus such that all the primers bind the same strand (such as using a forward primer for each target locus). This allows the PCR to amplify in a linear manner and reduces or eliminates amplification bias between amplicons due to sequence or length differences. In some embodiments, the amplicons are then amplified using a forward and reverse primer for each target locus.

Exemplary Primer Design Methods

If desired, multiplex PCR may be performed using primers with a decreased likelihood of forming primer dimers. In particular, highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing.

There are a number of ways to choose primers for a library where the amount of non-mapping primer dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

In some embodiments for selecting primers, an initial library of candidate primers is created by designing one or more primers or primer pairs to candidate target loci. A set of candidate target loci (such as SNPs) can selected based on publically available information about desired parameters for the target loci, such as frequency of the SNPs within a target population or the heterozygosity rate of the SNPs. In one embodiment, the PCR primers may be designed using the Primer3 program (the worldwide web at primer3.sourceforge.net; libprimer3 release 2.2.3, which is hereby incorporated by reference in its entirety). If desired, the primers can be designed to anneal within a particular annealing temperature range, have a particular range of GC contents, have a particular size range, produce target amplicons in a particular size range, and/or have other parameter characteristics. Starting with multiple primers or primer pairs per candidate target locus increases the likelihood that a primer or prime pair will remain in the library for most or all of the target loci. In one embodiment, the selection criteria may require that at least one primer pair per target locus remains in the library. That way, most or all of the target loci will be amplified when using the final primer library. This is desirable for applications such as screening for deletions or duplications at a large number of locations in the genome or screening for a large number of sequences (such as polymorphisms or other mutations) associated with a disease or an increased risk for a disease. If a primer pair from the library would produces a target amplicon that overlaps with a target amplicon produced by another primer pair, one of the primer pairs may be removed from the library to prevent interference.

In some embodiments, an "undesirability score" (higher score representing least desirability) is calculated (such as calculation on a computer) for most or all of the possible combinations of two primers from a library of candidate primers. In various embodiments, an undesirability score is calculated for at least 80, 90, 95, 98, 99, or 99.5% of the possible combinations of candidate primers in the library. Each undesirability score is based at least in part on the likelihood of dimer formation between the two candidate primers. If desired, the undesirability score may also be based on one or more other parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the target amplicon, GC content of the target amplicon, amplification efficiency of the target amplicon, size of the target amplicon, and distance from the center of a recombination hotspot. In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library. In some embodiments to increase the number of candidate primers to choose from, candidate primers that may mis-prime are not removed from the library. If multiple factors are considered, the undesirability score may be calculated based on a weighted average of the various parameters. The parameters may be assigned different weights based on their importance for the particular application that the primers will be used for. In some embodiments, the primer with the highest undesirability score is removed from the library. If the removed primer is a member of a primer pair that hybridizes to one target locus, then the other member of the primer pair may be removed from the library. The process of removing primers may be repeated as desired. In some embodiments, the selection method is performed until the undesirability scores for the candidate primer combinations remaining in the library are all equal to or below a minimum threshold. In some embodiments, the selection method is performed until the number of candidate primers remaining in the library is reduced to a desired number.

In various embodiments, after the undesirability scores are calculated, the candidate primer that is part of the greatest number of combinations of two candidate primers with an undesirability score above a first minimum threshold is removed from the library. This step ignores interactions equal to or below the first minimum threshold since these interactions are less significant. If the removed primer is a member of a primer pair that hybridizes to one target locus, then the other member of the primer pair may be removed from the library. The process of removing primers may be repeated as desired. In some embodiments, the selection method is performed until the undesirability scores for the candidate primer combinations remaining in the library are all equal to or below the first minimum threshold. If the number of candidate primers remaining in the library is higher than desired, the number of primers may be reduced by decreasing the first minimum threshold to a lower second minimum threshold and repeating the process of removing primers. If the number of candidate primers remaining in the library is lower than desired, the method can be continued by increasing the first minimum threshold to a higher second minimum threshold and repeating the process of removing primers using the original candidate primer library, thereby allowing more of the candidate primers to remain in the library. In some embodiments, the selection method is performed until the undesirability scores for the candidate primer combinations remaining in the library are all equal to or below the second minimum threshold, or until the number of candidate primers remaining in the library is reduced to a desired number.

If desired, primer pairs that produce a target amplicon that overlaps with a target amplicon produced by another primer pair can be divided into separate amplification reactions. Multiple PCR amplification reactions may be desirable for applications in which it is desirable to analyze all of the candidate target loci (instead of omitting candidate target loci from the analysis due to overlapping target amplicons).

These selection methods minimize the number of candidate primers that have to be removed from the library to achieve the desired reduction in primer dimers. By removing a smaller number of candidate primers from the library, more (or all) of the target loci can be amplified using the resulting primer library.

Multiplexing large numbers of primers imposes considerable constraint on the assays that can be included. Assays that unintentionally interact result in spurious amplification products. The size constraints of miniPCR may result in further constraints. In an embodiment, it is possible to begin with a very large number of potential SNP targets (between about 500 to greater than 1 million) and attempt to design primers to amplify each SNP. Where primers can be designed it is possible to attempt to identify primer pairs likely to form spurious products by evaluating the likelihood of spurious primer duplex formation between all possible pairs of primers using published thermodynamic parameters for DNA duplex formation. Primer interactions may be ranked by a scoring function related to the interaction and primers with the worst interaction scores are eliminated until the number of primers desired is met. In cases where SNPs likely to be heterozygous are most useful, it is possible to also rank the list of assays and select the most heterozygous compatible assays. Experiments have validated that primers with high interaction scores are most likely to form primer dimers. At high multiplexing it is not possible to eliminate all spurious interactions, but it is essential to remove the primers or pairs of primers with the highest interaction scores in silico as they can dominate an entire reaction, greatly limiting amplification from intended targets. We have performed this procedure to create multiplex primer sets of up to and in some cases more than 10,000 primers. The improvement due to this procedure is substantial, enabling amplification of more than 80%, more than 90%, more than 95%, more than 98%, and even more than 99% on target products as determined by sequencing of all PCR products, as compared to 10% from a reaction in which the worst primers were not removed. When combined with a partial semi-nested approach as previously described, more than 90%, and even more than 95% of amplicons may map to the targeted sequences.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed. In an embodiment, the method of primer design may be used in combination with the mini-PCR method described herein.

The use of tags on the primers may reduce amplification and sequencing of primer dimer products. In some embodiments, the primer contains an internal region that forms a loop structure with a tag. In particular embodiments, the primers include a 5' region that is specific for a target locus, an internal region that is not specific for the target locus and forms a loop structure, and a 3' region that is specific for the target locus. In some embodiments, the loop region may lie between two binding regions where the two binding regions are designed to bind to contiguous or neighboring regions of template DNA. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as a tag or a universal primer binding site) followed by a region that is specific for a target locus, an internal region that is not specific for the target locus and forms a loop structure, and a 3' region that is specific for the target locus. Tag-primers can be used to shorten necessary target-specific sequences to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging.

In an embodiment, the relative amount of nonproductive products in the multiplexed targeted PCR amplification can be reduced by raising the annealing temperature. In cases where one is amplifying libraries with the same tag as the target specific primers, the annealing temperature can be increased in comparison to the genomic DNA as the tags will contribute to the primer binding. In some embodiments reduced primer concentrations are used, optionally along with longer annealing times. In some embodiments the annealing times may be longer than 3 minutes, longer than 5 minutes, longer than 8 minutes, longer than 10 minutes, longer than 15 minutes, longer than 20 minutes, longer than 30 minutes, longer than 60 minutes, longer than 120 minutes, longer than 240 minutes, longer than 480 minutes, and even longer than 960 minutes. In certain illustrative embodiments, longer annealing times are used along with reduced primer concentrations. In various embodiments, longer than normal extension times are used, such as greater than 3, 5, 8, 10, or 15 minutes. In some embodiments, the primer concentrations are as low as 50 nM, 20 nM, 10 nM, 5 nM, 1 nM, and lower than 1 nM. This surprisingly results in robust performance for highly multiplexed reactions, for example 1,000-plex reactions, 2,000-plex reactions, 5,000-plex reactions, 10,000-plex reactions, 20,000-plex reactions, 50,000-plex reactions, and even 100,000-plex reactions. In an embodiment, the amplification uses one, two, three, four or five cycles run with long annealing times, followed by PCR cycles with more usual annealing times with tagged primers.

To select target locations, one may start with a pool of candidate primer pair designs and create a thermodynamic model of potentially adverse interactions between primer pairs, and then use the model to eliminate designs that are incompatible with other the designs in the pool.

In an embodiment, the invention features a method of decreasing the number of target loci (such as loci that may contain a polymorphism or mutation associated with a disease or disorder or an increased risk for a disease or disorder such as cancer) and/or increasing the disease load that is detected (e.g., increasing the number of polymorphisms or mutations that are detected). In some embodiments, the method includes ranking (such as ranking from highest to lowest) loci by frequency or reoccurrence of a polymorphism or mutation (such as a single nucleotide variation, insertion, or deletion, or any of the other variations described herein) in each locus among subjects with the disease or disorder such as cancer. In some embodiments, PCR primers are designed to some or all of the loci. During selection of PCR primers for a library of primers, primers to loci that have a higher frequency or reoccurrence (higher ranking loci) are favored over those with a lower frequency or reoccurrence (lower ranking loci). In some embodiments, this parameter is included as one of the parameters in the calculation of the undesirability scores described herein. If desired, primers (such as primers to high ranking loci) that are incompatible with other designs in the library can be included in a different PCR library/pool. In some embodiments, multiple libraries/pools (such as 2, 3, 4, 5 or more) are used in separate PCR reactions to enable amplification of all (or a majority) of the loci represented by all the libraries/pools. In some embodiment, this method is continued until sufficient primers are included in one or more libraries/pools such that the primers, in aggregate, enable the desired disease load to be captured for the disease or disorder (e.g., such as by detection of at least 80, 85, 90, 95, or 99% of the disease load).

Exemplary Primer Libraries

In one aspect, the invention features libraries of primers, such as primers selected from a library of candidate primers using any of the methods of the invention. In some embodiments, the library includes primers that simultaneously hybridize (or are capable of simultaneously hybridizing) to or that simultaneously amplify (or are capable of simultaneously amplifying) at least 100; 200; 500; 750; 1,000; 2,000; 5,000; 7,500; 10,000; 20,000; 25,000; 30,000;

40,000; 50,000; 75,000; or 100,000 different target loci in one reaction volume. In various embodiments, the library includes primers that simultaneously amplify (or are capable of simultaneously amplifying) between 100 to 500; 500 to 1,000; 1,000 to 2,000; 2,000 to 5,000; 5,000 to 7,500; 7,500 to 10,000; 10,000 to 20,000; 20,000 to 25,000; 25,000 to 30,000; 30,000 to 40,000; 40,000 to 50,000; 50,000 to 75,000; or 75,000 to 100,000 different target loci in one reaction volume, inclusive. In various embodiments, the library includes primers that simultaneously amplify (or are capable of simultaneously amplifying) between 1,000 to 100,000 different target loci in one reaction volume, such as between 1,000 to 50,000; 1,000 to 30,000; 1,000 to 20,000; 1,000 to 10,000; 2,000 to 30,000; 2,000 to 20,000; 2,000 to 10,000; 5,000 to 30,000; 5,000 to 20,000; or 5,000 to 10,000 different target loci, inclusive. In some embodiments, the library includes primers that simultaneously amplify (or are capable of simultaneously amplifying) the target loci in one reaction volume such that less than 60, 40, 30, 20, 10, 5, 4, 3, 2, 1, 0.5, 0.25, 0.1, or 0.5% of the amplified products are primer dimers. The various embodiments, the amount of amplified products that are primer dimers is between 0.5 to 60%, such as between 0.1 to 40%, 0.1 to 20%, 0.25 to 20%, 0.25 to 10%, 0.5 to 20%, 0.5 to 10%, 1 to 20%, or 1 to 10%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the targeted loci are amplified (e.g, amplified at least 5, 10, 20, 30, 50, or 100-fold compared to the amount prior to amplification). In various embodiments, the amount target loci that are amplified (e.g, amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 individual primers that each hybridize to a different target locus, wherein the individual primers are not part of primer pairs.

In various embodiments, the concentration of each primer is less than 100, 75, 50, 25, 20, 10, 5, 2, or 1 nM, or less than 500, 100, 10, or 1 uM. In various embodiments, the concentration of each primer is between 1 uM to 100 nM, such as between 1 uM to 1 nM, 1 to 75 nM, 2 to 50 nM or 5 to 50 nM, inclusive. In various embodiments, the GC content of the primers is between 30 to 80%, such as between 40 to 70%, or 50 to 60%, inclusive. In some embodiments, the range of GC content of the primers is less than 30, 20, 10, or 5%. In some embodiments, the range of GC content of the primers is between 5 to 30%, such as 5 to 20% or 5 to 10%, inclusive. In some embodiments, the melting temperature ($T_m$) of the test primers is between 40 to 80° C., such as 50 to 70° C., 55 to 65° C., or 57 to 60.5° C., inclusive. In some embodiments, the $T_m$ is calculated using the Primer3 program (libprimer3 release 2.2.3) using the built-in SantaLucia parameters (the world wide web at primer3.sourceforge.net). In some embodiments, the range of melting temperature of the primers is less than 15, 10, 5, 3, or 1° C. In some embodiments, the range of melting temperature of the primers is between 1 to 15° C., such as between 1 to 10° C., 1 to 5° C., or 1 to 3° C., inclusive. In some embodiments, the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the range of the length of the primers is less than 50, 40, 30, 20, 10, or 5 nucleotides. In some embodiments, the range of the length of the primers is between 5 to 50 nucleotides, such as 5 to 40 nucleotides, 5 to 20 nucleotides, or 5 to 10 nucleotides, inclusive. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the library does not comprise a microarray. In some embodiments, the library comprises a microarray.

In some embodiments, some (such as at least 80, 90, or 95%) or all of the adaptors or primers include one or more linkages between adjacent nucleotides other than a naturally-occurring phosphodiester linkage. Examples of such linkages include phosphoramide, phosphorothioate, and phosphorodithioate linkages. In some embodiments, some (such as at least 80, 90, or 95%) or all of the adaptors or primers include a thiophosphate (such as a monothiophosphate) between the last 3' nucleotide and the second to last 3' nucleotide. In some embodiments, some (such as at least 80, 90, or 95%) or all of the adaptors or primers include a thiophosphate (such as a monothiophosphate) between the last 2, 3, 4, or 5 nucleotides at the 3' end. In some embodiments, some (such as at least 80, 90, or 95%) or all of the adaptors or primers include a thiophosphate (such as a monothiophosphate) between at least 1, 2, 3, 4, or 5 nucleotides out of the last 10 nucleotides at the 3' end. In some embodiments, such primers are less likely to be cleaved or degraded. In some embodiments, the primers do not contain an enzyme cleavage site (such as a protease cleavage site).

Additional exemplary multiplex PCR methods and libraries are described in U.S. application Ser. No. 13/683,604, filed Nov. 21, 2012 (U.S. Publication No. 2013/0123120) and U.S. Ser. No. 61/994,791, filed May 16, 2014, which are each hereby incorporated by reference in its entirety). These methods and libraries can be used for analysis of any of the samples disclosed herein and for use in any of the methods of the invention.

Exemplary Primer Libraries for Detection of Recombination

In some embodiments, primers in the primer library are designed to determine whether or not recombination occurred at one or more known recombination hotspots (such as crossovers between homologous human chromosomes). Knowing what crossovers occurred between chromosomes allows more accurate phased genetic data to be determined for an individual. Recombination hotspots are local regions of chromosomes in which recombination events tend to be concentrated. Often they are flanked by "coldspots," regions of lower than average frequency of recombination. Recombination hotspots tend to share a similar morphology and are approximately 1 to 2 kb in length. The hotspot distribution is positively correlated with GC content and repetitive element distribution. A partially degenerated 13-mer motif CCNCCNTNNCCNC plays a role in some hotspot activity. It has been shown that the zinc finger protein called PRDM9 binds to this motif and initiates recombination at its location. The average distance between the centers of recombination hot spots is reported to be ~80 kb. In some embodiments, the distance between the centers of recombination hot spots ranges between ~3 kb to ~100 kb. Public databases include a large number of known human recombination hotspots, such as the HUMHOT and International HapMap Project databases (see, for example, Nishant et al., "HUMHOT: a database of human meiotic recombination hot spots," Nucleic Acids Research, 34: D25-D28, 2006, Database issue; Mackiewicz et al., "Distribution of Recombination Hotspots in the Human Genome—A Comparison of Computer Simulations with Real Data" PLoS ONE 8(6): e65272, doi:10.1371/journal.pone.0065272; and the world wide web at hapmap.ncbi.nlm.nih.gov/downloads/index.html.en, which are each hereby incorporated by reference in its entirety).

In some embodiments, primers in the primer library are clustered at or near recombination hotspots (such as known human recombination hotspots). In some embodiments, the corresponding amplicons are used to determine the sequence within or near a recombination hotspot to determine whether or not recombination occurred at that particular hotspot (such as whether the sequence of the amplicon is the sequence expected if a recombination had occurred or the sequence expected if a recombination had not occurred). In some embodiments, primers are designed to amplify part or all of a recombination hotspot (and optionally sequence flanking a recombination hotspot). In some embodiments, long read sequencing (such as sequencing using the Moleculo Technology developed by Illumina to sequence up to ~10 kb) or paired end sequencing is used to sequence part or all of a recombination hotspot. Knowledge of whether or not a recombination event occurred can be used to determine which haplotype blocks flank the hotspot. If desired, the presence of particular haplotype blocks can be confirmed using primers specific to regions within the haplotype blocks. In some embodiments, it is assumed there are no crossovers between known recombination hotspots. In some embodiments, primers in the primer library are clustered at or near the ends of chromosomes. For example, such primers can be used to determine whether or not a particular arm or section at the end of a chromosome is present. In some embodiments, primers in the primer library are clustered at or near recombination hotspots and at or near the ends of chromosomes.

In some embodiments, the primer library includes one or more primers (such as at least 5; 10; 50; 100; 200; 500; 750; 1,000; 2,000; 5,000; 7,500; 10,000; 20,000; 25,000; 30,000; 40,000; or 50,000 different primers or different primer pairs) that are specific for a recombination hotspot (such as a known human recombination hotspot) and/or are specific for a region near a recombination hotspot (such as within 10, 8, 5, 3, 2, 1, or 0.5 kb of the 5' or 3' end of a recombination hotspot). In some embodiments, at least 1, 5, 10, 20, 40, 60, 80, 100, or 150 different primer (or primer pairs) are specific for the same recombination hotspot, or are specific for the same recombination hotspot or a region near the recombination hotspot. In some embodiments, at least 1, 5, 10, 20, 40, 60, 80, 100, or 150 different primer (or primer pairs) are specific for a region between recombination hotspots (such as a region unlikely to have undergone recombination); these primers can be used to confirm the presence of haplotype blocks (such as those that would be expected depending on whether or not recombination has occurred). In some embodiments, at least 10, 20, 30, 40, 50, 60, 70, 80, or 90% of the primers in the primer library are specific for a recombination hotspot and/or are specific for a region near a recombination hotspot (such as within 10, 8, 5, 3, 2, 1, or 0.5 kb of the 5' or 3' end of the recombination hotspot). In some embodiments, the primer library is used to determine whether or not recombination has occurred at greater than or equal to 5; 10; 50; 100; 200; 500; 750; 1,000; 2,000; 5,000; 7,500; 10,000; 20,000; 25,000; 30,000; 40,000; or 50,000 different recombination hotspots (such as known human recombination hotspots). In some embodiments, the regions targeted by primers to a recombination hotspot or nearby region are approximately evenly spread out along that portion of the genome. In some embodiments, at least 1, 5, 10, 20, 40, 60, 80, 100, or 150 different primer (or primer pairs) are specific for the a region at or near the end of a chromosome (such as a region within 20, 10, 5, 1, 0.5, 0.1, 0.01, or 0.001 mb from the end of a chromosome). In some embodiments, at least 10, 20, 30, 40, 50, 60, 70, 80, or 90% of the primers in the primer library are specific for the a region at or near the end of a chromosome (such as a region within 20, 10, 5, 1, 0.5, 0.1, 0.01, or 0.001 mb from the end of a chromosome). In some embodiments, at least 1, 5, 10, 20, 40, 60, 80, 100, or 150 different primer (or primer pairs) are specific for the a region within a potential microdeletion in a chromosome. In some embodiments, at least 10, 20, 30, 40, 50, 60, 70, 80, or 90% of the primers in the primer library are specific for a region within a potential microdeletion in a chromosome. In some embodiments, at least 10, 20, 30, 40, 50, 60, 70, 80, or 90% of the primers in the primer library are specific for a recombination hotspot, a region near a recombination hotspot, a region at or near the end of a chromosome, or a region within a potential microdeletion in a chromosome.

Exemplary Multiplex PCR Methods

In one aspect, the invention features methods of amplifying target loci in a nucleic acid sample that involve (i) contacting the nucleic acid sample with a library of primers that simultaneously hybridize to least 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, the method also includes determining the presence or absence of at least one target amplicon (such as at least 50, 60, 70, 80, 90, 95, 96, 97, 98, 99, or 99.5% of the target amplicons). In some embodiments, the method also includes determining the sequence of at least one target amplicon (such as at least 50, 60, 70, 80, 90, 95, 96, 97, 98, 99, or 99.5% of the target amplicons). In some embodiments, at least 50, 60, 70, 80, 90, 95, 96, 97, 98, 99, or 99.5% of the target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold. In various embodiments, less than 60, 50, 40, 30, 20, 10, 5, 4, 3, 2, 1, 0.5, 0.25, 0.1, or 0.05% of the amplified products are primer dimers. In some embodiments, the method involves multiplex PCR and sequencing (such as high throughput sequencing).

In various embodiments, long annealing times and/or low primer concentrations are used. In various embodiments, the length of the annealing step is greater than 3, 5, 8, 10, 15, 20, 30, 45, 60, 75, 90, 120, 150, or 180 minutes. In various embodiments, the length of the annealing step (per PCR cycle) is between 5 and 180 minutes, such as 5 to 60, 10 to 60, 5 to 30, or 10 to 30 minutes, inclusive. In various embodiments, the length of the annealing step is greater than 5 minutes (such greater than 10, or 15 minutes), and the concentration of each primer is less than 20 nM. In various embodiments, the length of the annealing step is greater than 5 minutes (such greater than 10, or 15 minutes), and the concentration of each primer is between 1 to 20 nM, or 1 to 10 nM, inclusive. In various embodiments, the length of the annealing step is greater than 20 minutes (such as greater than 30, 45, 60, or 90 minutes), and the concentration of each primer is less than 1 nM.

At high level of multiplexing, the solution may become viscous due to the large amount of primers in solution. If the solution is too viscous, one can reduce the primer concentration to an amount that is still sufficient for the primers to bind the template DNA. In various embodiments, less than 60,000 different primers are used and the concentration of each primer is less than 20 nM, such as less than 10 nM or between 1 and 10 nM, inclusive. In various embodiments, more than 60,000 different primers (such as between 60,000 and 120,000 different primers) are used and the concentration of each primer is less than 10 nM, such as less than 5 nM or between 1 and 10 nM, inclusive.

It was discovered that the annealing temperature can optionally be higher than the melting temperatures of some or all of the primers (in contrast to other methods that use an annealing temperature below the melting temperatures of the primers). The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5 C below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing may be tolerated. In some embodiments of the present inventions, the $T_A$ is higher than ($T_m$), where at a given moment only a small fraction of the targets have a primer annealed (such as only ~1-5%). If these get extended, they are removed from the equilibrium of annealing and dissociating primers and target (as extension increases $T_m$ quickly to above 70 C), and a new ~1-5% of targets has primers. Thus, by giving the reaction long time for annealing, one can get ~100% of the targets copied per cycle. Thus, the most stable molecule pairs (those with perfect DNA pairing between the primer and the template DNA) are preferentially extended to produce the correct target amplicons. For example, the same experiment was performed with 57° C. as the annealing temperature and with 63° C. as the annealing temperature with primers that had a melting temperature below 63° C. When the annealing temperature was 57° C., the percent of mapped reads for the amplified PCR products was as low as 50% (with ~50% of the amplified products being primer-dimer). When the annealing temperature was 63° C., the percentage of amplified products that were primer dimer dropped to ~2%.

In various embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers. In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers, and the length of the annealing step (per PCR cycle) is greater than 1, 3, 5, 8, 10, 15, 20, 30, 45, 60, 75, 90, 120, 150, or 180 minutes In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers.

In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is between 50 to 70° C., such as between 55 to 60, 60 to 65, or 65 to 70° C., inclusive. In some embodiments, the annealing temperature is between 50 to 70° C., such as between 55 to 60, 60 to 65, or 65 to 70° C., inclusive, and either (i) the length of the annealing step (per PCR cycle) is greater than 3, 5, 8, 10, 15, 20, 30, 45, 60, 75, 90, 120, 150, or 180 minutes or (ii) the length of the annealing step (per PCR cycle) is between 5 and 180 minutes, such as 5 to 60, 10 to 60, 5 to 30, or 10 to 30 minutes, inclusive.

In some embodiments, one or more of the following conditions are used for empirical measurement of $T_m$ or are assumed for calculation of $T_m$: temperature: of 60.0° C., primer concentration of 100 nM, and/or salt concentration of 100 mM. In some embodiments, other conditions are used, such as the conditions that will be used for multiplex PCR with the library. In some embodiments, 100 mM KCl, 50 mM $(NH_4)_2SO_4$, 3 mM $MgCl_2$, 7.5 nM of each primer, and 50 mM TMAC, at pH 8.1 is used. In some embodiments, the $T_m$ is calculated using the Primer3 program (libprimer3 release 2.2.3) using the built-in SantaLucia parameters (the world wide web at primer3.sourceforge.net, which is hereby incorporated by reference in its entirety). In some embodiments, the calculated melting temperature for a primer is the temperature at which half of the primers molecules are expected to be annealed. As discussed above, even at a temperature higher than the calculated melting temperature, a percentage of primers will be annealed, and therefore PCR extension is possible. In some embodiments, the empirically measured $T_m$ (the actual $T_m$) is determined by using a thermostated cell in a UV spectrophotometer. In some embodiments, temperature is plotted vs. absorbance, generating an S-shaped curve with two plateaus. The absorbance reading halfway between the plateaus corresponds to $T_m$.

In some embodiments, the absorbance at 260 nm is measured as a function of temperature on an ultrospec 2100 pr UV/visible spectrophotometer (Amershambiosciences) (see, e.g., Takiya et al., "An empirical approach for thermal stability ($T_m$) prediction of PNA/DNA duplexes," Nucleic Acids Symp Ser (Oxf); (48):131-2, 2004, which is hereby incorporated by reference in its entirety). In some embodiments, absorbance at 260 nm is measured by decreasing the temperature in steps of 2° C. per minute from 95 to 20° C. In some embodiments, a primer and its perfect complement (such as 2 uM of each paired oligomer) are mixed and then annealing is performed by heating the sample to 95° C., keeping it there for 5 minutes, followed by cooling to room temperature during 30 minutes, and keeping the samples at 95° C. for at least 60 minutes. In some embodiments, melting temperature is determined by analyzing the data using SWIFT $T_m$ software. In some embodiments of any of the methods of the invention, the method includes empirically measuring or calculating (such as calculating with a computer) the melting temperature for at least 50, 80, 90, 92, 94, 96, 98, 99, or 100% of the primers in the library either before or after the primers are used for PCR amplification of target loci.

In some embodiments, the library comprises a microarray. In some embodiments, the library does not comprise a microarray.

In some embodiments, most or all of the primers are extended to form amplified products. Having all the primers consumed in the PCR reaction increases the uniformity of amplification of the different target loci since the same or similar number of primer molecules are converted to target amplicons for each target loci. In some embodiment, at least 80, 90, 92, 94, 96, 98, 99, or 100% of the primer molecules are extended to form amplified products. In some embodiments, for at least 80, 90, 92, 94, 96, 98, 99, or 100% of target loci, at least 80, 90, 92, 94, 96, 98, 99, or 100% of the primer molecules to that target loci are extended to form amplified products. In some embodiments, multiple cycles are performed until this percentage of the primers are consumed. In some embodiments, multiple cycles are performed until all or substantially all of the primers are consumed. If desired, a higher percentage of the primers can be consumed by decreasing the initial primer concentration and/or increasing the number of PCR cycles that are performed.

In some embodiments, the PCR methods may be performed with microliter reaction volumes, for which it can be harder to achieve specific PCR amplification (due to the lower local concentration of the template nucleic acids) compared to nanoliter or picoliter reaction volumes used in microfluidics applications. In some embodiments, the reaction volume is between 1 and 60 uL, such as between 5 and 50 uL, 10 and 50 uL, 10 and 20 uL, 20 and 30 uL, 30 and 40 uL, or 40 to 50 uL, inclusive.

In an embodiment, a method disclosed herein uses highly efficient highly multiplexed targeted PCR to amplify DNA followed by high throughput sequencing to determine the allele frequencies at each target locus. The ability to multiplex more than about 50 or 100 PCR primers in one reaction volume in a way that most of the resulting sequence reads map to targeted loci is novel and non-obvious. One technique that allows highly multiplexed targeted PCR to perform in a highly efficient manner involves designing primers that are unlikely to hybridize with one another. The PCR probes, typically referred to as primers, are selected by creating a thermodynamic model of potentially adverse interactions between at least 300; at least 500; at least 750; at least 1,000; at least 2,000; at least 5,000; at least 7,500; at least 10,000; at least 20,000; at least 25,000; at least 30,000; at least 40,000; at least 50,000; at least 75,000; or at least 100,000 potential primer pairs, or unintended interactions between primers and sample DNA, and then using the model to eliminate designs that are incompatible with other the designs in the pool. Another technique that allows highly multiplexed targeted PCR to perform in a highly efficient manner is using a partial or full nesting approach to the targeted PCR. Using one or a combination of these approaches allows multiplexing of at least 300, at least 800, at least 1,200, at least 4,000 or at least 10,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 60%, greater than 67%, greater than 80%, greater than 90%, greater than 95%, greater than 96%, greater than 97%, greater than 98%, greater than 99%, or greater than 99.5% DNA molecules that map to targeted loci.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one million to ten million. Prior attempts to multiplex more than 100 primers per pool have resulted in significant problems with unwanted side reactions such as primer-dimer formation.

Targeted PCR

In some embodiments, PCR can be used to target specific locations of the genome. In plasma samples, the original DNA is highly fragmented (typically less than 500 bp, with an average length less than 200 bp). In PCR, both forward and reverse primers anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as those containing SNPs, are typically designed such that the 3' end of the primer will hybridize to the base immediately adjacent to the polymorphic base or bases. In an embodiment of the present disclosure, the 3' ends of both the forward and reverse PCR primers are designed to hybridize to bases that are one or a few positions away from the variant positions (polymorphic sites) of the targeted allele. The number of bases between the polymorphic site (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic site.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 100, perhaps 200, or possibly 500 assays per reaction. Samples with large quantities of DNA can be split among multiple sub-reactions and then recombined before sequencing. For samples where either the overall sample or some subpopulation of DNA molecules is limited, splitting the sample would introduce statistical noise. In an embodiment, a small or limited quantity of DNA may refer to an amount below 10 pg, between 10 and 100 pg, between 100 μg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations a universal pre-amplification step may be used to increase the overall sample quantity. Ideally, this pre-amplification step should not appreciably alter the allelic distributions.

In an embodiment, a method of the present disclosure can generate PCR products that are specific to a large number of targeted loci, specifically 1,000 to 5,000 loci, 5,000 to 10,000 loci or more than 10,000 loci, for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. When detecting target sequences using microarrays with hybridization probes, primer dimers and other artifacts may be ignored, as these are not detected. However, when using sequencing as a method of detection, the vast majority of the sequencing reads would sequence such artifacts and not the desired target sequences in a sample. Methods described in the prior art used to multiplex more than 50 or 100 reactions in one reaction volume followed by sequencing will typically result in more than 20%, and often more than 50%, in many cases more than 80% and in some cases more than 90% off-target sequence reads.

In general, to perform targeted sequencing of multiple (n) targets of a sample (greater than 50, greater than 100, greater than 500, or greater than 1,000), one can split the sample into a number of parallel reactions that amplify one individual target. This has been performed in PCR multiwell plates or can be done in commercial platforms such as the FLUIDIGM ACCESS ARRAY (48 reactions per sample in microfluidic chips) or DROPLET PCR by RAIN DANCE TECHNOLOGY (100 s to a few thousands of targets). Unfortunately, these split-and-pool methods are problematic for samples with a limited amount of DNA, as there is often not enough copies of the genome to ensure that there is one copy of each region of the genome in each well. This is an especially severe problem when polymorphic loci are targeted, and the relative proportions of the alleles at the polymorphic loci are needed, as the stochastic noise introduced by the splitting and pooling will cause very poorly accurate measurements of the proportions of the alleles that were present in the original sample of DNA. Described here is a method to effectively and efficiently amplify many PCR reactions that is applicable to cases where only a limited amount of DNA is available. In an embodiment, the method may be applied for analysis of single cells, body fluids, mixtures of DNA such as the free floating DNA found in plasma, biopsies, environmental and/or forensic samples.

In an embodiment, the targeted sequencing may involve one, a plurality, or all of the following steps. a) Generate and amplify a library with adaptor sequences on both ends of DNA fragments. b) Divide into multiple reactions after library amplification. c) Generate and optionally amplify a library with adaptor sequences on both ends of DNA fragments. d) Perform 1000- to 10,000-plex amplification of selected targets using one target specific "Forward" primer per target and one tag specific primer. e) Perform a second amplification from this product using "Reverse" target specific primers and one (or more) primer specific to a universal tag that was introduced as part of the target specific forward primers in the first round. f) Perform a 1000-plex preamplification of selected target for a limited number of cycles. g) Divide the product into multiple aliquots and amplify subpools of targets in individual reactions (for example, 50 to 500-plex, though this can be used all the way down to singleplex. h) Pool products of parallel subpools reactions. i) During these amplifications primers may carry sequencing compatible tags (partial or full length) such that the products can be sequenced.

Highly Multiplexed PCR

Disclosed herein are methods that permit the targeted amplification of over a hundred to tens of thousands of target sequences (e.g., SNP loci) from a nucleic acid sample such as genomic DNA obtained from plasma. The amplified sample may be relatively free of primer dimer products and have low allelic bias at target loci. If during or after amplification the products are appended with sequencing compatible adaptors, analysis of these products can be performed by sequencing.

Performing a highly multiplexed PCR amplification using methods known in the art results in the generation of primer dimer products that are in excess of the desired amplification products and not suitable for sequencing. These can be reduced empirically by eliminating primers that form these products, or by performing in silico selection of primers. However, the larger the number of assays, the more difficult this problem becomes.

One solution is to split the 5000-plex reaction into several lower-plexed amplifications, e.g. one hundred 50-plex or fifty 100-plex reactions, or to use microfluidics or even to split the sample into individual PCR reactions. However, if the sample DNA is limited, such as in non-invasive prenatal diagnostics from pregnancy plasma, dividing the sample between multiple reactions should be avoided as this will result in bottlenecking.

Described herein are methods to first globally amplify the plasma DNA of a sample and then divide the sample up into multiple multiplexed target enrichment reactions with more moderate numbers of target sequences per reaction. In an embodiment, a method of the present disclosure can be used for preferentially enriching a DNA mixture at a plurality of loci, the method comprising one or more of the following steps: generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In an embodiment, a method of the present disclosure further includes performing a second amplification using "reverse" target specific primers and one or a plurality of primers specific to a universal tag that was introduced as part of the target specific forward primers in the first round. In an embodiment, the method may involve a fully nested, hemi-nested, semi-nested, one sided fully nested, one sided hemi-nested, or one sided semi-nested PCR approach. In an embodiment, a method of the present disclosure is used for preferentially enriching a DNA mixture at a plurality of loci, the method comprising performing a multiplex preamplification of selected targets for a limited number of cycles, dividing the product into multiple aliquots and amplifying subpools of targets in individual reactions, and pooling products of parallel subpools reactions. Note that this approach could be used to perform targeted amplification in a manner that would result in low levels of allelic bias for 50-500 loci, for 500 to 5,000 loci, for 5,000 to 50,000 loci, or even for 50,000 to 500,000 loci. In an embodiment, the primers carry partial or full length sequencing compatible tags.

The workflow may entail (1) extracting DNA such as plasma DNA, (2) preparing fragment library with universal adaptors on both ends of fragments, (3) amplifying the library using universal primers specific to the adaptors, (4) dividing the amplified sample "library" into multiple aliquots, (5) performing multiplex (e.g. about 100-plex, 1,000, or 10,000-plex with one target specific primer per target and a tag-specific primer) amplifications on aliquots, (6) pooling aliquots of one sample, (7) barcoding the sample, (8) mixing the samples and adjusting the concentration, (9) sequencing the sample. The workflow may comprise multiple sub-steps that contain one of the listed steps (e.g. step (2) of preparing the library step could entail three enzymatic steps (blunt ending, dA tailing and adaptor ligation) and three purification steps). Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mononucleosomal DNA fragments as the cell free fetal DNA (of placental origin) found in the circulation of pregnant women. Note that PCR assays can have the tags, for example sequencing tags, (usually a truncated form of 15-25 bases). After multiplexing, PCR multiplexes of a sample are pooled and then the tags are completed (including bar coding) by a tag-specific PCR (could also be done by ligation). Also, the full sequencing tags can be added in the same reaction as the multiplexing. In the first cycles targets may be amplified with the target specific primers, subsequently the tag-specific primers take over to complete the SQ-adaptor sequence. The PCR primers may carry no tags. The sequencing tags may be appended to the amplification products by ligation.

In an embodiment, highly multiplex PCR followed by evaluation of amplified material by clonal sequencing may be used for various applications such as the detection of fetal aneuploidy. Whereas traditional multiplex PCRs evaluate up to fifty loci simultaneously, the approach described herein may be used to enable simultaneous evaluation of more than 50 loci simultaneously, more than 100 loci simultaneously, more than 500 loci simultaneously, more than 1,000 loci simultaneously, more than 5,000 loci simultaneously, more than 10,000 loci simultaneously, more than 50,000 loci simultaneously, and more than 100,000 loci simultaneously. Experiments have shown that up to, including and more than 10,000 distinct loci can be evaluated simultaneously, in a single reaction, with sufficiently good efficiency and specificity to make non-invasive prenatal aneuploidy diagnoses and/or copy number calls with high accuracy. Assays may be combined in a single reaction with the entirety of a sample such as a cfDNA sample isolated from plasma, a fraction thereof, or a further processed derivative of the cfDNA sample. The sample (e.g., cfDNA or derivative) may also be split into multiple parallel multiplex reactions. The optimum sample splitting and multiplex is determined by trading off various performance specifications. Due to the limited amount of material, splitting the sample into multiple fractions can introduce sampling noise, handling time, and increase the possibility of error. Conversely, higher multiplexing can result in greater amounts of spurious amplification and greater inequalities in amplification both of which can reduce test performance.

Two crucial related considerations in the application of the methods described herein are the limited amount of original sample (e.g., plasma) and the number of original molecules in that material from which allele frequency or other measurements are obtained. If the number of original molecules falls below a certain level, random sampling noise becomes significant, and can affect the accuracy of the test. Typically, data of sufficient quality for making non-invasive prenatal aneuploidy diagnoses can be obtained if measurements are made on a sample comprising the equivalent of 500-1000 original molecules per target locus. There are a number of ways of increasing the number of distinct measurements, for example increasing the sample volume. Each manipulation applied to the sample also potentially results in losses of material. It is essential to characterize losses incurred by various manipulations and avoid, or as necessary improve yield of certain manipulations to avoid losses that could degrade performance of the test.

In an embodiment, it is possible to mitigate potential losses in subsequent steps by amplifying all or a fraction of the original sample (e.g., cfDNA sample). Various methods are available to amplify all of the genetic material in a sample, increasing the amount available for downstream procedures. In an embodiment, ligation mediated PCR (LM-PCR) DNA fragments are amplified by PCR after ligation of either one distinct adaptors, two distinct adapters, or many distinct adaptors. In an embodiment, multiple displacement amplification (MDA) phi-29 polymerase is used to amplify all DNA isothermally. In DOP-PCR and variations, random priming is used to amplify the original material DNA. Each method has certain characteristics such as uniformity of amplification across all represented regions of the genome, efficiency of capture and amplification of original DNA, and amplification performance as a function of the length of the fragment.

In an embodiment LM-PCR may be used with a single heteroduplexed adaptor having a 3-prime tyrosine. The heteroduplexed adaptor enables the use of a single adaptor molecule that may be converted to two distinct sequences on 5-prime and 3-prime ends of the original DNA fragment during the first round of PCR. In an embodiment, it is possible to fractionate the amplified library by size separations, or products such as AMPURE, TASS or other similar methods. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. The extension step of the PCR amplification may be limited from a time standpoint to reduce amplification from fragments longer than about 200 bp, about 300 bp, about 400 bp, about 500 bp or about 1,000 bp. A number of reactions were run using conditions as specified by commercially available kits; the resulted in successful ligation of fewer than 10% of sample DNA molecules. A series of optimizations of the reaction conditions for this improved ligation to approximately 70%.

Mini-PCR

The following Mini-PCR method is desirable for samples containing short nucleic acids, digested nucleic acids, or fragmented nucleic acids, such as cfDNA. Traditional PCR assay design results in significant losses of distinct fetal molecules, but losses can be greatly reduced by designing very short PCR assays, termed mini-PCR assays. Fetal cfDNA in maternal serum is highly fragmented and the fragment sizes are distributed in approximately a Gaussian fashion with a mean of 160 bp, a standard deviation of 15 bp, a minimum size of about 100 bp, and a maximum size of about 220 bp. The distribution of fragment start and end positions with respect to the targeted polymorphisms, while not necessarily random, vary widely among individual targets and among all targets collectively and the polymorphic site of one particular target locus may occupy any position from the start to the end among the various fragments originating from that locus. Note that the term mini-PCR may equally well refer to normal PCR with no additional restrictions or limitations.

During PCR, amplification will only occur from template DNA fragments comprising both forward and reverse primer sites. Because fetal cfDNA fragments are short, the likelihood of both primer sites being present the likelihood of a fetal fragment of length L comprising both the forward and reverse primers sites is ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp.

Note that in methods known in the prior art, short assays such as those described herein are usually avoided because they are not required and they impose considerable constraint on primer design by limiting primer length, annealing characteristics, and the distance between the forward and reverse primer.

Also note that there is the potential for biased amplification if the 3-prime end of the either primer is within roughly 1-6 bases of the polymorphic site. This single base difference at the site of initial polymerase binding can result in preferential amplification of one allele, which can alter observed allele frequencies and degrade performance. All of these constraints make it very challenging to identify primers that will amplify a particular locus successfully and furthermore, to design large sets of primers that are compatible in the same multiplex reaction. In an embodiment, the 3' end of the inner forward and reverse primers are designed to hybridize to a region of DNA upstream from the polymorphic site, and separated from the polymorphic site by a small number of bases. Ideally, the number of bases may be between 6 and 10 bases, but may equally well be between 4 and 15 bases, between three and 20 bases, between two and 30 bases, or between 1 and 60 bases, and achieve substantially the same end.

Multiplex PCR may involve a single round of PCR in which all targets are amplified or it may involve one round of PCR followed by one or more rounds of nested PCR or some variant of nested PCR. Nested PCR consists of a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. For samples such as plasma cfDNA, in which the DNA is highly fragmented, the larger assay size reduces the number of distinct cfDNA molecules from which a measurement can be obtained. In an embodiment, to offset this effect, one may use a partial nesting approach where one or both of the second round primers overlap the first binding sites extending internally some number of bases to achieve additional specificity while minimally increasing in the total assay size.

In an embodiment, a multiplex pool of PCR assays are designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively). In an embodiment, a multiplex pool of about 10,000 PCR assays (10,000-plex) are designed to amplify potentially heterozygous SNP loci on chromosomes X, Y, 13, 18, and 21 and 1 or 2 and these assays are used in a single reaction to amplify cfDNA obtained from a material plasma sample, chorion villus samples, amniocentesis samples, single or a small number of cells, other bodily fluids or tissues, cancers, or other genetic matter. The SNP frequencies of each locus may be determined by clonal or some other method of sequencing of the amplicons. Statistical analysis of the allele frequency distributions or ratios of all assays may be used to determine if the sample contains a trisomy of one or more of the chromosomes included in the test. In another embodiment the original cfDNA samples is split into two samples and parallel 5,000-plex assays are performed. In another embodiment the original cfDNA samples is split into n samples and parallel (~10,000/n)-plex assays are performed where n is between 2 and 12, or between 12 and 24, or between 24 and 48, or between 48 and 96. Data is collected and analyzed in a similar manner to that already described. Note that this method is equally well applicable to detecting translocations, deletions, duplications, and other chromosomal abnormalities.

In an embodiment, tails with no homology to the target genome may also be added to the 3-prime or 5-prime end of any of the primers. These tails facilitate subsequent manipulations, procedures, or measurements. In an embodiment, the tail sequence can be the same for the forward and reverse target specific primers. In an embodiment, different tails may be used for the forward and reverse target specific primers. In an embodiment, a plurality of different tails may be used for different loci or sets of loci. Certain tails may be shared among all loci or among subsets of loci. For example, using forward and reverse tails corresponding to forward and reverse sequences required by any of the current sequencing platforms can enable direct sequencing following amplification. In an embodiment, the tails can be used as common priming sites among all amplified targets that can be used to add other useful sequences. In some embodiments, the inner primers may contain a region that is designed to hybridize either upstream or downstream of the targeted locus (e.g, a polymorphic locus). In some embodiments, the primers may contain a molecular barcode. In some embodiments, the primer may contain a universal priming sequence designed to allow PCR amplification.

In an embodiment, a 10,000-plex PCR assay pool is created such that forward and reverse primers have tails corresponding to the required forward and reverse sequences required by a high throughput sequencing instrument (often referred to as a massively parallel sequencing instrument) such as the HISEQ, GAIIX, or MYSEQ available from ILLUMINA. In addition, included 5-prime to the sequencing tails is an additional sequence that can be used as a priming site in a subsequent PCR to add nucleotide barcode sequences to the amplicons, enabling multiplex sequencing of multiple samples in a single lane of the high throughput sequencing instrument.

In an embodiment, a 10,000-plex PCR assay pool is created such that reverse primers have tails corresponding to the required reverse sequences required by a high throughput sequencing instrument. After amplification with the first 10,000-plex assay, a subsequent PCR amplification may be performed using a another 10,000-plex pool having partly nested forward primers (e.g. 6-bases nested) for all targets and a reverse primer corresponding to the reverse sequencing tail included in the first round. This subsequent round of partly nested amplification with just one target specific primer and a universal primer limits the required size of the assay, reducing sampling noise, but greatly reduces the number of spurious amplicons. The sequencing tags can be added to appended ligation adaptors and/or as part of PCR probes, such that the tag is part of the final amplicon.

Tumor fraction affects performance of the test. There are a number of ways to enrich the tumor fraction of the DNA found in patient plasma. Tumor fraction can be increased by the previously described LM-PCR method already discussed as well as by a targeted removal of long fragments. In an embodiment, prior to multiplex PCR amplification of the target loci, an additional multiplex PCR reaction may be carried out to selectively remove long and largely maternal fragments corresponding to the loci targeted in the subsequent multiplex PCR. Additional primers are designed to anneal a site a greater distance from the polymorphism than is expected to be present among cell free fetal DNA fragments. These primers may be used in a one cycle multiplex PCR reaction prior to multiplex PCR of the target polymorphic loci. These distal primers are tagged with a molecule or moiety that can allow selective recognition of the tagged pieces of DNA. In an embodiment, these molecules of DNA may be covalently modified with a biotin molecule that allows removal of newly formed double stranded DNA comprising these primers after one cycle of PCR. Double stranded DNA formed during that first round is likely maternal in origin. Removal of the hybrid material may be accomplish by the used of magnetic streptavidin beads. There are other methods of tagging that may work equally well. In an embodiment, size selection methods may be used to enrich the sample for shorter strands of DNA; for example those less than about 800 bp, less than about 500 bp, or less than about 300 bp. Amplification of short fragments can then proceed as usual.

The mini-PCR method described in this disclosure enables highly multiplexed amplification and analysis of hundreds to thousands or even millions of loci in a single reaction, from a single sample. At the same, the detection of the amplified DNA can be multiplexed; tens to hundreds of samples can be multiplexed in one sequencing lane by using barcoding PCR. This multiplexed detection has been successfully tested up to 49-plex, and a much higher degree of multiplexing is possible. In effect, this allows hundreds of samples to be genotyped at thousands of SNPs in a single sequencing run. For these samples, the method allows determination of genotype and heterozygosity rate and simultaneously determination of copy number, both of which may be used for the purpose of aneuploidy detection. It may be used as part of a method for mutation dosage. This method may be used for any amount of DNA or RNA, and the targeted regions may be SNPs, other polymorphic regions, non-polymorphic regions, and combinations thereof.

In some embodiments, ligation mediated universal-PCR amplification of fragmented DNA may be used. The ligation mediated universal-PCR amplification can be used to amplify plasma DNA, which can then be divided into multiple parallel reactions. It may also be used to preferentially amplify short fragments, thereby enriching tumor fraction. In some embodiments the addition of tags to the fragments by ligation can enable detection of shorter fragments, use of shorter target sequence specific portions of the primers and/or annealing at higher temperatures which reduces unspecific reactions.

The methods described herein may be used for a number of purposes where there is a target set of DNA that is mixed with an amount of contaminating DNA. In some embodiments, the target DNA and the contaminating DNA may be from individuals who are genetically related. For example, genetic abnormalities in a fetus (target) may be detected from maternal plasma which contains fetal (target) DNA and also maternal (contaminating) DNA; the abnormalities include whole chromosome abnormalities (e.g. aneuploidy) partial chromosome abnormalities (e.g. deletions, duplications, inversions, translocations), polynucleotide polymorphisms (e.g. STRs), single nucleotide polymorphisms, and/or other genetic abnormalities or differences. In some embodiments, the target and contaminating DNA may be from the same individual, but where the target and contaminating DNA are different by one or more mutations, for example in the case of cancer. (see e.g. H. Mamon et al. *Preferential Amplification of Apoptotic DNA from Plasma: Potential for Enhancing Detection of Minor DNA Alterations in Circulating DNA*. Clinical Chemistry 54:9 (2008). In some embodiments, the DNA may be found in cell culture (apoptotic) supernatant. In some embodiments, it is possible to induce apoptosis in biological samples (e.g., blood) for subsequent library preparation, amplification and/or sequencing. A number of enabling workflows and protocols to achieve this end are presented elsewhere in this disclosure.

In some embodiments, the target DNA may originate from single cells, from samples of DNA consisting of less than one copy of the target genome, from low amounts of DNA, from DNA from mixed origin (e.g. cancer patient plasma and tumors: mix between healthy and cancer DNA, transplantation etc), from other body fluids, from cell cultures, from culture supernatants, from forensic samples of DNA, from ancient samples of DNA (e.g. insects trapped in amber), from other samples of DNA, and combinations thereof.

In some embodiments, a short amplicon size may be used. Short amplicon sizes are especially suited for fragmented DNA (see e.g. A. Sikora, et sl. Detection of increased amounts of cell-free fetal DNA with short PCR amplicons. *Clin Chem*, 2010 January; 56(1):136-8.)

The use of short amplicon sizes may result in some significant benefits. Short amplicon sizes may result in optimized amplification efficiency. Short amplicon sizes typically produce shorter products, therefore there is less chance for nonspecific priming. Shorter products can be clustered more densely on sequencing flow cell, as the clusters will be smaller. Note that the methods described herein may work equally well for longer PCR amplicons. Amplicon length may be increased if necessary, for example, when sequencing larger sequence stretches. Experiments with 146-plex targeted amplification with assays of 100 bp to 200 bp length as first step in a nested-PCR protocol were run on single cells and on genomic DNA with positive results.

In some embodiments, the methods described herein may be used to amplify and/or detect SNPs, copy number, nucleotide methylation, mRNA levels, other types of RNA expression levels, other genetic and/or epigenetic features. The mini-PCR methods described herein may be used along with next-generation sequencing; it may be used with other downstream methods such as microarrays, counting by digital PCR, real-time PCR, Mass-spectrometry analysis etc.

In some embodiment, the mini-PCR amplification methods described herein may be used as part of a method for accurate quantification of minority populations. It may be used for absolute quantification using spike calibrators. It may be used for mutation/minor allele quantification through very deep sequencing, and may be run in a highly multiplexed fashion. It may be used for standard paternity and identity testing of relatives or ancestors, in human, animals, plants or other creatures. It may be used for forensic testing. It may be used for rapid genotyping and copy number analysis (CN), on any kind of material, e.g. amniotic fluid and CVS, sperm, product of conception (POC). It may be used for single cell analysis, such as genotyping on samples biopsied from embryos. It may be used for rapid embryo analysis (within less than one, one, or two days of biopsy) by targeted sequencing using min-PCR.

In some embodiments, the mini-PCR amplification methods can be used for tumor analysis: tumor biopsies are often a mixture of healthy and tumor cells. Targeted PCR allows deep sequencing of SNPs and loci with close to no background sequences. It may be used for copy number and loss of heterozygosity analysis on tumor DNA. Said tumor DNA may be present in many different body fluids or tissues of tumor patients. It may be used for detection of tumor recurrence, and/or tumor screening. It may be used for quality control testing of seeds. It may be used for breeding, or fishing purposes. Note that any of these methods could equally well be used targeting non-polymorphic loci for the purpose of ploidy calling.

Some literature describing some of the fundamental methods that underlie the methods disclosed herein include: (1) Wang H Y, Luo M, Tereshchenko I V, Frikker D M, Cui X, Li J Y, Hu G, Chu Y, Azaro M A, Lin Y, Shen L, Yang Q, Kambouris M E, Gao R, Shih W, Li H. Genome Res. 2005 February; 15(2):276-83. Department of Molecular Genetics, Microbiology and Immunology/The Cancer Institute of New Jersey, Robert Wood Johnson Medical School, New Brunswick, New Jersey 08903, USA. (2) High-throughput genotyping of single nucleotide polymorphisms with high sensitivity. Li H, Wang H Y, Cui X, Luo M, Hu G, Greenawalt D M, Tereshchenko I V, Li J Y, Chu Y, Gao R. Methods Mol Biol. 2007; 396—PubMed PMID: 18025699. (3) A method comprising multiplexing of an average of 9 assays for sequencing is described in: Nested Patch PCR enables highly multiplexed mutation discovery in candidate genes. Varley K E, Mitra R D. Genome Res. 2008 November; 18(11):1844-50. Epub 2008 Oct. 10. Note that the methods disclosed herein allow multiplexing of orders of magnitude more than in the above references.

Exemplary Kits

In one aspect, the invention features a kit, such as a kit for amplifying target loci in a nucleic acid sample for detecting deletions and/or duplications of chromosome segments or entire chromosomes using any of the methods described herein). In some embodiments, the kit can include any of the primer libraries of the invention. In an embodiment, the kit comprises a plurality of inner forward primers and optionally a plurality of inner reverse primers, and optionally outer forward primers and outer reverse primers, where each of the primers is designed to hybridize to the region of DNA immediately upstream and/or downstream from one of the target sites (e.g., polymorphic sites) on the target chromosome(s) or chromosome segment(s), and optionally additional chromosomes or chromosome segments. In some embodiments, the kit includes instructions for using the primer library to amplify the target loci, such as for detecting one or more deletions and/or duplications of one or more chromosome segments or entire chromosomes using any of the methods described herein.

In certain embodiments, kits of the invention provide primer pairs for detecting chromosomal aneuploidy and CNV determination, such as primer pairs for massively multiplex reactions for detecting chromosomal aneuploidy such as CNV (CoNVERGe) (Copy Number Variant Events Revealed Genotypically) and/or SNVs. In these embodiments, the kits can include between at least 100, 200, 250, 300, 500, 1000, 2000, 2500, 3000, 5000, 10,000, 20,000, 25,000, 28,000, 50,000, or 75,000 and at most 200, 250, 300, 500, 1000, 2000, 2500, 3000, 5000, 10,000, 20,000, 25,000, 28,000, 50,000, 75,000, or 100,000 primer pairs that are shipped together. The primer pairs can be contained in a single vessel, such as a single tube or box, or multiple tubes or boxes. In certain embodiments, the primer pairs are pre-qualified by a commercial provider and sold together, and in other embodiments, a customer selects custom gene targets and/or primers and a commercial provider makes and ships the primer pool to the customer neither in one tube or a plurality of tubes. In certain exemplary embodiments, the kits include primers for detecting both CNVs and SNVs, especially CNVs and SNVs known to be correlated to at least one type of cancer.

Kits for circulating DNA detection according to some embodiments of the present invention, include standards and/or controls for circulating DNA detection. For example, in certain embodiments, the standards and/or controls are sold and optionally shipped and packaged together with primers used to perform the amplification reactions provided herein, such as primers for performing CoNVERGe. In certain embodiments, the controls include polynucleotides such as DNA, including isolated genomic DNA that exhibits one or more chromosomal aneuploidies such as CNV and/or includes one or more SNVs. In certain embodiments, the standards and/or controls are called PlasmArt standards and include polynucleotides having sequence identity to regions of the genome known to exhibit CNV, especially in certain inherited diseases, and in certain disease states such as cancer, as well as a size distribution that reflects that of cfDNA fragments naturally found in plasma. Exemplary methods for making PlasmArt standards are provided in the examples herein. In general, genomic DNA from a source known to include a chromosomal aneuoploidy is isolated, fragmented, purified and size selected.

Accordingly, artificial cfDNA polynucleotide standards and/or controls can be made by spiking isolated polynucleotide samples prepared as summarized above, into DNA samples known not to exhibit a chromosomal aneuploidy and/or SNVs, at concentrations similar to those observed for cfDNA in vivo, such as between, for example, 0.01% and 20%, 0.1 and 15%, or 0.4 and 10% of DNA in that fluid. These standards/controls can be used as controls for assay design, characterization, development, and/or validation, and as quality control standards during testing, such as cancer testing performed in a CLIA lab and/or as standards included in research use only or diagnostic test kits.

Exemplary Normalization/Correction Methods

In some embodiments, measurements for different loci, chromosome segments, or chromosomes are adjusted for bias, such as bias due to differences in GC content or bias due to other differences in amplification efficiency or adjusted for sequencing errors. In some embodiments, measurements for different alleles for the same locus are adjusted for differences in metabolism, apoptosis, histones, inactivation, and/or amplification between the alleles. In some embodiments, measurements for different alleles for the same locus in RNA are adjusted for differences in transcription rates or stability between different RNA alleles.

Exemplary Methods for Phasing Genetic Data

In some embodiments, genetic data is phased using the methods described herein or any known method for phasing genetic data (see, e.g., PCT Publ. No. WO2009/105531, filed Feb. 9, 2009, and PCT Publ. No. WO2010/017214, filed Aug. 4, 2009; U.S. Publ. No. 2013/0123120, Nov. 21, 2012; U.S. Publ. No. 2011/0033862, filed Oct. 7, 2010; U.S. Publ. No. 2011/0033862, filed Aug. 19, 2010; U.S. Publ. No. 2011/0178719, filed Feb. 3, 2011; U.S. Pat. No. 8,515,679, filed Mar. 17, 2008; U.S. Publ. No. 2007/0184467, filed Nov. 22, 2006; U.S. Publ. No. 2008/0243398, filed Mar. 17, 2008, and U.S. Ser. No. 61/994,791, filed May 16, 2014, which are each hereby incorporated by reference in its entirety). In some embodiments, the phase is determined for one or more regions that are known or suspected to contain a CNV of interest. In some embodiments, the phase is also determined for one or more regions flanking the CNV region(s) and/or for one or more reference regions. In one embodiment, genetic data of an individual is phased by inference by measuring tissue from the individual that is haploid, for example by measuring one or more sperm or eggs. In one embodiment, an individual's genetic data is phased by inference using the measured genotypic data of one or more first degree relatives, such as the individual's parents (e.g., sperm from the individual's father) or siblings.

In one embodiment, an individual's genetic data is phased by dilution where the DNA or RNA is diluted in one or a plurality of wells, such as by using digital PCR. In some embodiments, the DNA or RNA is diluted to the point where there is expected to be no more than approximately one copy of each haplotype in each well, and then the DNA or RNA in the one or more wells is measured. In some embodiments, cells are arrested at phase of mitosis when chromosomes are tight bundles, and microfluidics is used to put separate chromosomes in separate wells. Because the DNA or RNA is diluted, it is unlikely that more than one haplotype is in the same fraction (or tube). Thus, there may be effectively a single molecule of DNA in the tube, which allows the haplotype on a single DNA or RNA molecule to be determined. In some embodiments, the method includes dividing a DNA or RNA sample into a plurality of fractions such that at least one of the fractions includes one chromosome or one chromosome segment from a pair of chromosomes, and genotyping (e.g., determining the presence of two or more polymorphic loci) the DNA or RNA sample in at least one of the fractions, thereby determining a haplotype. In some embodiments, the genotyping involves sequencing (such as shotgun sequencing or single molecule sequencing), a SNP array to detect polymorphic loci, or multiplex PCR. In some embodiments, the genotyping involves use of a SNP array to detect polymorphic loci, such as at least 100; 200; 500; 750; 1,000; 2,000; 5,000; 7,500; 10,000; 20,000; 25,000; 30,000; 40,000; 50,000; 75,000; or 100,000 different polymorphic loci. In some embodiments, the genotyping involves the use of multiplex PCR. In some embodiments, the method involves contacting the sample in a fraction with a library of primers that simultaneously hybridize to at least 100; 200; 500; 750; 1,000; 2,000; 5,000; 7,500; 10,000; 20,000; 25,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data. In some embodiments, RNA (such as mRNA) is sequenced. Since mRNA contains only exons, sequencing mRNA allows alleles to be determined for polymorphic loci (such as SNPs) over a large distance in the genome, such as a few megabases. In some embodiments, a haplotype of an individual is determined by chromosome sorting. An exemplary chromosome sorting method includes arresting cells at phase of mitosis when chromosomes are tight bundles and using microfluidics to put separate chromosomes in separate wells. Another method involves collecting single chromosomes using FACS-mediated single chromosome sorting. Standard methods (such as sequencing or an array) can be used to identify the alleles on a single chromosome to determine a haplotype of the individual.

In some embodiments, a haplotype of an individual is determined by long read sequencing, such as by using the Moleculo Technology developed by Illumina. In some embodiments, the library prep step involves shearing DNA into fragments, such as fragments of ~10 kb size, diluting the fragments and placing them into wells (such that about 3,000 fragments are in a single well), amplifying fragments in each well by long-range PCR and cutting into short fragments and barcoding the fragments, and pooling the barcoded fragments from each well together to sequence them all. After sequencing, the computational steps involve separating the reads from each well based on the attached barcodes and grouping them into fragments, assembling the fragments at their overlapping heterozygous SNVs into haplotype blocks, and phasing the blocks statistically based on a phased reference panel and producing long haplotype contigs.

In some embodiments, a haplotype of the individual is determined using data from a relative of the individual. In some embodiments, a SNP array is used to determine the presence of at least 100; 200; 500; 750; 1,000; 2,000; 5,000; 7,500; 10,000; 20,000; 25,000; 30,000; 40,000; 50,000; 75,000; or 100,000 different polymorphic loci in a DNA or RNA sample from the individual and a relative of the individual. In some embodiments, the method involves contacting a DNA sample from the individual and/or a relative of the individual with a library of primers that simultaneously hybridize to at least 100; 200; 500; 750; 1,000; 2,000; 5,000; 7,500; 10,000; 20,000; 25,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data.

In one embodiment, an individual's genetic data is phased using a computer program that uses population based haplotype frequencies to infer the most likely phase, such as HapMap-based phasing. For example, haploid data sets can be deduced directly from diploid data using statistical methods that utilize known haplotype blocks in the general population (such as those created for the public HapMap Project and for the Perlegen Human Haplotype Project). A haplotype block is essentially a series of correlated alleles that occur repeatedly in a variety of populations. Since these haplotype blocks are often ancient and common, they may be used to predict haplotypes from diploid genotypes. Publicly available algorithms that accomplish this task include an imperfect phylogeny approach, Bayesian approaches based on conjugate priors, and priors from population genetics. Some of these algorithms use a hidden Markov model.

In one embodiment, an individual's genetic data is phased using an algorithm that estimates haplotypes from genotype data, such as an algorithm that uses localized haplotype clustering (see, e.g., Browning and Browning, "Rapid and Accurate Haplotype Phasing and Missing-Data Inference for Whole-Genome Association Studies By Use of Localized Haplotype Clustering" Am J Hum Genet. November 2007; 81(5): 1084-1097, which is hereby incorporated by reference in its entirety). An exemplary program is Beagle version: 3.3.2 or version 4 (available at the world wide web at hfaculty.washington.edu/browning/beagle/beagle.html, which is hereby incorporated by reference in its entirety).

In one embodiment, an individual's genetic data is phased using an algorithm that estimates haplotypes from genotype data, such as an algorithm that uses the decay of linkage disequilibrium with distance, the order and spacing of genotyped markers, missing-data imputation, recombination rate estimates, or a combination thereof (see, e.g., Stephens and Scheet, "Accounting for Decay of Linkage Disequilibrium in Haplotype Inference and Missing-Data Imputation" Am. J. Hum. Genet. 76:449-462, 2005, which is hereby incorporated by reference in its entirety). An exemplary program is PHASE v.2.1 or v2.1.1. (available at the world wide web at stephenslab.uchicago.edu/software.html, which is hereby incorporated by reference in its entirety).

In one embodiment, an individual's genetic data is phased using an algorithm that estimates haplotypes from population genotype data, such as an algorithm that allows cluster memberships to change continuously along the chromosome according to a hidden Markov model. This approach is flexible, allowing for both "block-like" patterns of linkage disequilibrium and gradual decline in linkage disequilibrium with distance (see, e.g., Scheet and Stephens, "A fast and flexible statistical model for large-scale population genotype data: applications to inferring missing genotypes and haplotypic phase." Am J Hum Genet, 78:629-644, 2006, which is hereby incorporated by reference in its entirety). An exemplary program is fastPHASE (available at the world wide web at stephenslab.uchicago.edu/software.html, which is hereby incorporated by reference in its entirety).

In one embodiment, an individual's genetic data is phased using a genotype imputation method, such as a method that uses one or more of the following reference datasets: HapMap dataset, datasets of controls genotyped on multiple SNP chips, and densely typed samples from the 1,000 Genomes Project. An exemplary approach is a flexible modelling framework that increases accuracy and combines information across multiple reference panels (see, e.g., Howie, Donnelly, and Marchini (2009) "A flexible and accurate genotype imputation method for the next generation of genome-wide association studies." PLoS Genetics 5(6): e1000529, 2009, which is hereby incorporated by reference in its entirety). Exemplary programs are IMPUTE or IMPUTE version 2 (also known as IMPUTE2) (available at the world wide web at mathgen.stats.ox.ac.uk/impute/impute_v2.html, which is hereby incorporated by reference in its entirety).

In one embodiment, an individual's genetic data is phased using an algorithm that infers haplotypes, such as an algorithm that infers haplotypes under the genetic model of coalescence with recombination, such as that developed by Stephens in PHASE v2.1. The major algorithmic improvements rely on the use of binary trees to represent the sets of candidate haplotypes for each individual. These binary tree representations: (1) speed up the computations of posterior probabilities of the haplotypes by avoiding the redundant operations made in PHASE v2.1, and (2) overcome the exponential aspect of the haplotypes inference problem by the smart exploration of the most plausible pathways (i.e., haplotypes) in the binary trees (see, e.g., Delaneau, Coulonges and Zagury, "Shape-IT: new rapid and accurate algorithm for haplotype inference," BMC Bioinformatics 9:540, 2008 doi:10.1186/1471-2105-9-540, which is hereby incorporated by reference in its entirety). An exemplary program is SHAPEIT (available at the world wide web at mathgen.stats.ox.ac.uk/genetics_software/shapeit/shapeit.html, which is hereby incorporated by reference in its entirety).

In one embodiment, an individual's genetic data is phased using an algorithm that estimates haplotypes from population genotype data, such as an algorithm that uses haplotype-fragment frequencies to obtain empirically based probabilities for longer haplotypes. In some embodiments, the algorithm reconstructs haplotypes so that they have maximal local coherence (see, e.g., Eronen, Geerts, and Toivonen, "HaploRec: Efficient and accurate large-scale reconstruction of haplotypes," *BMC Bioinformatics* 7:542, 2006, which is hereby incorporated by reference in its entirety). An exemplary program is HaploRec, such as HaploRec version 2.3. (available at the world wide web at cs.helsinki.fi/group/genetics/haplotyping.html, which is hereby incorporated by reference in its entirety).

In one embodiment, an individual's genetic data is phased using an algorithm that estimates haplotypes from population genotype data, such as an algorithm that uses a partition-ligation strategy and an expectation-maximization-based algorithm (see, e.g., Qin, Niu, and Liu, "Partition-Ligation-Expectation-Maximization Algorithm for Haplotype Inference with Single-Nucleotide Polymorphisms," Am J Hum Genet. 71(5): 1242-1247, 2002, which is hereby incorporated by reference in its entirety). An exemplary program is PL-EM (available at the world wide web at people.fas.harvard.edu/~junliu/plem/click.html, which is hereby incorporated by reference in its entirety).

In one embodiment, an individual's genetic data is phased using an algorithm that estimates haplotypes from population genotype data, such as an algorithm for simultaneously phasing genotypes into haplotypes and block partitioning. In some embodiments, an expectation-maximization algorithm is used (see, e.g., Kimmel and Shamir, "GERBIL: Genotype Resolution and Block Identification Using Likelihood," Proceedings of the National Academy of Sciences of the United States of America (PNAS) 102: 158-162, 2005, which is hereby incorporated by reference in its entirety). An exemplary program is GERBIL, which is available as part of the GEVALT version 2 program (available at the world wide web at acgt.cs.tau.ac.il/gevalt/, which is hereby incorporated by reference in its entirety).

In one embodiment, an individual's genetic data is phased using an algorithm that estimates haplotypes from population genotype data, such as an algorithm that uses an EM algorithm to calculate ML estimates of haplotype frequencies given genotype measurements which do not specify phase. The algorithm also allows for some genotype measurements to be missing (due, for example, to PCR failure). It also allows multiple imputation of individual haplotypes (see, e.g., Clayton, D. (2002), "SNPHAP: A Program for Estimating Frequencies of Large Haplotypes of SNPs", which is hereby incorporated by reference in its entirety). An exemplary program is SNPHAP (available at the world wide web at gene.cimr.cam.ac.uk/clayton/software/snphap.txt, which is hereby incorporated by reference in its entirety).

In one embodiment, an individual's genetic data is phased using an algorithm that estimates haplotypes from population genotype data, such as an algorithm for haplotype inference based on genotype statistics collected for pairs of SNPs. This software can be used for comparatively accurate phasing of large number of long genome sequences, e.g. obtained from DNA arrays. An exemplary program takes genotype matrix as an input, and outputs the corresponding haplotype matrix (see, e.g., Brinza and Zelikovsky, "2SNP: scalable phasing based on 2-SNP haplotypes," Bioinformatics. 22(3):371-3, 2006, which is hereby incorporated by reference in its entirety). An exemplary program is 2SNP (available at the world wide web at alla.cs.gsu.edu/~software/2SNP, which is hereby incorporated by reference in its entirety).

In various embodiments, an individual's genetic data is phased using data about the probability of chromosomes crossing over at different locations in a chromosome or chromosome segment (such as using recombination data such as may be found in the HapMap database to create a recombination risk score for any interval) to model dependence between polymorphic alleles on the chromosome or chromosome segment. In some embodiments, allele counts at the polymorphic loci are calculated on a computer based on sequencing data or SNP array data. In some embodiments, a plurality of hypotheses each pertaining to a different possible state of the chromosome or chromosome segment (such as an overrepresentation of the number of copies of a first homologous chromosome segment as compared to a second homologous chromosome segment in the genome of one or more cells from an individual, a duplication of the first homologous chromosome segment, a deletion of the second homologous chromosome segment, or an equal representation of the first and second homologous chromosome segments) are created (such as creation on a computer); a model (such as a joint distribution model) for the expected allele counts at the polymorphic loci on the chromosome is built (such as building on a computer) for each hypothesis; a relative probability of each of the hypotheses is determined (such as determination on a computer) using the joint distribution model and the allele counts; and the hypothesis with the greatest probability is selected. In some embodiments, building a joint distribution model for allele counts and the step of determining the relative probability of each hypothesis are done using a method that does not require the use of a reference chromosome.

In some embodiments, a sample (e.g., a biopsy such as a tumor biopsy, blood sample, plasma sample, serum sample, or another sample likely to contain mostly or only cells, DNA, or RNA with a CNV of interest) from the individual is analyzed to determine the phase for one or more regions that are known or suspected to contain a CNV of interest (such as a deletion or duplication). In some embodiments, the sample has a high tumor fraction (such as 30, 40, 50, 60, 70, 80, 90, 95, 98, 99, or 100%).

In some embodiments, the sample has a haplotypic imbalance or any aneuploidy. In some embodiments, the sample includes any mixture of two types of DNA where the two types have different ratios of the two haplotypes, and share at least one haplotype. For example, in the tumor case, the normal tissue is 1:1, and the tumor tissue is 1:0 or 1:2, 1:3, 1:4, etc. In some embodiments, at least 10; 100; 500; 1,000; 2,000; 3,000; 5,000; 8,000; or 10,000 polymorphic loci are analyzed to determine the phase of alleles at some or all of the loci. In some embodiments, a sample is from a cell or tissue that was treated to become aneuploidy, such as aneuploidy induced by prolonged cell culture.

In some embodiments, a large percent or all of the DNA or RNA in the sample has the CNV of interest. In some embodiments, the ratio of DNA or RNA from the one or more target cells that contain the CNV of interest to the total DNA or RNA in the sample is at least 80, 85, 90, 95, or 100%. For samples with a deletion, only one haplotype is present for the cells (or DNA or RNA) with the deletion. This first haplotype can be determined using standard methods to determine the identity of alleles present in the region of the deletion. In samples that only contain cells (or DNA or RNA) with the deletion, there will only be signal from the first haplotype that is present in those cells. In samples that also contain a small amount of cells (or DNA or RNA) without the deletion (such as a small amount of noncancerous cells), the weak signal from the second haplotype in these cells (or DNA or RNA) can be ignored. The second haplotype that is present in other cells, DNA, or RNA from the individual that lack the deletion can be determined by inference. For example, if the genotype of cells from the individual without the deletion is (AB,AB) and the phased data for the individual indicates that the first haplotype is (A,A); then, the other haplotype can be inferred to be (B,B).

For samples in which both cells (or DNA or RNA) with a deletion and cells (or DNA or RNA) without a deletion are present, the phase can still be determined. For example, plots can be generated in which the x-axis represents the linear position of the individual loci along the chromosome, and the y-axis represents the number of A allele reads as a fraction of the total (A+B) allele reads. In some embodiments for a deletion, the pattern includes two central bands that represent SNPs for which the individual is heterozygous (top band represents AB from cells without the deletion and A from cells with the deletion, and bottom band represents AB from cells without the deletion and B from cells with the deletion). In some embodiments, the separation of these two bands increases as the fraction of cells, DNA, or RNA with the deletion increases. Thus, the identity of the A alleles can be used to determine the first haplotype, and the identity of the B alleles can be used to determine the second haplotype.

For samples with a duplication, an extra copy of the haplotype is present for the cells (or DNA or RNA) with duplication. This haplotype of the duplicated region can be determined using standard methods to determine the identity of alleles present at an increased amount in the region of the duplication, or the haplotype of the region that is not duplicated can be determined using standard methods to determine the identity of alleles present at an decreased amount. Once one haplotype is determined, the other haplotype can be determined by inference.

For samples in which both cells (or DNA or RNA) with a duplication and cells (or DNA or RNA) without a duplication are present, the phase can still be determined using a method similar to that described above for deletions. For example, plots can be generated in which the x-axis represents the linear position of the individual loci along the chromosome, and the y-axis represents the number of A allele reads as a fraction of the total (A+B) allele reads. In some embodiments for a deletion, the pattern includes two central bands that represent SNPs for which the individual is heterozygous (top band represents AB from cells without the duplication and AAB from cells with the duplication, and bottom band represents AB from cells without the duplication and ABB from cells with the duplication). In some embodiments, the separation of these two bands increases as the fraction of cells, DNA, or RNA with the duplication increases. Thus, the identity of the A alleles can be used to determine the first haplotype, and the identity of the B alleles can be used to determine the second haplotype. In some embodiments, the phase of one or more CNV region(s) (such as the phase of at least 50, 60, 70, 80, 90, 95, or 100% of the polymorphic loci in the region that were measured) is determined for a sample (such as a tumor biopsy or plasma sample) from an individual known to have cancer and is used for analysis of subsequent samples from the same individual to monitor the progression of the cancer (such as monitoring for remission or reoccurrence of the cancer). In some embodiments, a sample with a high tumor fraction (such as a tumor biopsy or a plasma sample from an individual with a high tumor load) is used to obtain phased data that is used for analysis of subsequent samples with a lower tumor fraction (such as a plasma sample from an individual undergoing treatment for cancer or in remission).

In some embodiments, two or more of the methods described herein are used to phase genetic data of an individual. In some embodiments, both a bioinformatics method (such as using population based haplotype frequencies to infer the most likely phase) and a molecular biology method (such as any of the molecular phasing methods disclosed herein to obtain actual phased data rather than bioinformatics-based inferred phased data) are used. In some embodiments, phased data from other subjects (such as prior subjects) is used to refine the population data. For example, phased data from other subjects can be added to population data to calculate priors for possible haplotypes for another subject. In some embodiments, phased data from other subjects (such as prior subjects) is used to calculate priors for possible haplotypes for another subject.

In some embodiments, probabilistic data may be used. For example, due to the probabilistic nature of the representation of DNA molecules in a sample, as well as various amplification and measurement biases, the relative number of molecules of DNA measured from two different loci, or from different alleles at a given locus, is not always representative of the relative number of molecules in the mixture, or in the individual. If one were trying to determine the genotype of a normal diploid individual at a given locus on an autosomal chromosome by sequencing DNA from the plasma of the individual, one would expect to either observe only one allele (homozygous) or about equal numbers of two alleles (heterozygous). If, at that allele, ten molecules of the A allele were observed, and two molecules of the B allele were observed, it would not be clear if the individual was homozygous at the locus, and the two molecules of the B allele were due to noise or contamination, or if the individual was heterozygous, and the lower number of molecules of the B allele were due to random, statistical variation in the number of molecules of DNA in the plasma, amplification bias, contamination or any number of other causes. In this case, a probability that the individual was homozygous, and a corresponding probability that the individual was heterozygous could be calculated, and these probabilistic genotypes could be used in further calculations.

Note that for a given allele ratio, the likelihood that the ratio closely represents the ratio of the DNA molecules in the individual is greater the greater the number of molecules that are observed. For example, if one were to measure 100 molecules of A and 100 molecules of B, the likelihood that the actual ratio was 50% is considerably greater than if one were to measure 10 molecules of A and 10 molecules of B. In one embodiment, one uses use Bayesian theory combined with a detailed model of the data to determine the likelihood that a particular hypothesis is correct given an observation. For example, if one were considering two hypotheses—one that corresponds to a trisomic individual and one that corresponds to a disomic individual—then the probability of the disomic hypothesis being correct would be considerably higher for the case where 100 molecules of each of the two alleles were observed, as compared to the case where 10 molecules of each of the two alleles were observed. As the data becomes noisier due to bias, contamination or some other source of noise, or as the number of observations at a given locus goes down, the probability of the maximum likelihood hypothesis being true given the observed data drops. In practice, it is possible to aggregate probabilities over many loci to increase the confidence with which the maximum likelihood hypothesis may be determined to be the correct hypothesis. In some embodiments, the probabilities are simply aggregated without regard for recombination. In some embodiments, the calculations take into account cross-overs.

In an embodiment, probabilistically phased data is used in the determination of copy number variation. In some embodiments, the probabilistically phased data is population based haplotype block frequency data from a data source such as the HapMap data base. In some embodiments, the probabilistically phased data is haplotypic data obtained by a molecular method, for example phasing by dilution where individual segments of chromosomes are diluted to a single molecule per reaction, but where, due to stochaistic noise the identities of the haplotypes may not be absolutely known. In some embodiments, the probabilistically phased data is haplotypic data obtained by a molecular method, where the identities of the haplotypes may be known with a high degree of certainty.

Imagine a hypothetical case where a doctor wanted to determine whether or not an individual had some cells in their body which had a deletion at a particular chromosomal segment by measuring the plasma DNA from the individual. The doctor could make use of the knowledge that if all of the cells from which the plasma DNA originated were diploid, and of the same genotype, then for heterozygous loci, the relative number of molecules of DNA observed for each of the two alleles would fall into one distribution that was centered at 50% A allele and 50% B allele. However, if a fraction of the cells from which the plasma DNA originated had a deletion at a particular chromosome segment, then for heterozygous loci, one would expect that the relative number of molecules of DNA observed for each of the two alleles would fall into two distributions, one centered at above 50% A allele for the loci where there was a deletion of the chromosome segment containing the B allele, and one centered at below 50% for the loci where there was a deletion of the chromosome segment containing the A allele. The greater the proportion of the cells from which the plasma DNA originated contained the deletion, the further from 50% these two distributions would be.

In this hypothetical case, imagine a clinician who wants to determine if an individual had a deletion of a chromosomal region in a proportion of cells in the individual's body. The clinician may draw blood from the individual into a vacutainer or other type of blood tube, centrifuge the blood, and isolate the plasma layer. The clinician may isolate the DNA from the plasma, enrich the DNA at the targeted loci, possibly through targeted or other amplification, locus capture techniques, size enrichment, or other enrichment techniques. The clinician may analyze such as by measuring the number of alleles at a set of SNPs, in other words generating allele frequency data, the enriched and/or amplified DNA using an assay such as qPCR, sequencing, a microarray, or other techniques that measure the quantity of DNA in a sample. We will consider data analysis for the case where the clinician amplified the cell-free plasma DNA using a targeted amplification technique, and then sequenced the amplified DNA to give the following exemplary possible data at six SNPs found on a chromosome segment that is indicative of cancer, where the individual was heterozygotic at those SNPs:

SNP 1: 460 reads A allele; 540 reads B allele (46% A)
SNP 2: 530 reads A allele; 470 reads B allele (53% A)
SNP 3: 40 reads A allele; 60 reads B allele (40% A)
SNP 4: 46 reads A allele; 54 reads B allele (46% A)
SNP 5: 520 reads A allele; 480 reads B allele (52% A)
SNP 6: 200 reads A allele; 200 reads B allele (50% A)

From this set of data, it may be difficult to differentiate between the case where the individual is normal, with all cells being disomic, or where the individual may have a cancer, with some portion of cells whose DNA contributed towards the cell-free DNA found in the plasma having a deletion or duplication at the chromosome. For example, the two hypotheses with the maximum likelihood may be that the individual has a deletion at this chromosome segment, with a tumor fraction of 6%, and where the deleted segment of the chromosome has the genotype over the six SNPs of (A,B,A,A,B,B) or (A,B,A,A,B,A). In this representation of the individual's genotype over a set of SNPs, the first letter in the parentheses corresponds to the genotype of the haplotype for SNP 1, the second to SNP 2, etc.

If one were to use a method to determine the haplotype of the individual at that chromosome segment, and were to find that the haplotype for one of the two chromosomes was (A,B,A,A,B,B), this would agree with the maximum likelihood hypothesis, and the calculated likelihood that the individual has a deletion at that segment, and therefore may have cancerous or precancerous cells, would be considerably increased. On the other hand, if the individual were found to have the haplotype (A,A,A,A,A,A), then the likelihood that the individual has a deletion at that chromosome segment would be considerably decreased, and perhaps the likelihood of the no-deletion hypothesis would be higher (the actual likelihood values would depend on other parameters such as the measured noise in the system, among others).

There are many ways to determine the haplotype of the individual, many of which are described elsewhere in this document. A partial list is given here, and is not meant to be exhaustive. One method is a biological method where individual DNA molecules are diluted until approximately one molecule from each chromosomal region is in any given reaction volume, and then methods such as sequencing are used to measure the genotype. Another method is informatically based where population data on various haplotypes coupled with their frequency can be used in a probabilistic manner. Another method is to measure the diploid data of the individual, along with one or a plurality of related individuals who are expected to share haplotype blocks with the individual and to infer the haplotype blocks. Another method would be to take a sample of tissue with a high concentration of the deleted or duplicated segment, and determine the haplotype based on allelic imbalance, for example, genotype measurements from a sample of tumor tissue with a deletion can be used to determine the phased data for that deletion region, and this data can then be used to determine if the cancer has regrown post-resection.

In practice, typically more than 20 SNPs, more than 50 SNPs, more than 100 SNPs, more than 500 SNPs, more than 1,000 SNPs, or more than 5,000 SNPs are measured on a given chromosome segment.

Exemplary Mutations

Exemplary mutations associated with a disease or disorder such as cancer or an increased risk (such as an above normal level of risk) for a disease or disorder such as cancer include single nucleotide variants (SNVs), multiple nucleotide mutations, deletions (such as deletion of a 2 to 30 million base pair region), duplications, or tandem repeats. In some embodiments, the mutation is in DNA, such as cfDNA, cell-free mitochondrial DNA (cf mDNA), cell-free DNA that originated from nuclear DNA (cf nDNA), cellular DNA, or mitochondrial DNA. In some embodiments, the mutation is in RNA, such as cfRNA, cellular RNA, cytoplasmic RNA, coding cytoplasmic RNA, non-coding cytoplasmic RNA, mRNA, miRNA, mitochondrial RNA, rRNA, or tRNA. In some embodiments, the mutation is present at a higher frequency in subjects with a disease or disorder (such as cancer) than subjects without the disease or disorder (such as cancer). In some embodiments, the mutation is indicative of cancer, such as a causative mutation. In some embodiments, the mutation is a driver mutation that has a causative role in the disease or disorder. In some embodiments, the mutation is not a causative mutation. For example, in some cancers, multiple mutations accumulate but some of them are not causative mutations. Mutations (such as those that are present at a higher frequency in subjects with a disease or disorder than subjects without the disease or disorder) that are not causative can still be useful for diagnosing the disease or disorder. In some embodiments, the mutation is loss-of-heterozygosity (LOH) at one or more microsatellites.

In some embodiments, a subject is screened for one of more polymorphisms or mutations that the subject is known to have (e.g., to test for their presence, a change in the amount of cells, DNA, or RNA with these polymorphisms or mutations, or cancer remission or re-occurrence). In some embodiments, a subject is screened for one of more polymorphisms or mutations that the subject is known to be at risk for (such as a subject who has a relative with the polymorphism or mutation). In some embodiments, a subject is screened for a panel of polymorphisms or mutations associated with a disease or disorder such as cancer (e.g., at least 5, 10, 50, 100, 200, 300, 500, 750, 1,000, 1,500, 2,000, or 5,000 polymorphisms or mutations).

Many coding variants associated with cancer are described in Abaan et al., "The Exomes of the NCI-60 Panel: A Genomic Resource for Cancer Biology and Systems Pharmacology", *Cancer Research*, Jul. 15, 2013, and world wide web at dtp.nci.nih.gov/branches/btb/characterizationNCI60.html, which are each hereby incorporated by reference in its entirety). The NCI-60 human cancer cell line panel consists of 60 different cell lines representing cancers of the lung, colon, brain, ovary, breast, prostate, and kidney, as well as leukemia and melanoma. The genetic variations that were identified in these cell lines consisted of two types: type I variants that are found in the normal population, and type II variants that are cancer-specific.

Exemplary polymorphisms or mutations (such as deletions or duplications) are in one or more of the following genes: TP53, PTEN, PIK3CA, APC, EGFR, NRAS, NF2, FBXW7, ERBBs, ATAD5, KRAS, BRAF, VEGF, EGFR, HER2, ALK, p53, BRCA, BRCA1, BRCA2, SETD2, LRP1B, PBRM, SPTA1, DNMT3A, ARID1A, GRIN2A, TRRAP, STAG2, EPHA3/5/7, POLE, SYNE1, C20orf80, CSMD1, CTNNB1, ERBB2. FBXW7, KIT, MUC4, ATM, CDH1, DDX11, DDX12, DSPP, EPPK1, FAM186A, GNAS, HRNR, KRTAP4-11, MAP2K4, MLL3, NRAS, RB1, SMAD4, TTN, ABCC9, ACVR1B, ADAM29, ADAMTS19, AGAP10, AKT1, AMBN, AMPD2, ANKRD30A, ANKRD40, APOBR, AR, BIRC6, BMP2, BRAT1, BTNL8, C12orf4, C1QTNF7, C20orf186, CAPRIN2, CBWD1, CCDC30, CCDC93, CD5L, CDC27, CDC42BPA, CDH9, CDKN2A, CHD8, CHEK2, CHRNA9, CIZ1, CLSPN, CNTN6, COL14A1, CREBBP, CROCC, CTSF, CYP1A2, DCLK1, DHDDS, DHX32, DKK2, DLEC1, DNAH14, DNAH5, DNAH9, DNASE1L3, DUSP16, DYNC2H1, ECT2, EFHB, RRN3P2, TRIM49B, TUBB8P5, EPHA7, ERBB3, ERCC6, FAM21A, FAM21C, FCGBP, FGFR2, FLG2, FLT1, FOLR2, FRYL, FSCB, GAB1, GABRA4, GABRP, GH2, GOLGA6L1, GPHB5, GPR32, GPX5, GTF3C3, HECW1, HIST1H3B, HLA-A, HRAS, HS3ST1, HS6ST1, HSPD1, IDH1, JAK2, KDM5B, KIAA0528, KRT15, KRT38, KRTAP21-1, KRTAP4-5, KRTAP4-7, KRTAP5-4, KRTAP5-5, LAMA4, LATS1, LMF1, LPAR4, LPPR4, LRRFIP1, LUM, LYST, MAP2K1, MARCH1, MARCO, MB21D2, MEGF10, MMP16, MORC1, MRE11A, MTMR3, MUC12, MUC17, MUC2, MUC20, NBPF10, NBPF20, NEK1, NFE2L2, NLRP4, NOTCH2, NRK, NUP93, OBSCN, OR11H1, OR2B11, OR2M4, OR4Q3, OR5D13, OR8I2, OXSM, PIK3R1, PPP2R5C, PRAME, PRF1, PRG4, PRPF19, PTH2, PTPRC, PTPRJ, RAC1, RAD50, RBM12, RGPD3, RGS22, ROR1, RP11-671M22.1, RP13-996F3.4, RP1L1, RSBN1L, RYR3, SAMD3, SCN3A, SEC31A, SF1, SF3B1, SLC25A2, SLC44A1, SLC4A11, SMAD2, SPTA1, ST6GAL2, STK11, SZT2, TAF1L, TAX1BP1, TBP, TGFBI, TIF1, TMEM14B, TMEM74, TPTE, TRAPPC8, TRPS1, TXNDC6, USP32, UTP20, VASN, VPS72, WASH3P, WWTR1, XPO1, ZFHX4, ZMIZ1, ZNF167, ZNF436, ZNF492, ZNF598, ZRSR2, ABL1, AKT2, AKT3, ARAF, ARFRP1, ARID2, ASXL1, ATR, ATRX, AURKA, AURKB, AXL, BAP1, BARD1, BCL2, BCL2L2, BCL6, BCOR, BCORL1, BLM, BRIP1, BTK, CARD11, CBFB, CBL, CCND1, CCND2, CCND3, CCNE1, CD79A, CD79B, CDC73, CDK12, CDK4, CDK6, CDK8, CDKN1B, CDKN2B, CDKN2C, CEBPA, CHEK1, CIC, CRKL, CRLF2, CSF1R, CTCF, CTNNA1, DAXX, DDR2, DOT1L, EMSY (C11orf30), EP300, EPHA3, EPHA5, EPHB1, ERBB4, ERG, ESR1, EZH2, FAM123B (WTX), FAM46C, FANCA, FANCC, FANCD2, FANCE, FANCF, FANCG, FANCL, FGF10, FGF14, FGF19, FGF23, FGF3, FGF4, FGF6, FGFR1, FGFR2, FGFR3, FGFR4, FLT3, FLT4, FOXL2, GATA1, GATA2, GATA3, GID4 (C17orf39), GNA11, GNA13, GNAQ, GNAS, GPR124, GSK3B, HGF, IDH1, IDH2, IGF1R, IKBKE, IKZF1, IL7R, INHBA, IRF4, IRS2, JAK1, JAK3, JUN, KAT6A (MYST3), KDM5A, KDM5C, KDM6A, KDR, KEAP1, KLHL6, MAP2K2, MAP2K4, MAP3K1, MCL1, MDM2, MDM4, MED12, MEF2B, MEN1, MET, MITF, MLH1, MLL, MLL2, MPL, MSH2, MSH6, MTOR, MUTYH, MYC, MYCL1, MYCN, MYD88, NF1, NFKBIA, NKX2-1, NOTCH1, NPM1, NRAS, NTRK1, NTRK2, NTRK3, PAK3, PALB2, PAX5, PBRM1, PDGFRA, PDGFRB, PDK1, PIK3CG, PIK3R2, PPP2R1A, PRDM1, PRKAR1A, PRKDC, PTCH1, PTPN11, RAD51, RAF1, RARA, RET, RICTOR, RNF43, RPTOR, RUNX1, SMARCA4, SMARCB1, SMO, SOCS1, SOX10, SOX2, SPEN, SPOP, SRC, STAT4, SUFU, TET2, TGFBR2, TNFAIP3, TNFRSF14, TOP1, TP53, TSC1, TSC2, TSHR, VHL, WISP3, WT1, ZNF217, ZNF703, and combinations thereof (Su et al., J Mol Diagn 2011, 13:74-84; DOI:10.1016/j.jmoldx.2010.11.010; and Abaan et al., "The Exomes of the NCI-60 Panel: A Genomic Resource for Cancer Biology and Systems Pharmacology", *Cancer Research*, Jul. 15, 2013, which are each hereby incorporated by reference in its entirety). In some embodiments, the duplication is a chromosome 1p ("Chr1p") duplication associated with breast cancer. In some embodiments, one or more polymorphisms or mutations are in BRAF, such as the V600E mutation. In some embodiments, one or more polymorphisms or mutations are in K-ras. In some embodiments, there is a combination of one or more polymorphisms or mutations in K-ras and APC. In some embodiments, there is a combination of one or more polymorphisms or mutations in K-ras and p53. In some embodiments, there is a combination of one or more polymorphisms or mutations in APC and p53. In some embodiments, there is a combination of one or more polymorphisms or mutations in K-ras, APC, and p53. In some embodiments, there is a combination of one or more polymorphisms or mutations in K-ras and EGFR. Exemplary polymorphisms or mutations are in one or more of the following microRNAs: miR-15a, miR-16-1, miR-23a, miR-23b, miR-24-1, miR-24-2, miR-27a, miR-27b, miR-29b-2, miR-29c, miR-146, miR-155, miR-221, miR-222, and miR-223 (Calin et al. "A microRNA signature associated with prognosis and progression in chronic lymphocytic leukemia." N Engl J Med 353:1793-801, 2005, which is hereby incorporated by reference in its entirety).

In some embodiments, the deletion is a deletion of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the deletion is a deletion of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the duplication is a duplication of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the duplication is a duplication of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the tandem repeat is a repeat of between 2 and 60 nucleotides, such as 2 to 6, 7 to 10, 10 to 20, 20 to 30, 30 to 40, 40 to 50, or 50 to 60 nucleotides, inclusive. In some embodiments, the tandem repeat is a repeat of 2 nucleotides (dinucleotide repeat). In some embodiments, the tandem repeat is a repeat of 3 nucleotides (trinucleotide repeat).

In some embodiments, the polymorphism or mutation is prognostic. Exemplary prognostic mutations include K-ras mutations, such as K-ras mutations that are indicators of post-operative disease recurrence in colorectal cancer (Ryan et al. "A prospective study of circulating mutant KRAS2 in the serum of patients with colorectal neoplasia: strong prognostic indicator in postoperative follow up," Gut 52:101-108, 2003; and Lecomte T et al. Detection of free-circulating tumor-associated DNA in plasma of colorectal cancer patients and its association with prognosis," Int J Cancer 100:542-548, 2002, which are each hereby incorporated by reference in its entirety).

In some embodiments, the polymorphism or mutation is associated with altered response to a particular treatment (such as increased or decreased efficacy or side-effects). Examples include K-ras mutations are associated with decreased response to EGFR-based treatments in non-small cell lung cancer (Wang et al. "Potential clinical significance of a plasma-based KRAS mutation analysis in patients with advanced non-small cell lung cancer," Clin Canc Res 16:1324-1330, 2010, which is hereby incorporated by reference in its entirety).

K-ras is an oncogene that is activated in many cancers. Exemplary K-ras mutations are mutations in codons 12, 13, and 61. K-ras cfDNA mutations have been identified in pancreatic, lung, colorectal, bladder, and gastric cancers (Fleischhacker & Schmidt "Circulating nucleic acids (CNAs) and caner—a survey," Biochim Biophys Acta 1775: 181-232, 2007, which is hereby incorporated by reference in its entirety). [0739]$p^{53}$ is a tumor suppressor that is mutated in many cancers and contributes to tumor progression (Levine & Oren "The first 30 years of p53: growing ever more complex. Nature Rev Cancer," 9:749-758, 2009, which is hereby incorporated by reference in its entirety). Many different codons can be mutated, such as Ser249. p53 cfDNA mutations have been identified in breast, lung, ovarian, bladder, gastric, pancreatic, colorectal, bowel, and hepatocellular cancers (Fleischhacker & Schmidt "Circulating nucleic acids (CNAs) and caner—a survey," Biochim Biophys Acta 1775:181-232, 2007, which is hereby incorporated by reference in its entirety).

BRAF is an oncogene downstream of Ras. BRAF mutations have been identified in glial neoplasm, melanoma, thyroid, and lung cancers (Dias-Santagata et al. BRAF V600E mutations are common in pleomorphic xanthoastrocytoma: diagnostic and therapeutic implications. PLOS ONE 2011; 6:e17948, 2011; Shinozaki et al. Utility of circulating B-RAF DNA mutation in serum for monitoring melanoma patients receiving biochemotherapy. Clin Canc Res 13:2068-2074, 2007; and Board et al. Detection of BRAF mutations in the tumor and serum of patients enrolled in the AZD6244 (ARRY-142886) advanced melanoma phase II study. Brit J Canc 2009; 101:1724-1730, which are each hereby incorporated by reference in its entirety). The BRAF V600E mutation occurs, e.g., in melanoma tumors, and is more common in advanced stages. The V600E mutation has been detected in cfDNA.

EGFR contributes to cell proliferation and is misregulated in many cancers (Downward J. Targeting RAS signalling pathways in cancer therapy. Nature Rev Cancer 3:11-22, 2003; and Levine & Oren "The first 30 years of p53: growing ever more complex. Nature Rev Cancer," 9:749-758, 2009, which is hereby incorporated by reference in its entirety). Exemplary EGFR mutations include those in exons 18-21, which have been identified in lung cancer patients. EGFR cfDNA mutations have been identified in lung cancer patients (Jia et al. "Prediction of epidermal growth factor receptor mutations in the plasma/pleural effusion to efficacy of gefitinib treatment in advanced non-small cell lung cancer," J Canc Res Clin Oncol 2010; 136:1341-1347, 2010, which is hereby incorporated by reference in its entirety).

Exemplary polymorphisms or mutations associated with breast cancer include LOH at microsatellites (Kohler et al. "Levels of plasma circulating cell free nuclear and mitochondrial DNA as potential biomarkers for breast tumors," Mol Cancer 8:doi:10.1186/1476-4598-8-105, 2009, which is hereby incorporated by reference in its entirety), p53 mutations (such as mutations in exons 5-8)(Garcia et al." Extracellular tumor DNA in plasma and overall survival in breast cancer patients," Genes, Chromosomes & Cancer 45:692-701, 2006, which is hereby incorporated by reference in its entirety), HER2 (Sorensen et al. "Circulating HER2 DNA after trastuzumab treatment predicts survival and response in breast cancer," Anticancer Res 30:2463-2468, 2010, which is hereby incorporated by reference in its entirety), PIK3CA, MED1, and GAS6 polymorphisms or mutations (Murtaza et al. "Non-invasive analysis of acquired resistance to cancer therapy by sequencing of plasma DNA," Nature 2013; doi:10.1038/nature12065, 2013, which is hereby incorporated by reference in its entirety).

Increased cfDNA levels and LOH are associated with decreased overall and disease-free survival. p53 mutations (exons 5-8) are associated with decreased overall survival. Decreased circulating HER2 cfDNA levels are associated with a better response to HER2-targeted treatment in HER2-positive breast tumor subjects. An activating mutation in PIK3CA, a truncation of MED1, and a splicing mutation in GAS6 result in resistance to treatment.

Exemplary polymorphisms or mutations associated with colorectal cancer include p53, APC, K-ras, and thymidylate synthase mutations and p16 gene methylation (Wang et al. "Molecular detection of APC, K-ras, and p53 mutations in the serum of colorectal cancer patients as circulating biomarkers," World J Surg 28:721-726, 2004; Ryan et al. "A prospective study of circulating mutant KRAS2 in the serum of patients with colorectal neoplasia: strong prognostic indicator in postoperative follow up," Gut 52:101-108, 2003; Lecomte et al. "Detection of free-circulating tumor-associated DNA in plasma of colorectal cancer patients and its association with prognosis," Int J Cancer 100:542-548, 2002; Schwarzenbach et al. "Molecular analysis of the polymorphisms of thymidylate synthase on cell-free circulating DNA in blood of patients with advanced colorectal carcinoma," Int J Cancer 127:881-888, 2009, which are each hereby incorporated by reference in its entirety). Post-operative detection of K-ras mutations in serum is a strong predictor of disease recurrence. Detection of K-ras mutations and p16 gene methylation are associated with decreased survival and increased disease recurrence. Detection of K-ras, APC, and/or p53 mutations is associated with recurrence and/or metastases. Polymorphisms (including LOH, SNPs, variable number tandem repeats, and deletion) in the thymidylate synthase (the target of fluoropyrimidine-based chemotherapies) gene using cfDNA may be associated with treatment response.

Exemplary polymorphisms or mutations associated with lung cancer (such as non-small cell lung cancer) include K-ras (such as mutations in codon 12) and EGFR mutations. Exemplary prognostic mutations include EGFR mutations (exon 19 deletion or exon 21 mutation) associated with increased overall and progression-free survival and K-ras mutations (in codons 12 and 13) are associated with decreased progression-free survival (Jian et al. "Prediction of epidermal growth factor receptor mutations in the plasma/pleural effusion to efficacy of gefitinib treatment in advanced non-small cell lung cancer," J Canc Res Clin Oncol 136: 1341-1347, 2010; Wang et al. "Potential clinical significance of a plasma-based KRAS mutation analysis in patients with advanced non-small cell lung cancer," Clin Canc Res 16:1324-1330, 2010, which are each hereby incorporated by reference in its entirety). Exemplary polymorphisms or mutations indicative of response to treatment include EGFR mutations (exon 19 deletion or exon 21 mutation) that improve response to treatment and K-ras mutations (codons 12 and 13) that decrease the response to treatment. A resistance-conferring mutation in EFGR has been identified (Murtaza et al. "Non-invasive analysis of acquired resistance to cancer therapy by sequencing of plasma DNA," Nature doi:10.1038/nature12065, 2013, which is hereby incorporated by reference in its entirety).

Exemplary polymorphisms or mutations associated with melanoma (such as uveal melanoma) include those in GNAQ, GNA11, BRAF, and p53. Exemplary GNAQ and GNA11 mutations include R183 and Q209 mutations. Q209 mutations in GNAQ or GNA11 are associated with metastases to bone. BRAF V600E mutations can be detected in patients with metastatic/advanced stage melanoma. BRAF V600E is an indicator of invasive melanoma. The presence of the BRAF V600E mutation after chemotherapy is associated with a non-response to the treatment Exemplary polymorphisms or mutations associated with pancreatic carcinomas include those in K-ras and p53 (such as p53 Ser249). p53 Ser249 is also associated with hepatitis B infection and hepatocellular carcinoma, as well as ovarian cancer, and non-Hodgkin's lymphoma.

Even polymorphisms or mutations that are present in low frequency in a sample can be detected with the methods of the invention. For example, a polymorphism or mutation that is present at a frequency of 1 in a million can be observed 10 times by performing 10 million sequencing reads. If desired, the number of sequencing reads can be altered depending of the level of sensitivity desired. In some embodiments, a sample is re-analyzed or another sample from a subject is analyzed using a greater number of sequencing reads to improve the sensitivity. For example, if no or only a small number (such as 1, 2, 3, 4, or 5) polymorphisms or mutations that are associated with cancer or an increased risk for cancer are detected, the sample is re-analyzed or another sample is tested.

In some embodiments, multiple polymorphisms or mutations are required for cancer or for metastatic cancer. In such cases, screening for multiple polymorphisms or mutations improves the ability to accurately diagnose cancer or metastatic cancer. In some embodiments when a subject has a subset of multiple polymorphisms or mutations that are required for cancer or for metastatic cancer, the subject can be re-screened later to see if the subject acquires additional mutations.

In some embodiments in which multiple polymorphisms or mutations are required for cancer or for metastatic cancer, the frequency of each polymorphism or mutation can be compared to see if they occur at similar frequencies. For example, if two mutations required for cancer (denoted "A" and "B"), some cells will have none, some cells with A, some with B, and some with A and B. If A and B are observed at similar frequencies, the subject is more likely to have some cells with both A and B. If observer A and B at dissimilar frequencies, the subject is more likely to have different cell populations.

In some embodiments in which multiple polymorphisms or mutations are required for cancer or for metastatic cancer, the number or identity of such polymorphisms or mutations that are present in the subject can be used to predict how likely or soon the subject is likely to have the disease or disorder. In some embodiments in which polymorphisms or mutations tend to occur in a certain order, the subject may be periodically tested to see if the subject has acquired the other polymorphisms or mutations.

In some embodiments, determining the presence or absence of multiple polymorphisms or mutations (such as 2, 3, 4, 5, 8, 10, 12, 15, or more) increases the sensitivity and/or specificity of the determination of the presence or absence of a disease or disorder such as cancer, or an increased risk for with a disease or disorder such as cancer.

In some embodiments, the polymorphism(s) or mutation(s) are directly detected. In some embodiments, the polymorphism(s) or mutation(s) are indirectly detected by detection of one or more sequences (e.g., a polymorphic locus such as a SNP) that are linked to the polymorphism or mutation.

Exemplary Nucleic Acid Alterations

In some embodiments, there is a change to the integrity of RNA or DNA (such as a change in the size of fragmented cfRNA or cfDNA or a change in nucleosome composition) that is associated with a disease or disorder such as cancer, or an increased risk for a disease or disorder such as cancer. In some embodiments, there is a change in the methylation pattern RNA or DNA that is associated with a disease or disorder such as cancer, or an increased risk for with a disease or disorder such as cancer (e.g., hypermethylation of tumor suppressor genes). For example, methylation of the CpG islands in the promoter region of tumor-suppressor genes has been suggested to trigger local gene silencing. Aberrant methylation of the p16 tumor suppressor gene occurs in subjects with liver, lung, and breast cancer. Other frequently methylated tumor suppressor genes, including APC, Ras association domain family protein 1A (RASSF1A), glutathione S-transferase P1 (GSTP1), and DAPK, have been detected in various type of cancers, for example nasopharyngeal carcinoma, colorectal cancer, lung cancer, oesophageal cancer, prostate cancer, bladder cancer, melanoma, and acute leukemia. Methylation of certain tumor-suppressor genes, such as p16, has been described as an early event in cancer formation, and thus is useful for early cancer screening.

In some embodiments, bisulphite conversion or a non-bisulphite based strategy using methylation sensitive restriction enzyme digestion is used to determine the methylation pattern (Hung et al., J Clin Pathol 62:308-313, 2009, which is hereby incorporated by reference in its entirety). On bisulphite conversion, methylated cytosines remain as cytosines while unmethylated cytosines are converted to uracils. Methylation-sensitive restriction enzymes (e.g., BstUI) cleaves unmethylated DNA sequences at specific recognition sites (e.g., 5'-CG v CG-3' for BstUI), while methylated sequences remain intact. In some embodiments, the intact methylated sequences are detected. In some embodiments, stem-loop primers are used to selectively amplify restriction enzyme-digested unmethylated fragments without co-amplifying the non-enzyme-digested methylated DNA.

Exemplary Changes in mRNA Splicing

In some embodiments, a change in mRNA splicing is associated with a disease or disorder such as cancer, or an increased risk for a disease or disorder such as cancer. In some embodiments, the change in mRNA splicing is in one or more of the following nucleic acids associated with cancer or an increased risk for cancer: DNMT3B, BRCA1, KLF6, Ron, or Gemin5. In some embodiments, the detected mRNA splice variant is associated with a disease or disorder, such as cancer. In some embodiments, multiple mRNA splice variants are produced by healthy cells (such as non-cancerous cells), but a change in the relative amounts of the mRNA splice variants is associated with a disease or disorder, such as cancer. In some embodiments, the change in mRNA splicing is due to a change in the mRNA sequence (such as a mutation in a splice site), a change in splicing factor levels, a change in the amount of available splicing factor (such as a decrease in the amount of available splicing factor due to the binding of a splicing factor to a repeat), altered splicing regulation, or the tumor microenvironment.

The splicing reaction is carried out by a multi-protein/RNA complex called the spliceosome (Fackenthall and Godley, Disease Models & Mechanisms 1: 37-42, 2008, doi:10.1242/dmm.000331, which is hereby incorporated by reference in its entirety). The spliceosome recognizes intron-exon boundaries and removes intervening introns via two transesterification reactions that result in ligation of two adjacent exons. The fidelity of this reaction must be exquisite, because if the ligation occurs incorrectly, normal protein-encoding potential may be compromised. For example, in cases where exon-skipping preserves the reading frame of the triplet codons specifying the identity and order of amino acids during translation, the alternatively spliced mRNA may specify a protein that lacks crucial amino acid residues. More commonly, exon-skipping will disrupt the translational reading frame, resulting in premature stop codons. These mRNAs are typically degraded by at least 90% through a process known as nonsense-mediated mRNA degradation, which reduces the likelihood that such defective messages will accumulate to generate truncated protein products. If mis-spliced mRNAs escape this pathway, then truncated, mutated, or unstable proteins are produced.

Alternative splicing is a means of expressing several or many different transcripts from the same genomic DNA and results from the inclusion of a subset of the available exons for a particular protein. By excluding one or more exons, certain protein domains may be lost from the encoded protein, which can result in protein function loss or gain. Several types of alternative splicing have been described: exon skipping; alternative 5' or 3' splice sites; mutually exclusive exons; and, much more rarely, intron retention. Others have compared the amount of alternative splicing in cancer versus normal cells using a bioinformatic approach and determined that cancers exhibit lower levels of alternative splicing than normal cells. Furthermore, the distribution of the types of alternative splicing events differed in cancer versus normal cells. Cancer cells demonstrated less exon skipping, but more alternative 5' and 3' splice site selection and intron retention than normal cells. When the phenomenon of exonization (the use of sequences as exons that are used predominantly by other tissues as introns) was examined, genes associated with exonization in cancer cells were preferentially associated with mRNA processing, indicating a direct link between cancer cells and the generation of aberrant mRNA splice forms.

Exemplary Changes in DNA or RNA Levels

In some embodiments, there is a change in the total amount or concentration of one or more types of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA). In some embodiments, there is a change in the amount or concentration of one or more specific DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) molecules. In some embodiments, one allele is expressed more than another allele of a locus of interest. Exemplary miRNAs are short 20-22 nucleotide RNA molecules that regulate the expression of a gene. In some embodiments, there is a change in the transcriptome, such as a change in the identity or amount of one or more RNA molecules.

In some embodiments, an increase in the total amount or concentration of cfDNA or cfRNA is associated with a disease or disorder such as cancer, or an increased risk for a disease or disorder such as cancer. In some embodiments, the total concentration of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) increases by at least 2, 3, 4, 5, 6, 7, 8, 9, 10-fold, or more compared to the total concentration of that type of DNA or RNA in healthy (such as non-cancerous) subjects. In some embodiments, a total concentration of cfDNA between 75 to 100 ng/mL, 100 to 150 ng/mL, 150 to 200 ng/mL, 200 to 300 ng/mL, 300 to 400 ng/mgL, 400 to 600 ng/mL, 600 to 800 ng/mL, 800 to 1,000 ng/mL, inclusive, or a total concentration of cfDNA of more than 100 ng, mL, such as more than 200, 300, 400, 500, 600, 700, 800, 900, or 1,000 ng/mL is indicative of cancer, an increased risk for cancer, an increased risk of a tumor being malignant rather than benign, a decreased probably of the cancer going into remission, or a worse prognosis for the cancer. In some embodiments, the amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) having one or more polymorphisms/mutations (such as deletions or duplications) associated with a disease or disorder such as cancer or an increased risk for a disease or disorder such as cancer is at least 2, 3, 4, 5, 6, 7, 8, 9, 10, 11, 12, 14, 16, 18, 20, or 25% of the total amount of that type of DNA or RNA. In some embodiments, at least 2, 3, 4, 5, 6, 7, 8, 9, 10, 11, 12, 14, 16, 18, 20, or 25% of the total amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, mRNA, miRNA, mitochondrial RNA, rRNA, or tRNA) has a particular polymorphism or mutation (such as a deletion or duplication) associated with a disease or disorder such as cancer or an increased risk for a disease or disorder such as cancer.

In some embodiments, the cfDNA is encapsulated. In some embodiments, the cfDNA is not encapsulated.

In some embodiments, the fraction of tumor DNA out of total DNA (such as fraction of tumor cfDNA out of total cfDNA or fraction of tumor cfDNA with a particular mutation out of total cfDNA) is determined. In some embodiments, the fraction of tumor DNA may be determined for a plurality of mutations, where the mutations can be single nucleotide variants, copy number variants, differential methylation, or combinations thereof. In some embodiments, the average tumor fraction calculated for one or a set of mutations with the highest calculated tumor fraction is taken as the actual tumor fraction in the sample. In some embodiments, the average tumor fraction calculated for all of the mutations is taken as the actual tumor fraction in the sample. In some embodiments, this tumor fraction is used to stage a cancer (since higher tumor fractions can be associated with more advanced stages of cancer). In some embodiments, the tumor fraction is used to size a cancer, since larger tumors may be correlated with the fraction of tumor DNA in the plasma. In some embodiments, the tumor fraction is used to size the proportion of a tumor that is afflicted with a single or plurality of mutations, since there may be a correlation between the measured tumor fraction in a plasma sample and the size of tissue with a given mutation(s) genotype. For example, the size of tissue with a given mutation(s) genotype may be correlated with the fraction of tumor DNA that may be calculated by focusing on that particular mutation(s).

Exemplary Databases

The invention also features databases containing one or more results from a method of the invention. For example, the database may include records with any of the following information for one or more subjects: any polymorphisms/mutations (such as CNVs) identified, any known association of the polymorphisms/mutations with a disease or disorder or an increased risk for a disease or disorder, effect of the polymorphisms/mutations on the expression or activity level of the encoded mRNA or protein, fraction of DNA, RNA, or cells associated with a disease or disorder (such as DNA, RNA, or cells having polymorphism/mutation associated with a disease or disorder) out of the total DNA, RNA, or cells in sample, source of sample used to identify the polymorphisms/mutations (such as a blood sample or sample from a particular tissue), number of diseased cells, results from later repeating the test (such as repeating the test to monitor the progression or remission of the disease or disorder), results of other tests for the disease or disorder, type of disease or disorder the subject was diagnosed with, treatment(s) administered, response to such treatment(s), side-effects of such treatment(s), symptoms (such as symptoms associated with the disease or disorder), length and number of remissions, length of survival (such as length of time from initial test until death or length of time from diagnosis until death), cause of death, and combinations thereof.

In some embodiments, the database includes records with any of the following information for one or more subjects: any polymorphisms/mutations identified, any known association of the polymorphisms/mutations with cancer or an increased risk for cancer, effect of the polymorphisms/mutations on the expression or activity level of the encoded mRNA or protein, fraction of cancerous DNA, RNA or cells out of the total DNA, RNA, or cells in sample, source of sample used to identify the polymorphisms/mutations (such as a blood sample or sample from a particular tissue), number of cancerous cells, size of tumor(s), results from later repeating the test (such as repeating the test to monitor the progression or remission of the cancer), results of other tests for cancer, type of cancer the subject was diagnosed with, treatment(s) administered, response to such treatment(s), side-effects of such treatment(s), symptoms (such as symptoms associated with cancer), length and number of remissions, length of survival (such as length of time from initial test until death or length of time from cancer diagnosis until death), cause of death, and combinations thereof. In some embodiments, the response to treatment includes any of the following: reducing or stabilizing the size of a tumor (e.g., a benign or cancerous tumor), slowing or preventing an increase in the size of a tumor, reducing or stabilizing the number of tumor cells, increasing the disease-free survival time between the disappearance of a tumor and its reappearance, preventing an initial or subsequent occurrence of a tumor, reducing or stabilizing an adverse symptom associated with a tumor, or combinations thereof. In some embodiments, the results from one or more other tests for a disease or disorder such as cancer are included, such as results from screening tests, medical imaging, or microscopic examination of a tissue sample.

In one such aspect, the invention features an electronic database including at least 5, 10, $10^2$, $10^3$, $10^4$, $10^5$, $10^6$, $10^7$, $10^8$ or more records. In some embodiments, the database has records for at least 5, 10, $10^2$, $10^3$, $10^4$, $10^5$, $10^6$, $10^7$, $10^8$ or more different subjects.

In another aspect, the invention features a computer including a database of the invention and a user interface. In some embodiments, the user interface is capable of displaying a portion or all of the information contained in one or more records. In some embodiments, the user interface is capable of displaying (i) one or more types of cancer that have been identified as containing a polymorphism or mutation whose record is stored in the computer, (ii) one or more polymorphisms or mutations that have been identified in a particular type of cancer whose record is stored in the computer, (iii) prognosis information for a particular type of cancer or a particular a polymorphism or mutation whose record is stored in the computer (iv) one or more compounds or other treatments useful for cancer with a polymorphism or mutation whose record is stored in the computer, (v) one or more compounds that modulate the expression or activity of an mRNA or protein whose record is stored in the computer, and (vi) one or more mRNA molecules or proteins whose expression or activity is modulated by a compound whose record is stored in the computer. The internal components of the computer typically include a processor coupled to a memory. The external components usually include a mass-storage device, e.g., a hard disk drive; user input devices, e.g., a keyboard and a mouse; a display, e.g., a monitor; and optionally, a network link capable of connecting the computer system to other computers to allow sharing of data and processing tasks. Programs may be loaded into the memory of this system during operation.

In another aspect, the invention features a computer-implemented process that includes one or more steps of any of the methods of the invention.

Exemplary Risk Factors

In some embodiments, the subject is also evaluated for one or more risk factors for a disease or disorder, such as cancer. Exemplary risk factors include family history for the disease or disorder, lifestyle (such as smoking and exposure to carcinogens) and the level of one or more hormones or serum proteins (such as alpha-fetoprotein (AFP) in liver cancer, carcinoembryonic antigen (CEA) in colorectal cancer, or prostate-specific antigen (PSA) in prostate cancer). In some embodiments, the size and/or number of tumors is measured and use in determining a subject's prognosis or selecting a treatment for the subject.

Exemplary Screening Methods

If desired, the presence or absence of a disease or disorder such cancer can be confirmed, or the disease or disorder such as cancer can be classified using any standard method. For example, a disease or disorder such as cancer can be detected in a number of ways, including the presence of certain signs and symptoms, tumor biopsy, screening tests, or medical imaging (such as a mammogram or an ultrasound). Once a possible cancer is detected, it may be diagnosed by microscopic examination of a tissue sample. In some embodiments, a subject diagnosed undergoes repeat testing using a method of the invention or known testing for the disease or disorder at multiple time points to monitor the progression of the disease or disorder or the remission or reoccurrence of the disease or disorder.

Exemplary Cancers

Exemplary cancers that can be diagnosed, prognosed, stabilized, treated, prevented, for which a response to treatment can be predicted or monitored using any of the methods of the invention include solid tumors, carcinomas, sarcomas, lymphomas, leukemias, germ cell tumors, or blastomas. In various embodiments, the cancer is an acute lymphoblastic leukemia, acute myeloid leukemia, adrenocortical carcinoma, AIDS-related cancer, AIDS-related lymphoma, anal cancer, appendix cancer, astrocytoma (such as childhood cerebellar or cerebral astrocytoma), basal-cell carcinoma, bile duct cancer (such as extrahepatic bile duct cancer) bladder cancer, bone tumor (such as osteosarcoma or malignant fibrous histiocytoma), brainstem glioma, brain cancer (such as cerebellar astrocytoma, cerebral astrocytoma/malignant glioma, ependymo, medulloblastoma, supratentorial primitive neuroectodermal tumors, or visual pathway and hypothalamic glioma), glioblastoma, breast cancer, bronchial adenoma or carcinoid, burkitt's lymphoma, carcinoid tumor (such as a childhood or gastrointestinal carcinoid tumor), carcinoma central nervous system lymphoma, cerebellar astrocytoma or malignant glioma (such as childhood cerebellar astrocytoma or malignant glioma), cervical cancer, childhood cancer, chronic lymphocytic leukemia, chronic myelogenous leukemia, chronic myeloproliferative disorders, colon cancer, cutaneous t-cell lymphoma, desmoplastic small round cell tumor, endometrial cancer, ependymoma, esophageal cancer, ewing's sarcoma, tumor in the ewing family of tumors, extracranial germ cell tumor (such as a childhood extracranial germ cell tumor), extragonadal germ cell tumor, eye cancer (such as intraocular melanoma or retinoblastoma eye cancer), gallbladder cancer, gastric cancer, gastrointestinal carcinoid tumor, gastrointestinal stromal tumor, germ cell tumor (such as extracranial, extragonadal, or ovarian germ cell tumor), gestational trophoblastic tumor, glioma (such as brain stem, childhood cerebral astrocytoma, or childhood visual pathway and hypothalamic glioma), gastric carcinoid, hairy cell leukemia, head and neck cancer, heart cancer, hepatocellular (liver) cancer, hodgkin lymphoma, hypopharyngeal cancer, hypothalamic and visual pathway glioma (such as childhood visual pathway glioma), islet cell carcinoma (such as endocrine or pancreas islet cell carcinoma), kaposi sarcoma, kidney cancer, laryngeal cancer, leukemia (such as acute lymphoblastic, acute myeloid, chronic lymphocytic, chronic myelogenous, or hairy cell leukemia), lip or oral cavity cancer, liposarcoma, liver cancer (such as non-small cell or small cell cancer), lung cancer, lymphoma (such as AIDS-related, burkitt, cutaneous T cell, Hodgkin, non-hodgkin, or central nervous system lymphoma), macroglobulinemia (such as waldenström macroglobulinemia, malignant fibrous histiocytoma of bone or osteosarcoma, medulloblastoma (such as childhood medulloblastoma), melanoma, merkel cell carcinoma, mesothelioma (such as adult or childhood mesothelioma), metastatic squamous neck cancer with occult, mouth cancer, multiple endocrine neoplasia syndrome (such as childhood multiple endocrine neoplasia syndrome), multiple myeloma or plasma cell neoplasm. mycosis fungoides, myelodysplastic syndrome, myelodysplastic or myeloproliferative disease, myelogenous leukemia (such as chronic myelogenous leukemia), myeloid leukemia (such as adult acute or childhood acute myeloid leukemia), myeloproliferative disorder (such as chronic myeloproliferative disorder), nasal cavity or paranasal sinus cancer, nasopharyngeal carcinoma, neuroblastoma, oral cancer, oropharyngeal cancer, osteosarcoma or malignant fibrous histiocytoma of bone, ovarian cancer, ovarian epithelial cancer, ovarian germ cell tumor, ovarian low malignant potential tumor, pancreatic cancer (such as islet cell pancreatic cancer), paranasal sinus or nasal cavity cancer, parathyroid cancer, penile cancer, pharyngeal cancer, pheochromocytoma, pineal astrocytoma, pineal germinoma. pineoblastoma or supratentorial primitive neuroectodermal tumor (such as childhood pineoblastoma or supratentorial primitive neuroectodermal tumor), pituitary adenoma, plasma cell neoplasia, pleuropulmonary blastoma, primary central nervous system lymphoma, cancer, rectal cancer, renal cell carcinoma, renal pelvis or ureter cancer (such as renal pelvis or ureter transitional cell cancer, retinoblastoma, rhabdomyosarcoma (such as childhood rhabdomyosarcoma), salivary gland cancer, sarcoma (such as sarcoma in the ewing family of tumors, Kaposi, soft tissue, or uterine sarcoma), sézary syndrome, skin cancer (such as nonmelanoma, melanoma, or merkel cell skin cancer), small intestine cancer, squamous cell carcinoma, supratentorial primitive neuroectodermal tumor (such as childhood supratentorial primitive neuroectodermal tumor), T-cell lymphoma (such as cutaneous T-cell lymphoma), testicular cancer, throat cancer, thymoma (such as childhood thymoma), thymoma or thymic carcinoma, thyroid cancer (such as childhood thyroid cancer), trophoblastic tumor (such as gestational trophoblastic tumor), unknown primary site carcinoma (such as adult or childhood unknown primary site carcinoma), urethral cancer (such as endometrial uterine cancer), uterine sarcoma, vaginal cancer, visual pathway or hypothalamic glioma (such as childhood visual pathway or hypothalamic glioma), vulvar cancer, waldenström macroglobulinemia, or wilms tumor (such as childhood wilms tumor). In various embodiments, the cancer has metastasized or has not metastasized.

The cancer may or may not be a hormone related or dependent cancer (e.g., an estrogen or androgen related cancer). Benign tumors or malignant tumors may be diagnosed, prognosed, stabilized, treated, or prevented using the methods and/or compositions of the present invention.

In some embodiments, the subject has a cancer syndrome. A cancer syndrome is a genetic disorder in which genetic mutations in one or more genes predispose the affected individuals to the development of cancers and may also cause the early onset of these cancers. Cancer syndromes often show not only a high lifetime risk of developing cancer, but also the development of multiple independent primary tumors. Many of these syndromes are caused by mutations in tumor suppressor genes, genes that are involved in protecting the cell from turning cancerous. Other genes that may be affected are DNA repair genes, oncogenes and genes involved in the production of blood vessels (angiogenesis). Common examples of inherited cancer syndromes are hereditary breast-ovarian cancer syndrome and hereditary non-polyposis colon cancer (Lynch syndrome).

In some embodiments, a subject with one or more polymorphisms or mutations n K-ras, p53, BRA, EGFR, or HER2 is administered a treatment that targets K-ras, p53, BRA, EGFR, or HER2, respectively.

The methods of the invention can be generally applied to the treatment of malignant or benign tumors of any cell, tissue, or organ type.

Exemplary Treatments

If desired, any treatment for stabilizing, treating, or preventing a disease or disorder such as cancer or an increased risk for a disease or disorder such as cancer can be administered to a subject (e.g., a subject identified as having cancer or an increased risk for cancer using any of the methods of the invention). In various embodiments, the treatment is a known treatment or combination of treatments for a disease or disorder such as cancer, including but not limited to cytotoxic agents, targeted therapy, immunotherapy, hormonal therapy, radiation therapy, surgical removal of cancerous cells or cells likely to become cancerous, stem cell transplantation, bone marrow transplantation, photodynamic therapy, palliative treatment, or a combination thereof. In some embodiments, a treatment (such as a preventative medication) is used to prevent, delay, or reduce the severity of a disease or disorder such as cancer in a subject at increased risk for a disease or disorder such as cancer. In some embodiments, the treatment is surgery, first-line chemotherapy, adjuvant therapy, or neoadjuvant therapy.

In some embodiments, the targeted therapy is a treatment that targets the cancer's specific genes, proteins, or the tissue environment that contributes to cancer growth and survival. This type of treatment blocks the growth and spread of cancer cells while limiting damage to normal cells, usually leading to fewer side effects than other cancer medications.

One of the more successful approaches has been to target angiogenesis, the new blood vessel growth around a tumor. Targeted therapies such as bevacizumab (Avastin), lenalidomide (Revlimid), sorafenib (Nexavar), sunitinib (Sutent), and thalidomide (Thalomid) interfere with angiogenesis. Another example is the use of a treatment that targets HER2, such as trastuzumab or lapatinib, for cancers that overexpress HER2 (such as some breast cancers). In some embodiments, a monoclonal antibody is used to block a specific target on the outside of cancer cells. Examples include alemtuzumab (Campath-1H), bevacizumab, cetuximab (Erbitux), panitumumab (Vectibix), pertuzumab (Omnitarg), rituximab (Rituxan), and trastuzumab. In some embodiments, the monoclonal antibody tositumomab (Bexxar) is used to deliver radiation to the tumor. In some embodiments, an oral small molecule inhibits a cancer process inside of a cancer cell. Examples include dasatinib (Sprycel), erlotinib (Tarceva), gefitinib (Iressa), imatinib (Gleevec), lapatinib (Tykerb), nilotinib (Tasigna), sorafenib, sunitinib, and temsirolimus (Torisel). In some embodiments, a proteasome inhibitor (such as the multiple myeloma drug, bortezomib (Velcade)) interferes with specialized proteins called enzymes that break down other proteins in the cell.

In some embodiments, immunotherapy is designed to boost the body's natural defenses to fight the cancer. Exemplary types of immunotherapy use materials made either by the body or in a laboratory to bolster, target, or restore immune system function.

In some embodiments, hormonal therapy treats cancer by lowering the amounts of hormones in the body. Several types of cancer, including some breast and prostate cancers, only grow and spread in the presence of natural chemicals in the body called hormones. In various embodiments, hormonal therapy is used to treat cancers of the prostate, breast, thyroid, and reproductive system.

In some embodiments, the treatment includes a stem cell transplant in which diseased bone marrow is replaced by highly specialized cells, called hematopoietic stem cells. Hematopoietic stem cells are found both in the bloodstream and in the bone marrow.

In some embodiments, the treatment includes photodynamic therapy, which uses special drugs, called photosensitizing agents, along with light to kill cancer cells. The drugs work after they have been activated by certain kinds of light.

In some embodiments, the treatment includes surgical removal of cancerous cells or cells likely to become cancerous (such as a lumpectomy or a mastectomy). For example, a woman with a breast cancer susceptibility gene mutation (BRCA1 or BRCA2 gene mutation) may reduce her risk of breast and ovarian cancer with a risk reducing salpingo-oophorectomy (removal of the fallopian tubes and ovaries) and/or a risk reducing bilateral mastectomy (removal of both breasts). Lasers, which are very powerful, precise beams of light, can be used instead of blades (scalpels) for very careful surgical work, including treating some cancers.

In addition to treatment to slow, stop, or eliminate the cancer (also called disease-directed treatment), an important part of cancer care is relieving a subject's symptoms and side effects, such as pain and nausea. It includes supporting the subject with physical, emotional, and social needs, an approach called palliative or supportive care. People often receive disease-directed therapy and treatment to ease symptoms at the same time.

Exemplary treatments include actinomycin D, adcetris, Adriamycin, aldesleukin, alemtuzumab, alimta, amsidine, amsacrine, anastrozole, aredia, arimidex, aromasin, asparaginase, avastin, bevacizumab, bicalutamide, bleomycin, bondronat, bonefos, bortezomib, busilvex, busulphan, campto, capecitabine, carboplatin, carmustine, casodex, cetuximab, chimax, chlorambucil, cimetidine, cisplatin, cladribine, clodronate, clofarabine, crisantaspase, cyclophosphamide, cyproterone acetate, cyprostat, cytarabine, cytoxan, dacarbozine, dactinomycin, dasatinib, daunorubicin, dexamethasone, diethylstilbestrol, docetaxel, doxorubicin, drogenil, emcyt, epirubicin, eposin, Erbitux, erlotinib, estracyte, estramustine, etopophos, etoposide, evoltra, exemestane, fareston, femara, filgrastim, fludara, fludarabine, fluorouracil, flutamide, gefinitib, gemcitabine, gemzar, gleevec, glivec. gonapeptyl depot, goserelin, halaven, herceptin, hycamptin, hydroxycarbamide, ibandronic acid, ibritumomab, idarubicin, ifosfomide, interferon, imatinib mesylate, iressa, irinotecan, jevtana, lanvis, lapatinib, letrozole, leukeran, leuprorelin, leustat, lomustine, mabcampath, mabthera, megace, megestrol, methotrexate, mitozantrone, mitomycin, mutulane, myleran, navelbine, neulasta, neupogen, nexavar, nipent, nolvadex D, novantron, oncovin, paclitaxel, pamidronate, PCV, pemetrexed, pentostatin, perjeta, procarbazine, provenge, prednisolone, prostrap, raltitrexed, rituximab, sprycel, sorafenib, soltamox, streptozocin, stilboestrol, stimuvax, sunitinib, sutent, tabloid, tagamet, tamofen, tamoxifen, tarceva, taxol, taxotere, tegafur with uracil, temodal, temozolomide, thalidomide, thioplex, thiotepa, tioguanine, tomudex, topotecan, toremifene, trastuzumab, tretinoin, treosulfan, triethylenethiophorsphoramide, triptorelin, tyverb, uftoral, velcade, vepesid, vesanoid, vincristine, vinorelbine, xalkori, xeloda, yervoy, zactima, zanosar, zavedos, zevelin, zoladex, zoledronate, zometa zoledronic acid, and zytiga.

In some embodiments, the cancer is breast cancer and the treatment or compound administered to the individual is one or more of: Abemaciclib, Abraxane (Paclitaxel Albumin-stabilized Nanoparticle Formulation), Ado-Trastuzumab Emtansine, Afinitor (Everolimus), Anastrozole, Aredia (Pamidronate Disodium), Arimidex (Anastrozole), Aromasin (Exemestane), Capecitabine, Cyclophosphamide, Docetaxel, Doxorubicin Hydrochloride, Ellence (Epirubicin Hydrochloride), Epirubicin Hydrochloride, Eribulin Mesylate, Everolimus, Exemestane, 5-FU (Fluorouracil Injection), Fareston (Toremifene), Faslodex (Fulvestrant), Femara (Letrozole), Fluorouracil Injection, Fulvestrant, Gemcitabine Hydrochloride, Gemzar (Gemcitabine Hydrochloride), Goserelin Acetate, Halaven (Eribulin Mesylate), Herceptin (Trastuzumab), Ibrance (Palbociclib), Ixabepilone, Ixempra (Ixabepilone), Kadcyla (Ado-Trastuzumab Emtansine), Kisqali (Ribociclib), Lapatinib Ditosylate, Letrozole, Lynparza (Olaparib), Megestrol Acetate, Methotrexate, Neratinib Maleate, Nerlynx (Neratinib Maleate), Olaparib, Paclitaxel, Paclitaxel Albumin-stabilized Nanoparticle Formulation, Palbociclib, Pamidronate Disodium, Perjeta (Pertuzumab), Pertuzumab, Ribociclib, Tamoxifen Citrate, Taxol (Paclitaxel), Taxotere (Docetaxel), Thiotepa, Toremifene, Trastuzumab, Trexall (Methotrexate), Tykerb (Lapatinib Ditosylate), Verzenio (Abemaciclib), Vinblastine Sulfate, Xeloda (Capecitabine), Zoladex (Goserelin Acetate), Evista (Raloxifene Hydrochloride), Raloxifene Hydrochloride, Tamoxifen Citrate. In some embodiments, the cancer is breast cancer and the treatment or compound administered to the individual is a combination selected from: Doxorubicin Hydrochloride (Adriamycin) and Cyclophosphamide; Doxorubicin Hydrochloride (Adriamycin), Cyclophosphamide, and Paclitaxel (Taxol); Doxorubicin Hydrochloride (Adriamycin), Cyclophosphamide, and Fluorouracil; Methotrexate, Cyclophosphamide, and Fluorouracil; Epirubicin Hydrochloride, Cyclophosphamide, and Fluorouracil; and Doxorubicin Hydrochloride (Adriamycin), Cyclophosphamide, and Docetaxel (Taxotere).

For subjects that express both a mutant form (e.g., a cancer-related form) and a wild-type form (e.g., a form not associated with cancer) of an mRNA or protein, the therapy preferably inhibits the expression or activity of the mutant form by at least 2, 5, 10, or 20-fold more than it inhibits the expression or activity of the wild-type form. The simultaneous or sequential use of multiple therapeutic agents may greatly reduce the incidence of cancer and reduce the number of treated cancers that become resistant to therapy. In addition, therapeutic agents that are used as part of a combination therapy may require a lower dose to treat cancer than the corresponding dose required when the therapeutic agents are used individually. The low dose of each compound in the combination therapy reduces the severity of potential adverse side-effects from the compounds.

In some embodiments, a subject identified as having an increased risk of cancer may invention or any standard method), avoid specific risk factors, or make lifestyle changes to reduce any additional risk of cancer.

In some embodiments, the polymorphisms, mutations, risk factors, or any combination thereof are used to select a treatment regimen for the subject. In some embodiments, a larger dose or greater number of treatments is selected for a subject at greater risk of cancer or with a worse prognosis.

Other Compounds for Inclusion in Individual or Combination Therapies

If desired, additional compounds for stabilizing, treating, or preventing a disease or disorder such as cancer or an increased risk for a disease or disorder such as cancer may be identified from large libraries of both natural product or synthetic (or semi-synthetic) extracts or chemical libraries according to methods known in the art. Those skilled in the field or drug discovery and development will understand that the precise source of test extracts or compounds is not critical to the methods of the invention. Accordingly, virtually any number of chemical extracts or compounds can be screened for their effect on cells from a particular type of cancer or from a particular subject or screened for their effect on the activity or expression of cancer related molecules (such as cancer related molecules known to have altered activity or expression in a particular type of cancer). When a crude extract is found to modulate the activity or expression of a cancer related molecule, further fractionation of the positive lead extract may be performed to isolate chemical constituent responsible for the observed effect using methods known in the art.

Exemplary Assays and Animal Models for the Testing of Therapies

If desired, one or more of the treatment disclosed herein can be tested for their effect on a disease or disorder such as cancer using a cell line (such as a cell line with one or more of the mutations identified in the subject who has been diagnosed with cancer or an increased risk of cancer using the methods of the invention) or an animal model of the disease or disorder, such as a SCID mouse model (Jain et al., Tumor Models In Cancer Research, ed. Teicher, Humana Press Inc., Totowa, N.J., pp. 647-671, 2001, which is hereby incorporated by reference in its entirety). Additionally, there are numerous standard assays and animal models that can be used to determine the efficacy of particular therapies for stabilizing, treating, or preventing a disease or disorder such as cancer or an increased risk for a disease or disorder such as cancer. Therapies can also be tested in standard human clinical trials.

For the selection of a preferred therapy for a particular subject, compounds can be tested for their effect on the expression or activity on one or more genes that are mutated in the subject. For example, the ability of a compound to modulate the expression of particular mRNA molecules or proteins can be detected using standard Northern, Western, or microarray analysis. In some embodiments, one or more compounds are selected that (i) inhibit the expression or activity of mRNA molecules or proteins that promote cancer that are expressed at a higher than normal level or have a higher than normal level of activity in the subject (such as in a sample from the subject) or (ii) promote the expression or activity of mRNA molecules or proteins that inhibit cancer that are expressed at a lower than normal level or have a lower than normal level of activity in the subject. An individual or combination therapy that (i) modulates the greatest number of mRNA molecules or proteins that have mutations associated with cancer in the subject and (ii) modulates the least number of mRNA molecules or proteins that do not have mutations associated with cancer in the subject. In some embodiments, the selected individual or combination therapy has high drug efficacy and produces few, if any, adverse side-effects.

As an alternative to the subject-specific analysis described above, DNA chips can be used to compare the expression of mRNA molecules in a particular type of early or late-stage cancer (e.g., breast cancer cells) to the expression in normal tissue (Marrack et al., Current Opinion in Immunology 12, 206-209, 2000; Harkin, Oncologist. 5:501-507, 2000; Pelizzari et al., Nucleic Acids Res. 28(22):4577-4581, 2000, which are each hereby incorporated by reference in its entirety). Based on this analysis, an individual or combination therapy for subjects with this type of cancer can be selected to modulate the expression of the mRNA or proteins that have altered expression in this type of cancer.

In addition to being used to select a therapy for a particular subject or group of subjects, expression profiling can be used to monitor the changes in mRNA and/or protein expression that occur during treatment. For example, expression profiling can be used to determine whether the expression of cancer related genes has returned to normal levels. If not, the dose of one or more compounds in the therapy can be altered to either increase or decrease the effect of the therapy on the expression levels of the corresponding cancer related gene(s). In addition, this analysis can be used to determine whether a therapy affects the expression of other genes (e.g., genes that are associated with adverse side-effects). If desired, the dose or composition of the therapy can be altered to prevent or reduce undesired side-effects.

Exemplary Formulations and Methods of Administration

For stabilizing, treating, or preventing a disease or disorder such as cancer or an increased risk for a disease or disorder such as cancer, a composition may be formulated and administered using any method known to those of skill in the art (see, e.g., U.S. Pat. Nos. 8,389,578 and 8,389,557, which are each hereby incorporated by reference in its entirety). General techniques for formulation and administration are found in "Remington: The Science and Practice of Pharmacy," 21st Edition, Ed. David Troy, 2006, Lippincott Williams & Wilkins, Philadelphia, Pa., which is hereby incorporated by reference in its entirety). Liquids, slurries, tablets, capsules, pills, powders, granules, gels, ointments, suppositories, injections, inhalants, and aerosols are examples of such formulations. By way of example, modified or extended release oral formulation can be prepared using additional methods known in the art. For example, a suitable extended release form of an active ingredient may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Optionally, the finished tablet may be coated or uncoated.

Typical routes of administering such compositions include, without limitation, oral, sublingual, buccal, topical, transdermal, inhalation, parenteral (e.g., subcutaneous, intravenous, intramuscular, intrasternal injection, or infusion techniques), rectal, vaginal, and intranasal. In preferred embodiments, the therapy is administered using an extended release device. Compositions of the invention are formulated so as to allow the active ingredient(s) contained therein to be bioavailable upon administration of the composition. Compositions may take the form of one or more dosage units. Compositions may contain 1, 2, 3, 4, or more active ingredients and may optionally contain 1, 2, 3, 4, or more inactive ingredients.

Alternate Embodiments

Any of the methods described herein may include the output of data in a physical format, such as on a computer screen, or on a paper printout. Any of the methods of the invention may be combined with the output of the actionable data in a format that can be acted upon by a physician. Some of the embodiments described in the document for determining genetic data pertaining to a target individual may be combined with the notification of a potential chromosomal abnormality (such as a deletion or duplication), or lack thereof, with a medical professional. Some of the embodiments described herein may be combined with the output of the actionable data, and the execution of a clinical decision that results in a clinical treatment, or the execution of a clinical decision to make no action.

In some embodiments, a method is disclosed herein for generating a report disclosing a result of any method of the invention (such as the presence or absence of a deletion or duplication). A report may be generated with a result from a method of the invention, and it may be sent to a physician electronically, displayed on an output device (such as a digital report), or a written report (such as a printed hard copy of the report) may be delivered to the physician. In addition, the described methods may be combined with the actual execution of a clinical decision that results in a clinical treatment, or the execution of a clinical decision to make no action.

In certain embodiments, the present invention provides reagents, kits, and methods, and computer systems and computer media with encoded instructions for performing such methods, for detecting both CNVs and SNVs from the same sample using the multiplex PCR methods disclosed herein. In certain preferred embodiments the sample is a single cell sample or a plasma sample suspected of containing circulating tumor DNA. These embodiments take advantage of the discovery that by interrogating DNA samples from single cells or plasma for CNVs and SNVs using the highly sensitive multiplex PCR methods disclosed herein, improved cancer detection can be achieved, versus interrogating for either CNVs or SNVs alone, especially for cancers exhibiting CNV such as breast, ovarian, and lung cancer. The methods in certain illustrative embodiments for analyzing CNVs interrogate for between 50 and 100,000 or 50 and 10,000, or 50 and 1,000 SNPs and for SNVs interrogate for between 50 and 1000 SNVs or for between 50 and 500 SNVs or for between 50 and 250 SNVs. The methods provided herein for detecting CNVs and/or SNVs in plasma of subjects suspected of having cancer, including for example, cancers known to exhibit CNVs and SNVs, such as breast, lung, and ovarian cancer, provide the advantage of detecting CNVs and/or SNVs from tumors that often are composed of heterogeneous cancer cell populations in terms of genetic compositions. Thus, traditional methods, which focus on analyzing only certain regions of the tumors can often miss CNVs or SNVs that are present in cells in other regions of the tumor. The plasma samples act as liquid biopsies that can be interrogated to detect any of the CNVs and/or SNVs that are present in only subpopulations of tumor cells.

The following examples are put forth so as to provide those of ordinary skill in the art with a complete disclosure and description of how to use the embodiments provided herein, and are not intended to limit the scope of the disclosure nor are they intended to represent that the Examples below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

EXAMPLES

Example 1. Personalized Circulating Tumor DNA Analysis to Monitor Colorectal Cancer Early detection of disease recurrence has been shown to improve survival in patients with colorectal cancer (CRC). Detection of circulating tumor DNA (ctDNA) post-operatively defines a subset of CRC patients with very high risk of recurrence. Previous studies have performed ctDNA analysis to monitor tumor burden in early-stage CRC using small gene panel sequencing or digital droplet PCR.

The aim of this example was to use a personalized multiplex-PCR NGS platform targeting 16 tumor-specific mutations per patient to assess minimal residual disease postoperatively and to monitor treatment response in CRC.

130 patients with stage I-IV CRC, treated with curative surgery, and (optional) adjuvant chemotherapy were included (See Table 1). Plasma samples were collected longitudinally at baseline prior to surgery and at scheduled control visits after surgery (FIG. 20A). Whole-exome sequencing identified somatic mutations; following Signatera standard workflow, patient-specific multiplex-PCR assays targeting 16 somatic single-nucleotide and indel variants were assayed by massive parallel sequencing in plasma samples collected pre- and post-surgery, and during adjuvant therapy (FIG. 20B).

TABLE 1

Patient Characteristics and Demographics (N = 130)
Patients, N = 130, Age (years), median (range) = 69.9 (43.3-91),
Imaging follow-up, months, median = 12.3

| Gender, n (%) | | Histological grade, n (%) | |
| --- | --- | --- | --- |
| Female | 57 (43.1) | Moderatley differentiated | 100 (76.9) |
| Male | 74 (56.9)) | Poorly differentiated | 20 (15.5) |
| | | ND* | 10 (7.7) |
| Location, n (%) | | Adj. treatment, n (%) | |
| Colon | 124 (95.4)) | I | 0 (0) |
| Rectum | 6 (4.6) | II | 6 (14.3) |
| | | III | 71 (88.8) |
| | | IV | 2 (100) |
| | | Total | 79 (60.8) |
| Pathological stage, n (%) | | Relapse, n (%) | |
| I | 6 (4.7) | I | 0 (0) |
| II | 42 (3.2) | II | 3 (7.1) |
| III | 80 (62.5) | III | 19 (23.8) |
| IV | 2 (1.6) | IV | 0 (0) |
| | | Total | 22 (16.9) |
| Histological type, n (%) | | MSS/MSI | |
| Adenocarcinoma | 120 (92.3) | MSS | 104 (80) |
| Mucinous carcinoma | 10 (7.7) | MSI | 17 (13.1) |
| | | ND* | 9 (6.9) |

*ND = Not determined

Figure 22:
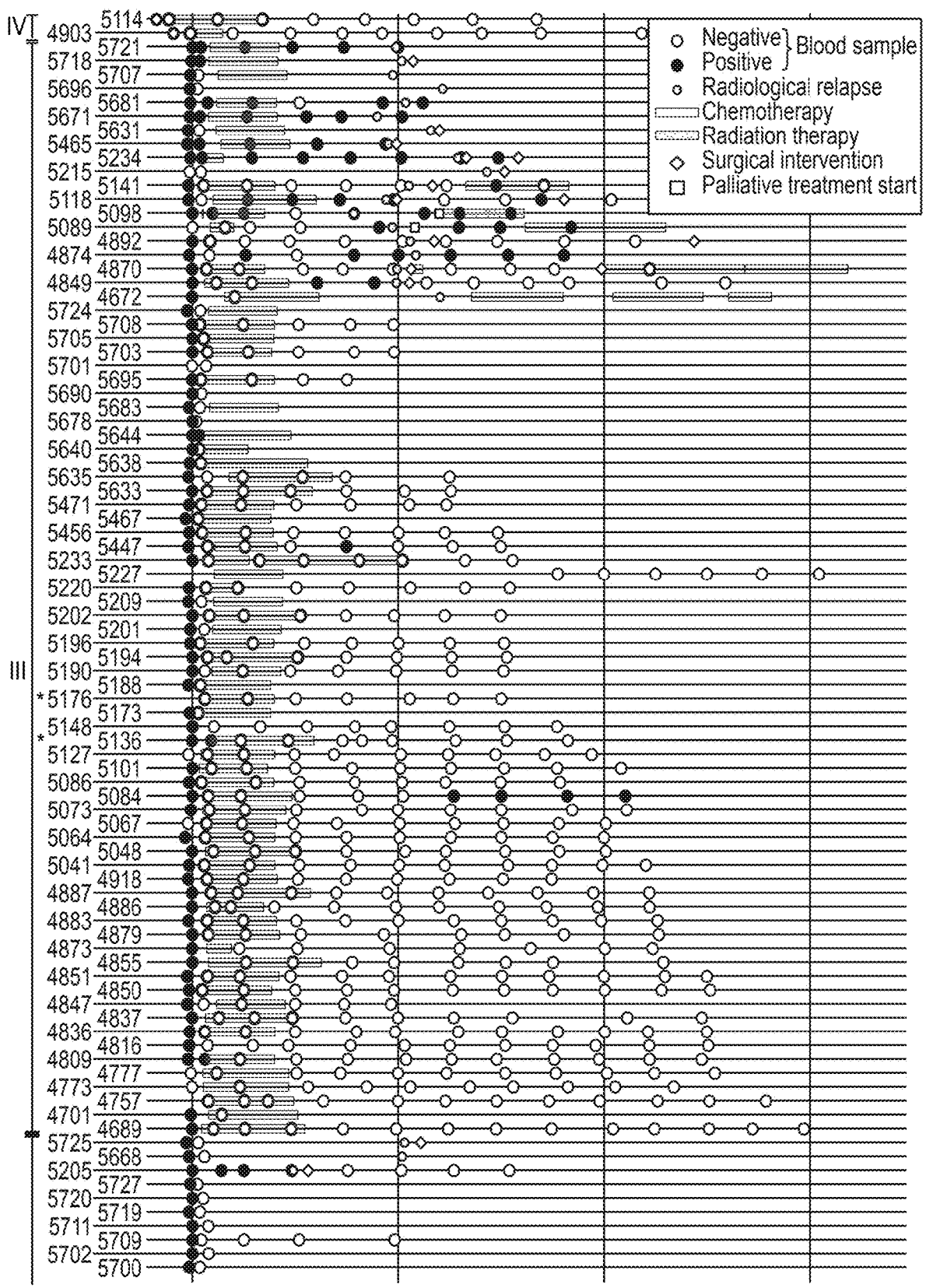
FIG. 22: Patient Summaries for 36 Months of Surveillance and Plasma Collection.
Figure 22:
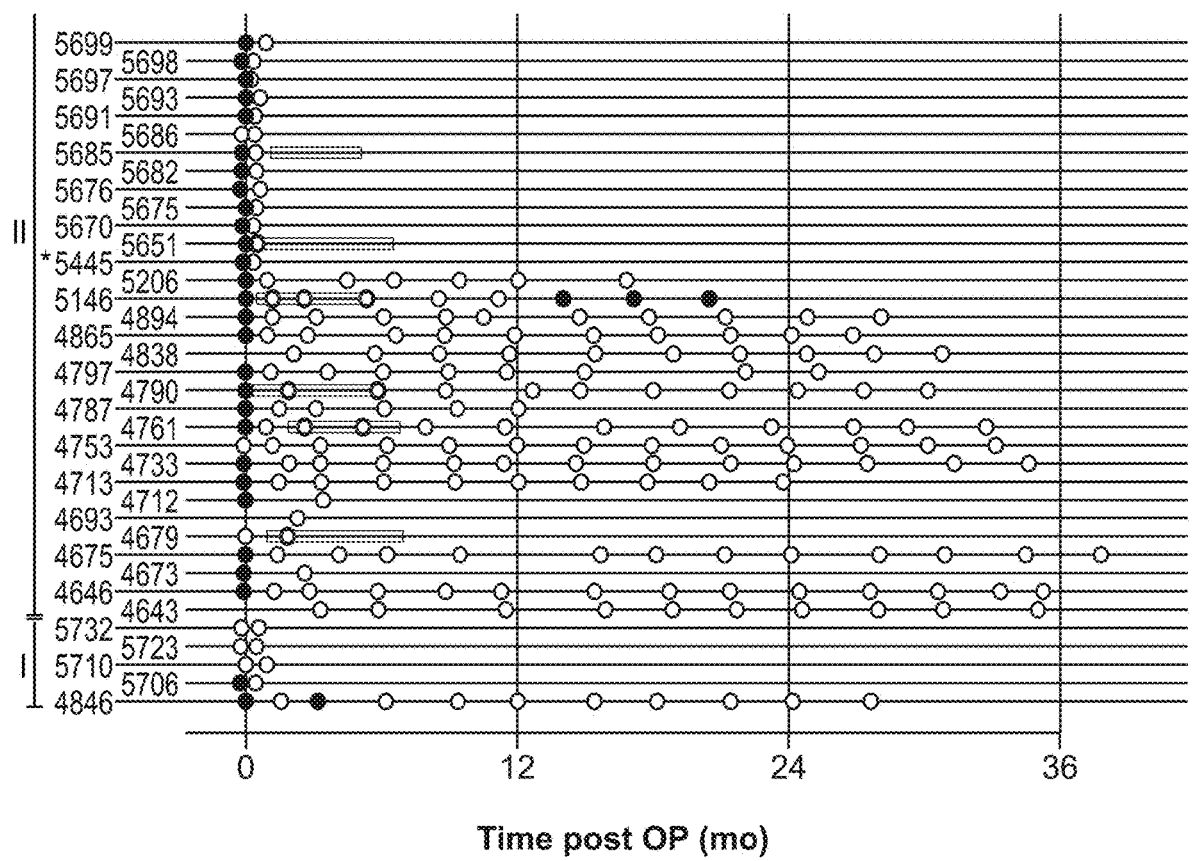
Figures 23A, 23B:
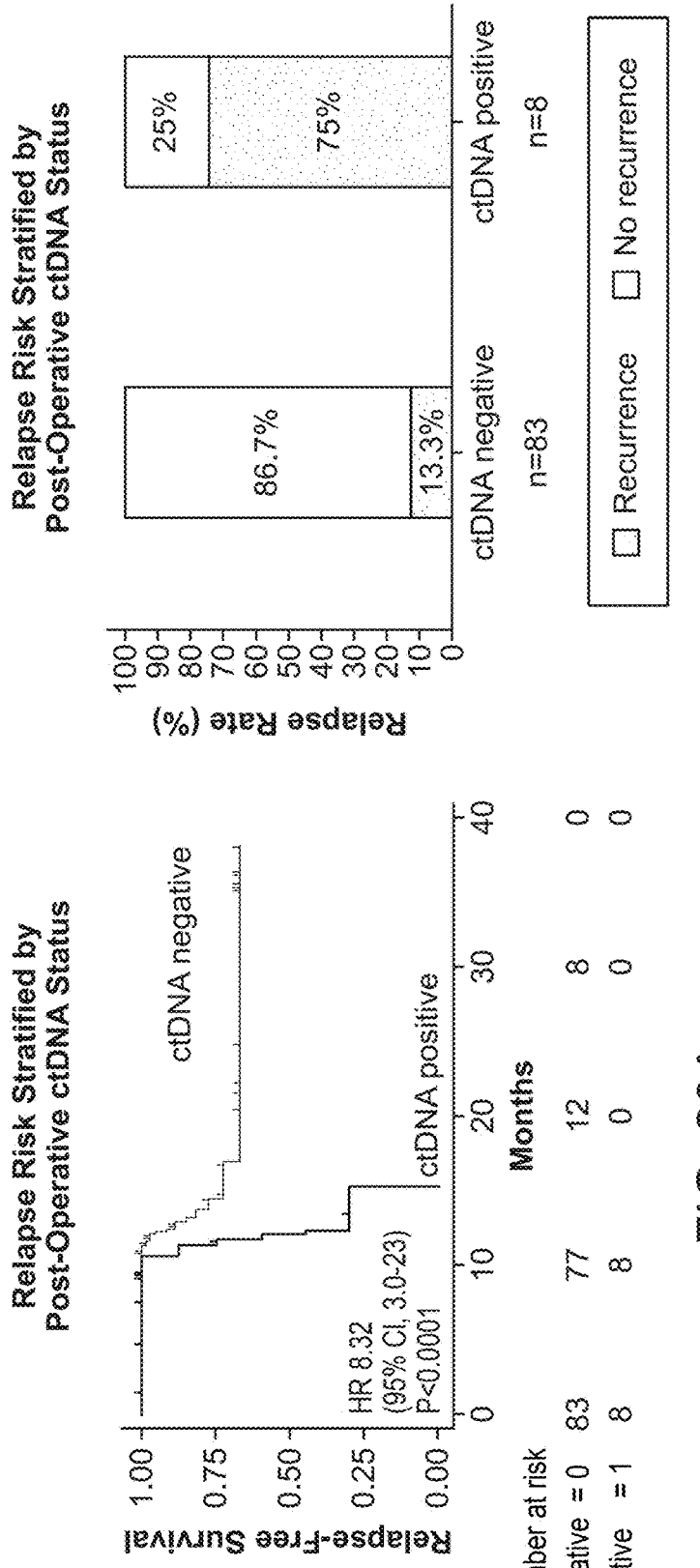
FIG. 23A-B: Relapse risk stratified by post-operative ctDNA status.

FIG. 22 provides a schematic overview of ctDNA profiling results of more than 800 plasma samples from 128 of 130 patients. FIG. 23A-B shows relapse risk stratified by post-operative ctDNA status. ctDNA status was established based on the first postoperative blood sample, which was drawn by week 6 and prior to start of ACT. FIG. 23(A) shows Kaplan Meier analysis of recurrence free survival stratified by ctDNA status. Patients without event were censored at end of follow-up. FIG. 23(B) shows relapse rates according to ctDNA status (no patients censored). Adjuvant chemotherapy was given to 58 patients, which probably affected the relapse rate of the ctDNA positive patients.

Figure 24B:
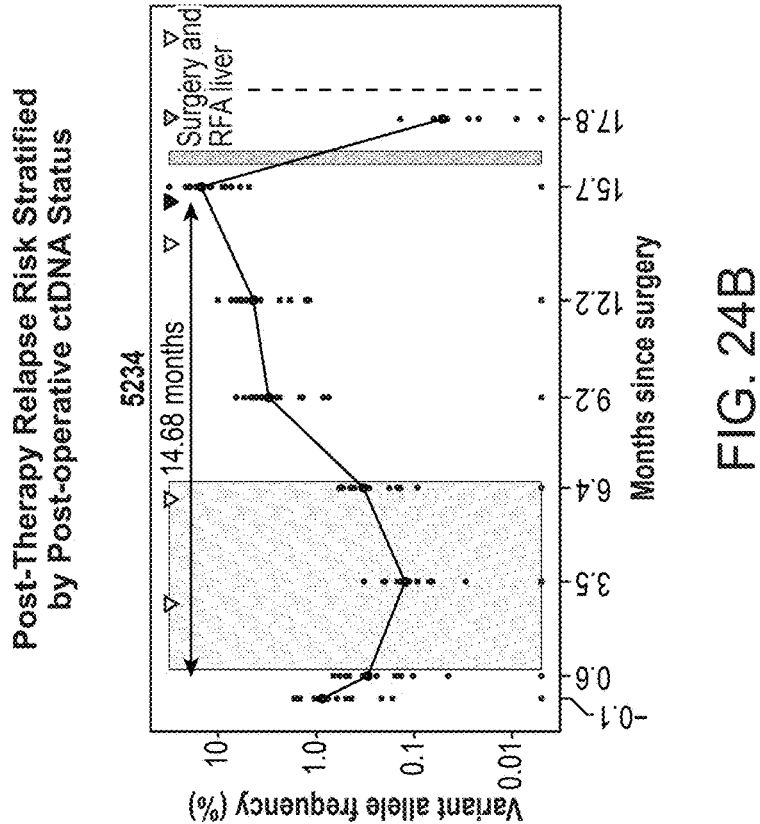
FIG. 24A-B: Post-therapy Relapse Risk Stratified by Postoperative ctDNA Status.
Figure 24A:
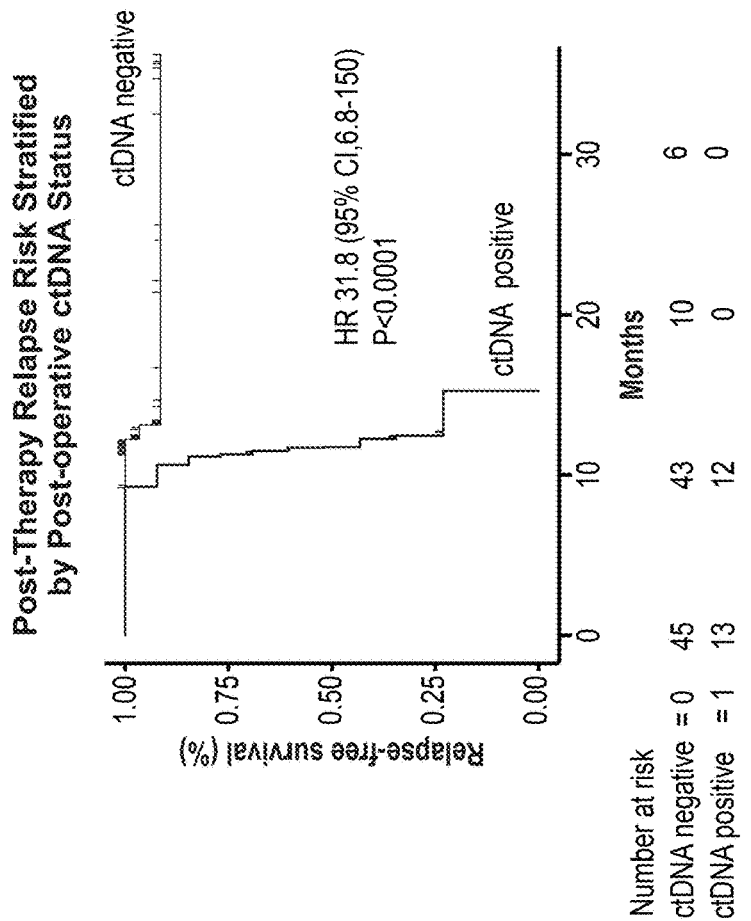

FIG. 24(A) shows relapse risk after post-adjuvant chemotherapy, stratified by post-adjuvant ctDNA status. Patients were scored ctDNA positive if any time-point post-adjuvant was positive and negative all post-adjuvant time-points were negative. FIG. 24(B) shows ctDNA profiling of a representative patient during adjuvant and post-adjuvant treatment.

Figure 25:
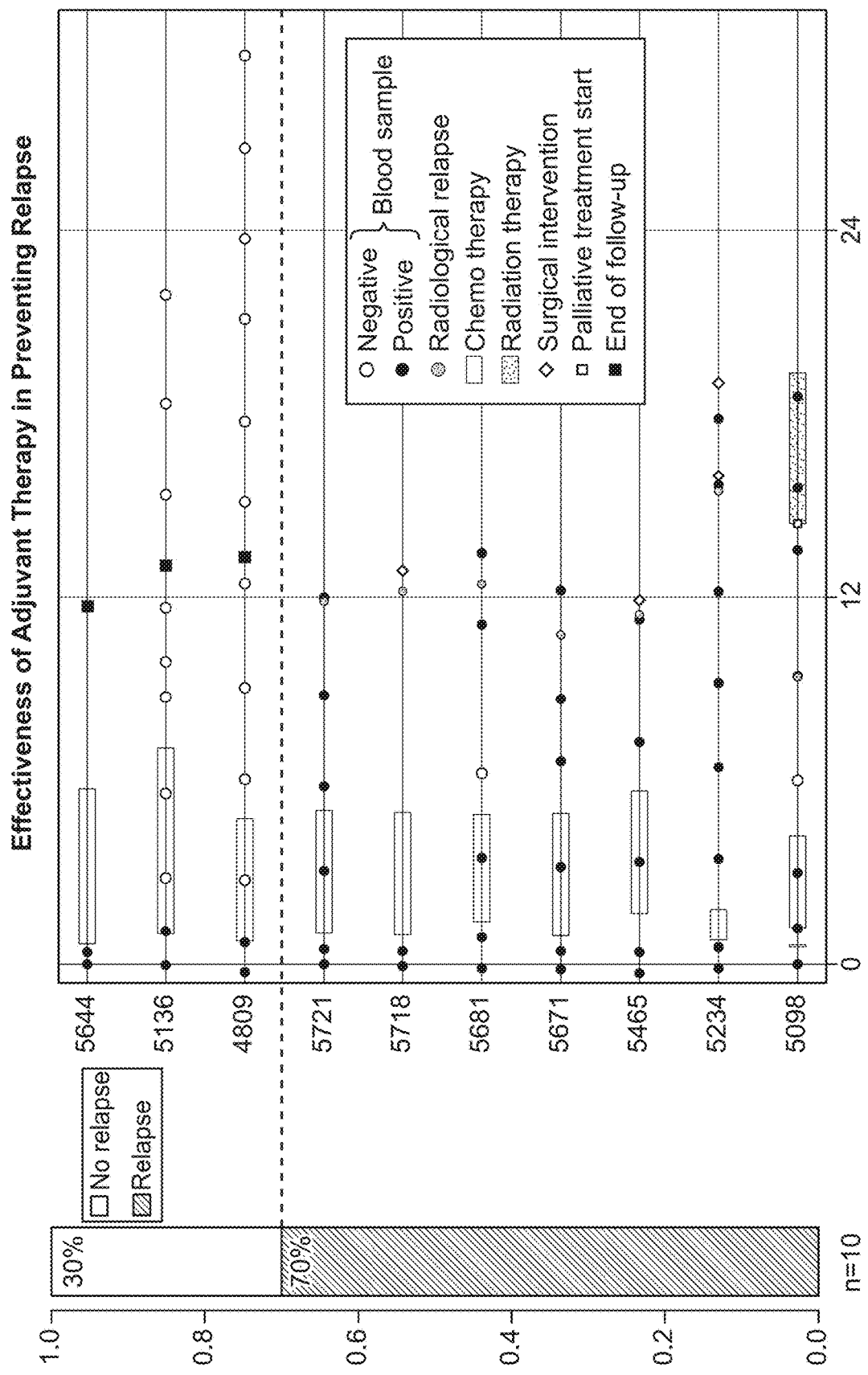
FIG. 25: Effectiveness of adjuvant therapy in preventing relapse.

FIG. 25 shows relapse rate of 10 patients post-operative ctDNA-positive prior to treatment with adjuvant chemotherapy, as well as how ctDNA was cleared by ACT for two of three non-relapsing ctDNA positive patients.

Figure 26B:
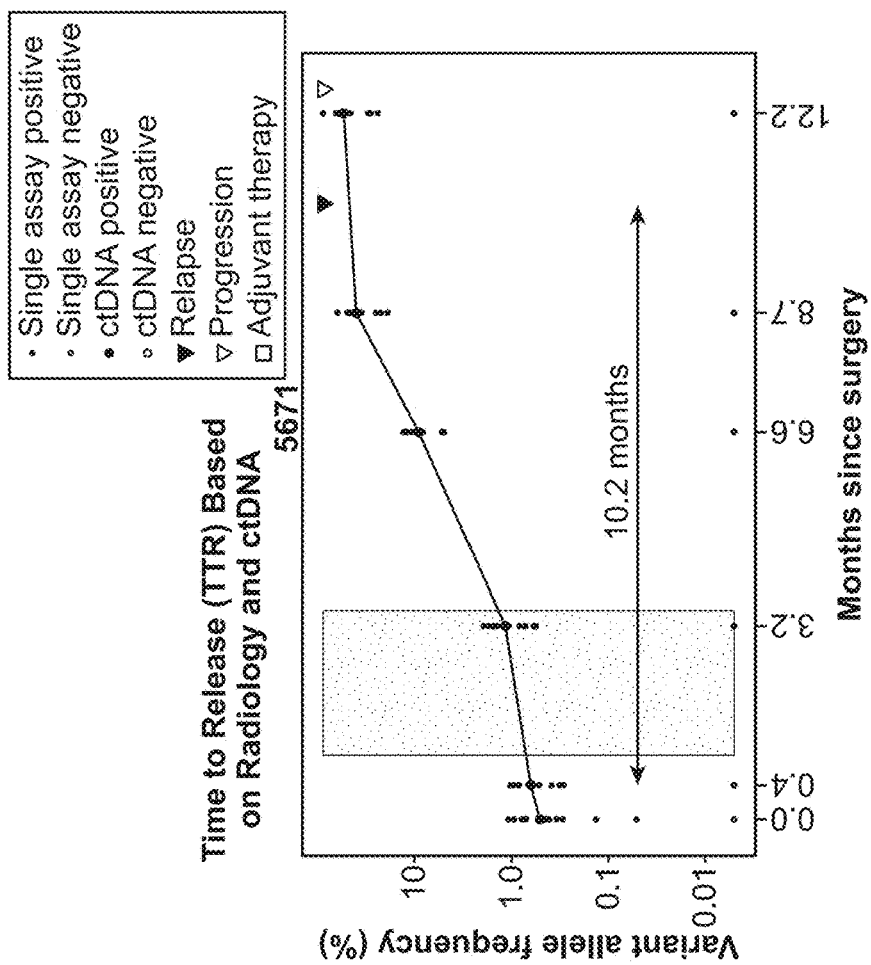
FIG. 26A-B: Time to Release Based on Radiology and ctDNA.
Figure 26A:
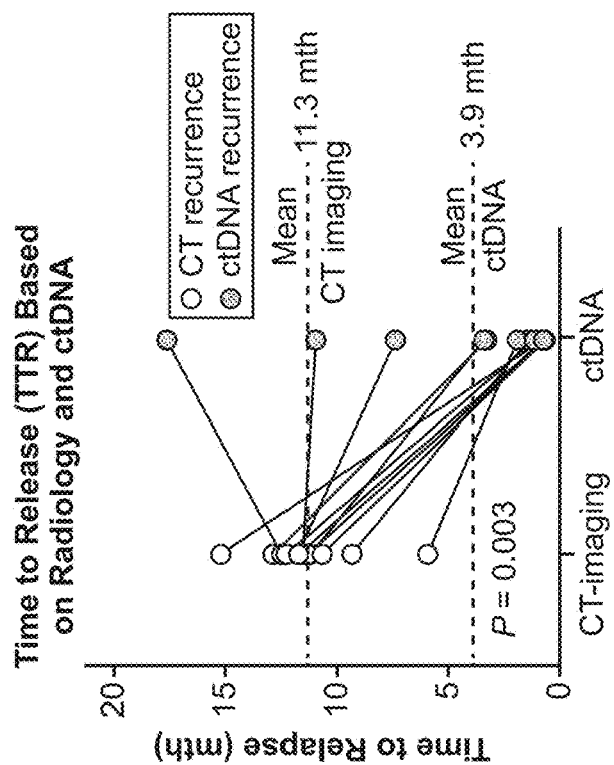
Figure 27A:
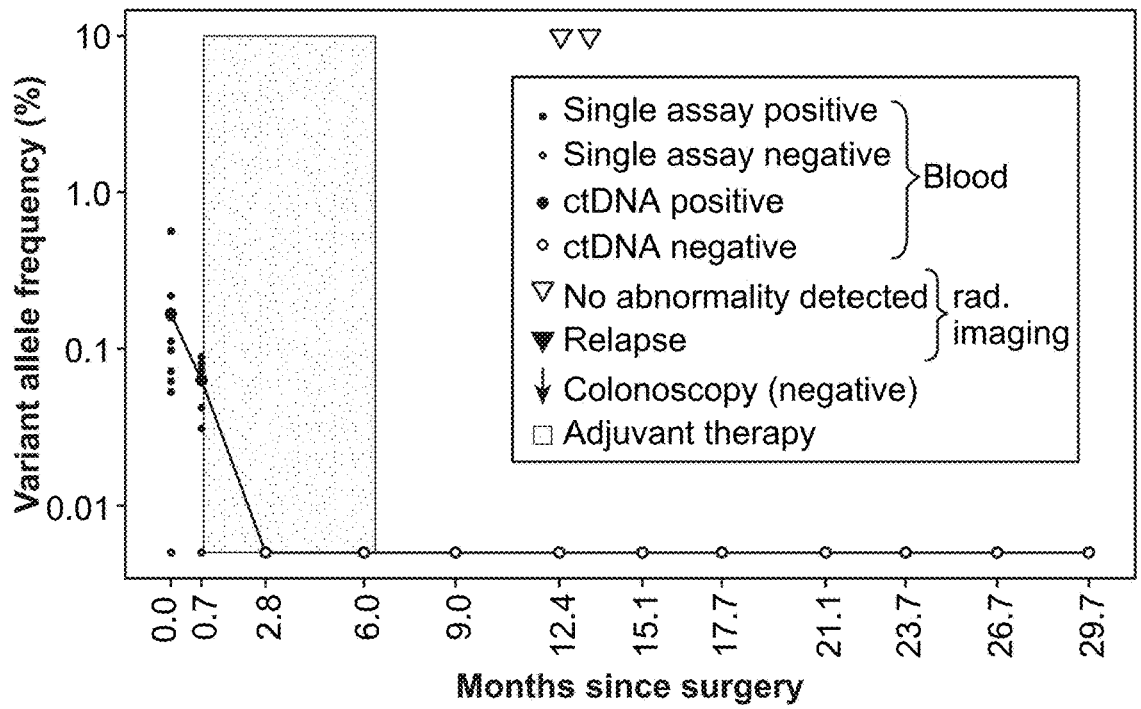
FIG. 27A-D: Early Detection of Relapse and Prediction of Treatment Response.
Figure 27B:
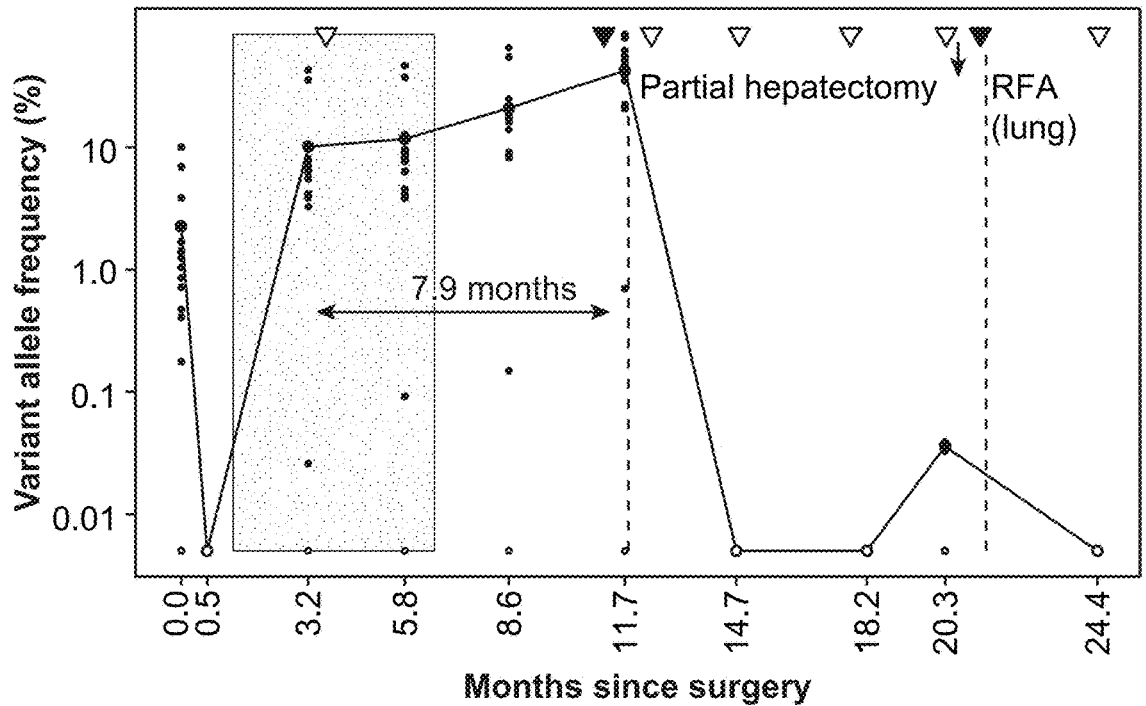
Figure 27C:
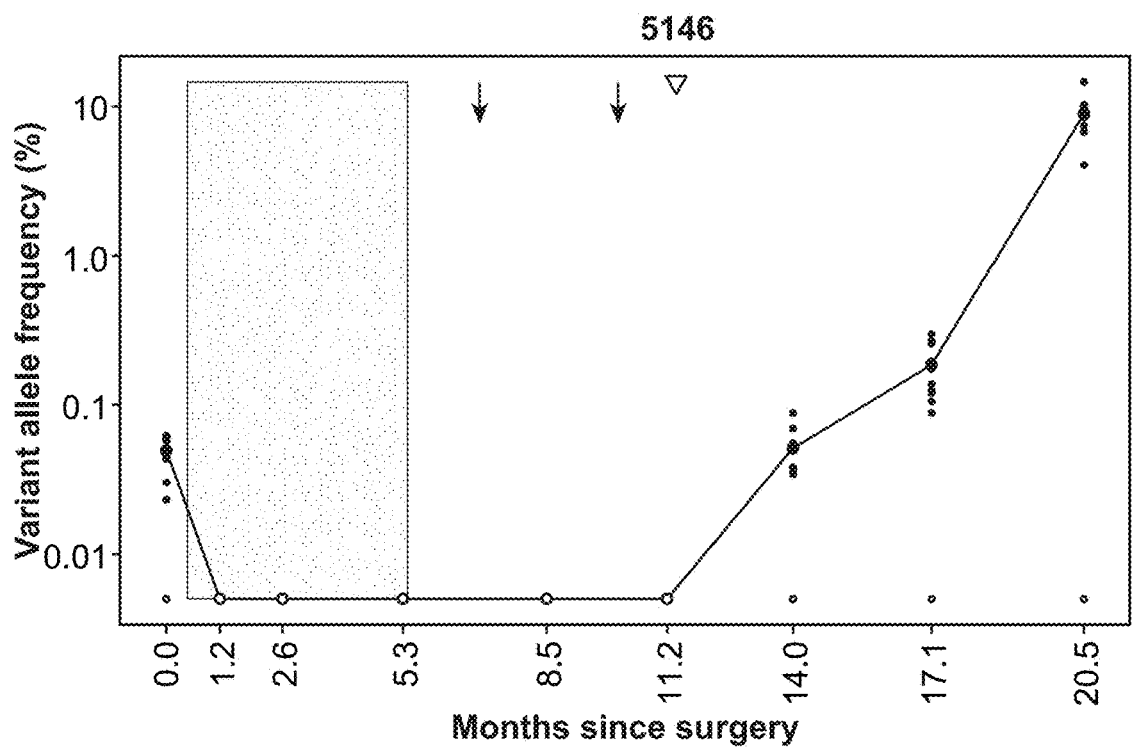
Figure 27D:
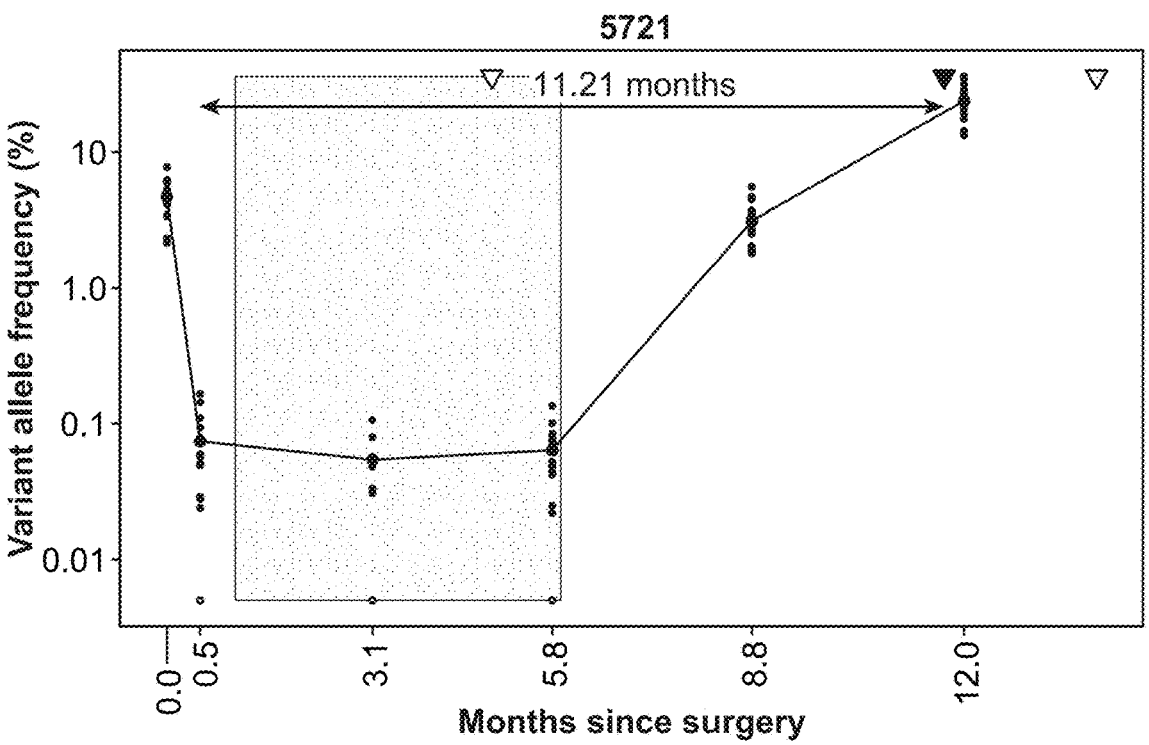

FIG. 26A-B shows comparison of time to recurrence (TTR) using ctDNA and CT-imaging: (A) comparison of TTR using ctDNA and CT-imaging for the 12 recurrence patients with recurrence was detected by both modalities; (B) serial ctDNA profiling of a representative recurrence patient with a 10.2 months ctDNA lead-time.

FIG. 27A-D shows serial ctDNA profiling of four representative patients.

In conclusion, the Signatera RUO approach for massive paralleled sequencing of personalized multiplex-PCR assays targeting tumor specific mutations is a highly sensitive and specific platform for detection and quantification of ctDNA. Post-operative ctDNA analysis enables stratification of CRC patients into subgroups with either very high or very low recurrence risk, both prior to and after ACT. Both prior to and after adjuvant chemotherapy. Longitudinal ctDNA analysis enables efficient post-operative treatment monitoring and early detection of recurrence ctDNA analysis has great utility in guiding treatment decisions, both in the adjuvant and post-adjuvant setting.

Example 2. Sequencing of Plasma cfDNA from Patients with Locally Advanced Bladder Cancer for Surveillance and Therapeutic Efficacy Monitoring Studies on different cancer types have shown that circulating tumor DNA (ctDNA) levels can be efficiently used to monitor treatment response to neoadjuvant therapy and/or detect disease recurrence earlier than clinical and radiological detection. In bladder cancer, mutations in plasma have been previously used to monitor response during treatment and identify early signs of metastatic disease. Recently, longitudinal ctDNA detection in patients with NSCLC was described and a personalized circulating tumor DNA (ctDNA) detection assay was developed (Signatera™ RUO).

The aim of the study was to use patient-specific mutations identified in the primary tumor to detect metastatic relapse, evaluate prognosis, and monitor treatment response in ctDNA from longitudinally-collected plasma samples.

Figure 28:
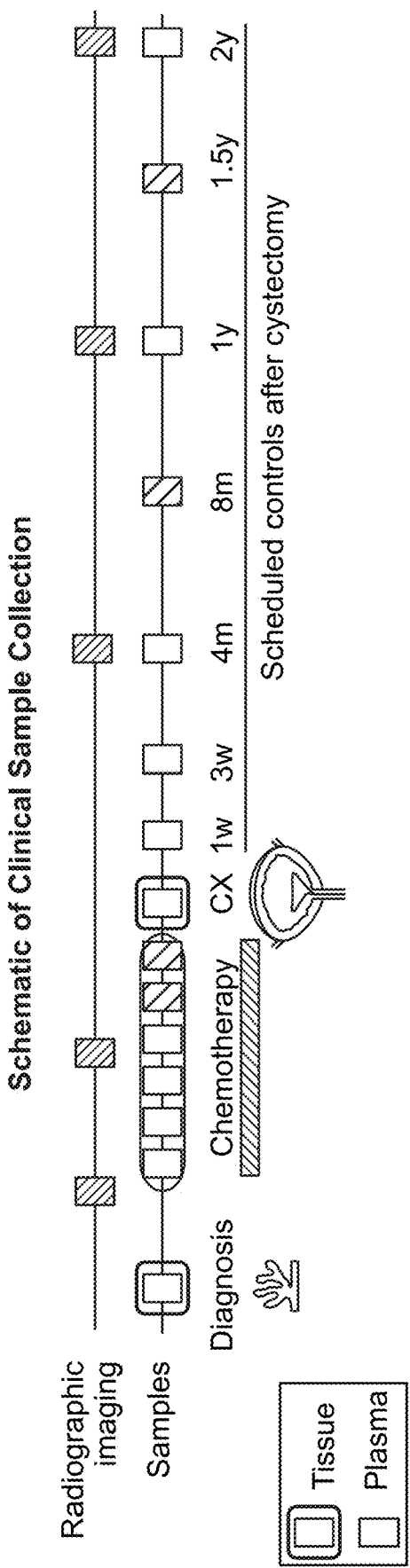
FIG. 28: Schematic of Clinical Sample Collection.

Clinical Protocol. Patients diagnosed with locally advanced muscle-invasive bladder cancer (MIBC) and scheduled for chemotherapy were prospectively recruited between 2013 and 2017. All patients were treated with neoadjuvant or first line chemotherapy before cystectomy (CX) and had up to 2 years follow-up (FIG. 28). Plasma samples were longitudinally collected pre- and post-systemic therapy and at scheduled control visits after CX.

Molecular Protocol. Patient-specific somatic mutations were identified by whole exome sequencing (WES) of tumor and matched normal samples. Personalized multiplex-PCR assays were used to detect patient-specific tumor DNA in plasma using cfDNA from longitudinally-collected plasma samples. For each patient, sequencing of 16 tumor-specific targets was performed and data were analyzed in a clinically-blinded fashion for the presence of ctDNA. Samples were considered ctDNA positive if and only if at least two positive patient-specific targets were called and met the qualifying confidence score threshold. Clinical results (radiographic imaging and treatment response) were unblinded and compared directly to the Signatera plasma call results.

A total of 50 patients were included in the study (Table 2).

TABLE 2

| Patient Characteristics and Demographics (N = 50) | | | |
|---|---|---|---|
| Age Years,[a] mean (range) | 65.5 (43-77) | | |
| Gender, n (%) | | Tumor stage at CX,[b] n (%) | |
| Females | 9 (18) | T0/Cis/Ta/T1 | 36 (72) |
| Male | 41 (82) | T2/T3/T4a | 12 (24) |
| Tumor stage at TUR-B, n (%) | | Metastasis,[c] n (%) | |
| T1/T2 | 43 (86) | Local relapse (pelvis, rectum, urethra) | 6 (12) |
| T4a/b | 7 (14) | Distant metastases (bone, lung, liver, skin) | 6 (12) |
| N stage before treatment, n (%) | | Clinical follow-up, days (range) | |
| N0 | 43 (86) | Disease free (CX; n = 38) | 434 (119-778) |
| N1/N2 | 7 (14) | Clinical relapse (CX; n = 10) | 347 (65-973) |
|  |  | Progression (CX unsuccessful; n = 2) | 280 (105-455) |

[a]At sampling;
[b]n = 48;
[c]n = 12.

Figures 29A, 29B:
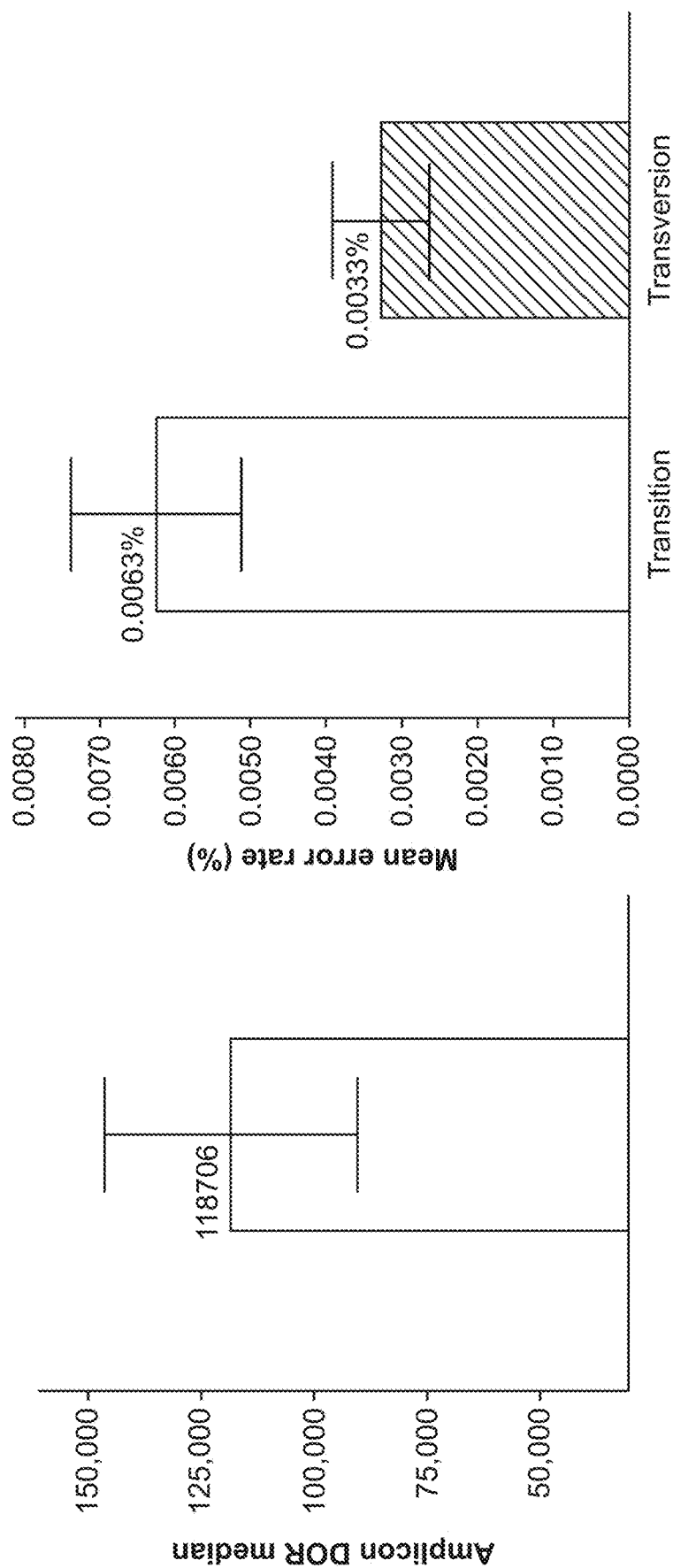
FIG. 29A-B: Plasma Sequencing QC.

In-line sequencing QC was performed across 5 HiSeq PE 2×50 runs; average per target depth-of-reads and background error rates are shown in FIG. 29A-B.

Early Detection of Relapse. Clinical relapse after CX was diagnosed for ten patients and ctDNA has been identified in plasma in nine of these patients with a median of 128 days prior to clinical relapse (Table 3). For one patient, the last control sample at 4 months post CX has not been analyzed yet.

TABLE 3

Molecular vs. Clinical Relapse (n = 9).

| Patient no. | Diagnosis stage | | CX stage | | ctDNA detection lead time (days) | Clin, Relapse after CX (days) | Location of metastasis |
|---|---|---|---|---|---|---|---|
| 1 | T2 | N0 | T2 | N0 | 0 | 973 | bone |
| 2 | T2 | N0 | T0 | N0 | 265 | 624 | local (urethra) |
| 3 | T4a | N0 | T4a | N0 | 0 | 119 | local (pelvis) |
| 4 | T2 | N0 | T3 | N0 | 152 | 208 | LN, lung, bone, local (pelvis) |
| 5 | T2 | N0 | T2 | N3 | 128 | 241 | Liver, bone |
| 6 | T2 | N0 | T4a | N0 | 96 | 379 | local (pelvis) |
| 7 | T2 | N0 | T1 | N3 | 245 | 309 | local |
| 8 | T4b | N0 | T3 | N0 | 186 | 324 | local (rectum) |
| 9 | T4b | N0 | T4a | N2 | 50 | 65 | sver |

Figure 30A:
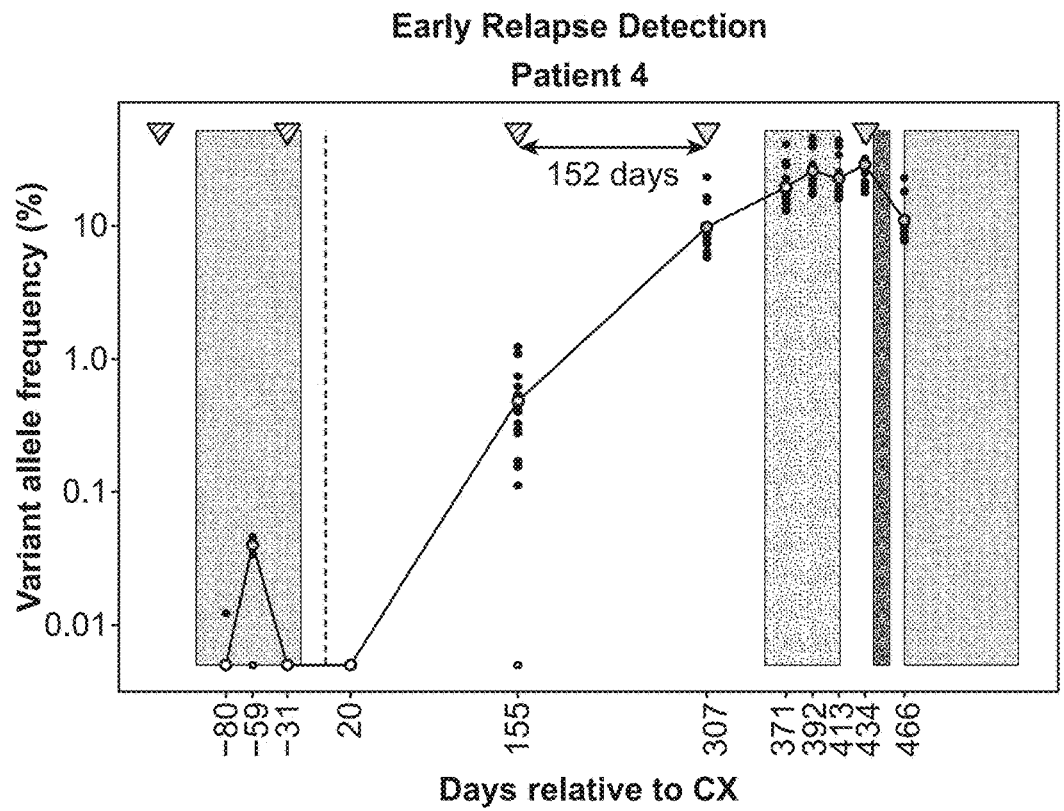
FIG. 30A-F: Early Relapse Detection.
Figure 30B:
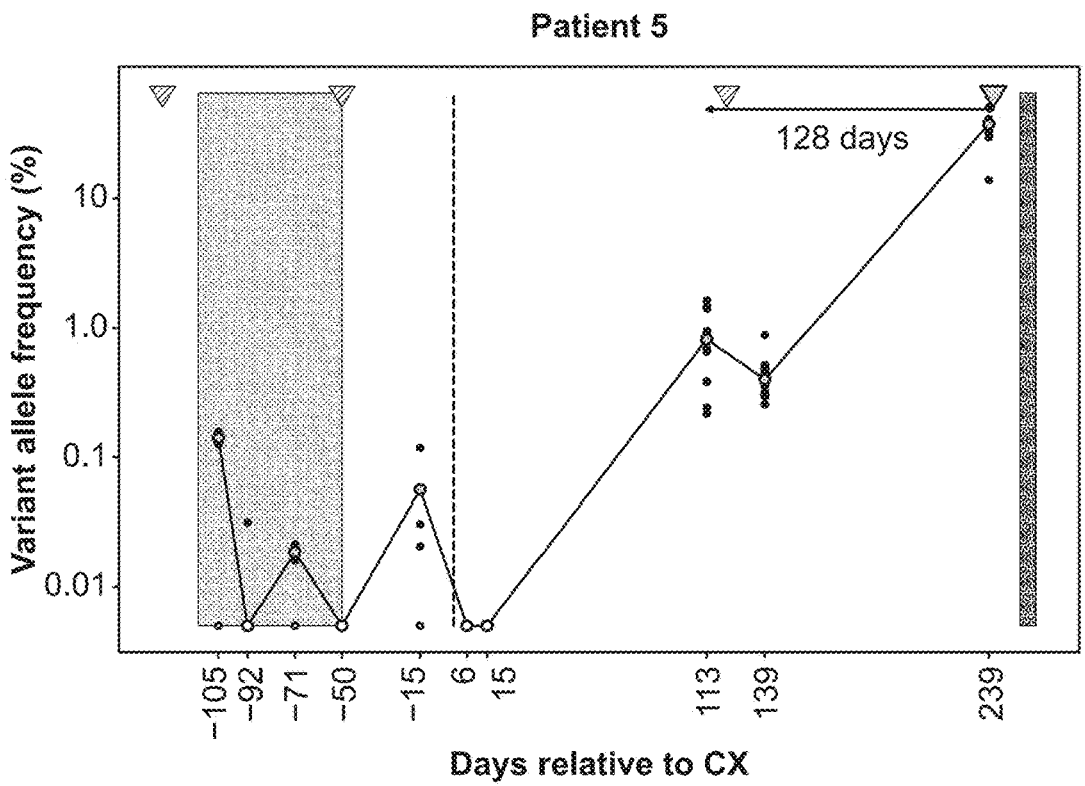
Figure 30C:
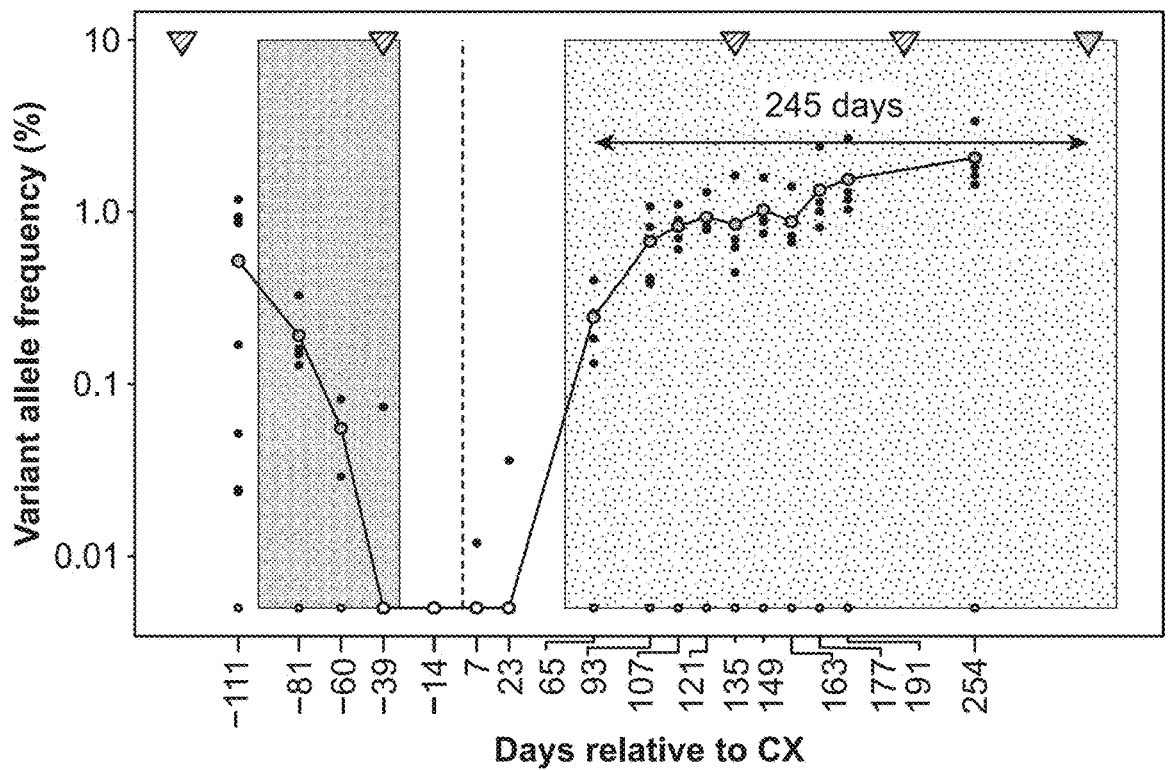
Figure 30D:
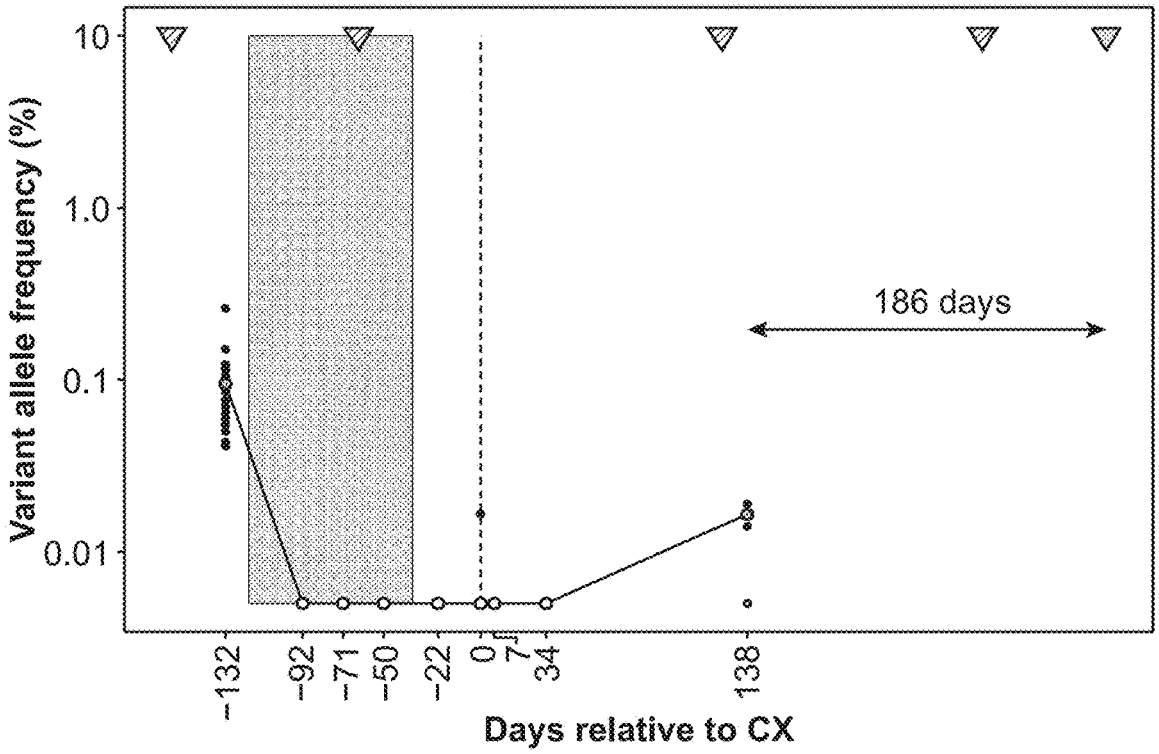
Figure 30E:
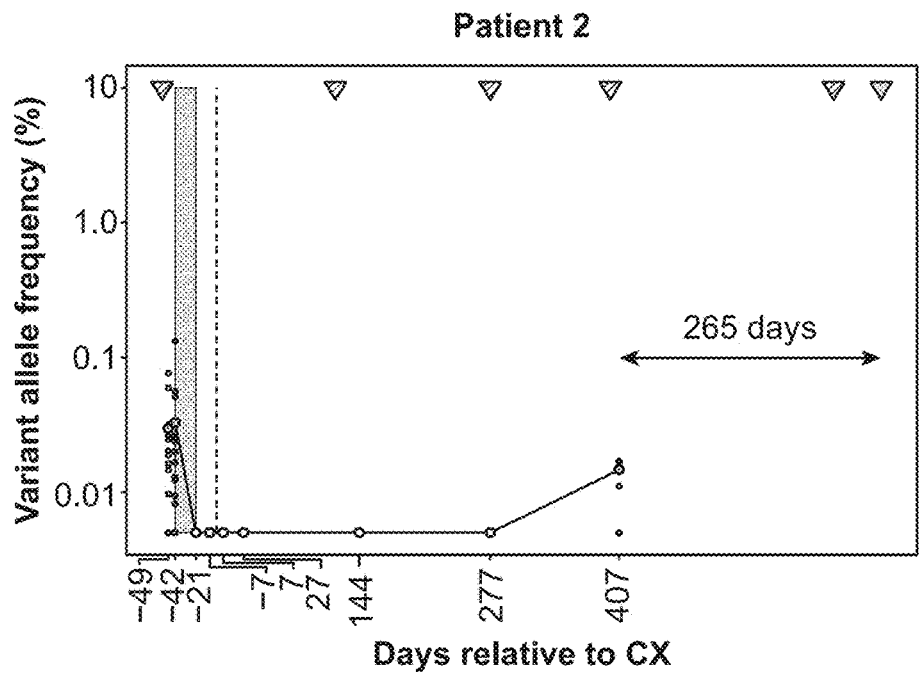
Figure 30F:
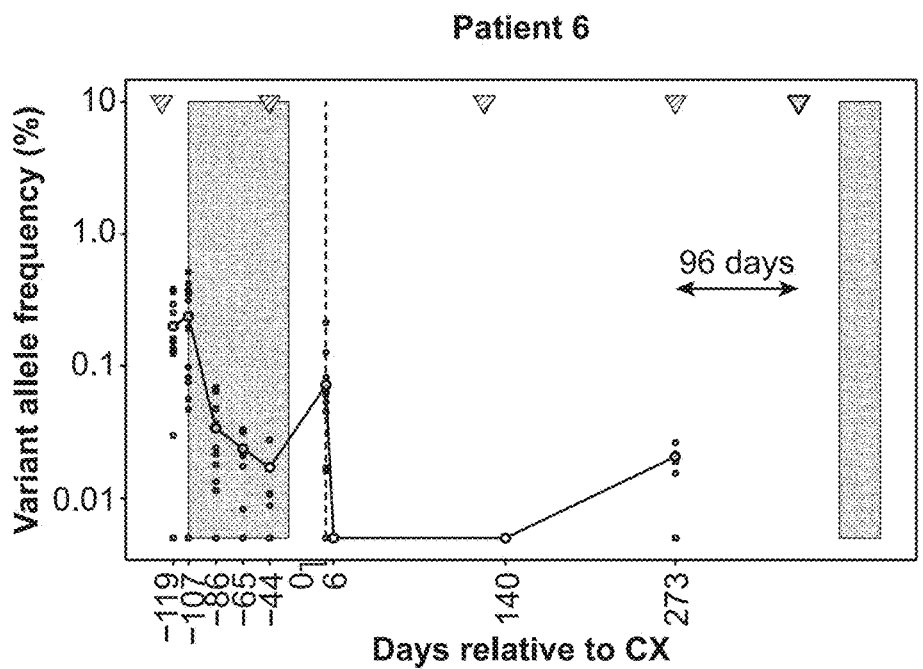
Figure 33:
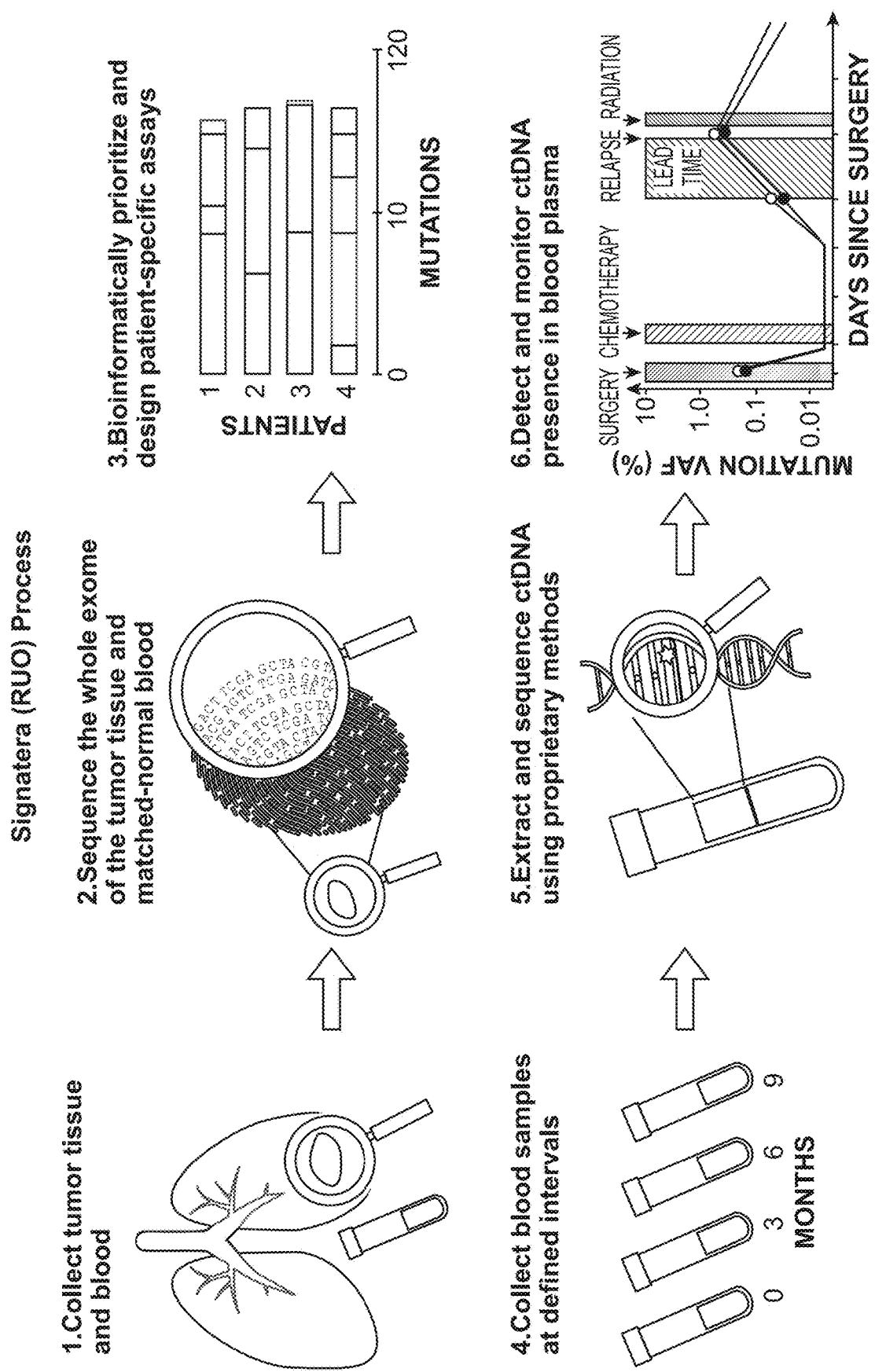
FIG. 33: Signatera (RUO) Process.

FIG. 30A-F depicts 6 patients that had early relapse detection. ctDNA was detected at VAFs as low as 0.02% at the time of molecular recurrence, which had a lead time of up to 265 days prior to clinical recurrence (FIGS. 30D, 30E and 30F). In most patients, response to chemotherapy corresponded to a decrease in ctDNA VAFs (Table 4).

TABLE 4

Prediction of Treatment Response following Chemotherapy

| Patient no. | Diagnosis stage | ctDNA VAF levels (%) | CX stage | ctDNA VAF levels (%) |
|---|---|---|---|---|
| 10[a] | T4a | 3.6 | T2, N0 | 0.02 |
| 11 | T2 | 0.1 | T0, N0 | ND |
| 12[b,c] | T1 | ND | T4a, N0 | 0.05 |
| 13 | T2 | 0.1 | T0, N0 | ND |
| 14 | T2 | 1.2 | CIS, N0 | ND |
| 15[a] | T1 | 0.3 | T2, N0 | ND |

[a]Received first line chemotherapy before CX.
[b]Underwent TUR-P before TUR-B, T1 tumor from Urethra, pars prostatica.
[c]Treatment response defined by advancement from inoperable to operable state after chemotherapy (despite clinical upstaging).
VAF, variant allele frequency; CX, cystectomy; ND, not detected.

FIG. 32A-B depicts two patients in which the treatment response was observed using ctDNA; ctDNA detected initially at diagnosis declined with neoadjuvant treatment and remained undetected after CX.

In conclusion, these data demonstrate that ctDNA analyses (e.g., via Signatera) can help inform on treatment response and identify disease recurrences up to 265 days earlier than radiographic imaging. Survival analyses identified significantly lower relapse free survival for patients with ctDNA at diagnosis or after cystectomy. Ultimately, ctDNA analysis could be incorporated into routine follow-up for early detection of relapse and consequently potentially earlier initiation of alternate treatment such as immunotherapy. The benefit in overall survival gained by ctDNA relapse detection should be assessed in randomized clinical trials.

Example 3. Highly-Sensitive Patient-Specific Multiplex PCR NGS-Based Non-Invasive Cancer Recurrence Detection and Therapy Monitoring Assay The identification of tumor mutations in circulating cell-free DNA holds great potential for the non-invasive detection of cancer relapse before clinical manifestation, detection of minimal residual disease after curative-intent treatment, and detection of therapeutically relevant mutations. To review and report analytical validation results for the detection of tumor-specific variants by the current version of the assay.

Signatera RUO. The Signatera™ (RUO) process starts with identifying and prioritizing somatic mutations from whole-exome sequencing of tumor and matched normal samples. Patient-specific multiplex-PCR assays targeting 16 somatic single-nucleotide and indel variants are then assayed by massively parallel sequencing in plasma samples collected throughout the patient's disease course to help detect and monitor circulating tumor DNA.

Analytical Validation. The analytical validation for the current version of the Signatera (RUO) assay was performed on two breast cancer cell lines (HCC2218, HCC1395), one lung cancer cell line (NCI-H1395) and their matched normal counterparts (HCC2218-BL, HCC1395-BL, and NCI-H1395-BL, respectively). Varying amounts of tumor cell line DNA (0%, 0.005%, 0.01%, 0.03%, 0.05%, 0.1%, 0.3%, 0.5%, 1%) were titrated into its respective matched normal cell line DNA. Multiplex-PCR assay primer pools (each consisting of 16 primer-pair assays specific to high-confidence somatic mutations) were designed using whole exome data from the corresponding tumor cell line DNA and its matched normal cell line DNA. The starting total input into library prep for each reaction was 20K genome equivalents; SNV and indel targets from the corresponding tumor DNA spike-in samples were amplified using the multiplex-PCR assay primer pools mentioned above. The mPCR products were barcoded, then pooled with other mPCR barcoded products, and subsequently sequenced on an Illumina HiSeq 2500 Rapid Run with 50 cycles of paired-end reads using the Illumina Paired End v2 kit with an average read depth of ~100,000/assay.

Figure 34A:
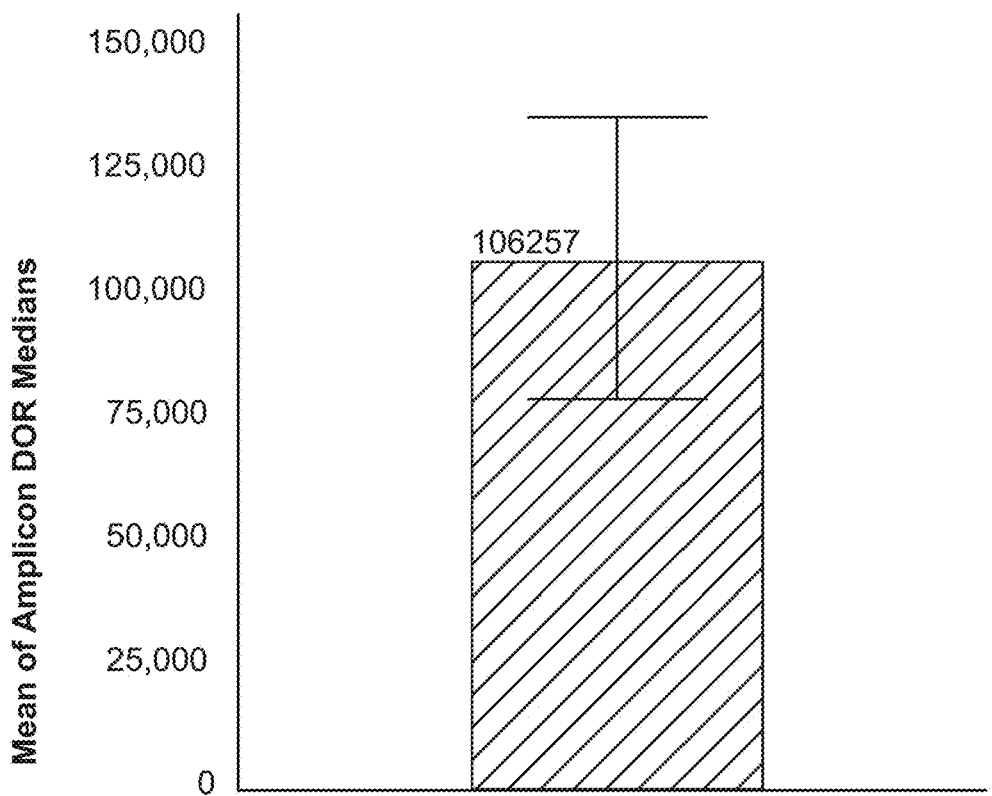
FIG. 34A-B: Plasma Sequencing QC.
Figure 34B:
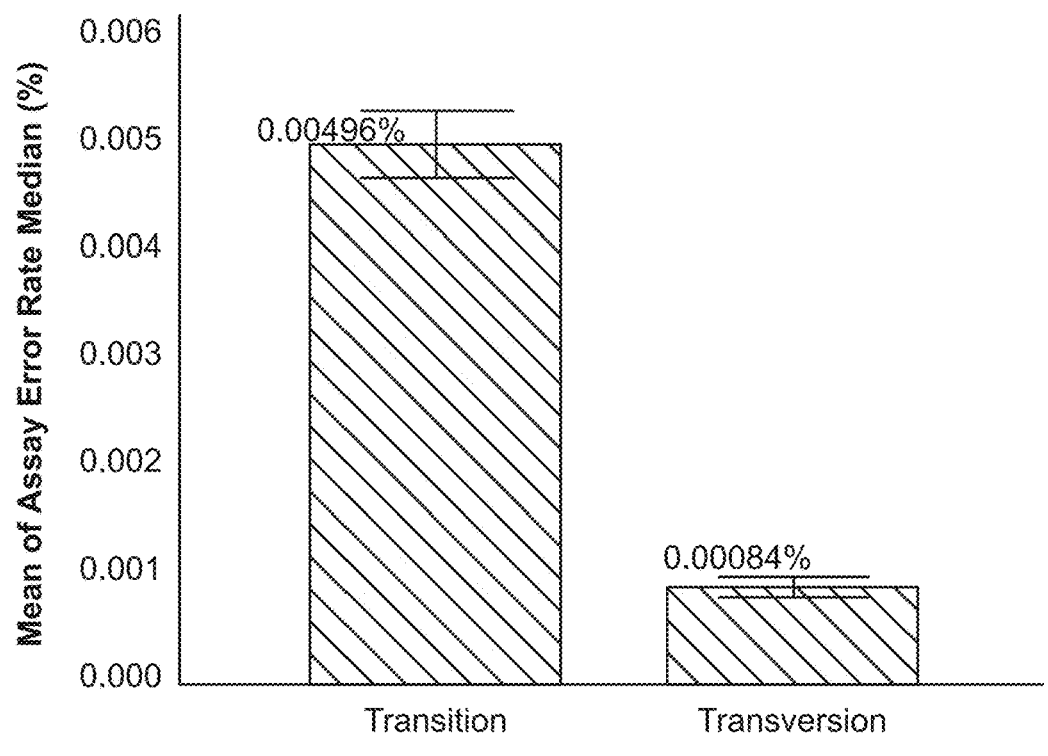
Figure 35:
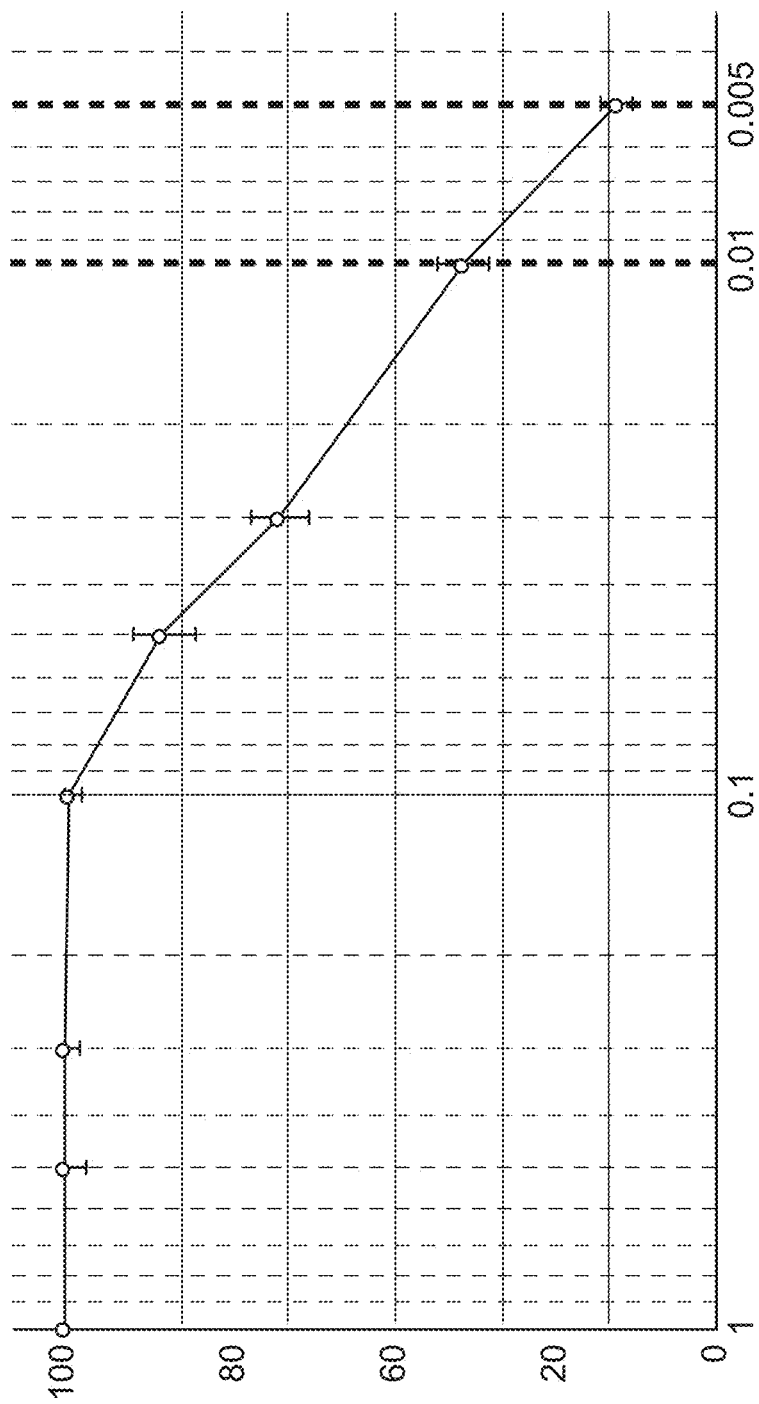
FIG. 35: Sensitivity of Single SNV Detection.
Figure 36A:
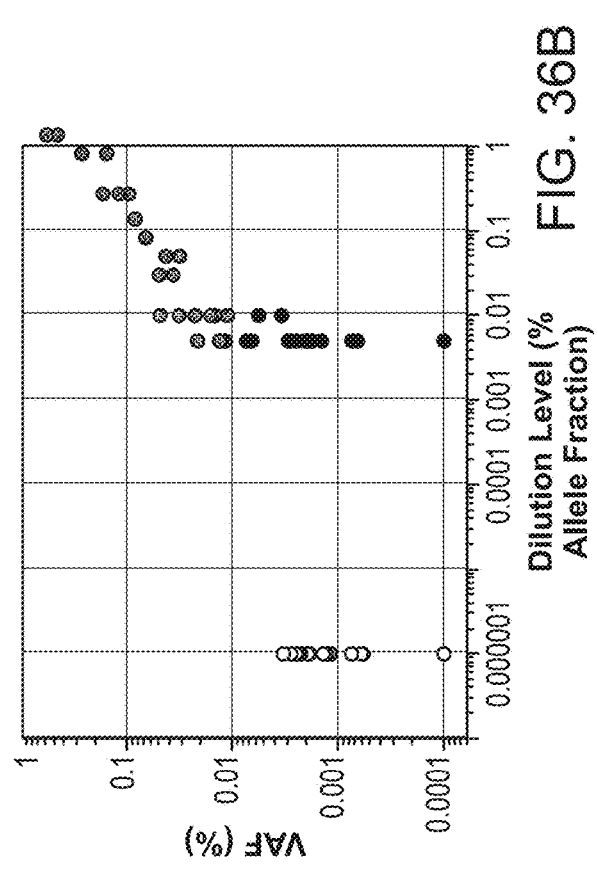
FIG. 36A-F: Expected Input vs Observed VAF with Signatera (RUO).
Figure 36B:
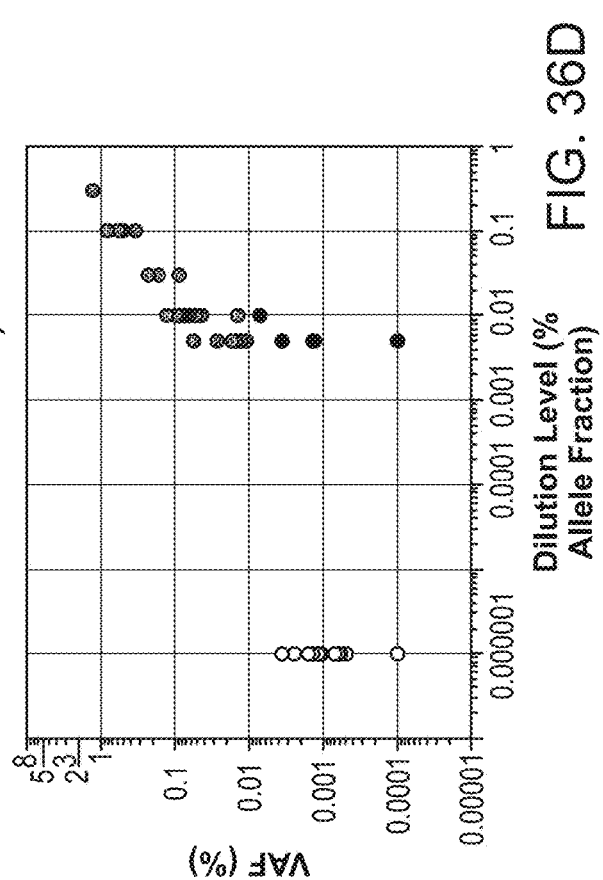
Figure 36C:
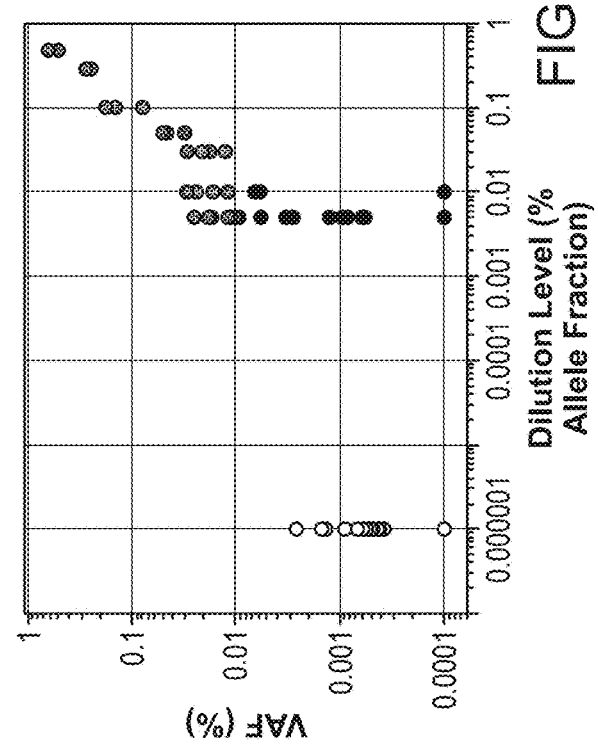
Figure 36D:
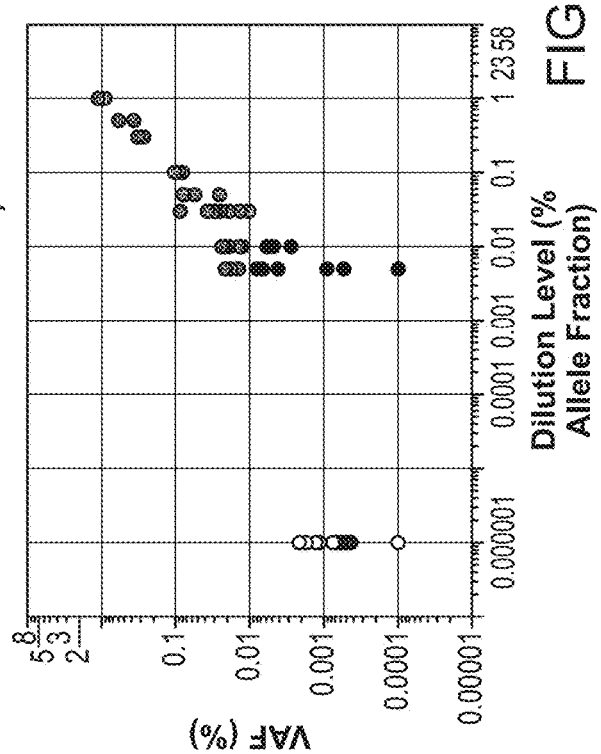
Figure 36F:
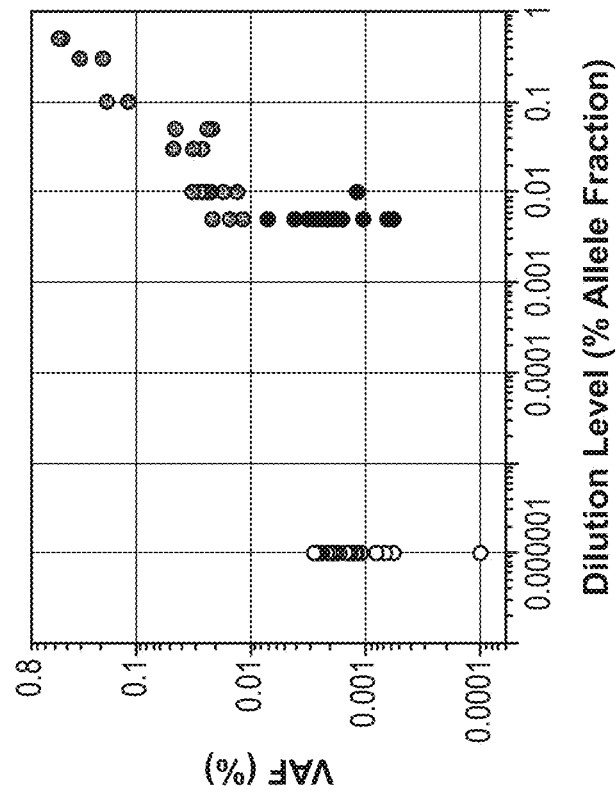
Figure 36E:
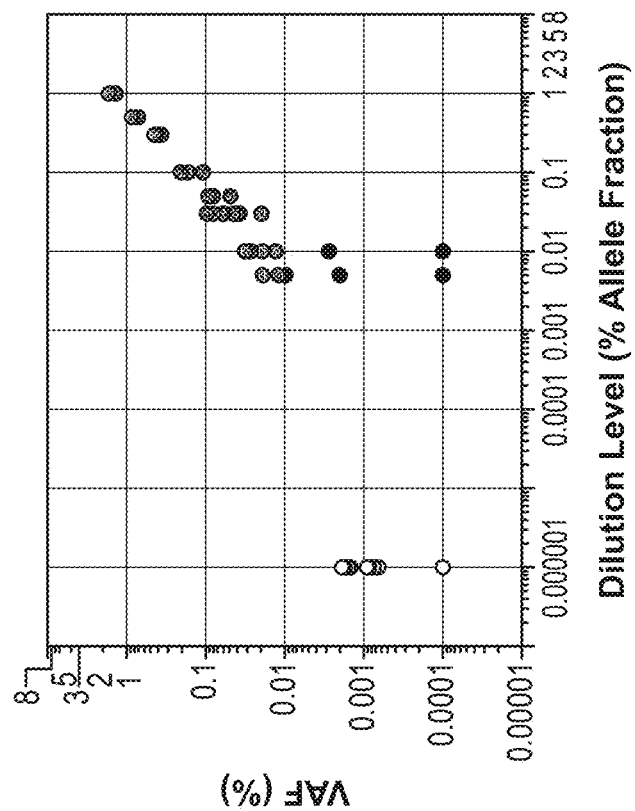

FIG. 34A-B depicts sequencing QC process checks across 4 HiSeq PE 2×50 runs, including, background transition and transversion error rates, and average per target depth-of-reads (DOR) of ~100K (where any targets receiving less than 5K reads were considered failed and not taken into account for calling).

An analytical sensitivity of ~60% for SNV detection at 0.03% spiked-in tumor DNA was achieved with Signatera (RUO) (Table 5).

TABLE 5

Analytical Sensitivity Results for the Current Version of Signatera (RUO)

| Tumor DNA Concentration (%) | Average Mutant Copies* | Detected SNVS | Total SNVs Used | Sensitivity | 95% CI |
|---|---|---|---|---|---|
| 0.006 | 1 | 120 | 794 | 15.1 | 12.7-17.8 |
| 0.010 | 2 | 246 | 635 | 36.7 | 34.9-42.7 |
| 0.030 | 6 | 291 | 433 | 67.2 | 62.6-71.6 |

TABLE 5-continued

Analytical Sensitivity Results for the Current Version of Signatera (RUO)

| Tumor DNA Concentration (%) | Average Mutant Copies* | Detected SNVS | Total SNVs Used | Sensitivity | 95% CI |
|---|---|---|---|---|---|
| 0.050 | 10 | 206 | 244 | 85.3 | 80.2-89.5 |
| 0.100 | 20 | 227 | 228 | 99.6 | 97.6-100 |
| 0.300 | 60 | 177 | 177 | 100 | 98-100 |
| 0.500 | 100 | 120 | 120 | 100 | 97-100 |
| 1.000 | 200 | 76 | 76 | 100 | 93-100 |

Figure 3:
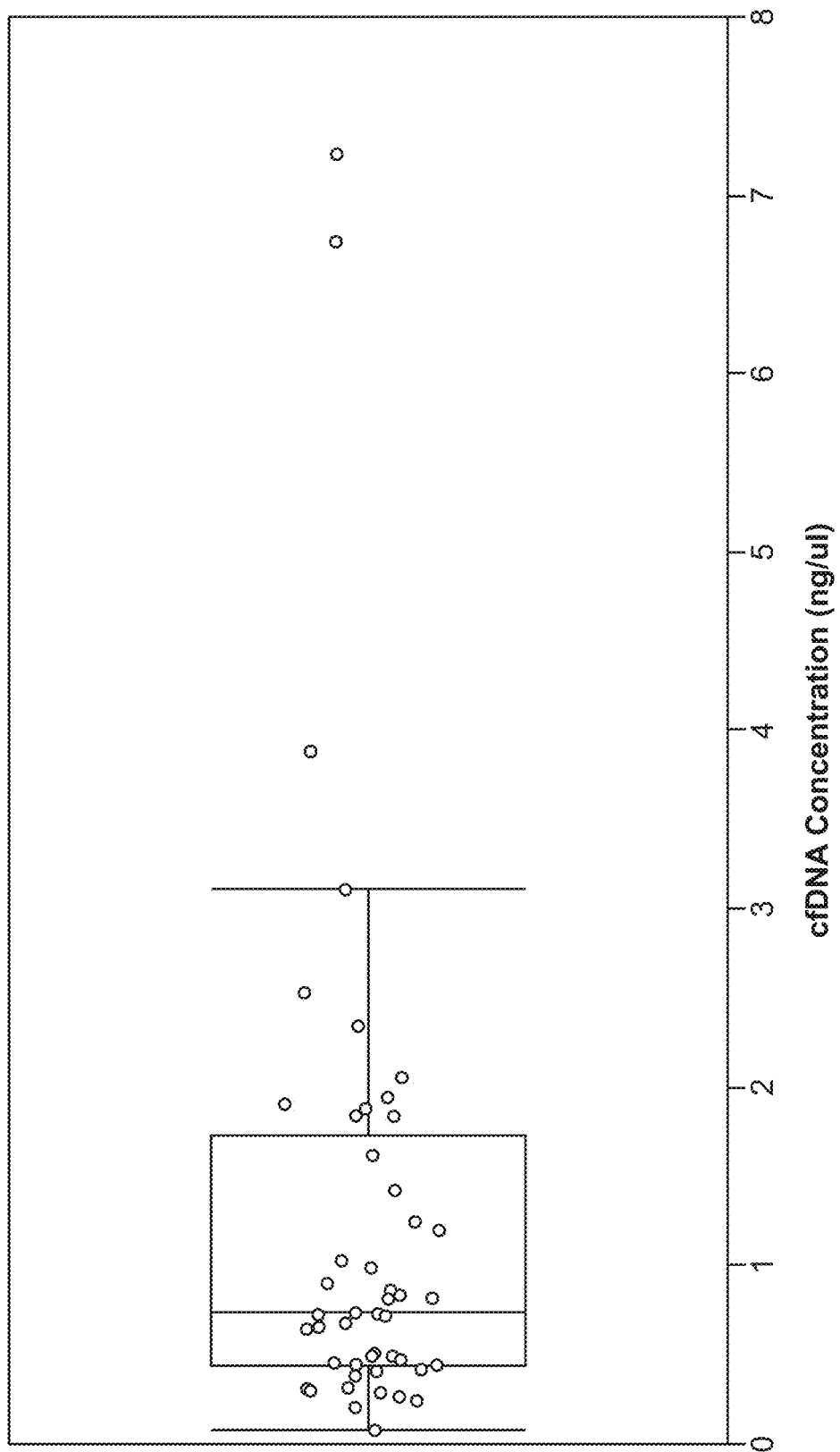
FIG. 3. Measured cfDNA concentration. Each data point refers to a plasma sample.
Figure 4:
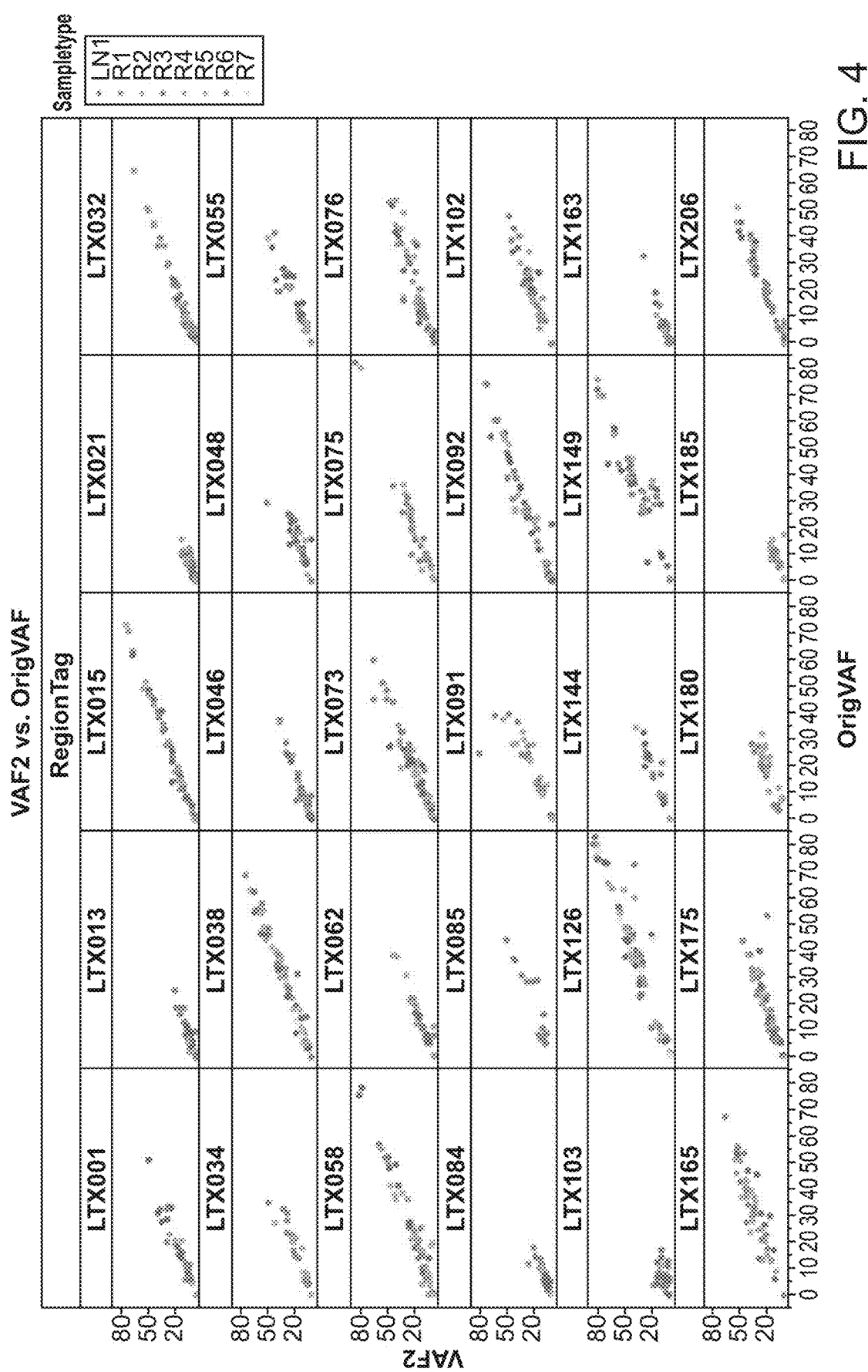
FIG. 4. Samples showing good correlation between tissue VAF measurements determined previously (x axis) and here using mPCR-NGS (y axis). Each sample is shown in a separate box, and the VAF data points are colored by tissue subsection.
Figure 5:
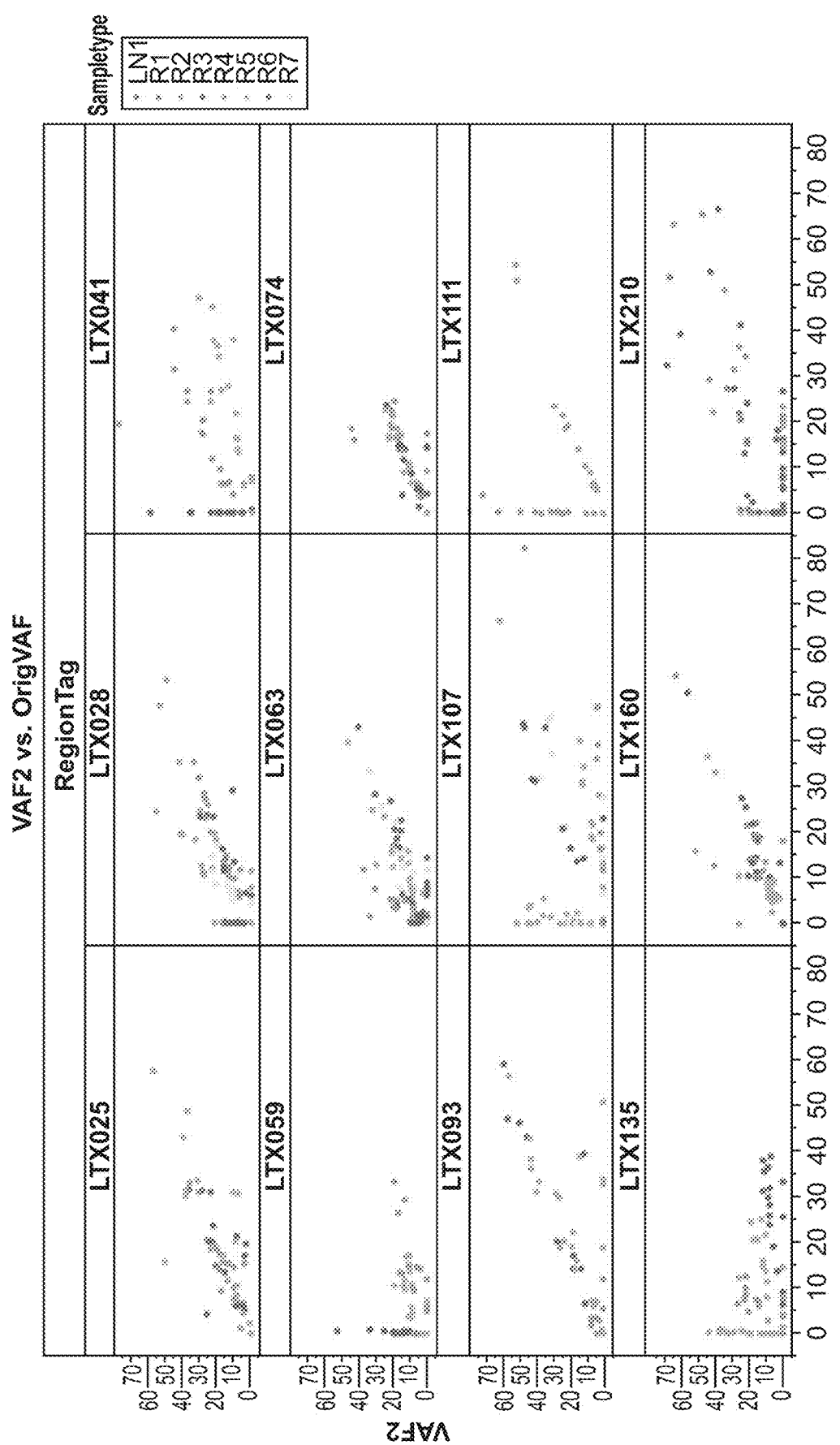
FIG. 5. Samples showing poor correlation between tissue VAF measurements determined previously (x axis) and here using mPCR-NGS (y axis). Each sample is shown in a separate box, and the VAF data points are colored by tissue subsection.
Figure 6A:
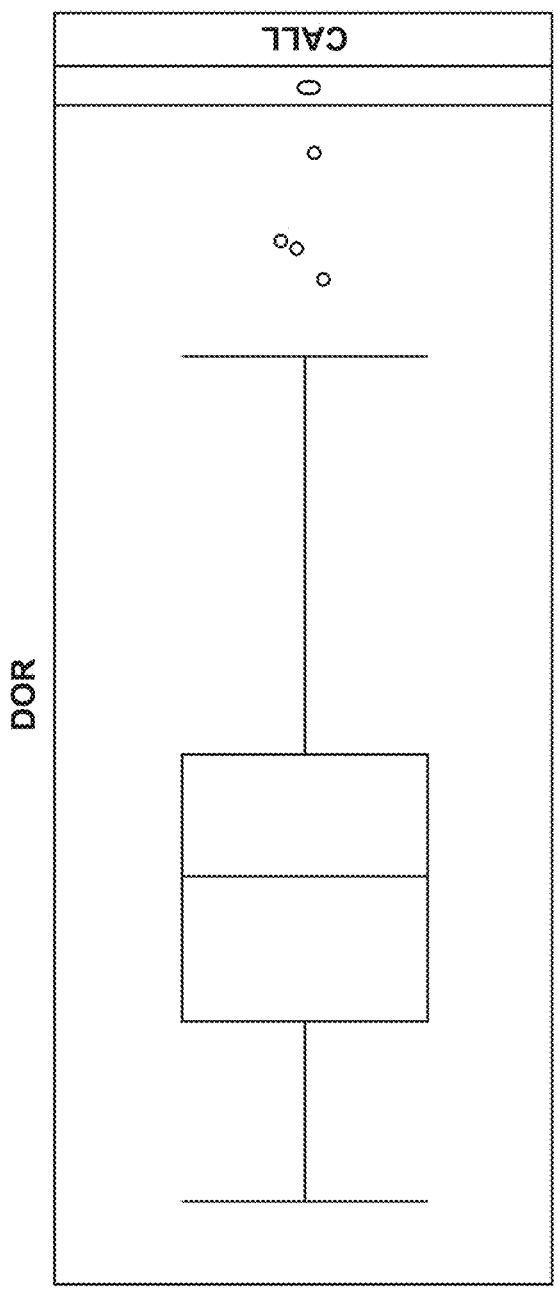
FIG. 6A-B. Depth of read histogram as a function of the resulting call. Top: the assay did not detect the expected plasma SNV. Bottom: the assay detected the expected plasma SNV.
Figure 6B:
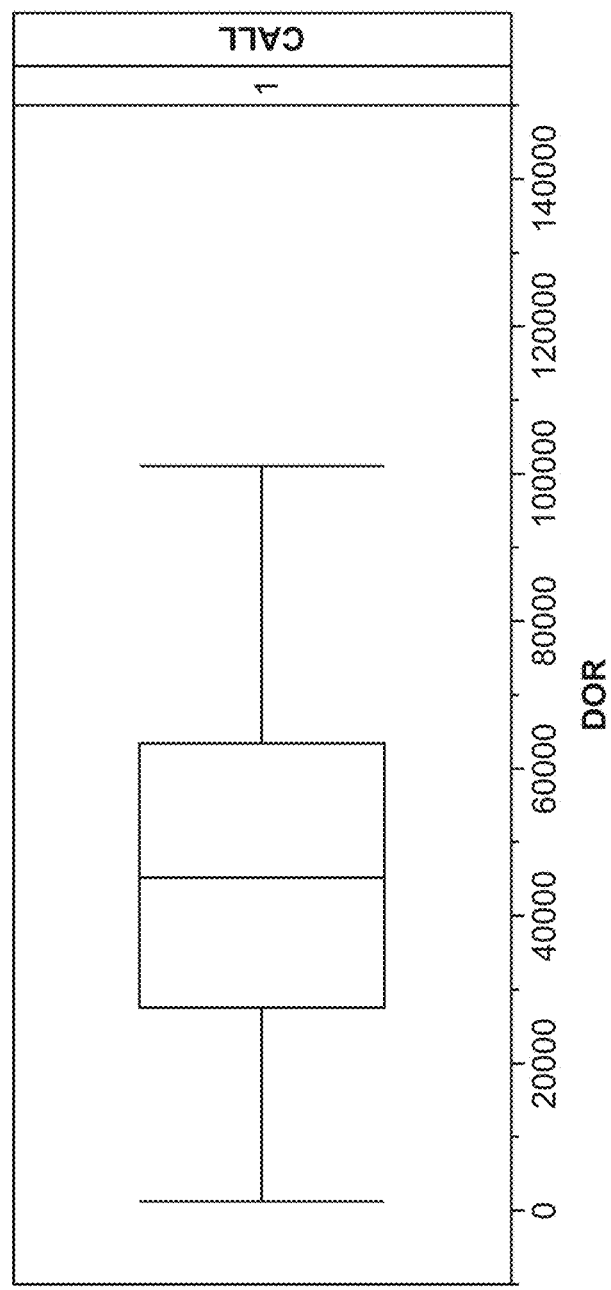
Figure 7:
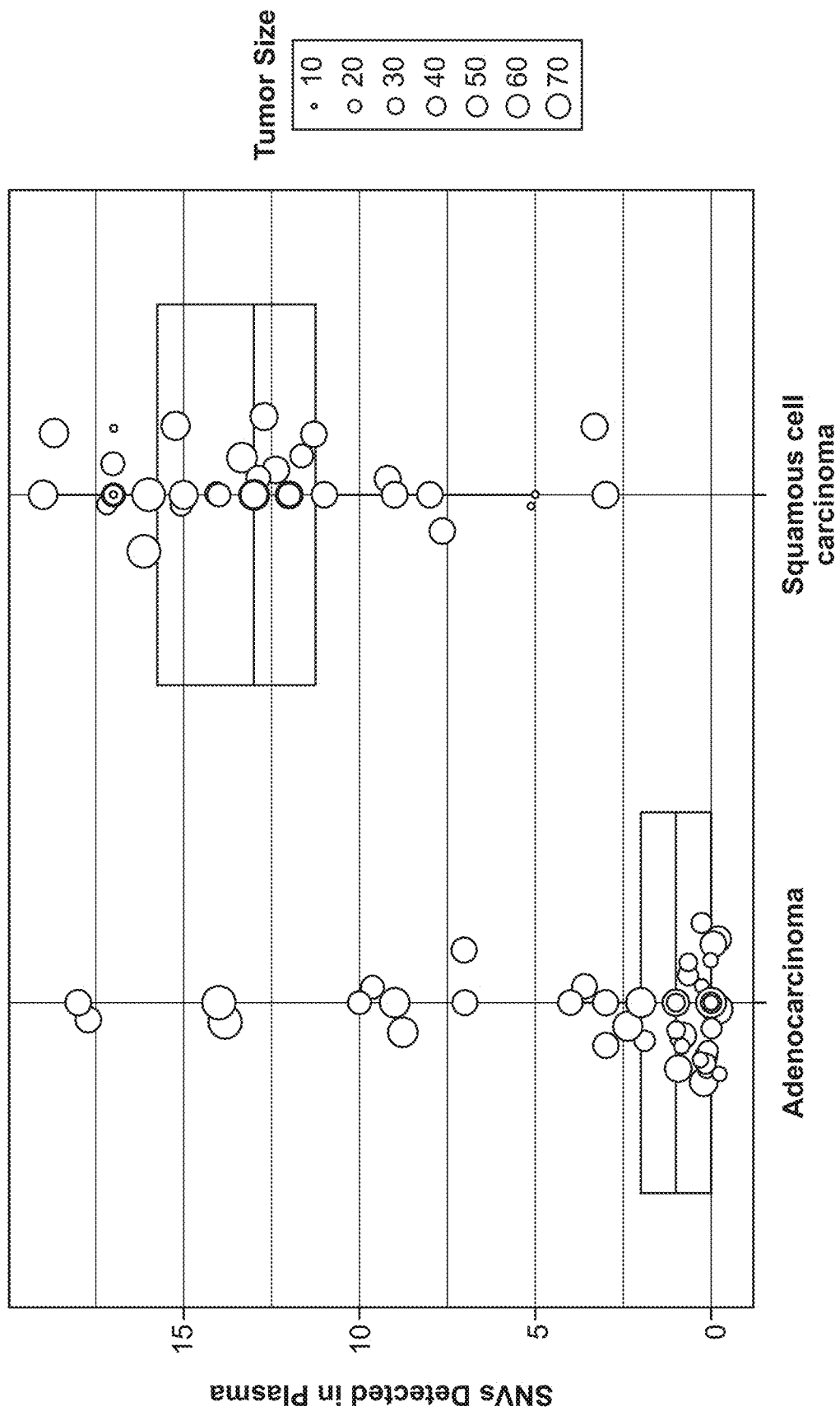
FIG. 7. Number of SNVs detected in plasma by histological type.
Figure 9:
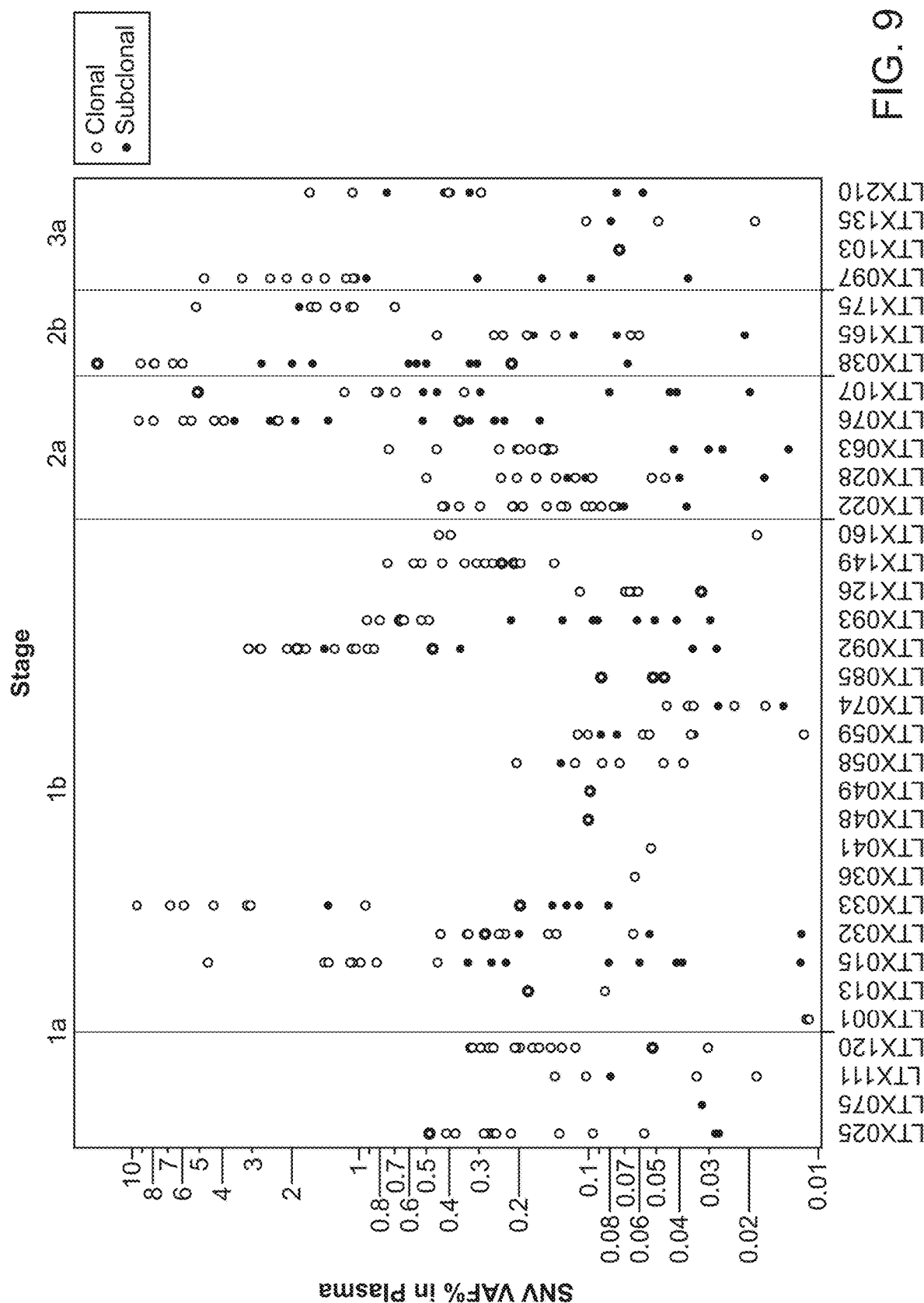
FIG. 9. Plasma VAF as a function of tumor stage and SNV clonality.
Figure 10:
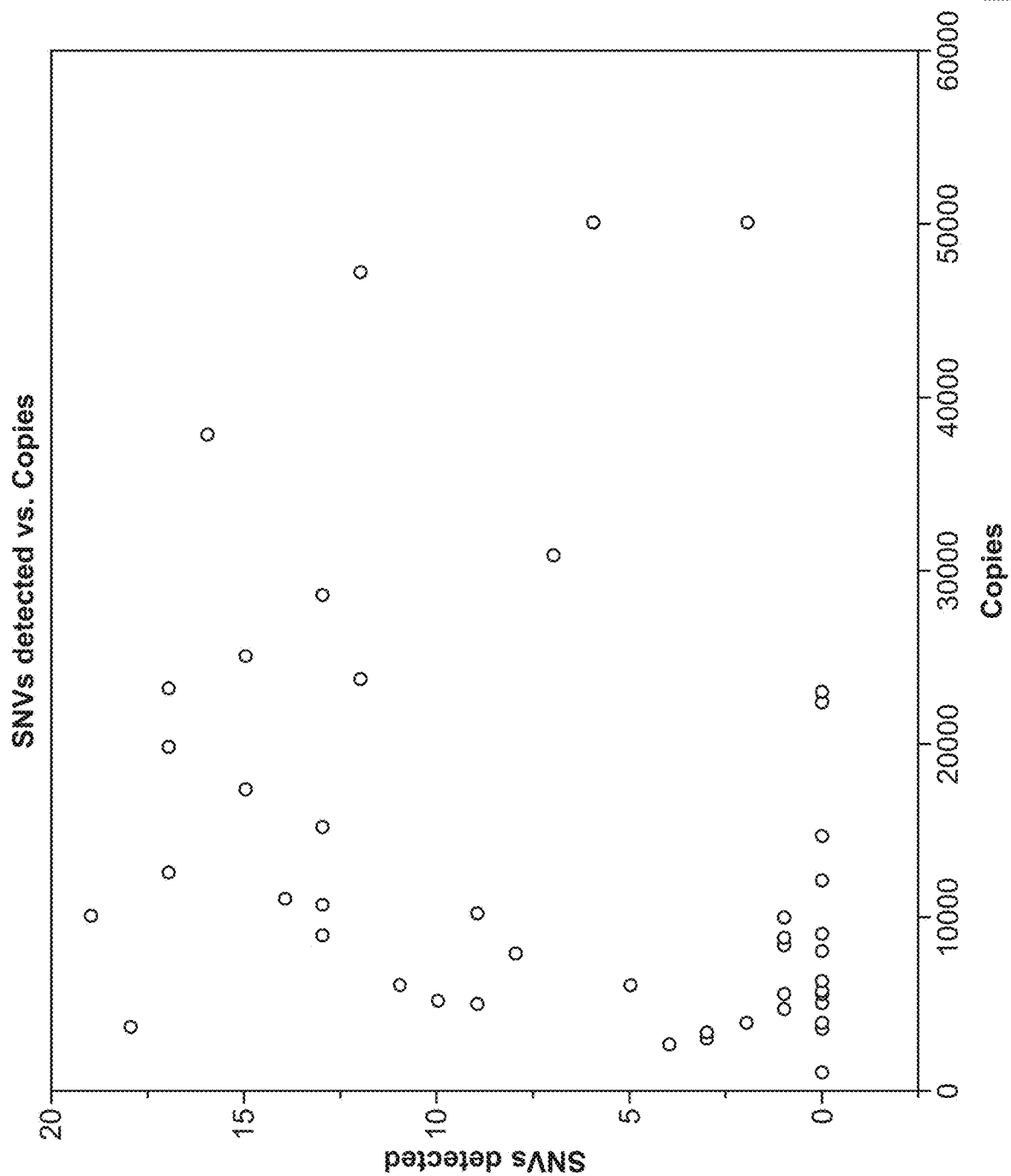
FIG. 10. Number of SNVs detected in plasma from each sample as a function of the cfDNA input amount.
Figure 11:
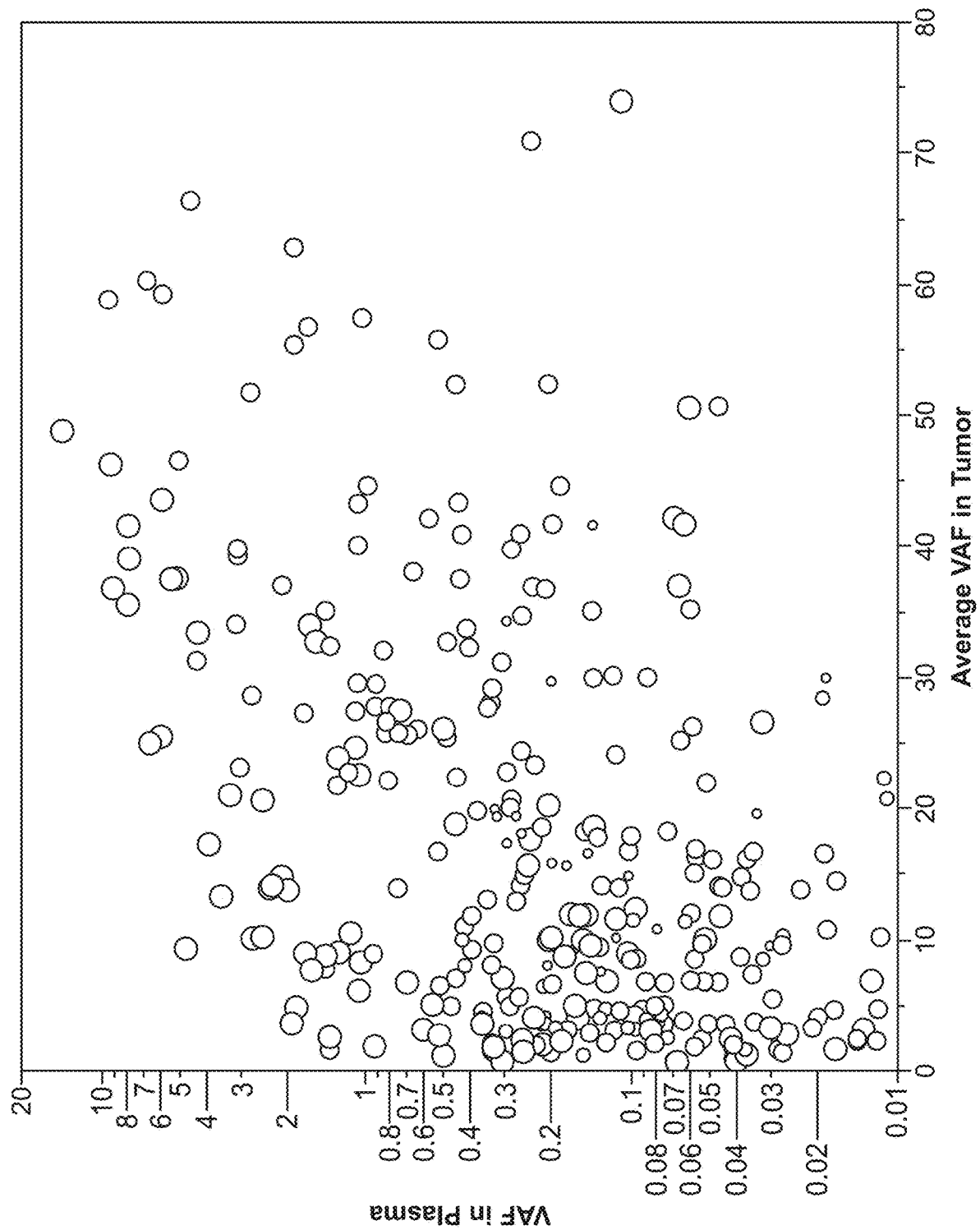
FIG. 11. Plasma VAF as a function of average tumor VAF. Average tumor VAF was calculated across all the tumor sub-sections analyzed from each tumor.

An assay specificity of 90.9% for normal (0% spike-in) cell line DNA was achieved (Table 1, FIG. 3).

For a given set of SNVs, the number of expected input percentages versus detected variant allele frequency (VAF) percentages for the differing spiked-in mutant DNA concentrations is shown across 6 targets, displaying high sensitivity above 0.03% tumor DNA concentrations (FIG. 36A-F). The false negatives shown at <0.01% SNV input (starting with <2 mutant copies) include mutant molecules lost due to sampling (FIG. 36A-F).

Estimated sample-level sensitivities for Signatera (RUO) when at least two SNVs are called from a set of 16 high-confidence SNVs, are listed in Table 6.

TABLE 6

Estimated Sample-Level Sensitivity

| Tumor DNA Concentration (%) | Sensitivity (%) |
|---|---|
| 0.005 | 49.97-72.02 |
| 0.010 | 94.55-99.56 |
| 0.030 | 99.97-99.99 |
| 0.050 | 100 |
| 0.100 | 100 |
| 0.300 | 100 |
| 0.500 | 100 |
| 1.000 | 100 |

In conclusion. The Signatera RUO assay provides a novel method of non-invasively detecting recurrence of personalized cancer signatures in plasma by ultra-deep sequencing of custom-made multiplex PCR assays (selected from a patient's tumor) with high sensitivity, high specificity, and low error rates. Based on the analytical validation results, the Signatera RUO assay, on an SNV level, has a 99.9% specificity and a greater than 65% sensitivity above 0.03% tumor fraction and a 100% sensitivity above 0.1% tumor fraction. On a sample-level, the Signatera RUO assay has greater than 95% sensitivity at 0.01% tumor fraction, nearly 100% sensitivity at 0.03% tumor fraction, and 100% sensitivity at 0.05% and above tumor fraction. These data demonstrate high rate of detection at single molecule mutant levels; they also suggest that lower plasma volumes may be utilized to achieve the same single-molecule detection with high specificity. The performance of the Signatera assay suggests the potential for it to determine chemotherapy treatment effectiveness.

Example 4. Longitudinal Assessment of Multiplex Patient-Specific ctDNA Biomarkers in Bladder Cancer for Diagnosis, Surveillance, and Recurrence Background. The use of circulating tumor DNA (ctDNA) as a biomarker for disease staging at diagnosis (DX), treatment response, and recurrence monitoring is an emerging field in many cancer types. In bladder cancer, the utility of ctDNA has shown promising results. Disclosed here is a highly sensitive and specific NGS-based approach to ctDNA monitoring.

Methods. A cohort of 50 patients with locally advanced muscle-invasive bladder cancer treated with neoadjuvant chemotherapy were included prospectively. For each patient, a panel of 16 tumor-specific mutations was designed (Signatera™ RUO) based on whole-exome sequencing of tumor and germline DNA. In total, we analyzed ctDNA from longitudinally collected plasma samples from 386 time points procured at diagnosis, during treatment, at cystectomy (Cx), and during monitoring until disease recurrence or up to 2 years follow-up. Results of ctDNA analyses were compared to radiographic imaging and clinical outcomes. ctDNA from longitudinally-collected urine samples can also be analyzed for treatment response and disease recurrence.

Results. At DX, plasma ctDNA status was strongly prognostic of recurrence-free survival. Specifically, 62% (8/13) of the ctDNA+ patients at DX recurred after neoadjuvant treatment and Cx; conversely, none (0/22) of the ctDNA– patients recurred (log-rank; p<0.0001). In addition, a strong correlation was also observed between presence of ctDNA after Cx and disease relapse. Specifically, relapse after Cx was detected in 100% (10/10) of ctDNA+ patients –120 days (0-245 days) prior to radiographic imaging, while 0% (0/38) of ctDNA– patients relapsed (log-rank; p<0.0001).

Conclusions. A strong prognostic potential of ctDNA in bladder cancer at time of DX was demonstrated, suggesting a role for ctDNA in the staging of bladder cancer. Furthermore, ctDNA was shown to be detected in all patients with disease recurrence after Cx. Incorporation of ctDNA analysis into routine follow-up for early detection of relapse allows earlier initiation of alternate treatment modalities.

Example 5. Serial Circulating Tumor DNA Analysis for Detection of Residual Disease, Assessment of Adjuvant Therapy Efficacy and for Early Recurrence Detection in Colorectal Cancer Background Early detection of disease recurrence has been shown to improve survival in patients with colorectal cancer (CRC). Previous studies have analyzed circulating tumor DNA (ctDNA) to monitor tumor burden in CRC using small gene panels and ddPCR. Here, a personalized multiplex-PCR and NGS platform (Signatera™ RUO) was used to detect ctDNA in serially collected plasma samples to assess if ctDNA detection defines the subset of patients with high risk of recurrence both before and after adjuvant chemotherapy (ACT).

Methods. A cohort of 130 patients with stage I-IV CRC, treated according to standard of care was analyzed. For each patient, tumor-specific panels of 16 mutations were designed using somatic mutation signatures obtained from WES. Plasma samples (n=829) collected pre- and post-surgery, and during ACT were analyzed. Recurrence-free survival was calculated for patients stratified by ctDNA status post-surgery (n=91) and post-ACT (n=58).

Results. ctDNA status after surgery, but prior to ACT, was assessed in 91 patients. Relapse was observed for 75% (6/8) of the ctDNA+, and only for 13% (11/83) of the ctDNA– patients. Effective ACT treatment was observed for 30% (3/10) of the post-operative ctDNA+ patients. These were consistently ctDNA– in post-ACT serially collected blood samples, and concordantly relapse free at end of follow-up. ctDNA status post-ACT was assessed in 58 patients. Radiologically confirmed relapse was observed for 77% (10/13) of the ctDNA+ and for 4% (2/45) of ctDNA− patients. On average ctDNA detected relapse 9.13 months earlier than standard-of-care CT-imaging.

Conclusions. Serial post-operative ctDNA analysis enables stratification of patients into high or low recurrence risk subgroups, assessment of ACT treatment efficacy, and early detection of recurrence. Importantly, it also indicates that ACT can eliminate residual disease in up to 30% of the post-operative ctDNA+ patients and therefore can be a treatment option for ctDNA+ patients. In summary, ctDNA analysis has great potential to guide treatment decisions, both in the adjuvant and post-adjuvant settings.

Example 6. Early Detection of Residual Breast Cancer (BC) Through a Robust, Scalable and Personalized Analysis of Circulating Tumor DNA (ctDNA) Antedates Overt Metastatic Recurrence Background Many BC patients relapse after primary treatment but there are no reliable tests to detect distant metastases before they become overt. Shown herein is earlier identification of recurring patients through personalised ctDNA analysis. The method is applicable to all patients and is not limited to hot-spot mutations typically detected by gene panels.

Methods. Forty-nine non-metastatic BC patients were recruited following surgery and adjuvant therapy. Plasma samples (n=208) were serially collected semi-annually. Using the analytically-validated Signatera™ workflow, mutational signatures were determined from primary tumor whole exome data and designed personalized assays targeting 16 variants with high sensitivity by ultra-deep sequencing (average >100,000×). The assay of each patient was used to determine whether the mutational signature was detectable in the plasma. All but 5 patients received chemotherapy, and the other 5 received radiotherapy.

Figure 37:
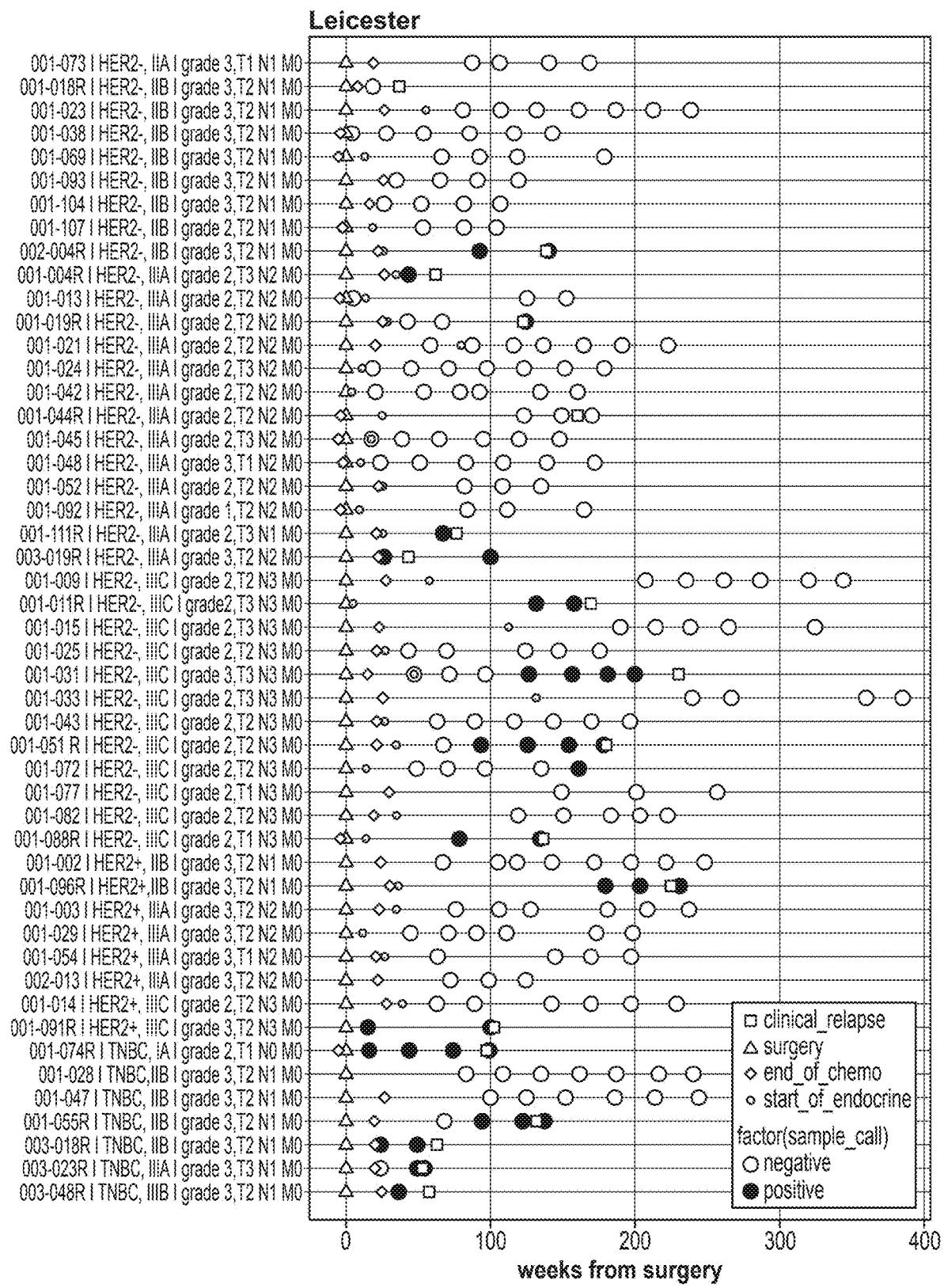
FIG. 37: Patient Summary for the breast cancer study in Example 6.
Figure 38C:
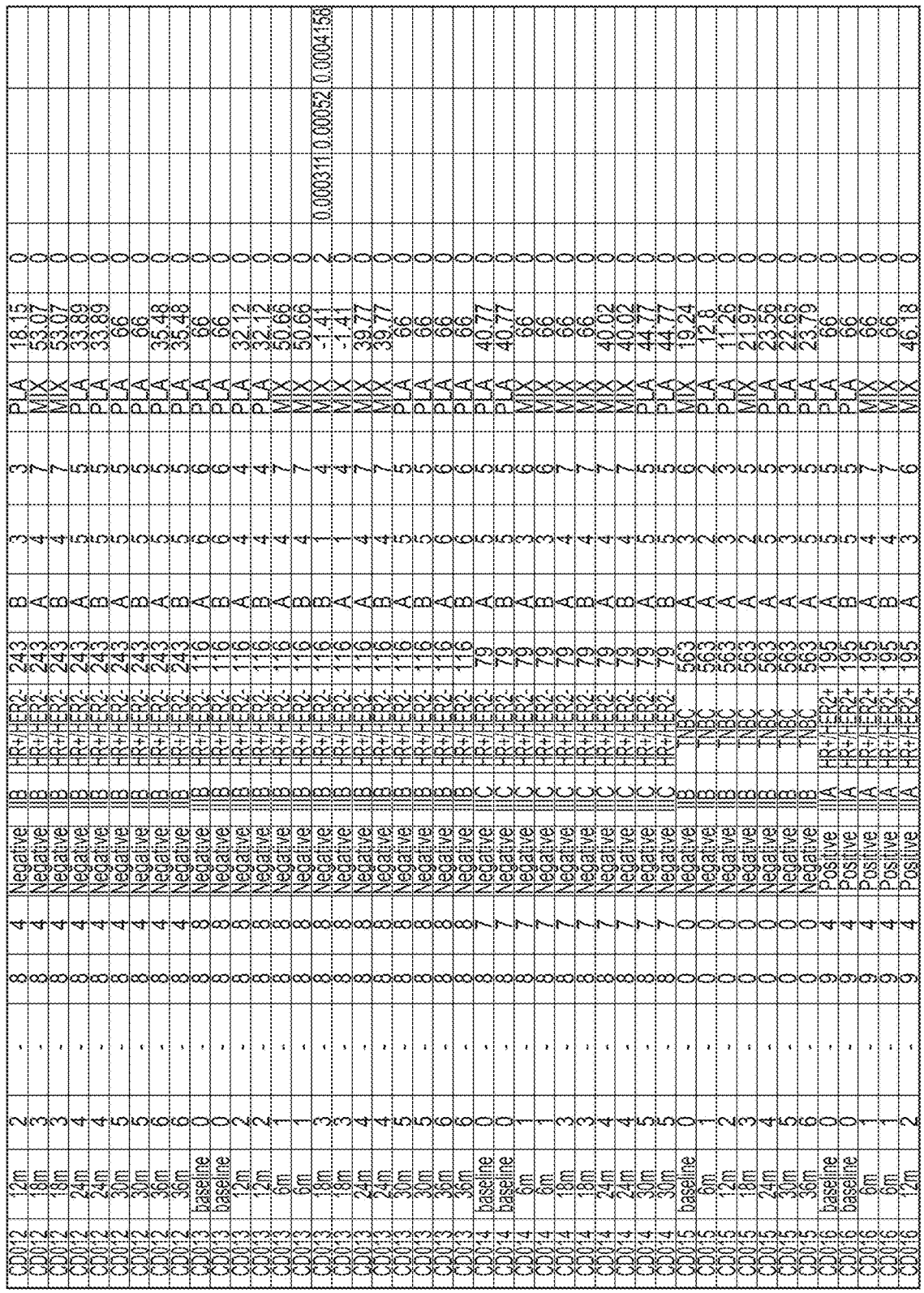
Figure 38D:
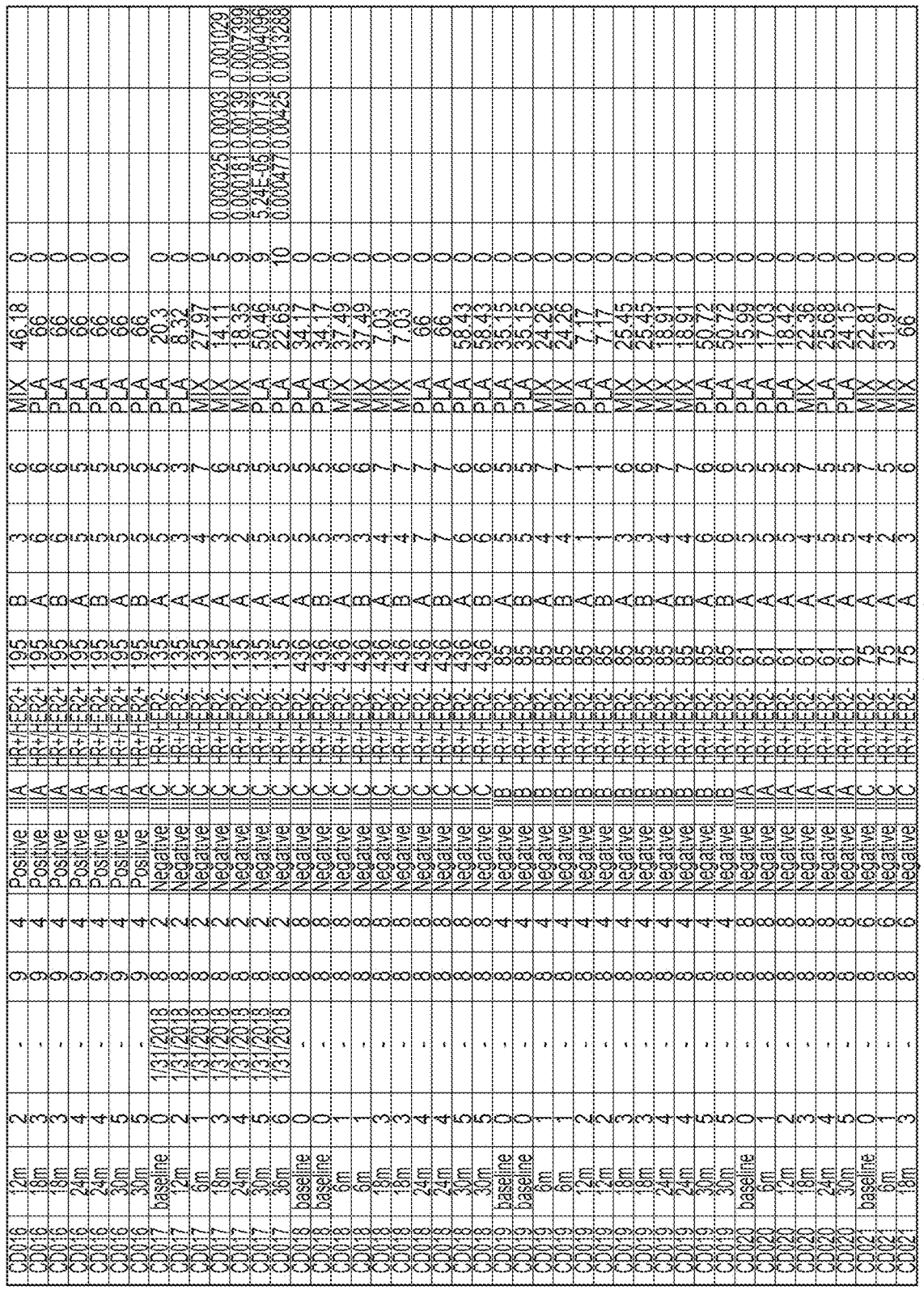
Figure 38E:
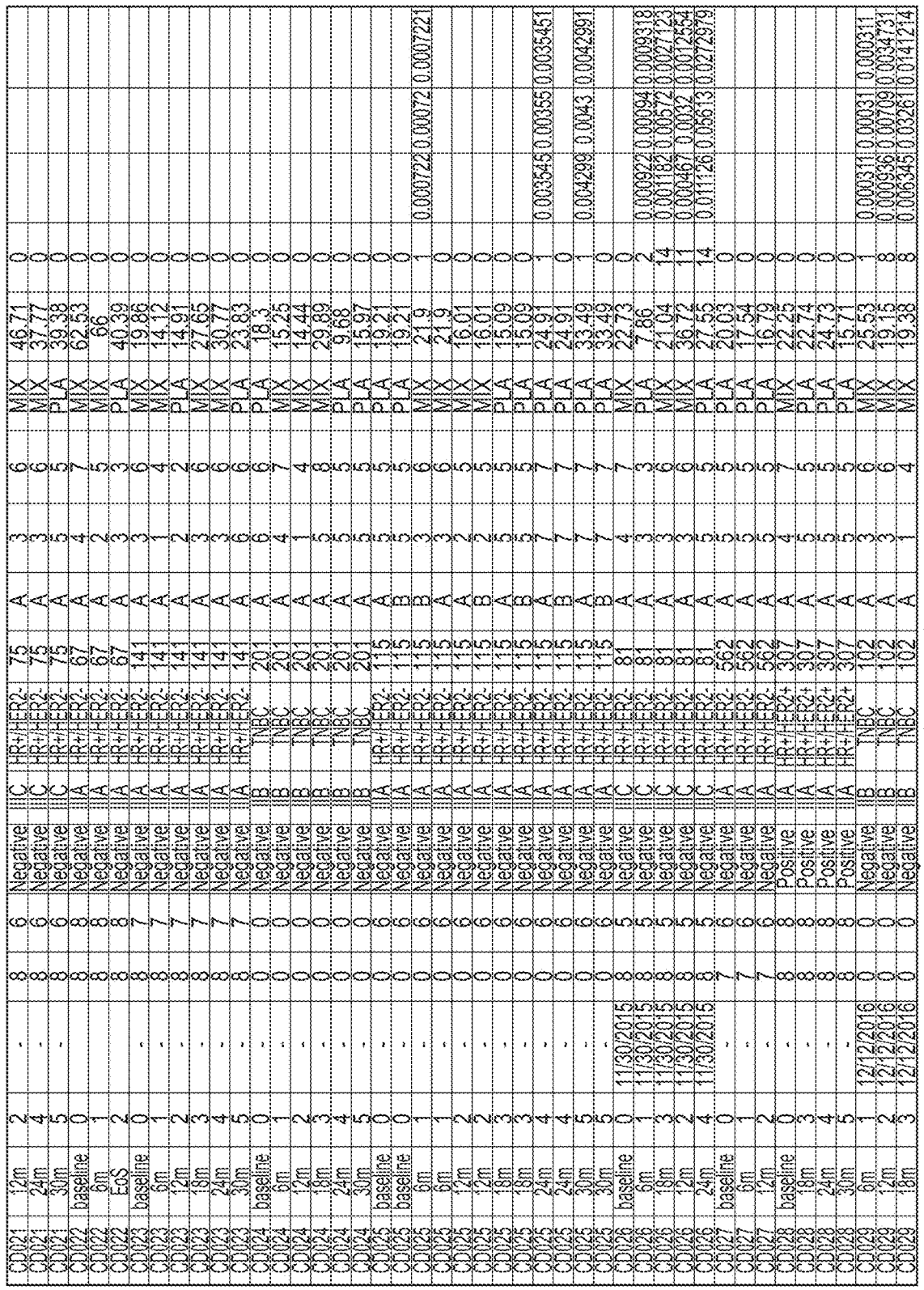
Figures 39, 40:
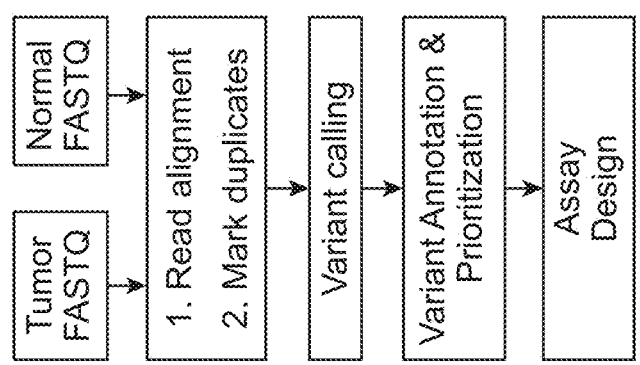
FIG. 39: Demographics of the patients in the breast cancer study of Example 6. 50 patients WES raw data (with driver variants for 35 patients) was received. 218 plasma samples at variable number of time points (between 1 and 8) were received. 108 extra extracted DNA samples were received. Relapse status was also collected. Blood samples were collected post adjuvant therapy with 6-month time intervals.
FIG. 40: Summary of WES analysis and pool design for breast cancer study in Example 6. Pool A is based on the Signatera method. Pool B contains 25 patients and is indicated with an asterisk in the box and whisker plot. 19 patients in Pool B had low tumor purity. 6 patients had extra early stage HER2− tumors. Pool B contains driver variants.
Figure 40:
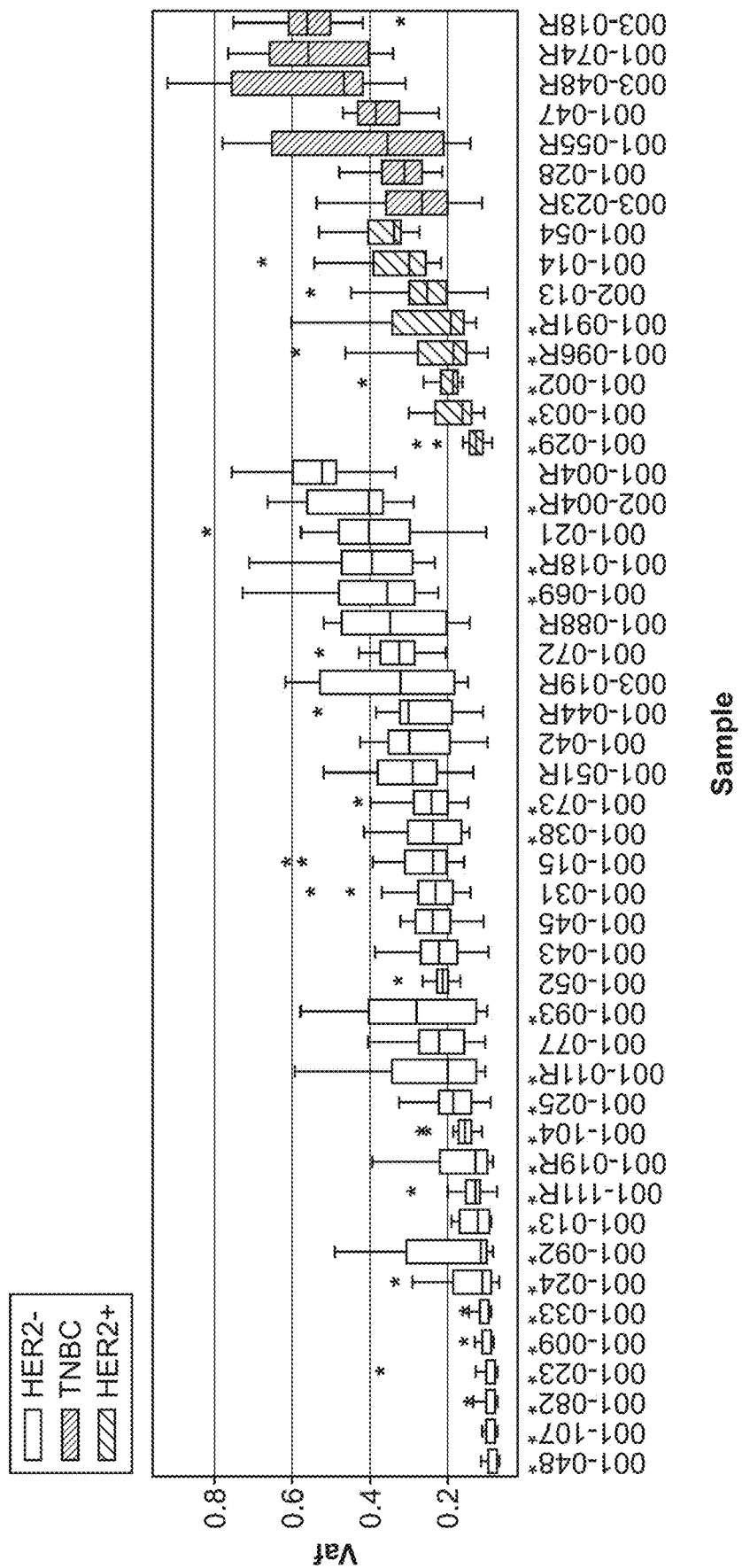
Figure 41:
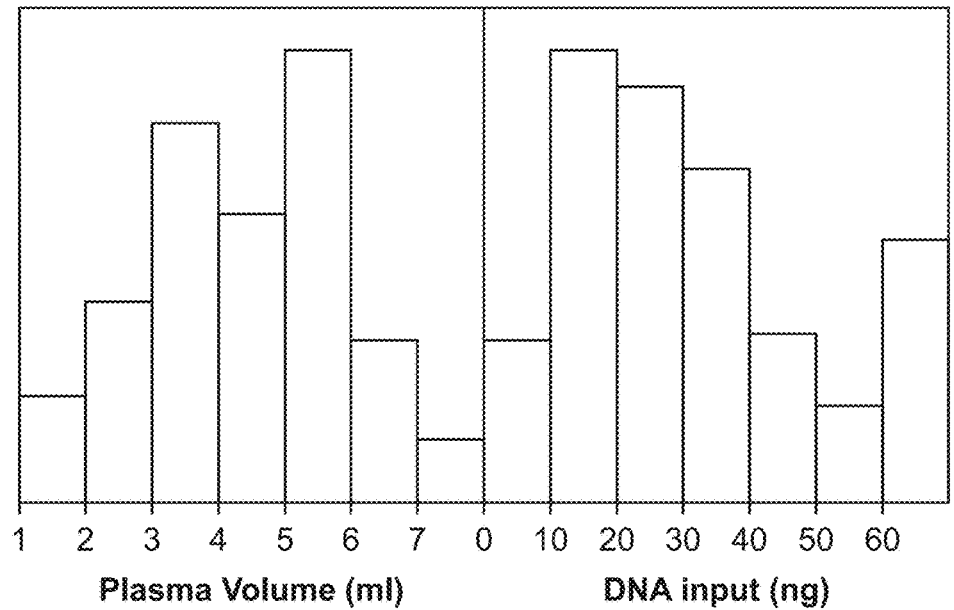
FIG. 41: Plasma samples for the breast cancer study in Example 6. The median plasma volume was 4 mL. Median DNA input was 26 ng. Median DNA input is lower than CRC and MIBC samples (45 ng and 66 ng respectively).
Figures 42A, 42B:
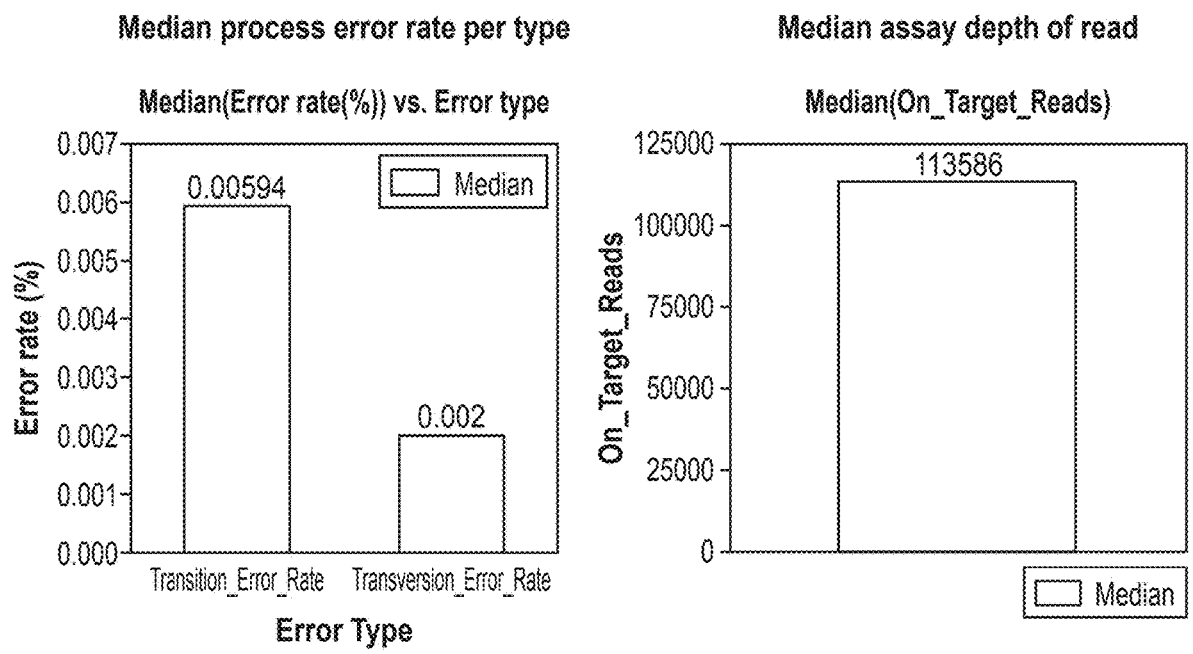
FIG. 42A-B: Sequencing quality control depicting median process error rate per type and median assay depth of read for the breast cancer study in Example 6. In total, 326 plasma sequencing samples were processed. Mutation calling FP rate is estimated to be 0.28%.
Figure 44:
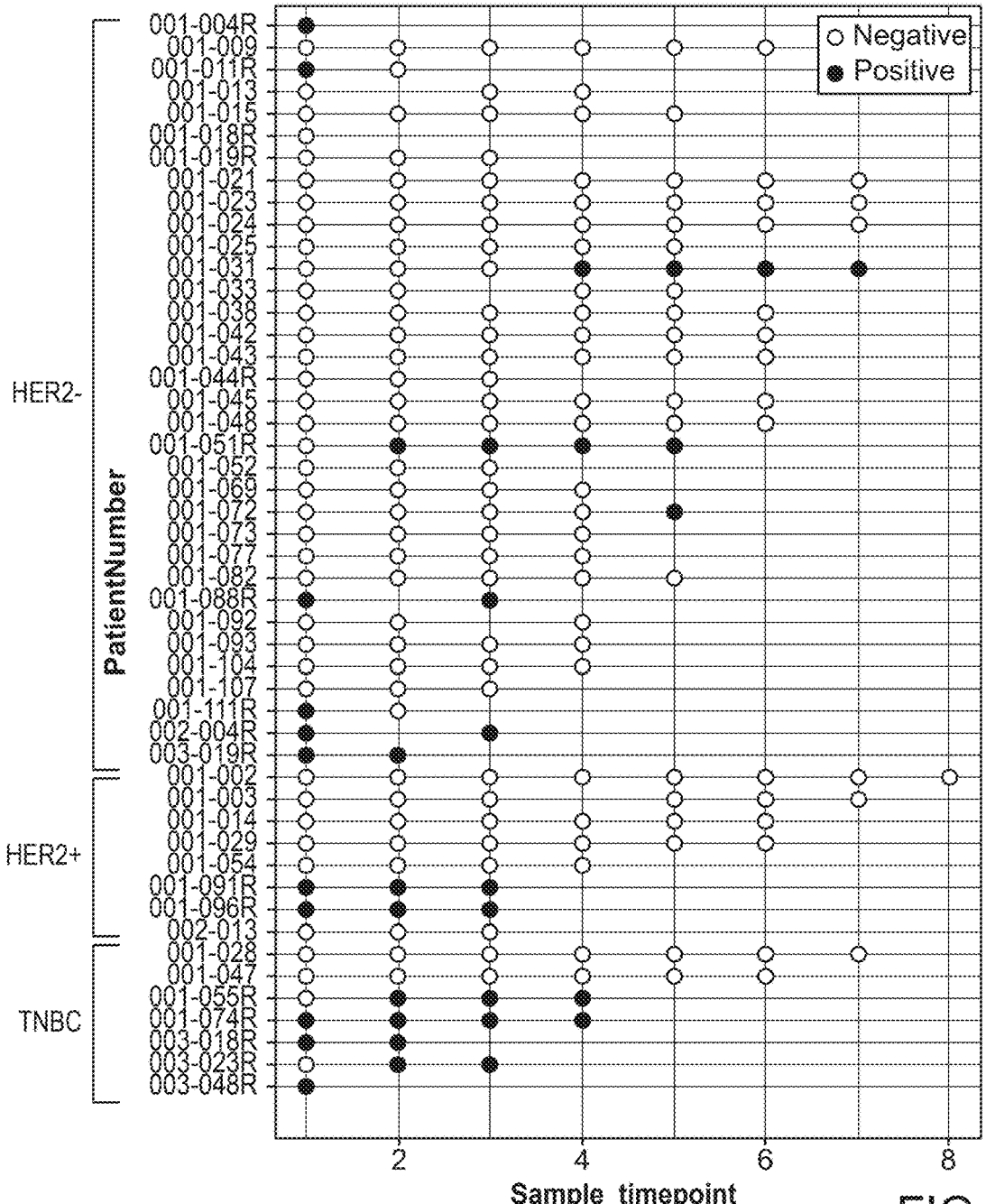
FIG. 44: Results from Pool A for the breast cancer study in Example 6. Out of 49 patients, 11 were baseline positive. 3 have only one time point. The remaining 8 patients stay positive all the time. Pool B and driver produced similar results. Driver information: 16 relapse samples have driver mutations. 11 relapse samples have at least one assay with driver.
Figure 46A:
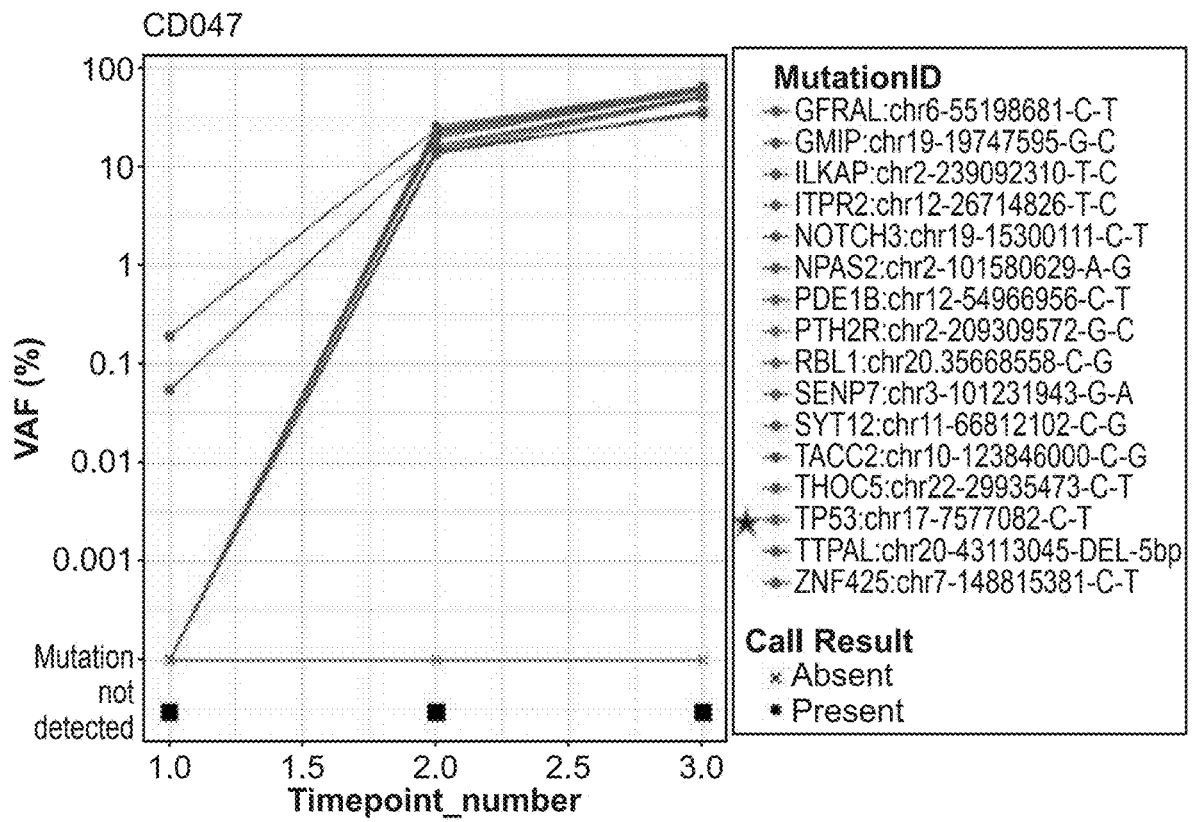
FIG. 46A-B: Graphical depiction of data corresponding to patient CD047 (TNBC) in FIG. 38.
Figure 46B:
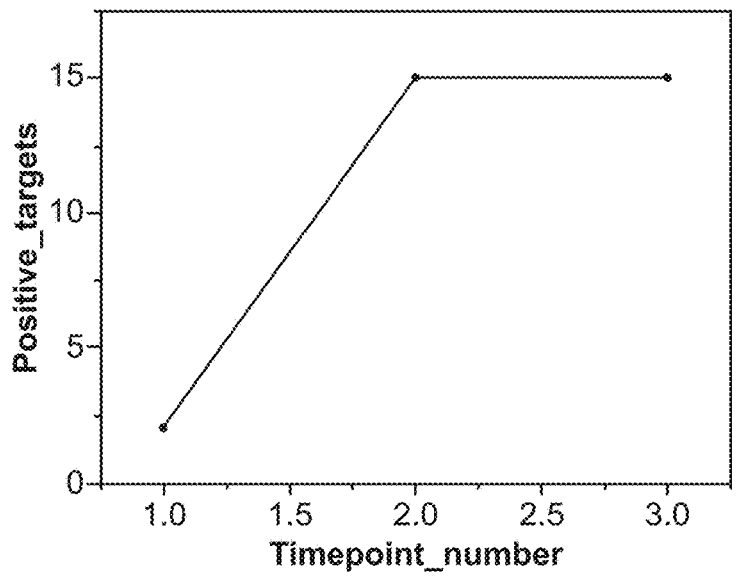
Figure 47A:
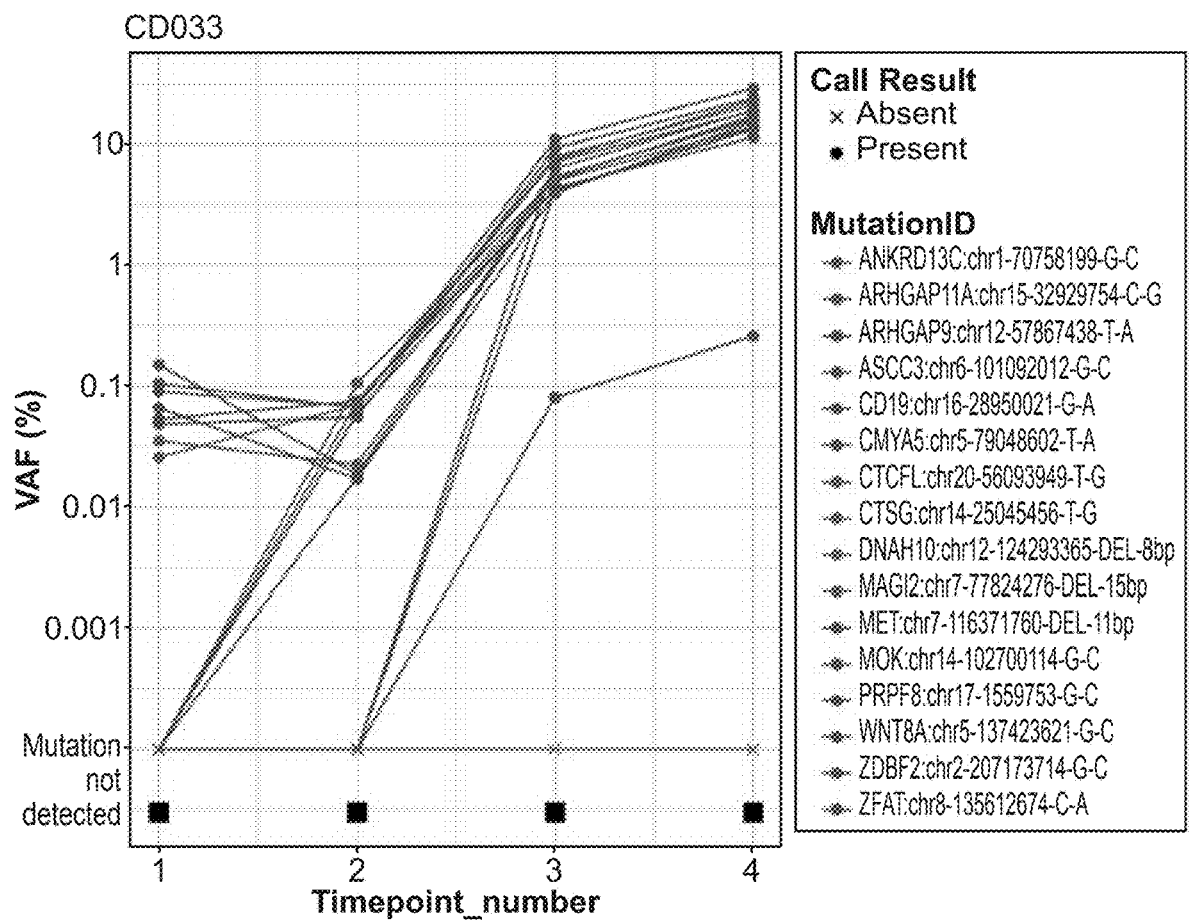
FIG. 47A-B: Graphical depiction of data corresponding to patient CD033 (TNBC) in FIG. 38.
Figure 47B:
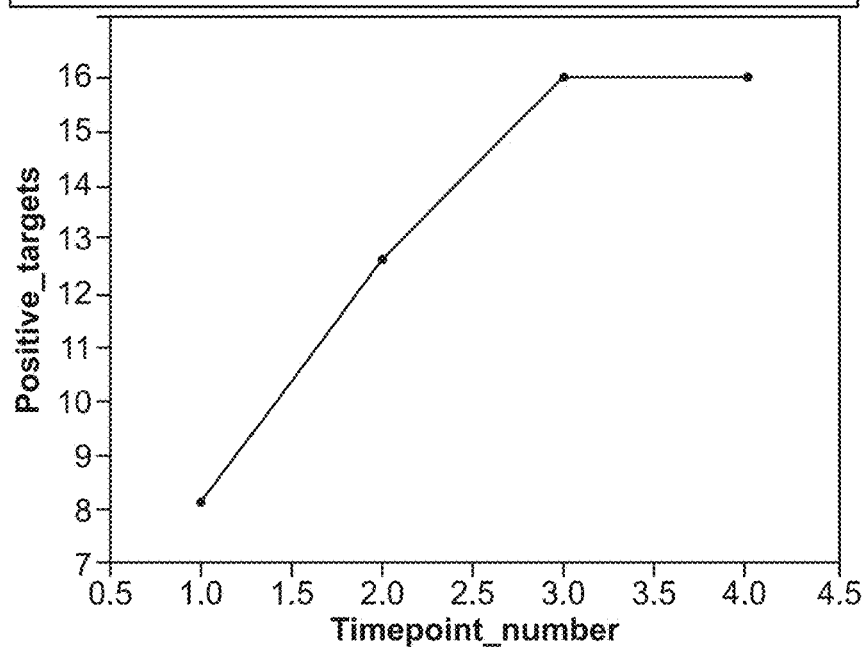
Figure 48A:
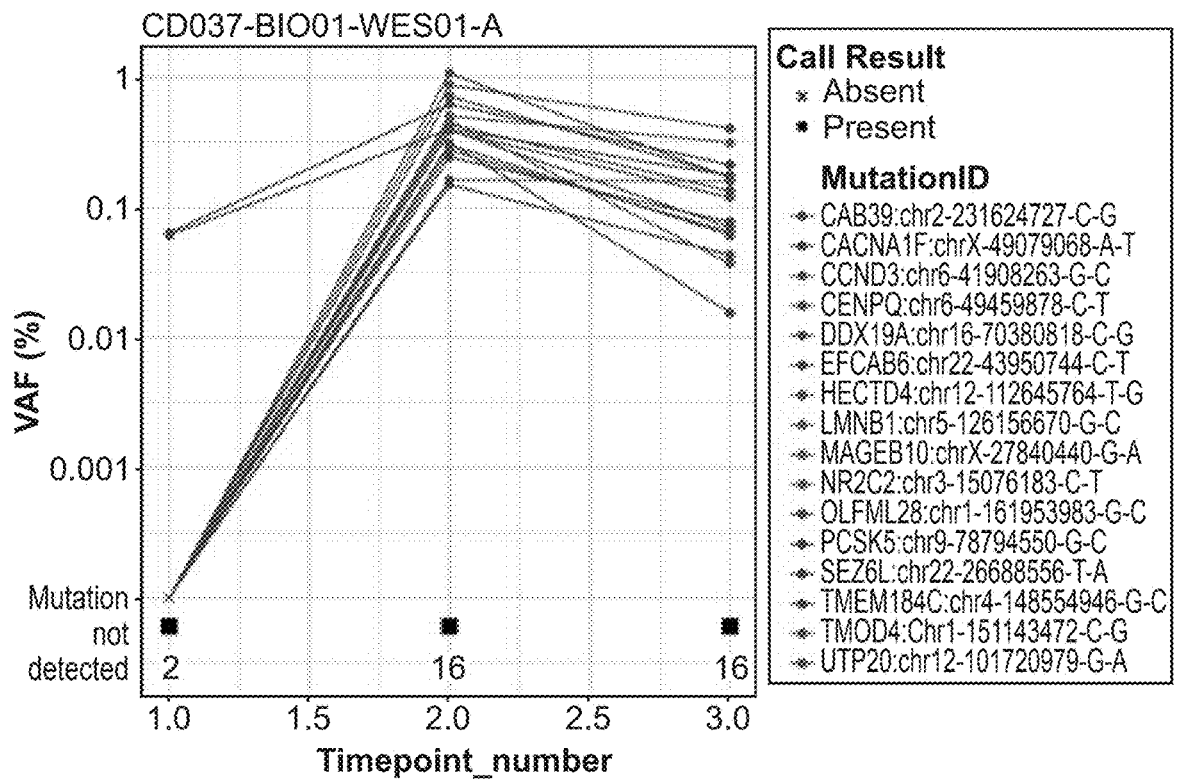
FIG. 48A-B: Graphical depiction of data corresponding to patient CD037 (HER2+) in FIG. 38.
Figure 48B:
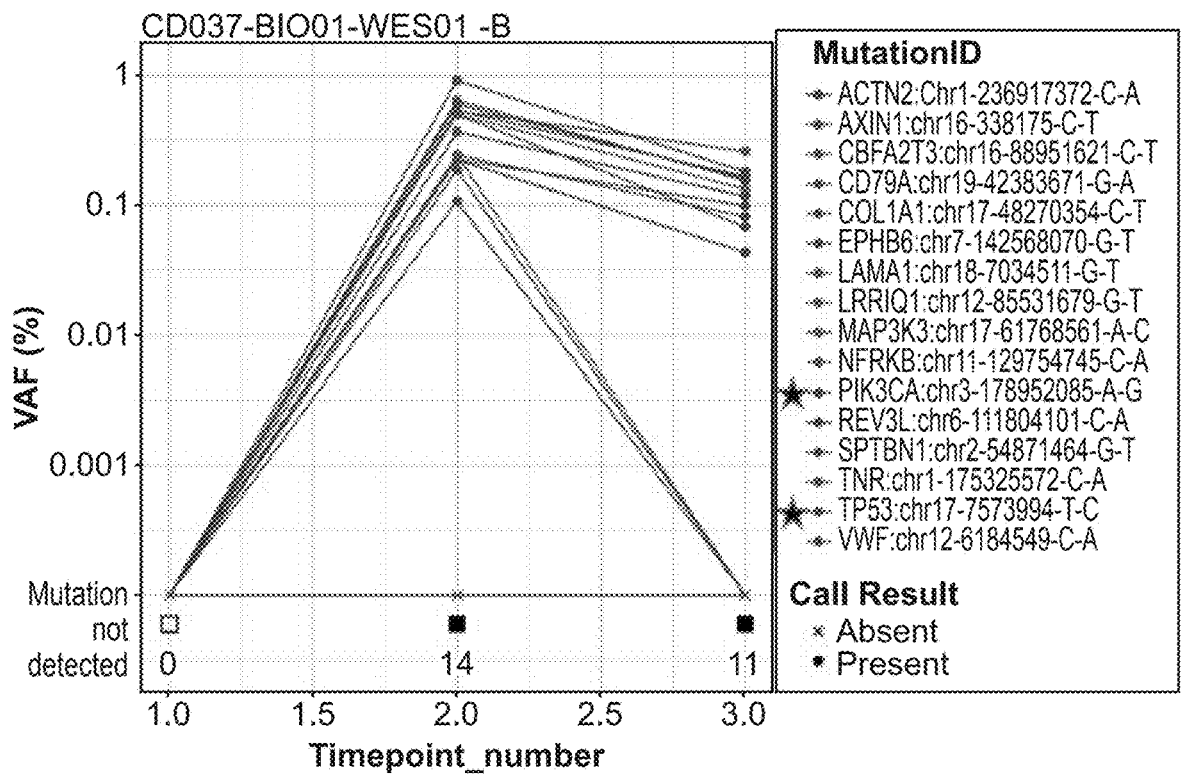
Figure 49A:
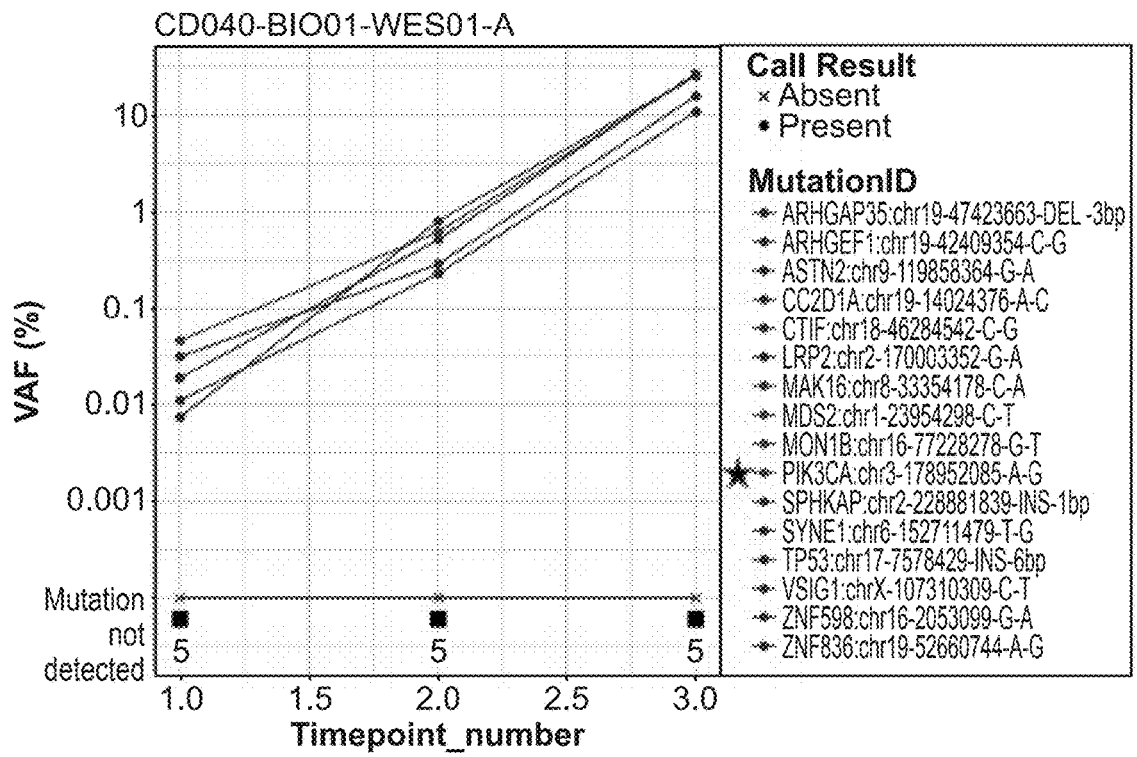
FIG. 49A-B: Graphical depiction of data corresponding to patient CD040 (HER2+) in FIG. 38.
Figure 49B:
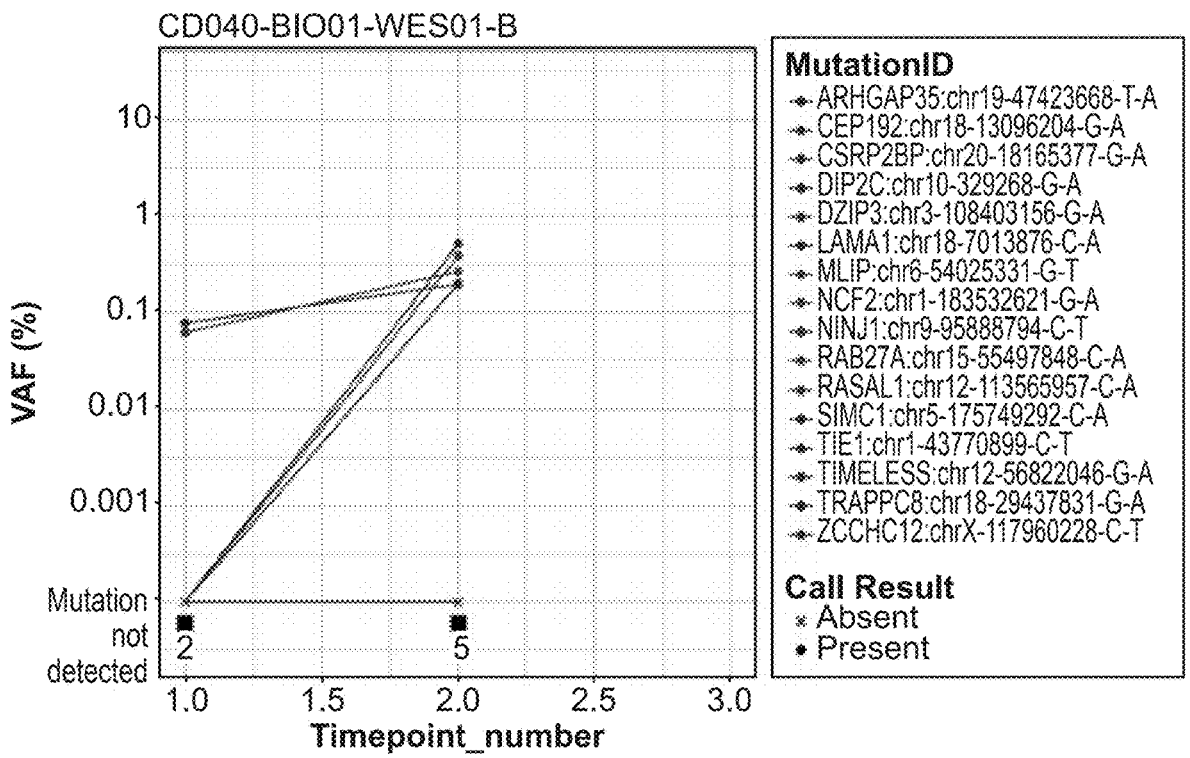
Figure 50A:
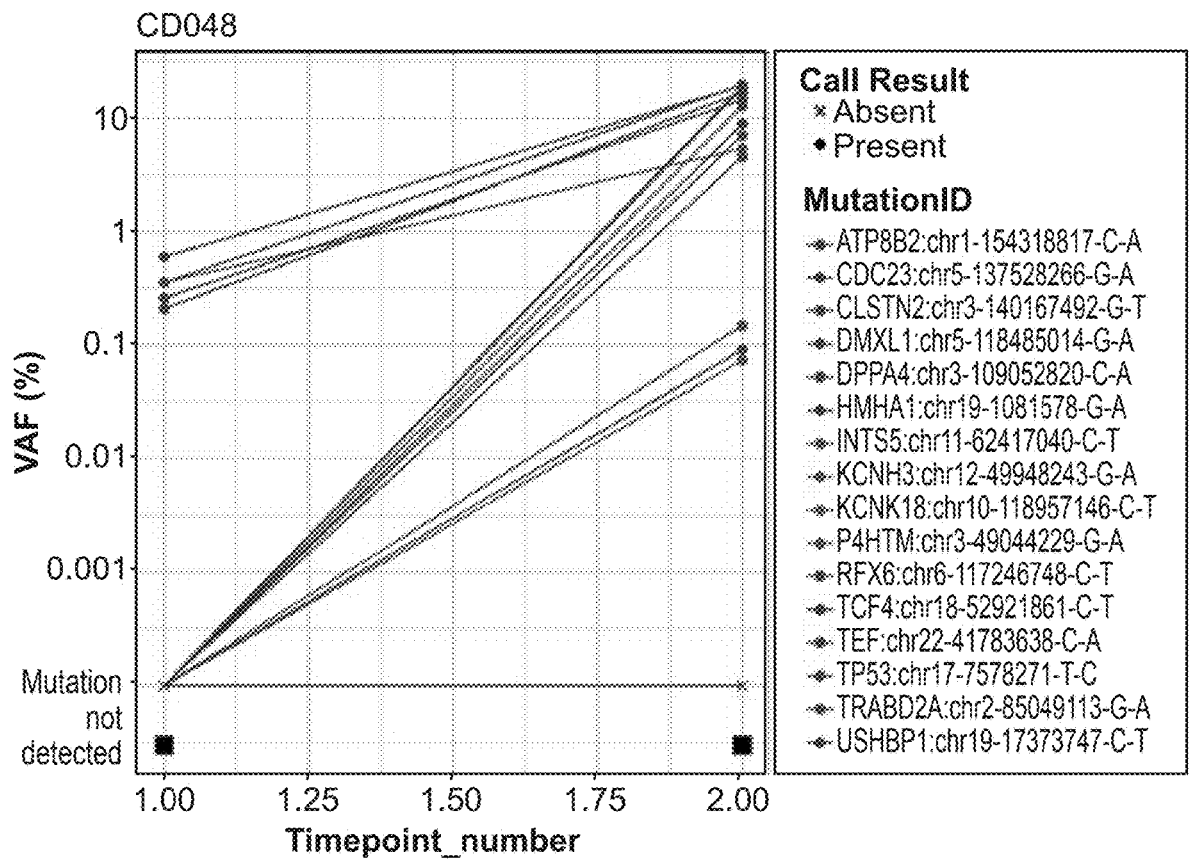
FIG. 50A-B: Graphical depiction of data corresponding to patient CD048 (HER2−) in FIG. 38.
Figure 50B:
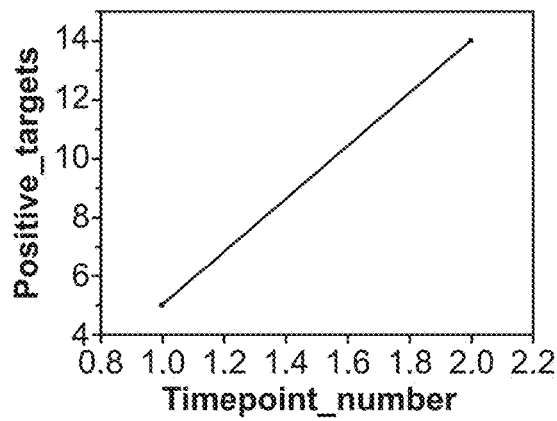
Figure 51A:
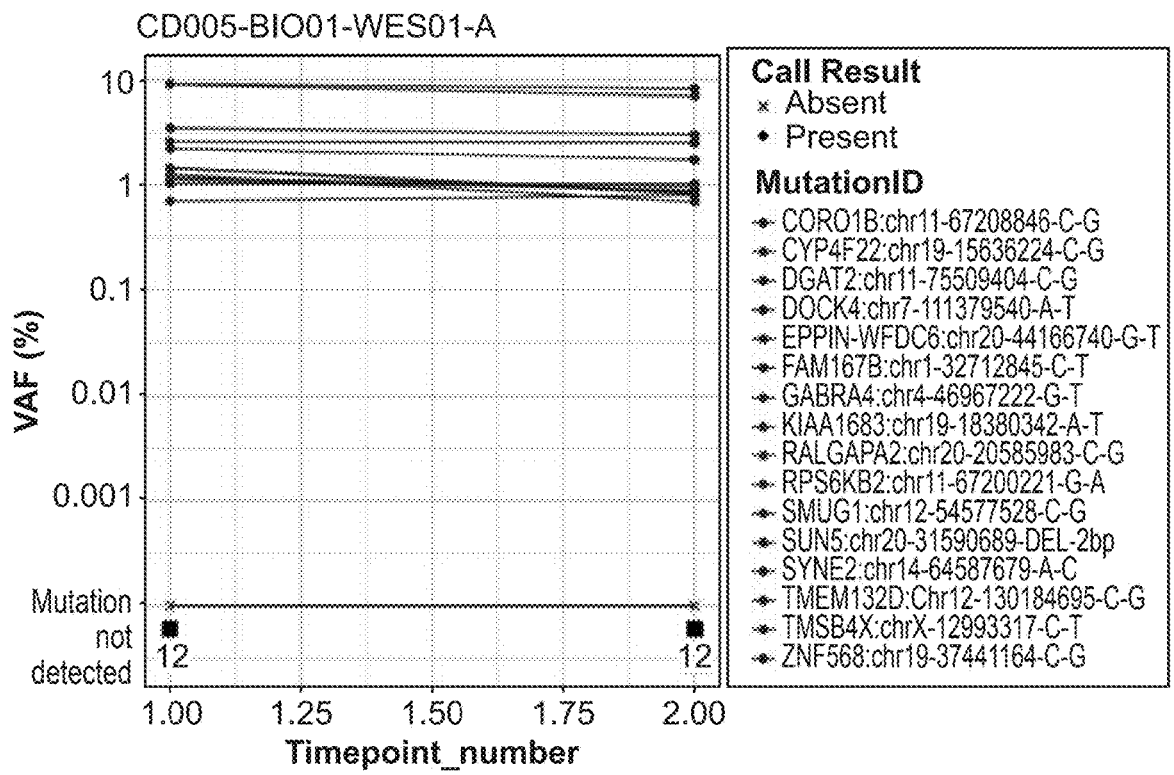
FIG. 51A-B: Graphical depiction of data corresponding to patient CD005 (HER2−) in FIG. 38.
Figure 51B:
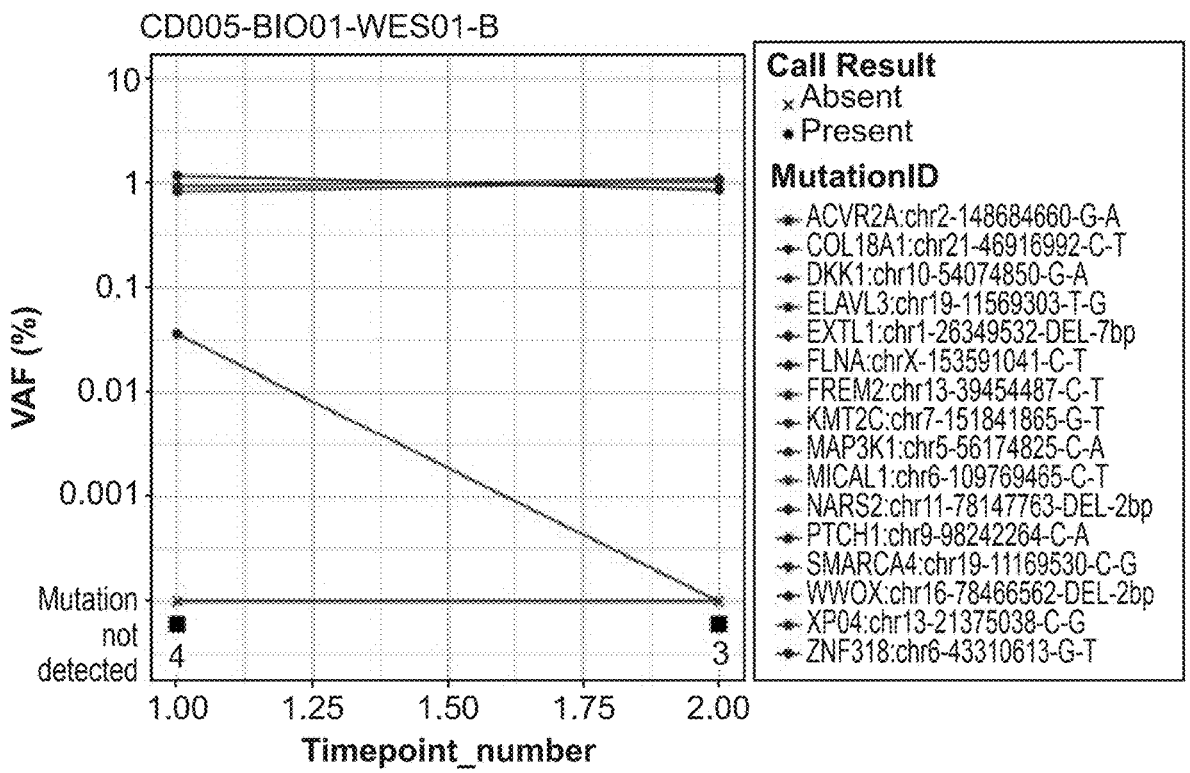
Figure 52A:
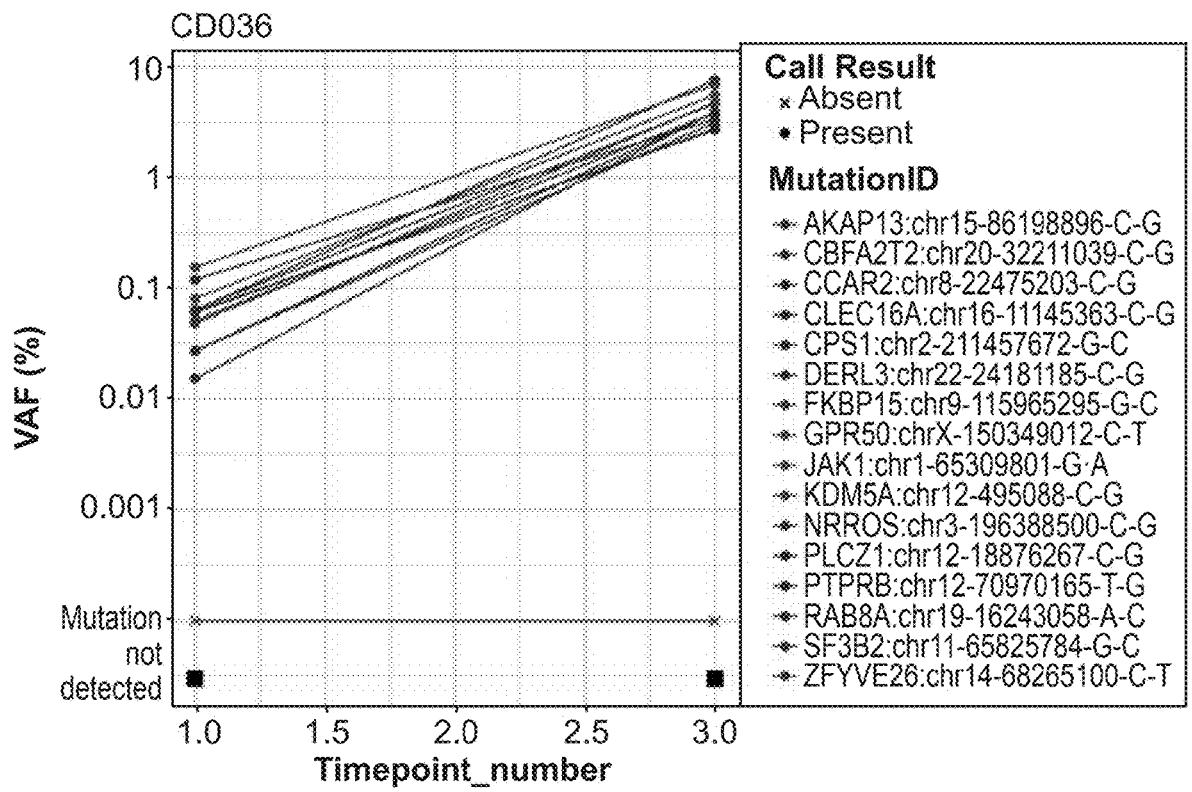
FIG. 52A-B: Graphical depiction of data corresponding to patient CD036 (HER2−) in FIG. 38.
Figure 52B:
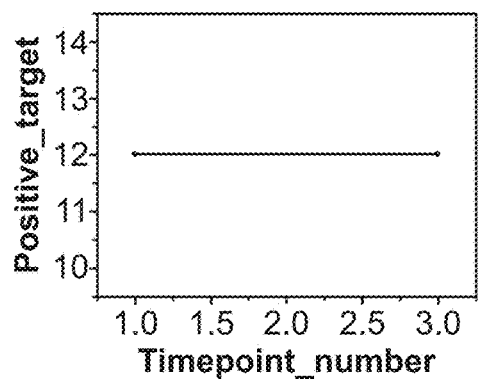
Figure 53A:
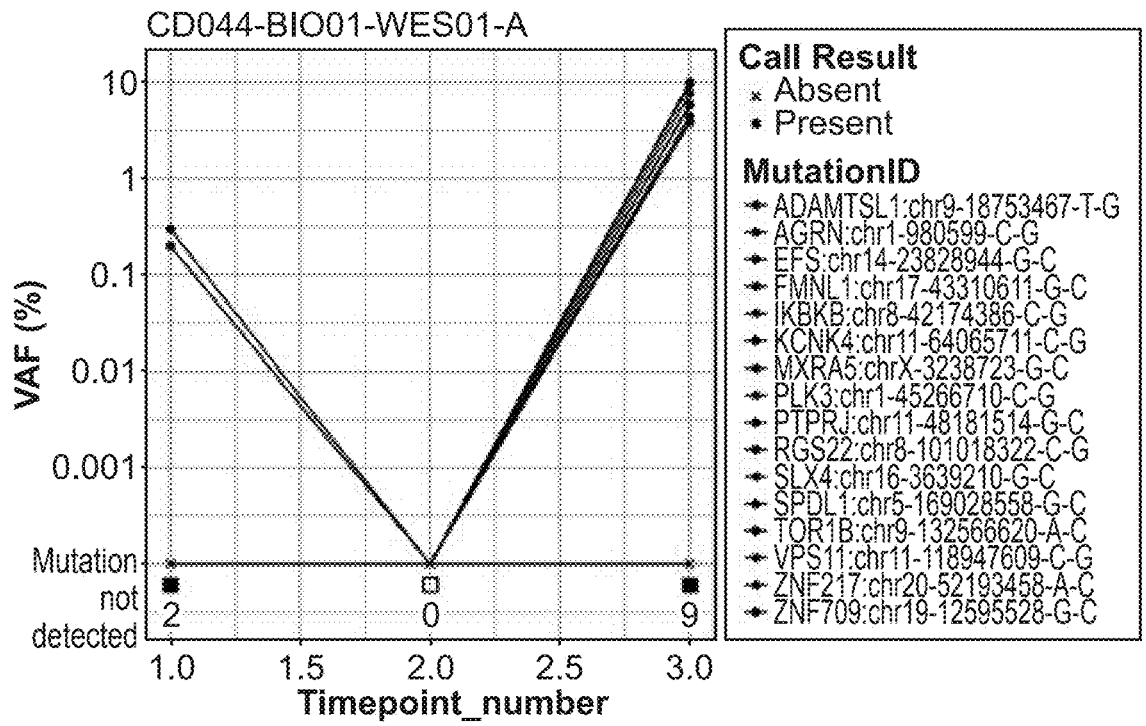
FIG. 53A-B: Graphical depiction of data corresponding to patient CD044 (HER2−) in FIG. 38.
Figure 53B:
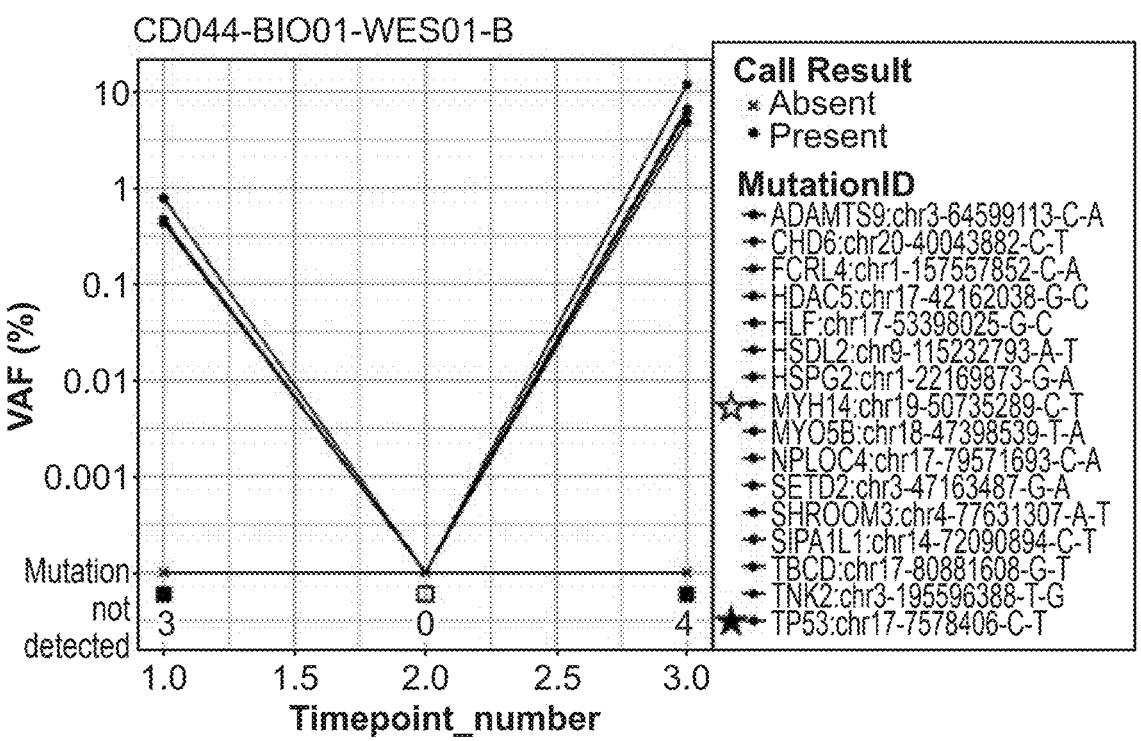
Figure 54A:
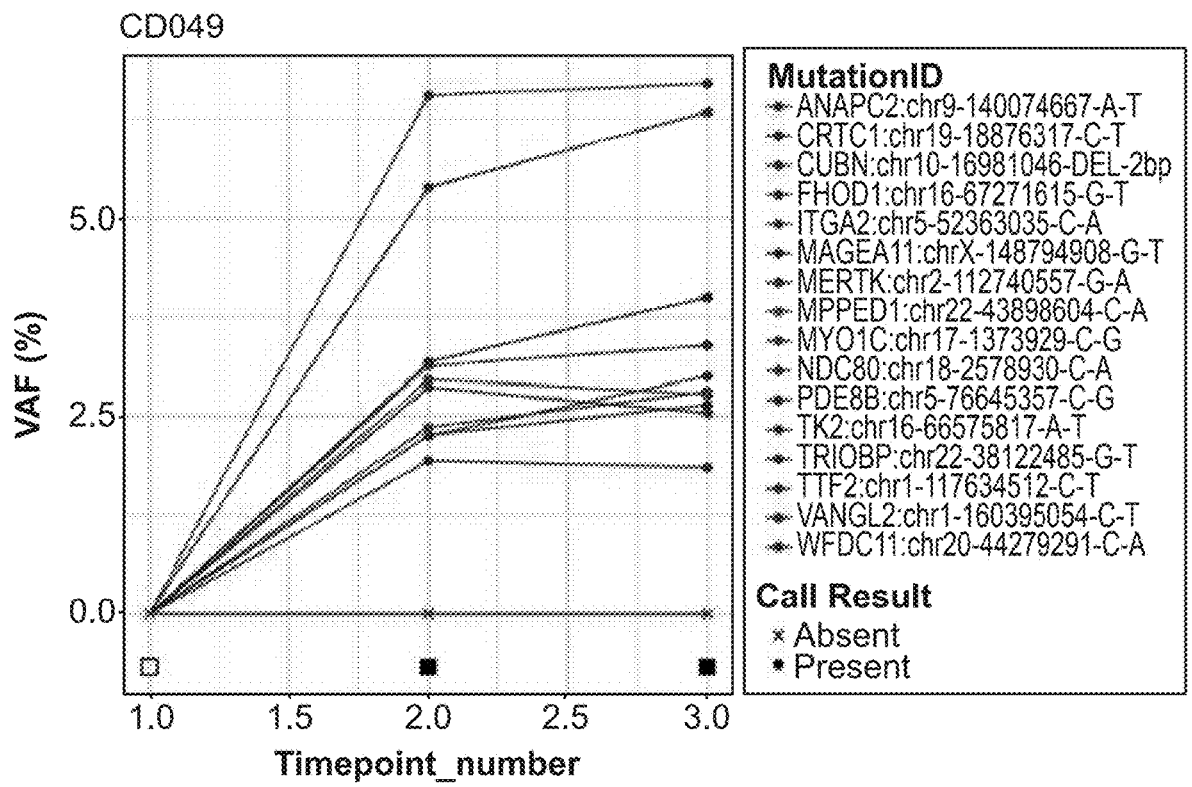
FIG. 54A-B: Graphical depiction of data corresponding to patient CD049 in FIG. 38.
Figure 54B:
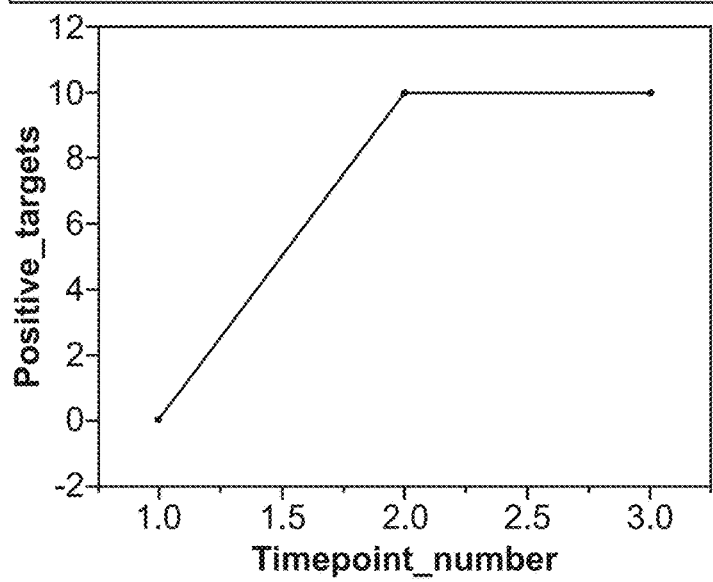
Figure 55A:
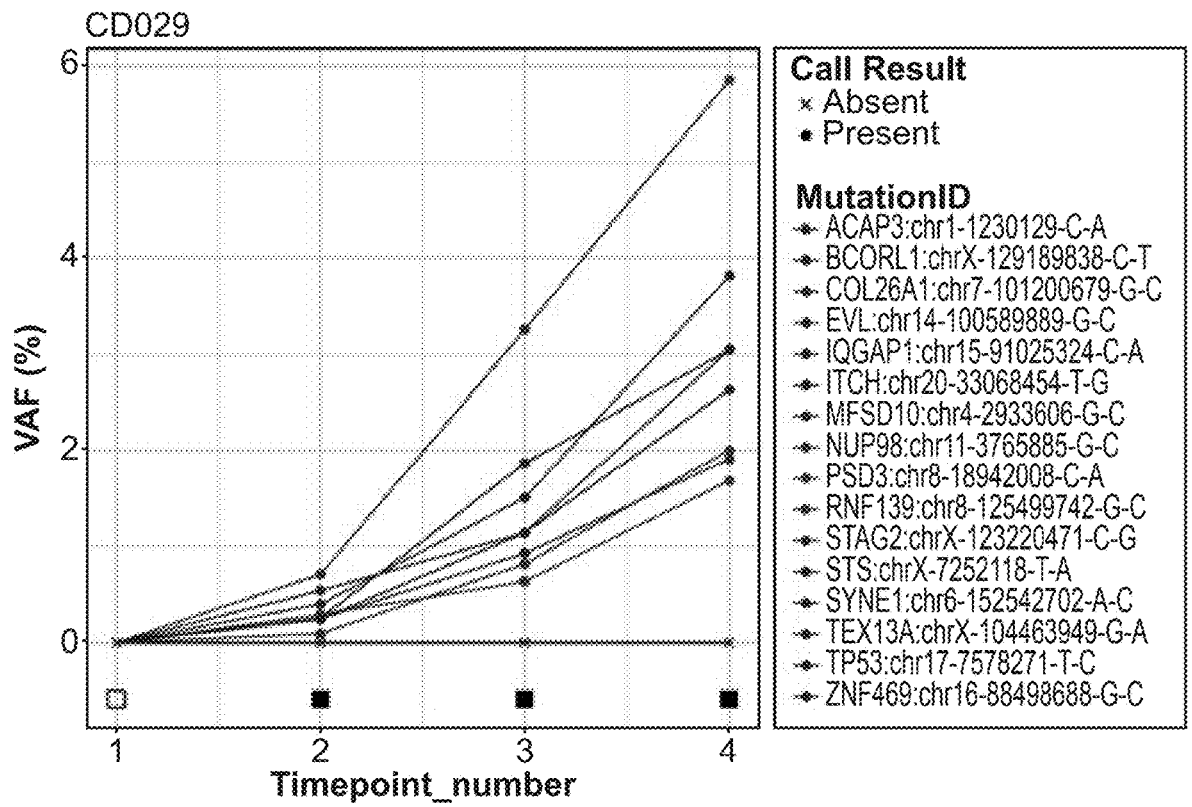
FIG. 55A-B: Graphical depiction of data corresponding to patient CD029 in FIG. 38.
Figure 55B:
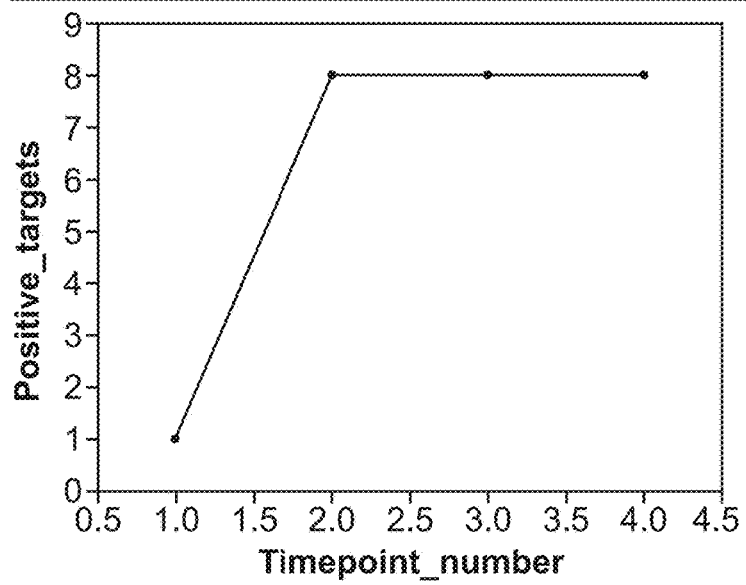
Figure 56A:
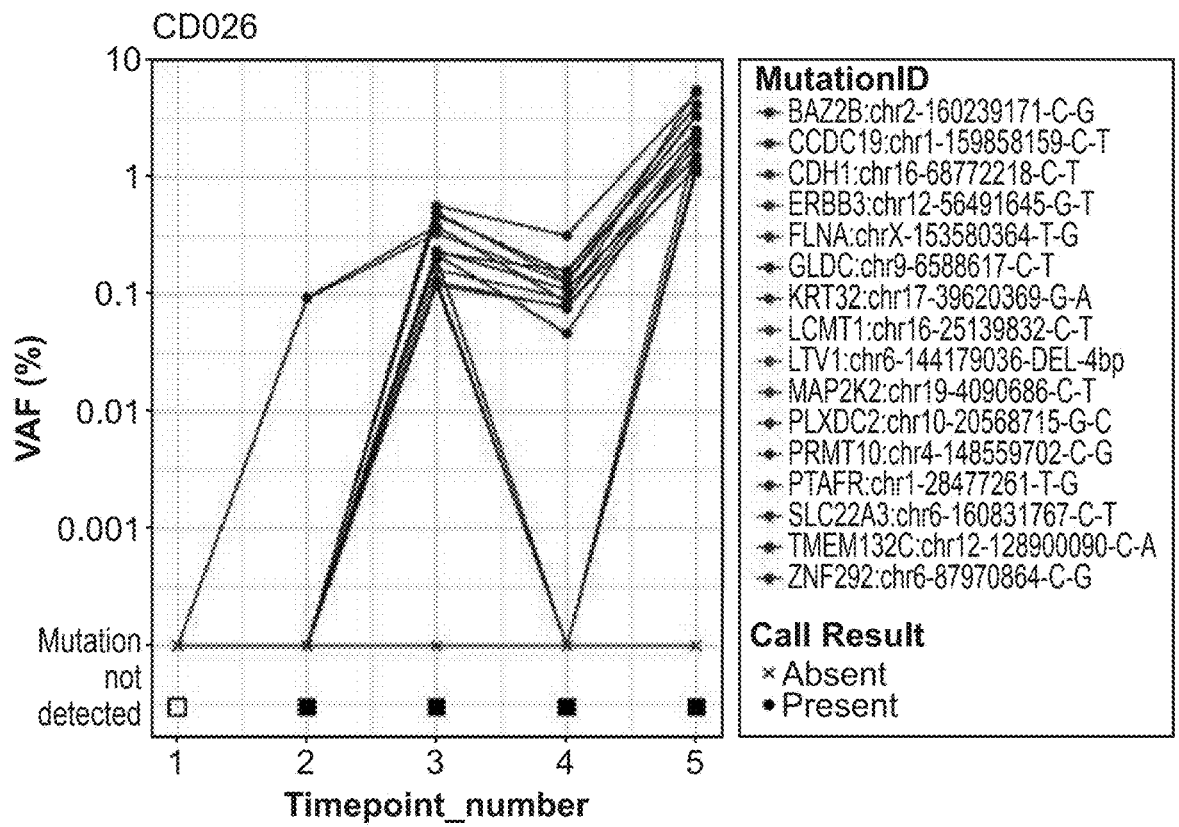
FIG. 56A-B: Graphical depiction of data corresponding to patient CD026 in FIG. 38.
Figure 56B:
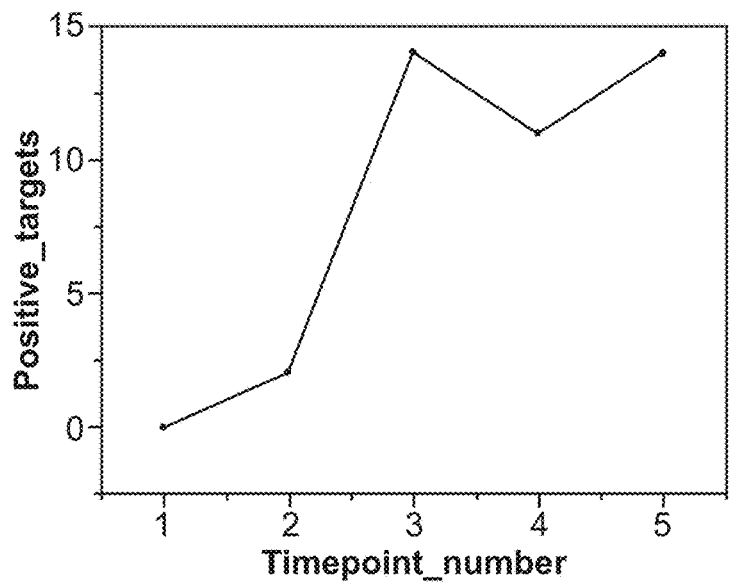
Figure 57A:
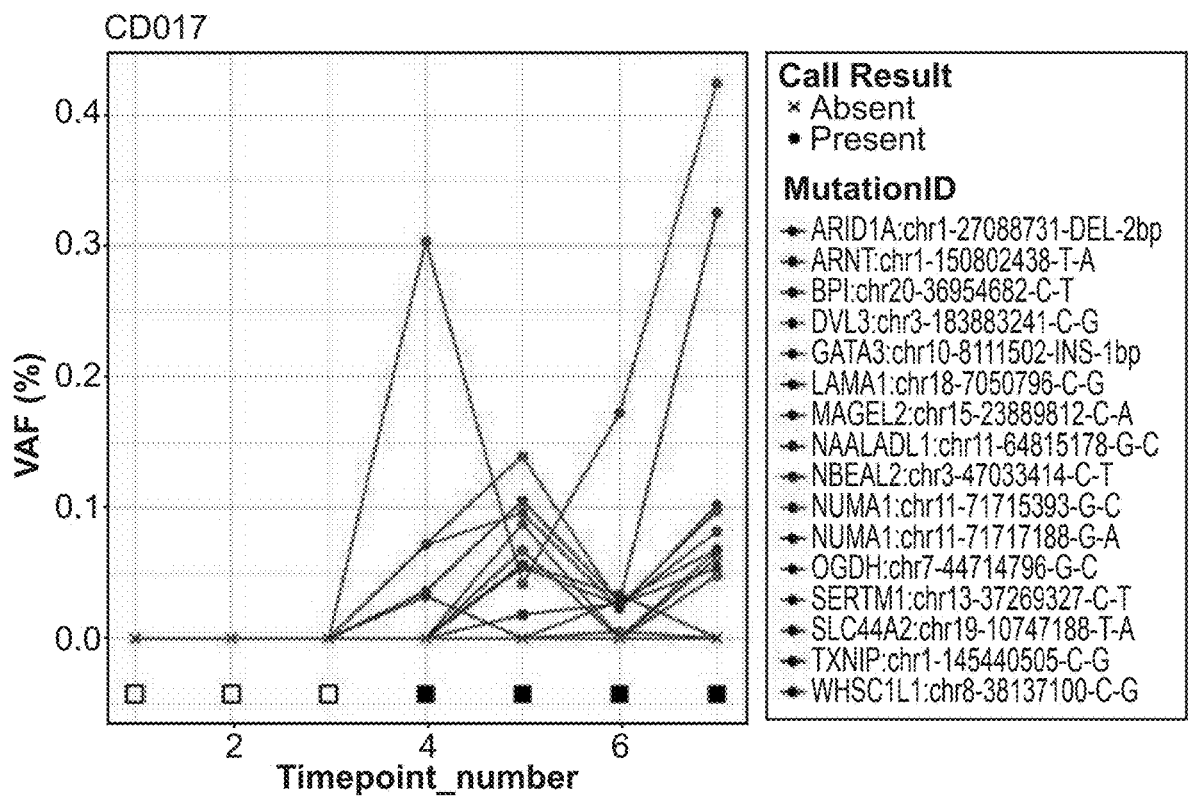
FIG. 57A-B: Graphical depiction of data corresponding to patient CD017 in FIG. 38.
Figure 57B:
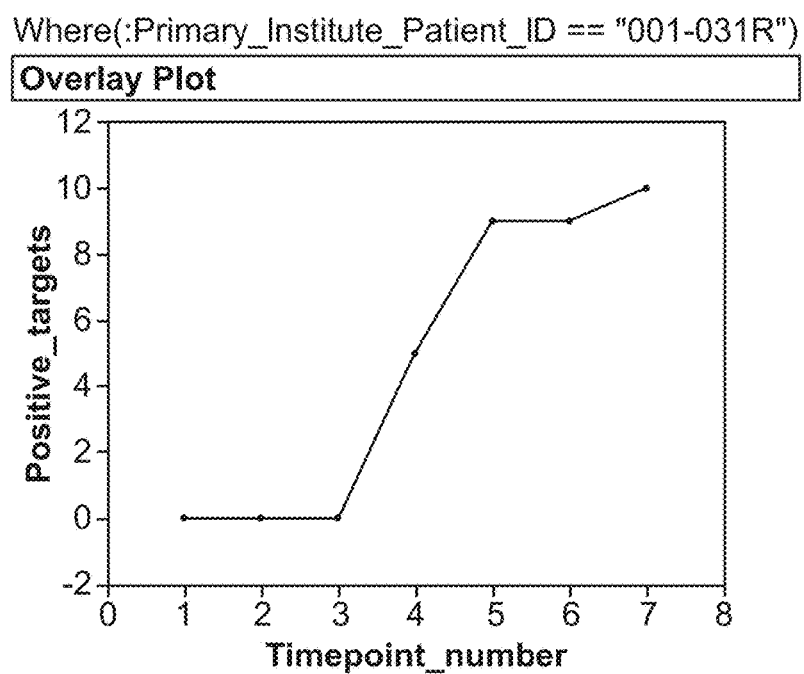
Figure 58:
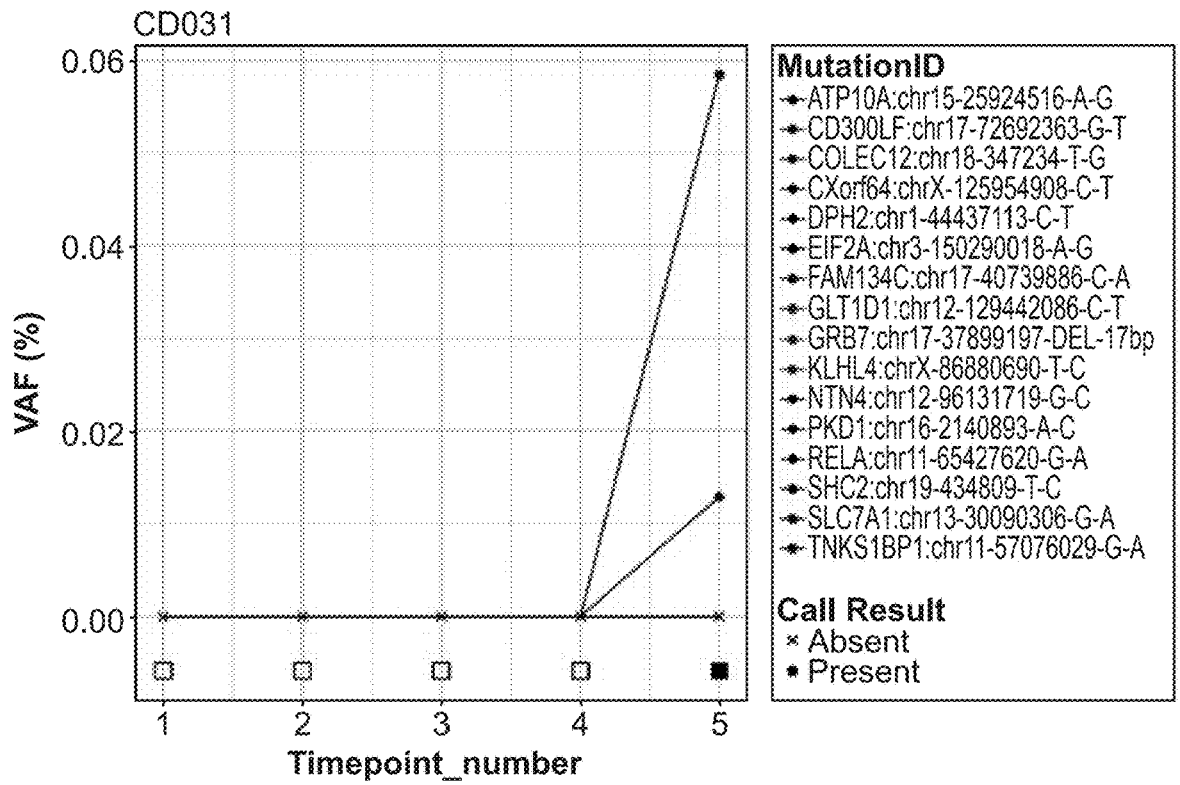
FIG. 58: Graphical depiction of data corresponding to patient CD031 in FIG. 38. HW: SHC2, PKD1, COLEC12.
Figure 59:
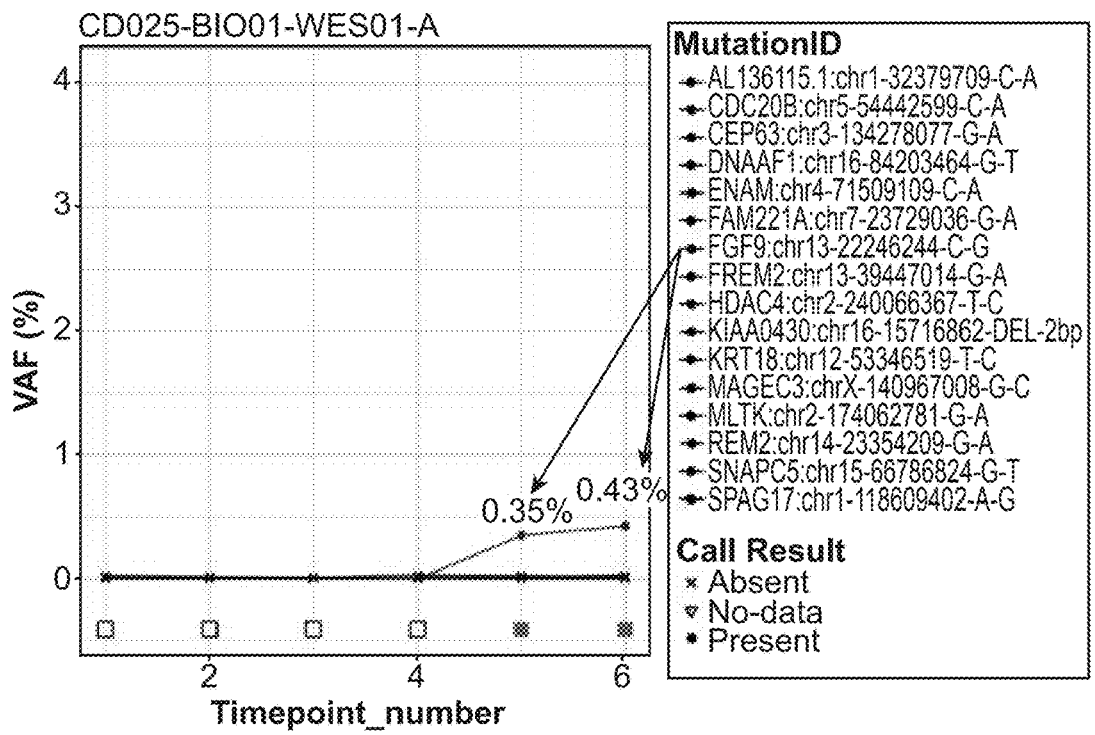
FIG. 59: Graphical depiction of data corresponding to patient CD025 in FIG. 38. In this patient, ctDNA was observed for a mutation in FGF9 for 2 consecutive time points. This patient may experience a relapse in the near future.

Results. In 16 of 18 (89%) clinically-relapsing patients ctDNA was detected ahead of metastatic relapse being diagnosed by clinical examination and biochemical (CA15-3) measurements, and remained ctDNA positive through follow-up. Of the 2 patients not detected, one had a local recurrence and the other had two primary tumours. None of the 33 non-relapsing patients were ctDNA positive at any time point (n=142). Metastatic relapse was predicted by Signatera with high accuracy and a lead time of up to 2 years (median=9.5 months). A summary of these results is provided in FIG. 37. Detailed results are shown in FIGS. 38-59.

Conclusions. The use of a scalable patient-specific ctDNA-based validated workflow identifies patients that will recur earlier. Accurate and earlier prediction by ctDNA analysis can provide a means of monitoring breast cancer patients in need second-line salvage adjuvant therapy in order to prevent overt life-threatening metastatic progression.

The results presented herein demonstrate that the methods are very sensitive in predicting breast cancer relapse based on detection of personalized cancer marker/circulating tumor DNA in patient's blood sample. For example, 16 of 18 relapse cases were correctly predicted and no false positives were identified. The methods are also very consistent. Once a positive detection is made, subsequence blood sample from the same patient stay consistently positive.

The methods are able to detect personalized cancer marker/circulating tumor DNA, and make prediction of relapse, for example, 27-610 days before relapse is detected via standard methods (e.g., imaging). The median time of detecting relapse is 9 months before relapse is detected via standard methods.

Example 7. Personalized Serial Circulating Tumor DNA (ctDNA) Analysis in High-Risk Early Stage Breast Cancer Patients to Monitor and Predict Response to Neoadjuvant Therapy (NAT) and Outcome in the I-SPY2 TRIAL Background ctDNA analysis offers a non-invasive approach for monitoring response and resistance to treatment. Serial ctDNA testing during NAT may provide early indicators of emerging resistance and disease progression. In this study, ctDNA was analyzed from high-risk early breast cancer patients who received NAT and definitive surgery in the I-SPY2 TRIAL (NCT01042379). The data collected in this example will be used to: (1) determine the relationship between ctDNA levels during early treatment and pCR/residual cancer burden/DRFS; (2) compare the performance of ctDNA vs. MRI imaging in predicting tumor response to therapy; and (3) examine the relationship of ctDNA levels before and after NAT with 3-year event-free survival (EFS).

Methods. ctDNA analysis was performed in 84 high-risk stage II and III breast cancer patients randomized to neo-adjuvant investigational agent (n=57), AKT inhibitor MK-2206 (M) in combination with paclitaxel (T) followed by doxorubicin and cyclophosphamide (AC) (M+T→AC), or standard-of-care (T→AC) (n=27). HER2+ patients received trastuzumab (H) in addition to T or M+T.

Serial plasma was collected before NAT, early treatment (3 weeks), between regimens (12 weeks), and after NAT prior to surgery. Mutational profiles derived from pretreatment tumor biopsy and germline DNA whole exome sequences were used to design personalized assays targeting 16 variants specific to a patients' tumor to detect ctDNA in plasma. In a subset of patients who did not achieve a pCR (n=18-22), mutations in residual cancers were compared to those found in pretreatment tumor.

Analysis: Of the 84 patients in this analysis, 15-25% were HR−HER2−, 40-60% HR+HER2−, and 35-35% in HER2+. 20-25% and 30-42% achieved a pCR in the control and treatment arms, respectively. Currently, data are collected to: (1) determine the relationship between ctDNA levels during early treatment and pCR/residual cancer burden/DRFS; (2) compare the performance of ctDNA vs. MRI imaging in predicting tumor response to therapy; (3) examine the relationship of ctDNA levels before and after NAT with 3-year event-free survival (EFS).

Conclusions. This study provides a platform to evaluate the clinical significance of ctDNA for serial monitoring of response to NAT. Accurate and early response prediction by highly sensitive ctDNA analysis can facilitate a timely and judicious change in treatment to improve patients' chances of achieving a pCR. Finally, personalized ctDNA testing can complement imaging and pathologic evaluation of tumor response to fine-tune pCR as a surrogate endpoint for improved EFS.

Example 8. Early Detection of Residual Breast Cancer Through a Scalable and Personalized Analysis of Circulating Tumor DNA (ctDNA) Antedates Overt Metastatic Recurrence Introduction Breast cancer is one of the most commonly diagnosed cancers worldwide and the second leading cause of cancer-related deaths in women. The current standard of care for women with non-metastatic breast cancer is surgery, often followed with adjuvant therapy to eliminate microscopic residual disease that can lead to relapse or further disease progression. Unfortunately, up to 30% of women who present with no evidence of disease following treatment with curative intent, eventually relapse and die of metastatic breast cancer as a result of micrometastases. Current tools for disease monitoring including imaging and/or biochemical methodologies (including serum levels of Cancer Antigen 15-3 (CA15-3)) have limited sensitivity and accuracy in detecting micrometastases. Late detection of metastasis is associated poor outcomes in many patients, underscoring the need to develop earlier and more sensitive measures of minimal residual disease (MRD).

Circulating tumor DNA (ctDNA) released by apoptotic and necrotic cancer cells has been shown to reflect the mutational signatures of the tumor and is emerging as a potential non-invasive biomarker for monitoring tumor progression across different cancer types. In breast cancer, the utility of ctDNA to detect minimal residual disease following surgery and/or adjuvant therapy, and to monitor metastatic disease has shown promising results. Specifically, plasma ctDNA levels have been shown to correlate with changes in tumor burden, thereby providing an earlier measure of treatment response, and to discriminate patients with and without eventual clinical recurrence post-surgery. While multiple studies have documented the potential use of ctDNA analysis in breast cancer, to date, there are no scalable tests capable of reliably detecting minimal residual disease in all patients.

A personalized tumor-specific approach for interrogating single nucleotide and INDEL variants in plasma cfDNA predicted relapse in patients with non-small cell lung cancer ahead of clinical detection, suggesting that this may also be suitable for monitoring minimal residual disease in breast cancer patients. Here, using an enhanced and scalable version of this approach, we sought to determine the use of serial ctDNA analysis in monitoring breast cancer recurrence following surgery and adjuvant therapy in comparison to conventional monitoring methods. The primary objective was to determine the "lead interval" between detection of ctDNA in blood plasma and clinical detection of overt metastatic disease in patients with primary breast cancer.

Methods
Patients and Samples

EBLIS is a multi-center, prospective cohort study, (NIHR REC number 13/LO/1152; IRAS: 126462) funded by Cancer Research UK and the National Institute for health Research (NIHR). All the patients gave written informed consent prior to entry into the trial. The trial protocol was approved by the Riverside Research Ethics Committee REC: 13/LO/115; IRAS: 126462. All research and technical staff were blinded as to the outcome of patients.

Figure 60:
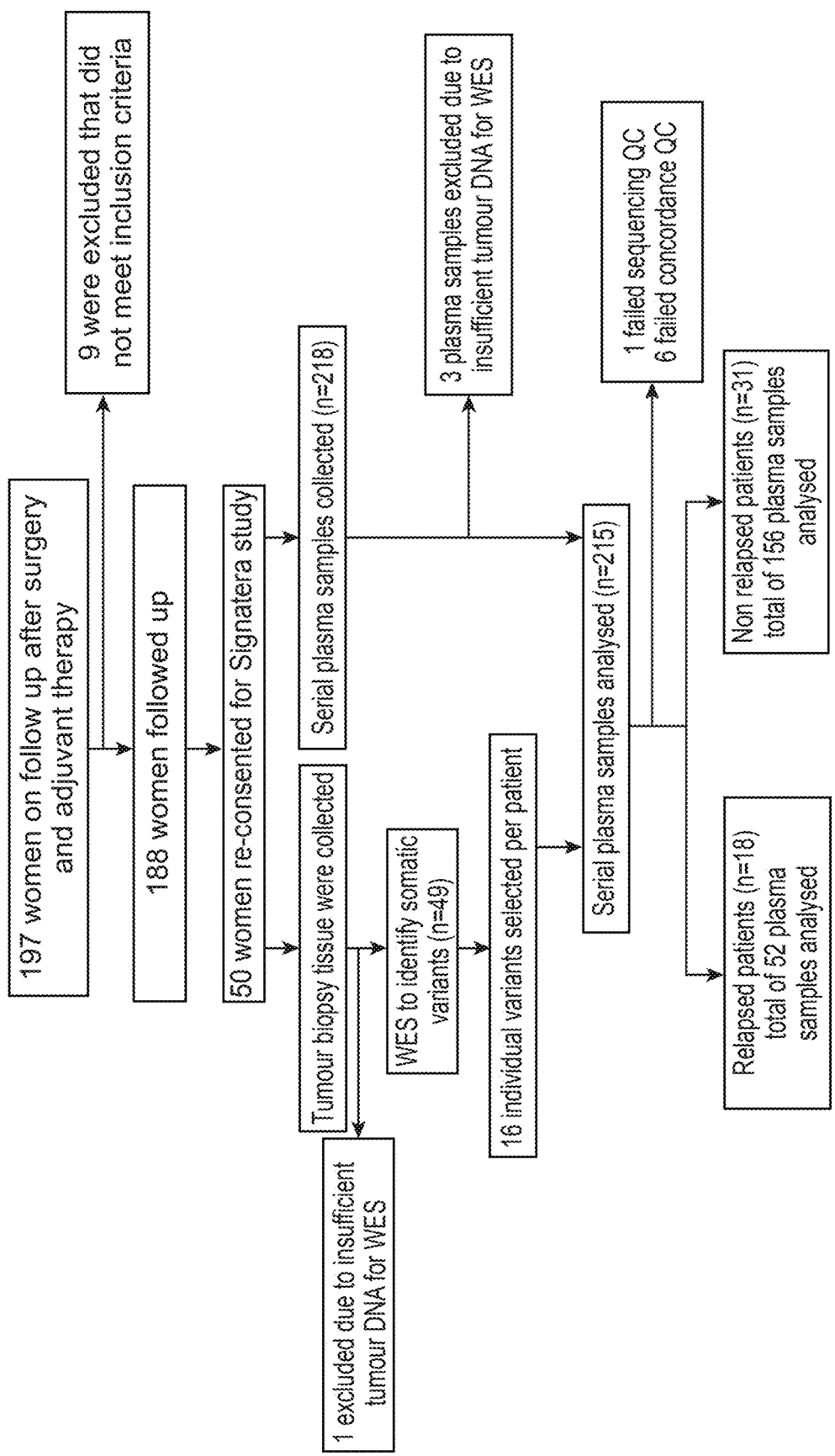
FIG. 60: Patient recruitment and Collection of Clinical Samples. For the 49 BC women monitored in this study, collected tumor tissue and serial plasma samples were analyzed using Signatera™ RUO workflow in a blinded manner. Exomic alterations were determined through paired-end sequencing of FFPE tumor-tissue specimens and matched normal DNA. Patient specific panels including 16 somatic mutations identified from WES were designed. Plasma samples were processed using their corresponding custom panels. 208 samples were analyzed for ctDNA detection.

We recruited a total of 197 patients from 3 centers in the UK. Nine patients did not fulfil the trial entry criteria; thus, a cohort of 188 patients were followed up with 6 monthly blood sampling for ctDNA, together with concomitant clinical examination, and biochemical measurements, including CA153 (FIG. 60). Eligible patients were to be 18 years or older, have no clinical evidence of metastatic disease, and therefore were considered free of disease after surgery and adjuvant chemotherapy. All had completed adjuvant chemotherapy within 5 years of entering the study. All had poor risk breast cancer (risk of mortality of >50% at 10 years without therapy, corresponding to a relapse rate of 65% at 10 years without treatment).

At the mid-point of the study (2 years), after an interim analysis and noting that there were 50% of predicted events, we elected to perform whole exome analysis of the primary tumor in the first 50 patients.

Blood samples were collected in K2-EDTA tubes. Samples were processed within 2 h of collection by double centrifugation of the blood, first for 10 min at 1,000 g, then the plasma for 10 min at 2000 g. Plasma was stored in 1 ml aliquots at −80° C.

Signatera™ RUO platform. All research and technical staff were blinded as to the outcome of patients and analyses were performed in a blinded manner. A strictly-controlled semi-automated lab process was performed by trained personnel with signed-off SOPs and witnessing. All reagents and equipment were controlled and qualified before entering the Signatera™ RUO pipeline. The process and reagent/equipment information were captured electronically and uploaded to a database with built-in integrity checks. Quality control was performed at every step of the workflow (FIG. 67A-D). Samples and amplicons which did not pass QC were excluded from analyses. For each patient, a set of 45 SNPs were genotyped in WES and plasma sequencing to ensure sample concordance. WES data was used to design patient specific panel of somatic mutations for all 49 patients. A total of 215 plasma samples were analyzed for ctDNA detection. For each target variant, a confidence score was calculated based on the mutant and reference alleles depth of read. A plasma sample with 2 or more high confident variants was considered ctDNA-positive. Details on steps of Signatera workflow are provided below.

Statistical Analyses

All data were presented descriptively as means, medians or proportions. Relapse free survival from the day of study enrolment was determined using the method of Kaplan-Meier. Cox Proportional Hazard regression was used to model the time to disease relapse. All statistical analyses were performed using Stata, release 12.0 (Stata Corp., College Station, Texas, USA) and survival plots generated using R version 3.5.1 ("survminer" package version 0.4.2.99).

A conservative strategy for handling missing continuous data was employed. If single data points were missing, the last observation was carried forward or if previous and subsequent data was available, then an average of these two values served as an estimate of the missing data.

Whole Exome Sequencing

The diagnostic FFPE blocks were checked by visual inspection and the block with the most residual tumor was used for DNA isolation. A single H & E tissue section was reviewed by a consultant histopathologist (D M) and a minimum of 2 regions of tumor was macrodissected using a 1 mm tissue microarray core needle. DNA was extracted from the FFPE tumor cores using the Gene Read kit (Qiagen) according to the manufacturer's instructions and DNA concentration was measured as described previously.

Illumina HiSeq was used to perform whole-exome sequencing on 200-500 ng pooled tumor DNA from 1-3 regions cored from each FFPE primary tumor block (Sequencing was carried out as a fee per service by Novogene, at an average deduplicated on-target read depth of 150× for all 49 tumor DNA and 50× for 49 matched germline samples. All sequencing data have been deposited in the European Genome-Phenome Archive.

Custom panel design. Patient specific somatic variants were identified by analyses of primary tumor and matched normal WES for all 49 patients. Clonality of variants was inferred based on the estimated proportion of cancer cells harboring the variant. Inferred clonality and types of variants were used to prioritized somatic SNVs and short Indels identified for each tumor. The standard Signatera assay design pipeline was used to generate PCR primers for the given set of variants. For each patient, 16 highly ranked compatible assays were selected for the custom patient-specific panel. The patient-specific 16-plex PCR assays were ordered from Integrated DNA Technologies.

cfDNA extraction and quantification. Up to 8 ml of plasma per case was available for this study (range, 1-8 ml; median 5 mL. The entire volume of plasma was used for cfDNA extraction. cfDNA was extracted using the QIAamp Circulating Nucleic Acid kit (Qiagen) and eluted into 50 L DNA Suspension Buffer (Sigma). Each cfDNA sample was quantified by Quant-iT High Sensitivity dsDNA Assay Kit (Invitrogen). In 49 patients, cfDNA was isolated from a total of 215 serial plasma samples.

cfDNA library preparation. Up to 66 ng (20,000 genome equivalents) of cfDNA from each plasma sample were used as input into the custom library preparation. Cell-free DNA was end-repaired, A-tailed, and ligated with custom adapters. The purified ligation product was amplified for 20 cycles, purified using Ampure XP beads (Agencourt/Beckman Coulter).

Plasma multiplex-PCR NGS workflow. An aliquot of each library was used as input into the associated patient-specific 16-plex PCR reaction. Samples were amplified using the Signatera tumor-specific assay and barcoded, then pooled. Sequencing was performed on an Illumina HiSeq 2500 Rapid Run with 50 cycles of paired-end reads using the Illumina Paired End v2 kit with an average read depth of >100,000× per amplicon.

Bioinformatics pipeline. All paired-end reads were merged using Pear software. Bases that did not match in forward and reverse reads or have a low quality score were filtered out to minimize sequencing errors. Merged reads were mapped to the hg19 reference genome with Novoalign version 2.3.4. Amplicons with <5,000 high quality reads were considered to have failed the QC. Quality control was performed using an in-house program checking for a wide list of statistics per sample that included total numbers of reads, mapped reads, on-target reads, number of failed targets and average error rate (FIG. 67A-D)

Plasma variant calling. A large set of negative control samples (~1000) were pre-processed to build a variant-specific background error model. A confidence score was calculated for each target variant using mutant and reference alleles on the basis of the error model, which is incorporated herein by reference in its entirety. A plasma sample with at least 2 variants with a confidence score above a predefined threshold (0.97) is called ctDNA positive.

Figures 68A, 68B:
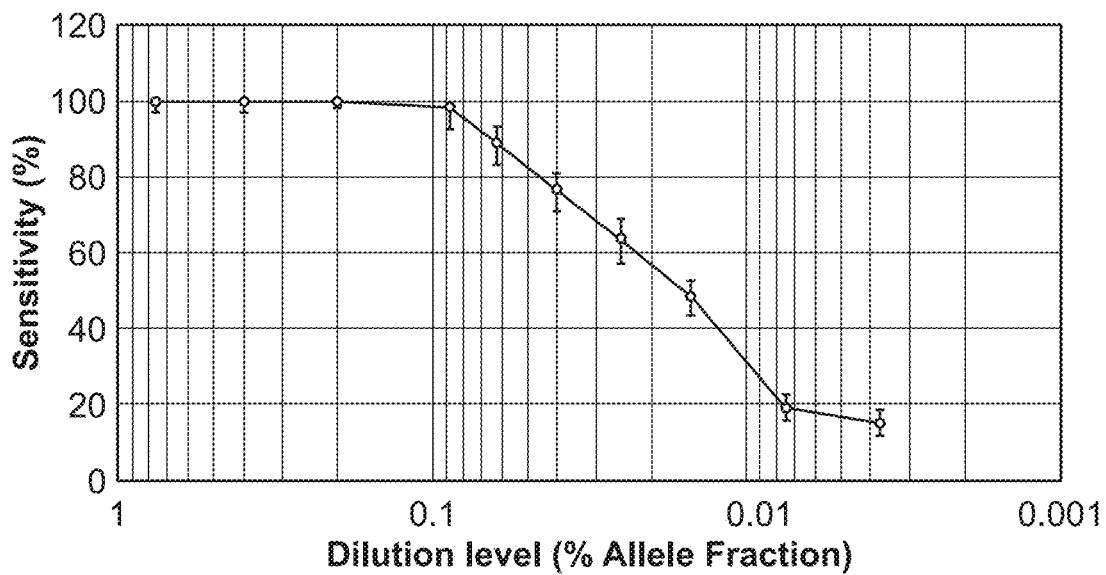
FIG. 68A-B: Analytical Validation Results. (A) Single target detection sensitivity. An analytical sensitivity of ~60% for mutation detection at ~0.03% spiked-in tumor DNA was achieved with Signatera. (B) Estimated sample-level sensitivities for Signatera when at least two mutations are detected from a set of 16 target variants.

Analytical validation. The analytical validation was performed using titrations of mononucleosomal DNA from three cancer cell lines into their matched normal counterparts (ATCC). Two breast cancer cell lines (HCC2218 & HCC1395), one lung cancer cell line (NCI-H1395), and their respective matched normal B lymphoblast-derived cell lines (HCC2218-BL, HCC1395-BL, and NCI-BL1395) were used. For each cell line pair DNA was exome-sequenced, target variants were selected, and two multiplex-PCR primer pools were designed using standard Signatera pipeline. Titrations of tumor into normal mononucleosomal DNAs were made at average VAFs (based on DNA input) of 1%, 0.5%, 0.3%, 0.1%, 0.05%, 0.03%, 0.01%, 0.005%, 0% (replicate numbers were from two to nine-increasing with the dilution factor). Due to the potential for heterogeneity and aneuploidy in the tumor cell lines the VAFs of the individual targets could differ from the average input VAFs. To accurately calculate the nominal VAF of each target in each titration step a separate experiment was performed with 10% VAF mixtures. The observed VAFs from this experiment were then used to calculate input correction factors (observed VAF/10%). The correction factors were applied to their respective targets in the dilution series. Additional negative samples were run using cfDNA isolated from 16 human plasmas (approximately 8 mL each). For the titration series 66 ng cfDNA (corresponding to 20,000 haploid genome equivalents) was used as input into the Signatera library preparation; for the plasma cfDNA samples all isolated DNA (ranged from 13-55 ng) was used as input. These libraries were then run through the Signatera plasma workflow (two primer pools for each titration sample and five primer pools for each cfDNA sample), sequenced, and analyzed with the Signatera analysis pipeline. FIG. 68A shows our estimated sensitivity for detecting targets in plasma at various level of concentration. A target specificity of >99.6% was achieved from negative samples. Assuming custom panel has between 10 to 16 clonal variants, sample-level sensitivity can be derived as reported in FIG. 68B. Sample-level specificity is estimated to be >99.8%.

Results

Here, we report the analysis of the first 50 patients entered into the EBLIS study (FIG. 60). One tumor sample was inadequate for exome sequencing and therefore we proceeded with 49 patients. Eighteen patients have relapsed and 31 remain disease-free at the reporting census date (30 Jun. 2018). All except 7 patients of the 49 patients received adjuvant or NACT chemotherapy with an anthracycline/taxane regimen (see FIG. 69 and Table A). Forty-one patients were receiving adjuvant endocrine therapy throughout the time of blood sampling (Table B1-B3). Although repeat scans were not required prior to trial entry, all except 3 patients had imaging studies at diagnosis or at the time of entry into the study, and all were within normal limits (Table B1-B3).

The non-relapsed patients were sequential patients recruited over the same time frame to those who relapsed, for whom we had sufficient tumor DNA isolated from the FFPE primary tumor block for exome profiling, and who had been followed up for a minimum of 2 years with serial blood sampling. We analyzed serial plasma samples in a blinded approach using the optimized Signatera workflow.

Of the 18 patients that relapsed, 10 were detected by CT, 3 by bone scan, and one each were detected by mammography, MRI, elevated liver enzymes, and ultrasound. One patient died of unknown cause.

Circulating Tumor DNA Detection and Lead Interval

We collected FFPE tumor samples from all patients: 39 had received no systemic therapy prior to biopsy; 10 had received neo-adjuvant chemotherapy (NACT) prior to their breast cancer resection (details of all systemic therapy, including timings of blood samples in FIG. 60 and Table B1-B3).

To assess the presence of circulating tumor DNA, for each patient, we designed patient-specific assays targeting 16 somatic SNV and INDEL variants from the somatic mutation profiles of each patient's tumor (FIG. 64A-C). We then applied the 49 respective personalized assays to each of the 208 plasma samples (range: 1-8 time points) from 49 patients.

Figure 61A:
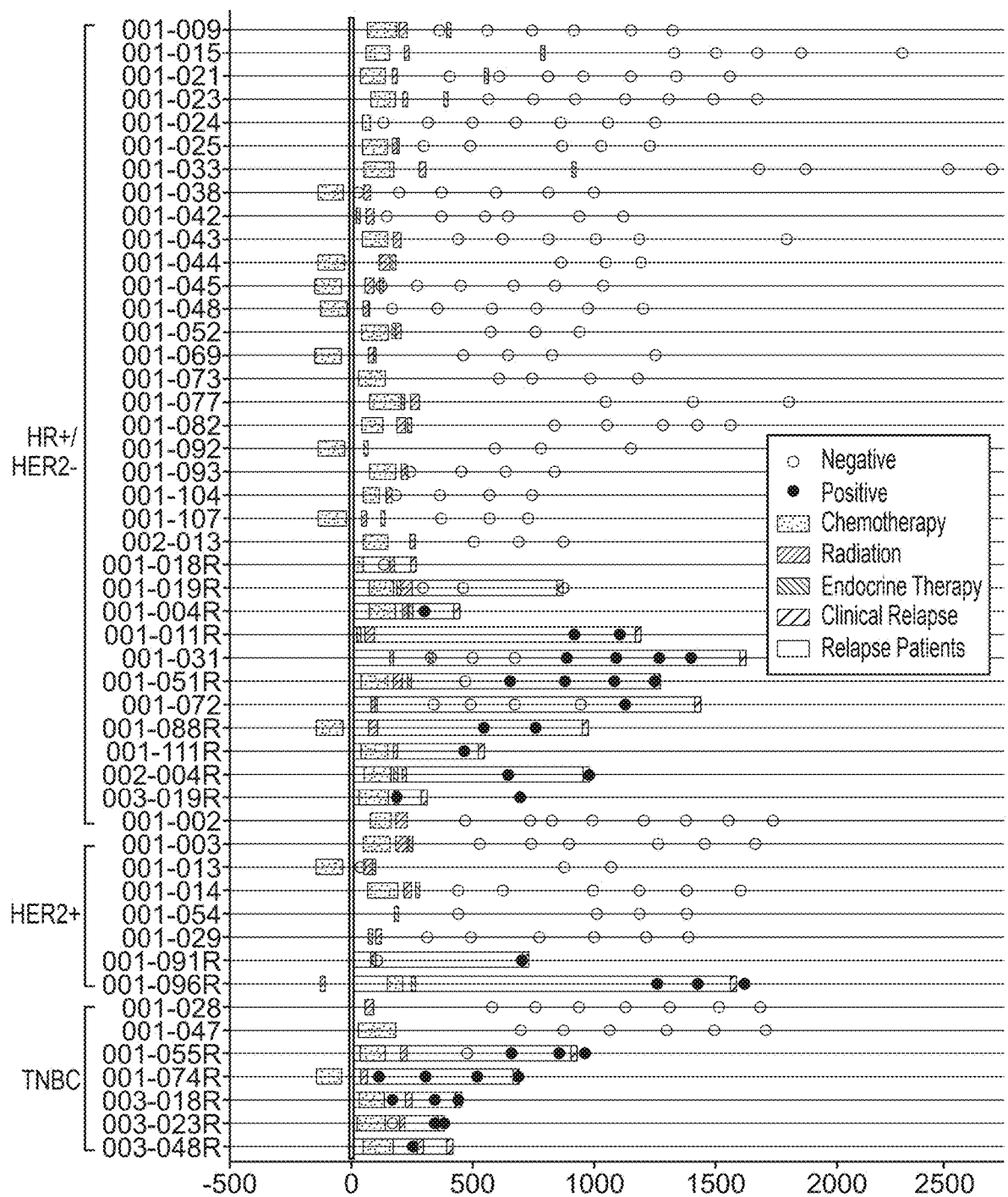
FIG. 61A-C: Summary overview and results of ctDNA analysis. (A) Summary of each patient's (n=49) treatment regimen along with results of serial plasma samples (n=208) analyzed. (B) Summary table showing total patients in each breast cancer subtype, number relapsed, percent detected by ctDNA analysis, and median lead time in days. (C) Comparison of molecular and clinical relapse colored by breast cancer subtype HR+, HER2+, TNBC using paired Wilcoxon signed rank test (p-value <0.001).
Figures 61B, 61C:
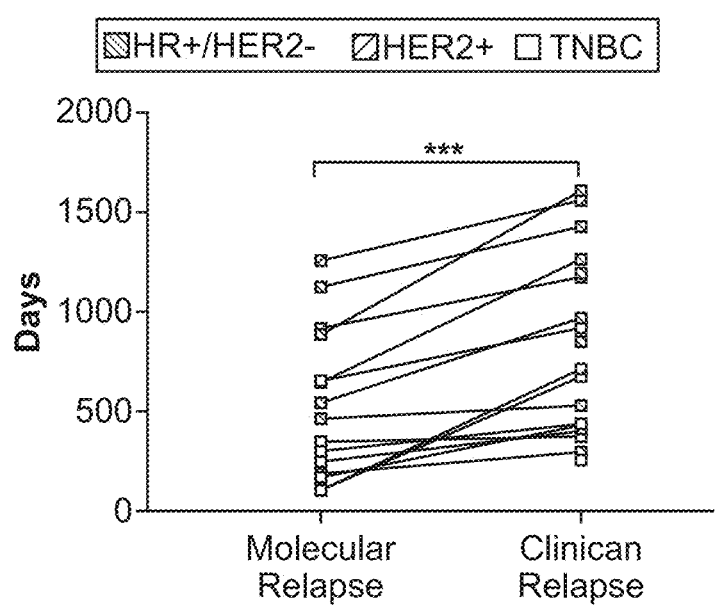
Figures 65A, 65B:
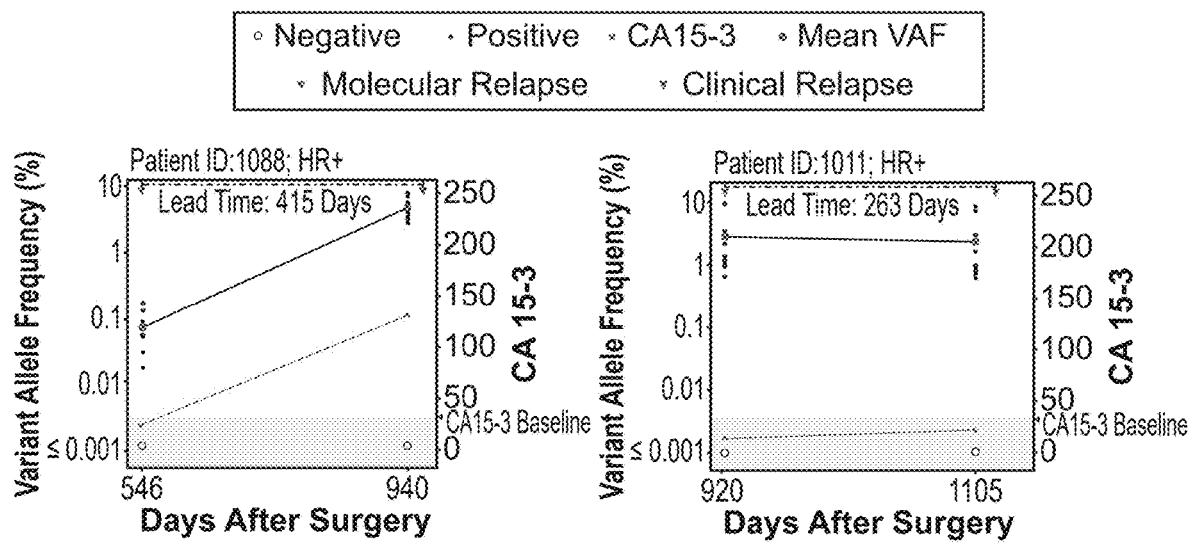
FIG. 65: (A-L) Plasma levels of ctDNA across multiple plasma time points for 12 (11 relapsed and 1 non-relapsed) breast cancer patients. Primary tumor and matched normal whole-exome sequencing identified patient-specific somatic mutations. Using the analytically-validated Signatera™ workflow, each patient specific assay was designed to target 16 somatic SNV and INDEL variants using massively parallel sequencing (median depth >100,000× per target) Mean VAFs are denoted by dark blue circle and solid line represent average VAF profile over time. The lead time is calculated by difference in clinical relapse and molecular relapse. CA15-3 levels is graphed over time and the baseline levels are marked in light shade.
Figures 65C, 65D:
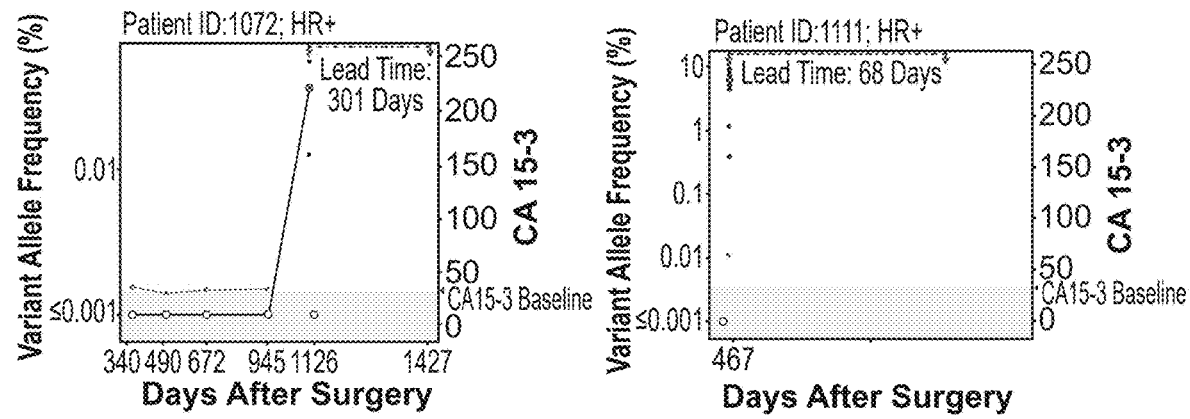
Figures 65E, 65F:
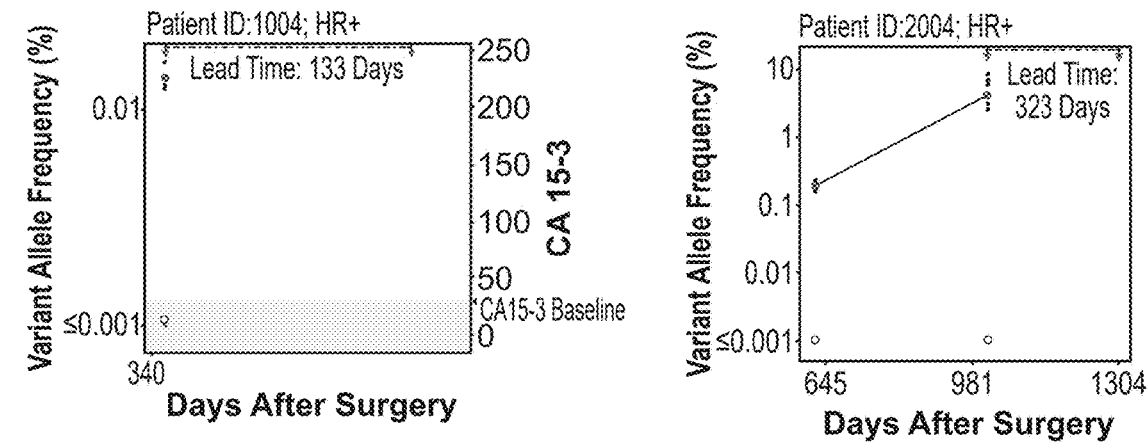
Figure 65G:
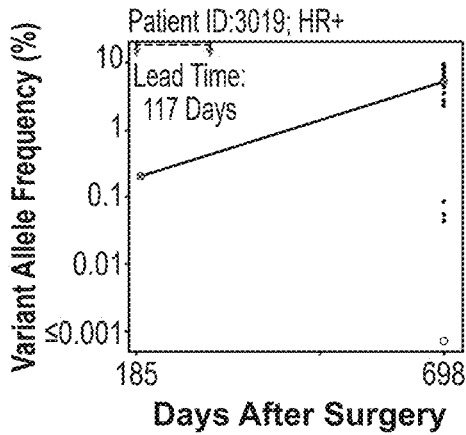
Figure 65H:
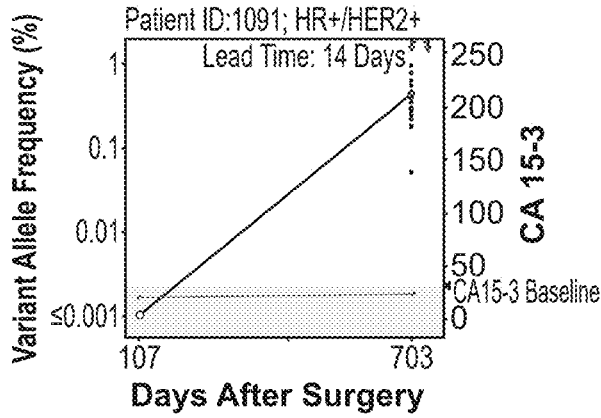
Figure 65I:
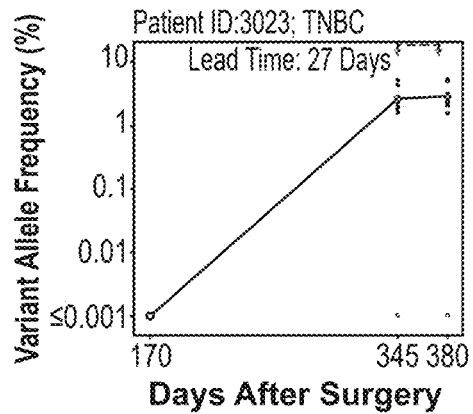
Figure 65J:
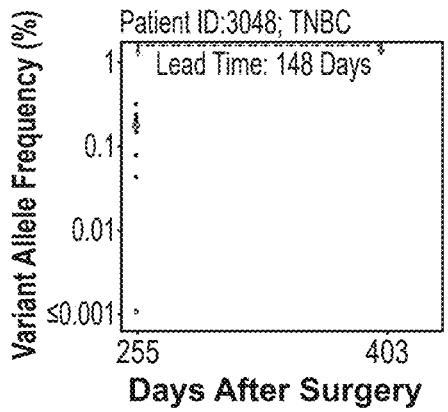
Figure 65K:
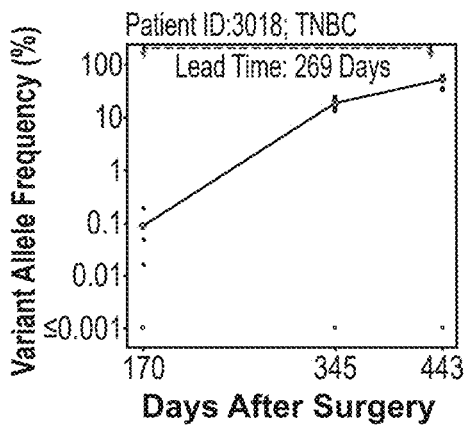
Figure 65L:
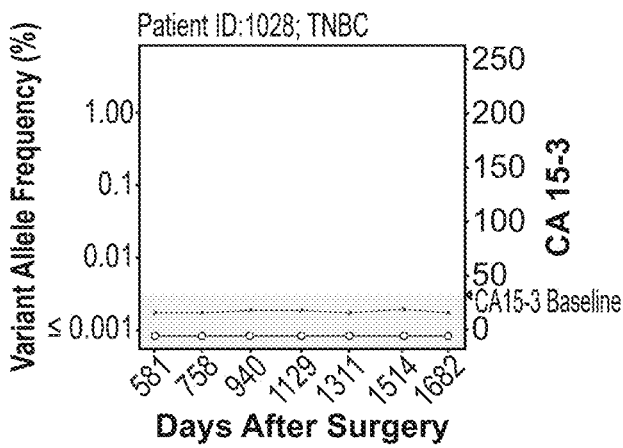

Circulating tumor DNA was detected in 89% (16 of 18) of the patients who relapsed; detection was 82%, 100%, and 100% in HR+/HER2−, HER2+ and triple negative breast cancers (TNBC), respectively (FIGS. 61A and B). Of the two relapsed patients who were not detected by ctDNA, one (1018) had three primary cancers and the other (1019) had a small local recurrence (subsequently resected) in the sternum (FIG. 61A, Table A). Notably, one patient (1072) initially had a normal blood profile but was positive for ctDNA at the last visit; the patient was disease free at the time of blood profiling, but the patient subsequently presented with distant metastases just prior to the census date (FIG. 61A and FIG. 65A). We detected recurrent disease up to 2 years prior to clinical relapse with a median of 266 days (8.9 months; FIG. 61B). When divided by subtype, the median lead times were 301, 164, and 258 days for HR+/HER2−, HER2+ and triple negative breast cancers (TNBC), respectively (FIGS. 61B and C). Strikingly, in two ER+PR+HER2− patients (1031 and 1051 FIG. 61A) there were up to four time points that were ctDNA positive prior to clinical relapse, translating to a lead interval of nearly 2 years.

Figure 62A:
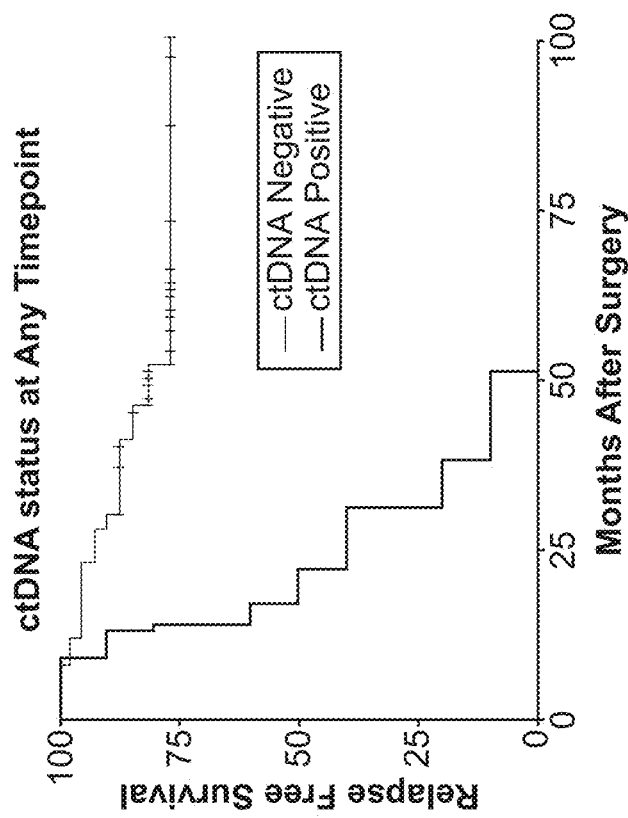
FIG. 62A-B: CtDNA detection in serial plasma samples predicts recurrence free survival (A) Recurrence-free survival according to the detection of ctDNA in any follow-up plasma samples post-surgery [HR:35.84 (7.9626-161.32]p-value <0.001. (B) Recurrence-free survival according to the detection of ctDNA in the first post-surgical plasma sample [HR: 11.784 (4.2784-32.457]. Data are from n=49 patients with p-value <0.001.
Figure 62B:
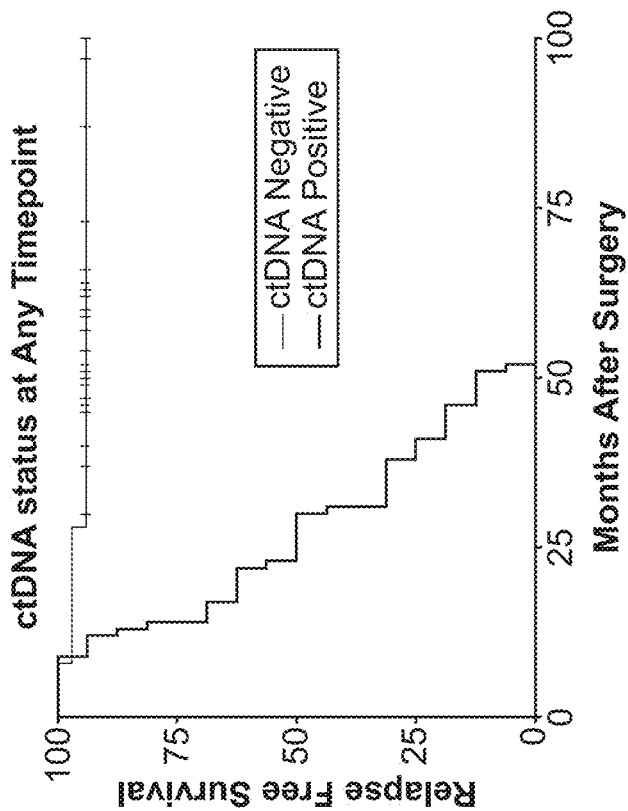

We did not detect ctDNA in any of the 156 plasma samples from the 31 patients who did not have disease recurrence (FIG. 61A). The presence of ctDNA was associated with significantly poor prognosis shown both by detection of ctDNA in the first post-surgical plasma sample (HR=11.8 (95% CI 4.3-32.5)) and in the follow-up plasma samples post-surgery (HR=35.8 (95% CI 8.0-161.3)) (FIG. 62A-B). All the patients that were ctDNA positive relapsed within 50 months after surgery.

For all patients, radiological and scanning examinations were negative for distant metastases until the date of overt relapse, generally preceded by patient symptoms. Many of the patients had follow-up scans to supplement scans done at presentation and these also were negative (Table B1-B3). Seven patients (1004, 1055, 1072, 1091, 3018, 3019, 3048) had scans done within 4 months of the ctDNA test first becoming positive and all were negative.

We also monitored CA15-3 in 43 of the 49 patients throughout the course of the study. Thirty-nine of these patients had normal results through the follow-up period. Twelve of the 18 patients who relapsed had normal CA15-3 levels through the monitoring period. Two patients (1051 and 1088) had progressive CA15-3 rise, but ctDNA was more sensitive than CA15-3 with ctDNA detected prior to elevated CA15-3 levels by 224 and 212 days, respectively (FIG. 63A and FIG. 65B). Patients 1111 and 1018 had a single blood sample taken prior to clinical relapse and had elevated CA15-3 measurements. Patient 1111 had a positive ctDNA test, while patient 1018 tested negative for ctDNA. Notably, six other patients (3 relapsed and 3 non-relapsed) had an occasional blood sample with slightly elevated CA15-3, but this fluctuated and did not reflect disease progression (Table B1-B3).

Characterization of Circulating Tumor DNA

Figures 66A, 66B:
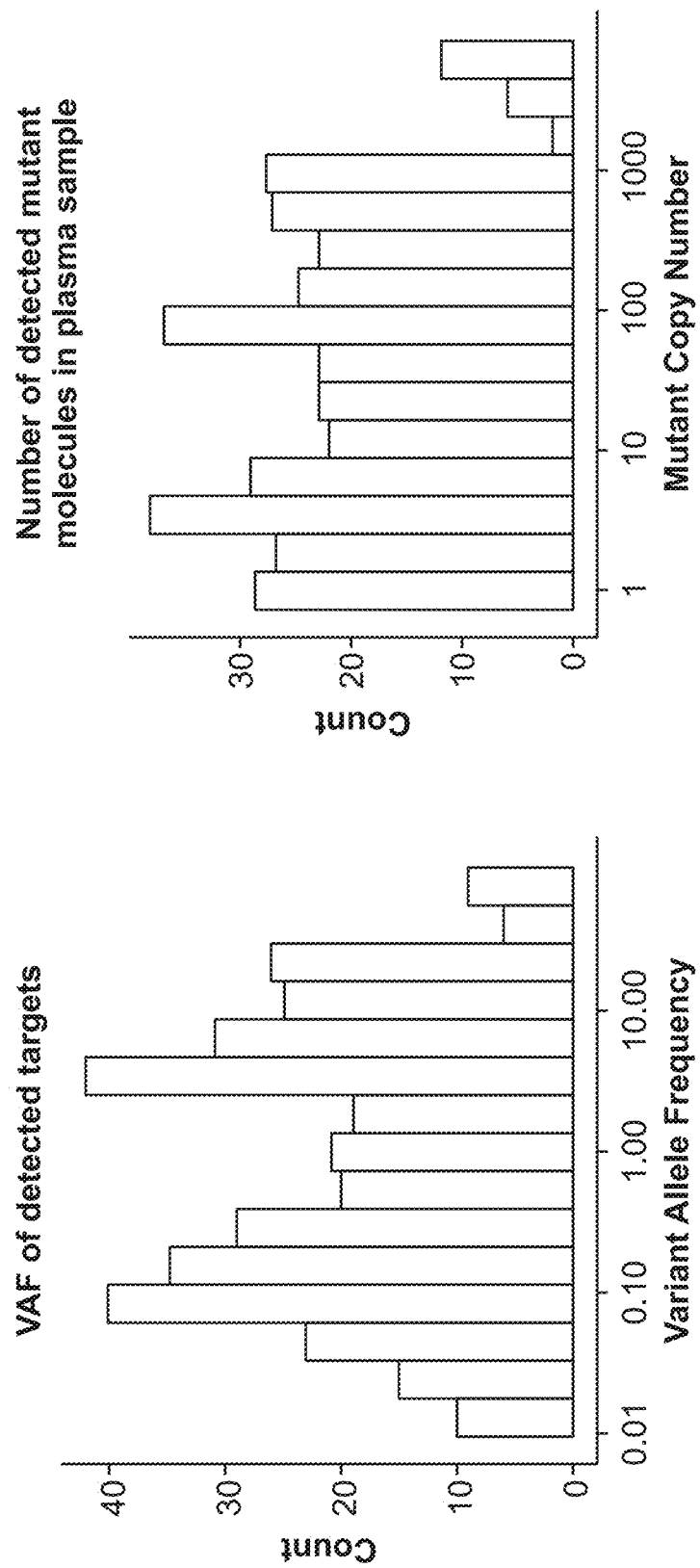
FIG. 66A-B: Distribution of VAFs and Mutant Counts. In total, 251 targets were detected in ctDNA positive plasma samples. The VAF of detected targets ranged from 0.01% to 64%, with a median of 0.82%. We used the observed mutant VAF and total number of DNA molecules in each sample to calculate the number of tumor molecules present in the patient's plasma sample. Number of detected mutant molecules in the 251 positive targets ranged from 1 to 6500 mutant molecules, with a median of 39 molecules.
Figure 67A:
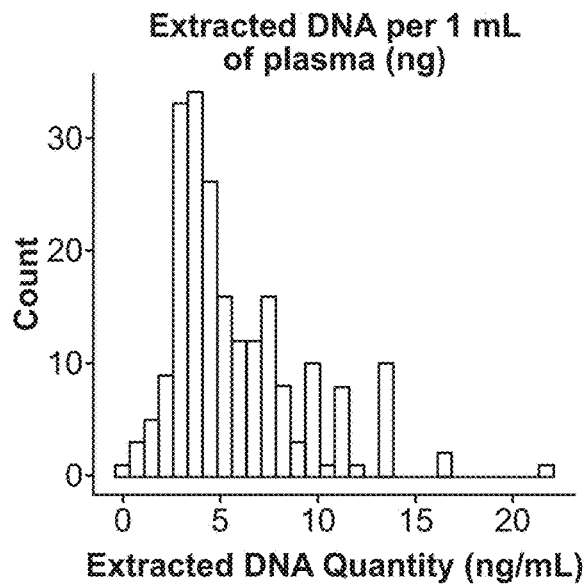
FIG. 67A-D: Signatera quality control process: Quality control was performed at every step of the workflow. In total out of 215 plasma samples 208 passed our sample QC process, and out of 784 unique assays designed there were 767 which passed our assay QC (corresponding to total of 3237 assays passing out of 3328 across all samples). A) Extracted cfDNA per mL. cfDNA extracted from each plasma sample was quantified by Quant-iT High Sensitivity dsDNA Assay Kit. Samples with quantified cfDNA amount <5 ng were flagged WARNING. Extracted cfDNA per mL ranged between 1 to 21.4 ng with the median of 4.7 ng. B) Library prep DNA input amount. Up to 66 ng of cfDNA from each plasma sample was used as input into library prep protocol. Library DNA input amount ranged between 1 to 66 ng with the median of 25.02. The purified libraries were QC'ed before proceeding to the next step. C) Sequencing coverage. Assays with coverage less than 5000× were excluded from analyses. Subsequently, samples with less than 8 passing assays failed sequencing coverage QC. The median depth of read for the assays passed coverage QC was 110,000×. D) Sample concordance. In order to track sample integrity, SNP tracers were used to measure concordance between patient's samples. For each plasma samples, a genotyping concordance score was calculated in comparison to its corresponding matched normal genotyping data. Samples are considered to be from the same patients when at least 85% of their SNPs had identical genotypes. Six plasma samples identified to be swapped were excluded from ctDNA analyses.
Figure 67B:
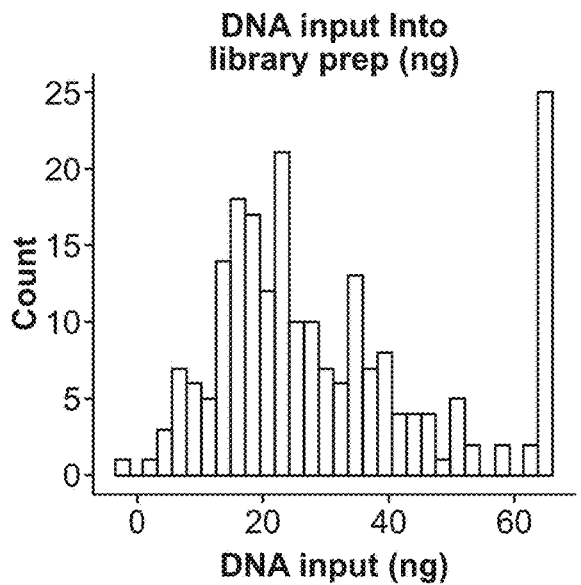
Figure 67C:
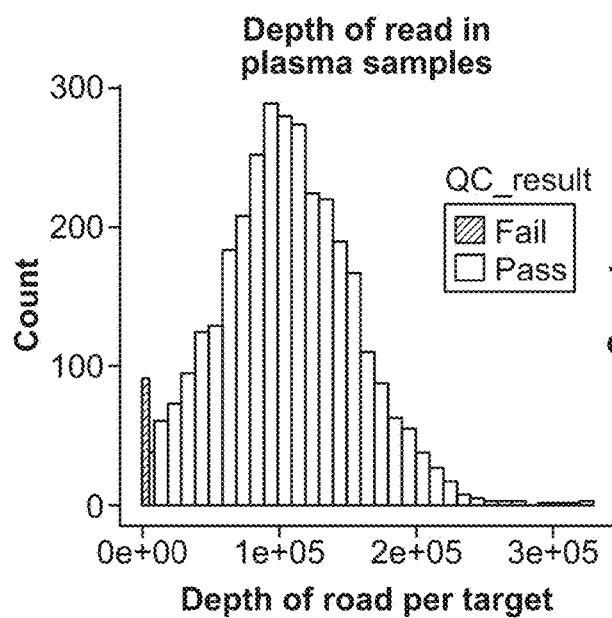
Figure 67D:
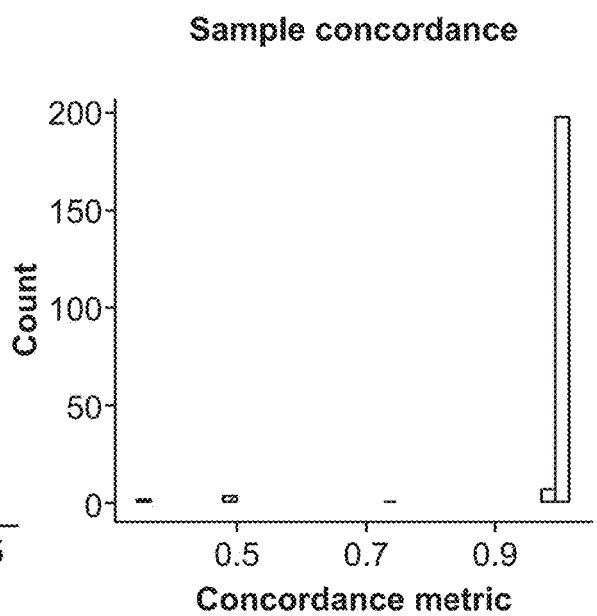

The Signatera assay is designed to target 16 patient-specific somatic SNV and INDEL variants that provide the highest likelihood of detection. All 16 relapsed patients detected by ctDNA are shown in FIG. 63 and FIG. 65. Ten plasma samples from eight relapsed patients had variant allele frequencies (VAFs) detected within 0.01-0.02%. The lowest variant allele frequency of 0.01% corresponds to detection of a single mutant molecule in the plasma sample (FIG. 66A-B). This level of sensitivity can be seen in four patients 1004, 01055, 1072, and 1096 (FIG. 63, FIG. 65, Table C). The greater than 99.5% specificity of the test is achieved by requiring that two or more variants are measured above the selected confidence threshold of the calling algorithm in order to be certain that ctDNA is present in the plasma. The specificity is underscored by the fact that none of the non-recurring patients' plasma samples were called positive.

In terms of changes in ctDNA profiles over time, of the 16 relapses detected through ctDNA, seven patients had a positive ctDNA test in all analyzed time points and showed an increase in both the number of variants detected and the percentage VAF over time; six patients that were initially ctDNA-negative later became positive, and three relapsed patients had only one plasma time point available for analysis, which were all ctDNA positive (FIG. 63 and FIG. 65).

Five of these patients are highlighted in FIG. 63 with at least one of each subtype-HR+/HER2− (1031 and 1051), HER2+(1096) and TNBC (1055 and 1074) being represented. Patients 1031, 1051, 1055 were initially ctDNA-negative, but ctDNA became detectable at a later time point (FIG. 63A-C). Two of these patients, both HR+(1031 and 1051), had the greatest lead time between molecular relapse detected by ctDNA and clinical relapse with 721 and 611 days, respectively (FIG. 63A-B). Patients 1031, 1055, 1074 and 1096 had variant allele frequencies detected in the range of 0.01 to 0.02% and showed a progressive rise in VAF correlating with disease progression (FIG. 63B-E). All patients remained positive through follow up once ctDNA had been detected (FIG. 63 and FIG. 65).

Overall, disease progression can be monitored by both the variant allele frequency and the number of detected variants as shown in FIG. 63F. Since the number of time points varied amongst the patients, the differences are highlighted by the first and last time points in the series of plasma samples from the same patient. The median variant allele frequency increased from 0.092% in the first time point (range: 0.01% to 9.2) to 3.9% (range: 0.05 to 64.4%), whereas the median number of variants detected at the first time point was 5 (range: 2-12) compared to 12 variants (range: 5-15) at the last time point. The low number of variants detected at early time points and the fact that these are present at very low copy numbers point to the importance of testing multiple mutations that are present in a patient's tumor in order to have a highly sensitive test for the presence of ctDNA in the plasma of a patient.

Discussion

This report describes a reliable and reproducible method of monitoring minimal residual disease in breast cancer patients across major subtypes. The approach uses genomic data from the tumor to design patient-specific assays. Sequencing of plasma cfDNA is then performed at extremely high depth to an average of >100,000 reads per target to achieve detection of sensitivity down to a single mutant molecule. This new transformative technology is robust and scalable for implementation in modern healthcare and is already productized for research use. This is especially timely, given, for example, the recent announcement that all cancers in the UK will receive genomic profiling from autumn 2018. The Signatera platform is capable of providing an individualized way of detecting micrometastatic disease, which is clearly supported by the results of this study in that all, but one, breast cancer patients who relapsed with distant metastases had a positive blood test before overt relapse, and in some cases demonstrating nearly a 2-year lead interval.

A previous study with a prototype of this technology showed promise in patients with non-small cell lung cancer (Abbosh et al. 2017, incorporated herein by reference in its entirety), and the workflow has been refined since to achieve a higher sensitivity of ctDNA detection and to be more economical. Here, we demonstrate the excellent reproducibility and accuracy of this system. Focusing on SNVs that are unique to the patient rather than known driver genes represents the most accurate and sensitive way of detecting MRD in patients with breast cancer to date.

The clinical application of ctDNA measurements in the management of early-stage cancer remains a highly contentious issue, and a recent ASCO and ACP joint review concluded that there is no evidence of clinical utility and little evidence of clinical validity in early-stage cancer of treatment monitoring or early residual disease detection. This conclusion may, in part, be due to the fact that all previous studies have been done in the absence of a comparison with conventional markers, such as has been done here.

There are several important points that emerge from this study. First, it is now possible to predict relapse with a high degree of accuracy in patients with no evidence of disease on imaging. Secondly, most patients are now followed up in US and UK centers by a combination of annual mammography and, in some cases, CA15-3 and liver function tests. These, with the exception of two cases of progressively elevated CA15-3 in the absence of detectable metastases, were all normal in our cohort until overt metastatic relapse, demonstrating the limitations of the current approaches used by clinicians. Seven of the patients who relapsed also had scans around the time of first detection of ctDNA and all were negative. Of note is the observation that some patients had transiently elevated CA15-3 and remain disease-free while the Signatera test was consistently positive once detected and there were no false positives. Thirdly, in spite of the fact that NACT reduced the primary cancer (on which exome sequencing was carried out), the mutation signature of the residual cancer reflects the residual metastatic disease in these patients, which suggests that personalized test designed based on the primary tumour mutation profile is not only possible, but effective.

However, there is a requirement for ctDNA to be shed into the plasma, and thus the test may be limited to those who have sufficiently aggressive disease at the outset, and thus may not be applicable to those patients with smaller and less aggressive breast cancers who often have a good prognosis. As the detection limit of our assay is down to a single molecule, the lack of detection is likely associated with tumor biology in which less aggressive tumors may release fewer ctDNA molecules. This is exemplified by one patient (1018) who relapsed with local resectable disease while being ctDNA negative. Further, in patients with multiple primary tumors, all will need to be profiled for monitoring disease progression. This is seen with patient 1019 who had three primary tumors; unfortunately, only one was subjected to exome sequencing due to limited available tissue. In this case, disease recurrence was not detected by ctDNA and our hypothesis is that the metastasis did not derive from the tumor that was sequenced. Finally, the test is not suitable for detecting a second primary breast cancer unless this is a recurrence of the original tumor; this is exemplified by the patient 1044 where a second contralateral primary cancer was found by routine mammography but plasma remained ctDNA negative throughout (Table A).

The analytic platform described here is not intended to identify tractable targets from the plasma. The majority of SNVs selected to be used for tumor DNA detection were unique to each patient, and were selected as a reflection of tumor burden rather than representing driver mutations that often contribute to cancer progression. However, this is also the advantage of the Signatera assay—choosing passenger and clonal mutations is imperative for monitoring disease burden since driver mutations often impart a selective advantage leading to changes tumor heterogeneity. While the 16-plex assays do not provide actionable targets, the tumor WES may provide such targets and plasma libraries may also be tested with other assays that identify tractable mutations.

Our results complement those of others in which actionable mutations for example in PIK3CA, are monitored throughout the neoadjuvant and adjuvant period. While choosing driver mutations could monitor the progression of some tumors (REFs), studies have shown that they are not useful in detecting early metastatic relapse in all patients since not all patients harbor the same targeted driver mutations in their tumor (REFs). In one previous study, only 78% (43 of 55) of the cases had one or more somatic mutation identified and were subsequently monitored using digital droplet PCR (ddPCR). We also analyzed an "off the shelf" breast cancer panel (Oncomine™ Breast cfDNA Assay) targeting >150 hotspots in 10 breast cancer genes and this panel identified ctDNA in only 73% of breast cancer patients. Since gene panels cannot represent the heterogeneity of all breast cancer cases, they are not inclusive or applicable to all breast cancer patients as seen in the two aforementioned examples. Therefore, the use of tumor exome profiling and Signatera bespoke approach should be used to detect minimal residual disease in all metastatic breast cancer patients; if positive, a secondary analysis should then be done for actionable mutations.

There are some important consequences of our study. Up until now, systemic treatment with targeted or cytotoxic therapies have been shown to be curative only when administered in the adjuvant setting; treatment of overt metastatic disease is rarely, if ever, curative (REF). The approach described here offers an alternative: that of attempting to salvage patients who have ctDNA with second-line therapies. Another application may be to assist in the evaluation of new drug therapies, especially those whose mechanism is to enhance the immune response. Up until now, an indirect measure of success has been used, that of time to progression; the Signatera ctDNA detection method will now enable another measure of success to be used as a yard-stick—that of reduction or clearance of ctDNA.

In conclusion, the Signatera platform is capable of detecting MRD in patients with breast cancer with a high degree of sensitivity. It out-performs conventional means of follow up and shows promise for monitoring patients for precision medicine. For the first time, this provides a blood based test that reassures patients that their disease is under control.

Summary

Many BC patients relapse after primary treatment but there are no reliable tests to detect distant metastases before they become overt. Here we show earlier identification of breast cancer recurrence through scalable personalized circulating tumor DNA (ctDNA) analysis. The method is applicable to all patients, and not limited to hot-spot mutations typically detected by gene panels.

Forty-nine non-metastatic BC patients were recruited following surgery and adjuvant therapy. Plasma samples (n=208) were serially collected semi-annually. Using the analytically-validated Signatera™ workflow, we determined mutational signatures from primary tumor whole exome data and designed personalized assays targeting 16 variants with high sensitivity by ultra-deep sequencing (average >100,000×). The patient-specific assay was used to detect the presence of ctDNA in the plasma.

In 16 of the 18 (89%) clinically-relapsing patients, ctDNA was detected ahead of metastatic relapse being diagnosed by clinical examination, radiological imaging and CA15-3 measurement, and remained ctDNA-positive through follow-up. Of the 2 patients not detected by ctDNA, one had a small local recurrence only (now resected) and the other had three primary tumors. None of the 31 non-relapsing patients were ctDNA-positive at any time point (n=156). Metastatic relapse was predicted by Signatera with and a lead time of up to 2 years (median=8.9 months, HR:35.84 (95% CI 7.9626-161.32)).

The use of a scalable patient-specific ctDNA-based validated workflow detects minimal residual disease before metastatic breast cancer recurrence ahead of clinical detection across major breast cancer sub-types. Accurate and earlier prediction by ctDNA analysis could provide a means of monitoring breast cancer patients in need of second-line salvage adjuvant therapy in an attempt to prevent overt life-threatening metastatic relapse.

TABLE A1

Clinical characteristics of all 49 patients.

| Case No | Age at diagnosis | Tumor Grade | ER Status | Her2 status | TNM staging | Time from first sample to relapse (days) | Date of relapse | Site of distant metastasis |
|---|---|---|---|---|---|---|---|---|
| E001 | 48 | 3 | − | + | T2 N1 M0 | − | NA | NA |
| E002 | 56 | 3 | + | + | T2 N2 M0 | − | NA | NA |
| E003 | 65 | 2 | + | − | T3 N2 M0 | 133 | Jun. 25, 2014 | Pleural Effusion |
| E004 | 50 | 2 | + | − | T2 N3 M0 | − | NA | NA |
| E005 | 69 | 2 | + | − | T3 N3 M0 | 263 | Jan. 2, 2015 | Nodal disease right hilum and mediastinum |
| E006 | 48 | 2 | + | − | T2 N2 M0 | − | NA | NA |
| E007 | 67 | 2 | + | + | T2 N3 M0 | − | NA | NA |
| E008 | 47 | 2 | + | − | T3 N3 M0 | − | NA | NA |
| E009 | 44 | 3 | + | − | T2 N1 M0 | 125 | Oct. 28, 2014 | Sternum, pelvis, vertebrae* |
| E010 | 38 | 2 | + | − | T2 N2 M0 | 561 | Jan. 8, 2016 | NA |
| E011 | 69 | 2 | + | − | T2 N2 M0 | − | NA | NA |
| E012 | 66 | 3 | + | − | T2 N1 M0 | − | NA | NA |
| E013 | 80 | 2 | + | − | T3 N2 M0 | − | NA | NA |
| E014 | 57 | 2 | + | − | T2 N3 M0 | − | NA | NA |
| E015 | 81 | 3 | − | − | T2 N1 M0 | − | NA | NA |
| E016 | 80 | 3 | − | + | T2 N2 M0 | − | NA | NA |
| E017 | 67 | 3 | + | − | T3 N3 M0 | 1281 | Jan. 31, 2018 | Sternoclavicular joint, skin, lung |
| E018 | 55 | 2 | + | − | T3 N3 M0 | − | NA | NA |
| E019 | 53 | 3 | + | − | T2 N1 M0 | − | NA | NA |
| E020 | 80 | 2 | + | − | T2 N2 M0 | − | NA | NA |
| E021 | 44 | 2 | + | − | T2 N3 M0 | − | NA | NA |
| E022 | 54 | 2 | + | − | T2 N2 M0 | − | NA | NA |
| E023 | 54 | 2 | + | − | T3 N2 M0 | − | NA | NA |
| E024 | 78 | 3 | − | − | T2 N1 M0 | − | NA | NA |
| E025 | 46 | 3 | − | − | T1 N2 M0 | − | NA | NA |
| E026 | 73 | 2 | + | − | T2 N3 M0 | 793 | Mar. 17, 2017 | Spine |
| E027 | 60 | 2 | + | − | T2 N2 M0 | − | NA | NA |
| E028 | 76 | 3 | + | + | T1 N2 M0 | − | NA | NA |
| E029 | 57 | 3 | − | − | T2 N1 M0 | 442 | Nov. 30, 2016 | Lung |
| E030 | 70 | 3 | + | − | T2 N1 M0 | − | NA | NA |
| E031 | 77 | 2 | + | − | T2 N3 M0 | 1087 | May 23, 2018 | Skin on right lower back |
| E032 | 39 | 3 | + | − | T1 N1 M0 | − | NA | NA |
| E033 | 57 | 2 | − | − | T1 N0 M0 | 570 | Dec. 30, 2016 | Intraclavicular fossa and sentinel lymph nodes |
| E034 | 66 | 2 | + | − | T1 N3 M0 | − | NA | NA |
| E035 | 59 | 2 | + | − | T2 N3 M0 | − | NA | NA |
| E036 | 46 | 2 | + | − | T1 N3 M0 | 415 | Oct. 13, 2016 | Bone and bladder |
| E037 | 78 | 3 | − | + | T2 N3 M0 | 610 | Jun. 7, 2017 | Lung |
| E038 | 63 | 1 | + | − | T2 N2 M0 | − | NA | NA |
| E039 | 48 | 3 | + | − | T2 N1 M0 | − | NA | NA |
| E040 | 55 | 3 | − | + | T2 N1 M0 | 313 | Sep. 5, 2016 | Bone |
| E041 | 67 | 3 | + | − | T2 N1 M0 | − | NA | NA |
| E042 | 49 | 2 | + | − | T2 N1 M0 | − | NA | NA |
| E043 | 41 | 2 | + | − | T3 N1 M0 | 68 | May 23, 2016 | Liver, Lung, Bone* |
| E044 | 46 | 3 | + | − | T2 N1 M0 | 323 | Feb. 4, 2016 | Local nodes |
| E045 | 46 | 3 | + | + | T2 N1 M0 | − | NA | NA |
| E046 | 57 | 3 | − | − | T2 N2 M0 | 269 | Feb. 8, 2016 | Bone, liver and pleura |
| E047 | 62 | 3 | + | − | T3 N1 M0 | 117 | Nov. 18, 2015 | Local nodes and intrapulmonal nodes |

TABLE A1-continued

Clinical characteristics of all 49 patients.

| Case No | Age at diagnosis | Tumor Grade | ER Status | Her2 status | TNM staging | Time from first sample to relapse (days) | Date of relapse | Site of distant metastasis |
|---|---|---|---|---|---|---|---|---|
| E048 | 52 | 3 | – | – | T2 N1 M0 | 202 | Dec. 31, 2015 | Bone and pleura |
| E049 | 45 | 3 | – | – | T2 N1 M0 | 148 | Oct. 8, 2016 | Not known* |

Those marked with an asterisk* are deceased.

TABLE B1

Plasma time point of patients.

| Case ID | #0 | #1 | #2 | #3 | #4 | #5 | #6 | #7 | #EoS |
|---|---|---|---|---|---|---|---|---|---|
| E001 | Jan.15, 2014 | Oct. 8, 2014 | Jan.7, 2015 | Jun. 24, 2015 | Jan. 20, 2016 | Jul. 13, 2016 | Jan. 4, 2017 | Jul. 5, 2017 | |
| E002 | Feb. 10, 2014 | Sep. 8, 2014 | Feb. 9, 2015 | Sep. 1, 2015 | Feb. 18, 2016 | Aug. 25, 2016 | Mar. 16, 2017 | | |
| E003 | Feb. 12, 2014 | | | | | | | | |
| E004 | Apr. 14, 2014 | Oct. 27, 2014 | Apr. 27, 2015 | Oct. 19, 2015 | Jun. 9, 2016 | Nov. 28, 2016 | | | |
| E005 | Apr. 14, 2014 | Oct. 16, 2014 | | | | | | | |
| E006 | May 7, 2014 | | | Dec. 9, 2015 | Aug. 23, 2016 | Mar. 1, 2017 | | | |
| E007 | May 12, 2014 | Nov. 11, 2014 | | Nov. 17, 2015 | May 26, 2016 | Dec. 8, 2016 | Jul. 16, 2017 | | |
| E008 | May 16, 2014 | Nov. 3, 2014 | Apr. 20, 2015 | Oct. 19, 2015 | | Dec. 12, 2016 | | | |
| E009 | Jun. 25, 2014 | | | | | | | | |
| E010 | Jun. 26, 2014 | Dec. 10, 2014 | | | | | | | Jan. 20, 2016 |
| E011 | Jul. 9, 2014 | Jan. 28, 2015 | Aug. 19, 2015 | Jan. 6, 2016 | Jul. 20, 2016 | Jan. 25, 2017 | Sep. 6, 2017 | | |
| E012 | Jul. 16, 2014 | Jan. 14, 2015 | Jul. 8, 2015 | Jan. 27, 2016 | Jul. 27, 2016 | Jan. 25, 2017 | Jul. 26, 2017 | | |
| E013 | Jul. 16, 2014 | Jan. 14, 2015 | Jul. 15, 2015 | Jan. 13, 2016 | Jul. 13, 2016 | Jan. 25, 2017 | Aug. 9, 2017 | | |
| E014 | Jul. 16, 2014 | Jan. 21, 2015 | | Feb. 3, 2016 | Jul. 12, 2016 | Jan. 31, 2017 | | | |
| E015 | Jul. 21, 2014 | Jan. 14, 2015 | Jul. 15, 2015 | Jan. 20, 2016 | Jul. 20, 2016 | Feb. 8, 2017 | Jul. 26, 2017 | | |
| E016 | Jul. 23, 2014 | Jan. 21, 2015 | Oct. 29, 2015 | Jun. 8, 2016 | Jan. 11, 2017 | Jul. 5, 2017 | | | |
| E017 | Jul. 30, 2014 | Jan. 14, 2015 | Jul. 8, 2015 | Feb. 10, 2016 | Aug. 31, 2016 | Feb. 22, 2017 | Jul. 4, 2017 | | |
| E018 | Aug. 11, 2014 | Feb. 16, 2015 | | Apr. 4, 2016 | Nov. 28, 2016 | May 24, 2017 | | | |
| E019 | Aug. 27, 2014 | Feb. 11, 2015 | Aug. 6, 2015 | Mar. 16, 2016 | Oct. 18, 2016 | Apr. 21, 2017 | | | |
| E020 | Sep. 4, 2014 | Apr. 20, 2015 | Oct. 15, 2015 | Jan. 14, 2016 | Nov. 3, 2016 | May 3, 2017 | | | |
| E021 | Sep. 9, 2014 | Mar. 10, 2015 | Sep. 15, 2015 | Mar. 24, 2016 | Sep. 22, 2016 | Mar. 30, 2017 | | | |
| E022 | Sep. 10, 2014 | Mar. 11, 2015 | Aug. 4, 2015 | | | | | | |
| E023 | Sep. 11, 2014 | Feb. 5, 2015 | Aug. 3, 2015 | Mar. 8, 2016 | Aug. 25, 2016 | Mar. 9, 2017 | | | |
| E024 | Sep. 24, 2014 | Mar. 18, 2015 | Sep. 23, 2015 | May 18, 2016 | Nov. 30, 2016 | Jun. 28, 2017 | | | |
| E025 | Nov. 5, 2014 | May 13, 2015 | Dec. 23, 2015 | Jun. 22, 2016 | Jan. 18, 2017 | Sep. 6, 2017 | | | |
| E026 | Jan. 14, 2015 | Jul. 15, 2015 | Feb. 24, 2016 | Sep. 13, 2016 | Feb. 28, 2017 | | | | |
| E027 | Feb. 3, 2015 | Aug. 4, 2015 | Feb. 4, 2016 | | | | | | |
| E028 | Feb. 11, 2015 | | | Aug. 30, 2016 | Feb. 21, 2017 | Sep. 5, 2017 | | | |
| E029 | Sep. 15, 2015 | Mar. 17, 2016 | Sep. 29, 2016 | | | | | | Jan. 12, 2017 |
| E030 | May 20, 2015 | Nov. 18, 2015 | May 18, 2016 | | Jul. 19, 2017 | | | | |
| E031 | Jun. 1, 2015 | Oct. 29, 2015 | Apr. 28, 2016 | Jan. 26, 2017 | Jul. 26, 2017 | | | | |
| E032 | Jun. 3, 2015 | Oct. 14, 2015 | Jun. 8, 2016 | Dec. 21, 2016 | | | | | |
| E033 | Jun. 9, 2015 | Dec. 22, 2015 | Jul. 21, 2016 | | | | | | Jan. 9, 2017 |
| E034 | Jun. 10, 2015 | Dec. 9, 2015 | Jun. 7, 2016 | | Jul. 4, 2017 | | | | |
| E035 | Jun. 18, 2015 | Jan. 21, 2016 | Sep. 9, 2016 | Jan. 30, 2017 | Jun. 12, 2017 | | | | |
| E036 | Aug. 25, 2015 | Mar. 24, 2016 | Sep. 22, 2016 | | | | | | |
| E037 | Oct. 6, 2015 | | | May 24, 2017 | | | | | May 24, 2017 |
| E038 | Oct. 7, 2015 | Apr. 13, 2016 | Oct. 19, 2016 | Apr. 19, 2017 | | | | | |
| E039 | Oct. 20, 2015 | May 18, 2016 | Nov. 16, 2016 | May 31, 2017 | | | | | |
| E040 | Oct. 28, 2015 | Apr. 13, 2016 | | | | | | | Oct. 19, 2016 |
| E041 | Jan. 20, 2016 | Jul. 20, 2016 | Feb. 8, 2017 | Aug. 4, 2017 | | | | | |
| E042 | Feb. 3, 2016 | Aug. 16, 2016 | Jan. 24, 2017 | | | | | | |
| E043 | Mar. 16, 2016 | | | | | | | | |
| E044 | Mar. 18, 2015 | Sep. 23, 2015 | | | | | | | Feb. 17, 2016 |
| E045 | Dec. 15, 2015 | Jun. 15, 2016 | Dec. 14, 2016 | | | | | | |
| E046 | May 15, 2015 | Nov. 6, 2015 | Feb. 12, 2016 | | | | | | |
| E047 | Jul. 24, 2015 | Dec. 16, 2016 | | | | | | | |
| E048 | Jun. 12, 2015 | Dec. 4, 2015 | | | | | | | Jan. 8, 2016 |
| E049 | May 1, 2016 | | | | | | | | |

TABLE B2

CA15-3 levels of patients.

| Case ID | #0 | #1 | #2 | #3 | #4 | #5 | #6 | #7 | #EoS |
|---|---|---|---|---|---|---|---|---|---|
| E001 | 7 | 20 | 19 | 22 | 20 | 18 | 17 | 20 | |
| E002 | 8 | 9 | 8 | 10 | 9 | 9 | 7 | | |
| E003 | 17 | | | | | | | | |
| E004 | 18 | 18 | ND | 18 | 18 | 19 | 17 | | |
| E005 | 22 | 26 | | | | | | | |
| E006 | 15 | 11* | 14* | 11 | 13 | 13 | | | |
| E007 | 15 | 14 | | 14 | 13 | 14 | 14 | | |
| E008 | 17 | 17 | 18 | 17 | 21 | 15 | | | |
| E009 | 51 | | | | | | | | 30* |
| E010 | 13 | 12 | | 16 | | | | | 16 |
| E011 | 9 | 8 | 7 | 8 | 9 | 9 | | | |
| E012 | 9 | 8 | 9 | 8 | 10 | 9 | 10 | | |
| E013 | 31 | 33 | 23 | 21 | 19 | 57 | 28 | | |
| E014 | 18 | 17 | | 18 | 18 | 20 | | | |
| E015 | 20 | 20 | 22 | 22 | 20 | 23 | 20 | | |
| E016 | 15 | 13 | 15 | 17 | 16 | 15 | | | |
| E017 | 13 | 13 | 13 | 14 | 15 | 17 | 17 | | |
| E018 | 5 | 6 | | 5 | 7 | 7 | | | |
| E019 | 29 | 23 | 29 | 26 | 29 | 29 | | | |
| E020 | 26 | 51 | 32 | 28 | 29 | 36 | | | |
| E021 | 14 | 14 | 14 | 14 | 14 | 14 | | | |
| E022 | 10 | 10 | 12 | | | | | | |
| E023 | 11 | 13 | 13 | 12 | 13 | 14 | | | |
| E024 | 23 | 23 | 28 | 24 | 25 | 22 | | | |
| E025 | 20 | 20 | 20 | 17 | 19 | 21 | | | |
| E026 | 24 | 31 | 46 | 58 | 104 | | | | 138 |
| E027 | 24 | 23 | 20 | | | | | | |
| E028 | 35 | | | 33 | 29 | | | | |
| E029 | 10 | 13 | 10 | 12 | | | | | 12 |
| E030 | 13 | 13 | 10 | | | | | | 14 |
| E031 | 34 | 27 | 31 | 32 | ND | | | | |
| E032 | 12 | 10 | 11 | 11 | 9* | | | | |
| E033 | 18 | 21 | 20 | | | | | | 22 |
| E034 | 26 | 25 | 23 | 27 | | | | | |
| E035 | 21 | 19 | 24 | 22 | 21 | | | | |
| E036 | 25 | 48 | 131 | | | | | | |
| E037 | 20 | | 22* | 21 | | | | | |
| E038 | 16 | 17 | 19 | 16 | | | | | |
| E039 | 14 | 12 | 11 | 13 | | | | | |
| E040 | 33 | 35 | | | | | | | 36 |
| E041 | 26 | 23 | 26 | 22 | | | | | |
| E042 | 5 | 5 | 5 | | | | | | |
| E043 | 65 | | | | | | | | |
| E044 | | | | | | | | | |
| E045 | | | | | | | | | |
| E046 | | | | | | | | | |
| E047 | | | | | | | | | |
| E048 | | | | | | | | | |
| E049 | | | | | | | | | |

TABLE B3

Endocrine therapy of patients.

| Case ID | Previous Chemo | #0 | #1 | #2 | #3 | #4 | #5 | #6 | #7 | #EoS |
|---|---|---|---|---|---|---|---|---|---|---|
| E001 | Yes | none | none | none | none | none | none | none | none | none |
| E002 | Yes | Letrozole | Letrozole | Letrozole | Letrozole | Letrozole | Letrozole | Letrozole | Letrozole | Letrozole |
| E003 | Yes | Letrozole | | | | | | | | Letrozole |
| E004 | Yes | Tamoxifen | Tamoxifen | Tamoxifen | Tamoxifen | Tamoxifen | Tamoxifen | | | |
| E005 | No | Anastrozole | Anastrozole | | | | | | | Anastrozole |
| E006 | Yes | Letrozole | Letrozole | Letrozole | Exemestane | Letrozole | Letrozole | | | |
| E007 | Yes | Anastrozole | Tamoxifen | no visit | Tamoxifen | Tamoxifen | Tamoxifen | Tamoxifen | | |
| E008 | Yes | Anastrozole/Zoladex | Anastrozole/Zoladex | Anastrazole | Exemestane | Exemestane | Exemestane | | | |
| E009 | Yes | none | | | | | | | | |
| E010 | Yes | Tamoxifen/zoladex | Tamoxifen/zoladex | | | | | | | |
| E011 | Yes | Letrozole | Letrozole | Letrozole | Letrozole | Letrozole | Letrozole | | | |
| E012 | Yes | Anastrozole | Anastrozole | Anastrozole | Anastrozole | Anastrozole | Anastrozole | Anastrozole | | |
| E013 | No | Letrozole | Letrozole | Letrozole | Letrozole | Letrozole | Letrozole | Letrozole | | |
| E014 | Yes | Letrozole | Letrozole | missed | Letrozole | Letrozole | Letrozole | | | |
| E015 | No | none | none | none | none | none | none | none | | |
| E016 | No | Anastrozole | Anastrozole | Anastrozole | Anastrozole | Anastrozole | Anastrozole | | | |
| E017 | Yes | Tamoxifen | Tamoxifen | Tamoxifen | Tamoxifen | Tamoxifen | Tamoxifen | Tamoxifen | | |
| E018 | Yes | Exemestane | Exemestane | missed | none | none | none | | | |
| E019 | Yes | none | Tamoxifen | Tamoxifen | Tamoxifen | Letrozole | Letrozole | | | |
| E020 | No | Tamoxifen | Tamoxifen | Tamoxifen | Tamoxifen | Tamoxifen | Tamoxifen | | | |
| E021 | Yes | Tamoxifen | Tamoxifen | Tamoxifen | Tamoxifen | Tamoxifen | Tamoxifen | | | |
| E022 | Yes | Anastrozole | Anastrozole | | | | | | | |
| E023 | Yes | Letrozole | Letrozole | Letrozole | Letrozole | Letrozole | Letrozole | | | |
| E024 | Yes | none | none | none | none | none | none | | | |
| E025 | Yes | Tamoxifen | Tamoxifen | Tamoxifen | Tamoxifen | Tamoxifen | Tamoxifen | | | |
| E026 | Yes | Letrozole | Letrozole | Letrozole | Letrozole | Letrozole | | | | |
| E027 | Yes | Anastrozole | Anastrozole | Anastrozole | | | | | | |
| E028 | Yes | Letrozole | missed | missed | Letrozole | Letrozole | Letrozole | | | |
| E029 | Yes | none | none | none | none | | | | | |
| E030 | Yes | Letrozole | Letrozole | Letrozole | | Letrozole | | | | |
| E031 | No | Anastrozole | Anastrozole | Anastrozole | Anastrozole | Anastrozole | | | | |
| E032 | Yes | none | none | None | none | | | | | |
| E033 | Yes | none | none | none | | | | | | |
| E034 | Yes | Letrozole | Letrozole | Letrozole | Letrozole | Letrozole | | | | |
| E035 | Yes | Anastrozole | Anastrozole | Anastrozole | Anastrozole | Anastrozole | | | | |
| E036 | Yes | Tamoxifen | Tamoxifen | Tamoxifen | | | | | | |

TABLE B3-continued

Endocrine therapy of patients.

| Case ID | Previous Chemo | Endocrine therapy #0 | #1 | #2 | #3 | #4 | #5 | #6 | #7 | #EoS |
|---|---|---|---|---|---|---|---|---|---|---|
| E037 | No | none | | | none | | | | | |
| E038 | Yes | Letrozole | Letrozole | Letrozole | Letrozole | | | | | |
| E039 | Yes | none | none | Letrozole | Letrozole | | | | | |
| E040 | Yes | Letrozole | Letrozole | | | | | | | |
| E041 | Yes | none | Tamoxifen | Tamoxifen | Tamoxifen | | | | | |
| E042 | Yes | Tamoxifen | Tamoxifen | Tamoxifen | | | | | | |
| E043 | Yes | Tamoxifen | | | | | | | | |
| E044 | Yes | Tamoxifen | Tamoxifen | | | | | | | Tamoxifen |
| E045 | Yes | Tamoxifen | Not Recorded | Not Recorded | | | | | | |
| E046 | Yes | None | None | None | | | | | | |
| E047 | Yes | Endocrine (TBC) | Endocrine (TBC) | | | | | | | |
| E048 | Yes | None | None | None | | | | | | |
| E049 | Yes | None | None | None | | | | | | |

TABLE C

Summary of sample levels and VAFs.

| Patient No. | Time point | Days from Surgery | ng of DNA to Library Prep | Number of Detected Targets | ctDNA status | Number of Assays Passed QC | Avg VAF (%) | Median VAF (%) | Max VAF (%) | Min VAF (%) |
|---|---|---|---|---|---|---|---|---|---|---|
| 1002 | 1 | 468 | 9.99 | 0 | Negative | 16 | NA | NA | NA | NA |
| 1002 | 2 | 734 | 6.84 | 0 | Negative | 16 | NA | NA | NA | NA |
| 1002 | 3 | 825 | 7.81 | 0 | Negative | 16 | NA | NA | NA | NA |
| 1002 | 4 | 993 | 6.36 | 0 | Negative | 16 | NA | NA | NA | NA |
| 1002 | 5 | 1203 | 8.93 | 0 | Negative | 16 | NA | NA | NA | NA |
| 1002 | 6 | 1378 | 11.83 | 0 | Negative | 16 | NA | NA | NA | NA |
| 1002 | 7 | 1553 | 14.74 | 0 | Negative | 16 | NA | NA | NA | NA |
| 1002 | 8 | 1735 | 10.68 | 0 | Negative | 16 | NA | NA | NA | NA |
| 1003 | 1 | 530 | 16.28 | 0 | Negative | 16 | NA | NA | NA | NA |
| 1003 | 2 | 740 | 21.77 | 0 | Negative | 16 | NA | NA | NA | NA |
| 1003 | 3 | 894 | 7.36 | 0 | Negative | 16 | NA | NA | NA | NA |
| 1003 | 5 | 1268 | 10.87 | 0 | Negative | 16 | NA | NA | NA | NA |
| 1003 | 6 | 1457 | 28.57 | 0 | Negative | 16 | NA | NA | NA | NA |
| 1003 | 7 | 1660 | 17.08 | 0 | Negative | 16 | NA | NA | NA | NA |
| 1004 | 1 | 302 | 32.98 | 3 | Positive | 16 | 0.015 | 0.014 | 0.018 | 0.013 |
| 1009 | 1 | 1452 | 35.74 | 0 | Negative | 16 | NA | NA | NA | NA |
| 1009 | 2 | 1648 | 18.31 | 0 | Negative | 16 | NA | NA | NA | NA |
| 1009 | 3 | 1830 | 16.79 | 0 | Negative | 16 | NA | NA | NA | NA |
| 1009 | 4 | 2005 | 22.25 | 0 | Negative | 16 | NA | NA | NA | NA |
| 1009 | 5 | 2239 | 41.96 | 0 | Negative | 16 | NA | NA | NA | NA |
| 1009 | 6 | 2411 | 21.3 | 0 | Negative | 16 | NA | NA | NA | NA |
| 1011 | 1 | 920 | 17.14 | 12 | Positive | 16 | 2.902 | 1.442 | 9.219 | 0.697 |
| 1011 | 2 | 1105 | 66 | 12 | Positive | 16 | 2.39 | 0.988 | 8.31 | 0.691 |
| 1013 | 1 | 37 | 21.44 | 0 | Negative | 16 | NA | NA | NA | NA |
| 1013 | 3 | 876 | 37.67 | 0 | Negative | 16 | NA | NA | NA | NA |
| 1013 | 4 | 1066 | 43.23 | 0 | Negative | 16 | NA | NA | NA | NA |
| 1014 | 1 | 440 | 22.19 | 0 | Negative | 16 | NA | NA | NA | NA |
| 1014 | 2 | 623 | 18.16 | 0 | Negative | 16 | NA | NA | NA | NA |
| 1014 | 3 | 994 | 17.33 | 0 | Negative | 16 | NA | NA | NA | NA |
| 1014 | 4 | 1185 | 13.01 | 0 | Negative | 16 | NA | NA | NA | NA |
| 1014 | 5 | 1381 | 27.12 | 0 | Negative | 16 | NA | NA | NA | NA |
| 1014 | 6 | 1601 | 9.01 | 0 | Negative | 16 | NA | NA | NA | NA |
| 1015 | 1 | 1330 | 18.83 | 0 | Negative | 16 | NA | NA | NA | NA |
| 1015 | 2 | 1501 | 27.39 | 0 | Negative | 16 | NA | NA | NA | NA |
| 1015 | 3 | 1669 | 9.04 | 0 | Negative | 16 | NA | NA | NA | NA |
| 1015 | 4 | 1851 | 13.65 | 0 | Negative | 16 | NA | NA | NA | NA |
| 1015 | 5 | 2271 | 23.95 | 0 | Negative | 16 | NA | NA | NA | NA |
| 1018 | 1 | 131 | 66 | 0 | Negative | 16 | NA | NA | NA | NA |
| 1019 | 1 | 296 | 35.69 | 0 | Negative | 16 | NA | NA | NA | NA |
| 1019 | 2 | 463 | 32.73 | 0 | Negative | 16 | NA | NA | NA | NA |
| 1019 | 3 | 869 | 66 | 0 | Negative | 16 | NA | NA | NA | NA |
| 1021 | 1 | 405 | 30.37 | 0 | Negative | 16 | NA | NA | NA | NA |
| 1021 | 2 | 608 | 51.4 | 0 | Negative | 16 | NA | NA | NA | NA |
| 1021 | 3 | 811 | 31.59 | 0 | Negative | 16 | NA | NA | NA | NA |
| 1021 | 4 | 951 | 35 | 0 | Negative | 16 | NA | NA | NA | NA |
| 1021 | 5 | 1147 | 45.12 | 0 | Negative | 16 | NA | NA | NA | NA |

TABLE C-continued

Summary of sample levels and VAFs.

| Patient No. | Time point | Days from Surgery | ng of DNA to Library Prep | Number of Detected Targets | ctDNA status | Number of Assays Passed QC | Avg VAF (%) | Median VAF (%) | Max VAF (%) | Min VAF (%) |
|---|---|---|---|---|---|---|---|---|---|---|
| 1021 | 6 | 1336 | 66 | 0 | Negative | 16 | NA | NA | NA | NA |
| 1021 | 7 | 1560 | 41.33 | 0 | Negative | 16 | NA | NA | NA | NA |
| 1023 | 1 | 565 | 23.61 | 0 | Negative | 16 | NA | NA | NA | NA |
| 1023 | 2 | 747 | 43.97 | 0 | Negative | 16 | NA | NA | NA | NA |
| 1023 | 3 | 922 | 18.15 | 0 | Negative | 16 | NA | NA | NA | NA |
| 1023 | 4 | 1125 | 53.07 | 0 | Negative | 16 | NA | NA | NA | NA |
| 1023 | 5 | 1307 | 33.89 | 0 | Negative | 16 | NA | NA | NA | NA |
| 1023 | 6 | 1489 | 66 | 0 | Negative | 16 | NA | NA | NA | NA |
| 1023 | 7 | 1671 | 35.48 | 0 | Negative | 16 | NA | NA | NA | NA |
| 1024 | 1 | 132 | 66 | 0 | Negative | 16 | NA | NA | NA | NA |
| 1024 | 2 | 496 | 32.12 | 0 | Negative | 16 | NA | NA | NA | NA |
| 1024 | 3 | 314 | 50.66 | 0 | Negative | 16 | NA | NA | NA | NA |
| 1024 | 4 | 678 | −1.41 | 0 | Negative | 16 | NA | NA | NA | NA |
| 1024 | 5 | 860 | 39.77 | 0 | Negative | 16 | NA | NA | NA | NA |
| 1024 | 6 | 1056 | 66 | 0 | Negative | 16 | NA | NA | NA | NA |
| 1024 | 7 | 1252 | 66 | 0 | Negative | 16 | NA | NA | NA | NA |
| 1025 | 1 | 300 | 40.77 | 0 | Negative | 16 | NA | NA | NA | NA |
| 1025 | 2 | 489 | 66 | 0 | Negative | 16 | NA | NA | NA | NA |
| 1025 | 3 | 867 | 66 | 0 | Negative | 15 | NA | NA | NA | NA |
| 1025 | 4 | 1027 | 40.02 | 0 | Negative | 15 | NA | NA | NA | NA |
| 1025 | 5 | 1230 | 44.77 | 0 | Negative | 15 | NA | NA | NA | NA |
| 1028 | 1 | 581 | 19.24 | 0 | Negative | 16 | NA | NA | NA | NA |
| 1028 | 2 | 758 | 12.8 | 0 | Negative | 16 | NA | NA | NA | NA |
| 1028 | 3 | 940 | 11.26 | 0 | Negative | 16 | NA | NA | NA | NA |
| 1028 | 4 | 1129 | 21.97 | 0 | Negative | 16 | NA | NA | NA | NA |
| 1028 | 5 | 1311 | 23.56 | 0 | Negative | 16 | NA | NA | NA | NA |
| 1028 | 6 | 1514 | 22.65 | 0 | Negative | 16 | NA | NA | NA | NA |
| 1028 | 7 | 1682 | 23.79 | 0 | Negative | 16 | NA | NA | NA | NA |
| 1029 | 1 | 311 | 66 | 0 | Negative | 16 | NA | NA | NA | NA |
| 1029 | 2 | 493 | 66 | 0 | Negative | 16 | NA | NA | NA | NA |
| 1029 | 3 | 774 | 46.18 | 0 | Negative | 16 | NA | NA | NA | NA |
| 1029 | 4 | 631 | 66 | 0 | Negative | 16 | NA | NA | NA | NA |
| 1029 | 5 | 1214 | 66 | 0 | Negative | 16 | NA | NA | NA | NA |
| 1029 | 6 | 1389 | 66 | 0 | Negative | 16 | NA | NA | NA | NA |
| 1031 | 1 | 330 | 20.3 | 0 | Negative | 15 | NA | NA | NA | NA |
| 1031 | 2 | 673 | 8.32 | 0 | Negative | 15 | NA | NA | NA | NA |
| 1031 | 3 | 498 | 27.97 | 0 | Negative | 15 | NA | NA | NA | NA |
| 1031 | 4 | 890 | 14.11 | 4 | Positive | 15 | 0.121 | 0.072 | 0.303 | 0.037 |
| 1031 | 5 | 1093 | 18.35 | 9 | Positive | 15 | 0.074 | 0.068 | 0.14 | 0.018 |
| 1031 | 6 | 1268 | 50.46 | 8 | Positive | 15 | 0.045 | 0.027 | 0.168 | 0.023 |
| 1031 | 7 | 1400 | 22.65 | 10 | Positive | 15 | 0.133 | 0.075 | 0.424 | 0.048 |
| 1033 | 1 | 1680 | 34.17 | 0 | Negative | 16 | NA | NA | NA | NA |
| 1033 | 2 | 1869 | 37.49 | 0 | Negative | 16 | NA | NA | NA | NA |
| 1033 | 4 | 2520 | 66 | 0 | Negative | 16 | NA | NA | NA | NA |
| 1033 | 5 | 2697 | 58.43 | 0 | Negative | 16 | NA | NA | NA | NA |
| 1038 | 1 | 29 | 35.15 | 0 | Negative | 16 | NA | NA | NA | NA |
| 1038 | 2 | 197 | 24.26 | 0 | Negative | 16 | NA | NA | NA | NA |
| 1038 | 3 | 373 | 7.17 | 0 | Negative | 15 | NA | NA | NA | NA |
| 1038 | 4 | 596 | 25.45 | 0 | Negative | 16 | NA | NA | NA | NA |
| 1038 | 5 | 812 | 18.91 | 0 | Negative | 16 | NA | NA | NA | NA |
| 1038 | 6 | 997 | 50.72 | 0 | Negative | 16 | NA | NA | NA | NA |
| 1042 | 1 | 147 | 15.99 | 0 | Negative | 15 | NA | NA | NA | NA |
| 1042 | 2 | 375 | 17.03 | 0 | Negative | 15 | NA | NA | NA | NA |
| 1042 | 3 | 553 | 18.42 | 0 | Negative | 15 | NA | NA | NA | NA |
| 1042 | 4 | 644 | 22.36 | 0 | Negative | 15 | NA | NA | NA | NA |
| 1042 | 5 | 938 | 25.68 | 0 | Negative | 15 | NA | NA | NA | NA |
| 1042 | 6 | 1119 | 24.15 | 0 | Negative | 15 | NA | NA | NA | NA |
| 1043 | 1 | 442 | 22.81 | 0 | Negative | 15 | NA | NA | NA | NA |
| 1043 | 2 | 624 | 31.97 | 0 | Negative | 15 | NA | NA | NA | NA |
| 1043 | 3 | 1004 | 66 | 0 | Negative | 15 | NA | NA | NA | NA |
| 1043 | 4 | 813 | 46.71 | 0 | Negative | 15 | NA | NA | NA | NA |
| 1043 | 5 | 1186 | 37.77 | 0 | Negative | 15 | NA | NA | NA | NA |
| 1043 | 6 | 1375 | 39.38 | 0 | Negative | 15 | NA | NA | NA | NA |
| 1044 | 1 | 862 | 62.53 | 0 | Negative | 16 | NA | NA | NA | NA |
| 1044 | 2 | 1044 | 66 | 0 | Negative | 16 | NA | NA | NA | NA |
| 1044 | 3 | 1190 | 40.39 | 0 | Negative | 16 | NA | NA | NA | NA |
| 1045 | 1 | 122 | 19.86 | 0 | Negative | 16 | NA | NA | NA | NA |
| 1045 | 2 | 269 | 14.12 | 0 | Negative | 16 | NA | NA | NA | NA |
| 1045 | 3 | 448 | 14.91 | 0 | Negative | 16 | NA | NA | NA | NA |
| 1045 | 4 | 666 | 27.65 | 0 | Negative | 16 | NA | NA | NA | NA |
| 1045 | 5 | 836 | 30.77 | 0 | Negative | 16 | NA | NA | NA | NA |
| 1045 | 6 | 1032 | 23.83 | 0 | Negative | 16 | NA | NA | NA | NA |
| 1047 | 1 | 698 | 18.3 | 0 | Negative | 16 | NA | NA | NA | NA |

TABLE C-continued

Summary of sample levels and VAFs.

| Patient No. | Time point | Days from Surgery | ng of DNA to Library Prep | Number of Detected Targets | ctDNA status | Number of Assays Passed QC | Avg VAF (%) | Median VAF (%) | Max VAF (%) | Min VAF (%) |
|---|---|---|---|---|---|---|---|---|---|---|
| 1047 | 2 | 873 | 15.25 | 0 | Negative | 16 | NA | NA | NA | NA |
| 1047 | 3 | 1062 | 14.44 | 0 | Negative | 16 | NA | NA | NA | NA |
| 1047 | 4 | 1300 | 29.89 | 0 | Negative | 16 | NA | NA | NA | NA |
| 1047 | 5 | 1496 | 9.68 | 0 | Negative | 16 | NA | NA | NA | NA |
| 1047 | 6 | 1706 | 15.97 | 0 | Negative | 16 | NA | NA | NA | NA |
| 1048 | 1 | 166 | 19.21 | 0 | Negative | 14 | NA | NA | NA | NA |
| 1048 | 2 | 355 | 21.9 | 0 | Negative | 15 | NA | NA | NA | NA |
| 1048 | 3 | 579 | 16.01 | 0 | Negative | 14 | NA | NA | NA | NA |
| 1048 | 4 | 761 | 15.09 | 0 | Negative | 15 | NA | NA | NA | NA |
| 1048 | 5 | 971 | 24.91 | 0 | Negative | 15 | NA | NA | NA | NA |
| 1048 | 6 | 1202 | 33.49 | 0 | Negative | 15 | NA | NA | NA | NA |
| 1051 | 1 | 470 | 22.73 | 0 | Negative | 14 | NA | NA | NA | NA |
| 1051 | 2 | 652 | 7.86 | 2 | Positive | 13 | 0.093 | 0.093 | 0.094 | 0.092 |
| 1051 | 3 | 1078 | 21.04 | 14 | Positive | 14 | 0.272 | 0.222 | 0.573 | 0.119 |
| 1051 | 4 | 876 | 36.72 | 11 | Positive | 14 | 0.125 | 0.11 | 0.321 | 0.046 |
| 1051 | 5 | 1246 | 27.55 | 14 | Positive | 14 | 2.737 | 2.37 | 5.617 | 1.111 |
| 1052 | 1 | 574 | 20.03 | 0 | Negative | 14 | NA | NA | NA | NA |
| 1052 | 2 | 756 | 17.54 | 0 | Negative | 14 | NA | NA | NA | NA |
| 1052 | 3 | 940 | 16.79 | 0 | Negative | 14 | NA | NA | NA | NA |
| 1054 | 1 | 443 | 22.25 | 0 | Negative | 14 | NA | NA | NA | NA |
| 1054 | 2 | 1009 | 22.74 | 0 | Negative | 14 | NA | NA | NA | NA |
| 1054 | 3 | 1184 | 24.73 | 0 | Negative | 14 | NA | NA | NA | NA |
| 1054 | 4 | 1380 | 15.71 | 0 | Negative | 14 | NA | NA | NA | NA |
| 1055 | 1 | 476 | 25.53 | 0 | Negative | 14 | NA | NA | NA | NA |
| 1055 | 2 | 660 | 19.15 | 9 | Positive | 14 | 0.312 | 0.256 | 0.711 | 0.022 |
| 1055 | 3 | 856 | 19.38 | 9 | Positive | 14 | 1.257 | 1.144 | 3.267 | 0.014 |
| 1055 | 4 | 961 | 17.58 | 8 | Positive | 14 | 3.006 | 2.844 | 5.871 | 1.69 |
| 1069 | 1 | 462 | 10.59 | 0 | Negative | 10 | NA | NA | NA | NA |
| 1069 | 2 | 644 | 27.48 | 0 | Negative | 16 | NA | NA | NA | NA |
| 1069 | 3 | 826 | 24.27 | 0 | Negative | 16 | NA | NA | NA | NA |
| 1069 | 4 | 1253 | 22.57 | 0 | Negative | 15 | NA | NA | NA | NA |
| 1072 | 1 | 340 | 13.83 | 0 | Negative | 13 | NA | NA | NA | NA |
| 1072 | 2 | 672 | 15 | 0 | Negative | 16 | NA | NA | NA | NA |
| 1072 | 3 | 490 | 21.88 | 0 | Negative | 16 | NA | NA | NA | NA |
| 1072 | 4 | 945 | 39.24 | 0 | Negative | 16 | NA | NA | NA | NA |
| 1072 | 5 | 1126 | 42.97 | 2 | Positive | 16 | 0.036 | 0.036 | 0.059 | 0.013 |
| 1073 | 1 | 610 | 15.91 | 0 | Negative | 15 | NA | NA | NA | NA |
| 1073 | 2 | 743 | 37.19 | 0 | Negative | 15 | NA | NA | NA | NA |
| 1073 | 3 | 981 | 25.62 | 0 | Negative | 15 | NA | NA | NA | NA |
| 1073 | 4 | 1177 | 35.93 | 0 | Negative | 15 | NA | NA | NA | NA |
| 1074 | 1 | 110 | 15.36 | 8 | Positive | 16 | 0.072 | 0.059 | 0.151 | 0.026 |
| 1074 | 2 | 306 | 26.05 | 12 | Positive | 16 | 0.054 | 0.063 | 0.105 | 0.017 |
| 1074 | 3 | 518 | 25.02 | 15 | Positive | 16 | 5.81 | 5.364 | 11.181 | 0.08 |
| 1074 | 4 | 690 | 35.86 | 15 | Positive | 16 | 16.936 | 16.54 | 29.448 | 0.261 |
| 1077 | 1 | 1044 | 16.64 | 0 | Negative | 13 | NA | NA | NA | NA |
| 1077 | 3 | 1407 | 14.63 | 0 | Negative | 13 | NA | NA | NA | NA |
| 1077 | 4 | 1799 | 34.01 | 0 | Negative | 13 | NA | NA | NA | NA |
| 1082 | 1 | 835 | 19.52 | 0 | Negative | 16 | NA | NA | NA | NA |
| 1082 | 2 | 1052 | 28.22 | 0 | Negative | 16 | NA | NA | NA | NA |
| 1082 | 3 | 1284 | 30.24 | 0 | Negative | 16 | NA | NA | NA | NA |
| 1082 | 4 | 1427 | 40.32 | 0 | Negative | 16 | NA | NA | NA | NA |
| 1082 | 5 | 1560 | 30.03 | 0 | Negative | 16 | NA | NA | NA | NA |
| 1088 | 1 | 546 | 35.77 | 12 | Positive | 16 | 0.065 | 0.062 | 0.154 | 0.016 |
| 1088 | 3 | 940 | 66 | 12 | Positive | 16 | 4.42 | 3.877 | 7.651 | 2.687 |
| 1091 | 1 | 107 | 4.91 | 0 | Negative | 16 | NA | NA | NA | NA |
| 1091 | 2 | 703 | 47.32 | 16 | Positive | 16 | 0.452 | 0.386 | 1.08 | 0.151 |
| 1091 | 3 | NA | 64.15 | 16 | Positive | 16 | 0.136 | 0.119 | 0.405 | 0.016 |
| 1092 | 1 | 590 | 25.27 | 0 | Negative | 16 | NA | NA | NA | NA |
| 1092 | 2 | 779 | 40.63 | 0 | Negative | 16 | NA | NA | NA | NA |
| 1092 | 4 | 1150 | 37.21 | 0 | Negative | 16 | NA | NA | NA | NA |
| 1093 | 1 | 243 | 57 | 0 | Negative | 16 | NA | NA | NA | NA |
| 1093 | 2 | 454 | 34.04 | 0 | Negative | 16 | NA | NA | NA | NA |
| 1093 | 3 | 636 | 66 | 0 | Negative | 16 | NA | NA | NA | NA |
| 1093 | 4 | 832 | 35.68 | 0 | Negative | 16 | NA | NA | NA | NA |
| 1096 | 1 | 1258 | 46.72 | 3 | Positive | 16 | 0.03 | 0.032 | 0.047 | 0.011 |
| 1096 | 2 | 1426 | 51.28 | 5 | Positive | 16 | 0.493 | 0.52 | 0.805 | 0.231 |
| 1096 | 3 | 1615 | 66 | 5 | Positive | 16 | 20.829 | 25.272 | 26.994 | 10.804 |
| 1104 | 1 | 183 | 39.36 | 0 | Negative | 15 | NA | NA | NA | NA |
| 1104 | 2 | 365 | 22.87 | 0 | Negative | 15 | NA | NA | NA | NA |
| 1104 | 3 | 568 | 47.98 | 0 | Negative | 15 | NA | NA | NA | NA |
| 1104 | 4 | 745 | 13.9 | 0 | Negative | 15 | NA | NA | NA | NA |
| 1107 | 1 | 373 | 18.46 | 0 | Negative | 16 | NA | NA | NA | NA |
| 1107 | 2 | 568 | 36.06 | 0 | Negative | 16 | NA | NA | NA | NA |

TABLE C-continued

Summary of sample levels and VAFs.

| Patient No. | Time point | Days from Surgery | ng of DNA to Library Prep | Number of Detected Targets | ctDNA status | Number of Assays Passed QC | Avg VAF (%) | Median VAF (%) | Max VAF (%) | Min VAF (%) |
|---|---|---|---|---|---|---|---|---|---|---|
| 1107 | 3 | 729 | 25.94 | 0 | Negative | 16 | NA | NA | NA | NA |
| 1111 | 1 | 467 | 66 | 11 | Positive | 16 | 6.388 | 6.206 | 11.209 | 0.415 |
| 2004 | 1 | 645 | 2.98 | 2 | Positive | 16 | 0.247 | 0.247 | 0.295 | 0.199 |
| 2004 | 3 | 981 | 18.36 | 9 | Positive | 16 | 6.148 | 5.801 | 10.105 | 3.842 |
| 2013 | 1 | 505 | 26.97 | 0 | Negative | 16 | NA | NA | NA | NA |
| 2013 | 2 | 688 | 4.3 | 0 | Negative | 16 | NA | NA | NA | NA |
| 2013 | 3 | 870 | 16.33 | 0 | Negative | 16 | NA | NA | NA | NA |
| 3018 | 1 | 170 | 16.2 | 3 | Positive | 16 | 0.088 | 0.055 | 0.192 | 0.016 |
| 3018 | 2 | 345 | 23.3 | 15 | Positive | 16 | 19.35 | 21.092 | 25.391 | 13.484 |
| 3018 | 3 | 443 | 66 | 15 | Positive | 16 | 53.703 | 57.854 | 64.446 | 34.164 |
| 3019 | 1 | 185 | 3.64 | 5 | Positive | 16 | 0.357 | 0.351 | 0.607 | 0.207 |
| 3019 | 2 | 696 | 23.18 | 14 | Positive | 16 | 10.495 | 10.841 | 19.652 | 0.074 |
| 3023 | 1 | 170 | 30.52 | 0 | Negative | 16 | NA | NA | NA | NA |
| 3023 | 2 | 345 | 26.79 | 10 | Positive | 16 | 3.295 | 2.917 | 6.581 | 1.949 |
| 3023 | 3 | 380 | 16.26 | 10 | Positive | 16 | 3.608 | 2.907 | 6.72 | 1.855 |
| 3048 | 1 | 255 | 30.79 | 11 | Positive | 16 | 0.157 | 0.148 | 0.292 | 0.039 |

Example 9. Early Detection of Metastatic Relapse and Monitoring of Therapeutic Efficacy by Ultra-Deep Sequencing of Serial Plasma Cell-Free DNA in Patients with Urothelial Bladder Carcinoma Introduction Bladder cancer is the most common malignancy of the urinary tract, and approximately 20-25% of patients with newly diagnosed urothelial carcinoma will develop muscle-invasive bladder cancer (MIBC), and 10-30% of patients diagnosed with non-MIBC (NMIBC) will progress to MIBC. The current standard method for treating MIBC is radical cystectomy. Unfortunately, 20% of patients with node-negative and 80% with node-positive disease at surgery will experience metastatic relapse, and overall survival (OS) is on average 50% over 5 years.

Neoadjuvant chemotherapy (NAC) improves survival of MIBC patients, and treatment with Gemcitabine and Cisplatin (GC) is the most commonly used neoadjuvant chemotherapy (NAC) of MIBC. Currently, treatment with Gemcitabine and Cisplatin leads to significant downstaging (pT<2 N0 at cystectomy) in about 40-50% of patients.

Early detection of metastatic relapse in patients with bladder cancer may offer new therapeutic approaches to increase survival. Identification of metastatic relapse after cystectomy at an early time point, when relapse is not detectable by radiographic imaging, could significantly improve identification of patients who may benefit from early/adjuvant treatment and improve the survival outcome for this patient group. In addition, early determination of relapse and metastasis could help preventing unnecessary and potentially harmful prolonged treatment of patients who are not responding to the treatment.

Currently, standard computed tomography (CT) imaging at scheduled intervals is used to detect relapse, metastasis, and monitor response to treatment. While imaging techniques offer an assessment of the tumor burden, the monitoring potential is restricted by a suboptimal detection limit and inherent variability in the measurements. Therefore, early detection of metastatic relapse and/or progression and evaluation of treatment efficacy remain a major clinical challenge.

The full potential of using circulating tumor DNA (ctDNA) as a biomarker for disease staging at diagnosis, tumor burden, early detection of metastatic relapse, and therapeutic treatment response remains unfulfilled. Recent promising studies have shown that cell-free DNA (cfDNA) may be used to monitor early stage lung cancer evolution and sub-clonal development in metastatic disease (Abbosh, et al., Nature 545, 446-451 (2017) ("Abbosh et al. 2017"), incorporated herein in its entirety). In bladder cancer, it was shown that ctDNA is detectable in plasma and urine and that high levels of ctDNA are associated with later detected clinical disease progression and metastatic disease (Birkenkamp-Demtröder et al., Eur. Urol. 70, 75-82 (2016); Christensen et al., Eur. Urol. 71, 961-969 (2017); Birkenkamp-Demtröder, K. et al. Eur. Urol. 73, 535-540 (2018); Patel, et al., Sci. Rep. 7, 5554 (2017)). However, these previous studies in bladder cancer were based on smaller selected cohorts and employed ddPCR assays that have relatively limited sensitivity compared to the Next Generation Sequencing (NGS) based method disclosed herein.

Here we report the results from a prospective study encompassing whole exome sequencing (WES) of primary tumors and matching germline DNA of 68 patients treated with neoadjuvant chemotherapy (n=56) or first line chemotherapy (n=12) before cystectomy. Sensitive, personalized multiplex-PCR NGS based assays specific to each respective patient's tumor mutational signature were designed and used to monitor somatic mutations in plasma samples that had been procured longitudinally, before, during, and after chemotherapy. The primary objective of this study was to develop a method of ctDNA detection to enable the use of ctDNA as a powerful biomarker for prognosis, early detection of metastatic disease and as a predictor of chemotherapy response.

Methods

Patients and Clinical Samples

Patients diagnosed with MIBC and receiving neoadjuvant chemotherapy prior to cystectomy, and patients receiving chemotherapy due to metastatic disease with or without prior cystectomy were enrolled between 2013 and 2017 at a single tertiary university hospital (Aarhus University Hospital, Denmark). Radical cystectomy was performed as open cystectomy or robotic assisted based on patient criteria and availability of the robot. In all patients, extended lymph node dissection was performed to the level of the aortic bifurcation.

Patients were treated according to Danish national guidelines. Neoadjuvant chemotherapy was administered as 4 series of Gemcitabine and Cisplatin (GC), given at three week intervals. Patients with metastasis or cT4b tumors at diagnosis were treated with up to 6 series of GC. Pathological downstaging after chemotherapy, administered prior to CX, was defined as <T1N0 after treatment. Cystectomy patients were followed with radiographic imaging by pre-therapeutic PET/CT and by CT of thorax and abdomen at scheduled controls at 4, 12 and 24 months after cystectomy for patients diagnosed with pT2N0 and additional controls at 8 and 18 months for patients diagnosed with >pT2 and/or N+. Patients treated for advanced disease were followed with CT at 3-4 month intervals. Detailed follow-up data were available for all patients, and clinical endpoints were the last recorded visit or the time of death obtained from the national personal registry. Patients were selected for whole exome sequencing based on the following criteria: 1) neo-adjuvant/first line chemotherapy for localized MIBC 2) number of visits with plasma samples taken before and during chemotherapy, before and after CX 3) availability of a tumor biopsy. All patients provided written informed consent, and the study was approved by The National Committee on Health Research Ethics (#1302183).

Sample Collection and DNA Extraction

We analysed material from blood, tumor biopsies, and longitudinally collected plasma samples. Tissue biopsies were obtained from TUR-B at the time of diagnosis. DNA was extracted as previously described, either from sections from TISSUE-TEK® O.C.T. Compound embedded tissue (Sakura) or from formalin-fixed paraffin embedded (FFPE) from a punch taken at the most representative localization with high carcinoma cell percentage 0.40 mL EDTA blood was collected at each visit or before each series of chemotherapy and was processed immediately. Samples were centrifuged at 3000×g for 10 minutes at room temperature, and plasma and buffy coat were stored separately at −80° C. Germline DNA was extracted from buffy coat leucocytes and concentration was measured by QUBIT® fluorometric quantitation. Plasma was stored at −80° C. Up to 9 ml of plasma per case was used for this study (range, 4-9 ml; average×mL). The entire volume of plasma was used for cfDNA extraction using the QIAAMP® Circulating Nucleic Acid kit (Qiagen) and eluted into 50 L DNA Suspension Buffer (Sigma). Each cfDNA sample was quantified by QUANT-IT® High Sensitivity dsDNA Assay Kit (Invitrogen).

Exome Sequencing and Bioinformatics Analysis

Libraries of tumor and matching germline DNA were prepared using 100-500 ng DNA and captured by SEQCA-PEZ® MedExomeV1_hg19 or MedExomePlusV1_hg19 panel (Roche). Exome sequencing metrics, carcinoma cell percentage and tissue type is shown.

All variants passing the applied filters were subjected to analyses on the activity of mutational signatures. Variants were initially loaded into a VRanges object and the sequence context was subsequently extracted using the SomaticSignatures R package (Obenchain et al., *Bioinformatics* 30, 2076-2078 (2014); Gehring et al., *Bioinformatics* 31, 3673-3675 (2015)). De novo extraction of mutation signatures was not applied due to the size of the cohort. The mutational profiles identified in our samples were instead projected onto the known COSMIC signatures using the MutationalPatterns R package (see cancer.sanger.ac.uk/cosmic/signatures and Blokzijl et al., *Genome Med.* 10, 33 (2018)). The mutational signatures 1, 2, 5, and 13 identified in Robertson et al., *Cell* 171, 540-556.e25 (2017) for bladder cancer were prioritized for the analyses.

DNA Damage Response Related Mutations

Selected DNA damage response genes were described in Teo et al., *Clin. Cancer Res.* 3610-3618 (2017). Mutations identified in these genes were analysed for being damaging or benign. All loss-of-function mutations were considered damaging. Missense mutations were subjected to further analysis using PolyPhen2 and MutationAssessor as described in Reva et al., *Nucleic Acids Res.* 39, e118 (2011), and Adzhubei et al., *Nature Methods* 7, 248-249 (2010). Variants identified as possibly damaging/probably damaging or medium/high in PolyPhen2 and MutationAssessor, respectively, were considered damaging.

Cell Free DNA Library Preparation

Preparation of cell free DNA (cfDNA) was previously described in Up to 66 ng (20,000 genome equivalents) of cell free DNA (cfDNA) from each plasma sample were used as input into the library preparation. The cfDNA was end-repaired, A-tailed, and ligated with custom adapters. The purified ligation product was amplified for 20 cycles and purified using AMPURE® XP beads (Agencourt/Beckman Coulter).

Plasma Multiplex-PCR Next Generation Sequencing (NGS) Workflow

An aliquot of each library was used as input into the associated patient-specific 16-plex PCR reaction. Samples were amplified using the SIGNATERA® tumor-specific assay and barcoded, followed by pooling. Sequencing was performed on an Illumina HISEQ® 2500 Rapid Run with 50 cycles of paired-end reads using the Illumina PAIRED END® v2 kit with an average read depth of >100,000× per amplicon as described in Abbosh et al., Phylogenetic ctDNA analysis depicts early-stage lung cancer evolution, Nature 545, 446-451 (2017).

Plasma Variant Calling

A large set of negative control samples (~1000) were pre-processed to build a background error model. For each target variant using mutant and reference alleles depth of read a confidence score was calculated on the basis of the error model as described in Abbosh et al. 2017. A ctDNA positive plasma sample was defined as having at least 2 variants with a confidence score above a predefined algorithm threshold (0.97) as described in Abbosh et al. 2017.

Plasma Whole Exome Sequencing

An aliquot of each plasma library was barcoded and captured using the SEQCAP® EZ MedExome Target Enrichment Kit. Sequencing was performed on an Illumina HISEQ® 2500 with 200 cycles of single-end reads using the Illumina TRUESEQ® v1 kit. The data was demultiplexed, adaptor trimmed, and mapping was performed with the Burrows-Wheeler Alignment (BWA-mem) tool and using hg19 as reference sequence. Duplicates were marked with the Picard tools for manipulating the sequencing data. The Bam files generated from this mapping were processed according to GATK best practices (ref). Variants were called using MuTect2, and variants passing the built-in filters were used to identify the genomic positions with alterations per patient. The called variants in both exomes per patient were subsequently used to analyze all the included positions manually using BAM-readcount (ref). Only bases and reads with qualities above 20 were included, and positions with fewer than 10 reads in both exomes were not included in the comparison.

RNA-Sequencing, Data Processing and Analysis

RNA sequencing was performed using the QUANT-SEQ® 3' mRNA-Seq Library Prep (Lexogen) with RNA input between 50-250 ng. Libraries were made according to the manufacturer's recommendations. Sequencing was performed as 70 bp single read on the Illumina NEXTSEQ® 500 platform. Sequence reads were aligned to the GRCh38 transcriptome (cDNA+ncRNA) using Salmon (Patro et al., Nature Methods, 14, 417-419 (2017)) with no gene length correction, and TPM gene expression data was normalized using edgeR (Robinson and Oshlack, Genome Biology, 11, R25 (2010)). Samples were classified according to MIBC consensus subtypes (manuscript in preparation).

Statistical Analyses

Survival analyses were carried out in R statistics using packages survminer and survival. Assessment of statistical significance was performed using Wilcoxon rank-sum test for continuous variables and Fisher's Exact test for categorical variables.

Results

Patient Characteristics and Primary Tumor Analysis

Figure 70:
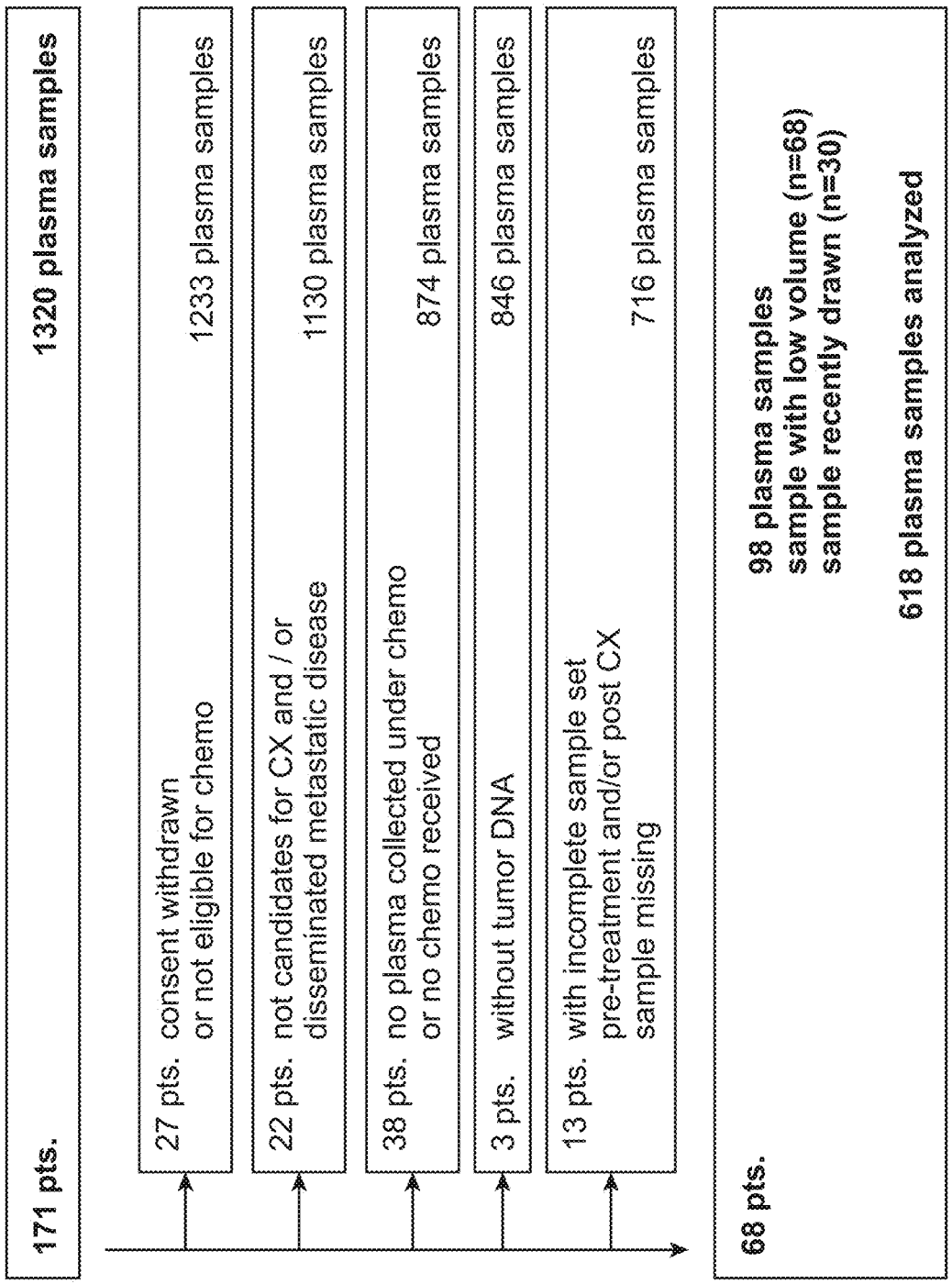
FIG. 70: Workflow diagram for the muscle invasive bladder cancer study in Example 9.
Figure 71F:
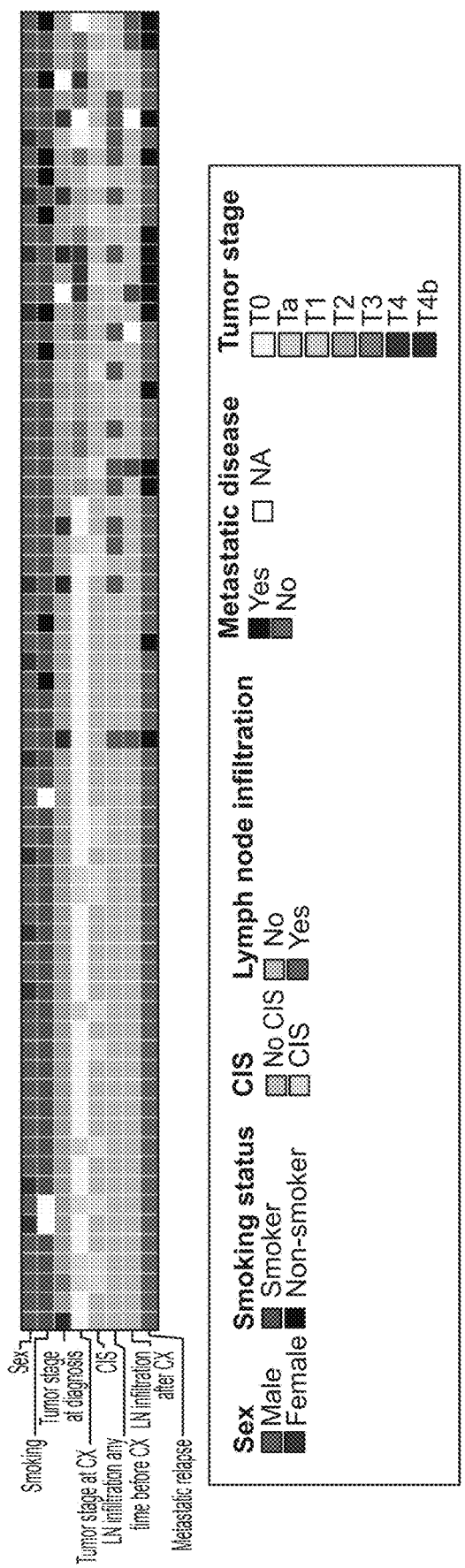
Figure 71G:
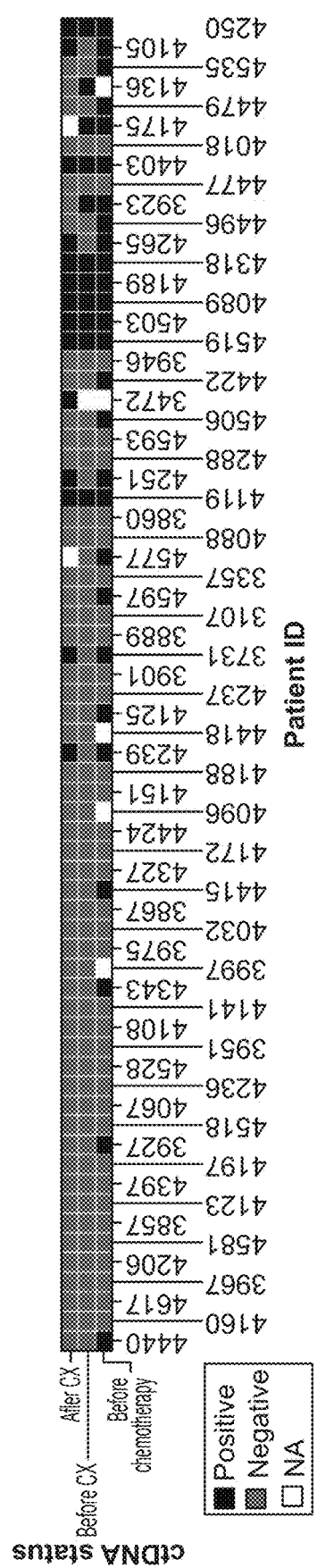

We enrolled patients with localized MIBC receiving chemotherapy before cystectomy between 2014 and 2017 at Aarhus University Hospital, Denmark (FIG. 70). In total, 68 patients fulfilled all inclusion criteria (see FIG. 70, FIG. 71A-G, and Table IA below).

TABLE IA

Patient Characteristics and Demographics.
Patients, N= 68 Age[a] (years), median (range) = 65.2 (43-79)

| Gender, n (%) | | Tumor stage at CX,[b] n (%) | |
|---|---|---|---|
| Female | 12 (17.6) | T0/Cis/Ta/T1 | 47 (69 .1) |
| Male | 56 (82.4) | T2/T3/T4a | 19 (27.9) |
| Tumor stage at TUR-B, n (%) | | Metastasis,[c] n (%) | |
| T1/T2 | 58 (85.3) | Local relapse (pelvis, rectum, urethra) | 6 (17.6) |
| T4a/b | 10 (14.7) | Distant metastases (bone, lung, liver, skin) | 8 (11.8) |
| N stage before treatment, n (%) | | Clinical follow-up, days (range) | |
| N0 | 58 (85.3) | Disease free (CX; n = 52) | 498 (103-991) |
| N1/N2 | 10 (14.7) | Clinical relapse (CX; n = 14) | 321 (57-1119) |
| | | Progression (CX unsuccessful; n = 2) | 263 |

*At sampling: *n = 66; *n = 14; CX, cystectomy

Figure 72:
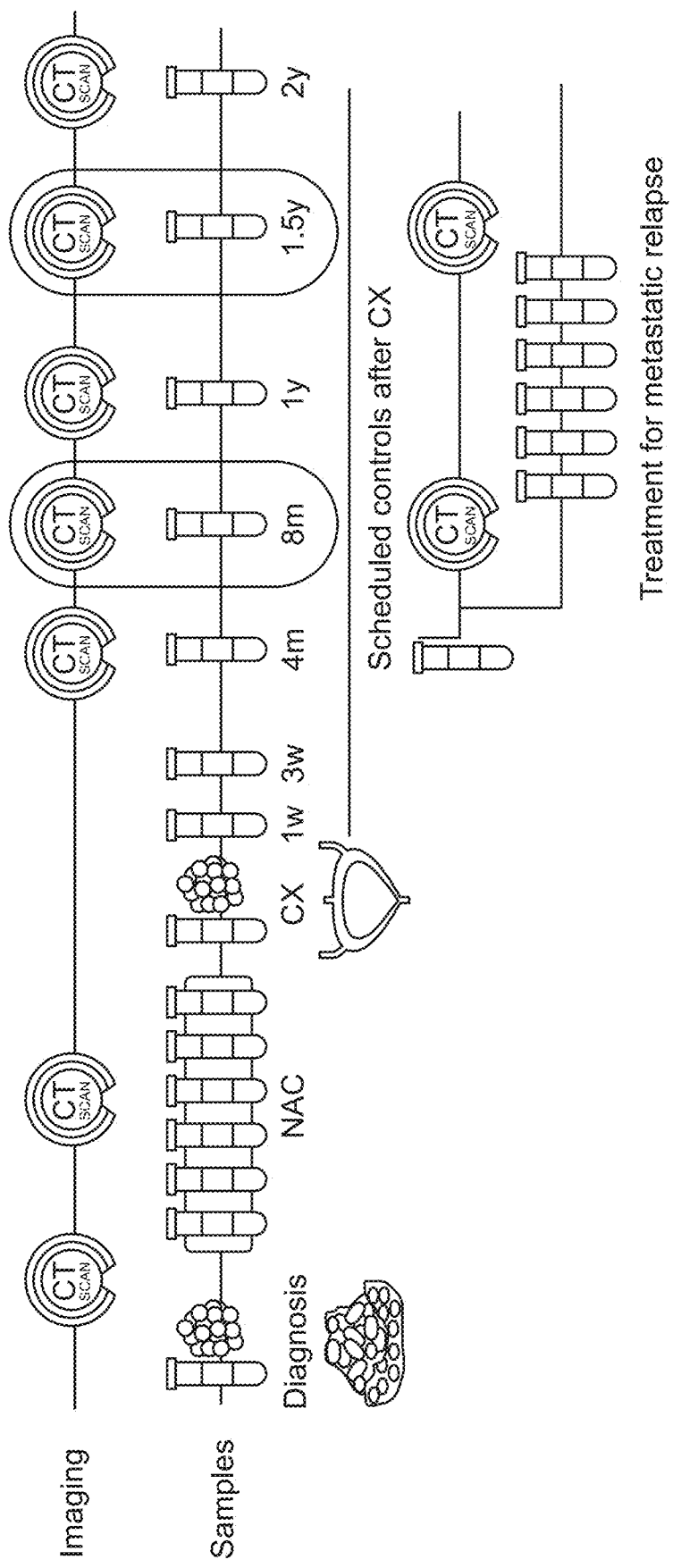
FIG. 72: Diagram outlining the clinical protocol and sampling schedule for the muscle invasive bladder cancer study in Example 9.

Whole exome sequencing (WES) of tumor and matched germline DNA was performed at a mean target coverage of 104× (31×-251×) for tumor samples and 66× (35×-120×) for germline samples identifying an average of 488 (11-3536) mutations per patient. In addition, RNA-Sequencing of 46 tumors was performed to determine bladder cancer subtypes, immune signatures and cellular compositions. A summary of molecular characteristics and clinical data for all patients is shown in FIG. 71A-G. An outline of the clinical protocol and sampling schedules for this study is shown in FIG. 72.

ctDNA Monitoring by Ultra-Deep Multiplex-PCR Based Next Generation Sequencing (NGS).

Figure 73:
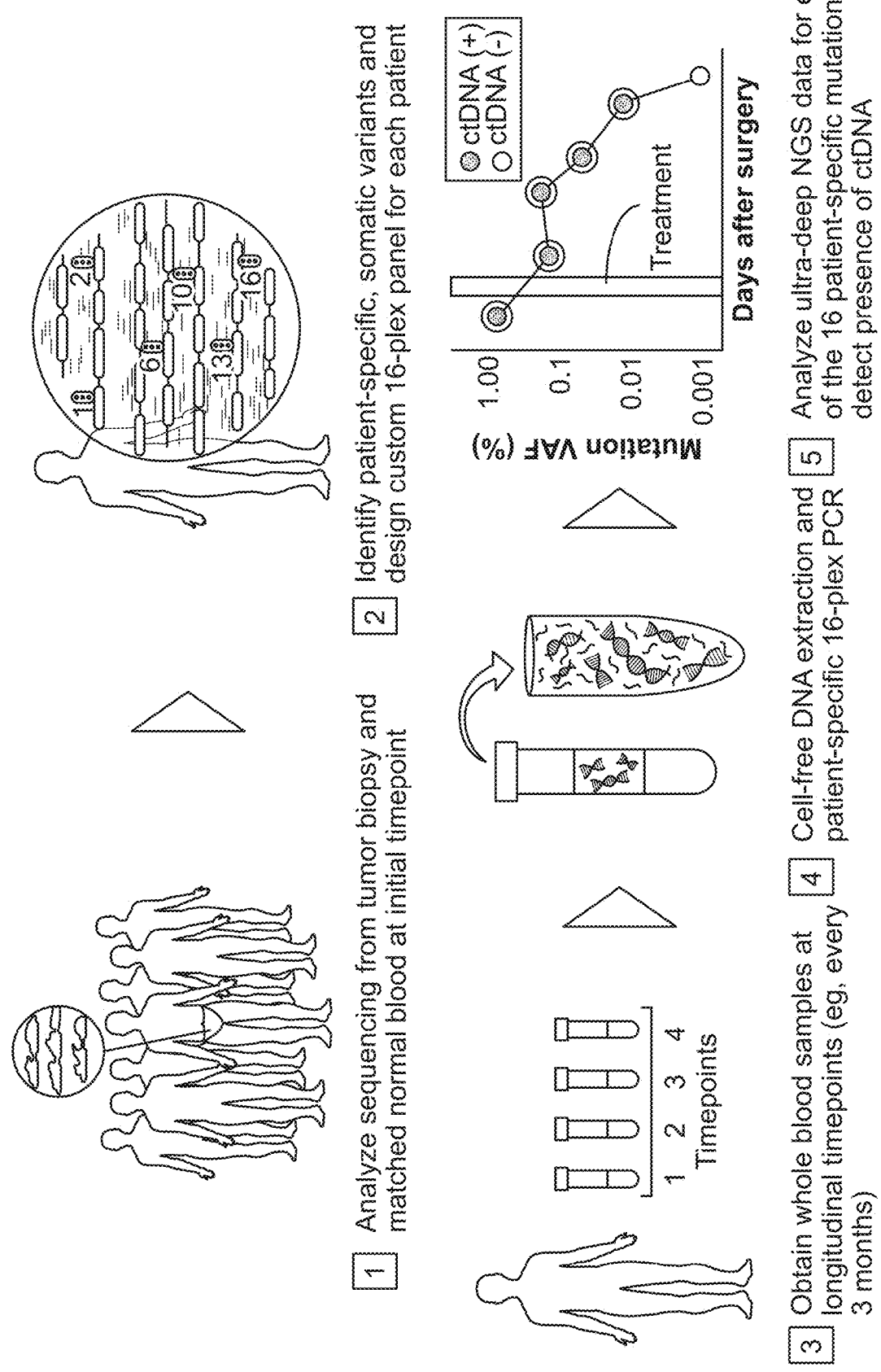
FIG. 73: Diagram outlining the Signatera™ workflow.
Figure 74:
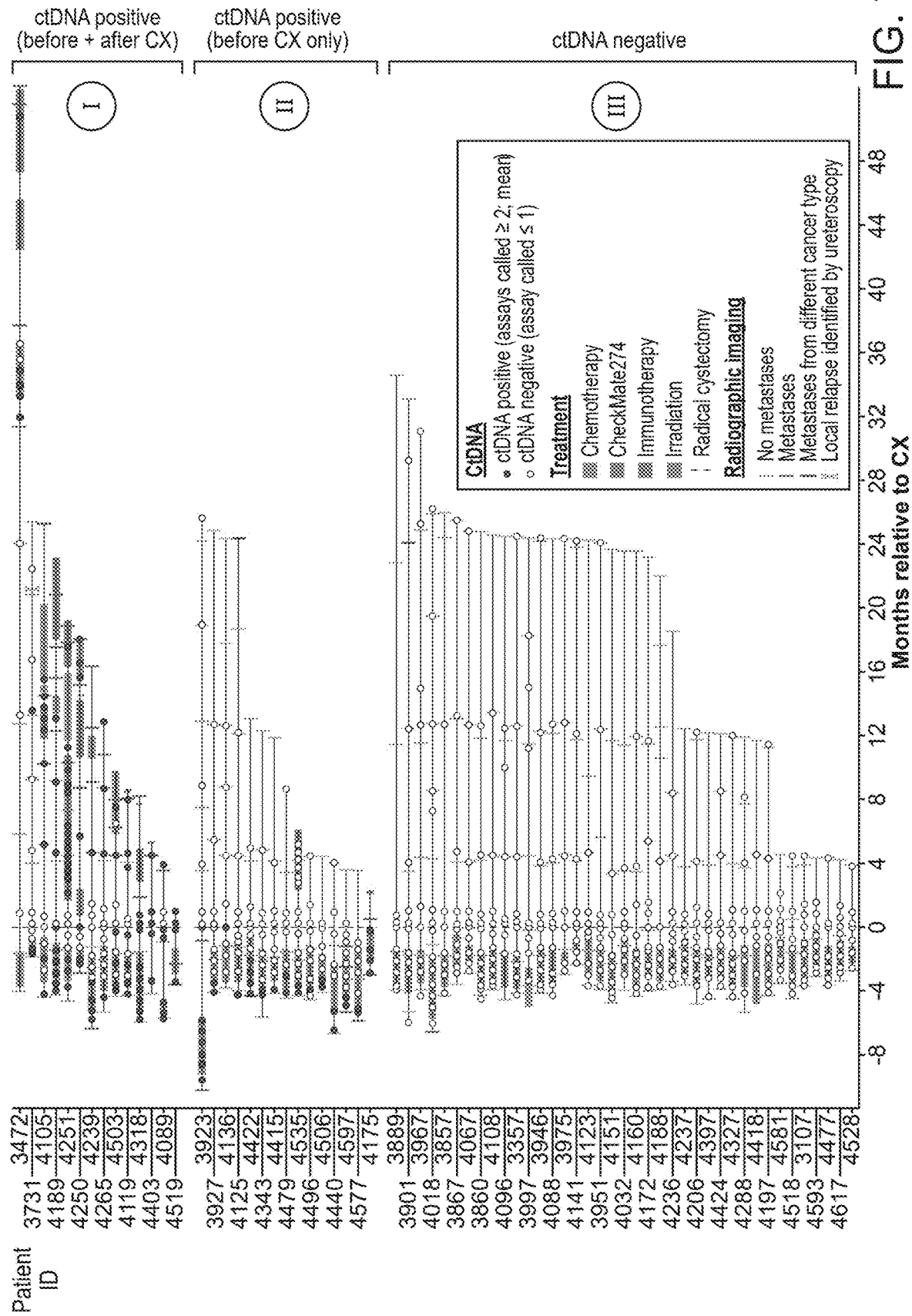
FIG. 74: Longitudinal representation of ctDNA results for all analyzed samples corresponding to the muscle invasive bladder cancer study in Example 9. Patients are separated into three groups based on ctDNA status: the upper panel shows patients ctDNA positive before and after cystectomy (CX); the middle panel shows patient ctDNA positive before CX only; the bottom panel shows ctDNA negative patient Horizontal lines represent each patients disease course and circles represent ctDNA status, line-through circles indicate samples with at least 2 positive assays. Treatment and imaging information is indicated for each patient.

A bespoke multiplex-PCR NGS approach was used for ctDNA detection. Somatic SNVs and short INDELs were prioritised from whole exome sequencing (WES) data based on observed variant allele frequency (VAF) in tissue and sequence context. Unique patient-specific assays were designed and synthesized for sixteen highly ranked somatic mutations as outlined in FIG. 73. Multiplex-PCR NGS was performed on plasma cfDNA. A sample was called ctDNA positive only if, at least two target variants were detected based on the previously developed calling algorithm disclosed in Abbosh et. al 2017. Sample-level analytical sensitivity (where 2 or more variants out of 16 are detected) was determined to be >95% at 0.01% variant allele frequencies.

Using this approach, ctDNA status was analysed in 618 plasma samples from the 68 patients included in the study (FIG. 70). Quality control was performed throughout the workflow. Samples and amplicons that failed QC were excluded from further analyses. For each patient, a set of 45 SNPs were genotyped in whole exome sequencing (WES) and in plasma sequencing to ensure sample concordance. The median target coverage was 120.000×.

ctDNA Detection for Prognosis and Relapse Detection

Throughout the whole disease course, presence or absence of ctDNA was strongly correlated with patient outcome (FIG. 74, FIG. 75A-C). The ctDNA status at the following three time points were of significant interest. The first time point of interest is the ctDNA status prior to NAC administration, and this time point was found to be strongly prognostic of outcome. In bladder cancer, the first intervention is TURBT (Transurethral Resection of Bladder Tumor), and therefore, this first time point was found to serve as a proxy to measure minimal residual disease. Strikingly, 94% (34/36) of the ctDNA negative patients at this first time point did not recur for the duration of the study. Contrarily, 44% (11/25) of patients that were ctDNA positive at this time point before NAC recurred after cystectomy. The detection of ctDNA at this early time point is thus a very strong prognostic factor for the long term clinical outcome after NAC and cystectomy (CX).

Figure 75B:
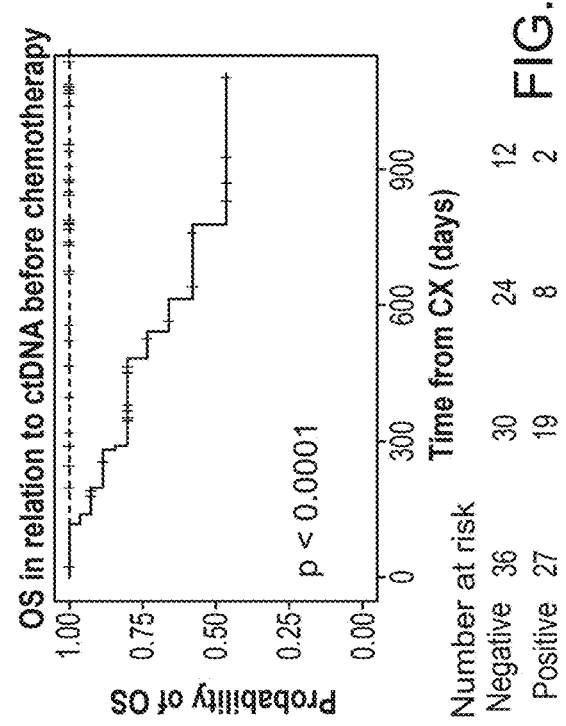
FIG. 75A-L: Graphical depiction of prognostic value of ctDNA detection for the muscle invasive bladder cancer study in Example 9. Kaplan-Meier survival analysis showing probability of recurrence-free survival (RFS) and overall survival (OS) stratified by ctDNA status before chemotherapy (FIG. 75A), before cystectomy (CX) (FIG. 75B), and after cystectomy (CX) (FIG. 75C).

The second time point was after NAC and prior to cystectomy, the ctDNA status at this time point was also prognostic of patient outcome. Among the ctDNA negative patients, only 7% (4/55; the 4 were positive after cystectomy (CX) and relapsed) of patients recurred compared to 70% (7/10) of ctDNA positive patients that experienced recurrence. ctDNA status before cystectomy (CX) was associated with pathology at CX because 100% of ctDNA positive patients at this time point had a residual T2+ tumor and/or lymph node metastases identified at cystectomy (FIG. 75B).

Figure 75D:
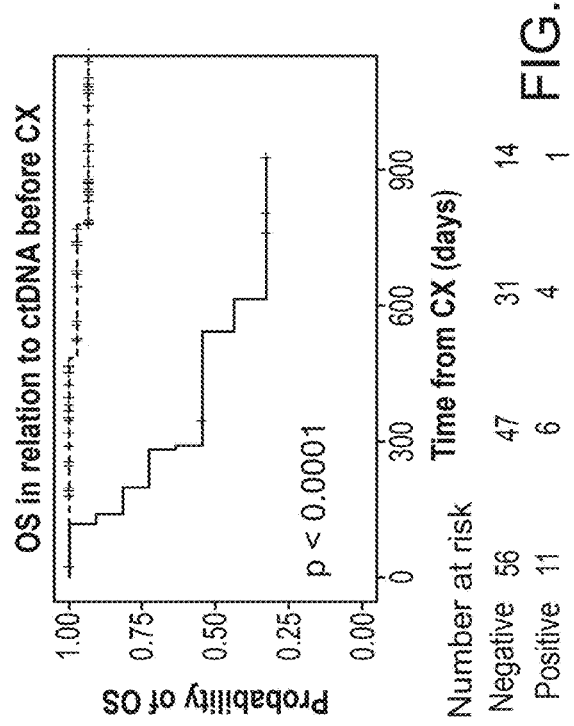
Figure 75A:
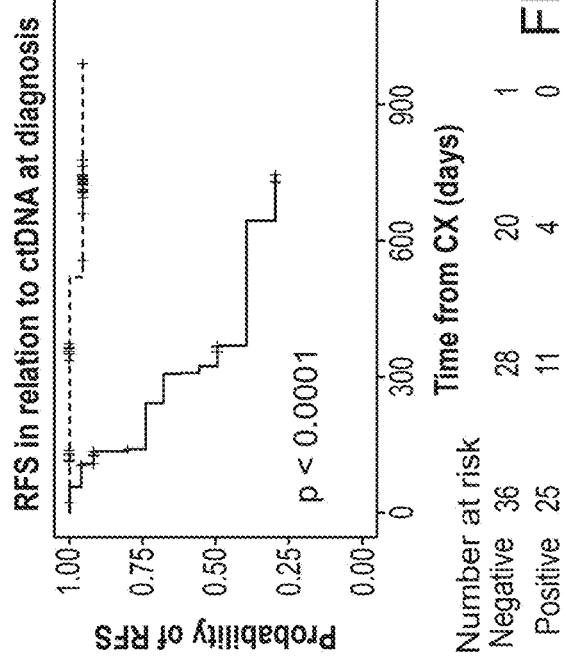
Figure 75C:
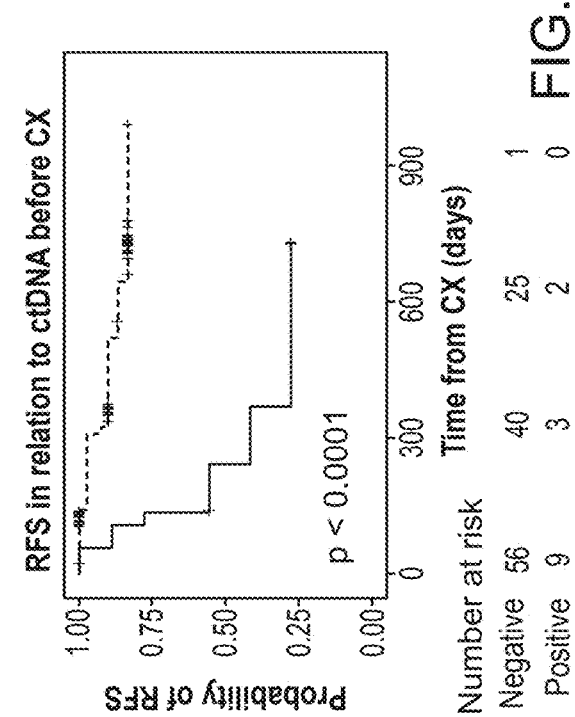
Figure 75E:
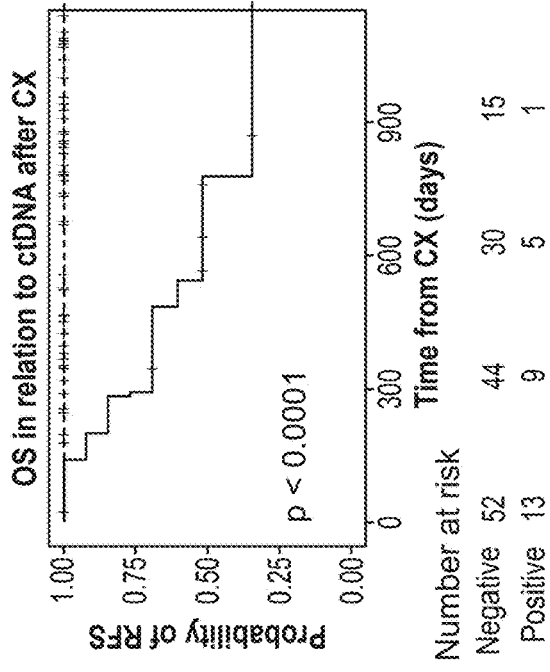
Figure 75G:
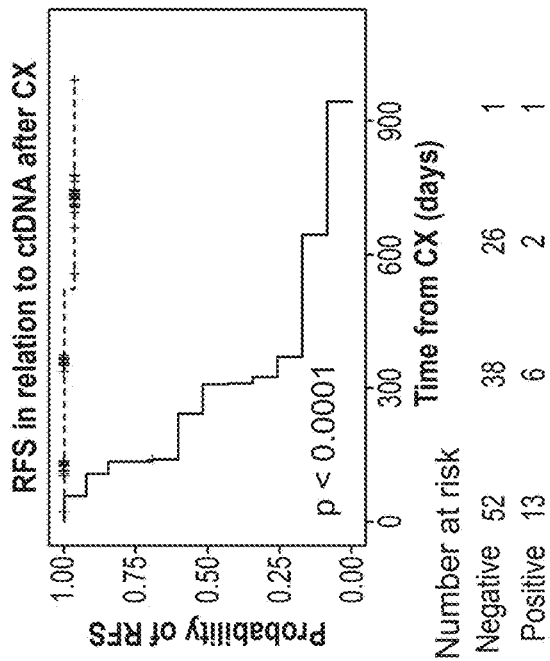
Figure 75F:
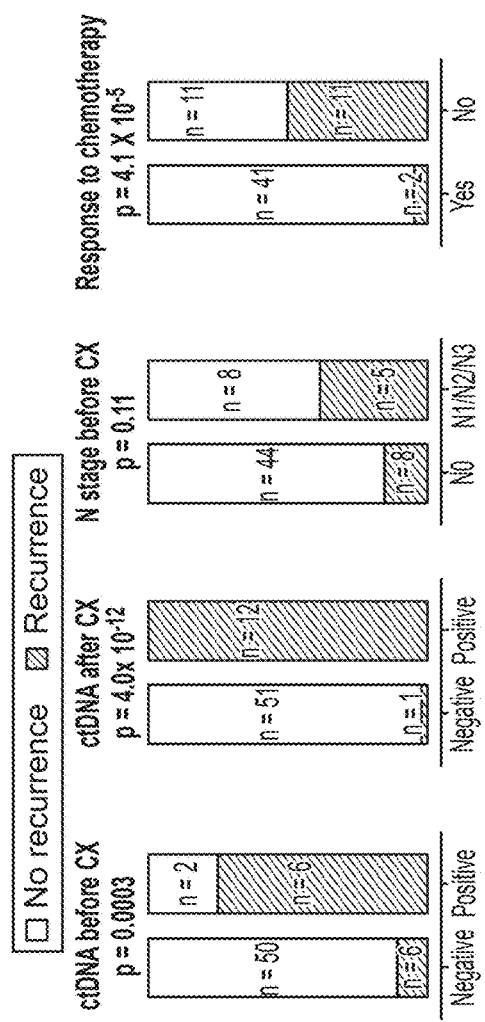
Figures 75H, 75I, 75J, 75K:
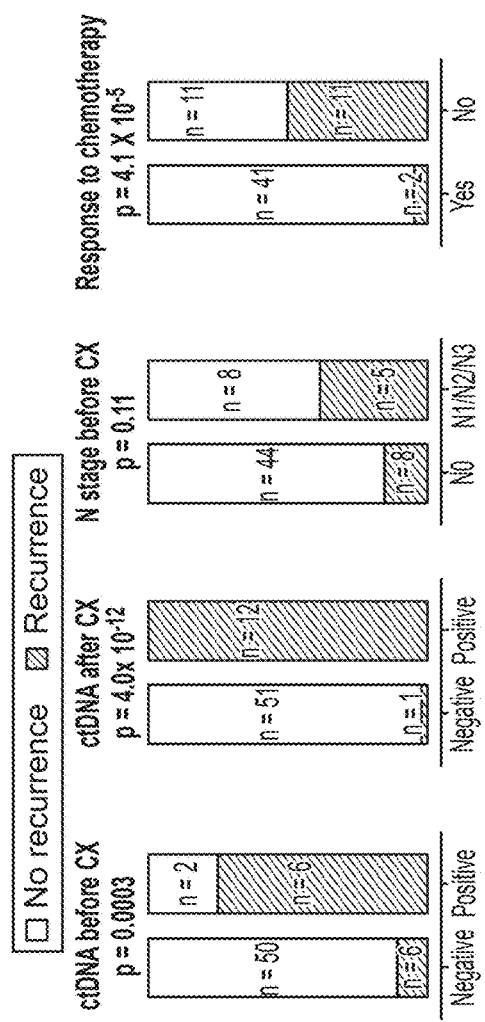
Figure 75L:
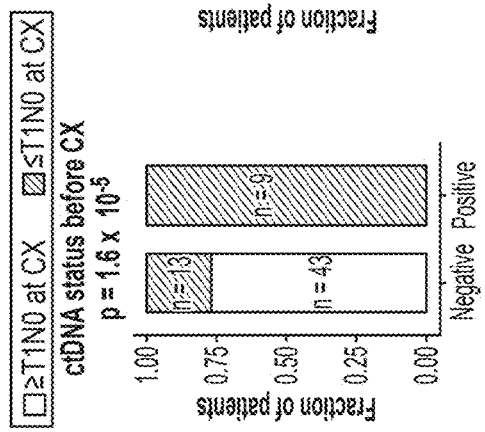
Figure 76B:
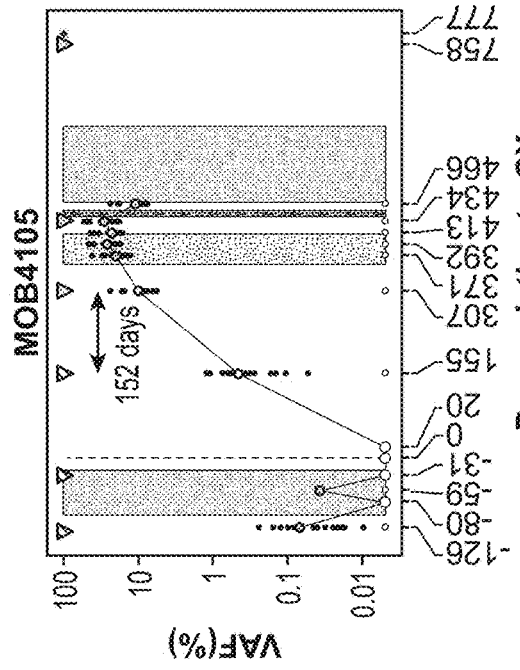
Figure 76A:
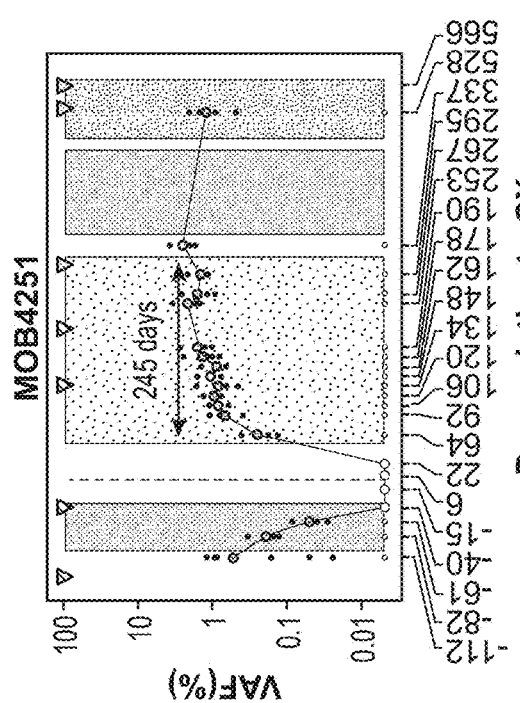
Figure 76D:
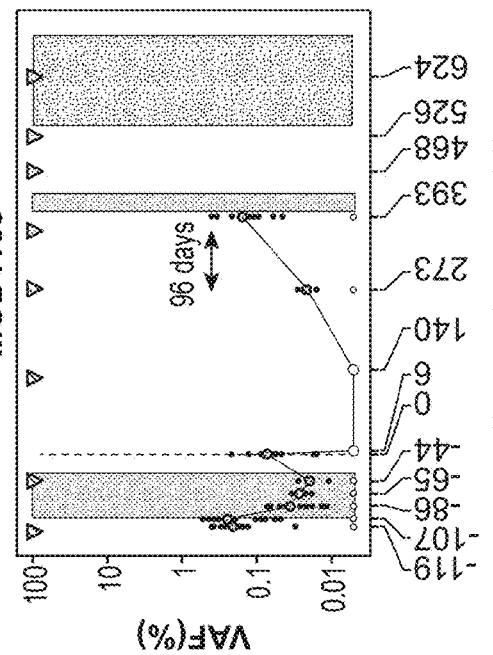
Figure 76C:
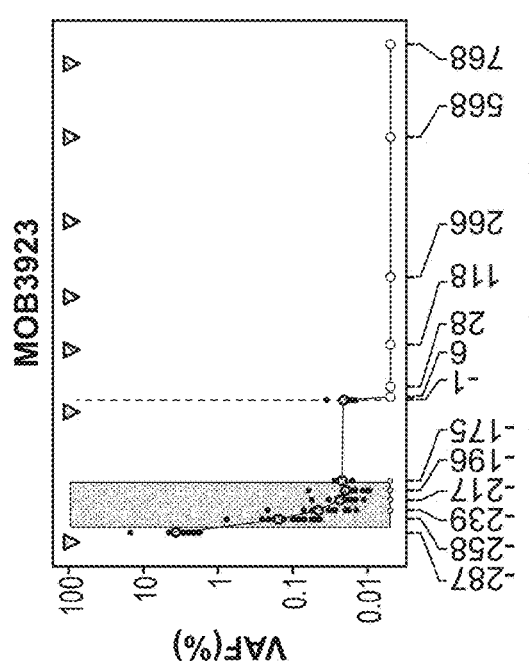

The third time was after cystectomy. Stratifying patients by ctDNA status after CX demonstrated a significantly worse outcome for ctDNA positive patients (FIG. 75C). The majority, 96% of the ctDNA negative patients (50/52) did not recur, however, 2/52 patients recurred >1.5 years after CX (ctDNA analysis not performed closer to relapse). In contrast, 92% (12/13) of ctDNA positive patients recurred. Notably, one patient died before clinical evaluation (FIG. 75D). Status of ctDNA after CX was found to be highly prognostic of disease recurrence, and a stronger predictive factor than any other predictive factor such as N stage before cystectomy and response to chemotherapy (FIG. 75E).

Serial ctDNA Measurements for Disease Surveillance

Figure 77:
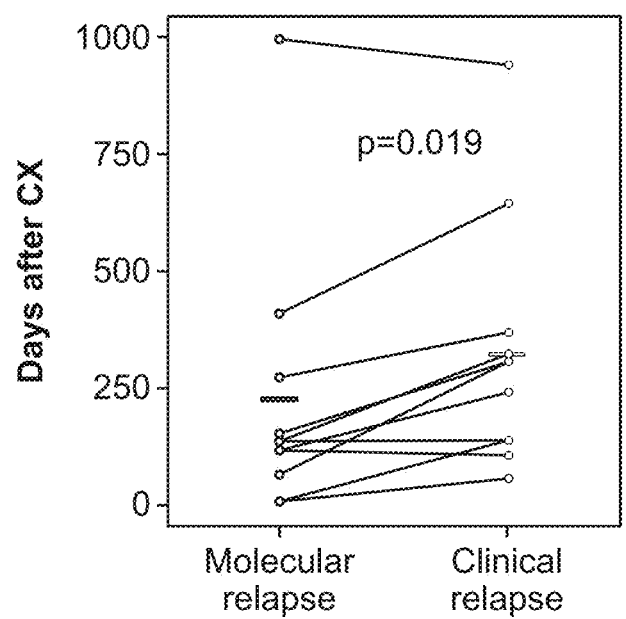
FIG. 77: Graphs showing time differences between molecular recurrence (ctDNA positivity) and clinical recurrence (radiographic imaging positive) for the muscle invasive bladder cancer study in Example 9. P-value was calculated using a paired Wilcoxon rank-sum test.

It is disclosed herein that serial measurement of ctDNA may be used for both monitoring therapy response as well as detecting relapse. In our study, serial plasma time points were collected after cystectomy while patients were disease-free to assess value of ctDNA in the surveillance setting. When including analysis of serial measurements of ctDNA during the disease courses we observed a sensitivity of 92% with 100% specificity (FIG. 76A-G). On average, the detection of ctDNA was observed 96 days (0-245 days) prior to detection by radiographic imaging. For example, for patient 4265, a drop in ctDNA during NAC was observed and then ctDNA was detected 138 days post CX; whereas clinically, the relapse was detected 186 days later (324 days after CX). Similarly, patient 4189 showed ctDNA positivity prior to CX, and was subsequently negative, and then ctDNA was again detected 273 days after CX; however, clinical relapse was detected on day 369, or 96 days later (see FIG. 76A-G). For the 12 patients with metastatic relapse, we found ctDNA analysis to have a median lead time of 103 days (range; p=0.019) over conventional imaging (FIG. 77) Lead-times may be biased by analysis of more frequent plasma sampling compared to imaging. Restricting our analyses to patients with simultaneous plasma and radiographic imaging identified eight patients, five of whom showed a lead-time in recurrence detection for ctDNA analyses. The remaining three patients showed simultaneous recurrence detection (FIG. 77), and the resulting average lead-time for all eight patients was found to be 106 days.

Serial Select ctDNA Measurements for Therapy Response Monitoring

Bladder cancer is treated with NAC, however, clinically useful predictive biomarkers of response to treatment before is currently not available, and pathological downstaging at CX is used as a proxy for treatment efficacy (ref). In our series, disease recurrence was significantly associated with chemotherapy response as expected (FIG. 78A), however, only 44% (x/y) of patients with no response had disease recurrence, indicating that pathological downstaging was suboptimal for evaluating treatment efficacy. Here, we found that serial measurements of ctDNA during NAC showed highly different distributions between responders and non-responders (p=xx; FIG. 78F-G). A total of 83% (34/41) of ctDNA negative patients showed response to chemotherapy and 53% (9/17) of patients that showed ctDNA clearance from initially positive tests responded, indicating that ctDNA levels may serve as better indicators of treatment efficacy during and after treatment. The ctDNA positive patients after NAC showed no response to chemotherapy. Overall, the ctDNA levels were reflective of the disease course characteristics observed in the cohort (FIG. 78G).

Figure 78B:
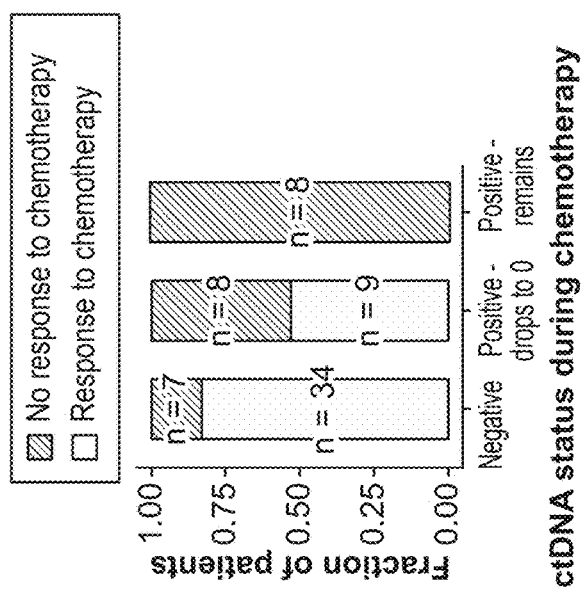
Figure 78C:
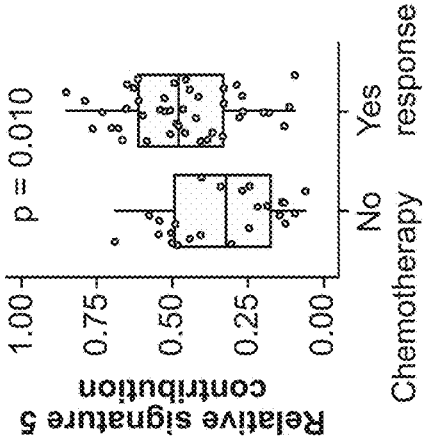
Figure 78A:
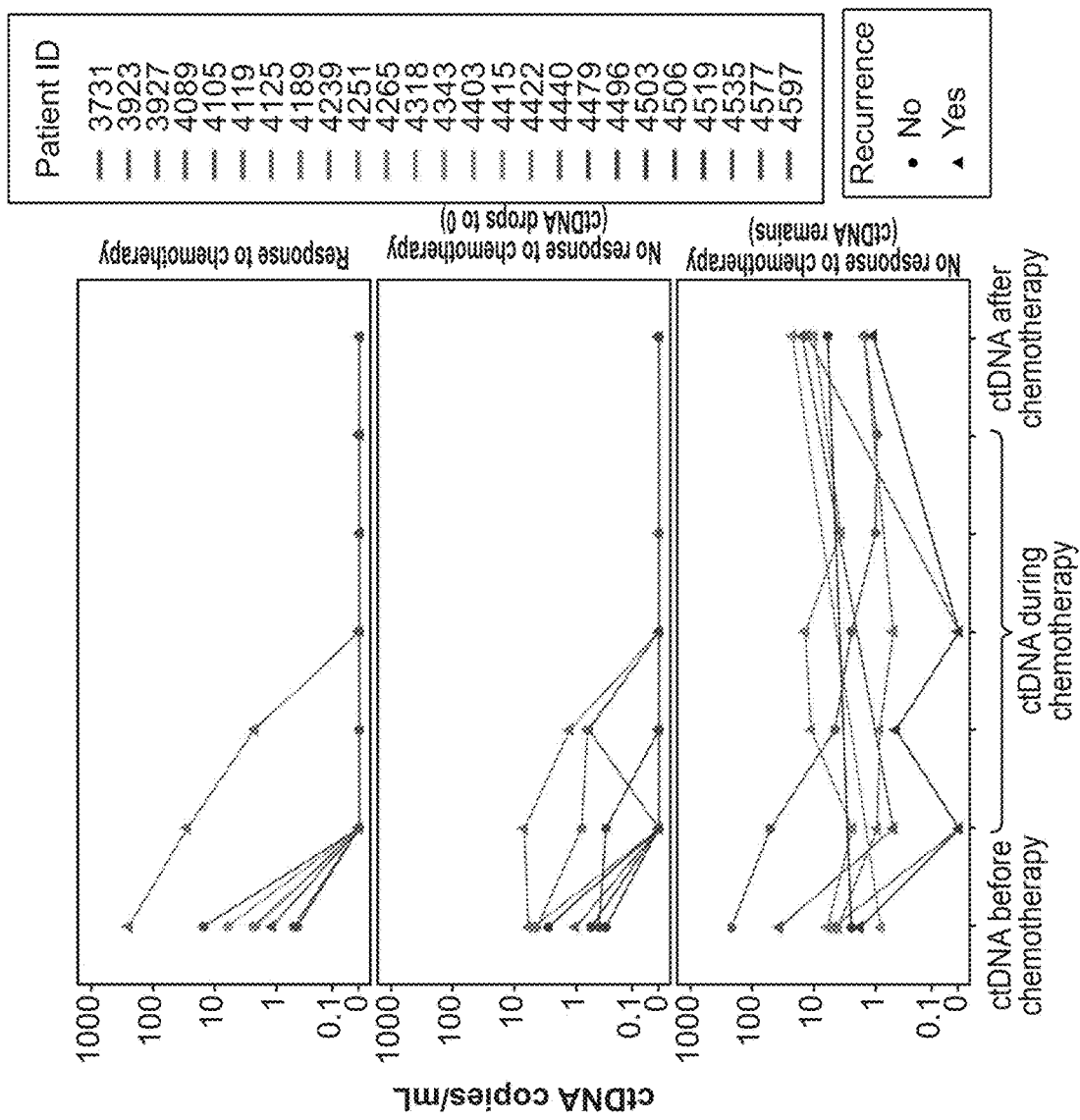
Figure 79A:
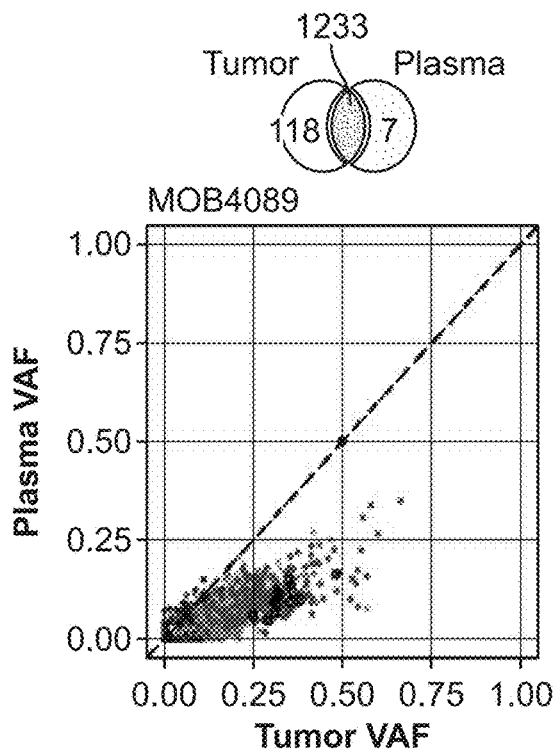
FIG. 79A-D: Graphs showing the total number of identified mutations per patient in relation to the ERCC2 status or the number of damaging DNA damage response (DDR) mutations for the muscle invasive bladder cancer study in Example 9.
Figure 79B:
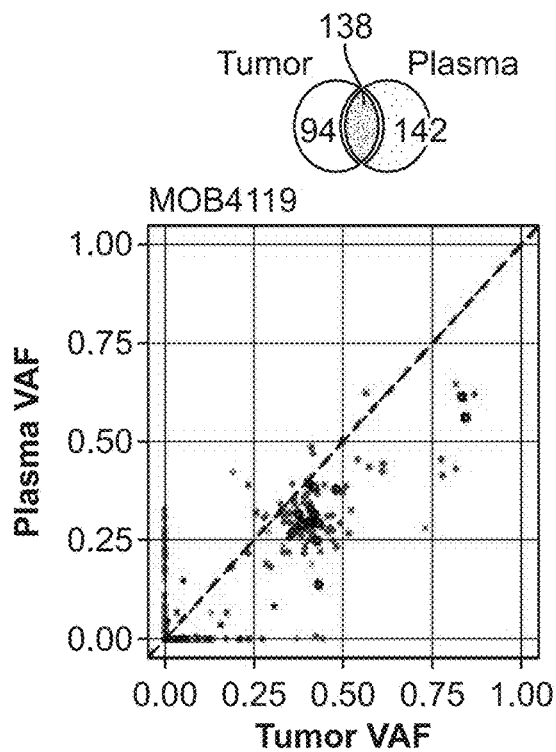
Figure 79C:
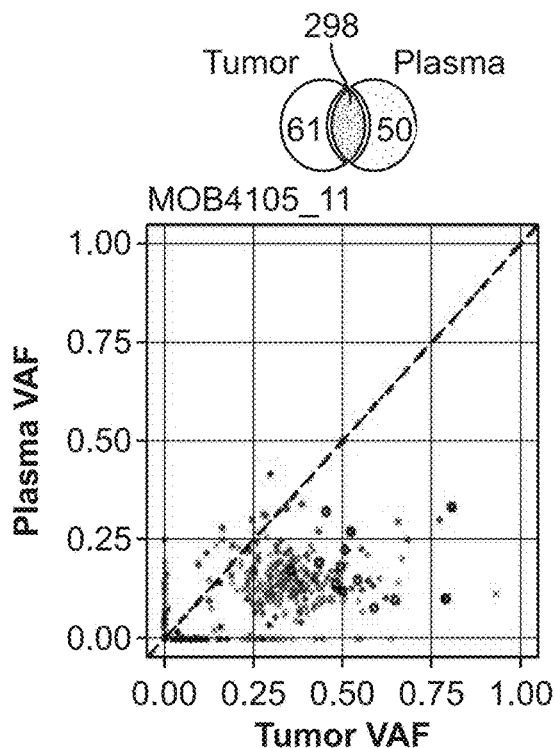
Figure 79D:
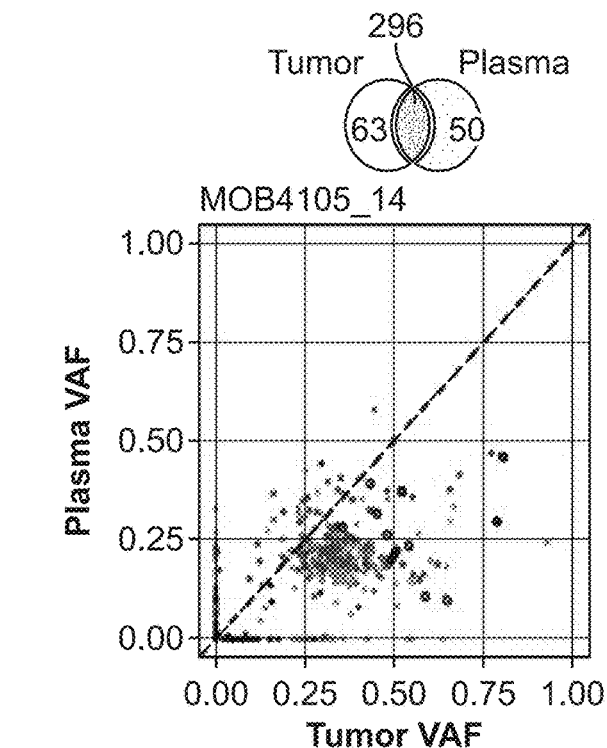
Figure 80A:
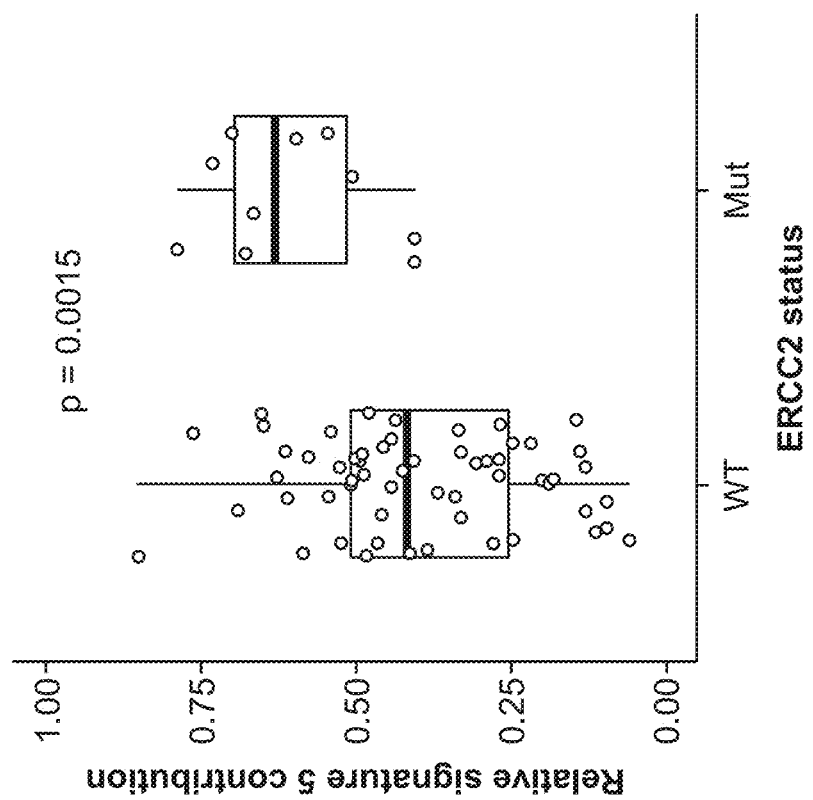
FIG. 80A-B: Graphs depicting genomic heterogeneity between primary tumor and metastatic relapse for the muscle invasive bladder cancer study in Example 9. Whole exome sequencing (WES) data of the primary tumors was compared to ctDNA. WES data from plasma samples with high ctDNA variant allele frequency (VAF) detected at metastatic relapse. Genomic positions with mutations identified in either plasma or tumor exome data were investigated for base counts. Resulting allele frequencies identified in plasma and tumor exome data are shown. Individual mutations are color coded according to statistical probability (strength) of the mutation call. Venn diagrams represent the number of mutations identified exclusively in the tumor, plasma or in both.
Figure 80B:
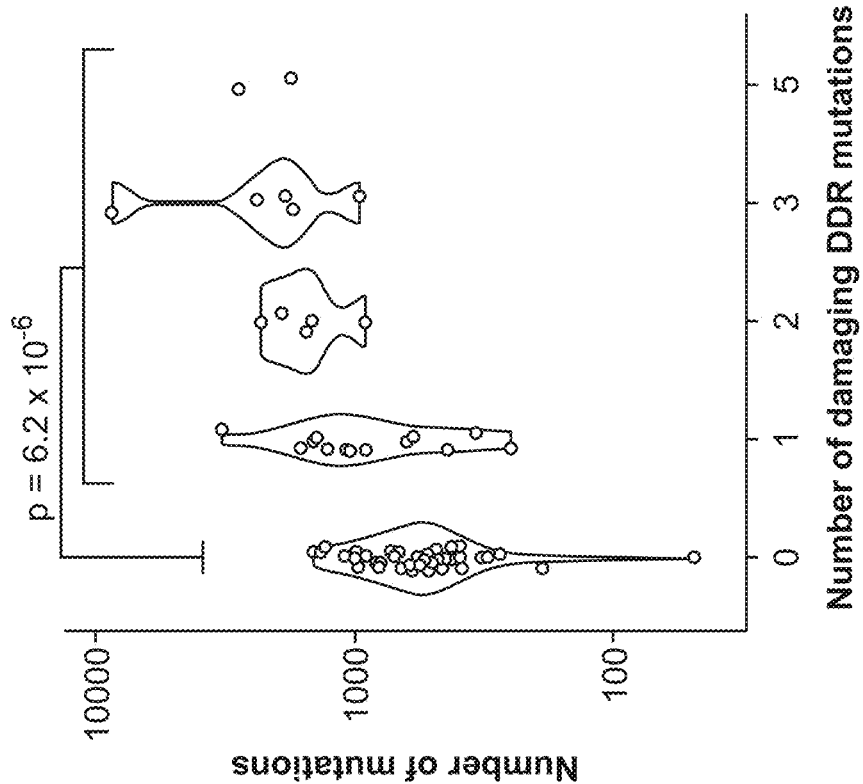
Figures 82A, 82B:
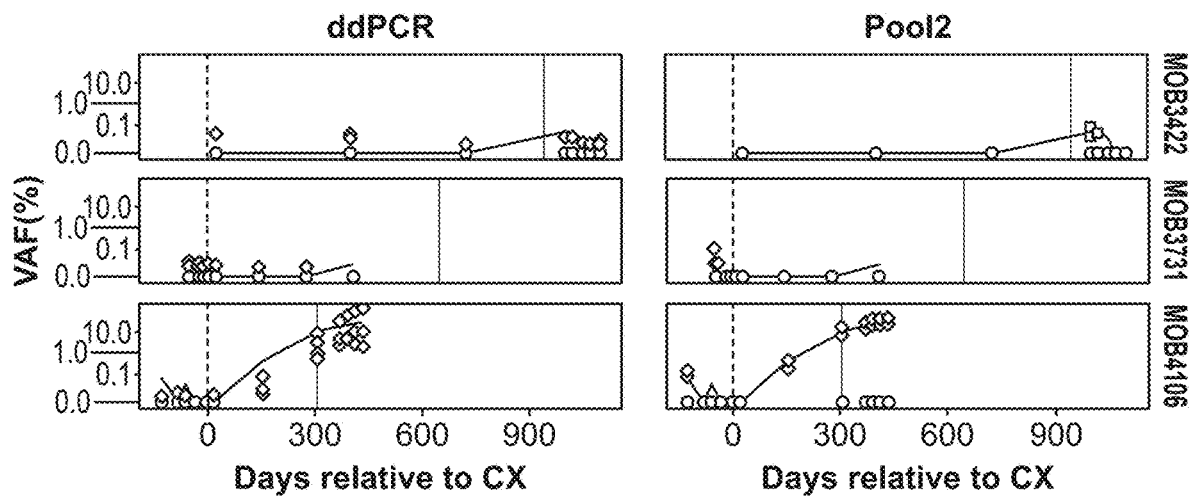
FIG. 82A-D: Graphs showing ctDNA level in plasma from 10 patients previously analyzed by ddPCR compared to ultra-deep sequencing for the muscle invasive bladder cancer study in Example 9.
Figures 82C, 82D:
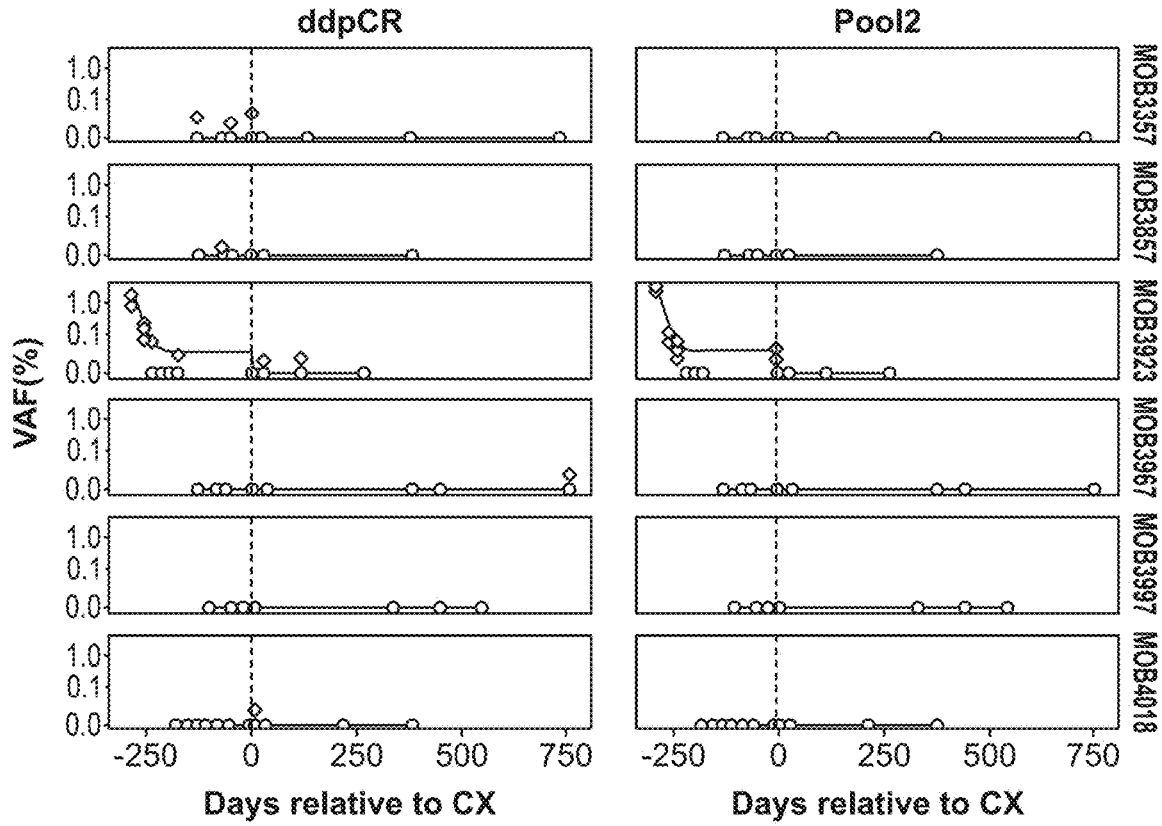
Figure 83C:
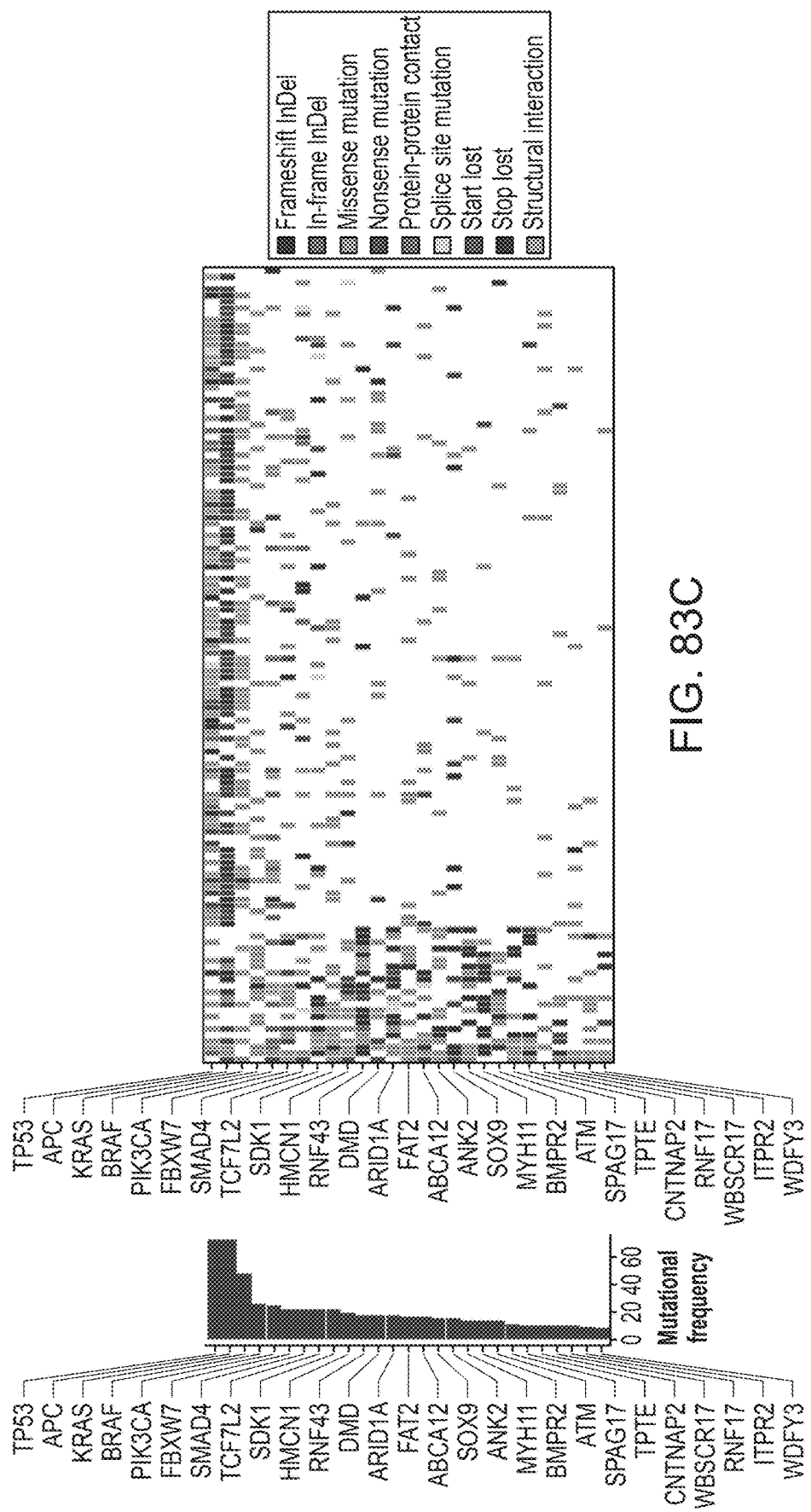
Figure 83D:
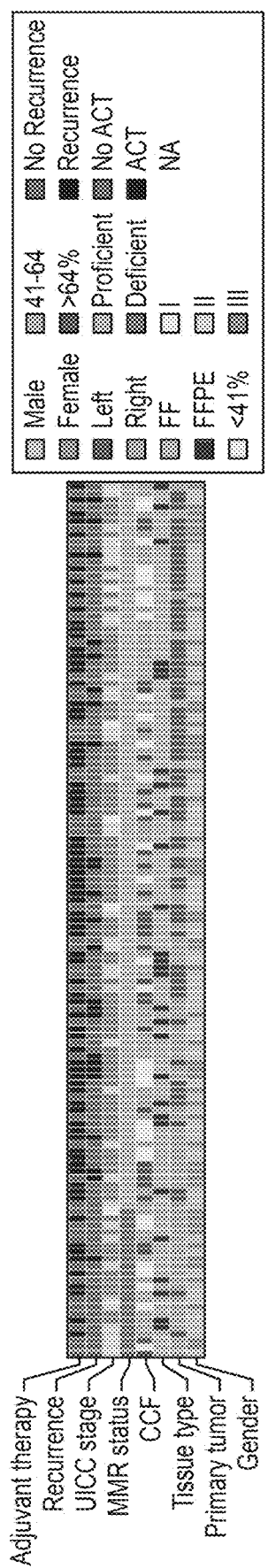
Figure 83E:
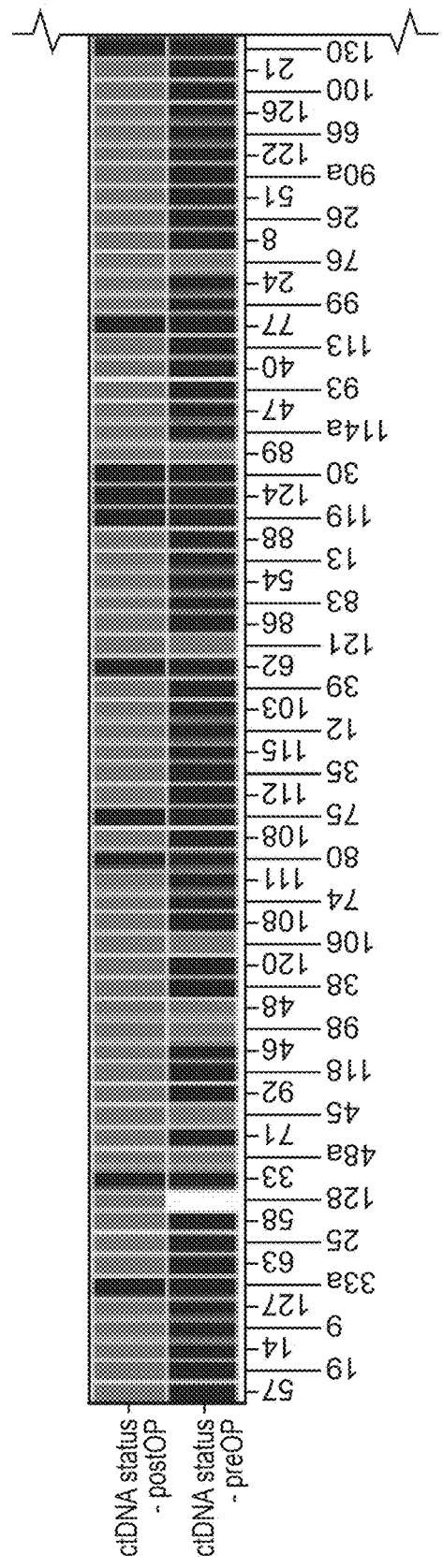
Figure 83E:
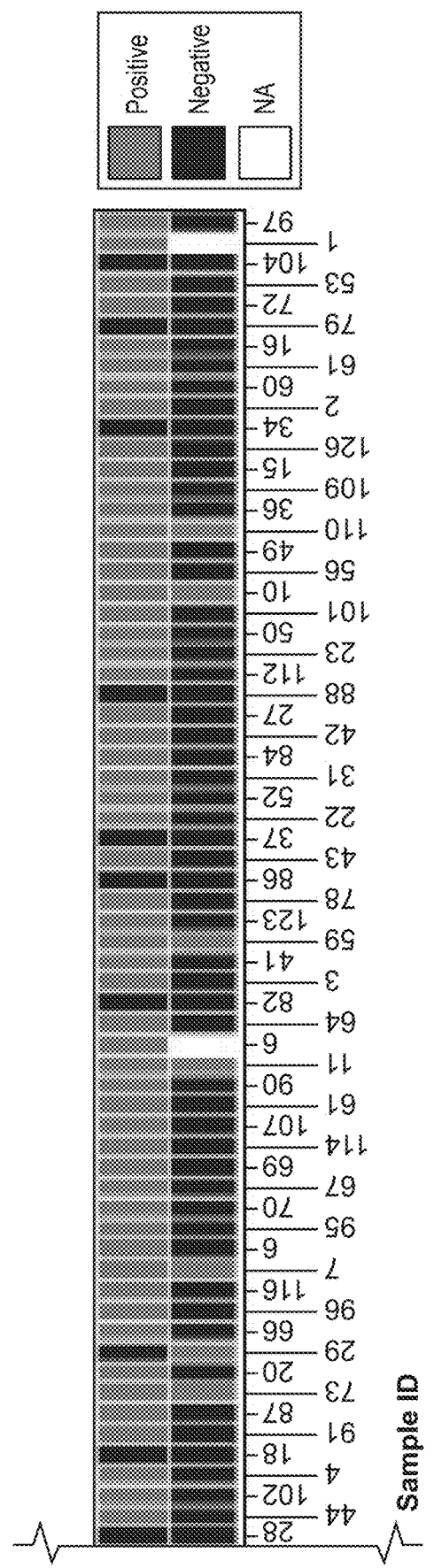
Figure 84:
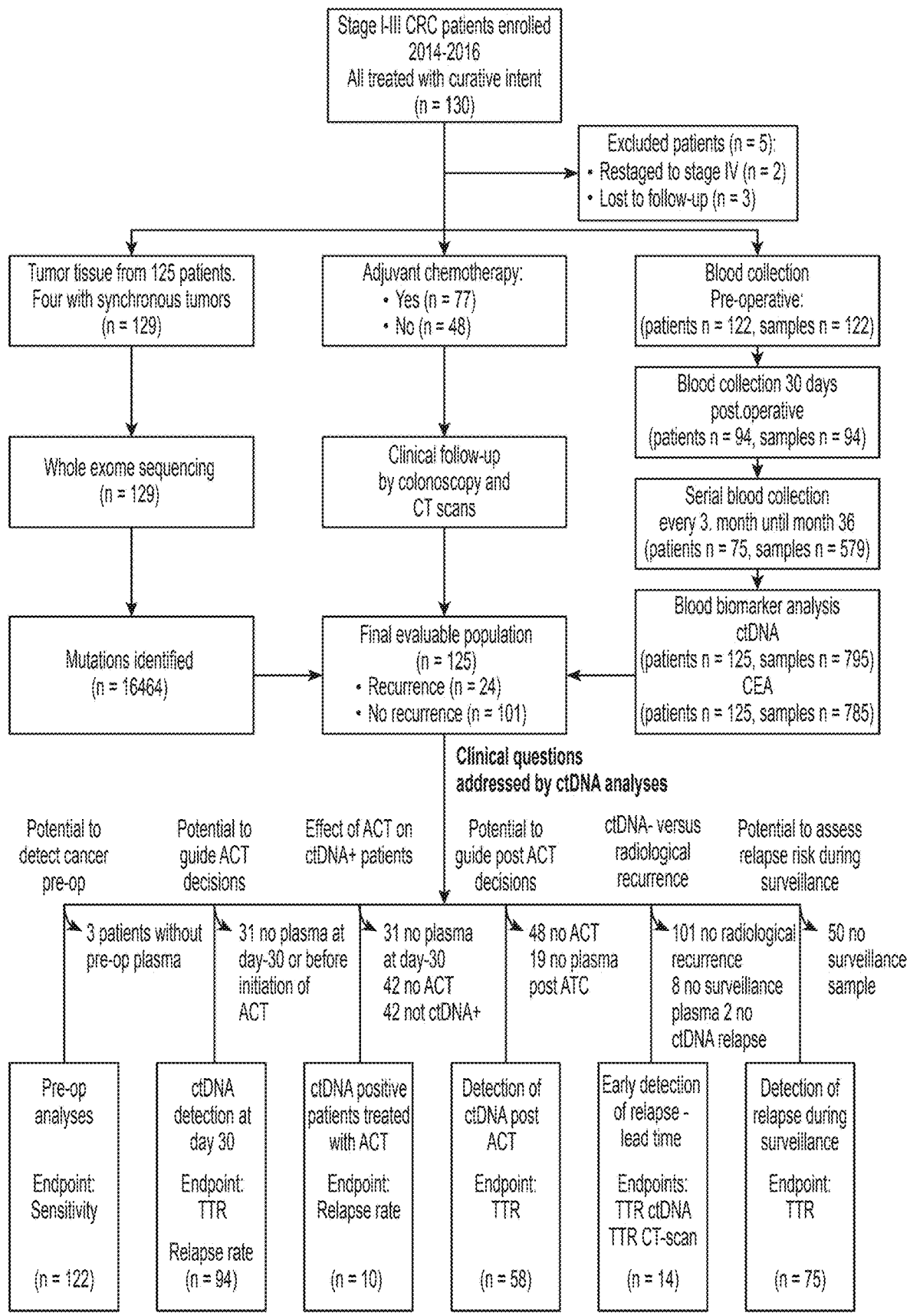
FIG. 84: Diagram showing patient enrollment, sample collection, and definitions of the patient subgroups used to address the defined clinical questions. Abbreviations: ctDNA, circulating tumor DNA; CT-scan, computed tomography scan; post-op, postoperative; TTR, time to recurrence.
Figure 85A:
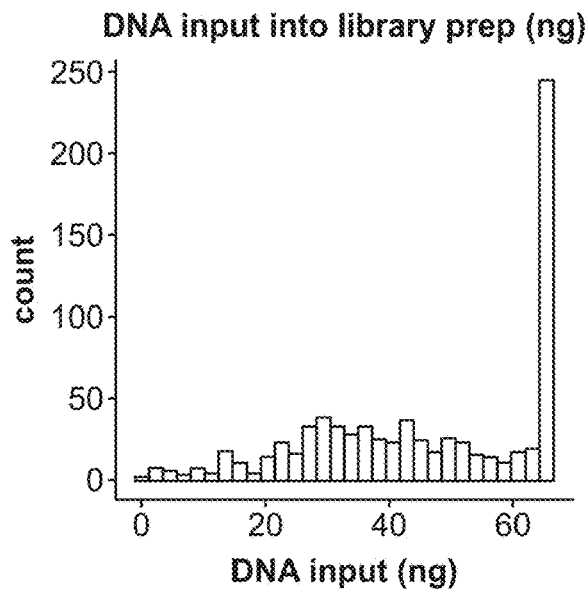
FIG. 85A-C: Graphs showing quality control (QC) tests of workflow for whole exome sequencing of the patient samples. 793 (99%) out of 795 plasma samples passed the sample QC process. 194 samples (from 70 patients) run with SNP tracer to check the concordance between the plasma sample and its corresponding tissue biopsy. All 194 plasma samples passed the concordance QC.
Figure 85B:
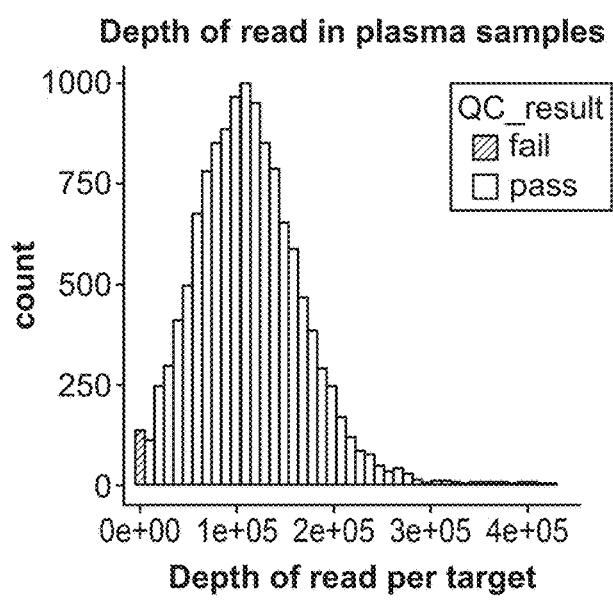
Figure 85C:
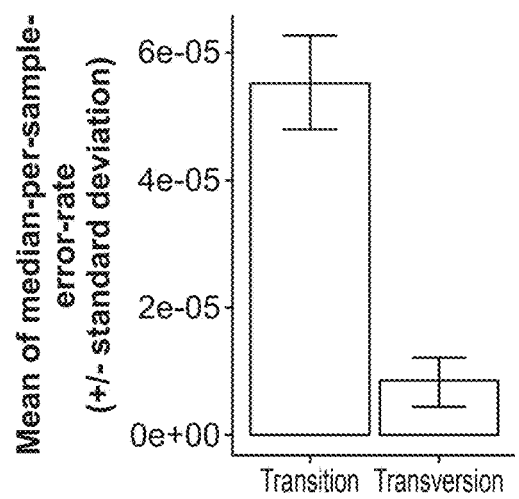
Figure 86A:
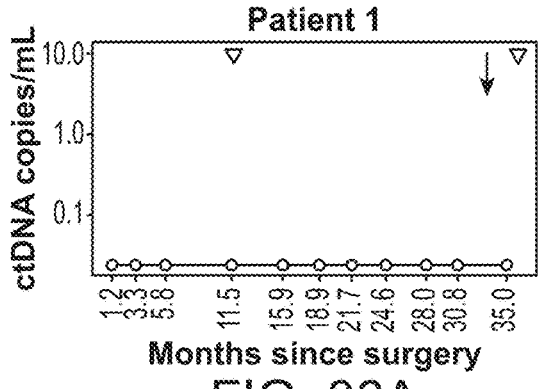
FIG. 86A-U4 shows circulating tumor DNA (ctDNA) results and dynamics for each individual patient.
Figure 86B:
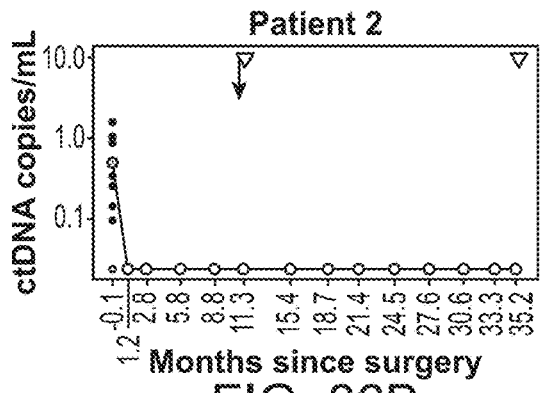
Figure 86C:
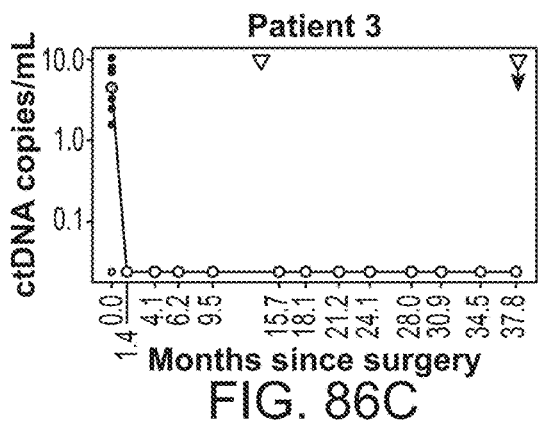
Figure 86D:
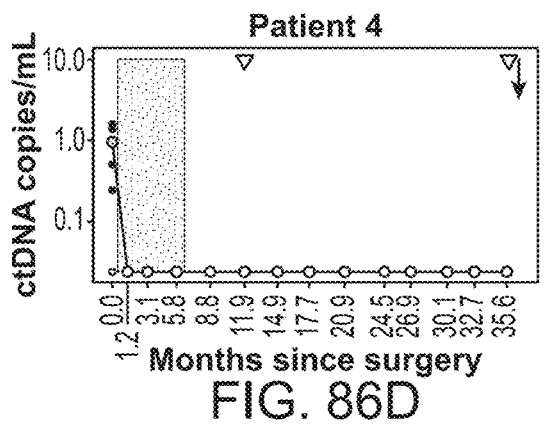
Figure 86E:
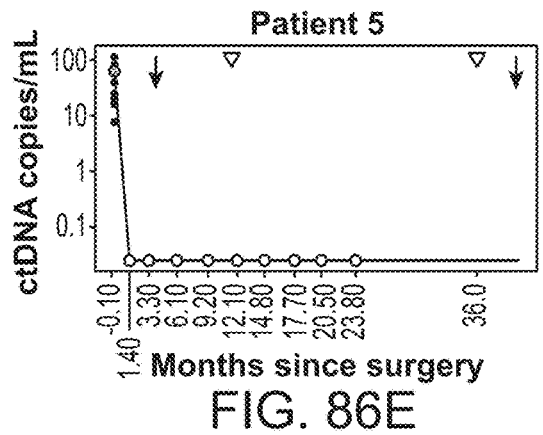
Figure 86F:
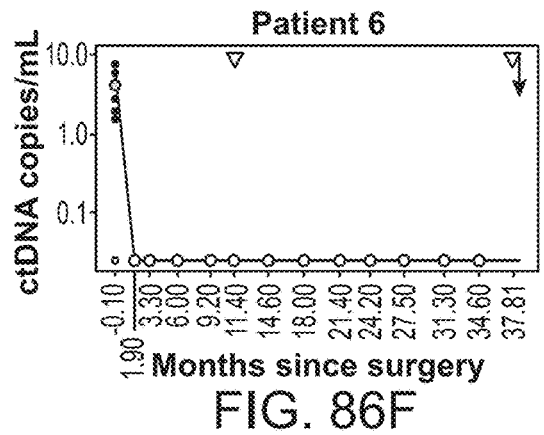
Figure 86G:
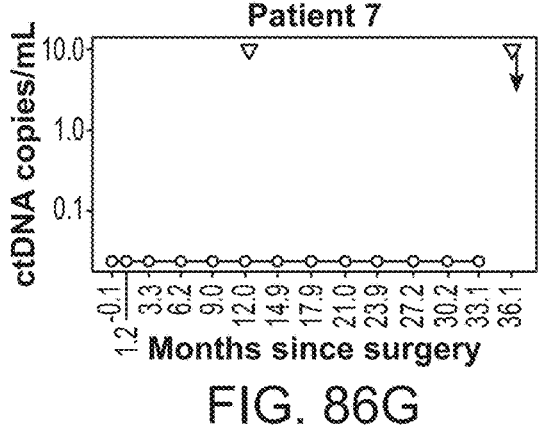
Figure 86H:
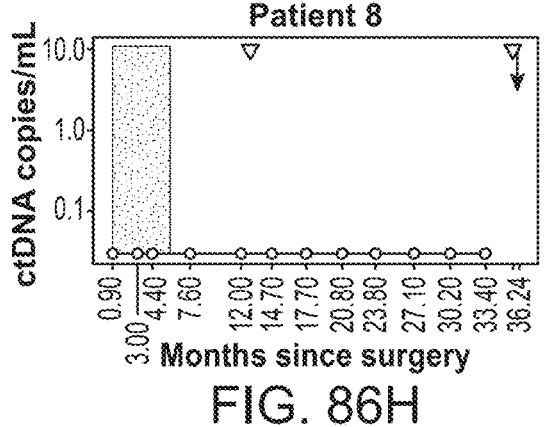
Figure 86I:
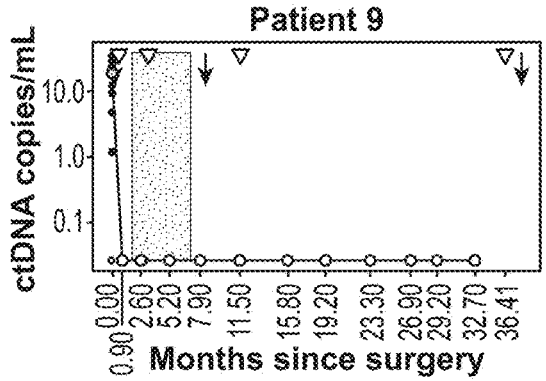
Figure 86J:
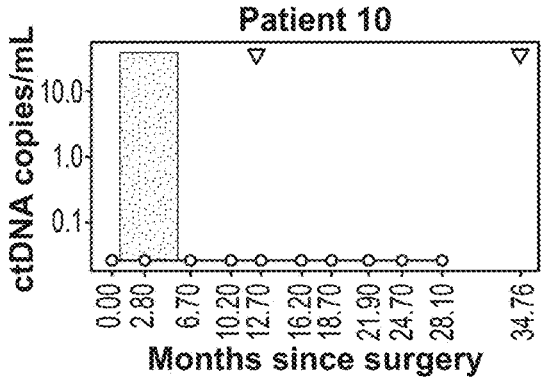
Figure 86K:
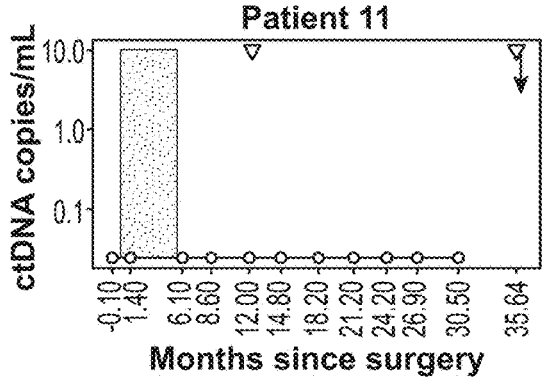
Figure 86L:
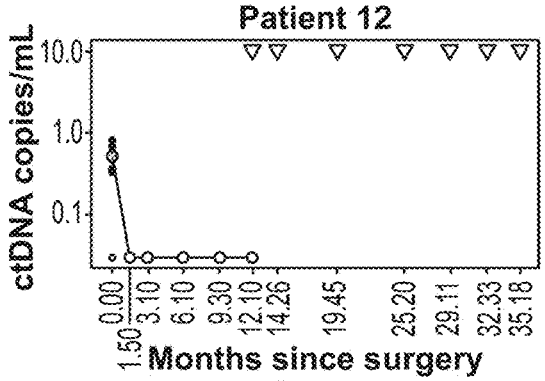
Figure 86M:
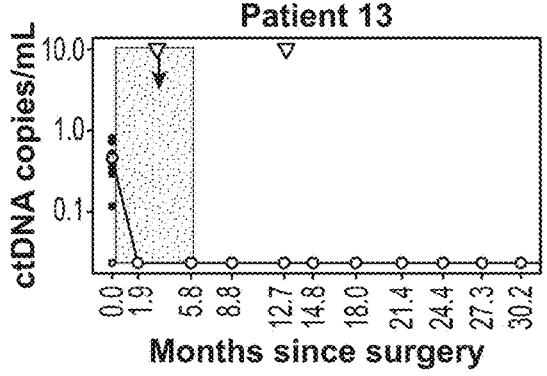
Figure 86N:
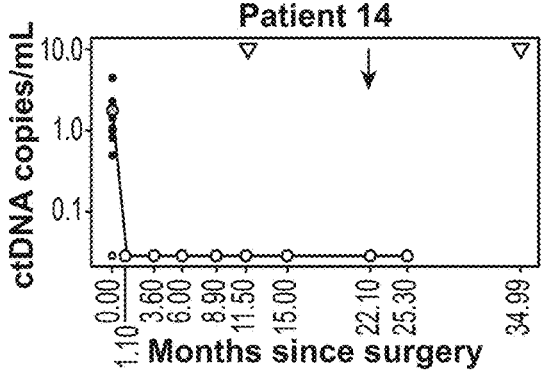
Figure 86O:
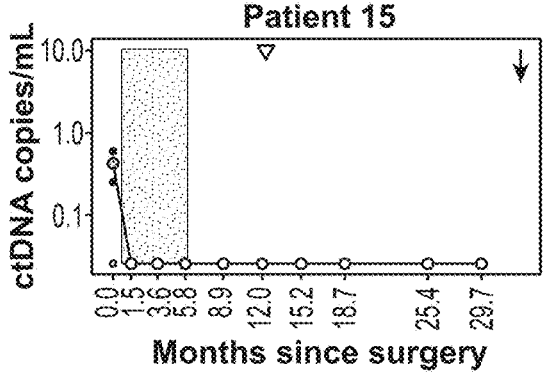
Figure 86P:
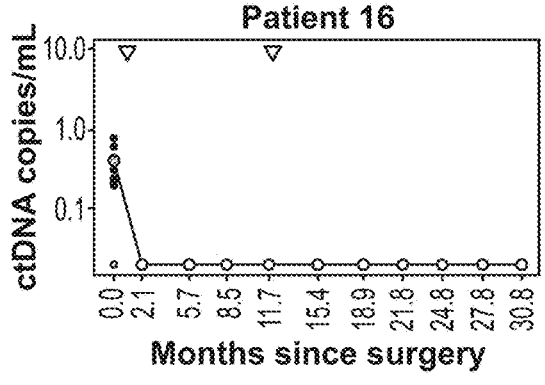
Figure 86Q:
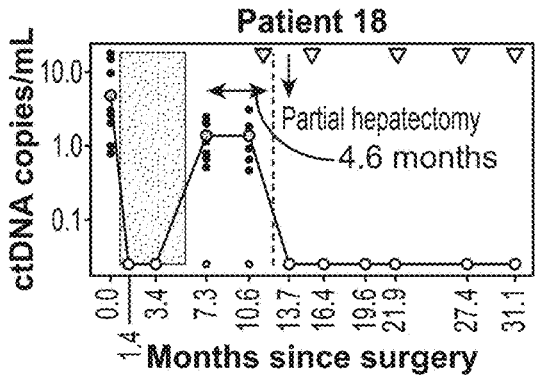
Figure 86R:
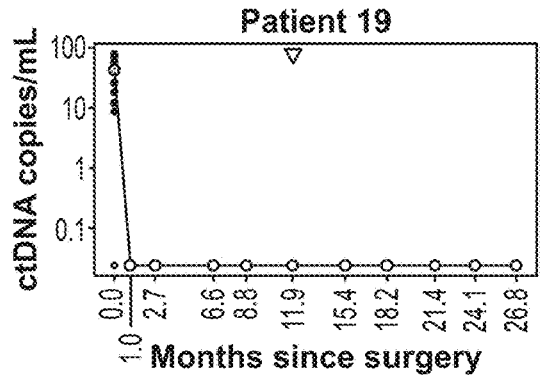
Figure 86S:
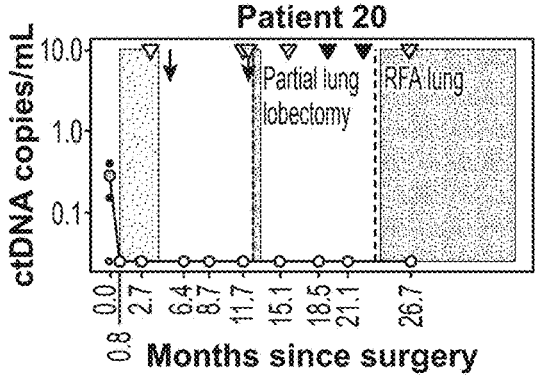
Figure 86T:
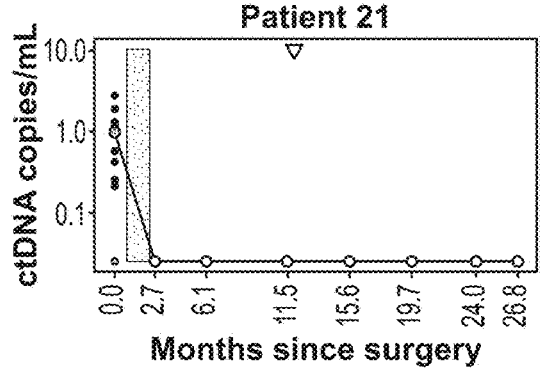
Figure 86U:
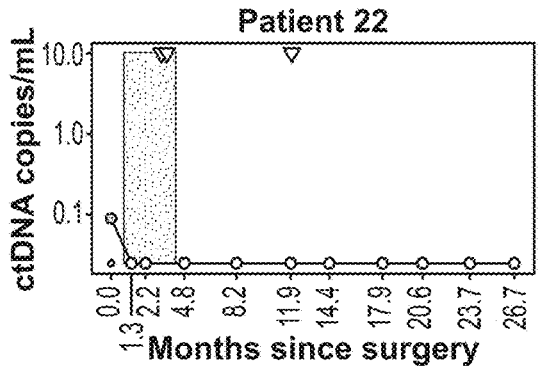
Figure 86V:
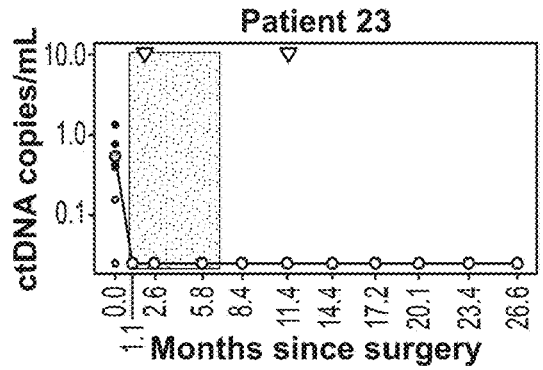
Figure 86W:
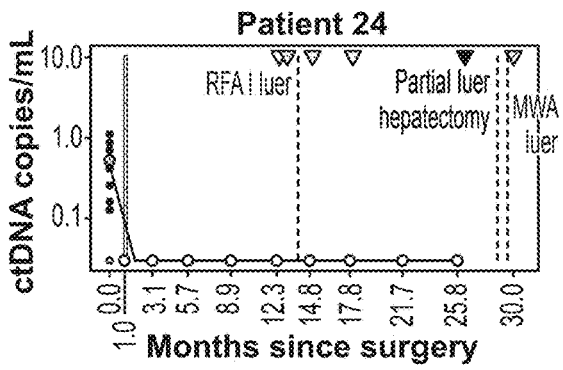
Figure 86X:
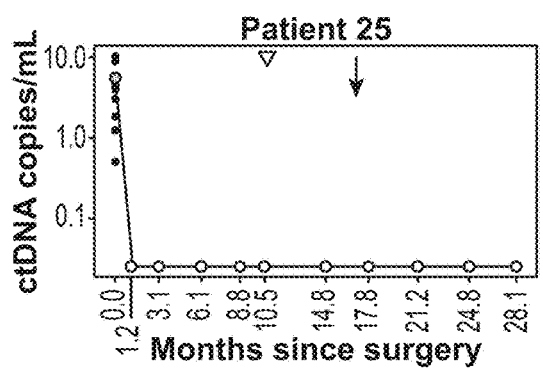

Analysis of molecular features in treatment naïve tumors showed significantly higher contribution of mutational signature 5 (p=0.01) in patients responding to chemotherapy (FIG. 78B). A high contribution of signature 5 was significantly associated with ERCC2 mutation status (FIG. 80A-B), indicating a correlation to DNA damage response (DDR) mechanisms, as previously reported 22. ERCC2 mutations in responders were, however, not significantly more prevalent (FIG. 78C). Overall, DDR mutation status was not a predictive biomarker for chemotherapy response (FIG. 78D). By stratifying tumors by molecular subtype (FIG. 78E), we found a significant correlation to survival (FIG. 78F), but the subtypes were not predictive of response to NAC (FIG. 78G). Tumors classified as "infiltrated" showed a higher rate of response to chemotherapy compared to other subtypes (FIG. 78G). This is in contrast to earlier reports highlighting basal like tumors to be most associated NAC treatment response.

Whole Exome Sequencing of Plasma ctDNA from Patients with Metastatic Disease

We performed whole exome sequencing (WES) of cfDNA from plasma samples with ctDNA targets measured at 10% allele frequency or above in the multiplex PCR NGS assays. Four samples from three patients were sequenced to a mean target coverage of 307× (272×-340×) and 508-1294 mutations were identified. We compared all mutations identified in the plasma WES data to the associated WES data from the primary tumor to assess mutational changes acquired during metastatic evolution (FIG. 79A-D). We found high similarities between the mutational landscapes of the primary tumors and the metastatic lesions, indicating a limited clonal evolution during the disease course of the selected patients. On average, we identified 62 mutations in ctDNA present at the time of metastases, which had not been detected in the primary tumors. Interestingly, we identified two CYP2C19 mutations in the plasma of patient 4119 both affecting codon 214. The resulting amino acid is situated in a canal involved in leading compounds to the active site of the protein. These mutations may have occurred during chemotherapy and may explain the lack of pathological downstaging observed in this patient.

Discussion

This report described a reliable and reproducible method for early detection and improved treatment of metastatic disease based on ctDNA detection and monitoring during prior to, during, and after treatment. In patients treated with curative-intent surgery, the detection of ctDNA serves as direct evidence of occult cancer cells and thus remnant disease.

Interestingly, it was discovered herein that detection of ctDNA often preceded detection of metastatic disease by imaging techniques. In particular, we discovered that all patients, who eventually presented with metastatic bladder cancer, were ctDNA positive after cystectomy, with an average lead-time of 103 days compared to imaging. The method of analysing provided herein ctDNA, therefore, offers a unique opportunity for initiation of treatment of metastatic relapse at an earlier time point. Importantly, initiating treatment against smaller volumes of metastatic disease might increase response rates and positively impact survival.

This study also described a reliable and reproducible method of identifying patients with low risk of metastatic relapse. It was found herein that all patients that remained disease-free were ctDNA negative after cystectomy (100% specificity). The 100% specificity of the test after cystectomy could be used to identify patients at low risk of metastatic relapse, and consequently reduce the need for continued surveillance with expensive radiographic imaging and associated patient anxiety. Accordingly, the present disclosure provide a superior association between ctDNA status and outcome compared to conventional methods, thereby moving ctDNA analyses closer to being clinically impactful.

It was also a discovery of the present disclosure that the dynamics of ctDNA can aid in identification of patients responding to NAC already during treatment. Patients with MIBC received NAC to decrease primary tumor burden and potentially eradicate micrometastasis prior to cystectomy, and a majority of patients experienced pathological downstaging after NAC. Lack of pathological downstaging, i.e. residual primary tumor or lymph node infiltration at the time of cystectomy, or prior lymph node infiltration are risk factors associated with disease recurrence after cystectomy. In our study, ctDNA was detected in 37% (25/68) of patients before or during NAC, and 53% of patients with a decline in ctDNA below our detection threshold showed pathological downstaging. Importantly, none of the patients with continually detectable ctDNA exhibited pathological downstaging. However, we observed a subset of patients with pathological downstaging that had disease recurrence and vice versa. These findings indicate that although clinical and histopathological parameters serve as prognostic risk factors, pathology-based risk stratification of patients is far from ideal.

The disclosure herein also provided that ctDNA status before and during chemotherapy could be implemented as a new powerful clinical risk factor and can potentially aid in selecting patients with early metastatic dissemination who might benefit from prolonged NAC and intensified surveillance regimens. Herein, it was demonstrated that no ctDNA negative patients before or during chemotherapy experienced disease recurrence after cystectomy, while 44% (11/25) of patients who were ctDNA positive before or during chemotherapy had disease recurrence. Presence of ctDNA even at an early time point can therefore be indicative of metastatic dissemination and aid in superior risk stratification of patients compared to the currently available risk factors for this patient cohort, which to our knowledge has not been demonstrated previously at a similar level of consistency. The subset of patients with initially detectable ctDNA but no evidence of eventual disease recurrence may represent cases where chemotherapy or cystectomy effectively eradicated the disease. Consequently, Patients with no evidence of early metastatic dissemination (ctDNA negative) and pathological downstaging after NAC may be eligible to bladder sparing approaches.

Notably, for many patients the ctDNA frequencies were quite low (few mutated copies), and NGS based ultra-deep sequencing approaches are required for reliable detection of these rare variants. The selection of clonal mutations based on WES of the primary tumor makes it possible to perform ultra-deep sequencing of the patient specific mutations in plasma ctDNA. Earlier work has shown genetic heterogeneity between primary tumors and metastases, indicating that gene panels of frequently mutated genes may be needed. By applying WES of cfDNA from plasma, we still observed heterogeneity between primary tumors and metastases, but importantly, all clonal mutations selected from the primary tumors were detected in the metastases.

In conclusion, the disclosure herein showed that detecting ctDNA levels in patients with bladder cancer was highly predictive of metastatic relapse and treatment response. In particular, the inventors of the present disclosure have herein provided accurate and reliable methods for monitoring the cancer patient's treatment response to reassure the patient that the disease is under control, and to detect relapse significantly earlier than conventional methods which may improve survival outcomes.

Example 10. Longitudinal Analysis of Plasma Cell-Free DNA by Ultra-Deep Sequencing in Stage I-III Colorectal Cancer Patients The purpose of this example was to show that longitudinal post-operative circulating tumor DNA (ctDNA) analysis enabled identification and monitoring of residual tumor burden in patients with no clinical evidence of disease. In particular, this example showed that ctDNA analysis enabled personalized and risk stratified post-operative management of stage I-III colorectal cancer patients.

Introduction

With 1.3 million newly diagnosed cases each year, colorectal cancer (CRC) is the third most common cancer worldwide, and the second leading cause of cancer-related deaths. Despite improved surgery, implementation of screening and advances in treatment regimens, the 5-year mortality rate for CRC patients remains high at about 40%, thereby representing a significant global health burden.

The current standard of care for patients with CRC includes surgical resection of the tumor, followed by adjuvant chemotherapy (ACT) in selected patients. The majority of stage II patients are not treated with ACT, however, ~10-15% have residual disease following surgery. If they could be identified, treatment with ACT could potentially reduce their risk of recurrence. Conversely, the majority of the stage III patients receive ACT. Despite, more than 50% already being cured by surgery. Furthermore, ~30% of the ACT-treated stage III patients experience recurrence, making them candidates for additional therapy. Thus, improved tools to identify the patient population who would benefit from ACT is greatly needed.

Early diagnosis of recurrent disease is another significant clinical unmet need in CRC. After completion of definitive treatment, recurrence surveillance is recommended in order to detect recurrence sufficiently early for potentially curative surgery. Despite surveillance, many recurrence events are detected late and only 10-20% of metachronous metastases are treated with curative intent. Therefore, there is a need for better biomarkers that can detect patients at high-risk of recurrence earlier, thereby enabling appropriate follow-up and therapeutic strategies to improve patient survival.

Methods

Patients

Patients with stage I to III CRC between 2014-2018 at the Surgical Departments of Aarhus University Hospital, Randers Hospital, and Herning Hospital were recruited. Tumor tissue was collected at surgery. Blood samples were collected prior to surgery (up to 14 days prior, pre-operative), and post-operatively at day 30 (allowing the sample to be drawn up to 14 days before or after), and then at every third month until death, patient withdrawal from the study, or month 36, whichever came first. Seventy-five patients provided serial blood samples (3 to 14 samples per patient), whereas the remaining 50 patients provided only two blood samples (pre-operative and post-operative day 30). Patient characteristics and demographics are shown in Table 12.1 below.

TABLE 12.1

Patient characteristics and demographics of eligible patients.

| | | |
|---|---|---|
| Patients, n | | 125 |
| Cancers, n | | 129* |
| Age (years), median (range) | | 69.9, (43.3-91) |
| Gender, n (%) | Female | 52 (41.6) |
| | Male | 73 (58.4) |
| Imaging follow-up (months), median (range) | | 12.5, 1.4-38.5 |
| Location, n (%) | Colon | 119 (95.2) |
| | Rectum | 6 (4.8) |
| Pathological UICC stage, n (%) | I | 5 (4) |
| | II | 39 (31.2) |
| | III | 81 (64.8) |

TABLE 12.1-continued

Patient characteristics and demographics of eligible patients.

| | | |
|---|---|---|
| Histological type, n (%) | Adenocarcinoma | 115 (92) |
| | Mucinous carcinoma | 10 (8.7) |
| Histological grade, n (%) | Moderatley differentiated | 96 (76.8) |
| | Poorly differentiated | 19 (15.2) |
| | ND | 10 (8) |
| Adjuvant therapy by UICC stage, n (%) | I | 0 (0.0) |
| | II | 6 (15.3) |
| | III | 71 (87.7) |
| | Total | 77 (61.6) |
| Relapse by UICC stage, n (%) | I | 0 (0.0) |
| | II | 4 (10.2) |
| | III | 20 (24.7) |
| | IV | 0 (0.0) |
| | Total | 24 (19.2) |
| MSS/MSI status, n (%) | MSS | 109 (87.2) |
| | MSI | 20 (16) |
| Smoking, n (%) | Never | 52 (41.6) |
| | Former | 57 (45.6) |
| | Current | 16 (12.8) |

*Four patients with synchronous cancers

Information on post-surgery clinical intervention and other clinicopathological information were collected for all patients as shown in Table 12.2 below. All patients in the study had undergone resection of the primary tumor.

TABLE 12.2

Clinicopathological information.

| Patient ID | Age | Sex | Primary tumor site | Primary tumor diameter, mm | UICC stage | TNMV | Adj. therapy |
|---|---|---|---|---|---|---|---|
| 1 | 68 | M | sigmoid | 52 | II | T3N0MxV0 | No |
| 2 | 70 | M | sigmoid | 54 | II | T3N0MxV0 | No |
| 3 | 67 | F | sigmoid | 32 | II | T3N0MxV0 | No |
| 4 | 64 | M | right flexure | 35 | III | T3N1MxV0 | Yes |
| 5 | 77 | M | sigmoid | 70 | II | T3N0MxV0 | No |
| 6 | 75 | M | cecum | 65 | II | T3N0MxV0 | No |
| 7 | 70 | M | ascending | 29 | II | T3N0M0V0 | No |
| 8 | 65 | F | sigmoid | 42 | III | T3N1M0V0 | Yes |
| 9 | 50 | M | sigmoid | 100 | II | T3N0M0V0 | Yes |
| 10 | 50 | F | sigmoid | 15 | III | T3N1M0V0 | Yes |
| 11 | 70 | M | right flexure | 40 | III | T3N2M0V1 | Yes |
| 12 | 67 | F | transversum | 50 | II | T3N0M0V0 | No |
| 13 | 66 | F | sigmoid | 40 | II | T4N0MxV0 | Yes |
| 14 | 68 | F | cecum | 63 | II | T3N0MxV0 | No |
| 15 | 48 | M | sigmoid | 42 | III | T3N2MxV0 | Yes |
| 16 | 68 | F | sigmoid | 50 | II | T3N0MxV0 | No |
| 18 | 67 | M | cecum | 45 | III | T2N2MxV0 | Yes |
| 19 | 69 | F | cecum | 58 | II | T3N0M0V0 | No |
| 20 | 73 | F | rectal middle, 5-10 cm | 55 | III | T3N1M0V2 | Yes |
| 21 | 68 | M | sigmoid | 55 | III | T3N1M0V0 | Yes |
| 22 | 67 | F | rectal high, 10-15 cm | 60 | III | T3N1M0V1 | Yes |
| 23 | 69 | M | rectal high, 10-15 cm | 53 | III | T4N1M0V1 | Yes |
| 24 | 82 | M | right flexure | 77 | III | T3N1M0V1 | Yes |
| 25 | 72 | F | right flexure | 95 | II | T3N0M0V0 | No |
| 26 | 66 | M | sigmoid | 82 | III | T4N1M0V0 | Yes |
| 27 | 68 | M | rectal high, 10-15 cm | 37 | III | T3N1M0V0 | Yes |
| 28 | 46 | F | sigmoid | 66 | III | T4N2M0V1 | Yes |
| 29 | 65 | F | rectal high, 10-15 cm | 37 | III | T3N1M0V1 | Yes |
| 30 | 52 | F | sigmoid | 47 | III | T3N2M0V2 | Yes |
| 31 | 54 | M | sigmoid | 25 | III | T3N1M0V0 | Yes |
| 33 | 47 | M | transversum (1) & ascending (2) | 170 (1) & 40 (2) | III | T3N1M0V1 (1) & T3N1M0V1 (2) | Yes |
| 34 | 69 | M | left flexure | 37 | II | T3N0M0V1 | Yes |
| 35 | 68 | M | ascending | 38 | III | T3N1M0V0 | Yes |
| 36 | 70 | M | sigmoid | 47 | III | T4N2M0V1 | Yes |
| 37 | 75 | M | sigmoid | 46 | II | T3N0M0V0 | No |
| 38 | 49 | F | ascending | 41 | II | T3N0M0V0 | No |
| 39 | 74 | M | cecum | 115 | III | T4N2M0V1 | Yes |
| 40 | 69 | M | cecum | 85 | III | T3N2M0V1 | Yes |
| 41 | 70 | M | sigmoid | 67 | II | T3N0M0V0 | No |
| 42 | 60 | M | left flexure | 73 | III | T4N2MxV1 | Yes |
| 43 | 48 | M | rectal high, 10-15 cm | 51 | II | T3N0MxV0 | No |
| 44 | 76 | F | sigmoid | 70 | II | T4N0M0V0 | Yes |
| 45 | 83 | F | transversum | 40 | II | T3N0MxV0 | No |

TABLE 12.2-continued

Clinicopathological information.

| Patient ID | Age | Sex | Primary tumor site | Primary tumor diameter, mm | UICC stage | TNMV | Adj. therapy |
|---|---|---|---|---|---|---|---|
| 46 | 72 | F | ascending | 70 | III | T4N2MxV1 | Yes |
| 47 | 73 | F | cecum | 7 | II | T3N0MxV0 | No |
| 48 | 91 | F | ascending (1) & transversum (2) | 55 (1) & 13 (2) | III | T3N1M0V1 (1) & TxN1M0Vx (2) | No |
| 49 | 80 | F | ascending | 20 | III | T4N1M0V0 | Yes |
| 50 | 64 | M | sigmoid | 83 | II | T4N0M0V2 | Yes |
| 51 | 60 | M | sigmoid | 70 | II | T3N0M0V0 | No |
| 52 | 81 | M | sigmoid | 30 | II | T3N0M0V0 | No |
| 53 | 80 | F | left flexure | 32 | III | T3N1M0V0 | No |
| 54 | 66 | M | sigmoid | 40 | III | T3N1M0V0 | No |
| 55 | 78 | M | sigmoid | 40 | II | T3N0M0V0 | No |
| 57 | 50 | M | ascending | 45 | II | T3N0M0V0 | No |
| 58 | 77 | M | ascending | 52 | II | T4N0M0V0 | No |
| 59 | 51 | F | sigmoid | 20 | I | T2N0M0V0 | No |
| 60 | 70 | F | sigmoid | 32 | II | T3N0M0V0 | No |
| 61 | 67 | M | sigmoid | 24 | II | T3N0M0V0 | No |
| 62 | 55 | M | descending | 30 | III | T4N1M0V1 | Yes |
| 63 | 82 | M | right flexure | 40 | III | T3N1MxV0 | No |
| 64 | 71 | F | sigmoid | 75 | III | T3N1MxV1 | Yes |
| 65 | 72 | M | right flexure | 55 | III | T4N1MxV1 | Yes |
| 66 | 72 | M | cecum | 90 | III | T3N2MxV0 | Yes |
| 67 | 71 | M | sigmoid | 35 | III | T4N1MxV0 | Yes |
| 68 | 83 | F | sigmoid | 75 | III | T3N2MxV1 | No |
| 69 | 56 | F | sigmoid | 25 | III | T3N1MxV1 | Yes |
| 70 | 66 | M | sigmoid | 20 | III | T3N2MxV0 | Yes |
| 71 | 77 | M | cecum | 90 | III | T3N1MxV0 | Yes |
| 72 | 49 | F | cecum | 41 | III | T3N1MxV0 | Yes |
| 73 | 43 | F | ascending | 64 | III | T4N2MxV1 | Yes |
| 74 | 72 | M | descending | 18 | III | T3N2MxV0 | Yes |
| 75 | 48 | F | ascending | 74 | III | T3N1MxV0 | Yes |
| 76 | 75 | M | sigmoid | 73 | III | T3N2MxV0 | Yes |
| 77 | 71 | F | cecum | 52 | III | T3N1MxV1 | Yes |
| 78 | 64 | F | descending | 50 | III | T4N2MxV0 | Yes |
| 79 | 50 | F | left flexure | 40 | III | T3N1MxV0 | Yes |
| 80 | 73 | F | cecum | 82 | III | T4N1MxV0 | Yes |
| 81 | 58 | F | sigmoid | 23 | III | T3N2MxV0 | Yes |
| 82 | 50 | F | sigmoid | 30 | III | T3N2M0V1 | Yes |
| 83 | 62 | F | sigmoid | 70 | III | T3N2MxV0 | Yes |
| 84 | 65 | F | descending | 100 | III | T3N1MxV2 | Yes |
| 85 | 61 | F | transversum | 35 | III | T3N2MxV0 | Yes |
| 86 | 79 | M | cecum | 90 | III | T3N2MxV1 | Yes |
| 87 | 70 | M | sigmoid | 145 | III | T3N1MxV2 | Yes |
| 88 | 64 | M | sigmoid | 60 | III | T3N2MxV1 | Yes |
| 89 | 75 | M | ascending | 40 | III | T3N2MxV0 | No |
| 90 | 87 | F | left flexure (1) & left flexure (2) | 62 (1) & NA (2) | III | T3N1MxV0 (1) & T3N1M0V0 (2) | No |
| 91 | 69 | M | sigmoid | 70 | III | T3N1MxV0 | Yes |
| 92 | 73 | F | cecum | 100 | III | T4N2MxV0 | Yes |
| 93 | 81 | M | ascending | 80 | III | T4N2MxV1 | Yes |
| 95 | 70 | M | sigmoid | 30 | I | T2N0MxV0 | No |
| 96 | 64 | M | left flexure | 40 | III | T4N2M0V1 | Yes |
| 97 | 67 | F | transversum | 60 | II | T4N0MxV0 | Yes |
| 98 | 78 | M | transversum | 30 | II | T3N0MxV0 | No |
| 99 | 79 | M | ascending | 40 | III | T4N2MxV0 | No |
| 100 | 59 | F | cecum | 100 | II | T4N0MxV1 | No |
| 101 | 72 | M | sigmoid | 40 | II | T3N0MxV2 | No |
| 102 | 69 | M | sigmoid | 35 | I | T2N0MxV0 | No |
| 103 | 70 | M | cecum | 100 | III | T3N1MxV1 | Yes |
| 104 | 50 | M | sigmoid | 30 | III | T3N1MxV2 | Yes |
| 105 | 72 | M | right flexure | 70 | II | T3N0MxV1 | No |
| 106 | 70 | F | ascending | 25 | I | T2N0MxV0 | No |
| 107 | 75 | M | descending | 30 | III | T3N2MxV0 | Yes |
| 108 | 72 | F | cecum | 61 | II | T3N0MxV0 | No |
| 109 | 74 | M | sigmoid | 50 | II | T3N0MxV0 | No |
| 110 | 67 | M | sigmoid | 35 | I | T2N0MxV0 | No |
| 111 | 52 | M | descending | 45 | III | T3N2M0V1 | Yes |
| 112 | 61 | M | cecum | 40 | III | T3N1MxV1 | Yes |
| 113 | 78 | M | sigmoid | 70 | III | T3N1MxV1 | No |
| 114 | 79 | M | cecum (1) & ascending (2) | 60 (1) & 35 (2) | III | T3N1MxV0 (1) & T3N1MxV0 (2) | Yes |

TABLE 12.2-continued

Clinicopathological information.

| Patient ID | Age | Sex | Primary tumor site | Primary tumor diameter, mm | UICC stage | TNMV | Adj. therapy |
| --- | --- | --- | --- | --- | --- | --- | --- |
| 115 | 78 | M | cecum | 35 | III | T3N2M0Vx | Yes |
| 116 | 75 | F | sigmoid | 70 | III | T4N1MxV0 | Yes |
| 117 | 84 | F | cecum | 56 | III | T3N1MxV0 | Yes |
| 118 | 69 | M | transversum | 80 | III | T4N2MxV0 | Yes |
| 119 | 69 | F | right flexure | 60 | III | T4N1MxV1 | Yes |
| 120 | 61 | F | transversum | 50 | III | T3N2MxV1 | Yes |
| 121 | 81 | F | cecum | 20 | III | T3N1MxV0 | No |
| 122 | 76 | M | ascending | 50 | III | T3N1MxV1 | Yes |
| 123 | 59 | M | left flexure | 50 | III | T4N1MxV0 | Yes |
| 124 | 71 | F | cecum | 47 | III | T3N2MxV2 | Yes |
| 125 | 78 | F | cecum | 40 | II | T4N0MxV0 | No |
| 126 | 71 | M | sigmoid | 60 | II | T3N0MxV0 | No |
| 127 | 67 | M | ascending | 30 | II | T3N0MxV0 | Nc |
| 128 | 51 | M | descending | 8 | III | T4N1M0V0 | Yes |
| 130 | 66 | M | ascending | 60 | III | T4N2M0V0 | Yes |

TABLE 12.3

Clinicopathological information continued.

| Patient ID | First relapse after OP. month | Relapse site | Relapse treatment | MSS/MSI | Perineural invasion | Perforation of tumor |
| --- | --- | --- | --- | --- | --- | --- |
| 1 | 0 | | | MSS | No | No |
| 2 | 0 | | | MSS | Yes | No |
| 3 | 0 | | | MSS | No | No |
| 4 | 0 | | | MSS | No | No |
| 5 | 0 | | | MSS | No | No |
| 6 | 0 | | | MSS | No | No |
| 7 | 0 | | | MSS | No | No |
| 8 | 0 | | | MSS | No | No |
| 9 | 0 | | | MSS | No | No |
| 10 | 0 | | | MSS | No | No |
| 11 | 0 | | | MSS | Yes | No |
| 12 | 0 | | | MSS | No | No |
| 13 | 0 | | | MSS | Yes | No |
| 14 | 0 | | | MSI | Yes | No |
| 15 | 0 | | | MSS | Yes | No |
| 16 | 0 | | | MSS | Yes | No |
| 18 | 12 | Liver | Partial hepatectomy | MSS | Yes | No |
| 19 | 0 | | | MSI | Yes | No |
| 20 | 12 | Lung | Partial lung lobectomy | MSS | Yes | No |
| 21 | 0 | | | MSS | Yes | No |
| 22 | 0 | | | MSS | Yes | No |
| 23 | 0 | | | MSS | Yes | No |
| 24 | 13 | Liver | RFA liver | MSS | Yes | No |
| 25 | 0 | | | MSI | Yes | No |
| 26 | 0 | | | MSS | Yes | No |
| 27 | 0 | | | MSS | Yes | No |
| 28 | 31 | Multiple | 5FU & Oxaliplatin & folinic acid | MSS | Yes | No |
| 29 | 12 | Lung | 5FU & Irinotecan & folinic acid | MSS | Yes | No |
| 30 | 9 | Bone | 5FU & Oxaliplatin & folinic acid | MSS | Yes | No |
| 31 | 0 | | | MSS | Yes | No |
| 33 | 0 | | | MSI | NA | No |
| 34 | 31 | Liver | Palliative | MSS | Yes | No |
| 35 | 0 | | | MSS | Yes | No |
| 36 | 0 | | | MSS | Yes | Yes |
| 37 | 6 | Liver | RFA liver | MSS | Yes | No |
| 38 | 0 | | | MSI | Yes | No |
| 39 | 0 | | | MSS | Yes | No |

TABLE 12.3-continued

Clinicopathological information continued.

| Patient ID | First relapse after OP. month | Relapse site | Relapse treatment | MSS/MSI | Perineural invasion | Perforation of tumor |
|---|---|---|---|---|---|---|
| 40 | 0 | | | MSS | Yes | No |
| 41 | 0 | | | MSS | Yes | No |
| 42 | 14 | Carsinosis | 5FU & Irinotecan & folinic acid | MSS | Yes | No |
| 43 | 0 | | | MSS | No | No |
| 44 | 0 | | | MSS | No | No |
| 45 | 0 | | | MSI | No | No |
| 46 | 0 | | | MSI | No | No |
| 47 | 0 | | | MSS | No | No |
| 48 | 0 | | | MSI | | No |
| 49 | 0 | | | MSS | Yes | Yes |
| 50 | 0 | | | MSS | Yes | No |
| 51 | 0 | | | MSS | Yes | No |
| 52 | 0 | | | MSS | No | No |
| 53 | 0 | | | MSS | Yes | No |
| 54 | 0 | | | MSS | Yes | No |
| 55 | 0 | | | MSS | Yes | No |
| 57 | 0 | | | MSS | Yes | No |
| 58 | 0 | | | MSI | Yes | No |
| 59 | 0 | | | MSS | No | No |
| 60 | 0 | | | MSS | Yes | No |
| 61 | 0 | | | MSS | Yes | No |
| 62 | 0 | | | MSS | No | No |
| 63 | 0 | | | MSI | No | No |
| 64 | 0 | | | MSS | No | No |
| 65 | 0 | | | MSS | Yes | No |
| 66 | 0 | | | MSS | No | No |
| 67 | 0 | | | MSS | No | No |
| 68 | 13 | Carcinosis | 5-FU | MSS | No | No |
| 69 | 0 | | | MSS | No | No |
| 70 | 0 | | | MSS | No | No |
| 71 | 0 | | | MSI | No | No |
| 72 | 0 | | | MSS | No | No |
| 73 | 0 | | | MSS | No | No |
| 74 | 0 | | | MSS | No | No |
| 75 | 11 | Lung | Partial hepatectomy | MSS | No | No |
| 76 | 0 | | | MSS | No | No |
| 77 | 13 | Lung | Partial lung lobectomy | MSS | Yes | No |
| 78 | 0 | | | MSS | No | No |
| 79 | 15 | Liver | Surgery and RFA liver | MSS | No | No |
| 80 | 0 | | | MSS | No | No |
| 81 | 0 | | | MSS | No | No |
| 82 | 11 | Lymph nodes | Surgery of lymph node (throat) | MSS | Yes | No |
| 83 | 0 | | | MSS | Yes | No |
| 84 | 0 | | | MSS | No | No |
| 85 | 11 | Liver & lung | None | MSS | No | No |
| 86 | 0 | | | MSS | No | No |
| 87 | 0 | | | MSS | No | No |
| 88 | 0 | | | MSS | No | No |
| 89 | 17 | Lung | Partial lung lobectomy | MSS | No | No |
| 90 | 0 | | | MSS | | No |
| 91 | 0 | | | MSS | No | No |
| 92 | 14 | Local | Surgery of anastomosis, small intestine, and mesentery | MSI | No | No |
| 93 | 0 | | | MSS | No | No |
| 95 | 0 | | | MSS | No | No |
| 96 | 0 | | | MSS | Yes | No |
| 97 | 0 | | | MSS | No | No |
| 98 | 0 | | | MSI | No | No |
| 99 | 15 | Multiple | Palliative | MSS | No | No |
| 100 | 0 | | | MSS | Yes | No |
| 101 | 0 | | | MSS | No | No |
| 102 | 0 | | | MSS | No | No |
| 103 | 12 | Multiple | None | MSS | No | No |
| 104 | 12 | Liver | RFA liver | MSS | No | No |

TABLE 12.3-continued

Clinicopathological information continued.

| Patient ID | First relapse after OP. month | Relapse site | Relapse treatment | MSS/MSI | Perineural invasion | Perforation of tumor |
|---|---|---|---|---|---|---|
| 105 | 0 | | | MSS | No | No |
| 106 | 0 | | | MSI | No | No |
| 107 | 0 | | | MSS | No | No |
| 108 | 12 | Liver | RFA liver | MSS | No | No |
| 109 | 0 | | | MSS | Yes | No |
| 110 | 0 | | | MSS | No | No |
| 111 | 0 | | | MSS | Yes | No |
| 112 | 0 | | | MSS | Yes | No |
| 113 | 0 | | | MSS | No | No |
| 114 | 0 | | | MSS | | No |
| 115 | 0 | | | MSS | No | No |
| 116 | 0 | | | MSS | No | No |
| 117 | 0 | | | MSS | No | No |
| 118 | 0 | | | MSI | Nc | Nc |
| 119 | 12 | Local | Pending | MSS | Yes | Yes |
| 120 | 0 | | | MSI | No | No |
| 121 | 0 | | | MSS | No | No |
| 122 | 0 | | | MSS | Yes | No |
| 123 | 0 | | | MSS | Yes | No |
| 124 | 12 | Multiple | Palliative | MSS | No | No |
| 125 | 12 | Lung | Palliative | MSS | No | No |
| 126 | 0 | | | MSS | No | No |
| 127 | 0 | | | MSI | No | No |
| 128 | 0 | | | MSI | Yes | NA |
| 130 | 0 | | | MSS | Yes | No |

TABLE 12.4

Clinicopathological information continued.

| Patient ID | Number of lymph nodes in resected specimen | Macroscopic Radical Resection | Microscopic Radical Resection | Radical resection | Ileus | Anastomotic leakage | Perforation | Tumor perforation | WHO status |
|---|---|---|---|---|---|---|---|---|---|
| 1 | 41 | Yes | Yes | Yes | No ileus | No leak | No | No | 1 |
| 2 | 31 | Yes | Yes | Yes | No ileus | No leak | No | No | 1 |
| 3 | 24 | Yes | Yes | Yes | No ileus | No leak | No | No | 1 |
| 4 | 39 | Yes | Yes | Yes | NA | No leak | No | No | 1 |
| 5 | 34 | Yes | Yes | Yes | No ileus | No leak | No | No | 1 |
| 6 | 23 | Yes | Yes | Yes | No ileus | No leak | No | No | 1 |
| 7 | 28 | Yes | Yes | Yes | No ileus | No leak | No | No | 1 |
| 8 | 32 | Yes | Yes | Yes | NA | No leak | No | No | 1 |
| 9 | 51 | Yes | Yes | Yes | No | NA | No | No | 1 |
| 10 | 27 | Yes | Yes | Yes | NA | No leak | No | No | 1 |
| 11 | 27 | Yes | Yes | Yes | NA | No leak | No | No | 1 |
| 12 | 41 | Yes | Yes | Yes | No ileus | No leak | No | No | 1 |
| 13 | 27 | Yes | Yes | Yes | No ileus | No leak | No | No | 1 |
| 14 | 28 | Yes | Yes | Yes | No ileus | No leak | No | No | 1 |
| 15 | 38 | Yes | Yes | Yes | NA | No leak | No | No | 1 |
| 16 | 28 | Yes | Yes | Yes | No ileus | No leak | No | No | 1 |
| 18 | 21 | Yes | No | No | NA | No leak | No | No | 1 |
| 19 | 28 | Yes | Yes | Yes | No ileus | No leak | No | No | 2 |
| 20 | 21 | Yes | Yes | Yes | NA | No leak | No | No | 1 |
| 21 | 26 | Yes | Yes | Yes | NA | No leak | No | No | 1 |
| 22 | 36 | Yes | Yes | Yes | NA | No leak | No | No | 1 |
| 23 | 41 | Yes | Yes | Yes | NA | No leak | No | No | 1 |
| 24 | 33 | Yes | Yes | Yes | NA | No leak | No | No | 1 |

TABLE 12.4-continued

Clinicopathological information continued.

| Patient ID | Number of lymph nodes in resected specimen | Macroscopic Radical Resection | Microscopic Radical Resection | Radical resection | Ileus | Anastomotic leakage | Perforation | Tumor perforation | WHO status |
|---|---|---|---|---|---|---|---|---|---|
| 25 | 62 | Yes | Yes | Yes | No ileus | No leak | No | No | 1 |
| 26 | 42 | Yes | Yes | Yes | NA | No leak | No | No | 1 |
| 27 | 27 | Yes | Yes | Yes | NA | No leak | No | No | 1 |
| 28 | 32 | Yes | Yes | Yes | NA | No leak | No | No | 1 |
| 29 | 15 | No | No | No | NA | No leak | No | No | 1 |
| 30 | 28 | Yes | No | No | NA | No leak | No | No | 1 |
| 31 | 28 | Yes | Yes | Yes | NA | No leak | No | No | 1 |
| 33 | 81 | Yes | Yes | Yes | NA | No leak | No | No | 1 |
| 34 | 35 | Yes | Yes | Yes | No ileus | No leak | No | No | 1 |
| 35 | 21 | Yes | Yes | Yes | NA | No leak | No | No | 1 |
| 36 | 37 | Yes | Yes | Yes | NA | No leak | No | No | 1 |
| 37 | 30 | Yes | Yes | Yes | No ileus | No leak | No | No | 1 |
| 38 | 27 | Yes | Yes | Yes | No ileus | No leak | No | No | 1 |
| 39 | 27 | Yes | No | No | NA | No leak | No | No | 1 |
| 40 | 23 | Yes | No | No | NA | No leak | No | No | 1 |
| 41 | 35 | Yes | Yes | Yes | No ileus | No leak | No | No | 1 |
| 42 | 36 | Yes | No | No | NA | No leak | No | No | 1 |
| 43 | 40 | Yes | Yes | Yes | Ileus | No leak | No | No | 1 |
| 44 | 19 | Yes | Yes | Yes | No ileus | No leak | No | No | 1 |
| 45 | 27 | Yes | Yes | Yes | No ileus | No leak | No | No | 2 |
| 46 | 37 | No | No | No | NA | No leak | Before surgery | Yes | 2 |
| 47 | 37 | Yes | Yes | Yes | No ileus | No leak | No | No | 2 |
| 48 | 32 | Yes | Yes | Yes | NA | No leak | No | No | 2 |
| 49 | 19 | Yes | No | No | NA | No leak | No | No | 1 |
| 50 | 40 | Yes | Yes | Yes | No ileus | No leak | No | No | 1 |
| 51 | 40 | Yes | Yes | Yes | No ileus | Leak | No | No | 1 |
| 52 | 17 | Yes | Yes | Yes | No ileus | No leak | No | No | 2 |
| 53 | 18 | Yes | No | No | NA | No leak | No | No | 2 |
| 54 | 17 | Yes | Yes | Yes | NA | Leak | No | No | NA |
| 55 | 18 | Yes | Yes | Yes | No ileus | No leak | No | No | 2 |
| 57 | 32 | Yes | Yes | Yes | No ileus | No leak | No | No | 1 |
| 58 | 24 | Yes | Yes | Yes | No ileus | No leak | No | No | 1 |
| 59 | 16 | Yes | Yes | Yes | NA | No leak | No | No | 1 |
| 60 | 14 | Yes | Yes | Yes | No ileus | No leak | No | No | 1 |
| 61 | 20 | Yes | Yes | Yes | No ileus | No leak | No | No | 1 |
| 62 | 19 | Yes | Yes | Yes | NA | No leak | No | No | 1 |
| 63 | 27 | Yes | Yes | Yes | NA | No leak | No | No | 1 |
| 64 | 19 | Yes | Yes | Yes | NA | No leak | No | No | 1 |
| 65 | 31 | Yes | No | No | NA | No leak | No | No | 1 |
| 66 | 49 | Yes | Yes | Yes | NA | No leak | No | No | 1 |
| 67 | 31 | Yes | Yes | Yes | NA | No leak | No | No | 2 |
| 68 | 24 | Yes | Yes | Yes | NA | No leak | No | No | 1 |
| 69 | 18 | Yes | Yes | Yes | NA | No leak | No | No | 2 |
| 70 | 37 | Yes | Yes | Yes | NA | No leak | No | No | 1 |
| 71 | 26 | Yes | Yes | Yes | NA | No leak | No | No | 2 |
| 72 | 16 | Yes | Yes | Yes | NA | No leak | No | No | 1 |
| 73 | 30 | Yes | Yes | Yes | NA | No leak | No | No | 1 |
| 74 | 25 | Yes | Yes | Yes | NA | No leak | No | No | 2 |
| 75 | 48 | Yes | Yes | Yes | NA | No leak | No | No | 2 |
| 76 | 26 | Yes | Yes | Yes | NA | No leak | No | No | 2 |
| 77 | 280 | Yes | Yes | Yes | NA | No leak | No | No | 2 |
| 78 | 23 | Yes | Yes | Yes | NA | No leak | No | No | 1 |
| 79 | 20 | Yes | Yes | Yes | NA | No leak | No | No | 1 |
| 80 | 47 | Yes | Yes | Yes | NA | No leak | No | No | 1 |
| 81 | 17 | Yes | Yes | Yes | NA | No leak | No | No | 1 |

TABLE 12.4-continued

Clinicopathological information continued.

| Patient ID | Number of lymph nodes in resected specimen | Macroscopic Radical Resection | Microscopic Radical Resection | Radical resection | Ileus | Anastomotic leakage | Perforation | Tumor perforation | WHO status |
|---|---|---|---|---|---|---|---|---|---|
| 82 | 29 | Yes | Yes | Yes | NA | No leak | No | No | NA |
| 83 | 23 | Yes | Yes | Yes | NA | No leak | No | No | 2 |
| 84 | 24 | Yes | Yes | Yes | NA | No leak | No | No | 1 |
| 85 | 27 | Yes | Yes | Yes | NA | No leak | No | No | 1 |
| 86 | 30 | Yes | Yes | Yes | NA | No leak | No | No | 1 |
| 87 | 17 | Yes | Yes | Yes | NA | No leak | No | No | 3 |
| 88 | 47 | Yes | Yes | Yes | NA | No leak | No | No | 1 |
| 89 | 12 | Yes | Yes | Yes | NA | No leak | No | No | 3 |
| 90 | 21 | Yes | No | No | Ileus | No leak | No | No | 3 |
| 91 | 15 | Yes | Yes | Yes | NA | No leak | No | No | 2 |
| 92 | 18 | Yes | No | No | NA | No leak | No | No | 2 |
| 93 | 28 | Yes | Yes | Yes | NA | No leak | No | No | 2 |
| 95 | 27 | Yes | Yes | Yes | NA | No leak | No | No | 1 |
| 96 | 33 | Yes | Yes | Yes | NA | No leak | No | No | 1 |
| 97 | 15 | Yes | Yes | Yes | No ileus | No leak | No | No | 1 |
| 98 | 15 | Yes | Yes | Yes | Ileus | No leak | No | No | 2 |
| 99 | 30 | Yes | Yes | Yes | NA | No leak | No | No | 1 |
| 100 | 12 | Yes | Yes | Yes | No ileus | No leak | No | No | 2 |
| 101 | 34 | Yes | Yes | Yes | No ileus | No leak | No | No | 2 |
| 102 | 13 | Yes | Yes | Yes | NA | No leak | No | No | 1 |
| 103 | 38 | Yes | No | No | NA | No leak | No | No | 3 |
| 104 | 24 | NA | NA | NA | NA | No leak | NA | No | NA |
| 105 | 36 | Yes | Yes | Yes | No ileus | No leak | No | No | 2 |
| 106 | 21 | Yes | Yes | Yes | NA | No leak | No | No | 1 |
| 107 | 17 | Yes | Yes | Yes | NA | No leak | No | No | 1 |
| 108 | 12 | Yes | Yes | Yes | No ileus | No leak | No | No | 3 |
| 109 | 24 | Yes | Yes | Yes | No ileus | No leak | No | No | 2 |
| 110 | 20 | Yes | Yes | Yes | NA | No leak | No | No | 2 |
| 111 | 31 | Yes | No | No | NA | No leak | Before surgery | Yes | 1 |
| 112 | 25 | Yes | No | No | NA | No leak | No | No | 1 |
| 113 | 22 | Yes | Yes | Yes | NA | No leak | No | No | 1 |
| 114 | 33 | Yes | Yes | Yes | NA | No leak | No | No | 1 |
| 115 | 24 | Yes | No | No | NA | No leak | No | No | 2 |
| 116 | 31 | Yes | Yes | Yes | NA | No leak | No | No | 1 |
| 117 | 19 | Yes | No | No | NA | No leak | No | No | 2 |
| 118 | 25 | Yes | Yes | Yes | NA | No leak | No | No | 1 |
| 119 | 29 | Yes | No | No | NA | No leak | Before surgery | Yes | 1 |
| 120 | 31 | Yes | Yes | Yes | NA | No leak | No | No | 1 |
| 121 | 14 | Yes | Yes | Yes | NA | No leak | No | No | 2 |
| 122 | 34 | Yes | Yes | Yes | NA | No leak | No | No | 1 |
| 123 | 24 | Yes | Yes | Yes | NA | No leak | No | No | 1 |
| 124 | 41 | Yes | NA | NA | NA | No leak | No | No | 2 |
| 125 | 31 | Yes | Yes | Yes | No ileus | No leak | No | No | 1 |
| 126 | 36 | Yes | Yes | Yes | No ileus | No leak | No | No | 1 |
| 127 | 23 | Yes | Yes | Yes | No ileus | No leak | No | No | 1 |
| 128 | 54 | Yes | NA | NA | NA | No leak | Before surgery | Yes | 2 |
| 130 | 19 | Yes | Yes | Yes | NA | No leak | No | No | 1 |

All patients received treatment and follow-up in compliance with Danish National Guidelines. The study was approved by the Committees on Biomedical Research Ethics in the Central Region of Denmark (1-16-02-453-14) and was performed in accordance with the Declaration of Helsinki. All participants provided written informed consent.

Carcinoembryonic Antigen (CEA) Analysis.

CEA analysis was performed on a Cobas e601 platform (Roche), according to the manufacturer's recommendations using 500 µL serum. The threshold levels were set to 4.0 µg/L and 6.0 µg/L for non-smokers and smokers, respectively, as recommended by the analysing hospital. A person who had not smoked for 8 weeks before sample collection was considered a former smoker.

Tissue Collection and Whole Exome Sequencing.

Tumor tissue was collected from all patients either as fresh frozen (n=102) or as formalin fixed and paraffin embedded tissue (FFPE) (n=27). Four patients presented with synchronous colorectal cancers (CRCs); from these patients, tissues from both tumors were collected. Metastatic tissue was collected from three patients with relapse. Constitutional DNA matching all patients was extracted from peripheral blood leukocytes.

Primary fresh frozen or formalin fixed paraffin embedded (FFPE) tissue samples, had a median pathological tumor cellularity of 50% (range 20-90%). (Suppl. Table 2). DNA was extracted using the Puregene® DNA purification kit (Gentra Systems) or using the QiAamp® DNA FFPE tissue kit (Qiagen).

Whole exome sequencing (WES) was performed on matched tumor DNA and buffy coat DNA. Summary of sample and WES information is shown in table 12.5 below. Cancer content was assessed by H&E evaluation of tissue sections cut before and after those used for extraction. Synchronous CRC are marked with S1 and S2 in the table.

TABLE 12.5

Summary of sample and whole exome sequencing information.

| Patient ID | Tissue type | Source of DNA | Tumor and metastatic tissue | | | Buffy coat | |
|---|---|---|---|---|---|---|---|
| | | | Cancer cell percentage | Input, ng | WES coverage | Input, ng | WES coverage |
| 1 | Primary tumor | FF | 60 | 500 | 100.8 | 500 | 41.9 |
| 2 | Primary tumor | FF | 60 | 500 | 94.3 | 500 | 36.5 |
| 3 | Primary tumor | FF | 60 | 500 | 101.8 | 500 | 45.3 |
| 4 | Primary tumor | FF | 60 | 500 | 98.4 | 500 | 45.5 |
| 5 | Primary tumor | FF | 25 | 500 | 167.8 | 500 | 40.9 |
| 6 | Primary tumor | FF | 50 | 500 | 93 | 500 | 46.1 |
| 7 | Primary tumor | FF | 50 | 500 | 91.2 | 500 | 40.8 |
| 8 | Primary tumor | FF | 85 | 500 | 89.9 | 500 | 43.2 |
| 9 | Primary tumor | FF | 60 | 500 | 91.3 | 500 | 36.1 |
| 10 | Primary tumor | FF | 55 | 500 | 140.4 | 500 | 41.8 |
| 11 | Primary tumor | FF | 60 | 500 | 104.3 | 500 | 39.4 |
| 12 | Primary tumor | FF | 60 | 500 | 106 | 500 | 40.8 |
| 13 | Primary tumor | FF | 45 | 500 | 97 | 500 | 47.2 |
| 14 | Primary tumor | FF | 70 | 500 | 106.6 | 500 | 61.3 |
| 15 | Primary tumor | FF | 40 | 500 | 105.2 | 500 | 39.2 |
| 16 | Primary tumor | FF | 80 | 250 | 122.7 | 500 | 92.2 |
| 18 | Primary tumor | FF | 80 | 500 | 98 | 500 | 49.4 |
| 19 | Primary tumor | FF | 40 | 500 | 100.3 | 500 | 37 |
| 20 | Primary tumor | FF | 80 | 500 | 112.2 | 500 | 44.7 |
| 21 | Primary tumor | FF | 70 | 500 | 117 | 500 | 56.5 |
| 22 | Primary tumor | FF | 82 | 500 | 102.2 | 500 | 54.9 |
| 23 | Primary tumor | FF | 60 | 500 | 104.9 | 500 | 43.1 |
| 24 | Primary tumor | FF | 90 | 500 | 104.2 | 500 | 46.5 |
| 25 | Primary tumor | FF | 35 | 500 | 106.1 | 500 | 43.6 |
| 26 | Primary tumor | FF | 80 | 500 | 150.9 | 500 | 46.5 |
| 27 | Primary tumor | FF | 50 | 500 | 149.2 | 500 | 54.9 |
| 28 | Primary tumor | FF | 70 | 500 | 129.2 | 500 | 60.9 |
| 29 | Primary tumor | FF | 45 | 500 | 86.1 | 500 | 45.1 |
| 30 | Primary tumor | FF | 20 | 500 | 222 | 500 | 40 |

TABLE 12.5-continued

Summary of sample and whole exome sequencing information.

| Patient ID | Tissue type | Source of DNA | Tumor and metastatic tissue | | | Buffy coat | |
|---|---|---|---|---|---|---|---|
| | | | Cancer cell percentage | Input, ng | WES coverage | Input, ng | WES coverage |
| 31 | Primary tumor | FFPE | 50 | 500 | 123.6 | 500 | 56.8 |
| 33 (S1) | Primary tumor | FF | 35 | 500 | 65.5 | 500 | 55.9 |
| 33 (S2) | Primary tumor | FFPE | 60 | 500 | 87.7 | 500 | 55.9 |
| 34 | Primary tumor | FF | 50 | 500 | 90.4 | 500 | 46.8 |
| 35 | Primary tumor | FF | 30 | 500 | 186.3 | 500 | 41.6 |
| 36 | Primary tumor | FF | 25 | 500 | 184.4 | 500 | 36.8 |
| 37 | Primary tumor | FF | 70 | 500 | 87.8 | 500 | 50.8 |
| 38 | Primary tumor | FF | 35 | 500 | 86.9 | 500 | 54.2 |
| 39 | Primary tumor | FF | 20 | 500 | 179.4 | 500 | 49.8 |
| 40 | Primary tumor | FF | 70 | 500 | 86.4 | 500 | 62.7 |
| 41 | Primary tumor | FF | 65 | 500 | 88.4 | 500 | 60.5 |
| 42 | Primary tumor | FF | 60 | 500 | 94.9 | 500 | 35.9 |
| 43 | Primary tumor | FF | 40 | 500 | 121.3 | 500 | 35.2 |
| 44 | Primary tumor | FF | 90 | 500 | 103.8 | 500 | 45.2 |
| 45 | Primary tumor | FF | 40 | 500 | 107.6 | 500 | 44.8 |
| 46 | Primary tumor | FF | 70 | 500 | 99 | 500 | 40.6 |
| 47 | Primary tumor | FF | 45 | 500 | 94.4 | 500 | 37.6 |
| 48 (S1) | Primary tumor | FF | 50 | 500 | 108.5 | 500 | 52.7 |
| 48 (S2) | Primary tumor | FFPE | 50 | 500 | 95 | 500 | 52.7 |
| 49 | Primary tumor | FF | 20 | 200 | 127.9 | 500 | 57.7 |
| 50 | Primary tumor | FF | 50 | 500 | 93.1 | 500 | 43.2 |
| 51 | Primary tumor | FFPE | 50 | 500 | 130.7 | 500 | 36.4 |
| 52 | Primary tumor | FFPE | 50 | 500 | 113 | 500 | 55.4 |
| 53 | Primary tumor | FF | 40 | 500 | 93.7 | 500 | 56 |
| 54 | Primary tumor | FF | 60 | 500 | 113.6 | 500 | 79.7 |
| 55 | Primary tumor | FF | 20 | 500 | 161 | 500 | 69.1 |
| 57 | Primary tumor | FF | 80 | 500 | 85 | 500 | 72.8 |
| 58 | Primary tumor | FF | 55 | 500 | 79.4 | 500 | 53.7 |
| 59 | Primary tumor | FF | 50 | 250 | 127.1 | 500 | 58.4 |
| 60 | Primary tumor | FFPE | 40 | 500 | 119.1 | 500 | 57.4 |
| 61 | Primary tumor | FF | 40 | 500 | 93.6 | 500 | 81.9 |
| 62 | Primary tumor | FFPE | 20 | 500 | 120.2 | 500 | 40 |
| 63 | Primary tumor | FF | 60 | 100 | 116.6 | 500 | 44.8 |
| 64 | Primary tumor | FF | 55 | 500 | 109 | 500 | 41.3 |
| 65 | Primary tumor | FFPE | 50 | 500 | 99.4 | 500 | 39.1 |
| 66 | Primary tumor | FF | 70 | 500 | 105.2 | 500 | 47.7 |

TABLE 12.5-continued

Summary of sample and whole exome sequencing information.

| | | Tumor and metastatic tissue | | | | Buffy coat | |
|---|---|---|---|---|---|---|---|
| Patient ID | Tissue type | Source of DNA | Cancer cell percentage | Input, ng | WES coverage | Input, ng | WES coverage |
| 67 | Primary tumor | FF | 77 | 500 | 82.1 | 500 | 50.2 |
| 68 | Primary tumor | FF | 50 | 500 | 102 | 500 | 42 |
| 69 | Primary tumor | FF | 60 | 500 | 97.3 | 500 | 44.9 |
| 70 | Primary tumor | FFPE | 20 | 500 | 150.4 | 500 | 39.8 |
| 71 | Primary tumor | FF | 25 | 500 | 160.4 | 500 | 39.2 |
| 72 | Primary tumor | FF | 50 | 500 | 126.8 | 500 | 57 |
| 73 | Primary tumor | FF | 45 | 500 | 90.3 | 500 | 55.3 |
| 74 | Primary tumor | FF | 65 | 500 | 127.3 | 500 | 44.7 |
| 75 | Primary tumor | FF | 85 | 500 | 108.8 | 500 | 36.5 |
| 76 | Primary tumor | FF | 85 | 250 | 111.8 | 500 | 55.6 |
| 77 | Primary tumor | FF | 50 | 500 | 124.5 | 500 | 42.1 |
| 78 | Primary tumor | FF | 53 | 500 | 94.2 | 500 | 53.5 |
| 79 | Primary tumor | FF | 65 | 500 | 101.2 | 500 | 54.1 |
| 80 | Primary tumor | FF | 80 | 500 | 93.8 | 500 | 44.8 |
| 81 | Primary tumor | FF | 45 | 500 | 101.8 | 500 | 38.3 |
| 82 | Primary tumor | FF | 30 | 500 | 219.9 | 500 | 69.3 |
| 83 | Primary tumor | FFPE | 50 | 200 | 38.6 | 500 | 52.2 |
| 84 | Primary tumor | FFPE | 50 | 500 | 69.2 | 500 | 39.6 |
| 85 | Primary tumor | FF | 60 | 500 | 107.6 | 500 | 63.3 |
| 86 | Primary tumor | FF | 80 | 200 | 116.2 | 500 | 38.3 |
| 87 | Primary tumor | FF | 40 | 500 | 120 | 500 | 39.7 |
| 88 | Primary tumor | FF | 18 | 500 | 192.4 | 500 | 45.4 |
| 89 | Primary tumor | FF | 63 | 500 | 91.7 | 500 | 56.5 |
| 90 (S1) | Primary tumor | FFPE | 50 | 500 | 94.6 | 500 | 41.3 |
| 90 (S2) | Primary tumor | FFPE | 50 | 500 | 70.8 | 500 | 41.3 |
| 91 | Primary tumor | FF | 43 | 500 | 82.8 | 500 | 84 |
| 92 | Primary tumor | FF | 55 | 500 | 132.1 | 500 | 54.1 |
| 93 | Primary tumor | FFPE | 50 | 500 | 118.4 | 500 | 41.1 |
| 95 | Primary tumor | FF | 80 | 100 | 148.6 | 500 | 52.3 |
| 96 | Primary tumor | FFPE | 40 | 500 | 48.3 | 500 | 52.9 |
| 97 | Primary tumor | FFPE | 50 | 500 | 73.2 | 500 | 33.1 |
| 98 | Primary tumor | FFPE | 50 | 500 | 96.8 | 500 | 41.6 |
| 99 | Primary tumor | FFPE | 50 | 500 | 125.1 | 500 | 38.4 |
| 100 | Primary tumor | FF | 45 | 500 | 81.5 | 500 | 38.4 |
| 101 | Primary tumor | FF | 40 | 500 | 88.1 | 500 | 43.3 |
| 102 | Primary tumor | FFPE | 50 | 500 | 127.7 | 500 | 32.9 |

TABLE 12.5-continued

Summary of sample and whole exome sequencing information.

| Patient ID | Tissue type | Source of DNA | Tumor and metastatic tissue | | | Buffy coat | |
|---|---|---|---|---|---|---|---|
| | | | Cancer cell percentage | Input, ng | WES coverage | Input, ng | WES coverage |
| 103 | Primary tumor | FF | 20 | 500 | 169.3 | 500 | 53.5 |
| 104 | Primary tumor | FF | 35 | 500 | 99.9 | 500 | 107.4 |
| 105 | Primary tumor | FF | 45 | 100 | 383.4 | 500 | 80.5 |
| 106 | Primary tumor | FF | 55 | 500 | 83.2 | 500 | 46.9 |
| 107 | Primary tumor | FFPE | 50 | 500 | 99.5 | 500 | 45.6 |
| 108 | Primary tumor | FF | 75 | 500 | 98.5 | 500 | 57.3 |
| 109 | Primary tumor | FF | 30 | 500 | 168.7 | 500 | 56.5 |
| 110 | Primary tumor | FF | 60 | 500 | 85.8 | 500 | 35.6 |
| 111 | Primary tumor | FFPE | 50 | 500 | 54.5 | 500 | 38.8 |
| 112 | Primary tumor | FF | 50 | 500 | 86.5 | 500 | 54.3 |
| 113 | Primary tumor | FFPE | 50 | 500 | 92.2 | 500 | 78.7 |
| 114 (S1) | Primary tumor | FF | 75 | 500 | 80.7 | 500 | 100.3 |
| 114 (S2) | Primary tumor | FF | 85 | 500 | 98.6 | 500 | 100.3 |
| 115 | Primary tumor | FF | 20 | 500 | 179.6 | 500 | 38.2 |
| 116 | Primary tumor | FF | 45 | 500 | 97.6 | 500 | 43.2 |
| 117 | Primary tumor | FF | 68 | 500 | 91.5 | 500 | 74.2 |
| 118 | Primary tumor | FF | 80 | 500 | 94.4 | 500 | 53 |
| 119 | Primary tumor | FFPE | 40 | 500 | 66 | 500 | 54.9 |
| 120 | Primary tumor | FF | 40 | 500 | 80.4 | 500 | 83 |
| 121 | Primary tumor | FFPE | 50 | 500 | 94.1 | 500 | 127 |
| 122 | Primary tumor | FFPE | 30 | 500 | 61.2 | 500 | 37.3 |
| 123 | Primary tumor | FF | 25 | 500 | 176.9 | 500 | 56.5 |
| 124 | Primary tumor | FF | 35 | 250 | 137.2 | 500 | 93.2 |
| 125 | Primary tumor | FF | 70 | 500 | 119.6 | 500 | 35 |
| 126 | Primary tumor | FF | 60 | 500 | 102.6 | 500 | 48.1 |
| 127 | Primary tumor | FFPE | 50 | 500 | 83.1 | 500 | 48.5 |
| 128 | Primary tumor | FFPE | 50 | 500 | 72.3 | 500 | 105.8 |
| 130 | Primary tumor | FF | 70 | 500 | 88.8 | 500 | 50.4 |

Library preparation, sequencing, and data analysis were carried out as described in Lamy et al. Paired Exome Analysis Reveals Clonal Evolution and Potential Therapeutic Targets in Urothelial Carcinoma. *Cancer Res.* 76(19): 5894-5906 (2016).

Blood Collection and Plasma Isolation

Blood samples were collected in K2-EDTA 10 ml tubes (BD 367525) at Aarhus University Hospital. All samples were processed within 2 hours of collection by double centrifugation of the blood at room temperature, first for 10 minutes at 3000 g, followed by centrifugation of plasma for 10 minutes at 3000 g. Plasma was aliquoted into 5 mL cryotubes and stored at −80° C.

Cell-Free DNA Extraction, Quantification, and Library Preparation.

Up to 10 ml of plasma per case was used for this study (range, 2-10 mL; median 8.5 mL) and cell-free DNA (cfDNA) was extracted using the QIAamp® Circulating Nucleic Acid kit (Qiagen) and eluted into 50 L DNA Suspension Buffer (Sigma). Each cfDNA sample was quantified by Quant-iT® High Sensitivity dsDNA Assay Kit (Invitrogen). In 125 patients, cfDNA was isolated from a total of 795 serial plasma samples.

Up to 66 ng (20,000 genome equivalents) of cfDNA from each plasma sample was used as input into library preparation. The cfDNA was end-repaired, A-tailed, and ligated with custom adapters, as described in Abbosh et al. Phylogenetic ctDNA analysis depicts early-stage lung cancer evolution. Nature 545(7655):446-451 (2017). The purified ligation product was amplified for 20 cycles and purified using Ampure® XP beads (Agencourt/Beckman Coulter).

Multiplex-PCR Assay Design

Patient-specific somatic variants were identified by analyses of primary tumour and matched normal WES samples for all patients. Clonality of variants was inferred based on the estimated proportion of cancer cells harboring the variant. Note that clonality inference from samples with low tumor cell fraction is limited due to a fairly flat distribution of variant allele frequency. Observed VAF in tissue and sequence context of variants were used to prioritize somatic SNVs and short INDELs identified for each tumour. The Signatera amplicon design pipeline was used to generate PCR primer pairs for the given set of variants. For each patient, 16 highly ranked compatible amplicons were selected for the custom patient-specific panel. The PCR primers were ordered from Integrated DNA Technologies.

Plasma-Multiplex-PCR Next Generation Sequencing Workflow

An aliquot of each library was used as input into the associated patient-specific 16-plex PCR reaction. Samples were amplified using the patient-specific assay and barcoded, followed by product pooling. Sequencing was performed on an Illumina HiSeq® 2500 Rapid Run with 50 cycles of paired-end reads using the Illumina Paired End v2 kit with an average read depth of >105,000× per amplicon.

Bioinformatics Pipeline

All paired-end reads were merged using Pear software as described in Zhang, BioinfoPtatics, 30(5): 614-620 (2014). Bases that did not match in forward and reverse reads or that had a low quality score were filtered out to minimize sequencing errors. Merged reads were mapped to the hg19 reference genome with Novoalign version 2.3.4 (worldwideweb.novocraft.com/). Amplicons with <5,000 high quality reads were considered to have failed sequencing quality control (QC). QC was performed using an in-house program checking for a wide list of statistics per sample that included total numbers of reads, mapped reads, on-target reads, number of failed targets and average error rate.

Plasma Variant Calling

A large set of negative control samples (~1000) were pre-processed to build a background error model. For each target variant using mutant and reference alleles depth of read a confidence score was calculated on the basis of the error model, as described in Abbosh et al. Phylogenetic ctDNA analysis depicts early-stage lung cancer evolution. Nature 545(7655):446-451 (2017). A plasma sample with at least 2 variants with a confidence score above a predefined algorithm threshold was defined as ctDNA positive as described in Abbosh et al, 2017, supra.

Statistical Analysis

The primary outcome measure was time to recurrence (TTR) assessed by standard radiologic criteria. TTR was measured from date of surgery to documented first radiologic recurrence (local or distant) or death as a result of colorectal cancer and was censored at last follow-up or non-colorectal cancer-related death. Survival analysis was performed using the Kaplan-Meier method. Cox proportional hazards regression analysis was used to assess the impact of ctDNA and CEA on TTR. Multivariate analysis was performed with clinical parameters that were statistically significant in univariate analysis. All P-values were based on two-sided testing and differences were considered significant at P<0.05. Statistical analysis was performed using STATA IC/12.1 and R Statistical software, version 2.4 for Windows.

Results

Figure 90A:
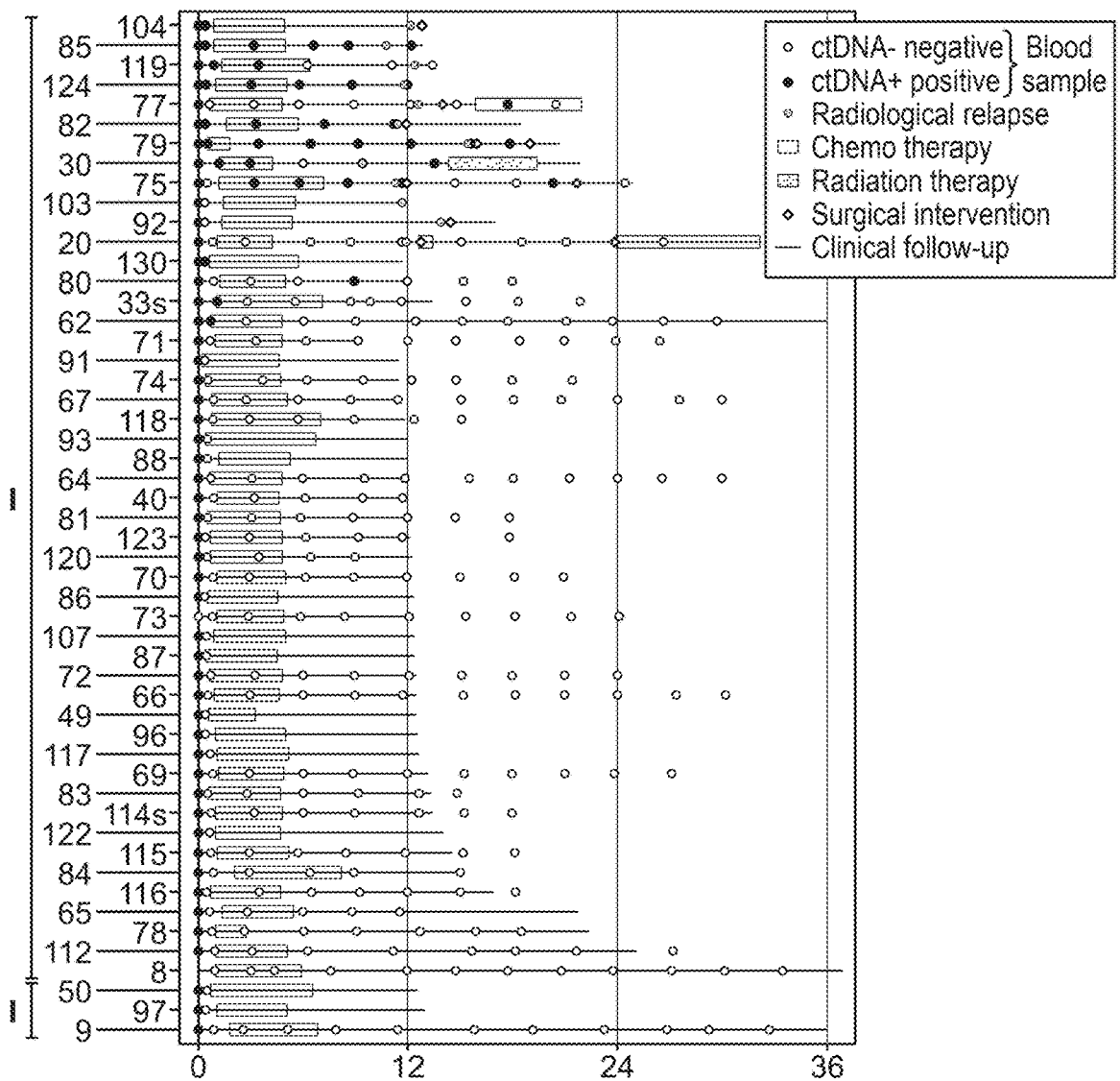
FIG. 90A-B shows a schematic overview of ctDNA profiling results of a subset of plasma samples included in the day 30 ctDNA analysis and receiving ACT ordered by recurrence status and disease stage. Patients marked by a (s) have synchronous CRC.
Figure 90B:
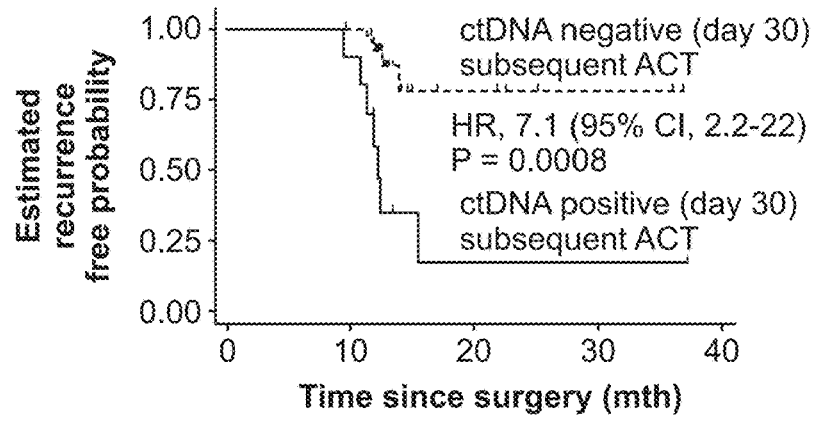
Figure 91:
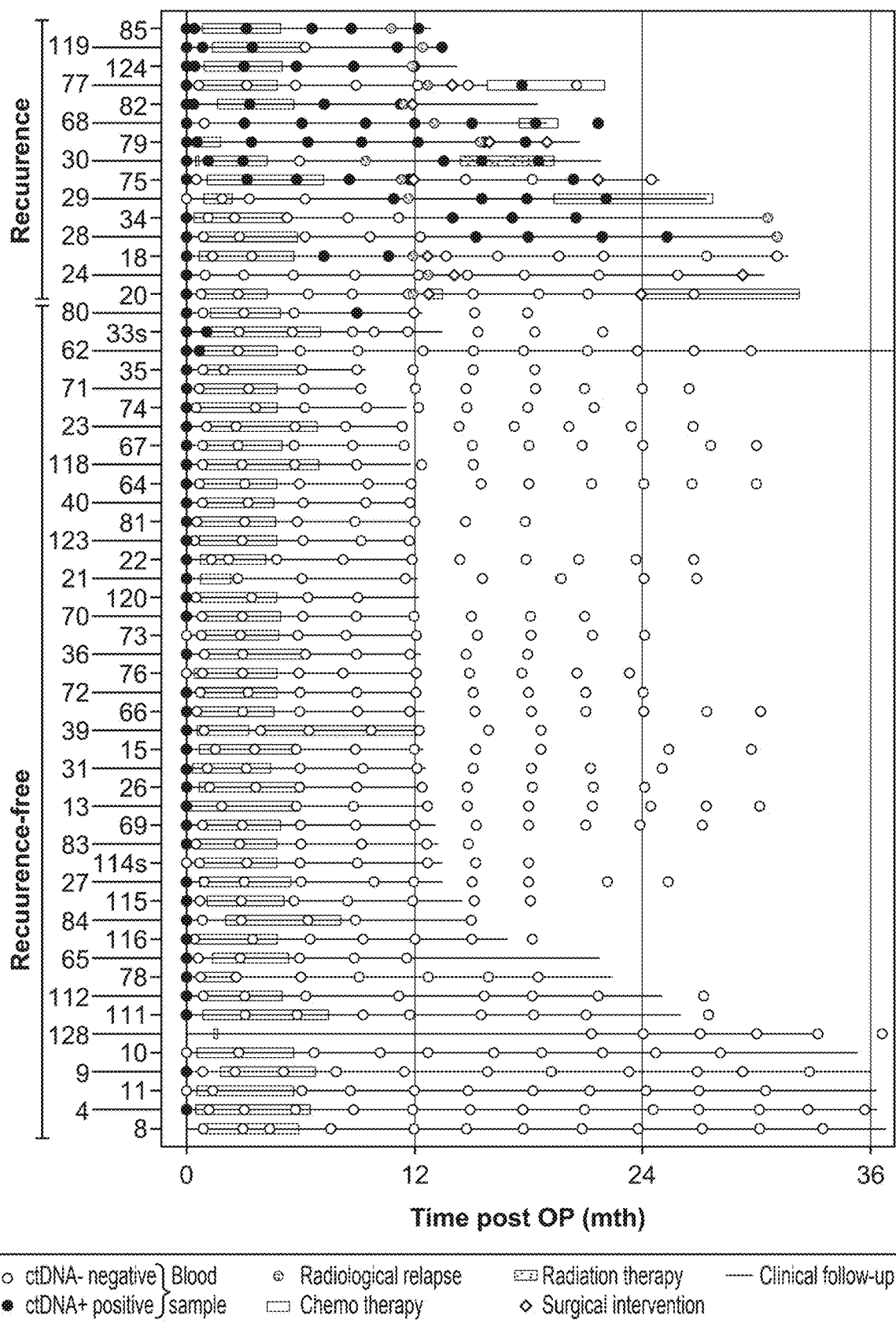
FIG. 91 shows a schematic overview of ctDNA profiling results of plasma samples included in the longitudinal post-ACT ctDNA analysis ordered by recurrence status, postoperative ctDNA status, and length of follow-up. Patients marked by a (s) have synchronous CRC (n=2). Plasma samples marked with ** are positive in the second pool only (n=1).

One hundred and thirty UICC stage I to III CRC patients were enrolled between 2014-2016. Five patients were subsequently excluded because they were either lost to follow-up (n=3) or reclassified to stage IV. Whole exome sequencing (WES) of tumor and matched germline DNA was used to identify somatic mutations as shown in FIG. 90A-B. Tumor specific multiplex-PCR assay panels targeting 16 mutations were designed for each patient. Ultra deep multiplex-PCR based NGS was used to analyze and quantify circulating tumor DNA in 795 plasma samples from 125 patients with a median follow-up of 12.5 months (range, 1.4 to 38.5 months). The workflow for this study is shown in FIG. 83A-E. Quality control was performed at every step of the workflow. The depth of read for the assays that passed coverage quality control was >105,000× as shown in FIG. 91. Detailed information regarding ctDNA results and dynamics for all 125 patients are listed in Table 12.6 and shown in FIG. 92. During the period of the patients were followed-up, 24 (19.2%) patients experienced radiologic recurrences.

Detection of ctDNA Preoperatively

Figures 87E, 87F:
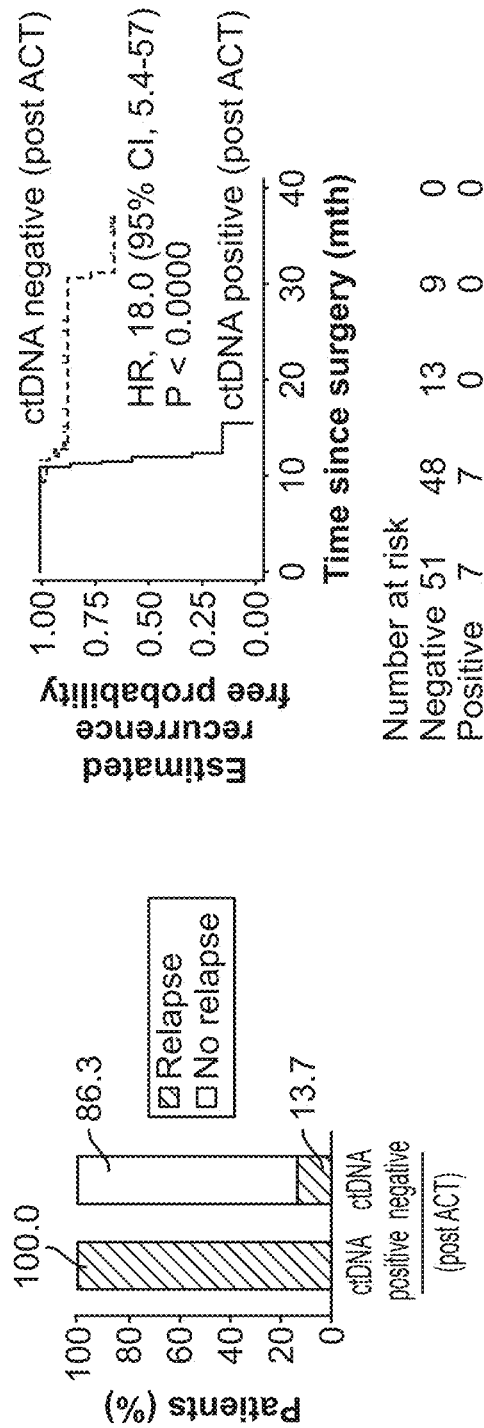
Figure 88:
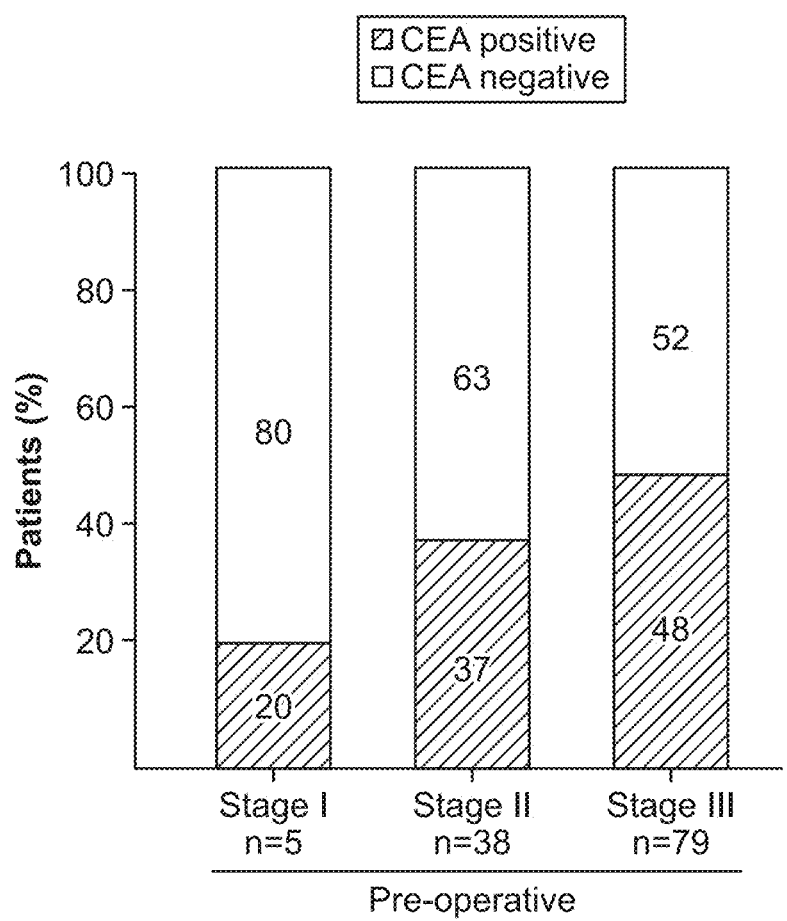
FIG. 88 shows pre-operative detection of carcinoembryonic antigen (CEA) in 125 stage i-Ill CRC patients.

In the baseline preoperative plasma samples (n=122), we detected ctDNA in 89% of the samples with sensitivity of 40%, 92%, and 90% in stages I, II, and III respectively as shown in FIG. 87A. Carcinoembryonic antigen (CEA) analysis performed on the same samples detected 43.3% of the cancers as shown in FIG. 88.

Post-Operative ctDNA Status at Day 30 Predicts Recurrence

Figure 89:
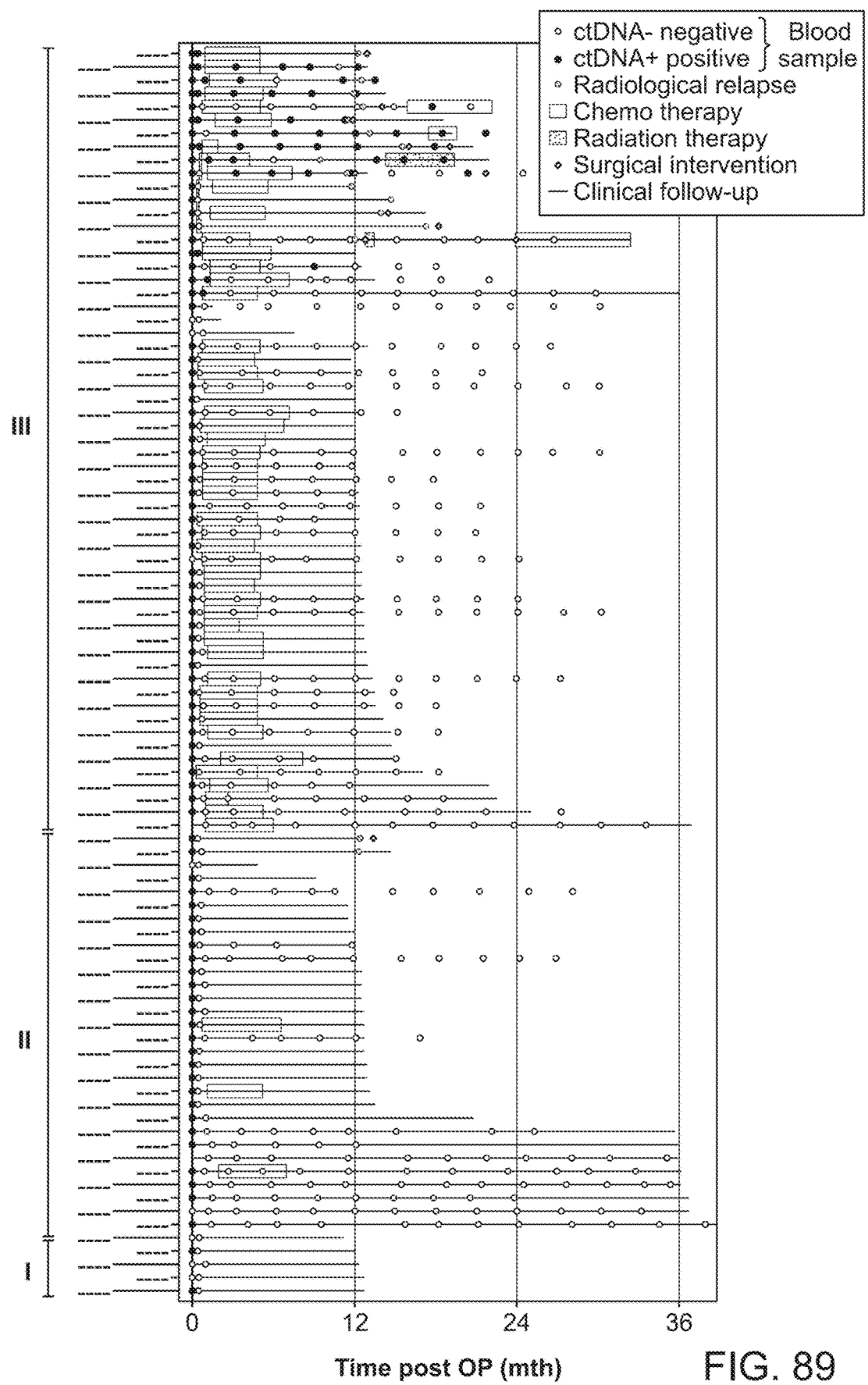
FIG. 89 shows a schematic overview of ctDNA profiling results of plasma samples included in the day 30 ctDNA analysis ordered by recurrence status and disease stage. Patients marked by a (s) have synchronous CRC. Plasma marked with ** are positive in the second pool only (n=1)

In order to assess its ability to detect residual disease and predict future recurrence, we performed ctDNA analysis of plasma samples collected post-operatively. Plasma collected at day 30, prior to the start of adjuvant chemotherapy, was available for 94 patients. Interestingly, the vast majority (89.4%) of the patients were ctDNA negative, and only 10.6% of the patients were positive for ctDNA after surgery as shown in FIG. 89. These ctDNA positive patients had a significantly higher recurrence rate (70%, 7/10) compared to those who were ctDNA negative after surgery (11.9%, 10/84) as shown in FIG. 87B. The presence of ctDNA was associated with a markedly reduced time to recurrence (TTR) as compared to ctDNA-negative patients (HR, 7.2; 95% CI, 2.7-19; P<0.0000) as shown in FIG. 87C. Compared with known prognostic factors such as stage and lymphovascular invasion, in a multivariate logistic regression model, ctDNA status was the only significant prognostic factor as shown in Table 12.7 below.

TABLE 12.7

Time to Recurrence Analysis by Clinicopathological Variables and Post-Op ctDNA Status at Day 30.

| Variable<br>All patients with a day<br>30 postoperative sample (n = 94) | Univariate analysis | | | Multivariate analysis* | | |
|---|---|---|---|---|---|---|
| | HR | (95% CI) | P | HR | (95% CI) | P |
| Age | | | | | | |
| < mean versus ≥ Mean | 1.4 | (0.52-3.8) | 0.508 | | | |
| Stage | | | | | | |
| Stage II versus stage III | 5.3 | (1.2-23) | 0.028 | 3.2 | (0.65-16) | 0.152 |
| Tumor site | | | | | | |
| Right versus left | 1.9 | (0.72-5.3) | 0.191 | | | |
| Lymphovascular invasion | | | | | | |
| No versus yes | 2.7 | (1.0-7.0) | 0.044 | 1.6 | (0.40-3.3) | 0.785 |
| MMR-status | | | | | | |
| Deficient versus proficient | 0.45 | (0.059-3.4) | 0.432 | | | |
| Radical resection (micro) | | | | | | |
| Yes versus no | 2.3 | (0.72-7.2) | 0.160 | | | |
| Histology | | | | | | |
| Adeno-versus mucinouscarcinoma | 1.6 | (0.35-7.2) | 0.531 | | | |
| Tumor differentiation | | | | | | |
| Medium/well versus poor | 0.86 | (0.19-3.8) | 0.847 | | | |
| Gender | | | | | | |
| Female versus male | 0.24 | (0.079-0.74) | 0.013 | | | |
| ctDNA status up to 6 weeks after OP (no ACT) | | | | | | |
| ctDNA-versus ctDNA+ | 7.2 | (2.7-19) | <0.0000 | 4.4 | (1.5-12.8) | 0.006 |

*Includes variables that were statistical significant in the univariate analysis, except gender.

A subset of the patients was treated with ACT (n=52), which can modify the prognostic value of ctDNA on outcome. However, even for this subset, ctDNA positivity was associated with a high risk of recurrence (HR, 7.1; 95% CI 2.2-22; P=0.0008) as shown in FIG. 90A-B. The relapse rate for ctDNA-negative patients was 11.9% independent of whether they were treated with ACT (5/42) or not (5/42). In summary, ctDNA status at 30 day post-surgery is a strong predictor of future recurrence, even for ACT treated patients. Adjuvant Chemotherapy Eliminates ctDNA in a Subfraction of Day 30 ctDNA Positive Patients.

While randomized studies have shown that adjuvant chemotherapy (ACT) can reduce the overall recurrence rate of stage III CRC 21-24, it is presently unknown if ACT can specifically prevent recurrences among the high-risk ctDNA-positive subfraction. The ten patients who were positive for ctDNA at day 30 were all subsequently treated with ACT as shown in FIG. 87D. Among these patients subsequently treated with ACT, 70% (n=7) relapsed, while 30% (n=3) were still disease free at the end of the follow-up period. This treatment efficacy is similar to that estimated when ACT is given to all stage III colon cancers as described in Upadhyay et al., Chemotherapy use in stage III colon cancer: a National Cancer Database analysis. *Ther Adv Med Oncol.* 7(5):244-251 (2015); André et al., Improved overall survival with oxaliplatin, fluorouracil, and leucovorin as adjuvant treatment in stage II or III colon cancer in the MOSAIC trial. *J Clin Oncol.* 27(19):3109-3116 (2009); Gill et al., Pooled analysis of fluorouracil-based adjuvant therapy for stage II and III colon cancer: who benefits and by how much? *J Clin Oncol.* 22(10):1797-1806 (2004); Haller et al., Capecitabine plus oxaliplatin compared with fluorouracil and folinic acid as adjuvant therapy for stage III colon cancer. *J Clin Oncol.* 29(11):1465-1471 (2011). Thus, the herein presented results presented in FIG. 87D showed that ACT can eliminate residual disease in a subfraction of high-risk ctDNA-positive patients.

For two out of three patients who did not recur, longitudinally collected plasma samples were available. Consistent with ACT eliminating the residual disease, these patients demonstrated complete clearance of ctDNA during therapy and remained ctDNA negative for the duration of the study. Conversely, the six recurrence patients with available longitudinal plasma either remained ctDNA positive during ACT or became ctDNA positive again shortly after completion of ACT.

Longitudinal ctDNA Monitoring Measures the Efficacy of ACT Treatment.

Longitudinally-collected blood samples were available for 8/10 patients who were ctDNA positive before the start of ACT. These longitudinally-collected blood samples were analysed to observe the changes in ctDNA levels during treatment. The ctDNA status became negative in 50% of the patients (n=4) as shown in FIG. 87D, while in the other four patients, ctDNA status remained positive throughout treatment. Strikingly, all four patients (100%) that did not clear ctDNA experienced disease recurrence, indicating that residual ctDNA predicted that ACT failed to eliminate the residual disease. Of the four patients that cleared ctDNA during treatment, two remained ctDNA negative in all post-ACT samples, and consistently have not relapsed, while the other two patients regained ctDNA positivity shortly after treatment and eventually relapsed as shown in FIG. 87D.

ctDNA Detection Post-ACT Defines a Patient Subgroup with Very High Recurrence Risk.

Since 100% of the patients who did not clear ctDNA during adjuvant chemotherapy (ACT), subsequently experienced disease relapse, we hypothesized that ctDNA analysis of the first blood sample drawn after ACT can be used to identify a subgroup of patients with continued residual disease who would benefit from further treatment. We found that all ctDNA positive patients (7/7) relapsed out of the 58 patients with post-ACT blood samples. In comparison, the relapse rate was 13.7% (7/51) for the ctDNA negative patients (Fisher exact test, P<0.0001) as shown in FIG. 87E. The ctDNA status post-ACT was a stronger predictor of incipient relapse compared to other predictive factor such as stage, lymphovascular invasion, micro-radical resection status, and CEA as shown in Table 12.8 below, and ctDNA status was a highly significant predictor of time to recurrence (TTR) (HR, 18.0; 95% CI, 5.4-57; P<0.0000) as shown in FIG. 87F.

TABLE 12.8

Time to recurrence analysis by clinicopathological variables, post-op ctDNA, and post-op CEA status at first timepoint post-ACT.

| Variable All patients with longitudinally collected plasma and ACT (n = 58) | Univariate analysis* | | |
|---|---|---|---|
| | HR | (95% CI) | P |
| Age | | | |
| < mean versus ≥ Mean Stage | 1.3 | (0.44-3.8) | 0.612 |
| Stage II versus stage III Tumor site | 1.3 | (0.17-10) | 0.794 |
| Right versus left | 1.8 | (0.63-5.3) | 0.265 |
| Lymphovascular invasion | | | |
| No versus yes MMR-status | 3.0 | (0.93-9.5) | 0.0664 |
| Deficient versus proficient Radical resection (micro) | 1.1 | (0.0-Inf) | 0.998 |
| Yes versus no Histology | 2.6 | (0.77-9) | 0.125 |
| Adeno-versus mucinouscarcinoma Tumor differentiation | 1.1 | (.14-8.3) | 0.943 |
| Medium/well versus poor Tumor perforation | 1.2 | (0.27-5.6) | 0.779 |
| No versus yes Gender | 0.91 | (0.12-7) | 0.929 |
| Female versus male CEA | 0.2 | (0.055-0.71) | 0.013 |
| CEA-versus CEA+ ctDNA | 2.4 | (0.74-7.9) | 0.141 |
| ctDNA-versus ctDNA+ | 18 | (5.4-57) | <0.0000 |

Figure 92:
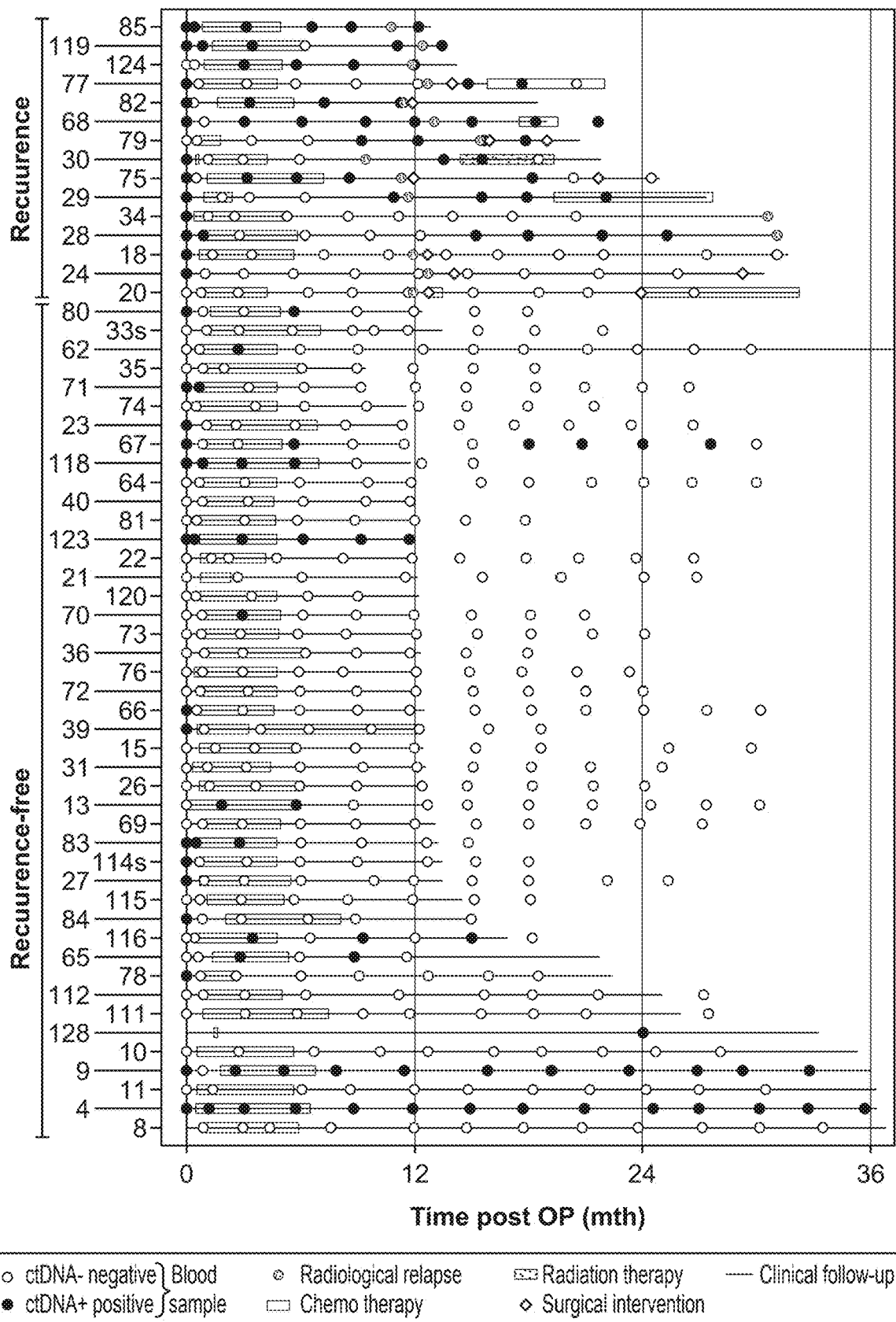
FIG. 92 shows a schematic overview of CEA profiling results of plasma samples included in the longitudinal post-ACT ctDNA analysis ordered by recurrence status, postoperative ctDNA status, and length of follow-up. Patients marked by a (s) have synchronous CRC (n=2). Plasma marked with ** are positive in the second pool only (n=1).

Longitudinal ctDNA analysis including all post-ACT blood samples, was an even stronger predictor of time to recurrence (HR, 29.0; 95% CI, 6.4-130; p<0.0000), and identified 13 ctDNA-positive patients of which 92.3% (12/13) relapsed as shown in FIG. 91. Although, longitudinal carcinoembryonic antigen (CEA) analysis was also a significant predictor of time to recurrence as shown in FIG. 92, following multivariate adjustment, longitudinal ctDNA status was the sole significant predictor of time to recurrence (HR, 26.9; 95% CI, 5.11-142; P=0.0001) as shown in Table 12.9 below.

TABLE 12.9

Time to Recurrence Analysis by Clinicopathological Variables, Post-Op ctDNA, and Post-Op CEA Status at all Timepoints Post-ACT.

| Variable All patients with longitudinally collected plasma and ACT (n = 58) | Univariate analysis* | | | Multivariate analysis* | | |
|---|---|---|---|---|---|---|
| | HR | (95% CI) | P | HR | (95% CI) | P |
| Age | | | | | | |
| < mean versus ≥ Mean Stage | 1.3 | (0.44-3.8) | 0.612 | | | |
| Stage II versus stage III Tumor site | 1.3 | (0.17-10) | 0.794 | | | |
| Right versus left Lymphovascular invasion | 1.8 | (0.63-5.3) | 0.265 | | | |
| No versus yes MMR-status | 3.0 | (0.93-9.5) | 0.0664 | | | |
| Deficient versus proficient | 1.1 | (0.0-Inf) | 0.998 | | | |

TABLE 12.9-continued

Time to Recurrence Analysis by Clinicopathological Variables, Post-Op ctDNA, and Post-Op CEA Status at all Timepoints Post-ACT.

| Variable | | | | Multivariate analysis* | | |
|---|---|---|---|---|---|---|
| All patients with longitudinally | Univariate analysis* | | | | (95% | |
| collected plasma and ACT (n = 58) | HR | (95% CI) | P | HR | CI) | P |
| Radical resection (micro) | | | | | | |
| Yes versus no | 2.6 | (0.77-9) | 0.125 | | | |
| Histology | | | | | | |
| Adeno-versus mucinouscarcinoma | 1.1 | (.14-8.3) | 0.943 | | | |
| Tumor differentiation | | | | | | |
| Medium/well versus poor | 1.2 | (0.27-5.6) | 0.779 | | | |
| Tumor perforation | | | | | | |
| No versus yes | 0.91 | (0.12-7) | 0.929 | | | |
| Gender | | | | | | |
| Female versus male | 0.2 | (0.055-0.71) | 0.013 | | | |
| CEA | | | | | | |
| CEA-versus CEA+ | 5.5 | (1.7-18) | 0.00449 | 1.1 | (0.31-4.2) | 0.854 |
| ctDNA | | | | | | |
| ctDNA-versus ctDNA+ | 29 | (6.4-130) | <0.0000 | 26.9 | (5.11-142) | <0.0000 |

*Includes variables that were statistical significant in the univariate analysis, except gender.

Longitudinal ctDNA Analysis Predicted Patient Outcome and Enabled Early Detection of Recurrence.

Figure 93A:
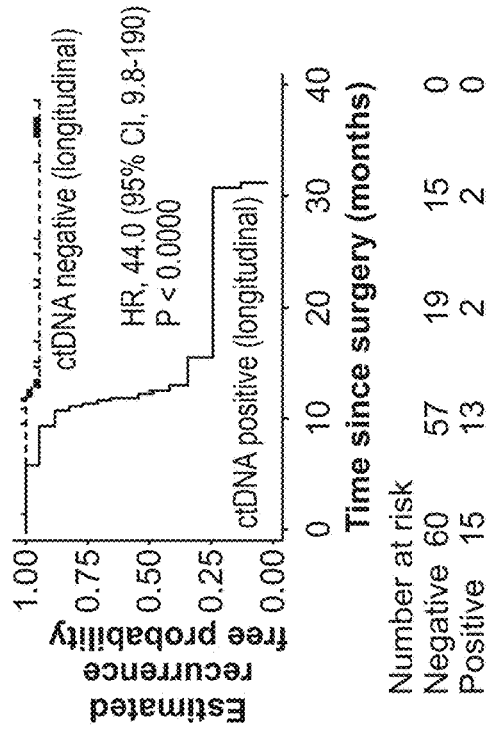
FIG. 93A-D: Graphs showing the association between ctDNA status and recurrence subsequent to definitive treatment.
Figure 93B:
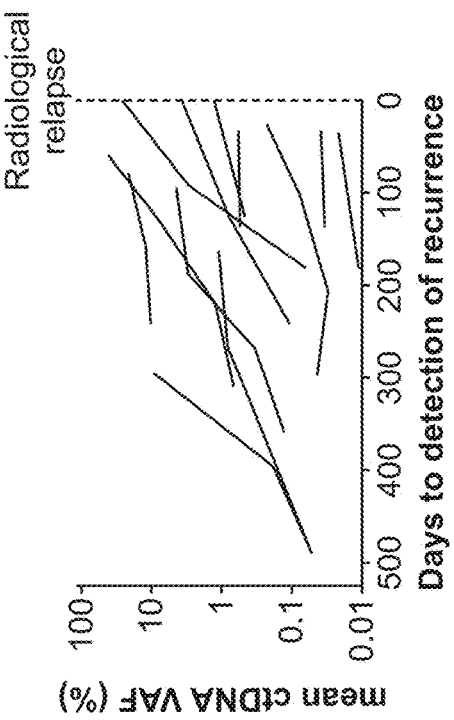
Figure 94:
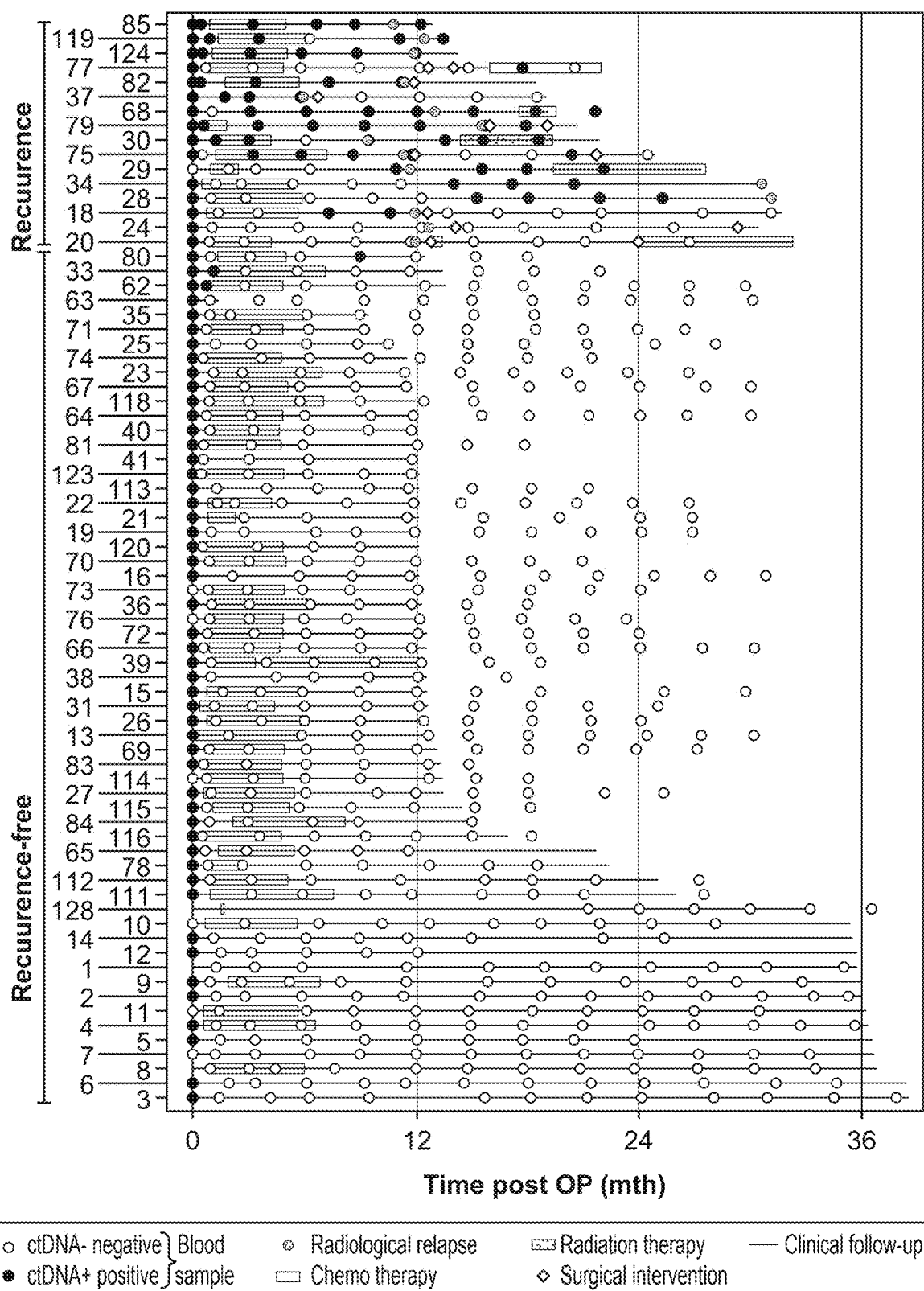
FIG. 94: Schematic overview of ctDNA profiling results of longitudinal plasma samples from relapsing vs. non-relapsing patients. Patients with just one positive plasma sample during surveillance is considered positive.

Serial ctDNA analysis during surveillance after definitive treatment of the 75 patients with longitudinal collected plasma samples identified metastatic relapse with 87.5% (14/16) sensitivity and 98.3% (58/59) specificity. Strikingly, 93.3% (14/15) of the ctDNA-positive patients recurred compared to a recurrence rate of only 3.3% (2/60) for patients who were ctDNA negative (Fisher's exact test, P<0.0001). The ctDNA-positive patients had a markedly reduced time to recurrence (TTR) (HR, 44.0; 95% CI, 9.8-190; P<0.0000) as shown in FIG. 93A-B. The disease courses and longitudinal ctDNA results for all 75 patients are shown in FIG. 94. The serial ctDNA analysis missed two relapse events (patients 20 and 24, FIG. 94). Whole exome sequencing of the two missed metastases, nevertheless, confirmed the presence of the mutations used for plasma screening as shown in Table 12.10 below.

TABLE 12.10

Matched Tumor and Metastatic WES on the Two Patients For Whom no ctDNA Were Detected and a Third Patient For Whom the Plasma Analysis Detected ctDNA Subsequent to Clinical Recurrence.

| | Patient ID | | |
|---|---|---|---|
| | 20 no ctDNA detected | 24 no ctDNA detected | 77 ctDNA detected after relapse |
| Mutations present in tumor also present in the metastasis (%) | 62.6 | 50.0 | 79.4 |
| Mutations screened in plasma also present in the metastasis (%) | 100.0 | 87.5 | 93.8 |

For the two recurrence patients (ID 20 and 24, Table 12.10), the longitudinal analysis detected no ctDNA post-op as shown in FIG. 90A-B. The same amount of plasma was analysed for these two patients as for the other patients. A possible sample swap could be rejected due to the 45 common SNPs in all tumors and plasma samples, which confirmed that no samples had been swapped. Next, we performed whole exome sequencing (WES) of the metastatic recurrence lesions for the two patients, and confirmed that the mutations selected for plasma profiling were present in the metastases Table 12.9. WES was also performed on the metastases from patient 77. For this patient the ctDNA longitudinal analysis did not detect ctDNA until after recurrence had been detected by radiological imaging as shown in FIG. 90A-B. Again, WES confirmed that the mutations selected for plasma profiling were present in the metastasis. In conclusion, the negative post-operative findings were caused by ctDNA levels below detection level and not that the selected markers were non-informative.

Figure 95:
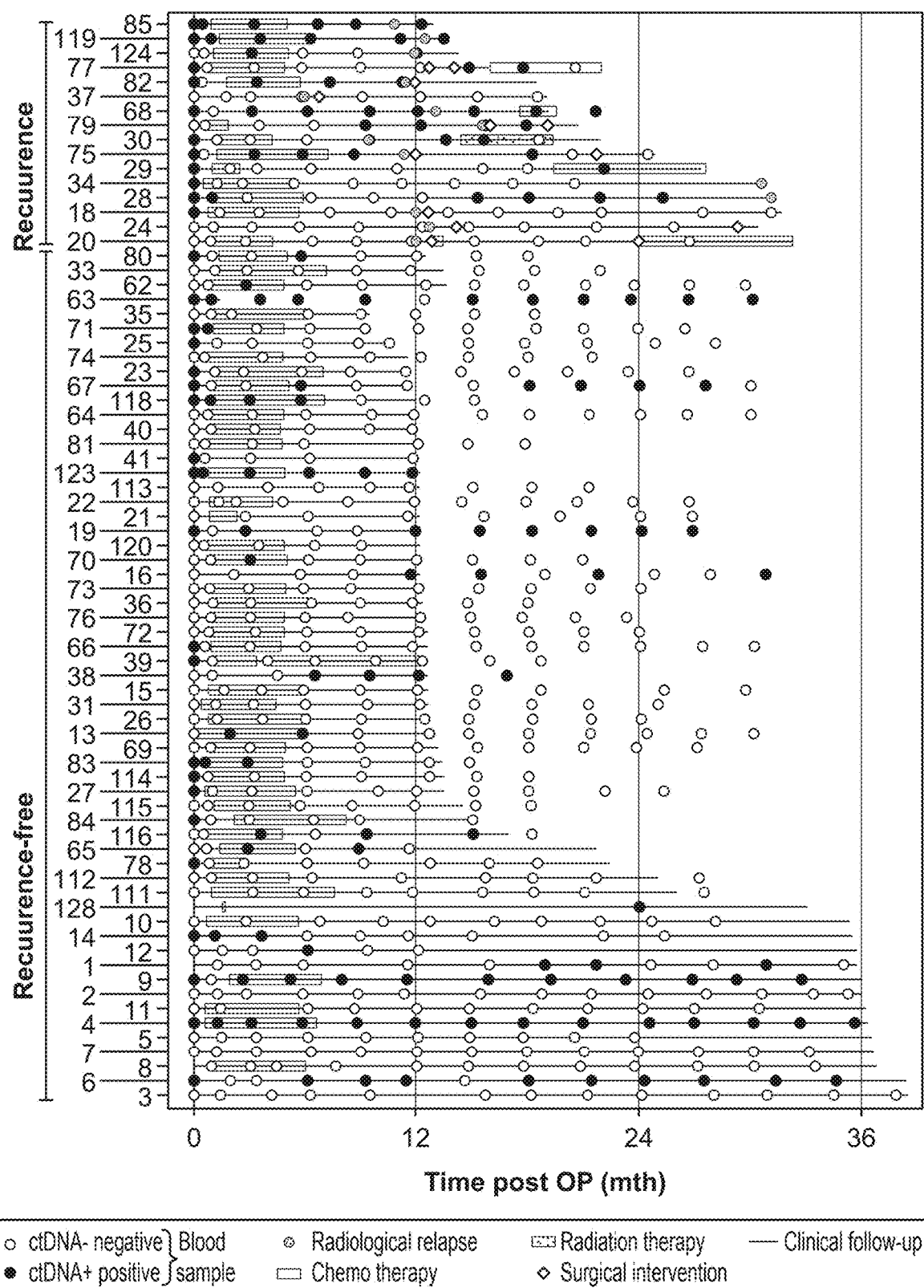
FIG. 95: Schematic overview of CEA profiling results of longitudinal serum samples from relapsing vs. non-relapsing patients. Patients with just one positive plasma sample during surveillance is considered positive.

Longitudinal CEA analysis of this same population identified relapse with a sensitivity of 68.8% (11/16) and specificity of 64.4% (38/59) as shown in FIG. 95. In multivariate analysis, ctDNA was the only significant predictor of time to recurrence (TTR) (HR, 41; 95% CI, 8.5-199; P<0.0000) as shown in Table 12.11 below.

TABLE 12.11

Time to Recurrence Analysis by Clinicopathological Variables and Post-Op ctDNA and CEA Status in Surveillance Samples.

| Variable All patients with longitudinally collected plasma (n = 75) | Univariate analysis* | | | Multivariate analysis* | | |
|---|---|---|---|---|---|---|
| | HR | (95% CI) | P | HR | (95% CI) | P |
| Age | | | | | | |
| < mean versus ≥ Mean | 1.0 | (0.39-2.8) | 0.947 | | | |
| Stage | | | | | | |
| Stage II versus stage III | 3.3 | (0.74-15) | 0.118 | | | |
| Tumor site | | | | | | |
| Right versus left | 1.2 | (0.45-3.2) | 0.722 | | | |
| Lymphovascular invasion | | | | | | |
| No versus yes | 4.1 | (1.4-12) | 0.010 | 1.1 | (0.35-3.4) | 0.875 |
| MMR-status | | | | | | |
| Deficient versus proficient | 1.2 | (0.0-Inf) | 0.998 | | | |
| Radical resection (micro) | | | | | | |
| Yes versus no | 2.9 | (0.88-9.3) | 0.080 | | | |
| Histology | | | | | | |
| Adeno-versus mucinouscarcinoma | 0.84 | (.84-6.4) | 0.868 | | | |
| Tumor differentiation | | | | | | |
| Medium/well versus poor | 0.92 | (0.21-4.1) | 0.911 | | | |
| Tumor perforation | | | | | | |
| No versus yes | 1.1 | (0.15-8.7) | 0.893 | | | |
| Gender | | | | | | |
| Female versus male | 0.25 | (0.08-0.8) | 0.018 | | | |
| CEA | | | | | | |
| CEA-versus CEA+ | 2.8 | (0.95-8.0) | 0.061 | | | |
| ctDNA | | | | | | |
| ctDNA-versus ctDNA+ | 44 | (9.8-190) | <0.0000 | 41 | (8.5-199) | <0.0000 |

*Includes variables that were statistical significant in the univariate analysis, except gender.

Figure 93C:
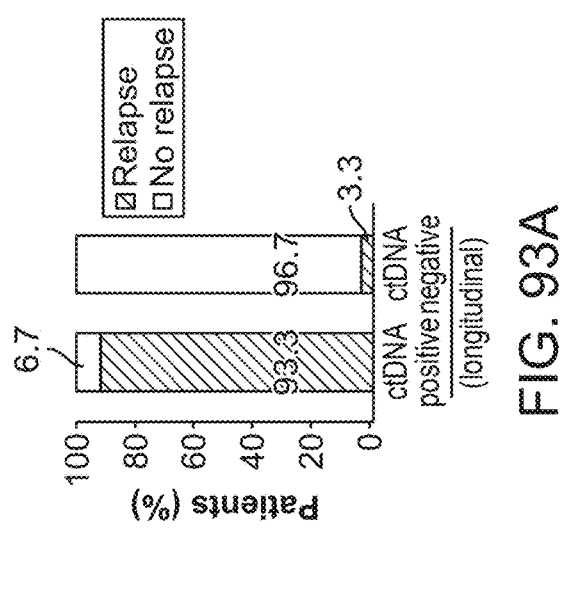
Figure 93D:
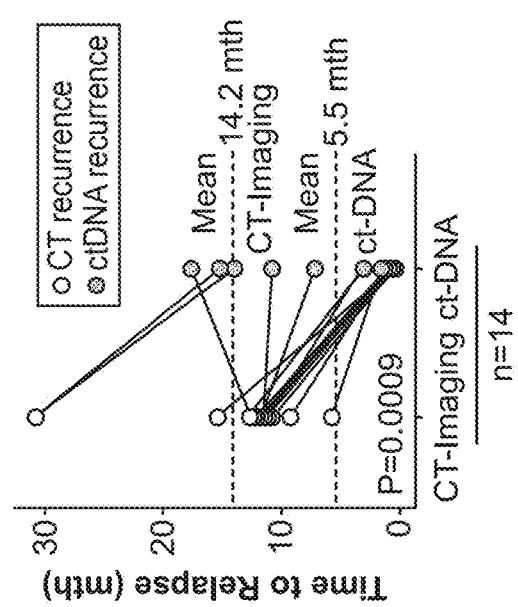
Figure 96:
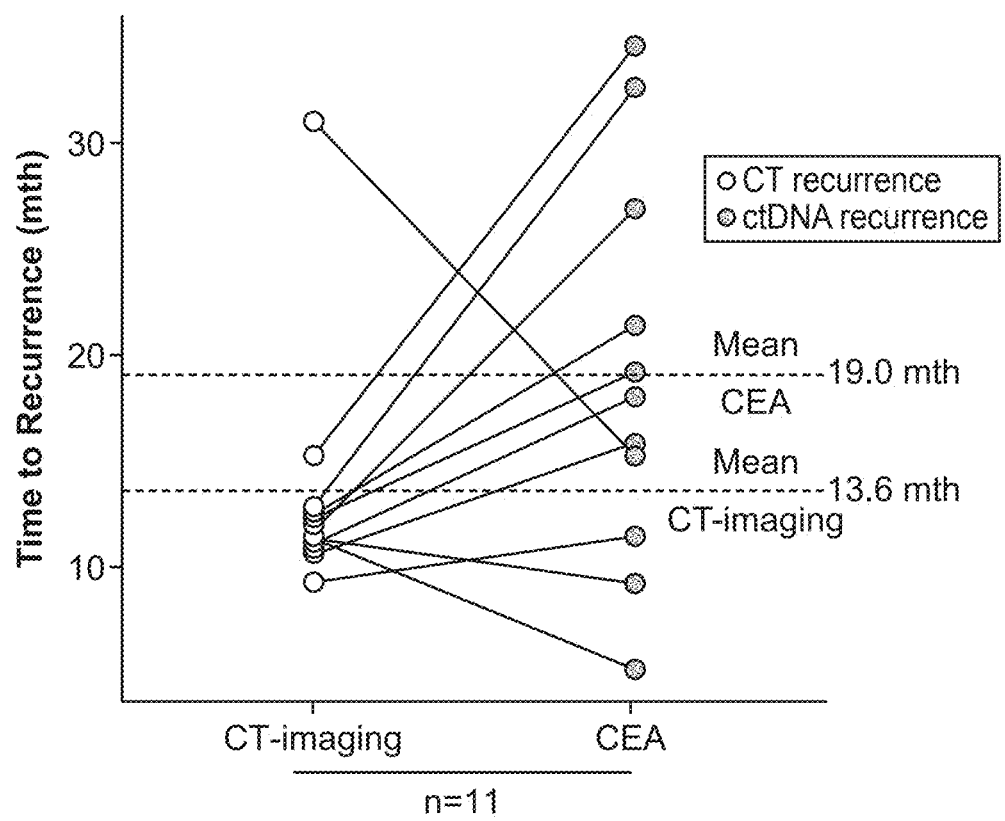
FIG. 96: Graph comparing time to radiological and CEA recurrence.

For patients with metastatic relapse and detectable ctDNA, it was found that ctDNA analysis had a mean lead time of 8.7 months (Wilcoxon signed rank test; P=0.0009) over standard-of-care CT-imaging as shown in FIG. 93C; whereas, no lead time could be established by using carcinoembryonic antigen (CEA) analysis as shown in FIG. 96. From ctDNA detection and until radiological relapse detection plasma samples remained ctDNA positive, and a 50-fold increase in the mean ctDNA VAF was observed, indicating that the tumor burden increased dramatically while the patients awaited radiological detection of the relapse as shown in FIG. 93D.

ctDNA Analysis Revealed Clinically Actionable Mutations

Having shown that longitudinal ctDNA analysis enabled early detection of micrometastatic disease, we next investigated if longitudinal ctDNA analysis could be used to obtain information about potentially actionable mutations present in the metastases.

11 patients with metastatic recurrence were identified from the available longitudinal samples, and clinically actionable mutations were identified by performing primary tumor whole exome sequencing (WES) as shown in Table 12.12 below.

TABLE 12.12

Patients with actionable mutations detected in the primary tumor.

| Pt. ID | Chr | Gene | POS | SNP ID | Nucleotide | Altnucleotide | POS change | Aminoacid change |
|---|---|---|---|---|---|---|---|---|
| 42 | chr14 | AKT1 | 105246551 | rs121434592 | C | T | c.49G > A | p.Glu17Lys |
| 42 | chr7 | BRAF | 140453136 | rs113488022 | A | T | c.1799T > A | p.Val600Glu |
| 18 | chr12 | KRAS | 25398284 | rs121913529 | C | T | c.35G > A | p.Gly12Asp |
| 20 | chr12 | KRAS | 25398284 | rs121913529 | C | T | c.35G > A | p.Gly12Asp |
| 20 | chr10 | PTEN | 89692981 | . | | TG | c.988dupG | p.Glu330fs |
| 68 | chr3 | PIK3CA | 178936091 | rs 104886003 | G | A | c.1633G > A | p.E545K |
| 68 | chr12 | KRAS | 25398284 | rs121913529 | C | T | c.35G > A | p.Gly12Asp |
| 24 | chr12 | KRAS | 25398284 | rs121913529 | C | A | c.35G > T | p.Gly12Val |
| 24 | chr18 | SMAD4 | 48604706 | | | G | T | c.1528G > T | p.Gly510* |

TABLE 12.12-continued

Patients with actionable mutations detected in the primary tumor.

| | | | | | | | | |
|---|---|---|---|---|---|---|---|---|
| 29 | chr12 | KRAS | 25398281 | rs112445441 | C | T | c.38G > A | p.Gly13Asp |
| 30 | chr3 | PIK3CA | 178936082 | . | G | A | c.1624G > A | E542K |
| 30 | chr12 | KRAS | 25398284 | rs121913529 | C | A | c.35G > T | p.Gly12Val |
| 30 | chr18 | SMAD4 | 48591928 | rs377767350 | T | G | c.1091T > G | p.Leu364Trp |
| 75 | chr17 | ERBB2 | 37880261 | . | G | T | c.2305G > T | p.Asp769Tyr |
| 75 | chr17 | ERBB2 | 37881000 | rs121913471 | G | T | c.2329G > T | p.Val777Leu |
| 77 | chr7 | BRAF | 140453136 | rs113488022 | A | T | c.1799T > A | p.Val600Glu |
| 37 | chr12 | KRAS | 25398285 | rs121913530 | C | T | c.34G > A | p.Gly12Ser |
| 89 | chr12 | KRAS | 25398285 | rs121913530 | C | A | c.34G > T | p.Gly12Cys |
| 125 | chr12 | KRAS | 25398284 | rs121913529 | C | A | c.35G > T | p.Gly12Val |
| 85 | chr3 | PIK3CA | 178938934 | . | G | A | c.2176G > A | p.Glu726Lys |
| 85 | chr12 | KRAS | 25398285 | rs121913530 | C | A | c.34G > T | p.Gly12Cys |
| 119 | chr12 | KRAS | 25398285 | rs121913530 | C | T | c.34G > A | p.Gly12Ser |
| 99 | chr12 | KRAS | 25380278 | . | A | T | c.180T > A | p.Gly60Gly |
| 99 | chr12 | KRAS | 25380277 | rs121913238 | G | T | c.181C > A | p.Gln61Lys |
| 104 | chr18 | SMAD4 | 48604701 | . | G | C | c.1523G > C | p.Gly508Ala |
| 124 | chr7 | BRAF | 140453136 | rs113488022 | A | T | c.1799T > A | p.Val600Glu |
| 108 | chr3 | PIK3CA | 178936094 | rs121913286 | C | A | c.1636C > A | Q546K |
| 108 | chr12 | KRAS | 25398285 | rs121913530 | C | A | c.34G > T | p.Gly12Cys |

| Pt. ID | POS | Cancer type | Drug | Ref. | Database | ctDNA + longitudinal plasma |
|---|---|---|---|---|---|---|
| 42 | 105246551 | Solid Tumors | AZD5363 | AKT Inhibition in Solid Tumors With AKT1 Mutations. | worldwideweb.mycancergenome.org/ | |
| 42 | 140453136 | Colorectal Cancer | RTK-Inhibitor + Trametinib | | oncokb.org/#/actionableGenes | |
| 18 | 25398284 | All Tumors | GDC-0994, KO-947, LY3214996 | | oncokb.org/#/actionableGenes | Yes |
| 20 | 25398284 | All Tumors | GDC-0994, KO-947, LY3214996 | | oncokb.org/#/actionableGenes | |
| 20 | 89692981 | Colorectal Cancer | GSK2636771 & AZD8186 | | oncokb.org/#/actionableGenes | |
| 68 | 178936091 | All Tumors | AZD8186 | Bendell et al. 2011). Clarke and Workman (2012) | worldwideweb.mycancergenome.org/ | Yes |
| 68 | 25398284 | All Tumors | GDC-0994, KO-947, LY3214996 | | oncokb.org/#/actionableGenes | Yes |
| 24 | 25398284 | Colorectal Cancer | GDC-0994, KO-947, LY3214996 | | oncokb.org/#/actionableGenes | |
| 24 | 48604706 | All Tumors | | Targeting the TGFβ pathway for cancer therapy | worldwideweb.mycancergenome.org/ | |
| 29 | 25398281 | Colorectal Cancer | GDC-0994, KO-947, LY3214996 | | oncokb.org/#/actionableGenes | Yes |
| 30 | 178936082 | Colorectal/ Breast cancer | Aspirin/PI3K inhibitors | Bendell et al. 2011). Clarke and Workman (2012) | worldwideweb.mycancergenome.org/ | Yes |
| 30 | 25398284 | Colorectal/ Breast cancer | GDC-0994, KO-947, LY3214996 | | oncokb.org/#/actionableGenes | Yes |
| 30 | 48591928 | Colorectal Cancer | | Targeting the TGFβ pathway for cancer therapy | worldwideweb.mycancergenome.org/ | Yes |
| 75 | 37880261 | All Tumors | Neratinib/ afatinib | HER2 activating mutations are targets | civicdb.org | Yes |

TABLE 12.12-continued

Patients with actionable mutations detected in the primary tumor.

| | | | | | | |
|---|---|---|---|---|---|---|
| 75 | 37881000 | All Tumors | Neratinib/ afatinib | for colorectal cancer treatment HER2 activating mutations are targets for colorectal cancer treatment | civicdb.org | Yes |
| 77 | 140453136 | Colorectal Cancer | RTK-Inhibitor + Trametinib | | oncokb.org/#/actionableGenes | Yes |
| 37 | 25398285 | Colorectal Cancer | GDC-0994, KO-947, LY3214996 | | oncokb.org/#/actionableGenes | Yes |
| 89 | 25398285 | Colorectal Cancer | GDC-0994, KO-947, LY3214996 | | oncokb.org/#/actionableGenes | |
| 125 | 253982 84 | Colorectal Cancer | GDC-0994, KO-947, LY3214996 | | oncokb.org/#/actionableGenes | |
| 85 | 178938934 | Colorectal Cancer | Aspirin/PI3K inhibitors | Bendell et al. 2011). Clarke and Workman (2012) | worldwideweb.mycancergenome.org/ | Yes |
| 85 | 25398285 | All Tumors | GDC-0994, KO-947, LY3214996 | | oncokb.org/#/actionableGenes | Yes |
| 11 | 25398285 | Colorectal Cancer | GDC-0994, KO-947, LY3214996 | | oncokb.org/#/actionableGenes | Yes |
| 99 | 25380278 | Colorectal Cancer | GDC-0994, KO-947, LY3214997 | | oncokb.org/#/actionableGenes | |
| 99 | 25380277 | Colorectal Cancer | GDC-0994, KO-947, LY3214998 | | oncokb.org/#/actionableGenes | |
| 104 | 48604701 | Colorectal Cancer | | Targeting the TGFβ pathway for cancer therapy HER2 | worldwideweb.mycancergenome.org/ | |
| 124 | 140453136 | Colorectal Cancer | RTK-Inhibitor + Trametinib | | oncokb.org/#/actionableGenes | |
| 108 | 178936094 | Colorectal Cancer | Aspirin/PI3K inhibitors | Bendell et al. 2011). Clarke and Workman (2012) | worldwideweb.mycancergenome.org/ | |
| 108 | 25398285 | Colorectal Cancer | GDC-0994, KO-947, LY3214996 | | oncokb.org/#/actionableGenes | |

Figure 97A:
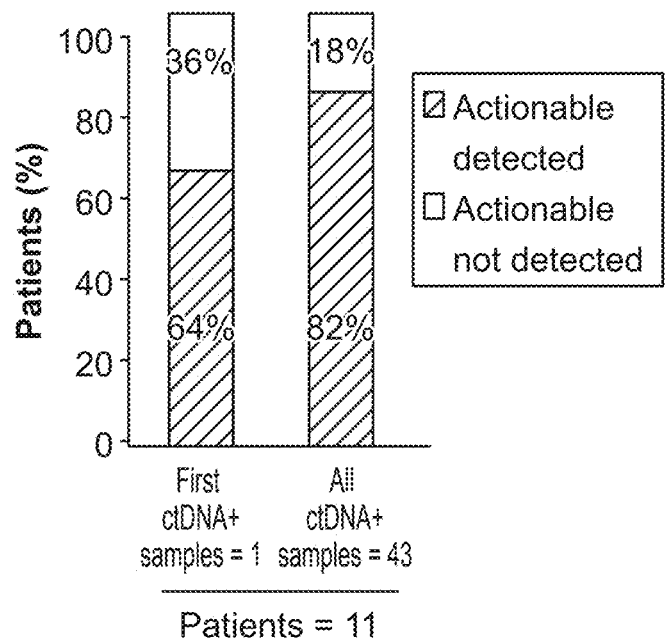
FIG. 97A-D: Detection of actionable mutation in recurrence patients.
Figure 97B:
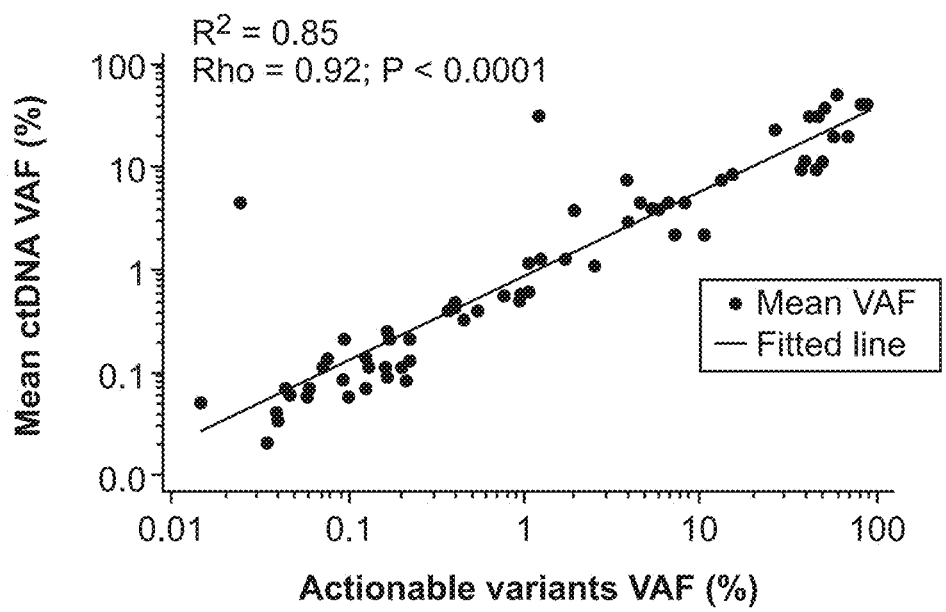
Figures 97C, 97D:
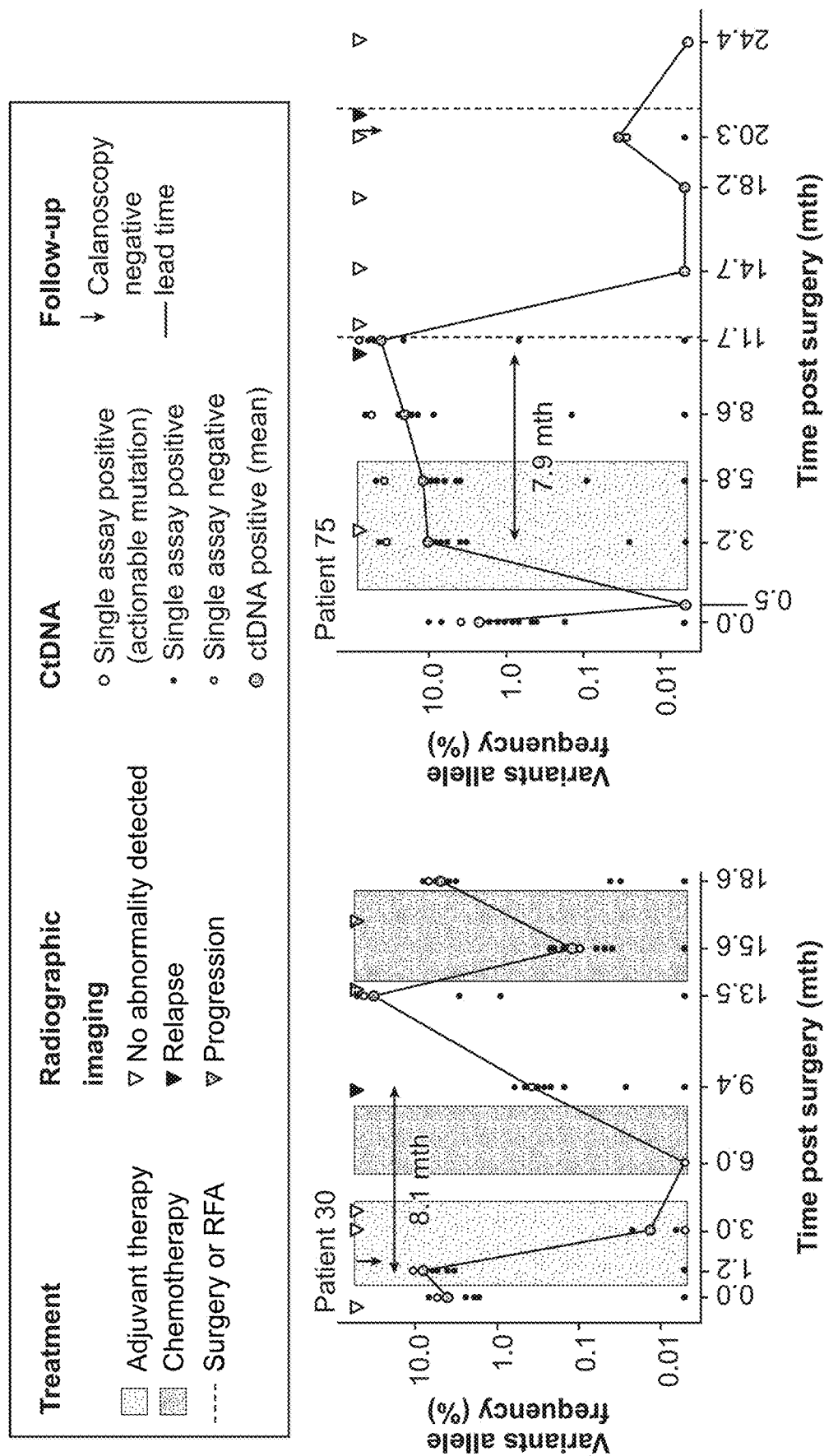
Figure 98:
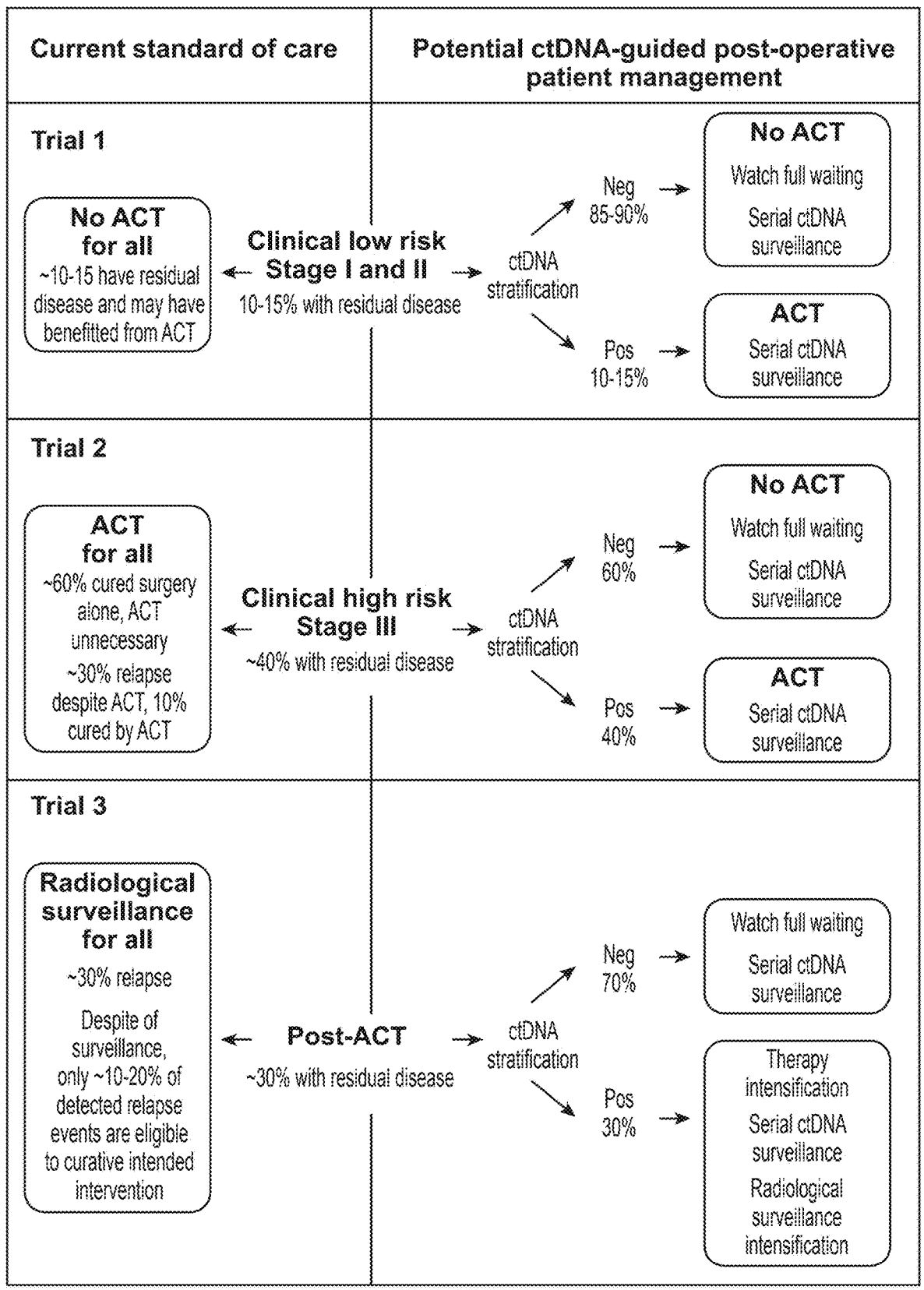
FIG. 98: Schematic comparison of current standard of care and potential ctDNA guided post-operative patient management.
Figure 99:
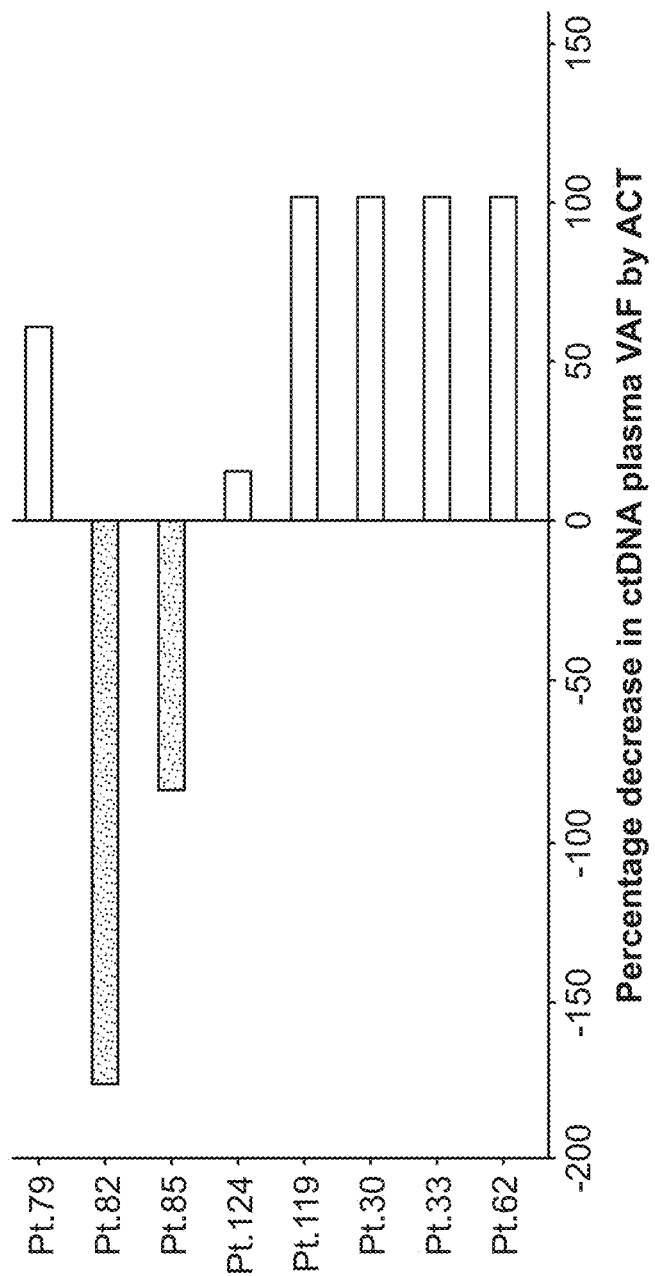
FIG. 99: Graph showing ctDNA decreased by adjuvant chemotherapy (ACT).

As a proof-of-concept, an additional multiplex-PCR panel targeting the actionable mutations were designed and applied to the longitudinal samples. An actionable mutation was detected in 82% (9/11) of the patients as shown in FIG. 97A. We observed a good correlation between the mean ctDNA VAFs and the VAFs of the actionable mutations as shown in FIG. 97B. The longitudinal changes in the actionable variant allele frequencies (VAFs) generally showed good correlation to treatment and very little inter mutation variation as shown in FIG. 97C.

Discussion

This example demonstrated that longitudinal ctDNA analysis in patients with stage I-III CRC can effectively detect and monitor changes in tumor burden throughout the clinical disease course. Specifically, it was demonstrated that ctDNA served as a robust biomarker for i) pre-operative CRC detection, ii) post-operative and post-ACT risk-stratification, iii) monitoring ACT efficacy, iv) detection of clinical actionable mutations, and v) early detection of recurrence. These observations have important and potentially paradigm-changing implications for the future of post-operative management of CRC patients, and laid the foundation for future intervention trials to investigate the clinical benefits of ctDNA-guided management.

In the pre-operative context, it was demonstrated the applicability of preoperative ctDNA measurements for disease detection.

In terms of patient stratification, ctDNA-analysis used herein divided patients into high- and low-relapse risk groups, which had potential implications on patient selection for adjuvant chemotherapy (ACT) treatment and for the decision of additional post-ACT treatment. Previously, decision making for ACT treatment was based on staging and clinical risk factors. However, the disclosure herein showed that ctDNA status is a stronger prognostic factor than stage, CEA and other high-risk features. Hence, in the future it may be possible to assign ctDNA-positive, but clinically low risk (stage I and II) patients, who would not receive ACT as the standard-of-care today, to ACT treatment based on the ctDNA analysis. The inventors of the present disclosure are currently conducting trial to assess the clinical benefit of ctDNA-based patient selection in this setting (e.g. IMPROVE-IT ClinicalTrials.gov: NCT03748680 and DYNAMIC Australian New Zealand Clinical Trials registry: ACTRN12615000381583).

The present disclosure also demonstrated that ctDNA negative patients have a low risk of relapsing, independent of whether ACT was administered (11.9%) or not (11.9%). Hence, in the future it may be possible to withhold ACT from ctDNA negative, but clinically high risk (stage III) patients, with minimal impact on their relapse risk. This patient group could be offered active ctDNA-based surveillance instead of ACT, thus sparing the many patients who are cured by surgery alone, from the toxicity of chemotherapy. Additionally, in the post-ACT setting where there are no current prognostic markers, we demonstrate that ctDNA analysis identifies patients who still have residual disease. This population may benefit from intensified therapeutic treatment.

The present disclosure also demonstrated that longitudinal ctDNA monitoring before, during and after ACT can provide a patient-level measurement of ACT efficacy. The 30% of patients who cleared ctDNA and remained negative in all subsequent samples, stayed disease free throughout the study. Thus, this example provided first line of evidence that ACT can reduce the risk of recurrence in ctDNA-positive patients. The present disclosure also demonstrated that all patients who did not clear ctDNA relapsed within a year of completion of ACT, and all patients with only transient clearance also relapsed. Future clinical trials that incorporate ctDNA clearance in the study design may allow for patient-level real-time measurement of therapy efficacy.

In the post-operative context, ctDNA monitoring show a significant improvement in relapse detection compared to standard-of-care radiological imaging, demonstrating a significant lead time of 8.7 months (P<0.001). Importantly, while awaiting radiological detection the ctDNA level increased by an average of 50 fold, indicating that tumor burden increases dramatically during the 8.7 months of lead time. Current guidelines recommend surveillance after curative CRC surgery, but the majority of relapse events are detected too late to be eligible for curative intervention. The early detection of residual disease by ctDNA analysis, may provide an opportunity for earlier radiological detection. In addition to detection of residual disease, ctDNA analysis also enabled identification of clinically actionable mutations. Hence, ctDNA has the potential to enable both early detection, and to guide treatment decisions.

In conclusion, the disclosure present in this example provided potentially paradigm-changing clinical applications of ctDNA in colorectal cancer. As aforementioned, additional clinical trials are being designed or already underway to investigate the clinical benefits of ctDNA-guided management. The results provided herein enables the use of circulating biomarkers for personalized risk stratification and therapy monitoring to ensure that the right treatment is given to the right patient at the right time and for the right duration.

Example 11. Whole Exome Plasma cfDNA Profiling Captures the Mutational Signatures of Pre-Clinical Relapse for Monitoring Disease Evolution The purpose of this example was to evaluate the use of whole-exome sequencing of plasma cell-free DNA (cfDNA-WES) for investigating mutational signatures and clonal evolution in patients with advanced cancers or patients with high circulating tumour DNA (ctDNA) burden. In particular, we demonstrated herein the use of cfDNA-WES profiling for detection of pre-clinical metastasis in patients with primary breast cancer.

Methods

Forty-nine primary breast cancer patients were recruited following surgery and adjuvant therapy. Serial plasma samples were collected every six months for ctDNA analysis using patient-specific assays targeting 16 variants by ultra-deep sequencing with Natera's Signatera workflow. Whole exome sequencing was performed on plasma cfDNA from all 17 relapsed patients before and around the time of clinical relapse in order to determine the concordance between variants identified in plasma and tumor biopsy, and understand tumor evolution during disease progression.

Results

Preliminary analysis of cfDNA-WES profiles from 3 relapsed patients showed a high degree of concordance between patient-specific variants identified in tumor biopsy and plasma. 34 out of 35 Signatera-detected variants were also identified by plasma WES and showed highly concordant variant allele frequencies (VAFs). The one variant that was not detected by cfDNA-WES was previously detected by Signatera at 0.2% VAF.

CONCLUSIONS

This examples showed that plasma WES can detect molecular residual disease in primary breast cancer patients. Analysis of WES plasma potentially provides evidence of cancer evolution, which may be important for treatment decision making.

Example 12. Use of Circulating Tumor DNA (ctDNA) as a Molecular Biomarker for the Assessment of Treatment Response in Lymphoma Here, in a biopharmaceutical pilot study, we evaluated the potential of a personalized, tumor-specific, multiplex PCR NGS-based approach (Signatera™) to detect ctDNA over the course of the patients' treatment regimen in order to correlate presence with the overall clinical response in a cohort with Non-Hodgkin's Lymphoma (NHL).

Methods

Blood samples collected from 8 Non-Hodgkin's Lymphoma (NHL) (6 diffuse large B-cell lymphoma and 2 follicular lymphoma) patients (pts) were available for ctDNA analysis. Patient-specific somatic variants were identified by analysis of whole exome sequencing (WES) data from primary tumor biopsy and matched normal samples. Plasma samples were then analyzed with the corresponding custom 16-plex assays using the Signatera workflow in a blinded manner. Samples were considered ctDNA positive if at least two patient-specific targets met the qualifying confidence score threshold.

Results

For Non-Hodgkin's Lymphoma (NHL), a median of 14.9 ng (range, 2.25-685 ng) of cfDNA was extracted from a median of 2.5 mL plasma. ctDNA was detected in 5 plasma time points from 4 patients. Of the 5 ctDNA+ plasma samples, 4 plasma samples correlated with either clinically progressive disease or partial response to therapy at blood collection. The 4 patients with no ctDNA detection at any time point displayed clinical complete response at blood collection.

CONCLUSIONS

A scalable patient-specific ctDNA monitoring assay can be applied for baseline detection, therapy monitoring and recurrence detection. Signatera's highly sensitive ctDNA detection analysis provides a non-invasive means of monitoring over the current standard of care.

What is claimed is:

1. A method for preparing a DNA fraction from a plasma sample of a cancer patient who has been diagnosed with colorectal cancer useful for assessing early relapse or metastasis of colorectal cancer, comprising
    performing whole exome sequencing on a tumor biopsy sample of the cancer patient who has been diagnosed with colorectal cancer to identify a plurality of patient-specific somatic mutations;
    longitudinally collecting one or more plasma samples from the cancer patient before and after the cancer patient has been treated with surgery, and extracting cell-free DNA from the one or more plasma samples;
    producing a DNA fraction by performing a targeted multiplex amplification reaction on the extracted cell-free DNA or DNA derived therefrom to generate a set of amplicons, wherein the set of amplicons each spans a single nucleotide variant locus of a set of at least 16 different patient-specific single nucleotide variant loci, and wherein the at least 16 different patient-specific single nucleotide variant loci each encompasses one of the somatic mutations identified in the tumor biopsy sample of the patient who has been diagnosed with the colorectal cancer by whole exome sequencing; and
    performing high-throughput sequencing to determine the sequence of at least a segment of each amplicon of the set of amplicons that comprises a patient-specific single nucleotide variant locus, wherein the patient-specific single nucleotide variant loci are each sequenced with a depth of read of at least 100,000 to obtain variant allele frequency (VAF) values of the patient-specific single nucleotide variant loci, wherein the presence of two or more patient-specific single nucleotide variant loci in the DNA fraction obtained from one or more plasma samples after surgery having a VAF value above a confidence threshold identifies early relapse or metastasis of colorectal cancer in the cancer patient.

2. The method of claim 1, wherein the presence of two or more patient-specific single nucleotide variant loci identifies early relapse or metastasis of colorectal cancer in the patient with a lead time of at least 9.13 months compared to clinical relapse or metastasis of cancer detectable by CT imaging.

3. The method of claim 1, wherein the method identifies the presence of two or more patient-specific single nucleotide variant loci in at least 95% of patients having early relapse or metastasis of colorectal cancer.

4. The method of claim 1, wherein the method identifies the presence of two or more patient-specific single nucleotide variant loci in at least 98% of patients having early relapse or metastasis of colorectal cancer.

5. The method of claim 1, wherein the method does not identify the presence of two or more patient-specific single nucleotide variant loci in at least 99% of patients not having early relapse or metastasis of colorectal cancer.

6. The method of claim 1, wherein the method has a specificity of at least 99.5% in identifying early relapse or metastasis of cancer when two or more patient-specific single nucleotide variant loci are identified above a confidence threshold of 0.97.

7. The method of claim 1, wherein the cancer patient has also been treated with an adjuvant chemotherapy before collection of at least one of the plasma samples.

8. The method of claim 1, wherein the colorectal cancer is stage I colorectal cancer.

9. The method of claim 1, wherein the colorectal cancer is stage II colorectal cancer.

10. The method of claim 1, wherein the colorectal cancer is stage III colorectal cancer.

11. The method of claim 1, wherein the presence of two or more patient-specific single nucleotide variant loci in the DNA fraction from two or more longitudinally collected plasma samples obtained at different time after surgery above a confidence threshold identifies early relapse or metastasis of colorectal cancer in the cancer patient.

12. The method of claim 1, wherein early relapse or metastasis of colorectal cancer in the cancer patient is determined when a percentage of the VAF for the two or more patient-specific single nucleotide variant loci in a plasma sample obtained after surgery is above a VAF percentage threshold value.

* * * * *